(12) United States Patent
Loy et al.

(10) Patent No.: US 10,246,417 B2
(45) Date of Patent: Apr. 2, 2019

(54) PICOLINAMIDES AS FUNGICIDES

(71) Applicant: Dow AgroSciences LLC, Indianapolis, IN (US)

(72) Inventors: Brian A. Loy, Indianapolis, IN (US);
Jared W. Rigoli, Indianapolis, IN (US);
Brannon Sam, Zionsville, IN (US);
Kevin G. Meyer, Zionsville, IN (US);
Chenglin Yao, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/862,769

(22) Filed: Jan. 5, 2018

(65) Prior Publication Data

US 2018/0186743 A1    Jul. 5, 2018

Related U.S. Application Data

(60) Provisional application No. 62/442,904, filed on Jan. 5, 2017, provisional application No. 62/442,914, filed on Jan. 5, 2017.

(51) Int. Cl.

| | | |
|---|---|---|
| *A01N 43/40* | (2006.01) | |
| *A01N 43/90* | (2006.01) | |
| *A01N 47/06* | (2006.01) | |
| *A01N 47/12* | (2006.01) | |
| *C07C 229/08* | (2006.01) | |
| *C07C 271/22* | (2006.01) | |
| *C07D 213/83* | (2006.01) | |
| *C07D 317/54* | (2006.01) | |
| *C07D 213/81* | (2006.01) | |
| *C07D 498/04* | (2006.01) | |

(52) U.S. Cl.
CPC .......... *C07D 213/81* (2013.01); *A01N 43/40* (2013.01); *A01N 43/90* (2013.01); *A01N 47/06* (2013.01); *A01N 47/12* (2013.01); *C07C 229/08* (2013.01); *C07C 271/22* (2013.01); *C07D 213/83* (2013.01); *C07D 317/54* (2013.01); *C07D 498/04* (2013.01); *C07B 2200/07* (2013.01); *C07C 2601/02* (2017.05); *C07C 2601/04* (2017.05); *C07C 2601/08* (2017.05); *C07C 2601/14* (2017.05)

(58) Field of Classification Search
CPC .. C07D 213/81; C07D 213/83; C07D 317/54; C07D 498/04; A01N 43/40; A01N 43/90; A01N 47/12; C07C 229/08; C07C 271/22
USPC ................................................... 514/230.5
See application file for complete search history.

(56) References Cited

U.S. PATENT DOCUMENTS

| | | | |
|---|---|---|---|
| 4,051,173 A | 9/1977 | Schact et al. | |
| 5,401,871 A | 3/1995 | Feldmann-Krane et al. | |
| 6,355,660 B1 | 3/2002 | Ricks et al. | |
| 6,410,572 B1 | 6/2002 | Schelberger et al. | |
| 6,436,421 B1 | 8/2002 | Schindler et al. | |
| 6,521,622 B1 | 2/2003 | Ricks et al. | |
| 6,706,740 B2 | 3/2004 | Ricks et al. | |
| 6,861,390 B2 | 3/2005 | Meyer et al. | |
| 6,903,219 B2 | 6/2005 | Niyaz et al. | |
| 6,916,932 B2 | 7/2005 | Meyer et al. | |
| 6,927,225 B2 | 8/2005 | Ricks | |
| 7,034,035 B2 | 4/2006 | Ricks et al. | |
| 7,183,278 B1 | 2/2007 | Sakanaka | |
| 7,241,804 B1 | 7/2007 | Hockenberry et al. | |
| 7,250,389 B1 | 7/2007 | Sakanaka | |
| RE39,991 E | 1/2008 | Ricks et al. | |
| 7,442,672 B2 | 12/2008 | Muller et al. | |
| 7,459,581 B2 | 12/2008 | Derrer et al. | |
| 7,560,565 B2 | 7/2009 | Bacque et al. | |
| 7,927,617 B2 | 4/2011 | Koltzenburg | |
| 8,008,231 B2 | 8/2011 | Leatherman | |
| 8,153,819 B2 | 4/2012 | Dietz | |
| 8,236,962 B2 | 8/2012 | Hoekstra et al. | |
| 8,349,877 B2 | 1/2013 | Brix et al. | |
| 8,415,274 B2 | 4/2013 | Wachendorff-Neumann et al. | |
| 8,470,840 B2 | 6/2013 | Klittich et al. | |
| 8,476,193 B2 | 7/2013 | Keeney et al. | |
| 8,586,550 B2 | 11/2013 | Lee et al. | |
| 8,604,215 B2 | 12/2013 | Phiasivongsa et al. | |
| 8,785,479 B2 | 7/2014 | Meyer et al. | |
| 8,835,462 B2 | 9/2014 | Meyer et al. | |
| 8,883,811 B2 | 11/2014 | Owen et al. | |

(Continued)

FOREIGN PATENT DOCUMENTS

| | | |
|---|---|---|
| CN | 102638989 | 8/2012 |
| EP | 1054011 | 11/2000 |

(Continued)

OTHER PUBLICATIONS

Hanafi, et al., "UK-2A, B, C and D, Novel Antifungal Antibiotics from *Streptomyces* sp. 517-02 II. Structural Elucidation", The Journal of Antibiotics, vol. 49, No. 12, pp. 1226-1231 (1996).

(Continued)

*Primary Examiner* — Yevgeny Valenrod

(57) ABSTRACT

This disclosure relates to picolinamides of Formula I and their use as fungicides.

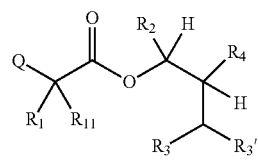

18 Claims, No Drawings

(56) References Cited

U.S. PATENT DOCUMENTS

| | | |
|---|---|---|
| 8,916,579 B2 | 12/2014 | Boebel |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,155,305 B2 | 10/2015 | Gary |
| 9,156,816 B2 | 10/2015 | Ito et al. |
| 9,179,674 B2 | 11/2015 | Martin et al. |
| 9,185,911 B2 | 11/2015 | Inami et al. |
| 9,198,419 B2 | 12/2015 | Owen et al. |
| 9,247,741 B2 | 2/2016 | DeLorbe et al. |
| 9,265,253 B2 | 2/2016 | Li et al. |
| 9,271,496 B2 | 3/2016 | Kemmit |
| 9,414,596 B2 | 8/2016 | Hoekstra et al. |
| 9,439,422 B2 | 9/2016 | Martin et al. |
| 9,549,555 B2 | 1/2017 | DeLorbe et al. |
| 9,549,556 B2 | 1/2017 | DeKorver et al. |
| 9,629,365 B2 | 4/2017 | Li et al. |
| 9,681,664 B2 | 6/2017 | LaLonde et al. |
| 9,686,984 B2 | 6/2017 | DeKorver et al. |
| 9,700,047 B2 | 7/2017 | Lu |
| 9,750,248 B2 | 9/2017 | Ouimette et al. |
| 2002/0119979 A1 | 8/2002 | Degenhardt et al. |
| 2002/0177578 A1 | 11/2002 | Ricks et al. |
| 2003/0018012 A1 | 1/2003 | Ricks |
| 2003/0018052 A1 | 1/2003 | Ricks |
| 2003/0022902 A1 | 1/2003 | Ricks et al. |
| 2003/0022903 A1 | 1/2003 | Ricks et al. |
| 2005/0239873 A1 | 10/2005 | Hockenberry et al. |
| 2007/0010401 A1 | 1/2007 | Noon |
| 2007/0066629 A1 | 3/2007 | Tormo i Biasco et al. |
| 2009/0203770 A1 | 8/2009 | Hockenberry et al. |
| 2009/0306142 A1 | 12/2009 | Carson et al. |
| 2010/0016163 A1 | 1/2010 | Keiper et al. |
| 2011/0070278 A1 | 3/2011 | Lopez |
| 2011/0082162 A1 | 4/2011 | Lorsbach et al. |
| 2012/0245031 A1 | 9/2012 | Gewehr et al. |
| 2013/0296372 A1 | 11/2013 | Owen et al. |
| 2014/0051678 A1 | 2/2014 | Clement-Schatlo et al. |
| 2014/0128411 A1 | 5/2014 | Ogawa et al. |
| 2014/0187587 A1 | 7/2014 | Ouimette et al. |
| 2014/0357713 A1 | 12/2014 | Damaj et al. |
| 2015/0018374 A1 | 1/2015 | Taggi et al. |
| 2015/0065529 A1 | 3/2015 | Owen et al. |
| 2015/0181868 A1 | 7/2015 | DeKorver et al. |
| 2015/0289508 A1 | 10/2015 | Meyer et al. |
| 2015/0322051 A1 | 11/2015 | Lu et al. |
| 2016/0007601 A1 | 1/2016 | Boebel et al. |
| 2016/0037774 A1 | 2/2016 | Schulz |
| 2016/0183526 A1 | 6/2016 | Hopkins et al. |
| 2016/0183527 A1 | 6/2016 | Hopkins et al. |
| 2016/0183528 A1 | 6/2016 | Hopkins et al. |
| 2017/0183324 A1 | 6/2017 | Li et al. |
| 2017/0273303 A1 | 9/2017 | DeKorver et al. |
| 2017/0273306 A1 | 9/2017 | LaLonde et al. |
| 2017/0290333 A1 | 10/2017 | Bravo-Altamirano et al. |
| 2017/0295792 A1 | 10/2017 | Bravo-Altamirano et al. |
| 2018/0037541 A1* | 2/2018 | Yao ................... C07C 271/22 |

FOREIGN PATENT DOCUMENTS

| | | |
|---|---|---|
| EP | 1516874 | 3/2005 |
| WO | WO/1996/37472 | 11/1996 |
| WO | WO/1999/40081 | 8/1999 |
| WO | WO/1999/011127 | 11/1999 |
| WO | WO/2001/014339 | 3/2001 |
| WO | WO/2001/014365 | 3/2001 |
| WO | WO/2003/011857 | 2/2003 |
| WO | WO/2003/035617 | 5/2003 |
| WO | WO/2007/017416 | 2/2007 |
| WO | WO/2009/040397 | 9/2008 |
| WO | WO/2011/028657 | 3/2011 |
| WO | WO/2011/044213 | 4/2011 |
| WO | WO/2011/069893 | 6/2011 |
| WO | WO/2012/016972 | 2/2012 |
| WO | WO/2012/016989 | 2/2012 |
| WO | WO/2012/020777 | 2/2012 |
| WO | WO/2012/070015 | 5/2012 |
| WO | WO/2013/110002 | 7/2013 |
| WO | WO/2013/116251 | 8/2013 |
| WO | WO/2013/169660 | 11/2013 |
| WO | WO2013/169662 | 11/2013 |
| WO | WO/2015/050818 | 4/2015 |
| WO | WO/2015/050819 | 4/2015 |
| WO | WO/2015/050820 | 4/2015 |
| WO | WO/2015/050822 | 4/2015 |
| WO | WO/2015/100182 | 7/2015 |
| WO | WO/2015/100183 | 7/2015 |
| WO | WO/2015/100184 | 7/2015 |
| WO | WO/2015/103161 | 7/2015 |
| WO | WO/2015/1001811 | 7/2015 |
| WO | WO/2015/171408 | 12/2015 |
| WO | WO/2016/007525 | 1/2016 |
| WO | WO/2016/07529 | 1/2016 |
| WO | WO/2016/007531 | 1/2016 |
| WO | WO/2016/109257 | 7/2016 |
| WO | WO/2016/109288 | 7/2016 |
| WO | WO/2016/109289 | 7/2016 |
| WO | WO/2016/109290 | 7/2016 |
| WO | WO/2016/109291 | 7/2016 |
| WO | WO/2016/109300 | 7/2016 |
| WO | WO/2016/109301 | 7/2016 |
| WO | WO/2016/109302 | 7/2016 |
| WO | WO/2016/109303 | 7/2016 |
| WO | WO/2016/109304 | 7/2016 |
| WO | WO/2016/109305 | 7/2016 |
| WO | WO/2016/122802 | 8/2016 |

OTHER PUBLICATIONS

Shibata, et al., "Uk-1, A Novel Cytotoxic Metabolite From *Streptomyces* sp. 517-02 II. Structural Eluciation", The Journal of Antibiotics, vol. 46, No. 7, pp. 1095-1100 (1993).

Shimano, et al., "Enantioselective Total Synthesis of the Antifungal Dilactone, UK-2A: The Determination of the Relative and Absolute Configurations", Tetrahedron Letters, vol. 39, pp. 4363-4366 (1998).

Shimano, et al., "Total Synthesis of the Antifungal Dilactones UK-2A and UK-3A: The Determination of their Relative and Absolute Configurations, Analog Synthesis and Antifungal Activities", Tetrahedron Letters, vol. 54, pp. 12745-12774 (1998).

Ueki, et al., "UK-1, A Novel Cytotoxic Metabolite from *Streptomyces* sp. 517-02 I. Taxonomy Fermentation, Isolation, Physico-Chemical and Biological Properites", The Journal of Antibiotics, vol. 50, No. 7, pp. 551-555 (1997).

Ueki, UK-2A, B, C and D, Novel Antifungal from *Streptomyces* sp. 517-02 I. Fermentation, Isolation and Biological Properties:, The Journal of Antibiotics, vol. 49, No. 7, pp. 639-643 (1996).

Ueki, et al., "UK-3A, a Novel Antifungal Antibiotic from *Streptomyces* sp. 517-02: Fermentation, Isolation, Structural Elucidation and Biological Properties":, The Journal of Antibiotics, vol. 50, No. 7, pp. 551-555 (1997).

Ueki, et al., "The Mode of Action of UK-2A and UK-3A, Novel Antifungal Antibiotics from *Streptomyces* sp. 517-02", The Journal of Antibiotics, vol. 50, No. 12, pp. 1052-1057 (1997).

Patent Abstracts of Japan vol. 1998, No. 06, Apr. 30, 1998 JP 10053583A (Mitsubishi Chem Corp) Feb. 24, 1998 abstract example 20.

Database Chemabs Online, Chemical Abstracts Service, Columbus, Ohio, US: accession No. CA63:16300d XP002164206.

International Search Authority, International Search Report and Written Opinion for PCT/US2005/028407, dated Aug. 5, 2015, 8 pages.

Thomas, S., International Search Report for PCT/US14/058067, dated Dec. 22, 2014, pp. 1-4, ISA/US.

Thomas, S., International Search Report for PCT/US14/058070, dated Dec. 15, 2014, pp. 1-4, ISA/US.

Thomas, S., Written Opinion for PCT/US14/058067, dated Dec. 22, 2014, pp. 1-5, ISA/US.

Thomas, S., Written Opinion for PCT/US14/058070, dated Dec. 15, 2014, pp. 1-5, ISA/US.

(56) References Cited

OTHER PUBLICATIONS

Anonymous, Synergistic Fungicidal Composition of Heterocyclic Aromatic Amides and Traizoles, ip.com Journal, ip.com, Electronic Publication, West Henrietta, NY, US Jul. 2004, 11 pages.
Backman, P., Fungicide Formulation: Relationship to Biological Activity, Ann. Rev. Phytophathol, 1978, 16, pp. 211-237.
BASF New Fungicide Xemium Got Full Approval in EU, Agronews, Jul. 18, 2012. Retrieved from the Internet: URL: http://news.agropages.com/News/NewsDetail---7386.htm, 1 page.
Bolton, M. et al., "Wheat leaf rust caused by Puccinia triticina," Molecular Plant Pathology, vol. 9, No. 5, 2008, pp. 563-575.
Davari, M. et al."Quantum Chemical Investigation of Intramolecular Thione-Thiol Tautomerism of 1,2,4-triazole-3-thione and its disubstituted derivatives," Journal of Molecular Modeling, Sep. 2009, 16(5), pp. 841-855.
FRAC Code List: Fungicides Sorted by Mode of Action (including FRAC Code numbering), Fungicide REsistance Action Committee, Dec. 2008, 10 pages.
Fungicidal Mixtures, IP.com Prior Art Database Technical Disclosure, (Jul. 5, 2005), XP055073888, COI: http://ip.com/pdf/ipcompad/IPCOM000126160D.pdf, 12 pages.
Gisi, U., "Synergistic Interaction of Fungicides in Mixtures," The American Phytophathological Society, vol. 86, No. 11, 1996, pp. 1273-1279.
Hu, Z. et al., "Synthesis of Novel Analogues of Antimycin A3," Tetrahedron Letters 49 (2008), pp. 5192-5195.
Huang, C. et al., :"Synergistic Interactions between Chitinase ChiCW and Fungicides Against Plant Fungal Pathogens,": J. Microbiol. Biotechnol., 2008, 18(4), pp. 784-787.
Kissling, E., "Crop Protection Pipeline Value Jumps to Euro 2.4 Billion," BASF SE, Mar. 10, 2011, Retrieved from the Internet:, URL:http://agro.basf.com/agri/AP-Internet/en/content/news_room/news/basf-crop-protection-pipleine-value,4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control," GCM, Jul. 2008, pp. 84-87.
Ueki, M., et al., "Uk-2A, B, C, and D, Novel Antifungal Antibiotics from *Streptomyces* sp. 517-02 I. Fermentation, Isolation, and Biological Properties," The Journal of Antibiotics, vol. 49, No. 87, Jul. 1996, pp. 639-643.

O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals,": Applied and Environmental Microbiology, vol. 77, No. 4, Feb. 2011, pp. 1460-1465.
PubChem: Open Chemistry Database, Substance Record for SID 74383515. Deposit Date Jun. 11, 2009. Retrieved from the Internet <URL:https://pubchem.ncbi.nlm.nih.gov/sustance/74383515#section=Top>, 5 pages.
Science for a Better Life, Bayer CropScience "positioned for Growth." Jun. 2008, 22 pages.
Calcium Dodecyl Benzene Sulfonate, CAS 26264-06-2, (http://www.hichem.com/product/showproduct.php?id=334639) Mar. 28, 2013, 4 pages.
Tani, K. et al., The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from *Streptomyces* sp. 517-02," Bioorganic & Medicinal Chemistry Letters, vol. 15, No. 8, 2005, pp. 2011-2014.
Usuki, Y. et al., Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruitcola and Botrytis cinerea," 1987, Plant Disease, vol. 71, No. 4, pp. 316-319.
Written Opinion and Search Report for PCT Patent Application No. PCT/US2015/067115 dated Mar. 11, 2016, 7 pages.
Gerald R. Stephenson, Ian G. Ferris, Patrick T. Holland, and Monica Nordberg, "Glossary of Terms Relating to Pesticides," in Pure and Applied Chemistry 2006, 78 (11), 2075-2154; International Union of Pure and Applied Chemistry.
D. J. Chitwood, "Nematicides," in Encyclopedia of Agrochemicals (3), pp. 1104-1115, John Wiley & Sons, New York, NY, 2003; http://naldc.nal.usda.gov/download/43874/PDF.

\* cited by examiner

PICOLINAMIDES AS FUNGICIDES

CROSS REFERENCE TO RELATED APPLICATIONS

This application claims priority under 35 U.S.C. § 119 of U.S. provisional patent application Ser. No. 62/442,914 filed Jan. 5, 2017, which application is hereby incorporated by reference in its entirety.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to picolinamides and their use as fungicides. The compounds of the present disclosure may offer protection against ascomycetes, basidiomycetes, deuteromycetes and oomycetes.

One embodiment of the present disclosure may include compounds of Formula I:

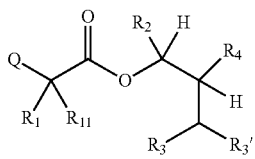

I wherein:
Q is

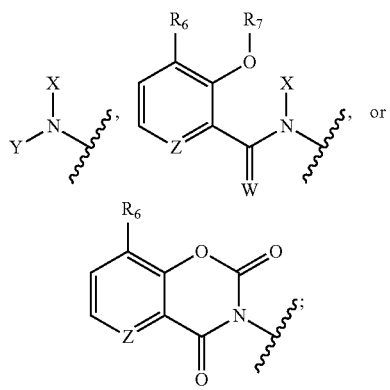

X is hydrogen or $C(O)R_5$;
Y is hydrogen or $C(O)R_5$;
Z is N or $N^+ \rightarrow O^-$ and W is O or S;
$R_1$ is hydrogen or alkyl, substituted with 0, 1 or multiple $R_8$;
$R_2$ is methyl;
$R_3$ and $R_{3'}$ are independently chosen from $C_3$-$C_6$ cycloalkyl, aryl or heteroaryl, each optionally substituted with 0, 1 or multiple $R_8$; Alternatively, $R_3$ and $R_{3'}$ may be taken together to form a 3-6 membered saturated or partially saturated carbocycle or heterocycle, optionally substituted with 0, 1 or multiple $R_8$;
$R_4$ is chosen from aryl or heteroaryl, each optionally substituted with 0, 1 or multiple $R_8$;
$R_5$ is chosen from alkoxy or benzyloxy, each optionally substituted with 0, 1, or multiple $R_8$;
$R_6$ is chosen from hydrogen, alkoxy, or halo, each optionally substituted with 0, 1, or multiple $R_8$;
$R_7$ is chosen from hydrogen, —$C(O)R_9$, or —$CH_2OC(O)R_9$;
$R_8$ is chosen from hydrogen, alkyl, aryl, acyl, halo, alkenyl, alkynyl, alkoxy, cyano, or heterocyclyl, each optionally substituted with 0, 1, or multiple $R_{10}$;
$R_9$ is chosen from alkyl, alkoxy, or aryl, each optionally substituted with 0, 1, or multiple $R_8$;
$R_{10}$ is chosen from hydrogen, alkyl, aryl, acyl, halo, alkenyl, alkoxy, or heterocyclyl; and
$R_{11}$ is chosen from hydrogen or alkyl, each substituted with 0, 1 or multiple $R_8$.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms The term "alkoxy" refers to an —OR substituent.
The term "acyloxy" refers to an —OC(O)R substituent.
The term "cyano" refers to a —C≡N substituent.
The term "hydroxyl" refers to a —OH substituent.
The term "amino" refers to an —$N(R)_2$ substituent.
The term "arylalkoxy" refers to —$O(CH_2)_n Ar$ where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —$NO_2$ substituent.
The term "thioalkyl" refers to a —SR substituent.

Throughout the disclosure, reference to the compounds of Formula I is read as also including all stereoisomers, for example diastereomers, enantiomers, and mixtures thereof.

In another embodiment, Formula (I) is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and used as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, *Bacillus subtilis*, *Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, fluindapyr, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetylaluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isofetamide, isoprothiolane, isopyrazam, isotianil, kasugamycin, kasugamycin hydrochloride hydrate, kresoxium-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pydiflumetofen, pyrametostrobin, pyraoxystrobin, pyraclostrobin, pyrazifulmid, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, coumoxystrobin, cufraneb, cupric hydrazinium sulfate, cuprobam, cyclafuramid, cypendazole, cyprofuram, decafentin, dichlobentiazox, dichlone, dichlozoline, diclobutrazol, dimethirimol, dinocton, dinosulfon, dinoterbon, dipymetitrone, dipyrithione, ditalimfos, dodicin, drazoxolon, EBP, enoxastrobin, ESBP, etaconazole, etem, ethirim, fenaminstrobin, fenaminosulf, fenapanil, fenitropan, fenpicoxamid, flufenoxystrobin, fluotrimazole, furcarbanil, furconazole, furconazole-cis, furmecyclox, furophanate, glyodine, griseofulvin, halacrinate, Hercules 3944, hexylthiofos, ICIA0858, ipfentrifluconazole, isopamphos, isovaledione, mandestrobin, mebenil, mecarbinzid, mefentrifluconazole, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyrisoxazole, pyroxychlor, pyroxyfur, quinacetol; quinacetol sulfate, quinazamid, quinconazole, quinofumelin, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, triclopyricarb, triflumezopyrim, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, aciflurofen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formula 1.3 and 1.4 wherein $R_4$ is as originally defined, can be prepared by the methods shown in Scheme 1, steps a-c. Compounds of Formula 1.1, wherein $R_4$ is as originally defined, can be prepared by treatment of halogens (X) of Formula 1.0, wherein $R_4$ is as originally defined, first under standard Grignard conditions, using magnesium metal and an alkali base, such as lithium chloride, in a polar, aprotic solvent such as tetrahydrofuran (THF) or diethyl ether (Et$_2$O), at a temperature of about 0° C. to about 70° C., to afford the Grignard intermediate. The solution is then treated with a metal catalyst, such as iron (III) acetylacetonate, followed by allyl chloride, in a polar aprotic solvent, such as THF, at a temperature of about 0° C. to about 70° C., to give compounds of Formula 1.1, wherein $R_4$ is as previously defined, and shown in step a. Generally, the composition of compounds of Formula 1.1 derived from this process is a mixture of allyl and E, Z isomers of the styrene derived products. Compounds of Formula 1.1, wherein $R_4$ is as previously defined, can be isomerized to compounds of Formula 1.2 by treating with a metal catalyst system, such as bis(dibenzylideneactone)palladium (O), a phosphine coordinating reagent, such as tri-tert-butylphosphine, and an acid chloride, such as isobutyryl chloride, in an aromatic hydrocarbon solvent such as toluene, at a temperature of about 25° C. to 100° C., to afford compounds of Formula 1.2, wherein $R_4$ is as originally defined, and shown in step b. Alternatively, compounds of Formula 1.2, wherein $R_4$ is as originally defined, can be isomerized using the conditions of Mayer, M.; Welther, A.; Jacobi von Wangelin, A. *Chem Cat Chem.* 2011, 3, 1567-1571, and shown in step b. Epoxides of Formulas 1.3 and 1.4, wherein $R_4$ is as previously defined, can be obtained by a catalytic asymmetric epoxidation method using oxone as oxidant and a fructose derived ketone as described by Wang, Z-X; Tu, Y.; Frohn, M.; Zhang, J-R.; Shi, Y. *J. Am. Chem. Soc.* 1997, 119, 11224-11235, and depicted in step c. It will be understood by those skilled in the art that epoxides of Formulae 1.3 and 1.4, wherein $R_4$ is as previously defined, can be prepared by other catalytic asymmetric epoxidation methods, including, but not limited to, dioxiranes derived from other chiral ketones; catalytic metal salen complexes using an oxidant, such as dioxygen or sodium hypochlorite; chiral iminium salts using oxone as the oxidizing species; chiral organic oxaziridine salts; and enzymatic epoxidation biocatalysts, such as monooxygenases and hydrolases.

Compounds of Formulas 2.1 and 2.2, wherein $R_3$, $R_{3'}$ and $R_4$ are as previously defined, and $R_3$ and $R_{3'}$ may or may not be equivalent, can be prepared by the method shown in Scheme 2, step a. Subjection of epoxides of Formulas 1.3 and 1.4, wherein $R_4$ is as previously defined, to an

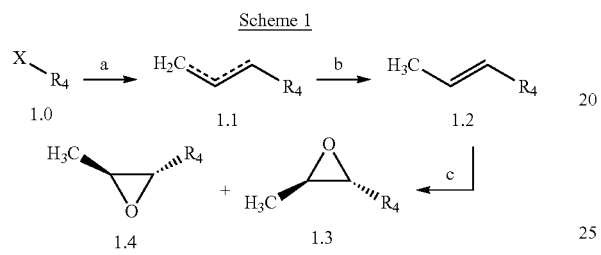

Scheme 1

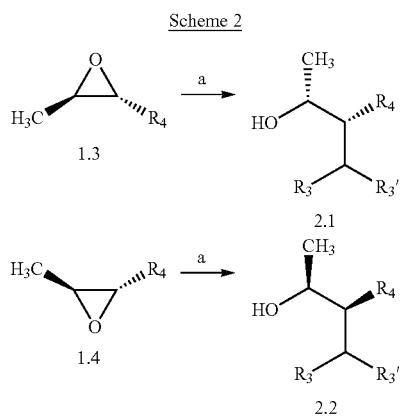

Scheme 2 organometallic nucleophile, such as an alkyl magnesium halide, in the presence of a metal halide, such as copper iodide, in a polar, aprotic solvent, such as THF or $Et_2O$, at a temperature of about −78° C. to 55° C., affords compounds of Formulas 2.1 and 2.2, wherein $R_3$, $R_{3'}$ and $R_4$ are as previously defined, and $R_3$ and $R_{3'}$ may or may not be equivalent, and shown in step a.

In certain cases, it is beneficial to employ an alkenyl organometallic reagent as the carbon nucleophile and shown in Scheme 3. Compounds of Formulas 3.1 and 3.3, wherein $R_3$ and $R_4$ are as previously defined, can be prepared by treating epoxides of Formulas 1.3 and 1.4, wherein $R_4$ is as previously defined, with an alkenyl magnesium halide, such as prop-1-en-2-ylmagnesium bromide, in the presence of a metal halide, such as copper iodide, in a polar, aprotic solvent, such as THF or $Et_2O$, at a temperature of about −78° C. to 25° C., and shown in step a. Compounds of

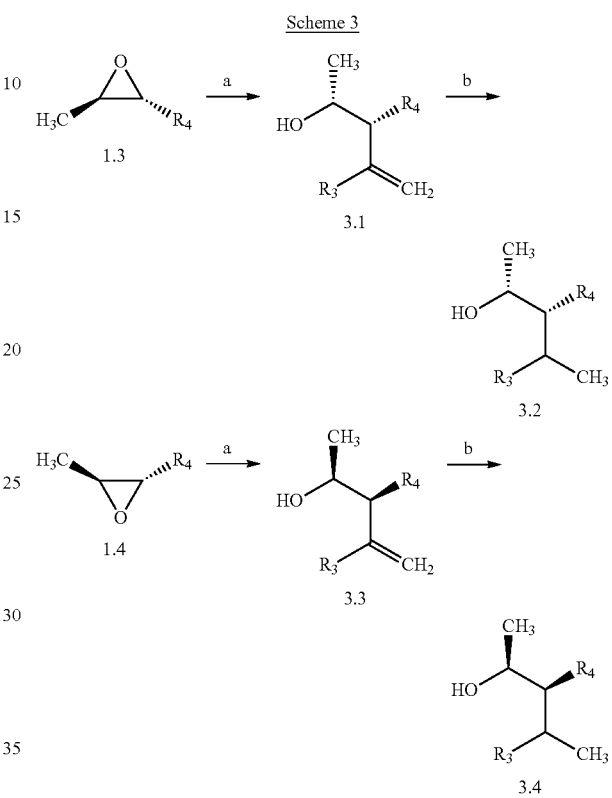

Scheme 3

Formulas 3.2 and 3.4, wherein $R_3$ and $R_4$ are as previously defined, can be prepared by treament of compounds of Formulas 3.1 and 3.3, wherein $R_3$ and $R_4$ are as previously defined, with a metal hydrogenation catalyst, such as tris(triphenylphosphine)rhodium(I) chloride (Wilkinson's catalyst) in a polar, aprotic solvent, such as THF, in the presence of a hydrogen atmosphere (1-4 atm); or, alternatively, with palladium absorbed on carbon, in a polar solvent, such as THF, in the presence of a hydrogen atmosphere (1-4 atm), and shown in step b.

In certain additional examples, compounds of Formula 4.2, wherein $R_3$, $R_{3'}$ and $R_4$ are as previously defined and $R_3$ and $R_{3'}$ may or may not be equivalent, can be prepared by the procedure shown in Scheme 4, steps a and b. Compounds of Formula 2.1, wherein $R_3$, $R_{3'}$ and $R_4$ are as previously defined and $R_3$ and $R_{3'}$ may or may not be equivalent, can be treated with an oxidizing reagent, such as the Dess-Martin periodinane, in a polar solvent such as dichloromethane ($CH_2Cl_2$), at a temperature of about 0° C. to 50° C., to give compounds of Formula 4.1, wherein $R_3$, $R_{3'}$ and $R_4$ are as previously defined and $R_3$ and $R_{3'}$ may or may not be equivalent, and shown in a. Compounds of Formula 4.1, wherein $R_3$, $R_{3'}$ and $R_4$ are as previously defined and $R_3$ and $R_{3'}$ may or may not be equivalent, can be treated with a chiral oxazaborolidine catalyst, such as (R)-1-methyl-3,3-diphenylhexahydropyrrolo[1,2-c][1,3,2]oxazaborole, in the presence of a boron hydride reducing agent, such as borane-dimethyl sulfide complex, in an aprotic solvent, such as toluene or

Scheme 4

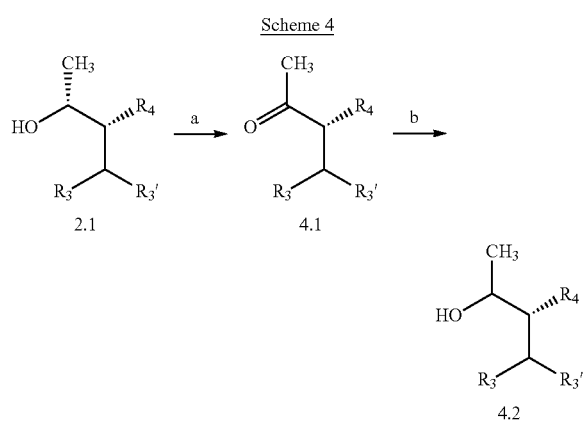

THF, at a temperature from about −78° C. to about room temperature, to afford compounds of Formula 4.2, wherein $R_3$, $R_{3'}$ and $R_4$ are as previously defined and $R_3$ and $R_{3'}$ may or may not be equivalent, and shown in b. Typical diastereomeric ratios obtained in b are generally in the 2:1 to 5:1 range with the anti isomer being favored over the syn. It will be understood by those skilled in the art that compounds of Formula 4.1, wherein $R_3$, $R_{3'}$ and $R_4$ are as previously defined and $R_3$ and $R_{3'}$ may or may not be equivalent, can be enantioselective reduced by other chiral catalyst/hydride reducing agent combinations, including, but not limited to, chirally modified lithium aluminum hydride or sodium borohydride reagents, phosphoramide catalysts, transfer hydrogenation catalyzed by chiral metal complexes, phase transfer catalysts, or enantioselective hydrogenation of pro-chiral ketones by enzymatic catalysis.

In certain additional examples, compounds of Formula 5.5 and 5.9, wherein $R_3$, $R_{3'}$ and $R_4$ are as previously defined and $R_3$ and $R_{3'}$ may or may not be equivalent, can be prepared by the procedure shown in Scheme 5, steps a-i. The compound of Formula 5.0 can be treated with an aryl or heteroaryl organometallic reagent, such as phenylmagnesium bromide, in a polar aprotic solvent, such as THF or $Et_2O$, at a temperature of about 0° C. to room temperature, to afford compounds of Formula 5.1, wherein $R_4$ is as originally defined, and shown in step a. Subjection of compounds of Formula 5.1 to an oxidization procedure, such as the Swern process (oxalyl chloride, DMSO, $Et_3N$, $CH_2Cl_2$), affords compounds of Formula 5.2, wherein $R_4$ is as originally defined, depicted in b. Compounds of Formula 5.3, wherein $R_3$, $R_{3'}$ and $R_4$ are as previously defined, and $R_3$ and $R_{3'}$ may or may not be equivalent, can be obtained by treating compounds of Formula 5.2, wherein $R_4$ is as originally defined, with an organometallic nucleophile, such as isopropylmagnesium bromide, in a polar aprotic solvent, such as THF or $Et_2O$, at a temperature of about 0° C. to room temperature, as depicted in step c. Compounds of Formula 5.4, wherein $R_3$, $R_{3'}$, and $R_4$ are as previously defined and $R_3$ and $R_{3'}$ may or may not be equivalent, and $R_4$ is not an electron-deficient aryl or heteroaryl group, can be obtained by treating the compounds of Formula 5.3, wherein $R_3$, $R_{3'}$ are as previously defined and may or may not be equivalent, and $R_4$ is not an electron-deficient aryl or heteroaryl group, with a

Scheme 5

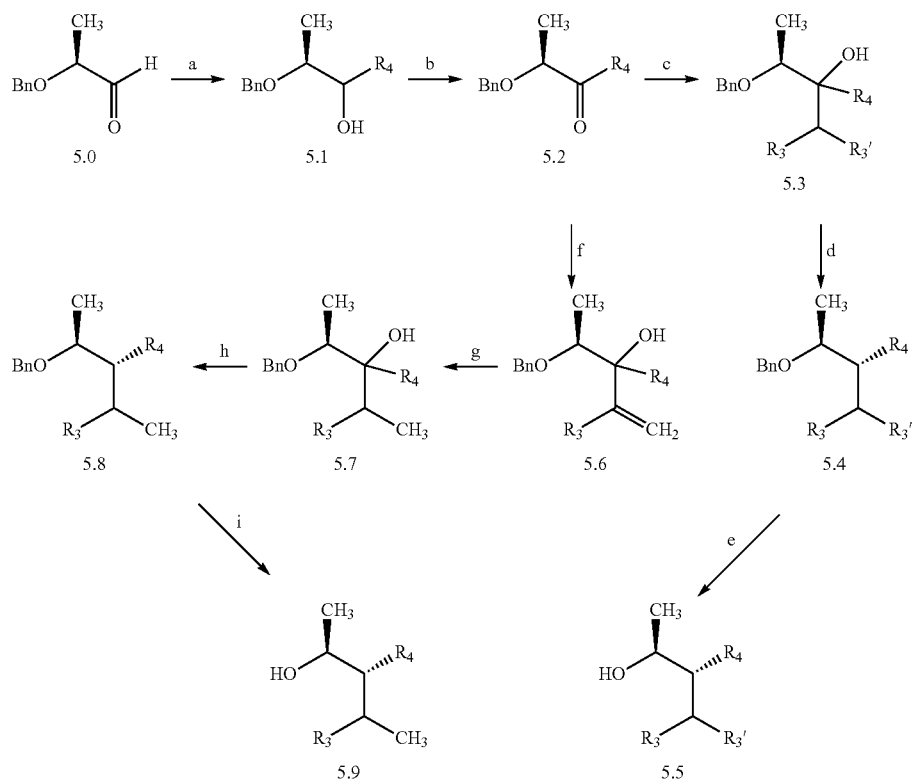

mixture of a hydride reagent, such as triethylsilane ($Et_3SiH$), and an acid, such as 2,2,2-trifluoroacetic acid (TFA) in a halogenated solvent such as dichloromethane (DCM) at a temperature of about 0° C. to 23° C., as depicted in d. Compounds of Formula 5.5, wherein $R_3$, $R_{3'}$, and $R_4$ are as originally defined and $R_3$ may or may not be equivalent to $R_{3'}$, can be prepared from compounds of Formula 5.4, wherein $R_3$, $R_{3'}$, and $R_4$ are as originally defined and $R_3$ may or may not be equivalent to $R_{3'}$, by treating with a metal catalyst such as palladium on carbon (Pd/C) in a polar protic solvent, such as ethanol (EtOH), in a hydrogen atmosphere (1-4 atm) at a temperature of about 25° C. to 65° C., or with an alternate source of hydrogen, such as cyclohexene, in a polar solvent such as EtOH, and shown in step e. In certain other cases, it is beneficial to synthesize compounds of Formula 5.9, wherein $R_3$ and $R_4$ are as originally defined, by the method shown in steps f-i. Compounds of Formula 5.2, wherein $R_4$ is as previously defined, can be treated with an alkenyl organometallic reagent, such as isopropenylmagnesium bromide, in a polar aprotic solvent, such as THF or $Et_2O$, at a temperature of about 0° C. to room temperature, to afford compounds of Formula 5.6, wherein $R_3$ and $R_4$ are as originally defined, and shown in step f. Compounds of Formula 5.7, wherein $R_3$ and $R_4$ are as previously defined, can be prepared by treatment of compounds of Formula 5.6, wherein $R_3$ and $R_4$ are as previously defined, with a metal hydrogenation catalyst, such as tris(triphenylphosphine)rhodium(I) chloride (Wilkinson's catalyst) in a polar, aprotic solvent, such as THF, in the presence of a hydrogen atmosphere (1-4 atm), and shown in g. Compounds of Formula 5.8, wherein $R_3$ and $R_4$ are as previously defined, and $R_4$ is not an electron-deficient aryl or heteroaryl group, can be obtained by treating the compounds of Formula 5.7, wherein $R_3$ and $R_4$ are as previously defined, and $R_4$ is not an electron-deficient aryl or heteroaryl group, with a mixture of a hydride reagent, such as triethylsilane ($Et_3SiH$), and an acid, such as 2,2,2-trifluoroacetic acid (TFA) in a halogenated solvent such as dichloromethane (DCM) at a temperature of about 0° C. to 23° C., as depicted in h. Compounds of Formula 5.9, wherein $R_3$ and $R_4$ are as previously defined, can be prepared by treatment of compounds of Formula 5.8, wherein $R_3$ and $R_4$ are as previously defined, with a metal hydrogenation catalyst, such as tris(triphenylphosphine)rhodium(I) chloride (Wilkinson's catalyst) in a polar, aprotic solvent, such as THF, in the presence of a hydrogen atmosphere (1-4 atm); or, alternatively, with palladium absorbed on carbon, in a polar solvent, such as THF, in the presence of a hydrogen atmosphere (1-4 atm), and shown in step i.

In certain other examples, compounds of Formula 5.5, wherein $R_3$, $R_{3'}$, and $R_4$ are as originally defined, and $R_3$ and $R_{3'}$ may or may not be equivalent, may also be prepared according to the method outlined in Scheme 6, steps a and b. Treatment of compounds of Formula 2.1, wherein $R_3$, $R_{3'}$, and $R_4$ are as originally defined, and $R_3$ and $R_{3'}$ may or may not be equivalent, with an Scheme 6

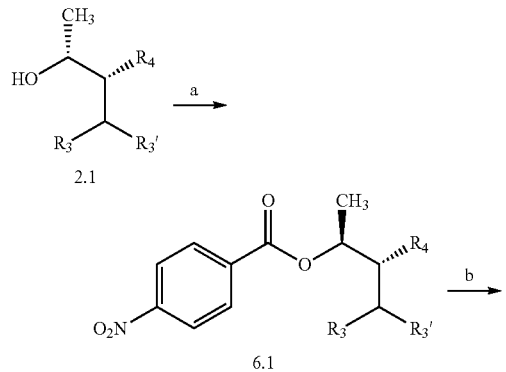

electron deficient benzoic acid, such as p-nitrobenzoic acid, a phosphine nucleophile, such as triphenylphosphine; and a diazene coupling reagent, such as diethyl (E)-diazene-1,2-dicarboxylate, in a polar, aprotic solvent, such as THF, at a temperature of about 0° C. to about 25° C. affords compounds of Formula 6.1, wherein $R_3$, $R_{3'}$, and $R_4$ are as originally defined, and $R_3$ and $R_{3'}$ may or may not be equivalent, as depicted in step a. In step b, compounds of Formula 6.1, wherein $R_3$, $R_{3'}$, and $R_4$ are as originally defined, and $R_3$ and $R_{3'}$ may or may not be equivalent, can be treated with an aqueous solution of an inorganic base, such as sodium hydroxide, in a polar aprotic solvent, such as THF, at a temperature of about 0° C. to about 40° C. to afford compounds of Formula 5.5, wherein $R_3$, $R_{3'}$, and $R_4$ are as originally defined, and $R_3$ and $R_{3'}$ may or may not be equivalent.

Compounds of Formula 7.2, wherein $R_1$, $R_3$, $R_{3'}$, $R_4$, and $R_{11}$, are as originally defined, and $R_3$ and $R_{3'}$ may or may not be equivalent, may be prepared according to the method outlined in Scheme 7, step a. Alcohols of Formula 5.5, wherein $R_3$, $R_{3'}$, and $R_4$, are as originally defined, and $R_3$ and $R_{3'}$ may or may not be equivalent, can be treated with compounds of Formula 7.1, wherein $R_1$ and $R_{11}$ are as originally defined, a coupling reagent, such as 3-(ethyliminomethyleneamino)-N,N-dimethylpropan-1-amine hydrochloride (EDC) or a polymer-supported carbodiimide (PS-CDI), and a catalyst, such as N,N-dimethylpyridin-4-amine (DMAP), in a halogenated or polar, aprotic solvent, such as $CH_2Cl_2$ or THF to afford compounds of Formula 7.2, wherein $R_1$, $R_3$, $R_{3'}$, $R_4$, and $R_{11}$, are as originally defined, and $R_3$ and $R_{3'}$ may or may not be equivalent, as shown in step a.

Scheme 7

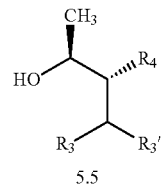

Compounds of Formula 7.2, wherein $R_1$, $R_3$, $R_{3'}$, $R_4$, and $R_{11}$, are as originally defined, and $R_3$ and $R_{3'}$ may or may not be equivalent, may also be prepared according to the method outlined in Scheme 8, step a. Alcohols of Formula 2.1, wherein $R_3$, $R_{3'}$, and $R_4$, are as originally

Scheme 8

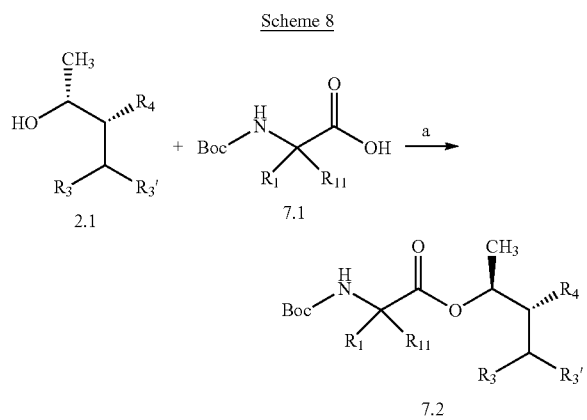

defined, and $R_3$ and $R_{3'}$ may or may not be equivalent, can be treated with with compounds of Formula 7.1, wherein Ru and Ru are as originally defined, a phosphine reagent, such as triphenylphosphine, and a diazine dicarboxylate electrophile, such as diisopropyl (E)-diazene-1,2-dicarboxylate (DIAD), in a polar aprotic solvent, such as THF, at a temperature of about 0° C. to 25° C. to afford compounds of Formula 7.2, wherein $R_1$, $R_3$, $R_{3'}$, $R_4$, and $R_{11}$, are as originally defined, and $R_3$ and $R_{3'}$ may or may not be equivalent, as shown in step a.

Compounds of Formula 9.5, wherein $R_1$, $R_2$, $R_3$, $R_{3'}$, $R_4$, $R_6$, and $R_{11}$, are as originally defined, and $R_3$ and $R_{3'}$ may or may not be equivalent, can be prepared according to the methods outlined in Scheme 9, steps a-d. Compounds of Formula 9.1, wherein $R_1$, $R_2$, $R_3$, $R_{3'}$, $R_4$, and $R_{11}$, are as originally defined, and $R_3$ and $R_{3'}$ may or may not be equivalent, but not alkenyl, can be treated with an acid, such as a 4 N solution of HCl in dioxane, in a halogenated solvent such as $CH_2Cl_2$ to afford compounds of Formula 9.2, wherein $R_1$, $R_2$, $R_3$, $R_{3'}$, $R_4$, and $R_{11}$, are as originally defined, and $R_3$ and $R_{3'}$ may or may not be equivalent, but not alkenyl, as shown in step a. Compounds of Formula 9.3, wherein $R_1$, $R_2$, $R_3$, $R_{3'}$, $R_4$, and $R_{11}$, are as originally defined, and $R_3$ and $R_{3'}$ may or may not be equivalent, can be prepared by treating compounds of Formula 9.1, wherein $R_1$, $R_2$, $R_3$, $R_{3'}$, $R_4$, and $R_{11}$, are as originally defined, and $R_3$ and $R_{3'}$ may or may not be equivalent, with an acid, such as 2,2,2-trifluoroacetic acid, in a halogenated solvent such as $CH_2Cl_2$, as shown in step c. Compounds of Formulas 9.2 and 9.3, wherein $R_1$, $R_2$, $R_3$, $R_{3'}$, $R_4$, and $R_{11}$, are as originally defined, and $R_3$ and $R_{3'}$ may or may not be equivalent, can be treated with compounds of Formula 9.4, wherein $R_6$ is as originally defined, in the presence of a base, such as diisopropylethylamine, and a peptide coupling reagent, such as benzotriazol-1-yl-oxytripyrrolidinophosphonium hexafluorophosphate (PyBOP) or O-(7-azabenzotriazol-1-yl)-N,N,N',N'-tetramethyluronium hexafluorophosphate (HATU), in an halogenated solvent such as $CH_2Cl_2$, to afford compounds of Formula 9.5, wherein $R_1$, $R_2$, $R_3$, $R_{3'}$, $R_4$, $R_6$ and $R_{11}$, are as originally defined, and $R_3$ and $R_{3'}$ may or may not be equivalent, as shown in steps b and d.

Scheme 9

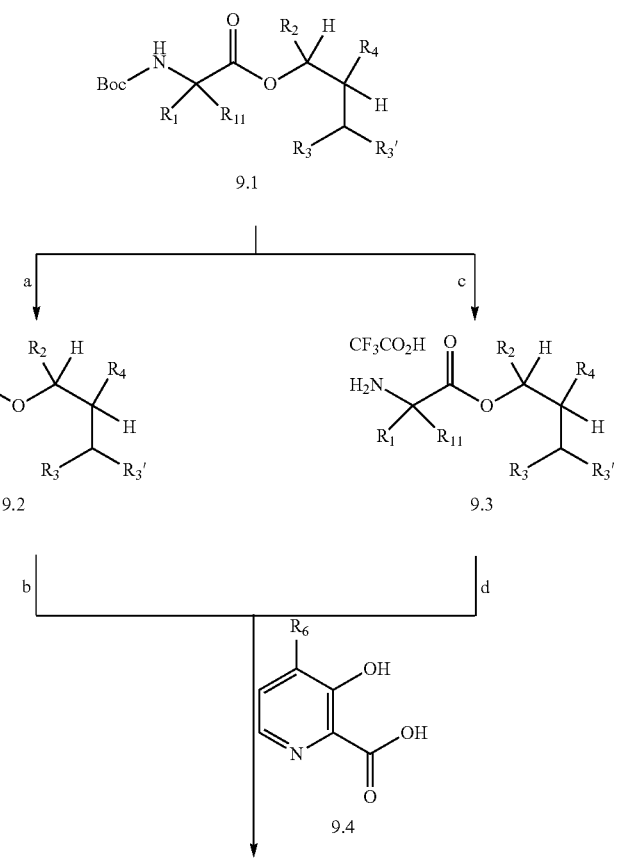

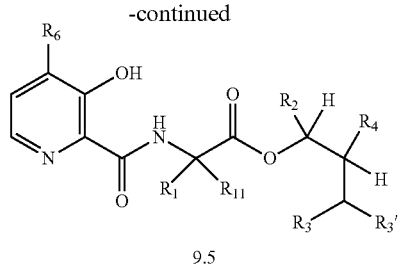

9.5

Compounds of Formula 10.1, wherein $R_1$, $R_2$, $R_3$, $R_{3'}$, $R_4$, $R_6$, $R_7$, and $R_{11}$, are as originally defined, and $R_3$ and $R_{3'}$ may or may not be equivalent, can be prepared according to the method outlined in Scheme 10, steps a or b. Compounds of Formula 9.5, wherein $R_1$, $R_2$, $R_3$, $R_{3'}$, $R_4$, $R_6$ and $R_{11}$, are as originally defined, and $R_3$ and $R_{3'}$ may or may not be equivalent, can be treated with an appropriate alkyl halide with or without a reagent such as sodium iodide (NaI) and an alkali carbonate base, such as sodium ($Na_2CO_3$) or potassium carbonate ($K_2CO_3$), in a solvent such as acetone, as shown in step a. Or, alternatively, by treatment with an acyl halide or anhydride in the presence of an amine base, such as pyridine, $NEt_3$, DMAP, or mixtures thereof, in an aprotic solvent, such as $CH_2Cl_2$, to afford compounds of Formula 10.1, wherein $R_1$, $R_2$, $R_3$, $R_{3'}$, $R_4$, $R_6$, $R_7$, and $R_{11}$, are as originally defined, and $R_3$ and $R_{3'}$ may or may not be equivalent, as shown in step b.

Scheme 10

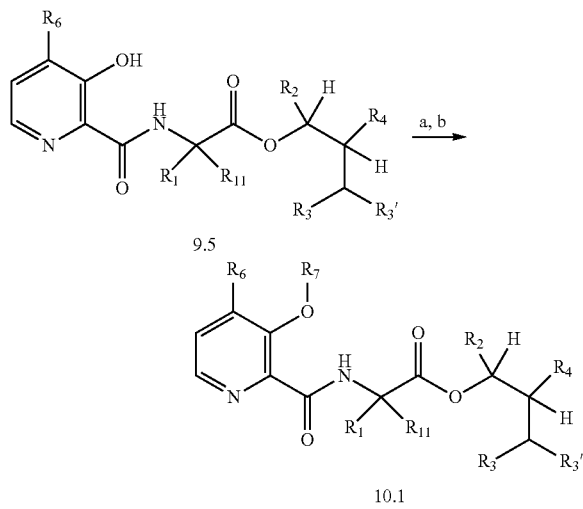

Compounds of Formula 11.1 and 11.2, wherein $R_1$, $R_2$, $R_3$, $R_{3'}$, $R_4$, $R_6$, $R_7$, and $R_{11}$, are as originally defined, and $R_3$ and $R_{3'}$ may or may not be equivalent, can be prepared according to the method outlined in Scheme 11, steps a and b. Compounds of Formula 9.5, wherein $R_1$, $R_2$, $R_3$, $R_{3'}$, $R_4$, $R_6$, and $R_{11}$, are as originally defined, and $R_3$ and $R_{3'}$ may or may not be equivalent, can be treated with a thionating reagent such as phosphorus pentasulfide, an additive, such as hexamethyldisiloxane, optionally in a polar aprotic solvent such as acetonitrile ($CH_3CN$), at a temperature of about 0° C. to 80° C. to afford compounds of Formula 11.1, wherein $R_1$, $R_2$, $R_3$, $R_{3'}$, $R_4$, $R_6$, and $R_{11}$, are as originally defined, and $R_3$ and $R_{3'}$ may or may not be equivalent, and shown in step a. It will be understood by those skilled in the art that compounds such as Formula 11.1 may also be prepared using other thionating agents including, but not limited to: sulfur, sulfhydric acid, sodium sulfide, sodium hydrosulfide, boron trisulfide, bis(diethylaluminum)sulfide, ammonium sulfide, Lawesson's reagent, ammonium O,O'-diethyl dithiophosphate, rhodanine, or a polymer supported thionating reagent. Additives can include, but not limited to, aluminum oxide ($Al_2O_3$); inorganic bases, such as potassium carbonate and sodium bicarbonate; organic bases, such as triethylamine, diethylaniline, pyridine and morpholine. Optional solvents can include, but not limited to, aliphatic, alicyclic or aromatic hydrocarbons, such as hexane, cyclohexane or toluene; halogenated hydrocarbons, such as dichloromethane, 1,2-dichloroethane and chlorobenzene; ethers, such as diethyl ether, 1,4-dioxane, THF and 1,2-dimethoxyethane; and other polar aprotic solvents such as pyridine and hexamethylphosphoramide (HMPA). In step b, treatment of compounds of Formula 11.1, wherein $R_1$, $R_2$, $R_3$, $R_{3'}$, $R_4$, $R_6$, and $R_{11}$, are as originally defined, and $R_3$ and $R_{3'}$ may or may not be equivalent, with an appropriate alkyl halide with or without a reagent such as sodium iodide (NaI) and an alkali carbonate base, such as sodium carbonate ($Na_2CO_3$) or potassium carbonate ($K_2CO_3$), in a solvent like acetone at a temperature of about 55° C., or by treatment with an acyl halide or anhydride in the presence of an amine base, such as pyridine, triethylamine ($Et_3N$), DMAP, or mixtures thereof, in an optional aprotic solvent such as DCM, at a temperature of about 23° C., can afford compounds of Formula 11.2 wherein $R_1$, $R_2$, $R_3$, $R_{3'}$, $R_4$, $R_6$, $R_7$, and $R_{11}$, are as originally defined, and $R_3$ and $R_{3'}$ may or may not be equivalent.

Scheme 11

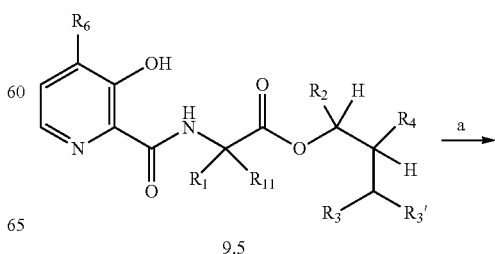

9.5

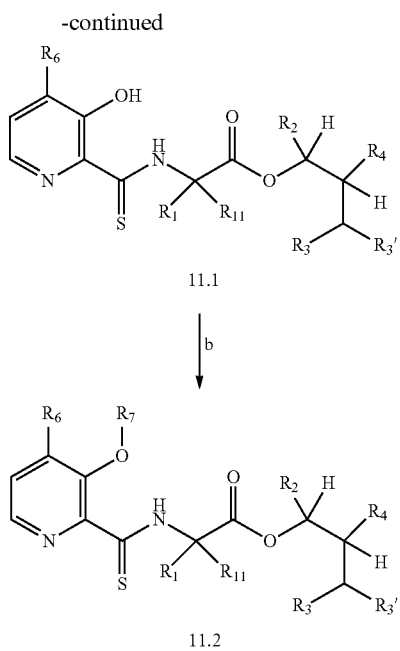

Compounds of Formula 12.1, wherein $R_1$, $R_2$, $R_3$, $R_{3'}$, $R_4$, $R_6$, and $R_{11}$, are as originally defined, and $R_3$ and $R_{3'}$ may or may not be equivalent, can be prepared according to the method outlined in Scheme 12, step a. Compounds of Formula 9.5, wherein $R_1$, $R_2$, $R_3$, $R_{3'}$, $R_4$, $R_6$, and $R_{11}$, are as originally defined, and $R_3$ and $R_{3'}$ may or may not be equivalent, can be treated with a oxidizing reagent such as m-chloroperbenzoic acid (mCPBA) in a polar solvent such as dichloromethane ($CH_2Cl_2$), at a temperature of about 0° C. to 50° C., to give compounds of Formula 12.1, as shown in a. It will be understood by those skilled in the art that compounds of Formula 12.1, wherein $R_1$, $R_2$, $R_3$, $R_{3'}$, $R_4$, $R_6$, and $R_{11}$, are as originally defined, and $R_3$ and $R_{3'}$ may or may not be equivalent, may also be prepared using other oxidizing agents, including, bit not limited to:

hydrogen peroxide, hydrogen peroxide-urea complex, magnesium monoperoxyphthalate hexahydrate (MMPP), peroxyacetic acid, oxone, sodium perchlorate or dimethyl dioxirane.

Compounds of Formula 13.1 wherein $R_1$, $R_2$, $R_3$, $R_{3'}$, $R_4$, $R_6$, and $R_{11}$, are as originally defined, and $R_3$ and $R_{3'}$ may or may not be equivalent, can be prepared according to the method outlined in Scheme 13, step a. Compounds of Formula 9.5, wherein $R_1$, $R_2$, $R_3$, $R_{3'}$, $R_4$, $R_6$, and $R_{11}$, are as originally defined, and $R_3$ and $R_{3'}$ may or may not be equivalent, can be treated with a diactivated carbonyl reagent such as triphosgene, with a base, such as pyridine, in a polar solvent, such as dichloromethane ($CH_2Cl_2$), at a temperature of about 0° C. to 50° C. to afford compounds of Formula 13.1, wherein $R_1$, $R_2$, $R_3$, $R_{3'}$, $R_4$, $R_6$, and $R_{11}$, are as originally defined, and $R_3$ and $R_{3'}$ may or may not be equivalent, as depicted in a.

Scheme 12

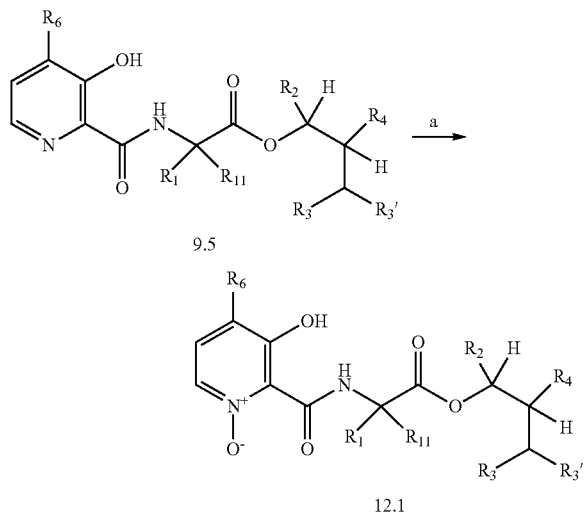

Scheme 13

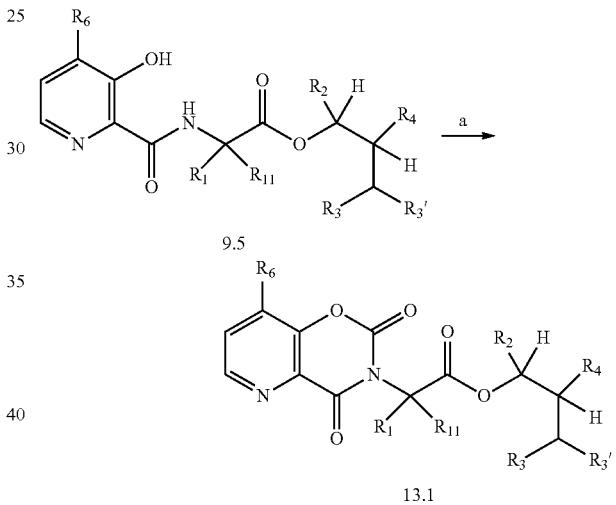

EXAMPLES

Example 1A: Preparation of (E)-1-methyl-4-(prop-1-en-1-yl)benzene

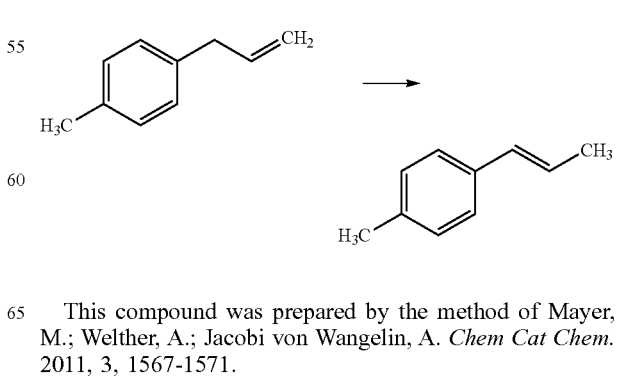

This compound was prepared by the method of Mayer, M.; Welther, A.; Jacobi von Wangelin, A. *Chem Cat Chem*. 2011, 3, 1567-1571.

Example 1B: Preparation of (E)-1-fluoro-4-(prop-1-en-1-yl)benzene

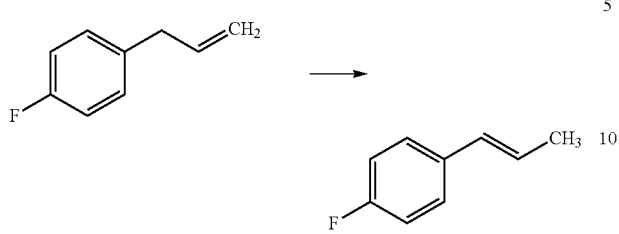

To a solution of 1-allyl-4-fluorobenzene (1.35 mL, 10 mmol) in toluene (20 mL) was added bis(dibenzylideneacetone)palladium (0.115 g, 0.200 mmol), tri-tert-butylphosphine (10% in hexane) (0.618 ml, 0.200 mmol) and isobutyryl chloride (0.021 ml, 0.200 mmol) in toluene (20.00 ml). The reaction was stirred at 80° C. overnight. The reaction mixture was purified by Isco chromatography (0 to 5% $Et_2O$ in pet ether) to provide the desired product as solution in toluene (20 mL) (1.36 g, 95%). $^1$H NMR (300 MHz, $CDCl_3$) δ 7.32-7.10 (m, 6H), 2.35 (s, 3H). $^{19}$F NMR (376 MHz, $CDCl_3$) δ-115.97.

Example 1C: Preparation of (E)-4-fluoro-2-methoxy-1-(prop-1-en-1-yl)benzene

Step 1: Preparation of (E,Z)-4-fluoro-2-methoxy-1-(prop-1-en-1-yl)benzene

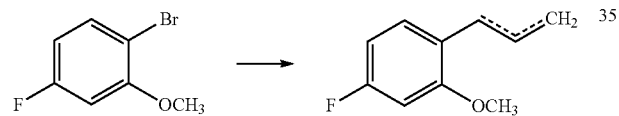

To a mixture of magnesium (0.79 g, 32.5 mmol) and lithium chloride (1.52 g, 35.80 mmol) in THF (33 ml) at room temperature was added 1-bromo-4-fluoro-2-methoxybenzene (3.13 mL, 24.39 mmol) and the reaction was stirred at 70° C. for 1.5 hr. The reaction was then cooled to 0° C., and Fe(acac)$_3$ (0.574 g, 1.63 mmol) was added. After 1 minute, allyl chloride (1.33 mL, 16.26 mmol) was added and the reaction was stirred at 0° C. for 30 min. The mixture was warmed to room temperature over 1 hr and was heated at 70° C. overnight. The reaction was cooled and diluted with petroleum ether (100 mL). The reaction was then quenched by the addition of a saturated $NH_4Cl$ solution (100 mL). The mixture was filtered through a Celite® pad and the layers were separated. The aqueous layer was extracted with petroleum ether (2×100 mL) and the combined organic phases were dried over $Na_2SO_4$ and carefully concentrated (25° C., 250 mbar). The residue was purified by Isco chromatography (100% pet ether as the eleuent) to provide (E,Z)-4-fluoro-2-methoxy-1-(prop-1-en-1-yl)benzene (2.25 g, 83% yield) as a colorless oil. This mixture was approximately a 3:1 mixture of E and Z isomers with a trace of the allyl isomer present. This material was used directly in the next step. $^1$H NMR (400 MHz, $CDCl_3$) δ 7.31 (dd, J=8.3, 6.8 Hz, 1H), 6.65-6.53 (m, 3H), 6.14 (dq, J=15.8, 6.6 Hz, 1H), 3.82 (s, 3H), 1.88 (dd, J=6.6, 1.7 Hz, 3H). $^{19}$F NMR (376 MHz, $CDCl_3$) δ-113.30.

Step 2: Preparation of (E)-4-fluoro-2-methoxy-1-(prop-1-en-1-yl)benzene.

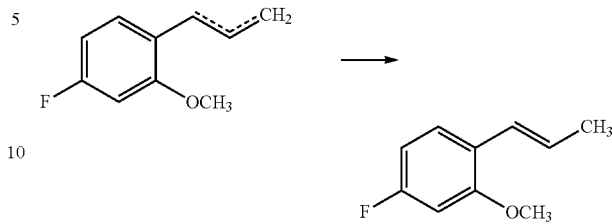

To a solution of (E,Z)-4-fluoro-2-methoxy-1-(prop-1-en-1-yl)benzene (2.25 g, 13.54 mmol) in toluene (27 mL) was added bis(dibenzylideneacetone)palladium (0.156 g, 0.271 mmol), tri-tert-butylphosphine (10% in hexane) (0.84 mL, 0.271 mmol) and isobutyryl chloride (0.028 mL, 0.271 mmol). The reaction was stirred at 80° C. overnight. The reaction mixture was purified by Isco chromatography (100% petroleum ether) to provide the title compound as a 20:1 mixture of E vs Z isomers (2.25 g, 100%). $^1$H NMR (400 MHz, $CDCl_3$) δ 7.31 (dd, J=8.3, 6.8 Hz, 1H), 6.65-6.53 (m, 3H), 6.14 (dq, J=15.8, 6.6 Hz, 1H), 3.82 (s, 3H), 1.88 (dd, J=6.6, 1.7 Hz, 3H). $^{19}$F NMR (376 MHz, $CDCl_3$) δ-113.30.

Example 1D: Preparation of (E)-2,4-dimethyl-1-(prop-1-en-1-yl)benzene

Step 1: Preparation of 1-allyl-2,4-dimethylbenzene.

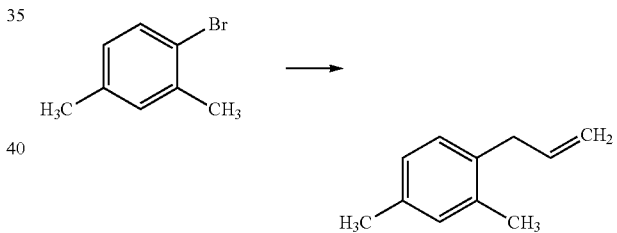

To a solution of magnesium (1.17 g, 48.0 mmol) and lithium chloride (2.20 g, 60.0 mmol) in THF (40 ml) at room temperature was added 1-bromo-2,4-dimethylbenzene (5.4 mL, 40.0 mmol) and the reaction was heated gently to reflux with a heat gun. The reaction was cooled to room temperature over 1 hr. The reaction was then cooled to 0° C., and Fe(acac)$_3$ (0.71 g, 2.00 mmol) dissolved in 5 mL of THF was added. After 5 minutes, allyl chloride (4.23 mL, 52.0 mmol) was added and the reaction was stirred at 0° C. for 30 min. The mixture was warmed to room temperature over 1 hr and was heated at 70° C. overnight. The reaction was cooled to 0° C. and quenched by the addition of a saturated $NaHCO_3$ solution (50 mL). The mixture was extracted with hexane (3×40 mL), the combined organic phases were washed with brine (50 mL), dried over $Na_2SO_4$ and carefully concentrated (25° C., 250 mbar). The residue was purified by Isco chromatography (100% hexane as the eluent) to provide 1-allyl-2,4-dimethylbenzene (2.75 g, 15.04 mmol, 38% yield) as a colorless oil. $^1$H NMR (400 MHz, $CDCl_3$) δ 7.11-6.87 (m, 3H), 5.93 (ddt, J=16.6, 10.1, 6.4 Hz, 1H), 5.19-4.85 (m, 2H), 3.33 (dd, J=6.4, 1.5 Hz, 2H), 2.29 (s, 3H), 2.25 (s, 3H).

Step 2: Preparation of (E)-2,4-dimethyl-1-(prop-1-en-1-yl)benzene.

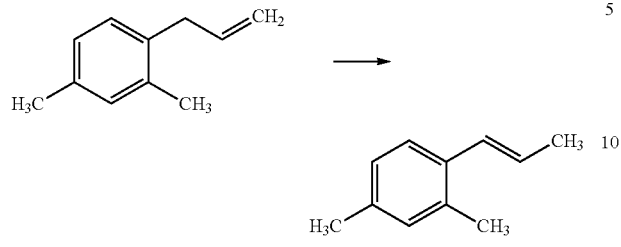

To a 250 mL round bottom flask charged with 1-allyl-2,4-dimethylbenzene (2.75 g, 18.81 mmol) and tris(((Z)-4-oxopent-2-en-2-yl)oxy)iron (0.332 g, 0.940 mmol) in THF (38 mL) was added phenylmagnesium bromide (1.0 M in THF) (9.40 mL, 9.40 mmol) at room temperature. After stirring overnight, the reaction mixture was cooled to 0° C. and quenched by the addition of a saturated solution of NaHCO$_3$ (50 mL). The combined organic layers were extracted with hexane (3×40 mL), washed with brine (50 mL) and dried over Na$_2$SO$_4$. Upon concentration in vacuo, the crude residue was purified via automated silica gel chromatography (100% hexanes as the eluent) to afford (E)-2,4-dimethyl-1-(prop-1-en-1-yl)benzene (2.71 g, 16.68 mmol, 89% yield) as a colorless oil. $^1$H NMR (400 MHz, CDCl$_3$) δ 7.30 (d, J=7.8 Hz, 1H), 7.05 6.86 (m, 2H), 6.56 (dd, J=15.6, 1.9 Hz, 1H), 6.06 (dq, J=15.6, 6.6 Hz, 1H), 2.30 (s, 3H), 2.29 (s, 3H), 1.89 (dd, J=6.6, 1.7 Hz, 3H).

Example 1E: Preparation of (E)-1-methyl-2-(prop-1-en-1-yl)benzene

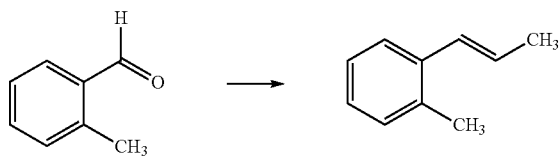

This compound was prepared by the method of Franzén (*Eur. J. Org. Chem.* 2015, 1834). To a solution of 2-methylbenzaldehyde (48.4 mL, 416 mmol) dissolved in CH$_2$Cl$_2$ (300 mL) was added 2-methylbut-2-ene (8.82 mL, 83 mmol) and triphenylmethylium tetrafluoroborate (5.50 g, 16.65 mmol). The reaction was stirred at room temperature for 20 hr. The reaction was quenched by the additon of saturated NaHCO$_3$ and diluted with excess CH$_2$Cl$_2$. The organic layer was separated, dried over MgSO$_4$, filtered and concentrated at low temperature and mild pressure. The resulting residue was purified by flash chromatography (ISCO, 330 g SiO$_2$ column, 100% pet ether as the eluent) to give (E)-1-methyl-2-(prop-1-en-1-yl)benzene (10 g, 71.9 mmol, 86% yield) as a clear liquid. $^1$H NMR (400 MHz, CDCl$_3$) δ 7.39 (d, J=7.0 Hz, 1H), 7.12 (qd, J=5.9, 2.1 Hz, 3H), 6.59 (dd, J=15.6, 1.9 Hz, 1H), 6.10 (dq, J=15.7, 6.6 Hz, 1H), 2.32 (s, 3H), 1.90 (dd, J=6.6, 1.8 Hz, 3H). $^{13}$C NMR (101 MHz, CDCl$_3$) δ 137.08, 134.77, 130.11, 128.92, 126.93, 126.70, 125.99, 125.44. EIMS m/z 132.

Example 2A: 2A Denotes that this Epoxide is Commercially Available

Example 2B: Preparation of (2S,3S)-2-methyl-3-(p-tolyl)oxirane

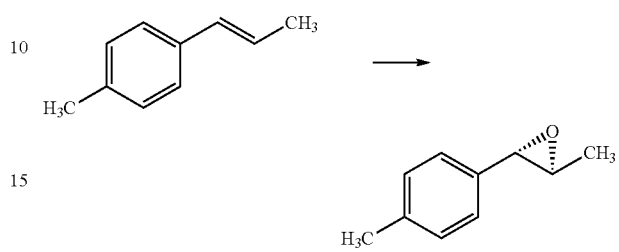

To a 500 mL round-bottom flask containing 75 mL of a buffer solution containing 0.05 M Na$_2$B$_4$O$_7$-10H$_2$O in 4×10$^{-4}$ M aqueous Na$_2$ (EDTA), was added acetonitrile (117 ml), (E)-1-methyl-4-(prop-1-en-1-yl)benzene (1.24 g, 7.69 mmol), tetrabutylammonium hydrogen sulfate (0.104 g, 0.308 mmol), and (3aS,4'R,7aS)-2,2,2',2'-tetramethyldihydrospiro[[1,3]dioxolo-[4,5-c]pyran-6,4'-[1,3]dioxolan]-7(7aH)-one (0.596 g, 2.307 mmol). The reaction mixture was cooled to 0° C. with an ice bath. A solution of oxone (6.53 g, 10.61 mmol) in aqueous Na$_2$(EDTA) (4×10$^{-4}$ M, 50 mL) and a solution of potassium carbonate (6.17 g, 44.6 mmol) in water (50 mL) were added dropwise through two syringe pumps over a period of 1.5 h (under these conditions, the reaction pH is around 10.5; it is recommended that both oxone and K$_2$CO$_3$ be added uniformly over 1.5 h). At this point, the reaction was immediately quenched by the addition of 100 mL each of petroleum ether and water. The layers were separated and the aqueous layer was extracted with petroleum ether (3×150 mL). The combined organic layers were washed with brine (150 mL), dried over Na$_2$SO$_4$ and concentrated under reduced pressure. The residue was purified by flash chromatography (0 to 10% acetone in hexanes as the eluent) to provide (2S,3S)-2-methyl-3-(p-tolyl)oxirane (1.09 g, 6.99 mmol, 91%) as a colorless oil. $^1$H NMR (300 MHz, CDCl$_3$) δ 7.15 (s, 4H), 3.54 (d, J=2.1 Hz, 1H), 3.03 (qd, J=5.1, 2.1 Hz, 1H), 2.34 (s, 3H), 1.44 (d, J=5.1 Hz, 3H). EIMS m/z 148.

Example 3A: Preparation of (1S,2R)-1-cyclobutyl-1-(4-fluoro-2-methylphenyl)propan-2-ol

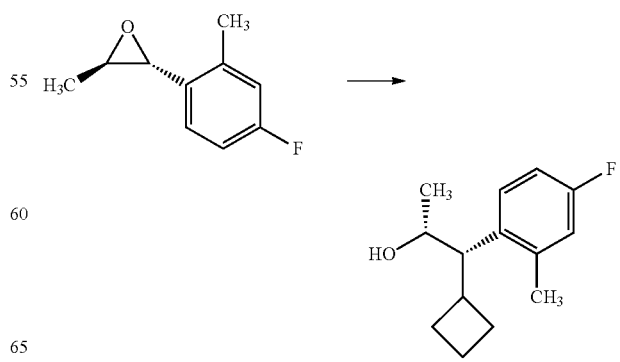

A suspension of magnesium (110 mg, 4.51 mmol) was prepared in THF (3 mL) and cooled to 0° C. After 5 min, bromocyclobutane (397 μL, 4.21 mmol) was added in one portion, and the resulting solution was vigorously stirred for 2 hr, slowly warming to room temperature. After 2 hr, the reaction was heated to 55° C. and stirred overnight. In a separate vial, a suspension of copper(I) iodide (401 mg, 2.106 mmol) in diethyl ether (7.5 mL) was cooled to −30° C. in a dry ice/acetonitrile bath. After ~5 min, the grignard solution was added via syringe over 30 seconds, and the resulting solution was stirred at −30° C. for 30 min, yielding a turbid dark grey/brown mixture. After 30 min, the reaction was cooled to −78° C. in a dry ice/acetone bath, and (2R,3R)-2-(4-fluoro-2-methylphenyl)-3-methyloxirane (250 mg, 1.504 mmol) was added dropwise via syringe as a solution in diethyl ether (1.5 mL with 2×0.5 mL washes). The reaction was then stirred overnight, slowly warming to room temperature. TLC indicated consumption of starting material. The reaction was quenched with sat. aq. NH$_4$Cl (20 mL) and extracted with diethyl ether (3×20 mL). The combined organic layers were dried over Na$_2$SO$_4$, filtered and concentrated to afford an oil. The oil was purified via silica gel Isco column chromatography (40 g silica gel column, 35 mL/min, 100% hexanes to 20% acetone:hexanes) to afford (1S,2R)-1-cyclobutyl-1-(4-fluoro-2-methylphenyl)propan-2-ol (133.4 mg, 0.600 mmol, 40% yield) as a clear, colorless oil. $^1$H NMR (400 MHz, CDCl$_3$) δ 7.14 (dd, J=8.2, 6.1 Hz, 1H), 6.86 (t, J=8.5 Hz, 2H), 3.89 (p, J=6.4 Hz, 1H), 2.84 (dd, J=10.4, 6.0 Hz, 1H), 2.77 2.64 (m, 1H), 2.35 (s, 3H), 2.24 2.12 (m, 1H), 1.86 1.58 (m, 4H), 1.44 1.24 (m, 2H), 1.13 (d, J=6.3 Hz, 3H). $^{19}$F NMR (376 MHz, CDCl$_3$) δ-117.58, −117.59. $_{13}$C NMR (101 MHz, CDCl$_3$) δ 160.94 (d, J=244.2 Hz), 139.81 (d, J=7.3 Hz), 134.60 (d, J=3.3 Hz), 128.53 (d, J=8.0 Hz), 116.78 (d, J=20.7 Hz), 112.84 (d, J=20.6 Hz), 70.25, 53.68, 38.03, 29.54, 27.08, 21.55, 20.55 (d, J=1.7 Hz), 18.16. IR (thin film) 3413, 2967, 1495, 1252, 1021, 955, 860 cm$^{-1}$.

Example 3B: Preparation of (2R,3S)-4-ethyl-3-(4-fluoro-2-methylphenyl)hexan-2-ol

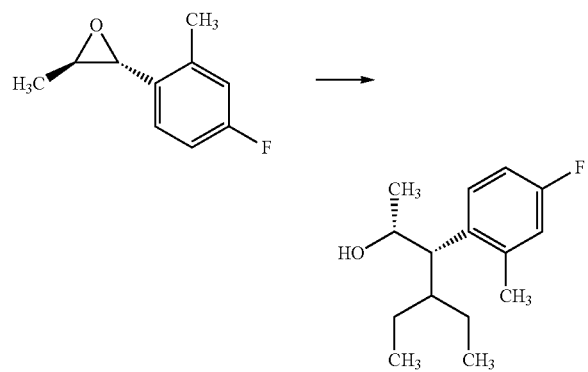

A suspension of copper(I) iodide (401 mg, 2.106 mmol) in anhydrous diethyl ether (7.5 mL) was cooled to −30° C. in a dry ice/acetonitrile bath. After ~5 min, pentan-3-ylmagnesium bromide (2M in Et$_2$O) (2106 μL, 4.21 mmol) was added via syringe over 30 seconds, and the resulting solution was stirred at −30° C. for 30 min, yielding a turbid dark grey/brown mixture. After 30 min, the reaction was cooled to −78° C. in a dry ice/acetone bath, and (2R,3R)-2-(4-fluoro-2-methylphenyl)-3-methyloxirane (250 mg, 1.504 mmol) was added dropwise via syringe as a solution in diethyl ether (1.5 mL with 2×0.5 mL washes). The reaction was then stirred overnight, slowly warming to room temperature. TLC indicated consumption of starting material. The reaction was quenched with sat. aq. NH$_4$Cl (20 mL) and extracted with diethyl ether (3×20 mL). The combined organic layers were dried over Na$_2$SO$_4$, filtered and concentrated to afford an oil. The oil was purified via silica gel Isco column chromatography (40 g silica gel column, 35 mL/min, 100% hexanes to 20% acetone:hexanes) to afford (2R,3S)-4-ethyl-3-(4-fluoro-2-methylphenyl)hexan-2-ol (116.7 mg, 0.490 mmol, 32.5% yield) as a yellow oil. $^1$H NMR (400 MHz, CDCl$_3$) δ 7.34 (dd, J=9.6, 6.1 Hz, 1H), 6.92-6.81 (m, 2H), 4.27 (dq, J=8.8, 4.7 Hz, 1H), 2.74 (dd, J=10.2, 3.6 Hz, 1H), 2.28 (s, 3H), 1.87 (qt, J=8.2, 3.6 Hz, 1H), 1.64 (dtd, J=14.9, 7.3, 4.4 Hz, 1H), 1.53 (tt, J=14.0, 6.7 Hz, 1H), 1.30 1.09 (m, 2H), 1.08 0.98 (m, 1H), 0.96 (d, J=6.4 Hz, 3H), 0.92 (t, J=7.5 Hz, 3H), 0.71 (t, J=7.4 Hz, 3H). $^{19}$F NMR (376 MHz, CDCl$_3$) d-118.01. $^{13}$C NMR (101 MHz, CDCl$_3$) δ 160.91 (d, J=243.7 Hz), 139.73 (d, J=7.1 Hz), 135.03 (d, J=3.3 Hz), 129.46 (d, J=7.9 Hz), 116.60 (d, J=20.5 Hz), 112.57 (d, J=20.4 Hz), 67.19, 47.45, 41.41, 22.08, 21.91, 21.53, 20.67 (d, J=1.6 Hz), 10.82, 9.78. IR (thin film) 3430, 2962, 1496, 1455, 1380, 1256, 956, 860, 801 cm$^{-1}$.

Example 4A: Preparation of (2R,3S)-3-(4-fluoro-2-methylphenyl)-4-methylpent-4-en-2-ol

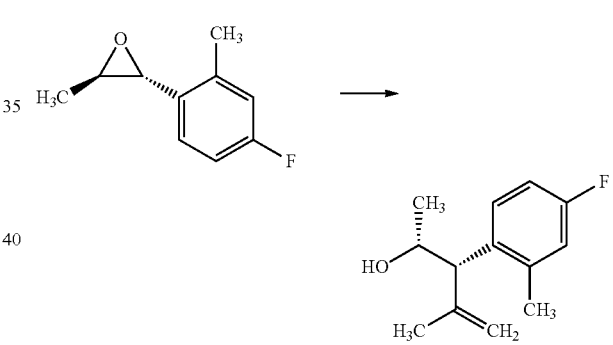

A suspension of copper(I) iodide (0.160 g, 0.842 mmol) in anhydrous diethyl ether (4.0 mL) was cooled to −20° C. After ~5 min, prop-1-en-2-ylmagnesium bromide (1M in 2-Me-THF) (1.685 mL, 1.685 mmol) was added via syringe over 30 seconds, and the resulting solution was stirred at −20° C. for 30 min. After 30 min, the reaction was cooled to −78° C. and (2R,3R)-2-(4-fluoro-2-methylphenyl)-3-methyloxirane (0.100 g, 0.602 mmol) was added dropwise via syringe as a solution in diethyl ether (1.0 mL with 2×0.5 mL washes). The reaction was then stirred overnight, slowly warming to room temperature. TLC indicated consumption of starting material. The reaction was quenched with sat. aq. NH$_4$Cl (20 mL) and extracted with diethyl ether (3×20 mL). The combined organic layers were dried over Na$_2$SO$_4$, filtered and concentrated to afford an oil. The oil was purified via silica gel Isco column chromatography (40 g silica gel column, 35 mL/min, 100% hexanes to 20% acetone:hexanes) to afford (2R,3S)-3-(4-fluoro-2-methylphenyl)-4-methylpent-4-en-2-ol (120.2 mg, 0.577 mmol, 96% yield) as a pale yellow oil. $^1$H NMR (400 MHz, CDCl$_3$) δ 7.37-7.30 (m, 1H), 6.93-6.86 (m, 2H), 4.89 (s, 2H), 4.32 (dq, J=8.8, 6.1 Hz, 1H), 3.42 (d, J=8.7 Hz, 1H), 2.34 (s, 3H), 1.59 (s, 3H), 1.52 (s, 1H), 1.30 (d, J=6.1 Hz, 3H). $^{19}$F NMR (376 MHz, CDCl$_3$) δ-116.95. $^{13}$C NMR (101 MHz, CDCl$_3$) δ 161.27 (d, J=244.8 Hz), 144.85, 140.40 (d, J=7.5 Hz), 133.79 (d, J=3.2 Hz), 128.19 (d, J=8.2 Hz), 117.47 (d, J=20.6 Hz), 113.12, 112.76 (d, J=20.8 Hz), 68.13, 56.04, 21.28, 21.22, 20.03 (d, J=1.5 Hz). IR (thin film) 3373, 2970, 1495, 1240, 958, 861 cm$^{-1}$.

Example 4B: Preparation of (2R,3S)-3-(4-fluoro-2-methylphenyl)-4-methylpentan-2-ol

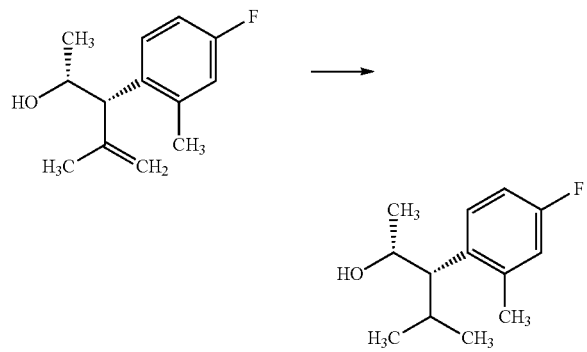

To a 20 mL vial containing (2R,3S)-3-(4-fluoro-2-methylphenyl)-4-methylpent-4-en-2-ol (120.2 mg, 0.577 mmol) and palladium on carbon (5%) (184 mg, 0.087 mmol) was added ethyl acetate (2886 μL). The black reaction mixture was flushed with H$_2$ gas via balloon. The resulting reaction was stirred at room temperature for 2 h, at which point TLC/UPLC indicated consumption of starting material. The reaction was filtered through a plug of celute, eluting with ethyl acetate (2×10 mL). The resulting solution was concentrated to afford an oil that was loaded directly onto a 25 g prepacked silica column in a minimal amount of dichloromethane and purified using Isco silica gel column chromatography (40 column, 40 mL/min, 100% hexanes to 30% ethyl acetate:hexanes) to afford (2R,3S)-3-(4-fluoro-2-methylphenyl)-4-methylpentan-2-ol (44.9 mg, 0.214 mmol, 37.0% yield) as a clear, colorless oil. $^1$H NMR (400 MHz, CDCl$_3$) δ 7.32 (dd, J=9.5, 6.1 Hz, 1H), 6.93-6.84 (m, 2H), 4.28 (qd, J=6.3, 4.4 Hz, 1H), 2.50 (dd, J=9.2, 4.4 Hz, 1H), 2.28 (s, 3H), 2.15 (dp, J=9.1, 6.6 Hz, 1H), 1.42-1.13 (m, 1H), 1.06 (d, J=6.6 Hz, 3H), 1.01 (d, J=6.3 Hz, 3H), 0.70 (d, J=6.7 Hz, 3H). $^{13}$C NMR (101 MHz, CDCl$_3$) δ 160.93 (d, J=243.8 Hz), 139.78 (d, J=7.2 Hz), 134.96 (d, J=3.3 Hz), 129.17 (d, J=8.0 Hz), 116.64 (d, J=20.4 Hz), 112.57 (d, J=20.4 Hz), 67.70, 52.62, 30.26, 21.76, 21.32, 20.77. $^{19}$F NMR (376 MHz, CDCl$_3$) δ-117.97.

Example 4C: Preparation of (2R,3S)-3-(4-fluoro-2-methylphenyl)-4-methylpentan-2-ol

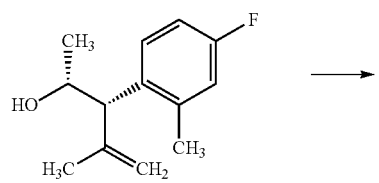

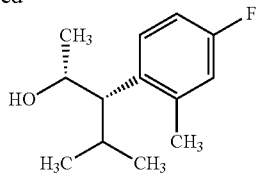

To a 250 mL round bottom flask containing (2R,3S)-3-(4-fluoro-2-methylphenyl)-4-methylpent-4-en-2-ol (1.16 g, 5.57 mmol) and Wilkinson's catalyst (1.288 g, 1.392 mmol) was added THF (55.7 ml). The reddish-brown reaction mixture was flushed with H$_2$ gas via balloon. The resulting reaction was stirred at room temperature overnight. The reaction was concentrated to a dark orange-brown oil, and the resulting oil was loaded directly onto a 25 g prepacked silica column in a minimal amount of dichloromethane and purified using Isco silica gel column chromatography (120 column, 85 mL/min, 100% hexanes to 30% ethyl acetate: hexanes) to afford (2R,3S)-3-(4-fluoro-2-methylphenyl)-4-methylpentan-2-ol (880 mg, 4.18 mmol, 75% yield) as a clear, colorless oil. $^1$H NMR (400 MHz, CDCl$_3$) δ 7.32 (dd, J=9.5, 6.0 Hz, 1H), 6.92-6.84 (m, 2H), 4.28 (qd, J=6.3, 4.4 Hz, 1H), 2.50 (dd, J=9.2, 4.4 Hz, 1H), 2.28 (s, 3H), 2.15 (ddd, J=13.2, 6.8, 2.3 Hz, 1H), 1.31-1.17 (m, 1H), 1.06 (d, J=6.6 Hz, 3H), 1.01 (d, J=6.3 Hz, 3H), 0.70 (d, J=6.7 Hz, 3H). $^{13}$C NMR (101 MHz, CDCl$_3$) δ 160.92 (d, J=243.8 Hz), 139.78 (d, J=7.2 Hz), 134.95 (d, J=3.2 Hz), 129.16 (d, J=7.8 Hz), 116.64 (d, J=20.4 Hz), 112.57 (d, J=20.3 Hz), 67.70, 52.62, 30.26, 21.76, 21.31, 20.76. $^{19}$F NMR (376 MHz, CDCl$_3$) δ-117.97.

Example 5: Preparation of (3S)-4-ethyl-3-phenylhexan-2-ol

Step 1: Preparation of (2R,3S)-4-ethyl-3-phenylhexan-2-ol.

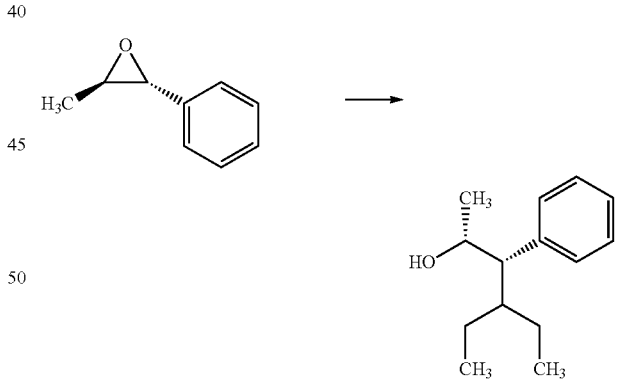

To a suspension of copper (I) iodide (667 mg, 3.50 mmol) in Et$_2$O (12.5 mL) cooled to −78° C. was added pentan-3-ylmagnesium bromide (2M in THF) (3.5 mL, 7.00 mmol). The reaction was warmed to −20° C. and stirred at that temperture for 30 min. The reaction was then cooled to −78° C. followed by the addition of (2R,3R)-2-methyl-3-phenyloxirane (335 mg, 2.5 mmol). The reaction was slowly warmed to room temperature and stirred overnight. The reaction was quenched by the addition of aqueous saturated NH$_4$Cl. The mixture was filtered through a pad of Celite, and the solution was extracted with Et$_2$O. The combined organic phases were dried over Na$_2$SO$_4$, filtered and concentrated under reduced pressure. The residue was purified by silica gel chromatography using a 0-10% acetone/hexane mixture as the eluent to provide the title compound as colorless oil (200 mg, 27%). $^1$H NMR (400 MHz, CDCl$_3$) δ 7.37-7.18 (m, 5H), 4.38-4.19 (m, 1H), 2.47 (dd, J=8.5, 5.1 Hz, 1H), 1.81 (ttd, J=8.8, 5.9, 3.2 Hz, 1H), 1.55-1.25 (m, 3H), 1.20 (d, J=5.6 Hz, 1H), 1.05 (d, J=6.3 Hz, 3H), 1.03-0.94 (m, 1H), 0.93 (t, J=7.4 Hz, 3H), 0.76 (t, J=7.4 Hz, 3H). ESIMS (m/z) 413 [2M+H]$^+$.

Step 2: Preparation of (S)-4-ethyl-3-phenylhexan-2-one.

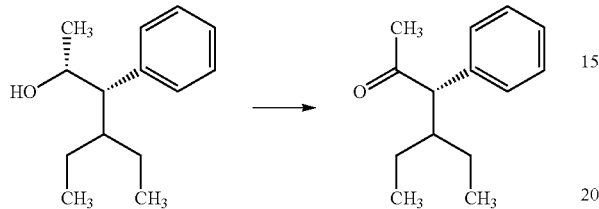

To a solution containing (2R,3S)-4-ethyl-3-phenylhexan-2-ol (190 mg, 0.921 mmol) dissolved in CH$_2$Cl$_2$ (4.6 mL) at 0° C. was added sodium bicarbonate (774 mg, 9.21 mmol) followed by Dess-Martin periodinane (781 mg, 1.842 mmol). The reaction was slowly warmed to room temperature over 3 hr. The reaction was quenched by the addition of aqueous saturated NaHCO$_3$ solution followed by extraction with CH$_2$Cl$_2$. The combined organic phases were dried over Na$_2$SO$_4$, filtered and concentrated under reduced pressure. The residue was purified by silica gel chromatography using a 0-5% acetone/hexane mixture as the eluent to provide the title compound as colorless oil (124 mg, 63%). $^1$H NMR (400 MHz, CDCl$_3$) δ 7.54-7.10 (m, 5H), 3.61 (d, J=10.8 Hz, 1H), 2.21 (dtt, J=11.1, 7.5, 3.9 Hz, 1H), 2.09 (s, 3H), 1.49-1.32 (m, 2H), 1.31-1.15 (m, 1H), 1.05-0.94 (m, 1H), 0.89 (t, J=7.4 Hz, 3H), 0.69 (t, J=7.4 Hz, 3H). $^{13}$C NMR (101 MHz, CDCl$_3$) δ 208.87, 137.71, 128.98, 128.66, 127.12, 63.12, 41.13, 30.15, 22.76, 21.03, 10.46, 9.47.

Step 3: Preparation of (3S)-4-ethyl-3-phenylhexan-2-ol.

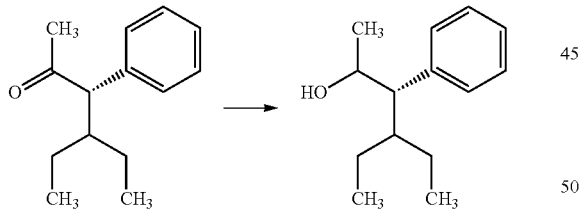

To a stirred solution containing (S)-4-ethyl-3-phenylhexan-2-one (120 mg, 0.587 mmol) and (R)-1-methyl-3,3-diphenylhexahydropyrrolo[1,2-c][1,3,2]oxazaborole (1 M in toluene) (58.7 μL, 0.059 mmol) dissolved in toluene (5.9 mL) at −78° C. was added BH$_3$-SMe$_2$ complex (61.3 μL, 0.646 mmol) dropwise. The reaction was slowly warmed to room temperature and stirred overnight. The reaction was then quenched carefully with methanol (475 μL, 11.75 mmol). The mixture was diluted with H$_2$O and extracted with Et$_2$O. The combined organic phases were dried over Na$_2$SO$_4$, filtered and concentrated under reduced pressure. The residue was purified by silica gel chromatography using a 0-10% acetone/hexane mixture as the eluent to provide the title compound as colorless oil (110 mg, 86%). $^1$H NMR shows a 3.3:1 mixture of diastereomers with the desired product being the major diastereomer. $^1$H NMR (major diastereomer) (300 MHz, CDCl$_3$) δ 7.37-7.04 (m, 5H), 4.22 (dt, J=13.8, 6.3 Hz, 1H), 2.75 (t, J=7.5 Hz, 1H), 1.85-1.73 (m, 1H), 1.55-1.21 (m, 3H), 1.18 (d, J=7.8 Hz, 1H), 1.05 (d, J=6.3 Hz, 3H), 1.03-0.97 (m, 1H), 0.94 (t, J=7.4 Hz, 3H), 0.81 (t, J=7.4 Hz, 3H). ESIMS (m/z) 413 [2M+H]$^+$.

Example 6: Preparation of (2S,3S)-3-(4-fluorophenyl)-4-methylpentan-2-ol

Step 1: Preparation of (2S)-2-(benzyloxy)-1-(4-fluorophenyl)propan-1-ol.

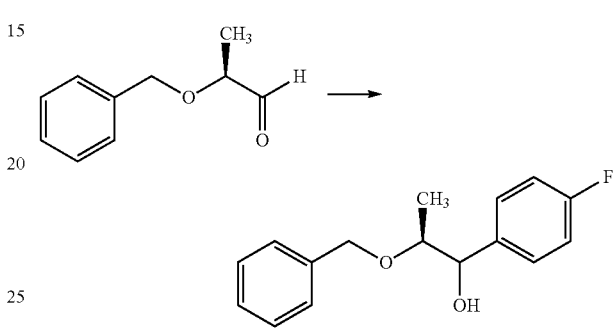

A round bottom flask was charged with (S)-2-(benzyloxy)propanal (1.0 g, 6.09 mmol) dissolved in anhydrous THF (6.77 mL). This solution was cooled in an ice bath under an atmosphere of N$_2$ and was treated dropwise with (4-fluorophenyl)magnesium bromide (6.70 mL, 6.70 mmol). The reaction was monitored by TLC (20% EtOAc in hexanes) until the reaction was complete. The reaction mixture was poured into saturated NH$_4$Cl and the phases separated. The aqueous phase was extracted with EtOAc. The organic fractions were dried with magnesium sulfate and concentrated under reduced pressure. The crude residue was purified by automated silica gel chromatography (0-25% EtOAc in hexanes) to provide (2S)-2-(benzyloxy)-1-(4-fluorophenyl)propan-1-ol (1.404 g, 5.34 mmol, 88% yield) as a colorless oil. $^1$H NMR analysis showed the mixure to be a 2:1 mixture of diastereomers. HRMS-ESI (m/z) [M+Na]+ calcd for C$_{16}$H$_{17}$FO$_2$Na, 283.1105; found, 283.1105.

Step 2: Preparation of (S)-2-(benzyloxy)-1-(4-fluorophenyl)propan-1-one.

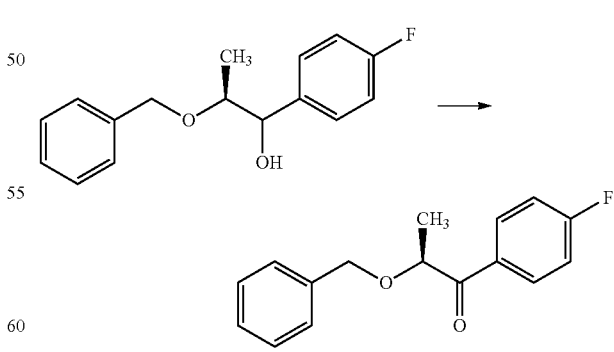

A 100 mL round bottom flask was charged with CH$_2$Cl$_2$ (12.26 mL), and oxalyl chloride (0.519 mL, 5.93 mmol). This solution was cooled in a dry ice/acetone bath under an atmosphere of N$_2$ and treated dropwise with DMSO (0.842 mL, 11.87 mmol). The resultant mixture was stirred for ~2 minutes and then treated dropwise with a solution of (2S)-2-(benzyloxy)-1-(4-fluorophenyl)propan-1-ol (1.404 g, 5.39 mmol) in 3 mL of $CH_2Cl_2$ (extra rinse with 1 mL). After stirring for ~15 minutes, the reaction mixture was treated dropwise with triethylamine (3.76 mL, 27.0 mmol). The reaction mixture was stirred for 5 minutes and then allowed to warm to room temperture. The reaction was monitored by TLC (20% EtOAc in hexanes). The reaction mixture was poured into $H_2O$ and the phases were separated. The aqueous phase was extracted with $CH_2Cl_2$. The combined organics were dried with sodium sulfate and concentrated. The crude residue was purified by silica gel chromatography (0-15% EtOAc in hexanes) to provide (S)-2-(benzyloxy)-1-(4-fluorophenyl)propan-1-one (1.1475 g, 4.44 mmol, 82% yield) as a colorless oil. $^1$H NMR (400 MHz, $CDCl_3$) δ 8.20-8.04 (m, 2H), 7.40-7.24 (m, 5H), 7.19-7.02 (m, 2H), 4.70 (q, J=6.9 Hz, 1H), 4.61 (d, J=11.6 Hz, 1H), 4.45 (d, J=11.6 Hz, 1H), 1.54 (d, J=6.9 Hz, 3H). $^{19}$F NMR (376 MHz, $CDCl_3$) δ-104.39. $^{13}$C NMR (126 MHz, $CDCl_3$) δ 199.27, 165.83 (d, J=255.3 Hz), 137.41, 131.69 (d, J=9.2 Hz), 131.08 (d, J=2.9 Hz), 128.46, 127.98, 127.93, 115.71 (d, J=21.8 Hz), 78.72, 71.65, 18.81. HRMS-ESI (m/z) [M+Na]+ calcd for $C_{16}H_{15}FO_2Na$, 281.0948; found, 281.0950.

Step 2A: Preparation of (S)-1-(benzo[d][1,3]dioxol-5-yl)-2-(benzyloxy)propan-1-one.

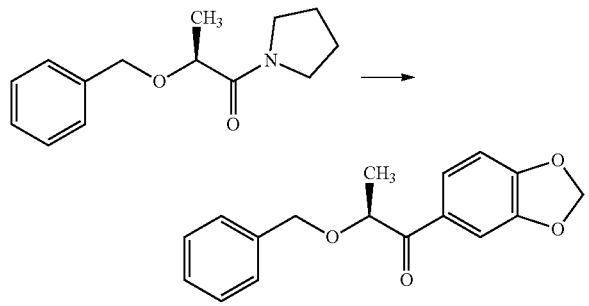

To a vial charged with (S)-2-(benzyloxy)-1-(pyrrolidin-1-yl)propan-1-one (1 g, 4.29 mmol) dissolved in anhydrous THF (12 mL) was added dropwise benzo[d][1,3]dioxol-5-ylmagnesium bromide (1M in 1:1 toluene/THF, 4.29 mL, 4.29 mmol) at −5° C. The mixture was allowed to warm to ambient temperature and stirred overnight. The mixture was quenched by the addition of 1 N HCl. The layers were separated, followed by extraction with ethyl ether (3×10 mL). The combined organic layers were washed with brine, dried over sodium sulfate, and concentrated in vacuo. The residue was purified via automated silica gel chromatography (Isco, 0-25% EtOAc/hexanes as the eluent) to afford (S)-1-(benzo[d][1,3]dioxol-5-yl)-2-(benzyloxy)propan-1-one (0.39 g, 30%) as yellow oil. $^1$H NMR (500 MHz, $CDCl_3$) δ 7.73 (dd, J=8.2, 1.7 Hz, 1H), 7.55 (d, J=1.6 Hz, 1H), 7.39-7.27 (m, 5H), 6.84 (d, J=8.2 Hz, 1H), 6.04 (s, 2H), 4.70 (q, J=6.9 Hz, 1H), 4.53 (dd, J=103.5, 11.6 Hz, 2H), 1.52 (d, J=6.9 Hz, 3H). $^{13}$C NMR (126 MHz, $CDCl_3$) δ 198.8, 152.0, 148.1, 137.6, 129.4, 128.4, 127.9, 127.8, 125.2, 108.6, 107.9, 101.8, 78.4, 71.5, 19.1. HRMS-ESI (m/z) [M+H]+ calcd for $C_{17}H_{17}O_4$, 285.1121; found, 285.1121.

Step 3: Preparation of (2S)-2-(benzyloxy)-3-(4-fluorophenyl)-4-methylpentan-3-ol.

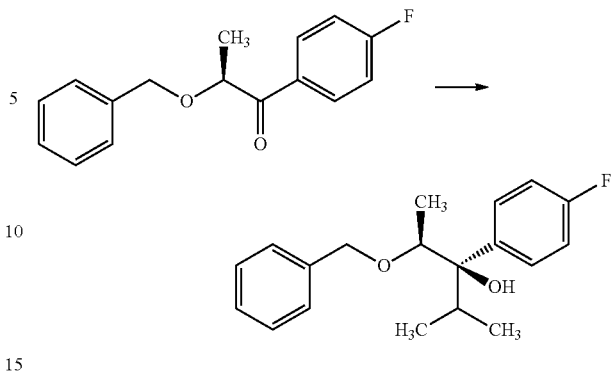

A solution of isopropylmagnesium bromide (1.936 mL, 3.87 mmol) was added to anhydrous THF (6.45 ml) cooled to 0° C. in an ice bath. A solution of (S)-2-(benzyloxy)-1-(4-fluorophenyl)propan-1-one (0.5 g, 1.936 mmol) in THF (2 mL+1 mL to rinse the syringe) was added dropwise. The reaction was stirred until complete by consumption of starting material by TLC (20% EtOAc in hexanes). The reaction was quenched by the addition of saturated ammonium chloride and the mixture was extracted with EtOAc. The combined organic fractions were dried over $MgSO_4$, filtered and concentrated. The crude residue was purified by automated silica gel chromatography (0-10% EtOAc in hexanes) to provide (2S)-2-(benzyloxy)-3-(4-fluorophenyl)-4-methylpentan-3-ol (201.9 mg, 0.634 mmol, 33% yield) as a white foam. $^1$H NMR data showed a 9.2:1 ratio of diastereomers. $^1$H NMR (400 MHz, $CDCl_3$) δ 7.43-7.20 (m, 7H), 7.00 (t, J=8.8 Hz, 2H), 4.72 (d, J=11.4 Hz, 1H), 4.49 (d, J=11.5 Hz, 1H), 4.09 (q, J=6.2 Hz, 1H), 2.46 (s, 1H), 2.35 (p, J=6.8 Hz, 1H), 1.00 (d, J=6.2 Hz, 3H), 0.77 (dd, J=8.8, 6.8 Hz, 6H). $^{19}$F NMR (376 MHz, $CDCl_3$) δ-117.13. $^{13}$C NMR (126 MHz, $CDCl_3$) δ 161.55 (d, J=244.4 Hz), 138.28, 136.60 (d, J=3.2 Hz), 128.45, 128.14 (d, J=7.7 Hz), 127.80, 114.09 (d, J=20.9 Hz), 80.56, 70.91, 34.79, 17.93, 16.87, 13.63. HRMS-ESI (m/z) [M+Na]+ calcd for $C_{19}H_{23}FO_2Na$, 325.1574; found, 325.1574.

Step 4: Preparation of 1-((2S,3S)-2-(benzyloxy)-4-methylpentan-3-yl)-4-fluorobenzene.

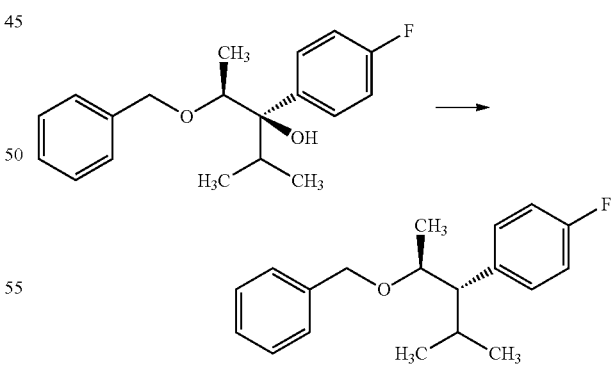

To a solution of (2S)-2-(benzyloxy)-3-(4-fluorophenyl)-4-methylpentan-3-ol (0.2 g, 0.661 mmol) dissolved in $CH_2Cl_2$ (2.205 ml) at 0° C. was added triethylsilane (1.056 mL, 6.61 mmol) followed by trifluoroacetic acid (0.510 mL, 6.61 mmol). The mixture was stirred at 0° C. for 1 hr. The mixture was then allowed to slowly warm to room temperature and stirred overnight. The reaction was carefully quenched by the addition of a saturated sodium bicarbonate solution and extracted with CH₂Cl₂. The combined organic layers were then dried over sodium sulfate, filtered and concentrated under reduced pressure. The crude residue was purified by automated silica gel chromatography (0-5% EtOAc in hexanes) to provide 1-((2S,3S)-2-(benzyloxy)-4-methylpentan-3-yl)-4-fluorobenzene (152.2 mg, 0.505 mmol, 76% yield) as a colorless oil. ¹H NMR data revealed a 7.2:1 ratio of diastereomers. ¹H NMR (400 MHz, CDCl₃) δ 7.39-7.26 (m, 5H), 7.07-6.91 (m, 4H), 4.66 (d, J=11.6 Hz, 1H), 4.50 (d, J=11.6 Hz, 1H), 3.88 (dq, J=8.5, 6.1 Hz, 1H), 2.61 (d, J=14.4 Hz, 1H), 2.37 (dq, J=13.4, 6.7 Hz, 1H), 1.01 (d, J=6.1 Hz, 3H), 0.80 (d, J=6.8 Hz, 3H), 0.74 (d, J=6.8 Hz, 3H). ¹³C NMR (126 MHz, CDCl₃) δ 161.48 (d, J=243.8 Hz), 138.84, 135.66 (d, J=3.3 Hz), 131.08 (d, J=7.6 Hz), 128.35, 127.71, 127.49, 114.48 (d, J=20.8 Hz), 75.31, 70.71, 57.21, 27.57, 21.59, 18.36, 17.35. HRMS-ESI (m/z) [M+Na]+ calcd for C₁₉H₂₃FONa, 309.1625; found, 309.1629.

Step 5: Preparation of (2S,3S)-3-(4-fluorophenyl)-4-methylpentan-2-ol.

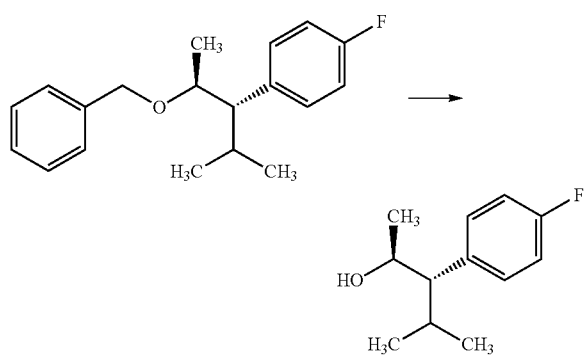

A flask containing 1-((2S)-2-(benzyloxy)-4-methylpentan-3-yl)-4-fluorobenzene (0.15 g, 0.524 mmol) was charged with 5% palladium on carbon (0.056 g, 0.026 mmol) and then suspended in ethanol (2.62 mL). The reaction atmosphere was replaced with hydrogen gas via a balloon (1 atm) and montinored until complete by TLC (25% EtOAc in hexanes). The reaction was filtered through a pad of Celite© and the pad was washed with ethyl acetate. The filtrate was concentrated under reduced pressure. The crude residue was purified by automated column chromatography (0-20% EtOAc in hexanes as the eluent) to provide (2S,3S)-3-(4-fluorophenyl)-4-methylpentan-2-ol (76.9 mg, 0.388 mmol, 74.1% yield) as a white foam. ¹H NMR (500 MHz, CDCl₃) d 7.11-7.05 (m, 2H), 7.03-6.97 (m, 2H), 4.17 (dq, J=7.5, 6.2 Hz, 1H), 2.47 (t, J=7.5 Hz, 1H), 2.18 (dp, J=13.6, 6.8 Hz, 1H), 1.19 (d, J=7.2 Hz, 1H), 1.03 (d, J=6.3 Hz, 3H), 0.90 (d, J=6.7 Hz, 3H), 0.79 (d, J=6.7 Hz, 3H). ¹³C NMR (126 MHz, CDCl₃) δ 161.65 (d, J=244.4 Hz), 135.15 (d, J=3.4 Hz), 131.11 (d, J=7.6 Hz), 114.76 (d, J=20.9 Hz), 68.13, 59.08, 28.28, 21.34, 20.53, 19.47. IR (thin film) 3348, 2960, 2929, 2872, 1604, 1508, 1465, 1368, 1223, 1160, 833 cm⁻¹.

Step 6: Preparation of (4S)-4-(benzyloxy)-3-(4-fluorophenyl)-2-methylpent-1-en-3-ol.

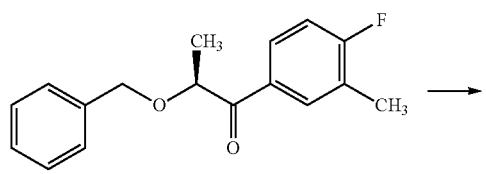

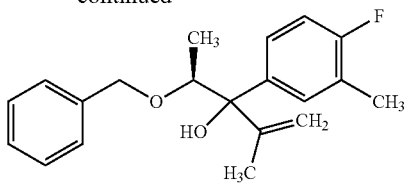

To a solution containing prop-1-en-2-ylmagnesium bromide (1 M in 2-Me-THF) (4.29 mL, 4.29 mmol) dissolved in THF (21.44 mL) and cooled to 0° C. in an ice/water bath was added (S)-2-(benzyloxy)-1-(4-fluoro-3-methylphenyl) propan-l-one (0.584 g, 2.144 mmol) dropwise over 5 minutes as a solution in THF (3 mL). The resulting solution was stirred for 1 hr, at which point an additional 2.1 mL (1 equivalent) of the Grignard reagent was added, and the reaction was stirred for an additional hour. The reaction was quenched with saturated aqueous NH₄Cl (50 mL) solution and extracted with EtOAc (3×50 mL). The combined organic layers were dried over Na₂SO₄, filtered, and concentrated to an oil. The oil was loaded onto a prepacked 25 g silica gel column and purified using Isco silica gel column chromatography (40 column, 35 mL/min, 100% hexanes to 20% ethyl acetate:hexanes) to afford the title compound (671 mg, 100%) as a clear, colorless oil. ¹H NMR (400 MHz, CDCl₃) δ 7.40-7.23 (m, 6H), 7.16 (ddd, J=7.9, 4.9, 2.4 Hz, 1H), 6.92 (t, J=9.0 Hz, 1H), 5.17 (t, J=1.0 Hz, 1H), 4.98 (p, J=1.4 Hz, 1H), 4.69 (d, J=11.4 Hz, 1H), 4.51 (d, J=11.4 Hz, 1H), 4.21 (q, J=6.1 Hz, 1H), 2.81 (s, 1H), 2.26 (d, J=1.9 Hz, 3H), 1.63 (t, J=1.0 Hz, 3H), 0.99 (d, J=6.1 Hz, 3H). ¹⁹F NMR (376 MHz, CDCl₃) d-120.68. IR (thin film) 3500, 2977, 2923, 1499, 1242, 1114, 1097, 894, 818, 733, 697 cm⁻¹. HRMS-ESI (m/z) [M+H]+ calcd for C₂₀H₂₃FNaO₂, 337.1574; found, 337.1584.

Step 7: Preparation of (2S)-2-(benzyloxy)-3-(4-fluorophenyl)-4-methylpentan-3-ol.

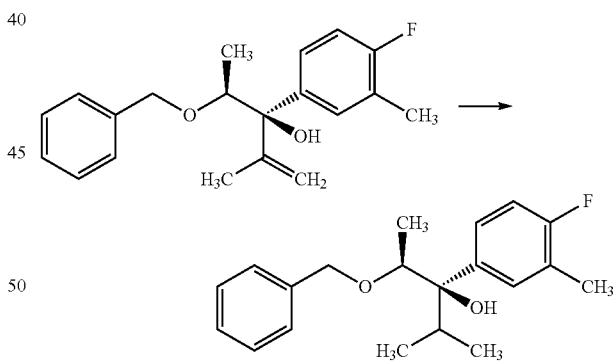

A solution containing (3S,4S)-4-(benzyloxy)-3-(4-fluoro-3-methylphenyl)-2-methylpent-1-en-3-ol (0.6713 g, 2.135 mmol) and Wilkinson's catalyst (0.593 g, 0.641 mmol) dissolved in THF (14.23 mL) was flushed with hydrogen gas via balloon. The resulting reaction was stirred at room temperature overnight. The reaction mixture was concentrated to a dark orange-brown oil under reduced pressure. The resulting oil was loaded directly onto a 25 g prepacked silica column in a minimal amount of dichloromethane and purified using Isco silica gel column chromatography (40 column, 35 mL/min, 100% hexanes to 20% ethyl acetate: hexanes) to afford the title compound (659 mg, 98%) as a clear, colorless oil. ¹H NMR (400 MHz, CDCl₃) δ 7.41-7.28

(m, 5H), 7.16 (dd, J=7.6, 2.3 Hz, 1H), 7.05 (ddd, J=7.8, 5.0, 2.4 Hz, 1H), 6.92 (t, J=9.0 Hz, 1H), 4.72 (d, J=11.4 Hz, 1H), 4.49 (d, J=11.4 Hz, 1H), 4.08 (q, J=6.2 Hz, 1H), 2.44 (s, 1H), 2.34 (p, J=6.8 Hz, 1H), 2.27 (d, J=1.9 Hz, 3H), 1.01 (d, J=6.1 Hz, 3H), 0.77 (dd, J=10.6, 6.8 Hz, 6H). $^{19}$F NMR (376 MHz, CDCl$_3$) δ -121.44. $^{13}$C NMR (101 MHz, CDCl$_3$) δ 160.12 (d, J=243.5 Hz), 138.39, 136.31 (d, J=3.5 Hz), 129.74 (d, J=4.9 Hz), 128.45, 127.79, 127.75, 125.35 (d, J=7.8 Hz), 123.40 (d, J=17.0 Hz), 113.69 (d, J=22.1 Hz), 80.55, 77.07, 70.95, 34.84, 18.01, 16.94, 14.80 (d, J=3.5 Hz), 13.71. IR (thin film) 3564, 2962, 2935, 1501, 1374, 1243, 1105, 1089, 817, 757, 697 cm$^{-1}$. HRMS-ESI (m/z) [M+H]+ calcd for C$_{20}$H$_{25}$FNaO$_2$, 339.1731; found, 339.1728.

Example 6A: Preparation of (2R,3S)-3-(2,5-dimethylphenyl)-4-methylpentan-2-ol Step 1: Preparation of 2-(2,5-dimethylphenyl)-3-methylbutanoic acid.

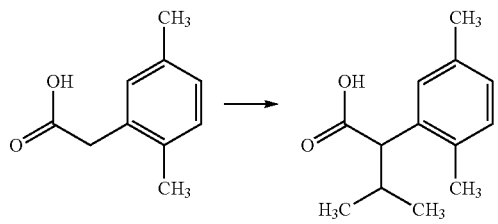

A solution of isopropylmagnesium chloride (2 M in THF, 5.79 mL, 11.57 mmol) was added slowly to a solution of 2-(2,5-dimethylphenyl)acetic acid (0.95 g, 5.79 mmol) in THF (11.57 mL) at room temperature. The resulting thick suspension was stirred for 1 hr and treated with 2-iodopropane (1.736 mL, 17.36 mmol). The reaction was heated to 70° C. and stirred overnight. The reaction was quenched by the addition of 1N HCl and extracted with EtOAc. The organic layer was dried over magnesium sulfate, filtered and concentrated under reduced pressure. The residue was purified by automated column chromatography (Isco, 0-30% EtOAc in hexanes as the eluent) to provide 2-(2,5-dimethylphenyl)-3-methylbutanoic acid (670 mg, 53.3%) as a white solid. $^1$H NMR (500 MHz, CDCl$_3$) δ 11.32 (bs, 1H), 7.21 (s, 1H), 7.04 (d, J=7.7 Hz, 1H), 6.95 (d, J=8.5 Hz, 1H), 3.46 (d, J=10.9 Hz, 1H), 2.40-2.34 (m, 1H), 2.33 (s, 3H), 2.29 (s, 3H), 1.11 (d, J=6.4 Hz, 3H), 0.69 (d, J=6.7 Hz, 3H). $^{13}$C NMR (126 MHz, CDCl$_3$) δ 179.72, 136.08, 135.79, 133.69, 130.22, 127.82, 127.67, 54.23, 31.46, 21.62, 21.12, 19.75, 19.69. HRMS-ESI (m/z) [2M+H]+ calcd for C$_{13}$H$_{18}$O$_2$, 413.2686; found, 413.2674.

Step 2: Preparation of 2-(2,5-dimethylphenyl)-N-methoxy-N,3-dimethylbutanamide.

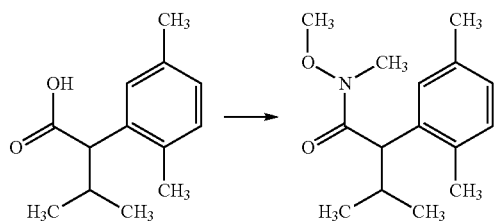 [SMILES: Cc1ccc(C)c(C(C(=O)O)C(C)C)c1 ; CON(C)C(=O)C(c1cc(C)ccc1C)C(C)C]

To a solution containing 2-(2,5-dimethylphenyl)-3-methylbutanoic acid (0.66 g, 3.20 mmol) dissolved in 32 mL of CH$_2$Cl$_2$ at 0° C. was added 4-methylmorpholine (0.70 mL, 6.40 mmol) and N,O-dimethylhydroxylamine hydrochloride (0.624 g, 5.71 mmol). 3-(((Ethylimino)methylene)amino)-N,N-dimethylpropan-1-amine hydrochloride (EDC, 1.23 g, 6.40 mmol) was added and the reaction was warmed to room temperature and stirred overnight. The reaction was concentrated under reduced pressure and the residue was purified by automated silica gel chromatography (Isco, 0-25% EtOAc in hexanes as the eluent) to provide 2-(2,5-dimethylphenyl)-N-methoxy-N,3-dimethylbutanamide (694 mg, 83%) as a colorless oil. $^1$H NMR (500 MHz, CDCl$_3$) δ 7.27 (s, 1H), 7.01 (d, J=7.7 Hz, 1H), 6.93-6.89 (m, 1H), 3.84 (d, J=10.3 Hz, 1H), 3.48 (s, 3H), 3.14 (s, 3H), 2.41-2.35 (m, 1H), 2.34 (s, 3H), 2.27 (s, 3H), 1.05 (d, J=6.4 Hz, 3H), 0.68 (d, J=6.8 Hz, 3H). $^{13}$C NMR (126 MHz, CDCl$_3$) δ 137.49, 135.69, 133.14, 129.89, 127.88, 127.23, 60.95, 49.90, 32.65, 32.21, 22.25, 21.11, 19.51. HRMS-ESI (m/z) [M+H]+ calcd for C$_{15}$H$_{23}$NO$_2$, 250.1802; found, 250.1799.

Step 3: Preparation of 3-(2,5-dimethylphenyl)-4-methylpentan-2-one.

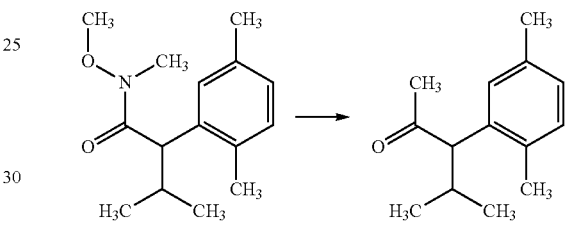

A solution containing 2-(2,5-dimethylphenyl)-N-methoxy-N,3-dimethylbutanamide (0.685 g, 2.75 mmol) dissolved in THF (18.31 mL) was cooled to 0° C. Methylmagnesium bromide (3.0 M in diethyl ether, 2.75 ml, 8.24 mmol) was added dropwise and the reaction was allowed to warm to room temperature and stirred overnight. The reaction was quenched by the addition of saturated ammonium chloride solution and was extracted with EtOAc. The organic layer was dried over magnesium sulfate, filtered and concentrated under reduced pressure to provide 3-(2,5-dimethylphenyl)-4-methylpentan-2-one (573.3 mg, 97%) as a yellow oil. $^1$H NMR (500 MHz, CDCl$_3$) δ 7.27 (s, 1H), 7.06 (d, J=7.6 Hz, 1H), 6.94 (d, J=7.7 Hz, 1H), 3.58 (d, J=10.5 Hz, 1H), 2.44-2.38 (m, 1H), 2.37 (s, 3H), 2.27 (s, 3H), 2.02 (s, 3H), 1.01 (d, J=6.4 Hz, 3H), 0.65 (d, J=6.8 Hz, 3H). $^{13}$C NMR (126 MHz, CDCl$_3$) δ 208.55, 136.24, 135.95, 133.52, 130.48, 127.83, 127.61, 62.29, 30.53, 30.09, 21.86, 21.04, 19.91, 19.51. HRMS-ESI (m/z) [M+H]+ calcd for C$_{14}$H$_{20}$O, 205.1587; found, 205.1578.

Step 4: Preparation of (2R,3S)-3-(2,5-dimethylphenyl)-4-methylpentan-2-ol and (2S,3R)-3-(2,5-dimethylphenyl)-4-methylpentan-2-ol.

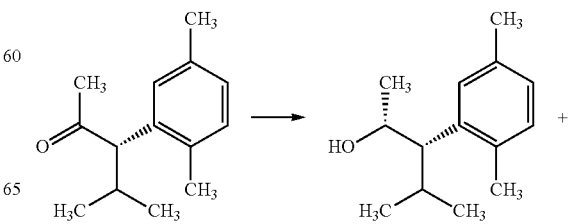

-continued

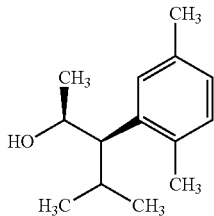

Lithium aluminum hydride (2.80 mL, 2.80 mmol) as a solution (1.0 M in THF) was added to a flask containing THF (28.0 mL) cooled to −78° C. A solution of 3-(2,5-dimethylphenyl)-4-methylpentan-2-one (0.573 g, 2.80 mmol) in THF (3 mL) was added dropwise. The reaction was warmed to room temperature and stirred overnight. The reaction was cooled to 0° C. and quenched by the addition of 0.1 mL H₂O, 0.1 mL 1N NaOH, followed by an additional 0.3 mL of H₂O. The mixture was stirred vigorously for 15 min. The reaction was filtered and the solids were washed with EtOAc. The filtrate was concentrated under reduced pressure to provide a racemic mixture of (2R,3S)-3-(2,5-dimethylphenyl)-4-methylpentan-2-ol and (2S,3R)-3-(2,5-dimethylphenyl)-4-methylpentan-2-ol (491 mg, 72%) as a colorless oil. The syn product is the exclusive product as predicted by Cram's rule. ¹H NMR (500 MHz, CDCl₃) δ 7.12 (s, 1H), 7.05 (d, J=7.7 Hz, 1H), 6.94-6.91 (m, 1H), 4.32-4.20 (m, 1H), 2.55 (dd, J=8.9, 4.7 Hz, 1H), 2.31 (s, 3H), 2.25 (s, 3H), 2.17 (ddt, J=13.3, 8.8, 6.7 Hz, 1H), 1.26 (d, J=6.1 Hz, 1H), 1.05 (d, J=2.3 Hz, 3H), 1.04 (d, J=2.0 Hz, 3H), 0.72 (d, J=6.7 Hz, 3H). ¹³C NMR (126 MHz, CDCl₃) δ 138.84, 135.13, 134.66, 130.18, 128.14, 126.71, 67.91, 62.20, 53.16, 30.01, 21.76, 21.36, 20.75, 20.29. ESIMS (m/z) 207 [M+H]⁺.

Step 5: Preparation of (2R,3S) and (2S,3R)-3-(2,5-dimethylphenyl)-4-methylpentan-2-yl (S)-2-methoxy-2-phenylacetate.

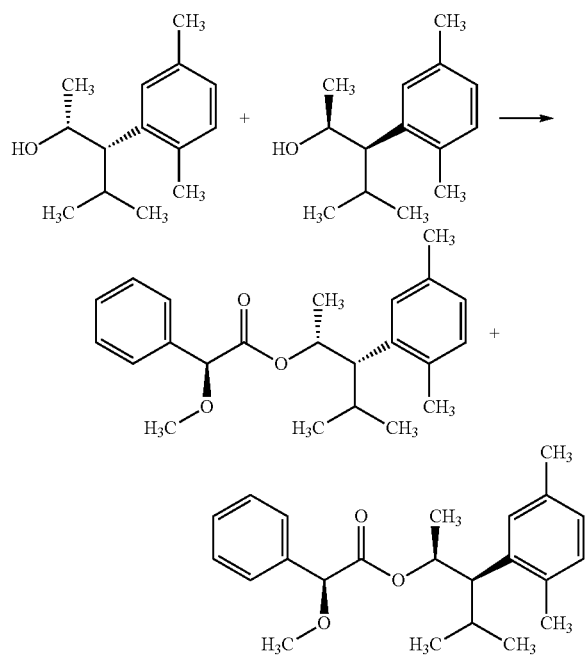

To a racemic mixture containing (2R,3S) and (2S,3R)-3-(2,5-dimethylphenyl)-4-methylpentan-2-ol (0.491 g, 2.380 mmol) dissolved in 16 mL of CH₂Cl₂ was added N,N-dimethylpyridin-4-amine (0.029 g, 0.238 mmol) and (S)-2-methoxy-2-phenylacetic acid (0.514 g, 3.09 mmol). The reaction was cooled to 0° C. followed by addition of 3-(((ethylimino)methylene)amino)-N,N-dimethylpropan-1-amine hydrochloride (0.912 g, 4.76 mmol) was added and the reaction was warmed to room temperature and stirred overnight. The mixture was concentrated under reduced pressure. The residue was purified by automated silica gel chromatography (Isco, 80 g SiO₂ column, 0-10% MTBE in hexanes as the eluent) to provide (2R,3S)-3-(2,5-dimethylphenyl)-4-methylpentan-2-yl (S)-2-methoxy-2-phenylacetate (284.7 mg 32%) and (2S,3R)-3-(2,5-dimethylphenyl)-4-methylpentan-2-yl (S)-2-methoxy-2-phenylacetate as colorless oils. Only the desired (2R,3S) diastereomer was characterized. ¹H NMR (500 MHz, CDCl₃) δ 7.44-7.37 (m, 2H), 7.36-7.27 (m, 3H), 7.18 (s, 1H), 7.00 (d, J=7.7 Hz, 1H), 6.93-6.80 (m, 1H), 5.42-5.34 (m, 1H), 4.74 (s, 1H), 3.40 (s, 3H), 2.62 (dd, J=9.7, 4.3 Hz, 1H), 2.30 (s, 3H), 2.21 (s, 3H), 2.05-1.92 (m, 1H), 0.93 (d, J=6.5 Hz, 3H), 0.87 (d, J=6.3 Hz, 3H), 0.68 (d, J=6.7 Hz, 3H). ¹³C NMR (126 MHz, CDCl₃) δ 170.32, 139.03, 136.46, 134.96, 133.92, 129.67, 128.80, 128.51, 126.90, 126.67, 82.86, 72.23, 57.31, 51.06, 30.54, 21.31, 21.00, 20.93, 20.23, 17.82. HRMS-ESI (m/z) [M+Na]+ calcd for C₂₃H₃₀O₃, 377.2087; found, 377.2089.

Step 6: Preparation of (2R,3S)-3-(2,5-dimethylphenyl)-4-methylpentan-2-ol.

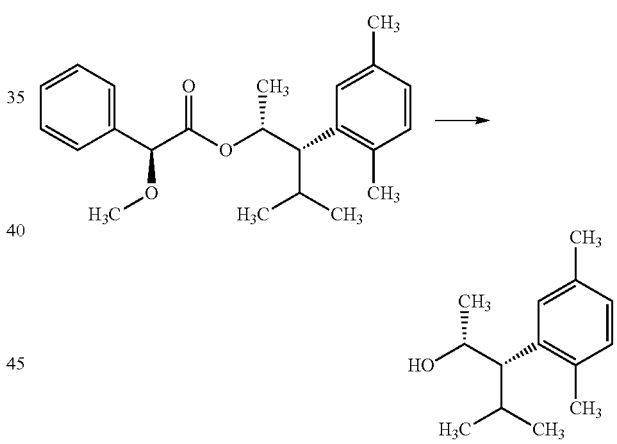

To a solution containing (2R,3S)-3-(2,5-dimethylphenyl)-4-methylpentan-2-yl(S)-2-methoxy-2-phenylacetate (0.28 g, 0.790 mmol) dissolved in MeOH (7.90 mL) was added potassium carbonate (0.327 g, 2.370 mmol). The reaction was heated to 55° C. and stirred overnight. The reaction was cooled to room temperature, diluted with water and extracted with CH₂Cl₂. The combined organic layers were dried over sodium sulfate, filtered and concentrated under reduced pressure. The crude material was purified by automated silica gel chromatography (Isco, 0-20% EtOAc in hexanes as the eluent) to provide (2R,3S)-3-(2,5-dimethylphenyl)-4-methylpentan-2-ol (139 mg, 81%) as a colorless oil. ¹H NMR (500 MHz, CDCl₃) δ 7.12 (s, 1H), 7.05 (d, J=7.7 Hz, 1H), 6.96-6.87 (m, 1H), 4.33-4.19 (m, 1H), 2.55 (dd, J=8.9, 4.7 Hz, 1H), 2.31 (s, 3H), 2.25 (s, 3H), 2.17 (ddt, J=13.4, 8.8, 6.7 Hz, 1H), 1.26 (d, J=6.1 Hz, 1H), 1.05 (d, J=2.1 Hz, 3H), 1.04 (d, J=1.8 Hz, 3H), 0.72 (d, J=6.7 Hz, 3H). IR (thin film) 3429 (b), 2956, 2925, 2868, 1500, 1457, 1382, 1151, 1027, 905, 806, 787 cm$^{-1}$. HRMS-ESI (m/z) [M+NH$_4$]+ calcd for C$_{14}$H$_{22}$O, 224.2009; found, 224.2001.

Example 7: Preparation of (2S,3S)-3-(4-fluoro-2-methylphenyl)-4-methylpentan-2-ol Step 1: Preparation of (2S,3S)-3-(4-fluoro-2-methylphenyl)-4-methylpentan-2-yl4-nitrobenzoate.

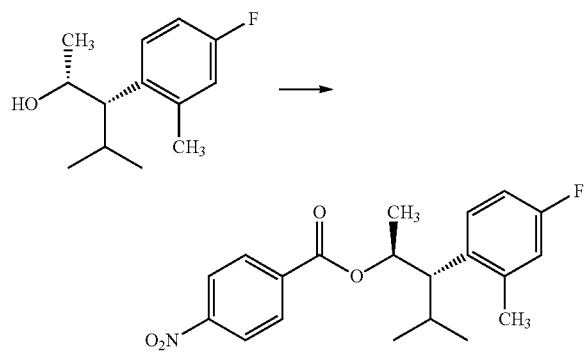

In a 250 mL round bottom flask, a solution of (2R,3S)-3-(4-fluoro-2-methylphenyl)-4-methylpentan-2-ol (0.880 g, 4.18 mmol), triphenylphosphine (4.17 g, 15.90 mmol) and 4-nitrobenzoic acid (2.87 g, 17.16 mmol) was prepared in anhydrous THF (41.8 ml) and cooled to 0° C. in an ice/water bath. After ~5 min, diethyl (E)-diazene-1,2-dicarboxylate (2.97 ml, 18.83 mmol) was added dropwise, and the mixture was allowed to slowly warm to room temperature overnight. After 18 hr, TLC indicated ~75% conversion to a single higher Rf spot. The reaction was then heated to 40° C. and stirred for an additional 12 hr. The mixture was cooled to room temperature and quenched with a saturated aqueous solution of NH$_4$Cl (40 mL) and extracted with CH$_2$Cl$_2$ (3×40 mL). The combined organic layers were passed through a phase separator and concentrated to an oil. The residue was purified via silica gel Isco column chromatography (80 g silica gel column, 60 mL/min, 100% hexanes to 20% acetone:hexanes) to afford (2S,3S)-3-(4-fluoro-2-methylphenyl)-4-methylpentan-2-yl4-nitrobenzoate (1.34 g, 3.73 mmol, 89% yield) as a yellow oil. $^1$H NMR (400 MHz, CDCl$_3$) δ 8.33-8.26 (m, 2H), 8.17-8.11 (m, 2H), 7.14 (dd, J=9.5, 5.9 Hz, 1H), 6.98-6.86 (m, 2H), 5.65 (dq, J=8.2, 6.3 Hz, 1H), 3.18 (t, J=7.8 Hz, 1H), 2.30 (s, 3H), 2.19-2.09 (m, 1H), 1.19 (d, J=6.3 Hz, 3H), 0.98 (d, J=6.7 Hz, 3H), 0.80 (d, J=6.8 Hz, 3H). $^{19}$F NMR (376 MHz, CDCl$_3$) δ-117.11. IR (thin film) 3353, 2961, 1719, 1528, 1277, 1102, 720 cm$^{-1}$. ESIMS (m/z) 359.1 [M+H]$^+$.

Step 2: Preparation of (2S,3S)-3-(4-fluoro-2-methylphenyl)-4-methylpentan-2-ol.

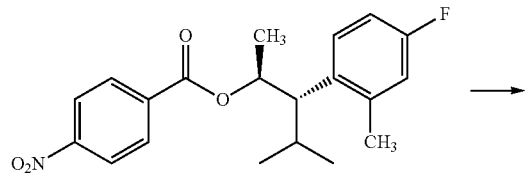

-continued

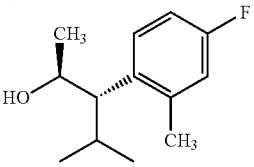

In a 250 mL round-bottom flask, a solution of (2S,3S)-3-(4-fluoro-2-methylphenyl)-4-methylpentan-2-yl 4-nitrobenzoate (1.34 g, 3.73 mmol) was prepared in THF (49.7 mL) and cooled to 0° C. in an ice/water bath. After ~5 min, sodium hydroxide (10% aqueous solution) (44 mL, 3.73 mmol) (39.7 mL water+4.4 mL 50% w/w/NaOH) was added dropwise, and the mixture was allowed to slowly warm to room temperature over 1 hr and then heated to 40° C. and stirred for 2 days. The reaction was cooled to ambient temperature. The reaction was quenched by the addition of a saturated aqueous solution of NH$_4$Cl (100 mL) and extracted with CH$_2$Cl$_2$ (3×100 mL). Additional product remained in aqueous layer as evidenced by TLC, so 100 mL brine was added to aqueous layer, and the aqueous layer was extracted again with CH$_2$Cl$_2$ (2×100 mL), after which no additional product was observed in the aqueous layer. The combined organic layers were then passed through a phase separator and concentrated to afford an oil that was purified via silica gel Isco column chromatography (120 g silica gel column, 85 mL/min, 100% hexanes to 30% acetone: hexanes) to afford (2S,3S)-3-(4-fluoro-2-methylphenyl)-4-methylpentan-2-ol (460 mg, 2.187 mmol, 58.7% yield) (52% over 2 steps) as a clear, colorless oil. $^1$H NMR (400 MHz, CDCl$_3$) δ7.02 (dd, J=8.6, 6.0 Hz, 1H), 6.94-6.81 (m, 2H), 4.25-4.12 (m, 1H), 2.88 (t, J=7.6 Hz, 1H), 2.35 (s, 3H), 2.25-2.12 (m, 1H), 1.21 (d, J=6.0 Hz, 1H), 1.04 (d, J=6.3 Hz, 3H), 0.94 (d, J=6.7 Hz, 3H), 0.80 (d, J=6.7 Hz, 3H). $^{19}$F NMR (376 MHz, CDCl$_3$) δ-117.86. $^{13}$C NMR (101 MHz, CDCl$_3$) d 160.86 (d, J=243.9 Hz), 140.35 (d, J=7.4 Hz), 134.42 (d, J=3.1 Hz), 129.29 (d, J=6.8 Hz), 116.88 (d, J=20.3 Hz), 112.20 (d, J=20.6 Hz), 69.48, 29.72, 21.12, 21.00, 20.99, 20.65, 19.98. IR (thin film) 3382, 2960, 2927, 1716, 1497, 1365, 1225, 736 cm$^{-1}$.

Example 8: (2S,3S)-3-(4-fluorophenyl)-4-methylpentan-2-yl(tert-butoxycarbonyl)-L-alaninate

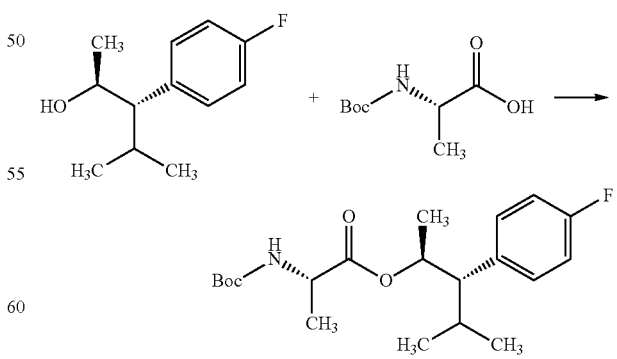

To a stirred solution of (2S,3S)-3-(4-fluorophenyl)-4-methylpentan-2-ol (0.075 g, 0.382 mmol), (tert-butoxycarbonyl)-L-alanine (0.108 g, 0.573 mmol) and DMAP (4.67 mg, 0.038 mmol) dissolved in CH$_2$Cl$_2$ (3.82 mL) at 0° C. in an ice bath was added N¹-((ethylimino)methylene)-N³,N³-dimethylpropane-1,3-diamine hydrochloride (EDC; 0.147 g, 0.764 mmol) and the reaction was monitored until complete by TLC (25% EtOAc in hexanes). The reaction was purified by automated column chromatography (0-10% EtOAc in hexanes) to provide (2S,3S)-3-(4-fluorophenyl)-4-methylpentan-2-yl (tert-butoxycarbonyl)-L-alaninate (137.5 mg, 0.370 mmol, 97% yield) as colorless oil. $^1$H NMR (400 MHz, CDCl$_3$) δ 7.06 (dd, J=8.7, 5.6 Hz, 2H), 7.02-6.92 (m, 2H), 5.36 (dq, J=8.7, 6.3 Hz, 1H), 5.05 (s, 1H), 4.37-4.19 (m, 1H), 2.69 (dd, J=8.7, 6.4 Hz, 1H), 2.08 (h, J=6.7 Hz, 1H), 1.45 (s, 9H), 1.38 (d, J=7.2 Hz, 3H), 1.06 (d, J=6.2 Hz, 3H), 0.86 (d, J=6.8 Hz, 3H), 0.74 (d, J=6.8 Hz, 3H). $^{13}$C NMR (126 MHz, CDCl$_3$) δ 172.79, 161.75 (d, J=244.8 Hz), 155.03, 134.29, 131.03 (d, J=7.6 Hz), 114.82 (d, J=21.0 Hz), 79.79, 72.32, 55.88, 49.50, 28.34, 28.18, 21.30, 18.81, 18.41, 17.74. IR (thin film) 3352, 2964, 2932, 1712, 1605, 1509, 1452, 1366, 1224, 1160, 835 cm$^{-1}$. HRMS-ESI (m/z) [M+Na]+ calcd for C$_{20}$H$_{30}$FNNaO$_4$, 390.2051; found, 390.2044.

Example 9: Preparation of (2S,3S)-3-(4-fluoro-2-methylphenyl)-4-methylpentan-2-yl (tert-butoxycarbonyl)-L-alaninate

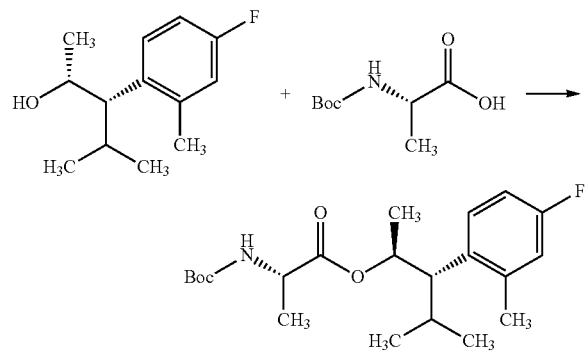

In a small vial, (2R,3S)-3-(4-fluoro-2-methylphenyl)-4-methylpentan-2-ol (115.5 mg, 0.549 mmol), (tert-butoxycarbonyl)-L-alanine (125 mg, 0.659 mmol) and triphenylphosphine (173 mg, 0.659 mmol) were dissolved in THF (2.75 mL) under a N$_2$ atmosphere and cooled to 0° C. in an ice/water bath. After ~5 min, diisopropyl (E)-diazene-1,2-dicarboxylate (130 μL, 0.659 mmol) was added in dropwise via syringe over 3 min, and the resulting pale orange reaction was stirred overnight, slowly warming to room temperature as the ice melted. After 18 hr, the reaction was concentrated under reduced pressure to afford an oil. The oil was loaded directly onto a 12 g prepacked silica column in a minimal amount of dichloromethane and purified using Isco silica gel column chromatography (120 column, 85 mL/min, 100% pet ether to 40% MTBE:pet ether) to afford (2S,3S)-3-(4-fluoro-2-methylphenyl)-4-methylpentan-2-yl (tert-butoxycarbonyl)-L-alaninate (35.0 mg, 0.092 mmol, 17% yield) as a clear, colorless oil. $^1$H NMR (400 MHz, CDCl$_3$) δ 7.05 (dd, J=8.5, 6.0 Hz, 1H), 6.87 (ddt, J=11.6, 8.3, 4.1 Hz, 2H), 5.33 (dq, J=9.1, 6.2 Hz, 1H), 5.05 (d, J=8.1 Hz, 1H), 4.28 (d, J=7.6 Hz, 1H), 3.08 (dd, J=9.2, 6.2 Hz, 1H), 2.32 (s, 3H), 2.18-2.06 (m, 1H), 1.45 (s, 9H), 1.39 (d, J=7.2 Hz, 3H), 1.03 (d, J=6.2 Hz, 3H), 0.85 (d, J=6.8 Hz, 3H), 0.78 (d, J=6.9 Hz, 3H). $^{19}$F NMR (376 MHz, CDCl$_3$) δ-117.34. IR (thin film) 3355, 2965, 1714, 1499, 1366, 1167, 1052, 735 cm$^{-1}$. HRMS-ESI (m/z) [M+Na]+ calcd for C$_{21}$H$_{32}$FNNaO$_4$, 404.2208; found, 404.2201.

Example 10: Preparation of (2S,3S)-3-(4-fluoro-2-methylphenyl)-4-methylpentan-2-yl (3-hydroxy-4-methoxypicolinoyl)-L-alaninate Step 1: Preparation of (2S,3S)-3-(4-fluoro-2-methylphenyl)-4-methylpentan-2-yl-L-alaninate hydrochloride.

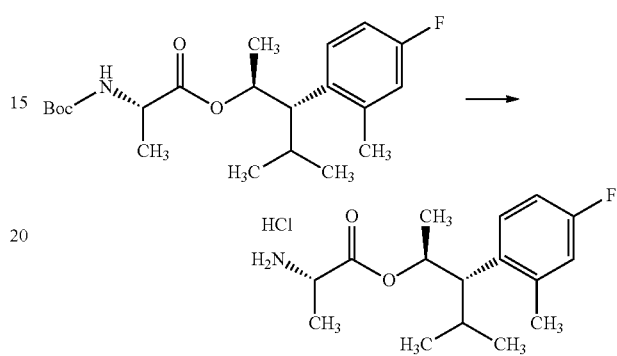

In a small vial, (2S,3S)-3-(4-fluoro-2-methylphenyl)-4-methylpentan-2-yl-(tert-butoxycarbonyl)-L-alaninate (35.0 mg, 0.092 mmol) was dissolved in CH$_2$Cl$_2$ (2 mL). Hydrogen chloride (4M in dioxane) (0.344 mL, 1.376 mmol) was added in one portion via syringe. The resulting clear, colorless reaction was stirred at room temperature for 3 hr. After 3 hr, TLC indicated complete consumption of the starting material and conversion to a baseline product by TLC. The reaction was concentrated under a stream of N$_2$ and dried in a vacuum oven to provide (2S,3S)-3-(4-fluoro-2-methylphenyl)-4-methylpentan-2-yl-L-alaninate (26.1 mg, 0.092 mmol, 100% yield) as a clear, colorless oil. ESIMS (m/z) 282.1 [M+H]$^+$. This material was used directly in the next step without further purification.

Step 2: Preparation of (2S,3S)-3-(4-fluoro-2-methylphenyl)-4-methylpentan-2-yl (3-hydroxy-4-methoxypicolinoyl)-L-alaninate.

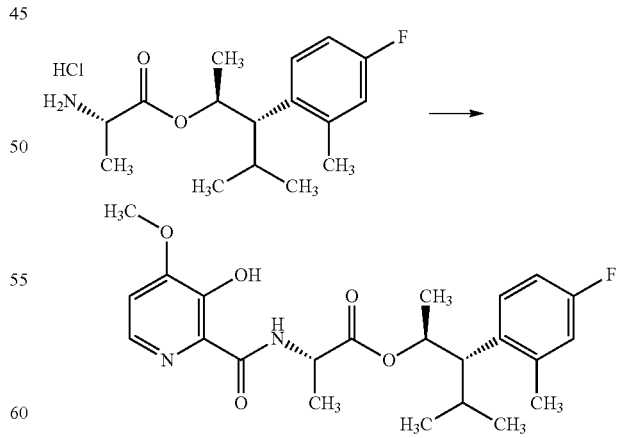

To a vial containing (2S,3S)-3-(4-fluoro-2-methylphenyl)-4-methylpentan-2-yl-L-alaninate (26.1 mg, 0.093 mmol) was added 3-hydroxy-4-methoxypicolinic acid (23.53 mg, 0.139 mmol) and ((1H-benzo[d][1,2,3]triazol-1-yl)oxy)tri(pyrrolidin-1-yl)phosphonium hexafluorophosphate(V) (72.4 mg, 0.139 mmol). Dichloromethane (1.86 mL) was added followed by N-ethyl-N-isopropylpropan-2-amine (121 µL, 0.696 mmol) dropwise over 45 seconds. After 10 min, most of the solids solubilized and the resultant pale pink colored reaction was stirred at room temperature overnight. TLC/UPLC indicated consumption of the starting material and formation of a major spot that glowed blue under UV. The reaction was then concentrated under reduced pressure to yield an orange oil. The oil was loaded directly onto a 12 g prepacked silica column in a minimal amount of dichloromethane and purified using Isco silica gel column chromatography (24 column, 30 mL/min, 100% hexanes to 50% acetone:hexanes) to afford (2S,3S)-3-(4-fluoro-2-methylphenyl)-4-methylpentan-2-yl-(3-hydroxy-4-methoxypicolinoyl)-L- alaninate (24.4 mg, 0.056 mmol, 60.8% yield) as a clear, colorless oil. $^1$H NMR (400 MHz, CDCl$_3$) δ 12.13 (s, 1H), 8.45 (d, J=8.0 Hz, 1H), 7.99 (d, J=5.2 Hz, 1H), 7.05 (dd, J=8.6, 5.9 Hz, 1H), 6.93-6.77 (m, 3H), 5.38 (dq, J=8.9, 6.3 Hz, 1H), 4.76-4.65 (m, 1H), 3.95 (s, 3H), 3.09 (dd, J=8.9, 6.5 Hz, 1H), 2.29 (s, 3H), 2.11 (h, J=6.8 Hz, 1H), 1.55 (d, J=7.2 Hz, 3H), 1.08 (d, J=6.2 Hz, 3H), 0.86 (d, J=6.8 Hz, 3H), 0.78 (d, J=6.7 Hz, 3H). $^{19}$F NMR (376 MHz, CDCl$_3$) δ-117.30. IR (thin film) 3366, 2961, 1734, 1650, 1529, 1264, 1183, 1049, 955, 801, 735 cm$^{-1}$. HRMS-ESI (m/z) [M+H]+ calcd for C$_{23}$H$_{30}$FN$_2$O$_5$, 433.2133; found, 433.2129.

Example 11A: Preparation of (2S,3R)-3-(2,4-dimethylphenyl)-4-methylpentan-2-yl (3-acetoxy-4-methoxypicolinoyl)-L-alaninate

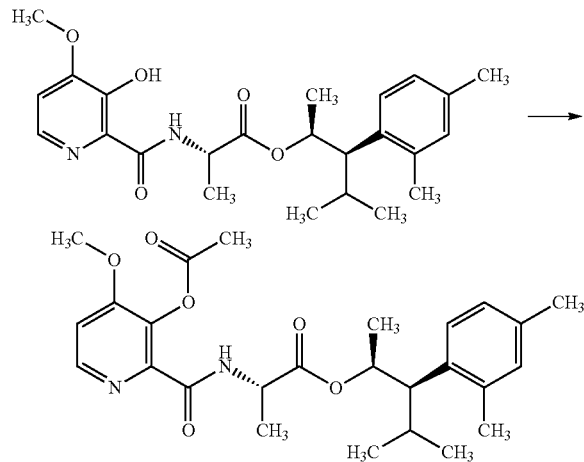

To a 20 mL vial charged with (2S,3R)-3-(2,4-dimethylphenyl)-4-methylpentan-2-yl (3-hydroxy-4-methoxypicolinoyl)-L-alaninate (30 mg, 0.070 mmol) dissolved in pyridine (1 mL, 12.36 mmol) was added acetic anhydride (25 µL, 2.65 mmol) at room temperature. After stirring for 45 min, the mixture was concentrated in vacuo and purified via automated silica gel chromatography (0-40% acetone/hexanes as the eluent) to afford (2S,3R)-3-(2,4-dimethylphenyl)-4-methylpentan-2-yl (3-acetoxy-4-methoxypicolinoyl)-L-alaninate (32 mg, 0.061 mmol, 87% yield) as colorless oil. $^1$H NMR (500 MHz, CDCl$_3$) δ 8.56 (s, 1H), 8.35 (d, J=5.4 Hz, 1H), 7.19 (d, J=7.9 Hz, 1H), 7.00 (d, J=5.4 Hz, 1H), 6.94 (d, J=1.9 Hz, 1H), 6.90 (dd, J=7.9, 1.9 Hz, 1H), 5.41 (qd, J=6.3, 4.7 Hz, 1H), 4.77-4.61 (m, 1H), 3.91 (s, 3H), 2.68 (dd, J=9.3, 4.8 Hz, 1H), 2.39 (s, 3H), 2.27 (s, 3H), 2.25 (s, 3H), 2.03 (dp, J=9.2, 6.6 Hz, 1H), 1.38 (d, J=7.2 Hz, 3H), 1.05 (d, J=6.3 Hz, 3H), 0.99 (d, J=6.6 Hz, 3H), 0.69 (d, J=6.8 Hz, 3H). IR (thin film) 3383, 2969, 1772, 1733, 1679, 1200, 1176 cm$^{-1}$. HRMS-ESI (m/z) [M+H]+ calcd for C$_{26}$H$_{35}$N$_2$O$_6$, 471.2490; found, 471.2485.

Example 11B: Preparation of (2S,3R)-3-(2,4-dimethylphenyl)-4-methylpentan-2-yl (3-(acetoxymethoxy)-4-methoxypicolinoyl)-L-alaninate

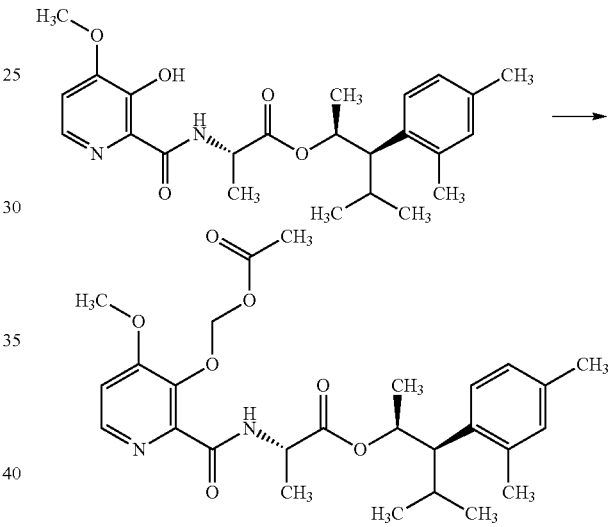

To a 20 mL vial charged with in (2S,3R)-3-(2,4-dimethylphenyl)-4-methylpentan-2-yl (3-hydroxy-4-methoxypicolinoyl)-L-alaninate (30 mg, 0.070 mmol) and potassium carbonate (19.35 mg, 0.140 mmol) dissolved in acetone (1.5 mL) was added bromomethyl acetate (0.014 mL, 0.140 mmol) at room temperature. After stirring for 2 hr at 50° C., the mixture was concentrated in vacuo and purified via automated silica gel chromatography (0-40% acetone/hexanes as the eluent) to afford (2S,3R)-3-(2,4-dimethylphenyl)-4-methylpentan-2-yl(3-(acetoxymethoxy)-4-methoxypicolinoyl)-L-alaninate (21 mg, 0.038 mmol, 54% yield) as colorless oil. $^1$H NMR (500 MHz, CDCl$_3$) δ 8.38 (d, J=7.9 Hz, 1H), 8.29 (d, J=5.4 Hz, 1H), 7.20 (d, J=7.9 Hz, 1H), 7.00-6.87 (m, 3H), 5.80-5.69 (m, 2H), 5.42 (qd, J=6.2, 4.7 Hz, 1H), 4.71 (p, J=7.2 Hz, 1H), 3.91 (s, 3H), 2.69 (dd, J=9.2, 4.9 Hz, 1H), 2.27 (s, 3H), 2.25 (s, 3H), 2.10-1.97 (m, 1H), 2.06 (s, 3H), 1.39 (d, J=7.2 Hz, 3H), 1.07 (d, J=6.3 Hz, 3H), 0.99 (d, J=6.6 Hz, 3H), 0.70 (d, J=6.7 Hz, 3H). IR (thin film) 3380, 2969, 1732, 1675, 1502, 1200, 1003, 967, 829 cm$^{-1}$. HRMS-ESI (m/z) [M+H]+ calcd for C$_{27}$H$_{37}$N$_2$O$_7$, 501.2595; found, 501.2589.

Example 11C: Preparation of (2S,3S)-3-(3-fluoro-4-methoxyphenyl)-4-methylpentan-2-yl (4-methoxy-3-((3-methoxypropanoyl)oxy)picolinoyl)-L-alaninate

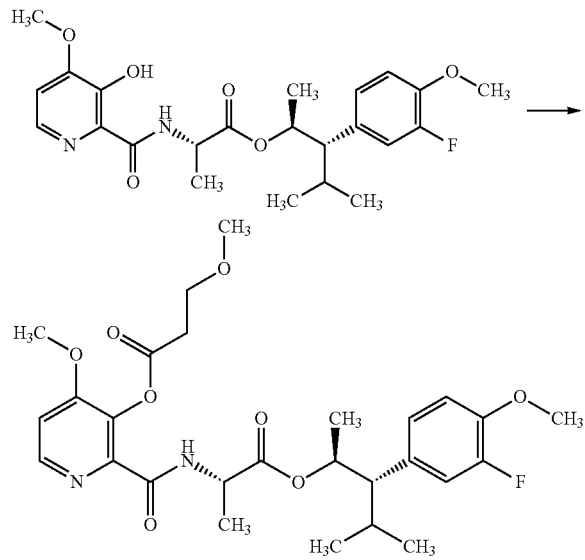

To a stirred solution of (2S,3S)-3-(3-fluoro-4-methoxyphenyl)-4-methylpentan-2-yl (3-hydroxy-4-methoxypicolinoyl)-L-alaninate (59.3 mg, 0.132 mmol) and 4-(dimethylamino)pyridine (3.23 mg, 0.026 mmol) dissolved in $CH_2Cl_2$ (2.0 mL) was added triethylamine (0.037 mL, 0.264 mmol) followed by 3-methoxypropanoyl chloride (0.022 mL, 0.198 mmol). The reaction was allowed to stir at room temperature overnight. The reaction was concentrated under a stream of nitrogen. The residue was loaded directly onto a 12 g prepacked silica column in a minimal amount of dichloromethane and purified using Isco silica gel column chromatography (24 g column, 35 mL/min, 100% hexanes to 50% acetone:hexanes as the eluent) to afford the title compound (58.5 mg, 83% yield) as a pale yellow oil. $^1$H NMR (400 MHz, CDCl$_3$) δ 8.51 (d, J=7.9 Hz, 1H), 8.34 (d, J=5.4 Hz, 1H), 7.01 (d, J=5.5 Hz, 1H), 6.92-6.75 (m, 3H), 5.34 (dq, J=8.3, 6.2 Hz, 1H), 4.66 (dt, J=8.1, 7.1 Hz, 1H), 3.90 (s, 3H), 3.86 (s, 3H), 3.81 (t, J=6.6 Hz, 2H), 3.40 (s, 3H), 2.99 (t, J=6.6 Hz, 2H), 2.64 (dd, J=8.6, 6.5 Hz, 1H), 2.05 (h, J=6.8 Hz, 1H), 1.49 (d, J=7.2 Hz, 3H), 1.09 (d, J=6.3 Hz, 3H), 0.87 (d, J=6.7 Hz, 3H), 0.75 (d, J=6.7 Hz, 3H). $^{13}$C NMR (101 MHz, CDCl$_3$) δ 172.19, 169.42, 162.36, 159.51, 151.94 (d, J=245.0 Hz), 146.73, 146.25 (d, J=10.8 Hz), 141.62, 137.42, 131.84 (d, J=5.6 Hz), 125.47 (d, J=3.6 Hz), 117.15 (d, J=18.2 Hz), 113.05-112.84 (m), 109.77, 72.51, 67.62, 58.76, 56.33, 56.24, 55.74, 48.21, 34.67, 28.35, 21.25, 18.77, 18.63, 17.47. $^{19}$F NMR (376 MHz, CDCl$_3$) δ-135.76. HRMS-ESI (m/z) [M+H]$^+$ calcd for $C_{27}H_{36}FN_2O_8$, 535.2450; found, 535.2444.

Example 12: Preparation of (1R,2S)-1-cyclopentyl-1-phenylpropan-2-yl(3-acetoxy-4-methoxypyridine-2-carbonothioyl)-L-alaninate Step 1: Preparation of (1R,2S)-1-cyclopentyl-1-phenylpropan-2-yl (3-hydroxy-4-methoxypyridine-2-carbonothioyl)-L-alaninate.

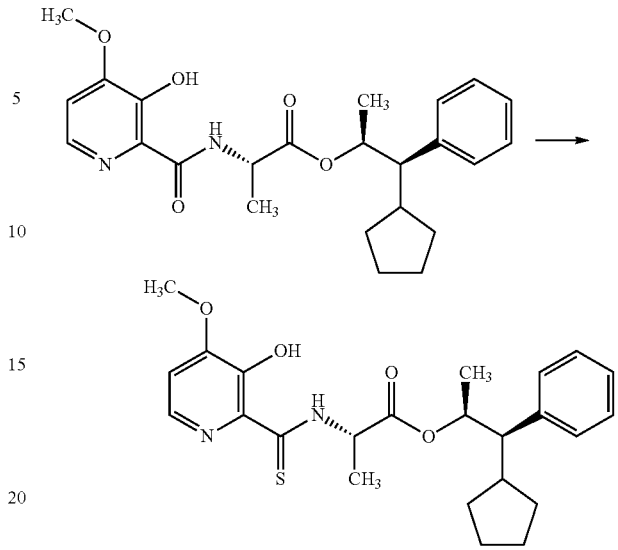

To a 30 mL vial charged with (1R,2S)-1-cyclopentyl-1-phenylpropan-2-yl (3-hydroxy-4-methoxypicolinoyl)-L-alaninate (99 mg, 0.232 mmol) dissolved in acetonitrile (2.32 mL) was added phosphorous pentasulfide (103 mg, 0.464 mmol) and 1,1,1,3,3,3-hexamethyldisiloxane (248 µL, 1.161 mmol). After stirring for 45 min at 45° C., sat. NaHCO$_3$ (15 mL) was added followed by aqueous extraction with dichloromethane (3×15 mL). The organics were dried over MgSO$_4$, filtered, and concentrated in vacuo. The crude residue was purified via flash chromatography (0-45% acetone/hexanes as the eluent) to furnish (1R,2S)-1-cyclopentyl-1-phenylpropan-2-yl (3-hydroxy-4-methoxypyridine-2-carbonothioyl)-L-alaninate (72 mg, 0.155 mmol, 66.6% yield) as a yellow oil. $^1$H NMR (500 MHz, CDCl$_3$) δ 12.94 (s, 1H), 10.71 (s, 1H), 8.01 (d, J=15.0 Hz, 1H), 7.22-7.17 (m, 3H), 7.15 (dd, J=6.7, 3.0 Hz, 2H), 6.89 (d, J=5.0 Hz, 1H), 5.39 (qd, J=6.4, 4.0 Hz, 1H), 5.12-5.03 (m, 1H), 3.97 (s, 3H), 2.41 (dd, J=10.4, 4.0 Hz, 1H), 2.25-2.14 (m, 1H), 1.95-1.84 (m, 1H), 1.69-1.59 (m, 1H), 1.56 (d, J=7.2 Hz, 3H), 1.54-1.45 (m, 2H), 1.44-1.28 (m, 2H), 1.19 (dq, J=12.3, 9.1 Hz, 1H), 1.09 (d, J=6.4 Hz, 3H), 0.92 (ddt, J=12.5, 10.0, 8.5 Hz, 1H). IR (thin film) 2951, 2868, 1733, 1581, 1514, 1480, 1454, 1377, 1342, 1274, 1249, 1211, 1131, 1095, 992, 913, 860, 801, 736, 703 cm$^{-1}$. HRMS-ESI (m/z) [M+Na]+ calcd for $C_{24}H_{30}N_2O_4SNa$, 465.1818; found, 465.1830.

Step2: Preparation of (1R,2S)-1-cyclopentyl-1-phenylpropan-2-yl (3-acetoxy-4-methoxypyridine-2-carbonothioyl)-L-alaninate.

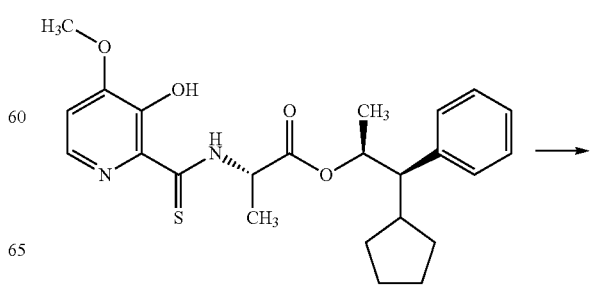

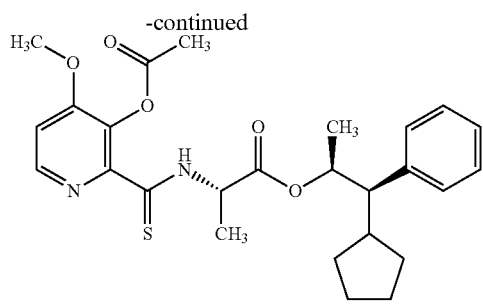

To a solution of (1R,2S)-1-cyclopentyl-1-phenylpropan-2-yl (3-hydroxy-4-methoxypyridine-2-carbonothioyl)-L-alaninate (55 mg, 0.124 mmol) dissolved in pyridine (1 mL, 0.124 mmol) was added acetic anhydride (0.25 mL, 0.124 mmol). After stirring for 1 hr at room temperature, the mixture was concentrated in vacuo and purified via automated column chromatography (0-50% acetone/hexanes as the eluent) to furnish (1R,2S)-1-cyclopentyl-1-phenylpropan-2-yl (3-acetoxy-4-methoxypyridine-2-carbonothioyl)-L-alaninate (34 mg, 0.060 mmol, 48.0% yield) as a brown oil. $^1$H NMR (500 MHz, CDCl$_3$) δ 9.98 (d, J=7.3 Hz, 1H), 8.35 (d, J=5.4 Hz, 1H), 7.25-7.13 (m, 5H), 7.01 (d, J=5.5 Hz, 1H), 5.39 (qd, J=6.3, 4.1 Hz, 1H), 5.16 (p, J=7.2 Hz, 1H), 3.91 (s, 3H), 2.42 (dd, J=10.3, 4.0 Hz, 1H), 2.35 (s, 3H), 2.28-2.19 (m, 1H), 1.93-1.83 (m, 1H), 1.68-1.59 (m, 1H), 1.52 (d, J=7.2 Hz, 3H), 1.50-1.31 (m, 4H), 1.20 (dq, J=12.5, 9.1 Hz, 1H), 1.08 (d, J=6.4 Hz, 3H), 0.97-0.90 (m, 1H). IR (thin film) 2950, 2868, 1770, 1731, 1585, 1496, 1438, 1365, 1311, 1278, 1193, 1175, 1131, 1102, 1040, 1010, 909, 847, 824, 759, 703 cm$^{-1}$. HRMS-ESI (m/z) [M+Na]+ calcd for C$_{26}$H$_{32}$N$_2$O$_5$SNa, 507.1924; found, 507.1920.

Example 13: Preparation of 2-(((S)-1-(((2S,3R)-3-(2,4-dimethylphenyl)-4-methylpentan-2-yl)oxy)-1-oxopropan-2-yl)carbamoyl)-3-hydroxy-4-ethoxy-pyridine 1-oxide

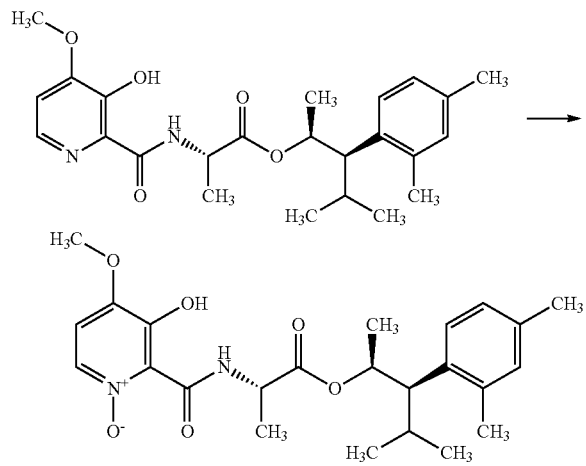

To a 25 mL vial charged with (2S,3R)-3-(2,4-dimethylphenyl)-4-methylpentan-2-yl (3-hydroxy-4-methoxypicolinoyl)-L-alaninate (38 mg, 0.089 mmol) dissolved in CH$_2$Cl$_2$ (1182 μL) was added 3-chlorobenzoperoxoic acid (mCPBA, 43.7 mg, 0.177 mmol) at room temperature. After stirring overnight, the reaction mixture was concentrated in vacuo and purified via automated silica gel chromatography (0-50% acetone/hexanes as the eluent) to afford 2-(((S)-1-(((2S,3R)-3-(2,4-dimethylphenyl)-4-methylpentan-2-yl)oxy)-1-oxopropan-2-yl)carbamoyl)-3-hydroxy-4-methoxy-pyridine 1-oxide (27 mg, 0.055 mmol, 61.6% yield) as colorless oil. $^1$H NMR (500 MHz, CDCl$_3$) δ 14.37 (s, 1H), 12.78 (d, J=7.0 Hz, 1H), 7.88 (d, J=7.1 Hz, 1H), 7.15 (d, J=7.7 Hz, 1H), 6.90 (d, J=8.0 Hz, 2H), 6.77 (d, J=7.2 Hz, 1H), 5.42 (qd, J=6.3, 5.0 Hz, 1H), 4.69-4.61 (m, 1H), 3.96 (s, 3H), 2.69 (dd, J=9.1, 5.0 Hz, 1H), 2.25 (s, 3H), 2.23 (s, 3H), 2.00 (dp, J=8.8, 6.6 Hz, 1H), 1.44 (d, J=7.2 Hz, 3H), 1.08 (d, J=6.3 Hz, 3H), 0.98 (d, J=6.6 Hz, 3H), 0.69 (d, J=6.8 Hz, 3H). IR (thin film) 2964, 1734, 1644, 1571, 1480, 1302, 1216 cm$^{-1}$. HRMS-ESI (m/z) [M+H]+ calcd for C$_{24}$H$_{33}$N$_2$O$_6$, 445.2333; found, 445.2370.

Example 14: Preparation of (2S,3R)-3-(2,4-dimethylphenyl)-4-methylpentan-2-yl (S)-2-(8-methoxy-2,4-dioxo-2H-pyrido[2,3-e][1,3]oxazin-3(4H)-yl)propanoate

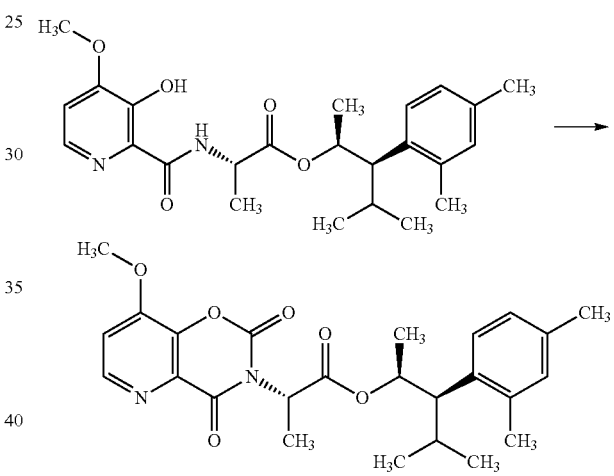

To a 20 mL vial charged with (2S,3R)-3-(2,4-dimethylphenyl)-4-methylpentan-2-yl (3-hydroxy-4-methoxypicolinoyl)-L-alaninate (30 mg, 0.070 mmol) and triphosgene (41.5 mg, 0.140 mmol) dissolved in CH$_2$Cl$_2$ (0.75 mL) was added pyridine (0.1 mL, 1.236 mmol) at room temperature. After stirring for 45 min at room temperature, the crude LCMS revealed a complete conversion to the desired mass. The reaction mixture was quenched by the addition of a saturated NaHCO$_3$ solution and was extracted with EtOAc (3×10 mL). The combined organic layers were washed with brine (10 mL). The organic solution was dried over Na$_2$SO$_4$, filtered and concentrated in vacuo. The residue was purified via automated silica gel chromatography (0-40% acetone/hexanes as the eluent) to afford (2S,3R)-3-(2,4-dimethylphenyl)-4-methylpentan-2-yl(S)-2-(8-methoxy-2,4-dioxo-2H-pyrido[2,3-e][1,3]oxazin-3(4H)-yl)propanoate (28 mg, 0.059 mmol, 84% yield) as orange oil. $^1$H NMR (500 MHz, CDCl$_3$) δ 8.62 (d, J=5.3 Hz, 1H), 7.15 (d, J=5.4 Hz, 1H), 6.90 (d, J=7.9 Hz, 1H), 6.87-6.83 (m, 1H), 6.32-6.24 (m, 1H), 5.65 (q, J=7.1 Hz, 1H), 5.43 (qd, J=6.4, 3.2 Hz, 1H), 4.05 (s, 3H), 2.53 (dd, J=10.4, 3.2 Hz, 1H), 2.18 (s, 3H), 2.10 (s, 3H), 2.06-1.96 (m, 1H), 1.71 (d, J=7.0 Hz, 3H), 1.04 (d, J=6.5 Hz, 3H), 0.95 (d, J=6.3 Hz, 3H), 0.60 (d, J=6.6 Hz, 3H). IR (thin film) 2958, 1770, 1715, 1371, 1244, 734 cm$^{-1}$. HRMS-ESI (m/z) [M+H]+ calcd for $C_{25}H_{31}N_2O_6$, 455.2177; found, 455.2171.

Example A: Evaluation of Fungicidal Activity: Leaf Blotch of Wheat (*Zymoseptoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia triticina*; Synonym: *Puccinia recondita* f. sp. *tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two week old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example D: Evaluation of Fungicidal Activity: Tomato Early Blight (*Alternaria solani*; Bayer Code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example E: Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example F: Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

Example G: Evaluation of Fungicidal Activity: Wheat Glume Blotch (*Parastagonospora nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Parastagonospora nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example H: Evaluation of Fungicidal Activity: Cucumber Downy Mildew (*Pseudoperonospora cubensis*; Bayer Code PSPECU)

Cucumber seedlings (variety Bush Pickle) were grown in soil-less Metro mix, with one plant per pot, and used in the test when 12 to 14 days old. Plants were inoculated with a spore suspension 24 hr following fungicide treatments. Test plants were inoculated with an aqueous spore suspension of *Pseudoperonospora cubensis* 24 hr after fungicide treatments. After inoculation the plants were kept in a dew room at 22° C. with 100% relative humidity for 24 hr to permit spores to germinate and infect the leaf. The plants were then transferred to a greenhouse set at 20° C. until disease was fully expressed. Fungicide formulation, application and disease assessment on the sprayed leaves followed the procedures as described in the Example A.

Example I: Evaluation of Fungicidal Activity: Rice Blast (*Magnaporthe grisea*; Anamorph: *Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation, the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example J: Evaluation of Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example K: Evaluation of Fungicidal Activity: Grape Powdery Mildew (*Uncinula necator*; Bayer Code UNCINE)

Grape seedlings (variety Carignane) were grown in soil-less Metro mix, with one plant per pot, and used in the test when approximately 1 month old. Plants were inoculated 24 hr after fungicide treatment by shaking spores from infected leaves over test plants. Plants were maintained in a greenhouse set at 20° C. until disease was fully developed. Fungicide formulation, application and disease assessment on sprayed leaves followed the procedures as described in the Example A.

TABLE 1

| Compound Structure, Appearance, and Preparation Method | | | |
|---|---|---|---|
| Cmpd. No. | Structure | As Prepared According To | Appearance |
| 1 | [structure] | Example 2A Example 3B Example 8 | Colorless Oil |
| 2 | [structure] | Example 2A Example 3B Example 8 | Colorless Oil |
| 3 | [structure] | Example 2A Example 3B Example 9 | Colorless Oil |

TABLE 1-continued

Compound Structure, Appearance, and Preparation Method

| Cmpd. No. | Structure | As Prepared According To | Appearance |
|---|---|---|---|
| 4 | 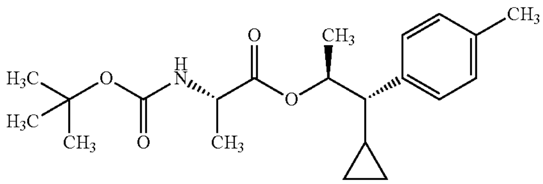 [SMILES: Cc1ccc([C@H](C2CC2)[C@H](C)OC(=O)[C@H](C)NC(=O)OC(C)(C)C)cc1] | Example 1A<br>Example 2B<br>Example 3B<br>Example 8 | Colorless Oil |
| 5 | 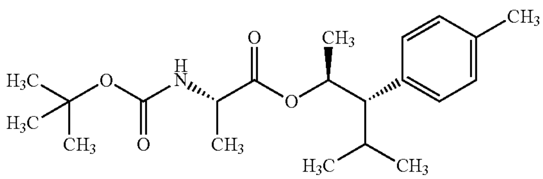 [SMILES: Cc1ccc([C@H](C(C)C)[C@H](C)OC(=O)[C@H](C)NC(=O)OC(C)(C)C)cc1] | Example 1A<br>Example 2B<br>Example 3B<br>Example 8 | Pale Yellow Oil |
| 6 | 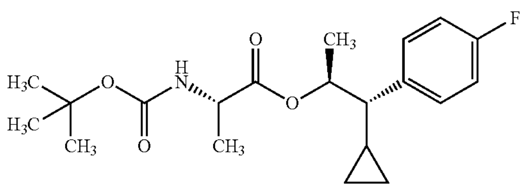 [SMILES: C[C@H](NC(=O)OC(C)(C)C)C(=O)O[C@@H](C)[C@H](c1ccc(F)cc1)C1CC1] | Example 1B<br>Example 2B<br>Example 3B<br>Example 8 | Colorless Oil |
| 7 | 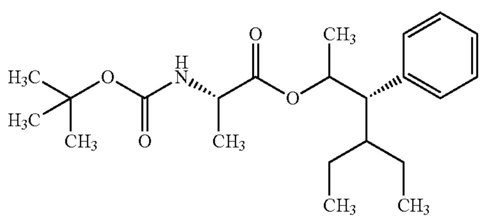 [SMILES: CCC(CC)[C@@H](c1ccccc1)C(C)OC(=O)[C@H](C)NC(=O)OC(C)(C)C] | Example 2A<br>Example 5<br>Example 8 | Colorless Oil |
| 8 | 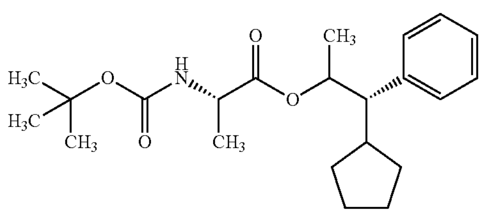 [SMILES: CC(OC(=O)[C@H](C)NC(=O)OC(C)(C)C)[C@H](c1ccccc1)C1CCCC1] | Example 2A<br>Example 5<br>Example 8 | Colorless Oil |
| 9 | 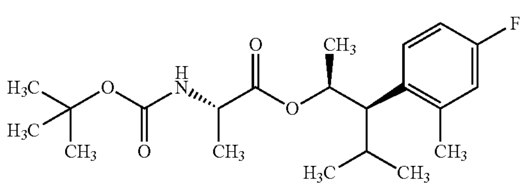 [SMILES: Cc1cc(F)ccc1[C@@H](C(C)C)[C@H](C)OC(=O)[C@H](C)NC(=O)OC(C)(C)C] | Example 1C; Step 1<br>Example 2B<br>Example 3B<br>Example 8 | Clear, Colorless Oil |
| 10 | 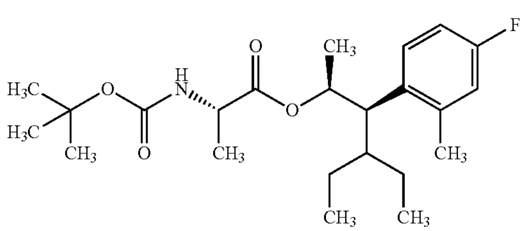 [SMILES: CCC(CC)[C@H](c1ccc(F)cc1C)[C@H](C)OC(=O)[C@H](C)NC(=O)OC(C)(C)C] | Example 1C; Step 1<br>Example 2B<br>Example 3B<br>Example 8 | Clear, Colorless Oil |

TABLE 1-continued

Compound Structure, Appearance, and Preparation Method

| Cmpd. No. | Structure | As Prepared According To | Appearance |
|---|---|---|---|
| 11 | 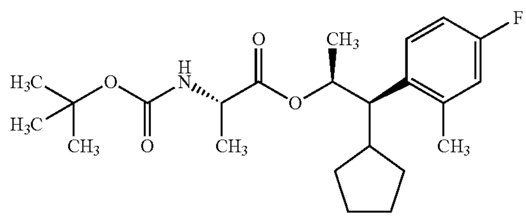 [SMILES: Cc1cc(F)ccc1[C@@H](C1CCCC1)[C@H](C)OC(=O)[C@H](C)NC(=O)OC(C)(C)C] | Example 1C; Step 1<br>Example 2B<br>Example 3B<br>Example 8 | Clear, Colorless Oil |
| 12 | 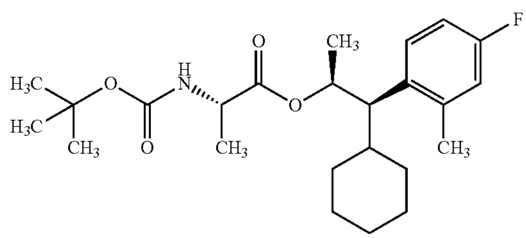 [SMILES: Cc1cc(F)ccc1[C@@H](C1CCCCC1)[C@H](C)OC(=O)[C@H](C)NC(=O)OC(C)(C)C] | Example 1C; Step 1<br>Example 2B<br>Example 3B<br>Example 8 | Clear, Colorless Oil |
| 13 | 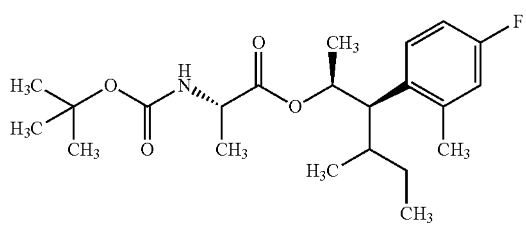 [SMILES: CCC(C)[C@H](c1ccc(F)cc1C)[C@H](C)OC(=O)[C@H](C)NC(=O)OC(C)(C)C] | Example 1C; Step 1<br>Example 2B<br>Example 3B<br>Example 8 | Clear, Colorless Oil |
| 14 | 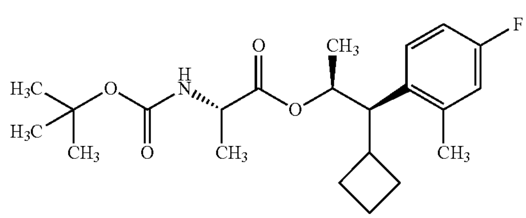 [SMILES: Cc1cc(F)ccc1[C@@H](C1CCC1)[C@H](C)OC(=O)[C@H](C)NC(=O)OC(C)(C)C] | Example 1C; Step 1<br>Example 2B<br>Example 3A<br>Example 8 | Clear, Colorless Oil |
| 15 | 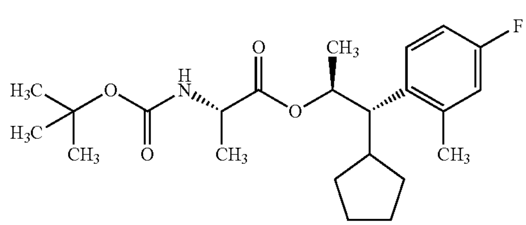 [SMILES: Cc1cc(F)ccc1[C@H](C1CCCC1)[C@H](C)OC(=O)[C@H](C)NC(=O)OC(C)(C)C] | Example 1C; Step 1<br>Example 2B<br>Example 3B<br>Example 9 | Clear, Colorless Oil |
| 16 | 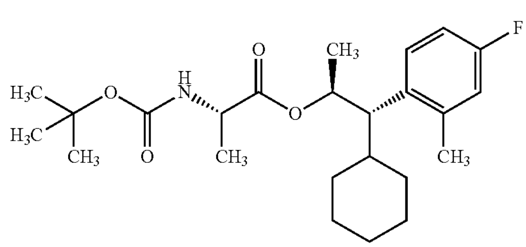 [SMILES: Cc1cc(F)ccc1[C@H](C1CCCCC1)[C@H](C)OC(=O)[C@H](C)NC(=O)OC(C)(C)C] | Example 1C; Step 1<br>Example 2B<br>Example 3B<br>Example 9 | Clear, Colorless Oil |
| 17 | 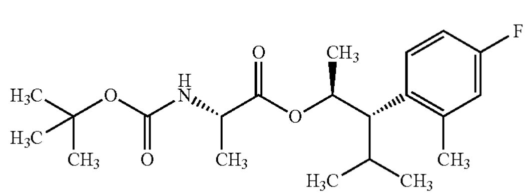 [SMILES: Cc1cc(F)ccc1[C@H](C(C)C)[C@H](C)OC(=O)[C@H](C)NC(=O)OC(C)(C)C] | Example 1C; Step 1<br>Example 2B<br>Example 4A<br>Example 4C<br>Example 9 | Clear, Colorless Oil |

TABLE 1-continued

Compound Structure, Appearance, and Preparation Method

| Cmpd. No. | Structure | As Prepared According To | Appearance |
|---|---|---|---|
| 18 | 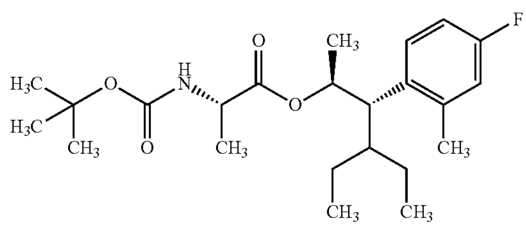 [SMILES: CCC(CC)[C@@H](c1ccc(F)cc1C)[C@H](C)OC(=O)[C@H](C)NC(=O)OC(C)(C)C] | Example 1C; Step 1<br>Example 2B<br>Example 3B<br>Example 9 | Clear, Colorless Oil |
| 19 | 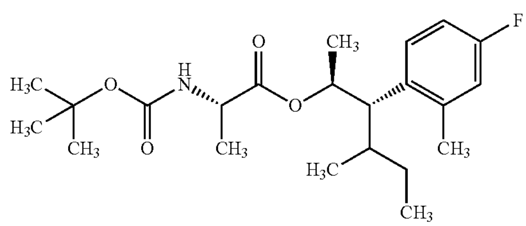 [SMILES: CCC(C)[C@@H](c1ccc(F)cc1C)[C@H](C)OC(=O)[C@H](C)NC(=O)OC(C)(C)C] | Example 1C; Step 1<br>Example 2B<br>Example 3B<br>Example 9 | Clear, Colorless Oil |
| 20 | 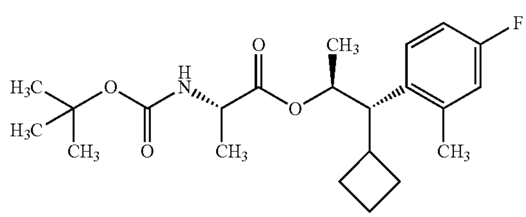 [SMILES: Cc1cc(F)ccc1[C@H](C1CCC1)[C@H](C)OC(=O)[C@H](C)NC(=O)OC(C)(C)C] | Example 1C; Step 1<br>Example 2B<br>Example 3A<br>Example 9 | Clear, Colorless Oil |
| 21 | 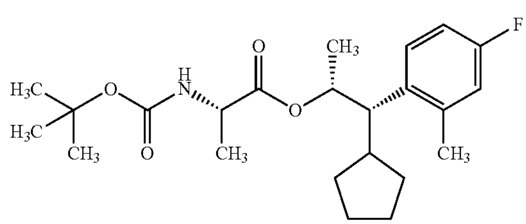 [SMILES: Cc1cc(F)ccc1[C@H](C1CCCC1)[C@@H](C)OC(=O)[C@H](C)NC(=O)OC(C)(C)C] | Example 1C; Step 1<br>Example 2B<br>Example 3B<br>Example 8 | Clear, Colorless Oil |
| 22 | 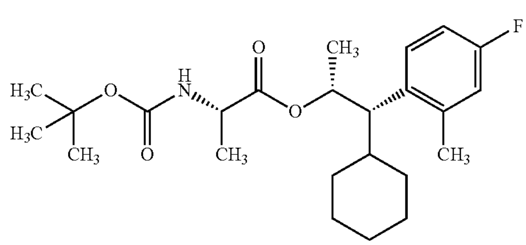 [SMILES: Cc1cc(F)ccc1[C@H](C1CCCCC1)[C@@H](C)OC(=O)[C@H](C)NC(=O)OC(C)(C)C] | Example 1C; Step 1<br>Example 2B<br>Example 3B<br>Example 8 | Clear, Colorless Oil |
| 23 | 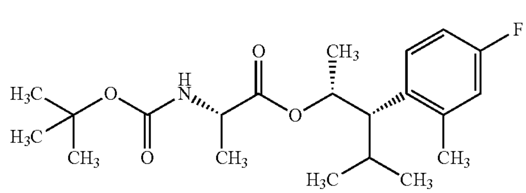 [SMILES: Cc1cc(F)ccc1[C@H](C(C)C)[C@@H](C)OC(=O)[C@H](C)NC(=O)OC(C)(C)C] | Example 1C; Step 1<br>Example 2B<br>Example 4A<br>Example 4B<br>Example 8 | Clear, Colorless Oil |
| 24 | 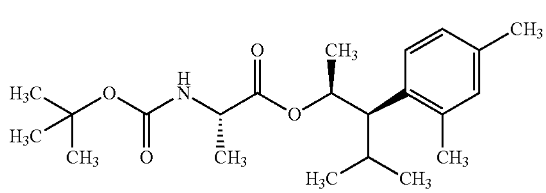 [SMILES: Cc1ccc([C@@H](C(C)C)[C@H](C)OC(=O)[C@H](C)NC(=O)OC(C)(C)C)c(C)c1] | Example 1D<br>Example 2B<br>Example 3B<br>Example 8 | Yellow Oil |

TABLE 1-continued

Compound Structure, Appearance, and Preparation Method

| Cmpd. No. | Structure | As Prepared According To | Appearance |
|---|---|---|---|
| 25 | 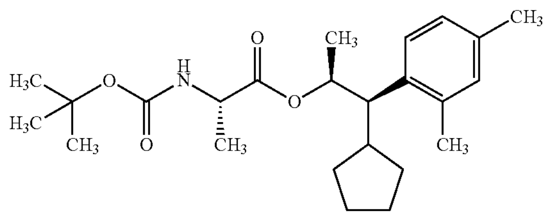 [SMILES: Cc1ccc([C@@H](C2CCCC2)[C@H](C)OC(=O)[C@H](C)NC(=O)OC(C)(C)C)c(C)c1] | Example 1D Example 2B Example 3B Example 8 | Colorless Oil |
| 26 | 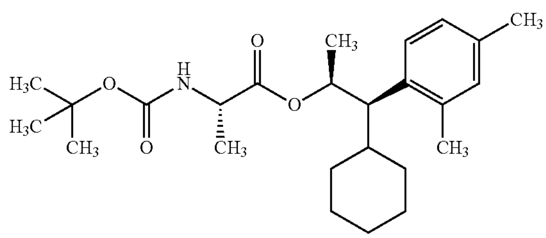 [SMILES: Cc1ccc([C@@H](C2CCCCC2)[C@H](C)OC(=O)[C@H](C)NC(=O)OC(C)(C)C)c(C)c1] | Example 1D Example 2B Example 3B Example 8 | Colorless Oil |
| 27 | 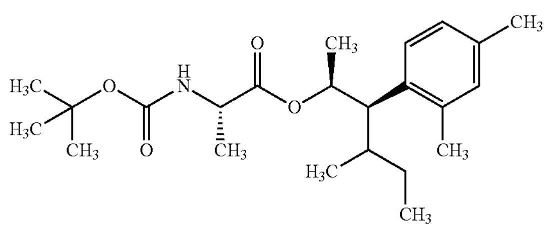 [SMILES: CCC(C)[C@H](c1ccc(C)cc1C)[C@H](C)OC(=O)[C@H](C)NC(=O)OC(C)(C)C] | Example 1D Example 2B Example 3B Example 8 | Colorless Oil |
| 28 | 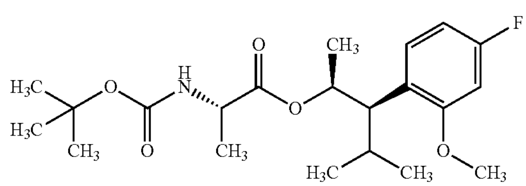 [SMILES: COc1cc(F)ccc1[C@@H](C(C)C)[C@H](C)OC(=O)[C@H](C)NC(=O)OC(C)(C)C] | Example 1C Example 2B Example 3B Example 8 | Clear, Colorless Oil |
| 29 | 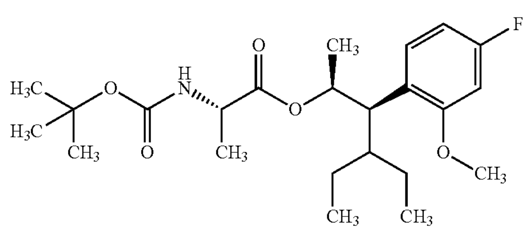 [SMILES: CCC(CC)[C@H](c1ccc(F)cc1OC)[C@H](C)OC(=O)[C@H](C)NC(=O)OC(C)(C)C] | Example 1C Example 2B Example 3B Example 8 | Clear, Colorless Oil |
| 30 | 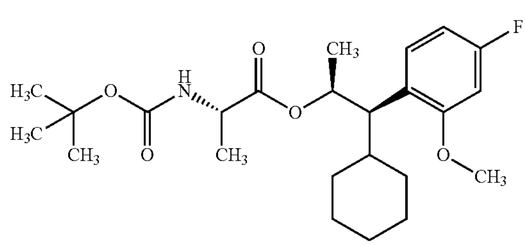 [SMILES: COc1cc(F)ccc1[C@@H](C1CCCCC1)[C@H](C)OC(=O)[C@H](C)NC(=O)OC(C)(C)C] | Example 1C Example 2B Example 3B Example 8 | Clear, Colorless Oil |

TABLE 1-continued

Compound Structure, Appearance, and Preparation Method

| Cmpd. No. | Structure | As Prepared According To | Appearance |
|---|---|---|---|
| 31 | 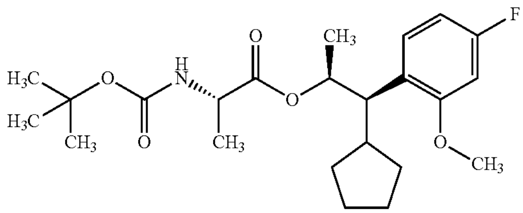 [SMILES: COc1cc(F)ccc1[C@@H](C1CCCC1)[C@H](C)OC(=O)[C@H](C)NC(=O)OC(C)(C)C] | Example 1C<br>Example 2B<br>Example 3B<br>Example 8 | Clear, Colorless Oil |
| 32 | 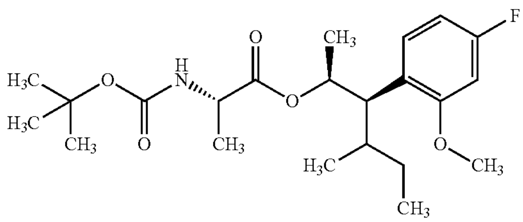 [SMILES: CCC(C)[C@H](c1ccc(F)cc1OC)[C@H](C)OC(=O)[C@H](C)NC(=O)OC(C)(C)C] | Example 1C<br>Example 2B<br>Example 3B<br>Example 8 | Clear, Colorless Oil |
| 33 | 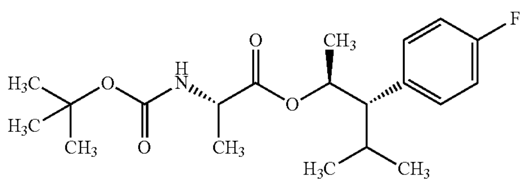 [SMILES: CC(C)[C@@H](c1ccc(F)cc1)[C@H](C)OC(=O)[C@H](C)NC(=O)OC(C)(C)C] | Example 6 Steps 1, 2, 3, 4, 5<br>Example 8 | Colorless Oil |
| 34 | 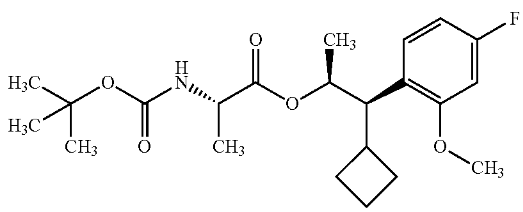 [SMILES: COc1cc(F)ccc1[C@@H](C1CCC1)[C@H](C)OC(=O)[C@H](C)NC(=O)OC(C)(C)C] | Example 1C<br>Example 2B<br>Example 3A<br>Example 8 | Clear, Colorless Oil |
| 35 | 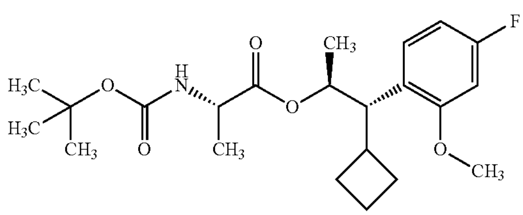 [SMILES: COc1cc(F)ccc1[C@H](C1CCC1)[C@H](C)OC(=O)[C@H](C)NC(=O)OC(C)(C)C] | Example 1C<br>Example 2B<br>Example 3B<br>Example 7<br>Example 8 | Clear, Colorless Oil |
| 36 | 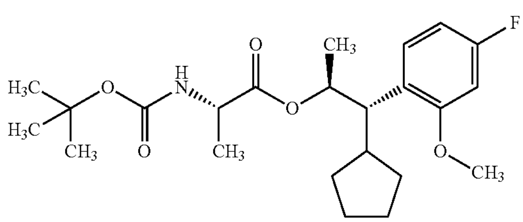 [SMILES: COc1cc(F)ccc1[C@H](C1CCCC1)[C@H](C)OC(=O)[C@H](C)NC(=O)OC(C)(C)C] | Example 1C<br>Example 2B<br>Example 3B<br>Example 7<br>Example 8 | Clear, Colorless Oil |
| 37 | 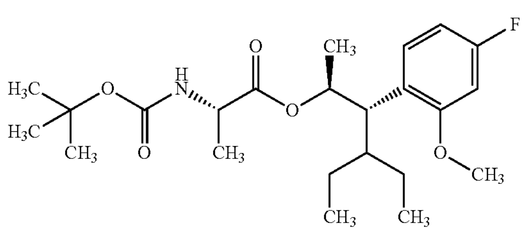 [SMILES: CCC(CC)[C@@H](c1ccc(F)cc1OC)[C@H](C)OC(=O)[C@H](C)NC(=O)OC(C)(C)C] | Example 1C<br>Example 2B<br>Example 3B<br>Example 7<br>Example 8 | Clear, Colorless Oil |

TABLE 1-continued

Compound Structure, Appearance, and Preparation Method

| Cmpd. No. | Structure | As Prepared According To | Appearance |
|---|---|---|---|
| 38 | 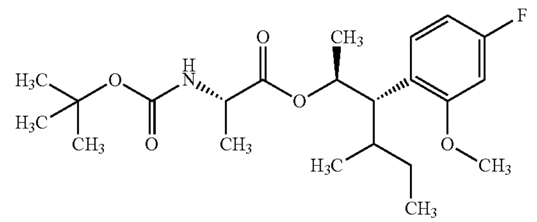 [SMILES: CCC(C)[C@@H](c1ccc(F)cc1OC)[C@H](C)OC(=O)[C@H](C)NC(=O)OC(C)(C)C] | Example 1C<br>Example 2B<br>Example 3B<br>Example 7<br>Example 8 | Clear, Colorless Oil |
| 39 | 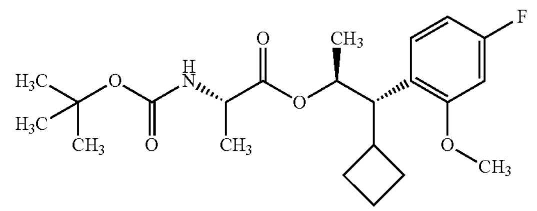 [SMILES: COc1cc(F)ccc1[C@H](C1CCC1)[C@H](C)OC(=O)[C@H](C)NC(=O)OC(C)(C)C] | Example 1C<br>Example 2B<br>Example 3A<br>Example 7<br>Example 8 | Clear, Colorless Oil |
| 40 | 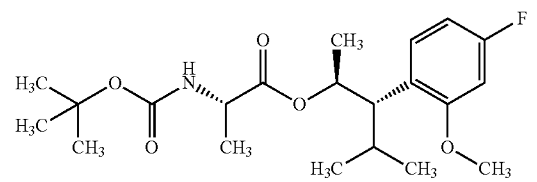 [SMILES: COc1cc(F)ccc1[C@H](C(C)C)[C@H](C)OC(=O)[C@H](C)NC(=O)OC(C)(C)C] | Example 1C<br>Example 2B<br>Example 4A<br>Example 4C<br>Example 7<br>Example 8 | Clear, Colorless Oil |
| 41 | 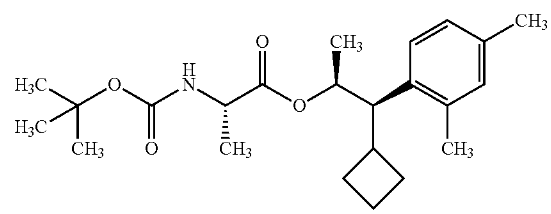 [SMILES: Cc1ccc([C@@H](C2CCC2)[C@H](C)OC(=O)[C@H](C)NC(=O)OC(C)(C)C)c(C)c1] | Example 1D<br>Example 2B<br>Example 3A<br>Example 8 | Colorless Oil |
| 42 | 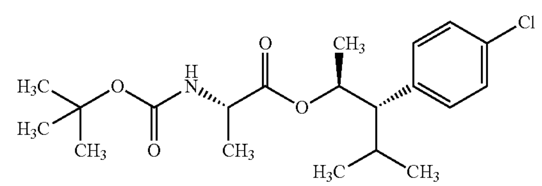 [SMILES: CC(C)[C@@H](c1ccc(Cl)cc1)[C@H](C)OC(=O)[C@H](C)NC(=O)OC(C)(C)C] | Example 6<br>Steps 1, 2, 3, 4, 5<br>Example 8 | Colorless Oil |
| 43 | 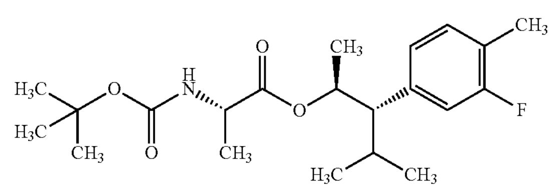 [SMILES: Cc1ccc([C@H](C(C)C)[C@H](C)OC(=O)[C@H](C)NC(=O)OC(C)(C)C)cc1F] | Example 6<br>Steps 1, 2, 3, 4, 5<br>Example 8 | Colorless Oil |
| 44 | 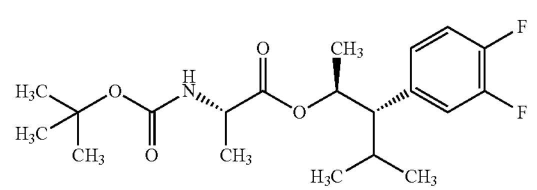 [SMILES: CC(C)[C@@H](c1ccc(F)c(F)c1)[C@H](C)OC(=O)[C@H](C)NC(=O)OC(C)(C)C] | Example 6<br>Steps 1, 2, 3, 4, 5<br>Example 8 | Colorless Oil |

TABLE 1-continued

Compound Structure, Appearance, and Preparation Method

| Cmpd. No. | Structure | As Prepared According To | Appearance |
|---|---|---|---|
| 45 | 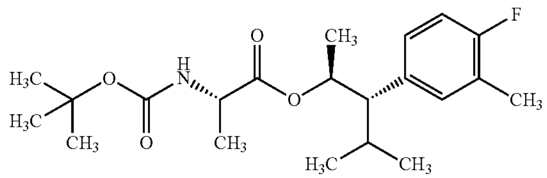 [SMILES: Cc1cc([C@H](C(C)C)[C@H](C)OC(=O)[C@H](C)NC(=O)OC(C)(C)C)ccc1F] | Example 6 Steps 1, 2, 3, 4, 5 Example 8 | Pale Yellow Oil |
| 46 | 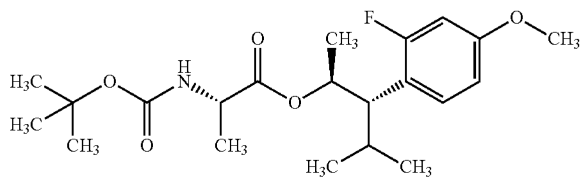 [SMILES: COc1ccc([C@H](C(C)C)[C@H](C)OC(=O)[C@H](C)NC(=O)OC(C)(C)C)c(F)c1] | Example 6 Steps 1, 2, 3, 4, 5 Example 8 | Clear, Colorless Oil |
| 47 | 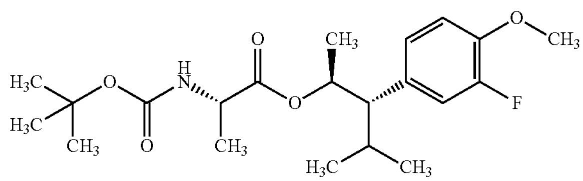 [SMILES: COc1ccc([C@H](C(C)C)[C@H](C)OC(=O)[C@H](C)NC(=O)OC(C)(C)C)cc1F] | Example 6 Steps 1, 2, 3, 4, 5 Example 8 | Clear, Colorless Oil |
| 48 | 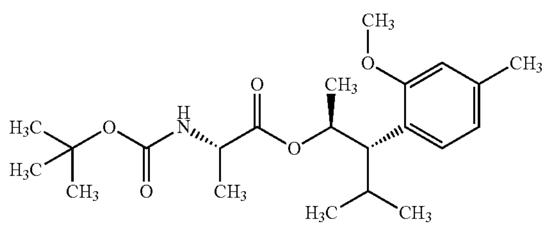 [SMILES: COc1cc(C)ccc1[C@H](C(C)C)[C@H](C)OC(=O)[C@H](C)NC(=O)OC(C)(C)C] | Example 6 Steps 1, 2, 3, 4, 5 Example 8 | Pale Yellow Oil |
| 49 | 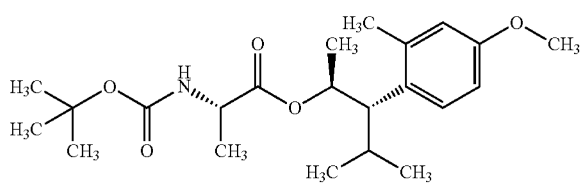 [SMILES: COc1ccc([C@H](C(C)C)[C@H](C)OC(=O)[C@H](C)NC(=O)OC(C)(C)C)c(C)c1] | Example 6 Steps 1, 2, 3, 4, 5 Example 8 | Clear, Colorless Oil |
| 50 | 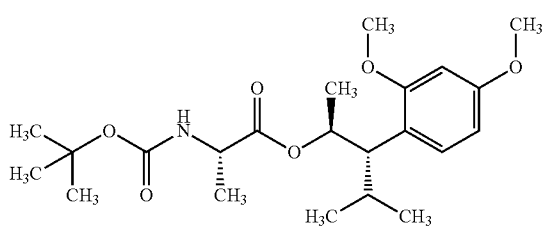 [SMILES: COc1ccc([C@H](C(C)C)[C@H](C)OC(=O)[C@H](C)NC(=O)OC(C)(C)C)c(OC)c1] | Example 6 Steps 1, 2, 3, 4, 5 Example 8 | Colorless Oil |
| 51 | 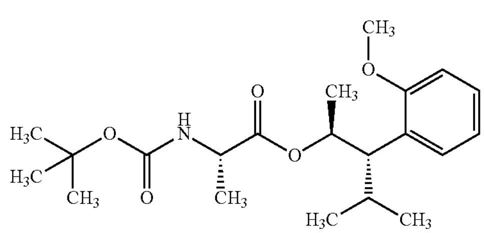 [SMILES: COc1ccccc1[C@H](C(C)C)[C@H](C)OC(=O)[C@H](C)NC(=O)OC(C)(C)C] | Example 6 Steps 1, 2, 3, 4, 5 Example 8 | Colorless Oil |

TABLE 1-continued

Compound Structure, Appearance, and Preparation Method

| Cmpd. No. | Structure | As Prepared According To | Appearance |
|---|---|---|---|
| 52 | 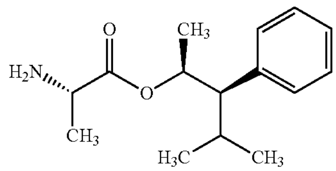 [SMILES: CC(C)[C@H](c1ccccc1)[C@H](C)OC(=O)[C@H](C)N] | Example 10 Steps 1 | Colorless Oil |
| 53 | 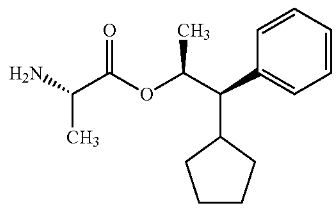 [SMILES: C[C@H](N)C(=O)O[C@@H](C)[C@@H](c1ccccc1)C1CCCC1] | Example 10 Steps 1 | Colorless Oil |
| 54 | 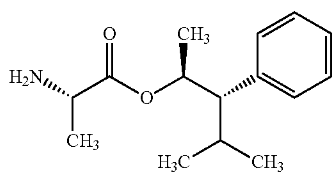 [SMILES: CC(C)[C@@H](c1ccccc1)[C@H](C)OC(=O)[C@H](C)N] | Example 10 Steps 1 | Colorless Oil |
| 55 | 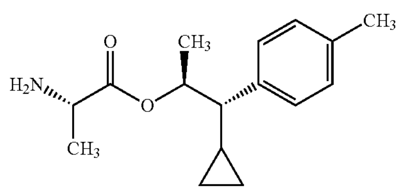 [SMILES: Cc1ccc([C@H](C2CC2)[C@H](C)OC(=O)[C@H](C)N)cc1] | Example 10 Steps 1 | Colorless Oil |
| 56 | 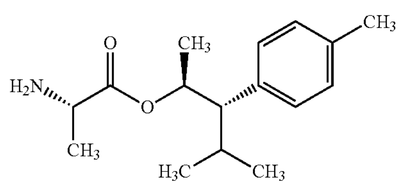 [SMILES: Cc1ccc([C@H](C(C)C)[C@H](C)OC(=O)[C@H](C)N)cc1] | Example 10 Steps 1 | White Semisolid |
| 57 | 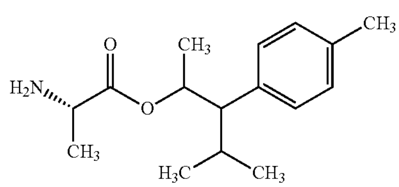 [SMILES: Cc1ccc(C(C(C)C)C(C)OC(=O)[C@H](C)N)cc1] | Example 10 Steps 1 | Colorless Oil |
| 58 | 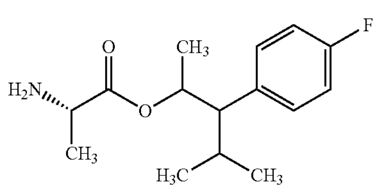 [SMILES: CC(C)C(c1ccc(F)cc1)C(C)OC(=O)[C@H](C)N] | Example 10 Steps 1 | Colorless Oil |
| 59 | 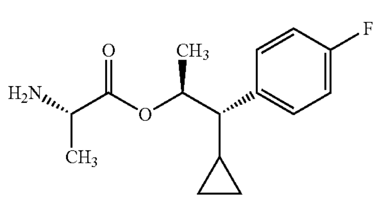 [SMILES: C[C@H](N)C(=O)O[C@@H](C)[C@H](c1ccc(F)cc1)C1CC1] | Example 10 Steps 1 | Colorless Oil |

TABLE 1-continued

Compound Structure, Appearance, and Preparation Method

| Cmpd. No. | Structure | As Prepared According To | Appearance |
|---|---|---|---|
| 60 | 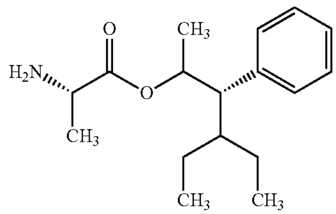 [SMILES: CCC(CC)[C@@H](c1ccccc1)C(C)OC(=O)[C@H](C)N] | Example 10 Steps 1 | Colorless Oil |
| 61 | 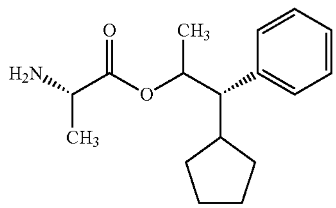 [SMILES: CC(OC(=O)[C@H](C)N)[C@H](c1ccccc1)C1CCCC1] | Example 10 Steps 1 | Colorless Oil |
| 62 | 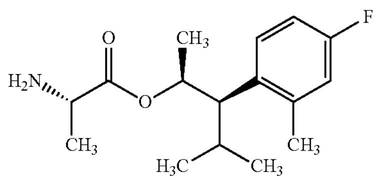 [SMILES: Cc1cc(F)ccc1[C@@H](C(C)C)[C@H](C)OC(=O)[C@H](C)N] | Example 10 Steps 1 | Clear, Colorless Oil |
| 63 | 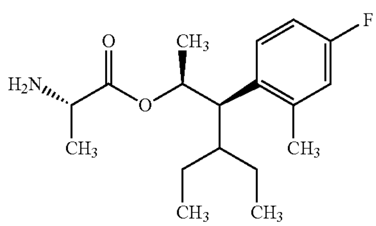 [SMILES: CCC(CC)[C@H](c1ccc(F)cc1C)[C@H](C)OC(=O)[C@H](C)N] | Example 10 Steps 1 | Clear, Colorless Oil |
| 64 | 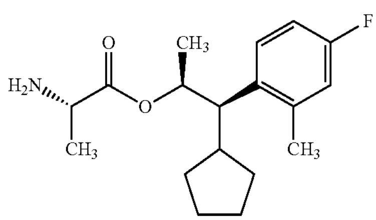 [SMILES: Cc1cc(F)ccc1[C@@H](C1CCCC1)[C@H](C)OC(=O)[C@H](C)N] | Example 10 Steps 1 | Pale Yellow Oil |
| 65 | 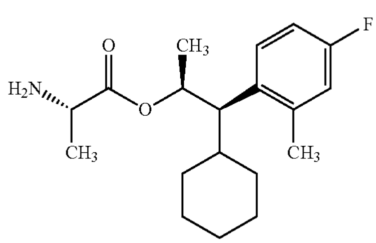 [SMILES: Cc1cc(F)ccc1[C@@H](C1CCCCC1)[C@H](C)OC(=O)[C@H](C)N] | Example 10 Steps 1 | Clear, Colorless Oil |
| 66 | 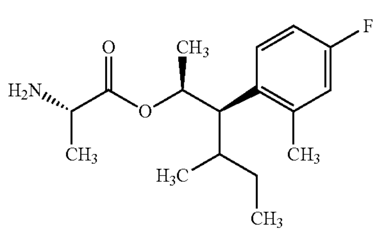 [SMILES: CCC(C)[C@H](c1ccc(F)cc1C)[C@H](C)OC(=O)[C@H](C)N] | Example 10 Steps 1 | Clear, Colorless Oil |

TABLE 1-continued

Compound Structure, Appearance, and Preparation Method

| Cmpd. No. | Structure | As Prepared According To | Appearance |
|---|---|---|---|
| 67 | 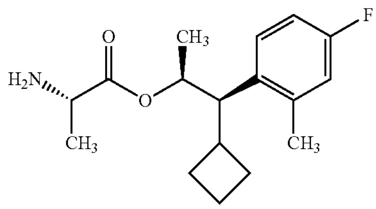 [SMILES: Cc1cc(F)ccc1[C@@H](C1CCC1)[C@H](C)OC(=O)[C@H](C)N] | Example 10 Steps 1 | Clear, Colorless Oil |
| 68 | 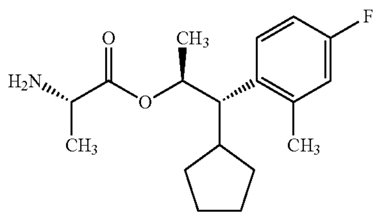 [SMILES: Cc1cc(F)ccc1[C@H](C1CCCC1)[C@H](C)OC(=O)[C@H](C)N] | Example 10 Steps 1 | Pale Yellow Oil |
| 69 | 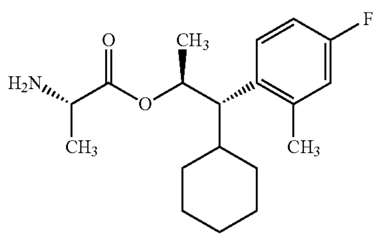 [SMILES: Cc1cc(F)ccc1[C@H](C1CCCCC1)[C@H](C)OC(=O)[C@H](C)N] | Example 10 Steps 1 | Clear, Colorless Oil |
| 70 | 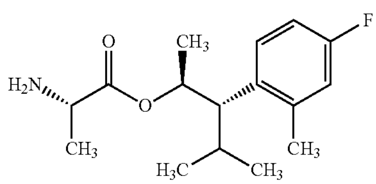 [SMILES: Cc1cc(F)ccc1[C@H](C(C)C)[C@H](C)OC(=O)[C@H](C)N] | Example 10 Steps 1 | Clear, Colorless Oil |
| 71 | 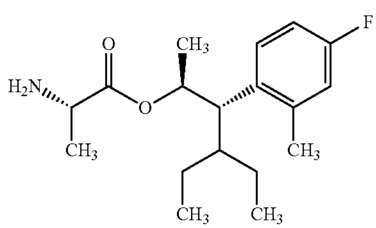 [SMILES: CCC(CC)[C@@H](c1ccc(F)cc1C)[C@H](C)OC(=O)[C@H](C)N] | Example 10 Steps 1 | Pale Yellow Oil |
| 72 | 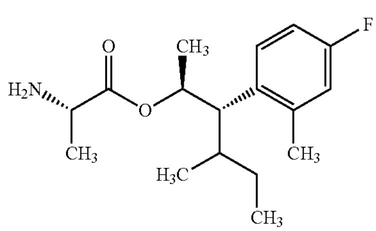 [SMILES: CCC(C)[C@@H](c1ccc(F)cc1C)[C@H](C)OC(=O)[C@H](C)N] | Example 10 Steps 1 | Pale Yellow Oil |
| 73 | 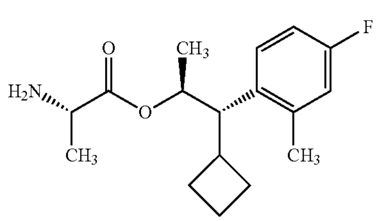 [SMILES: Cc1cc(F)ccc1[C@H](C1CCC1)[C@H](C)OC(=O)[C@H](C)N] | Example 10 Steps 1 | Pale Yellow Oil |

TABLE 1-continued

Compound Structure, Appearance, and Preparation Method

| Cmpd. No. | Structure | As Prepared According To | Appearance |
|---|---|---|---|
| 74 | 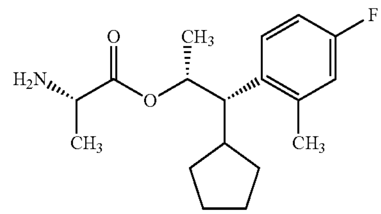 [SMILES: Cc1cc(F)ccc1[C@H](C1CCCC1)[C@@H](C)OC(=O)[C@H](C)N] | Example 10 Steps 1 | Clear, Colorless Oil |
| 75 | 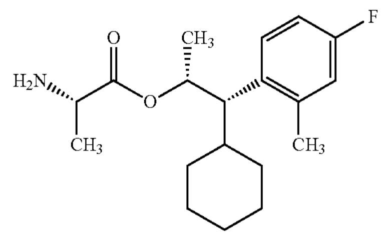 [SMILES: Cc1cc(F)ccc1[C@H](C1CCCCC1)[C@@H](C)OC(=O)[C@H](C)N] | Example 10 Steps 1 | Clear, Colorless Oil |
| 76 | 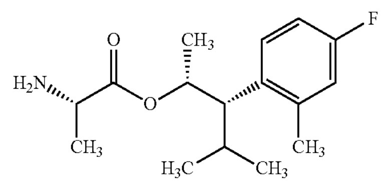 [SMILES: Cc1cc(F)ccc1[C@H](C(C)C)[C@@H](C)OC(=O)[C@H](C)N] | Example 10 Steps 1 | Clear, Colorless Oil |
| 77 | 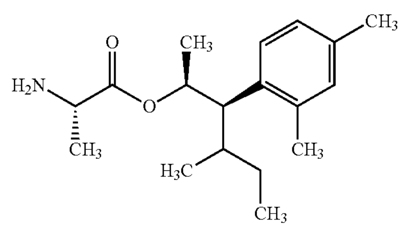 [SMILES: CCC(C)[C@H](c1ccc(C)cc1C)[C@H](C)OC(=O)[C@H](C)N] | Example 10 Steps 1 | Yellow Oil |
| 78 | 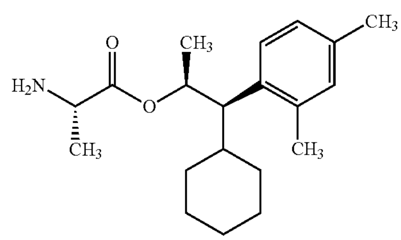 [SMILES: Cc1ccc([C@@H](C2CCCCC2)[C@H](C)OC(=O)[C@H](C)N)c(C)c1] | Example 10 Steps 1 | Yellow Oil |
| 79 | 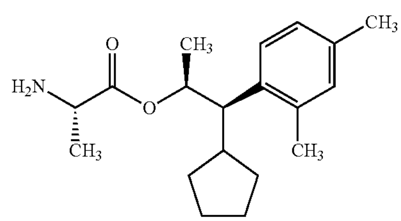 [SMILES: Cc1ccc([C@@H](C2CCCC2)[C@H](C)OC(=O)[C@H](C)N)c(C)c1] | Example 10 Steps 1 | Yellow Oil |
| 80 | 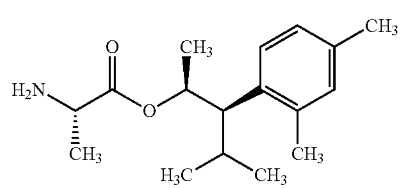 [SMILES: Cc1ccc([C@@H](C(C)C)[C@H](C)OC(=O)[C@H](C)N)c(C)c1] | Example 10 Steps 1 | Yellow Oil |

TABLE 1-continued

Compound Structure, Appearance, and Preparation Method

| Cmpd. No. | Structure | As Prepared According To | Appearance |
|---|---|---|---|
| 81 | 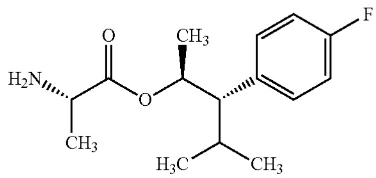 [SMILES: CC(C)[C@@H](c1ccc(F)cc1)[C@H](C)OC(=O)[C@H](C)N] | Example 10 Steps 1 | Thick Oil |
| 82 | 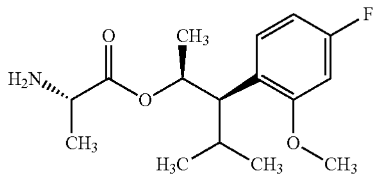 [SMILES: COc1cc(F)ccc1[C@@H](C(C)C)[C@H](C)OC(=O)[C@H](C)N] | Example 10 Steps 1 | Pale Yellow Oil |
| 83 | 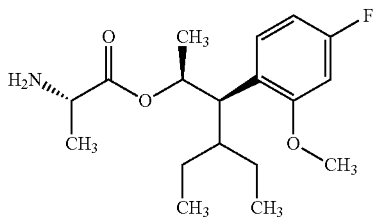 [SMILES: CCC(CC)[C@H](c1ccc(F)cc1OC)[C@H](C)OC(=O)[C@H](C)N] | Example 10 Steps 1 | Clear, Colorless Oil |
| 84 | 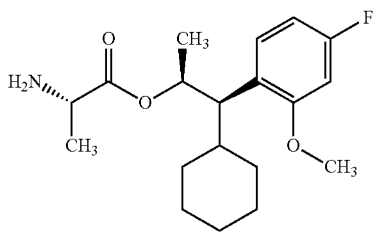 [SMILES: COc1cc(F)ccc1[C@@H](C1CCCCC1)[C@H](C)OC(=O)[C@H](C)N] | Example 10 Steps 1 | Clear, Colorless Oil |
| 85 | 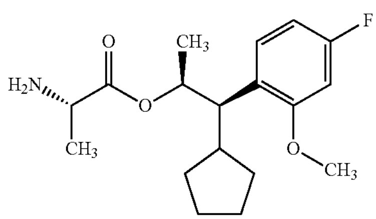 [SMILES: COc1cc(F)ccc1[C@@H](C1CCCC1)[C@H](C)OC(=O)[C@H](C)N] | Example 10 Steps 1 | Clear, Colorless Oil |
| 86 | 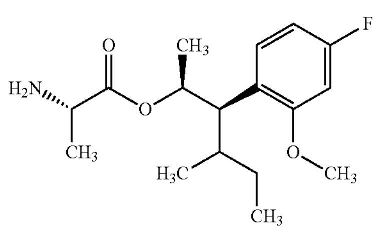 [SMILES: CCC(C)[C@H](c1ccc(F)cc1OC)[C@H](C)OC(=O)[C@H](C)N] | Example 10 Steps 1 | Clear, Colorless Oil |
| 87 | 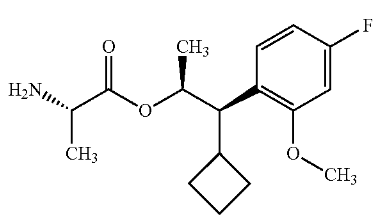 [SMILES: COc1cc(F)ccc1[C@@H](C1CCC1)[C@H](C)OC(=O)[C@H](C)N] | Example 10 Steps 1 | Clear, Colorless Oil |

TABLE 1-continued
Compound Structure, Appearance, and Preparation Method
| Cmpd. No. | Structure | As Prepared According To | Appearance |
|---|---|---|---|
| 88 | 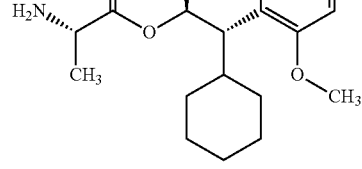 | Example 10 Steps 1 | Clear, Colorless Oil |
| 89 | 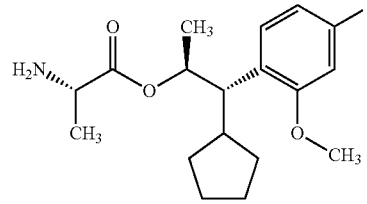 | Example 10 Steps 1 | White Semisolid |
| 90 | 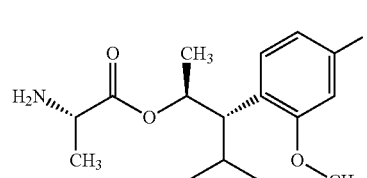 | Example 10 Steps 1 | Off-White Semisolid |
| 91 | 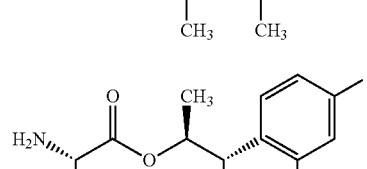 | Example 10 Steps 1 | Clear, Colorless Oil |
| 92 | 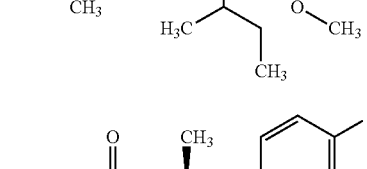 | Example 10 Steps 1 | Clear, Colorless Oil |
| 93 | 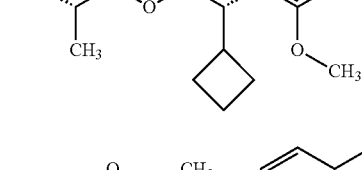 | Example 10 Steps 1 | Clear, Colorless Oil |
| 94 | 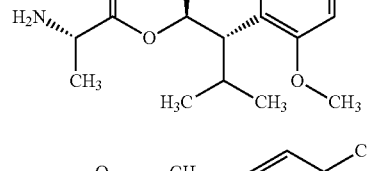 | Example 10 Steps 1 | Yellow Oil |

TABLE 1-continued

Compound Structure, Appearance, and Preparation Method

| Cmpd. No. | Structure | As Prepared According To | Appearance |
|---|---|---|---|
| 95 | 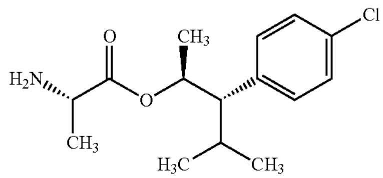 [SMILES: CC(C)[C@@H](c1ccc(Cl)cc1)[C@H](C)OC(=O)[C@H](C)N] | Example 10 Steps 1 | Thick Oil |
| 96 | 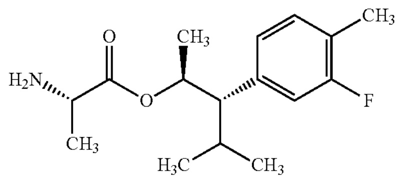 [SMILES: Cc1ccc([C@H](C(C)C)[C@H](C)OC(=O)[C@H](C)N)cc1F] | Example 10 Steps 1 | Thick Oil |
| 97 | 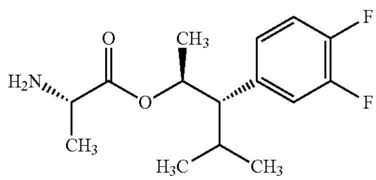 [SMILES: CC(C)[C@@H](c1ccc(F)c(F)c1)[C@H](C)OC(=O)[C@H](C)N] | Example 10 Steps 1 | Thick Oil |
| 98 | 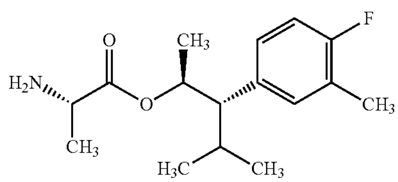 [SMILES: Cc1cc([C@H](C(C)C)[C@H](C)OC(=O)[C@H](C)N)ccc1F] | Example 10 Steps 1 | Pale Yellow Oil |
| 99 | 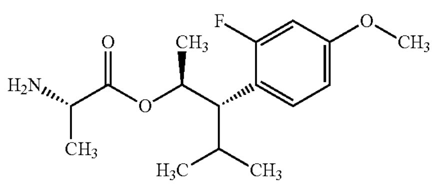 [SMILES: COc1ccc([C@H](C(C)C)[C@H](C)OC(=O)[C@H](C)N)c(F)c1] | Example 10 Steps 1 | White Semisolid |
| 100 | 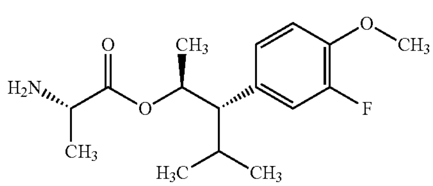 [SMILES: COc1ccc([C@H](C(C)C)[C@H](C)OC(=O)[C@H](C)N)cc1F] | Example 10 Steps 1 | Clear, Colorless Oil |
| 101 | 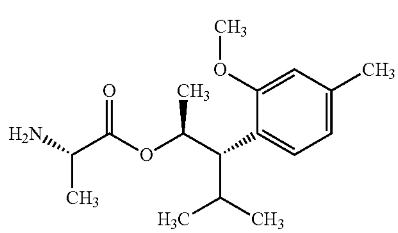 [SMILES: COc1cc(C)ccc1[C@H](C(C)C)[C@H](C)OC(=O)[C@H](C)N] | Example 10 Steps 1 | Pale Yellow Oil |
| 102 | 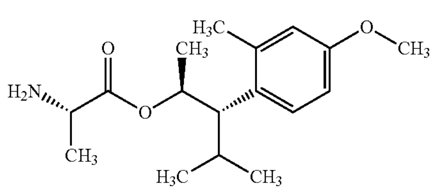 | Example 10 Steps 1 | Clear, Colorless Oil |

TABLE 1-continued

Compound Structure, Appearance, and Preparation Method

| Cmpd. No. | Structure | As Prepared According To | Appearance |
|---|---|---|---|
| 103 | 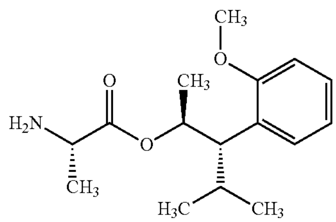 [SMILES: COc1ccccc1[C@H](C(C)C)[C@H](C)OC(=O)[C@H](C)N] | Example 10 Steps 1 | Yellow Oil |
| 104 | 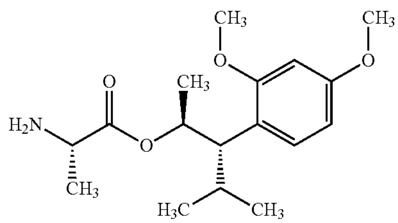 [SMILES: COc1ccc([C@H](C(C)C)[C@H](C)OC(=O)[C@H](C)N)c(OC)c1] | Example 10 Steps 1 | Yellow Oil |
| 105 | 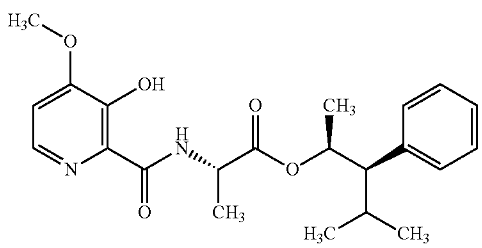 [SMILES: COc1ccnc(C(=O)N[C@@H](C)C(=O)O[C@@H](C)[C@@H](c2ccccc2)C(C)C)c1O] | Example 10 Steps 2 | Colorless Gel |
| 106 | 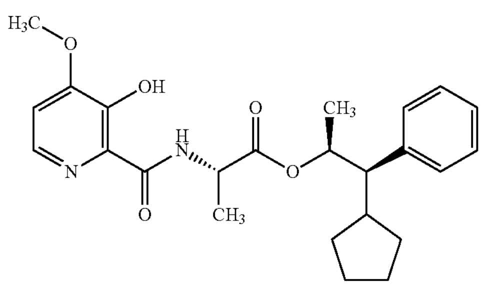 [SMILES: COc1ccnc(C(=O)N[C@@H](C)C(=O)O[C@@H](C)[C@@H](c2ccccc2)C2CCCC2)c1O] | Example 10 Steps 2 | Colorless Gel |
| 107 | 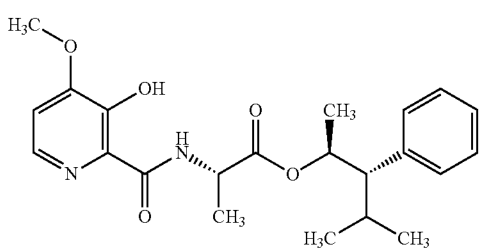 [SMILES: COc1ccnc(C(=O)N[C@@H](C)C(=O)O[C@@H](C)[C@H](c2ccccc2)C(C)C)c1O] | Example 10 Steps 2 | Colorless Oil |
| 108 | 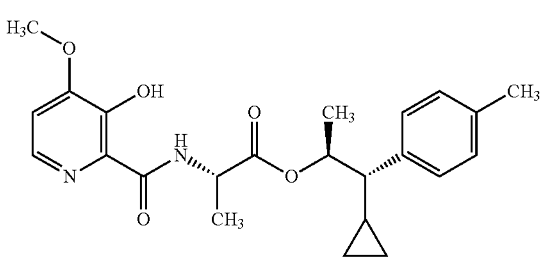 [SMILES: COc1ccnc(C(=O)N[C@@H](C)C(=O)O[C@@H](C)[C@H](c2ccc(C)cc2)C2CC2)c1O] | Example 10 Steps 2 | Colorless Oil |

TABLE 1-continued

Compound Structure, Appearance, and Preparation Method

| Cmpd. No. | Structure | As Prepared According To | Appearance |
|---|---|---|---|
| 109 | 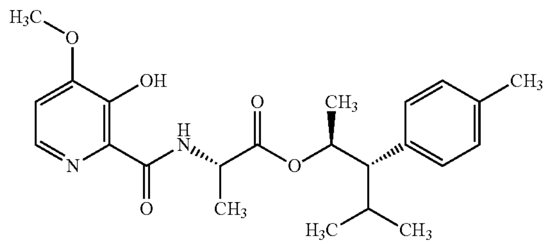 [SMILES: COc1ccnc(C(=O)N[C@@H](C)C(=O)O[C@@H](C)[C@H](c2ccc(C)cc2)C(C)C)c1O] | Example 10 Steps 2 | Clear, Colorless Oil |
| 110 | 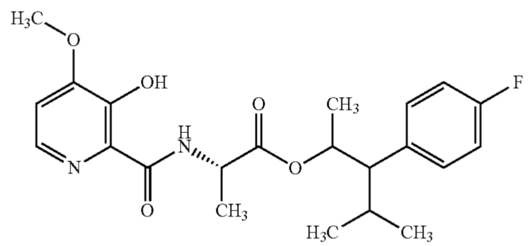 [SMILES: COc1ccnc(C(=O)N[C@@H](C)C(=O)OC(C)C(c2ccc(F)cc2)C(C)C)c1O] | Example 10 Steps 2 | Colorless Oil |
| 111 | 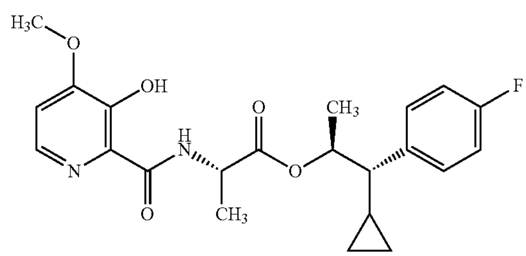 [SMILES: COc1ccnc(C(=O)N[C@@H](C)C(=O)O[C@@H](C)[C@H](c2ccc(F)cc2)C2CC2)c1O] | Example 10 Steps 2 | Colorless Oil |
| 112 | 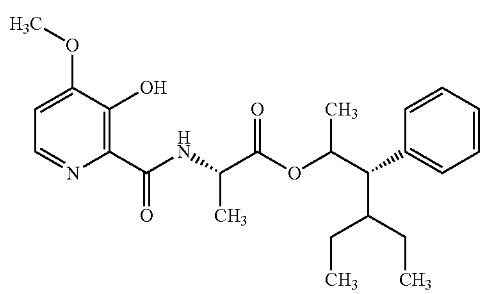 [SMILES: CCC(CC)[C@@H](c1ccccc1)C(C)OC(=O)[C@H](C)NC(=O)c1nccc(OC)c1O] | Example 10 Steps 2 | Colorless Oil |
| 113 | 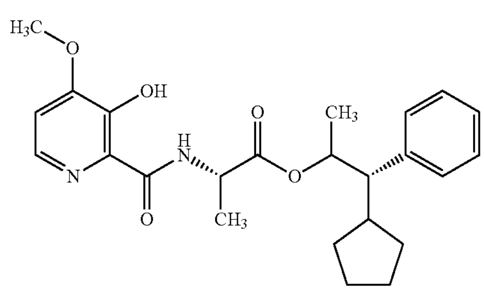 [SMILES: COc1ccnc(C(=O)N[C@@H](C)C(=O)OC(C)[C@H](c2ccccc2)C2CCCC2)c1O] | Example 10 Steps 2 | Colorless Oil |

TABLE 1-continued

Compound Structure, Appearance, and Preparation Method

| Cmpd. No. | Structure | As Prepared According To | Appearance |
|---|---|---|---|
| 114 | 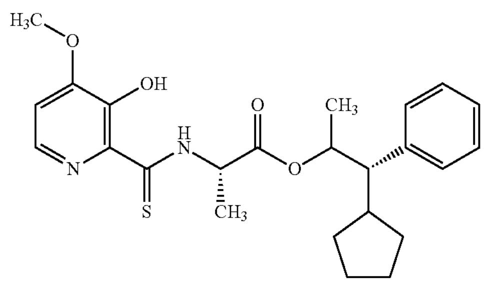 [SMILES: COc1ccnc(C(=S)N[C@@H](C)C(=O)OC(C)[C@H](c2ccccc2)C2CCCC2)c1O] | Example 10 Steps 2 | Yellow Solid |
| 115 | 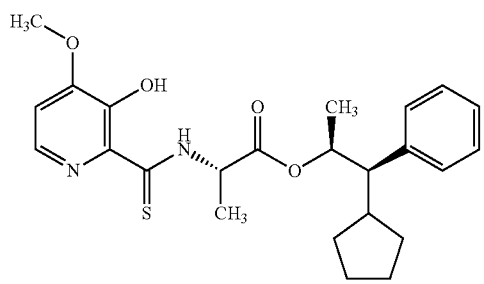 [SMILES: COc1ccnc(C(=S)N[C@@H](C)C(=O)O[C@@H](C)[C@@H](c2ccccc2)C2CCCC2)c1O] | Example 10 Steps 2 | Yellow Oil |
| 116 | 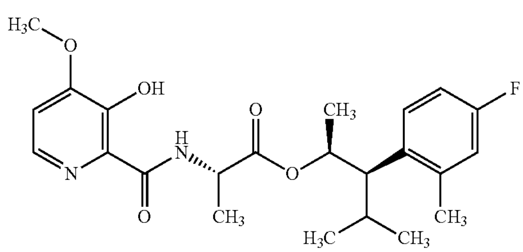 [SMILES: COc1ccnc(C(=O)N[C@@H](C)C(=O)O[C@@H](C)[C@@H](c2ccc(F)cc2C)C(C)C)c1O] | Example 10 Steps 2 | Clear, Colorless Oil |
| 117 | 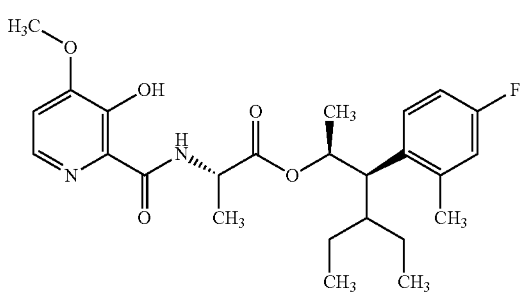 [SMILES: CCC(CC)[C@H](c1ccc(F)cc1C)[C@H](C)OC(=O)[C@H](C)NC(=O)c1nccc(OC)c1O] | Example 10 Steps 2 | Clear, Colorless Oil |
| 118 | 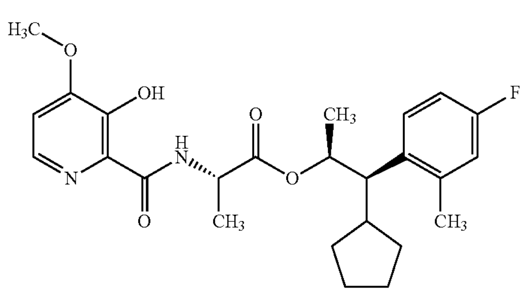 [SMILES: COc1ccnc(C(=O)N[C@@H](C)C(=O)O[C@@H](C)[C@@H](c2ccc(F)cc2C)C2CCCC2)c1O] | Example 10 Steps 2 | Clear, Colorless Oil |

TABLE 1-continued

Compound Structure, Appearance, and Preparation Method

| Cmpd. No. | Structure | As Prepared According To | Appearance |
|---|---|---|---|
| 119 | 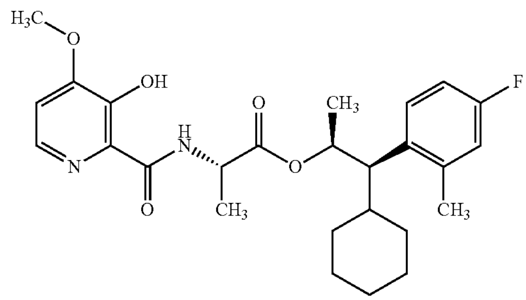 [SMILES: COc1ccnc(C(=O)N[C@@H](C)C(=O)O[C@@H](C)[C@@H](c2ccc(F)cc2C)C2CCCCC2)c1O] | Example 10 Steps 2 | Clear, Colorless Oil |
| 120 | 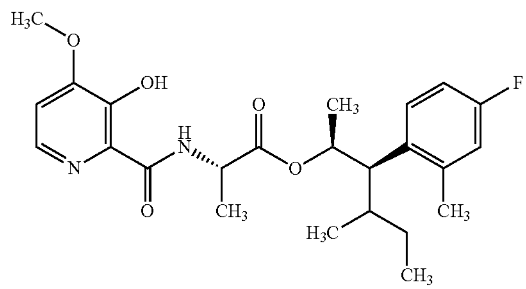 [SMILES: CCC(C)[C@H](c1ccc(F)cc1C)[C@H](C)OC(=O)[C@H](C)NC(=O)c1nccc(OC)c1O] | Example 10 Steps 2 | Clear, Colorless Oil |
| 121 | 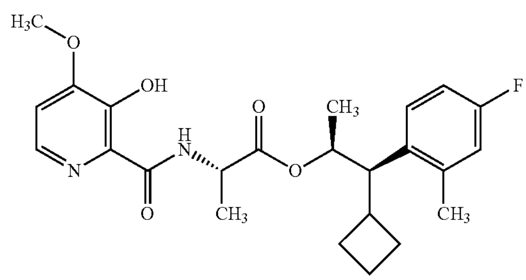 [SMILES: COc1ccnc(C(=O)N[C@@H](C)C(=O)O[C@@H](C)[C@@H](c2ccc(F)cc2C)C2CCC2)c1O] | Example 10 Steps 2 | Clear, Colorless Oil |
| 122 | 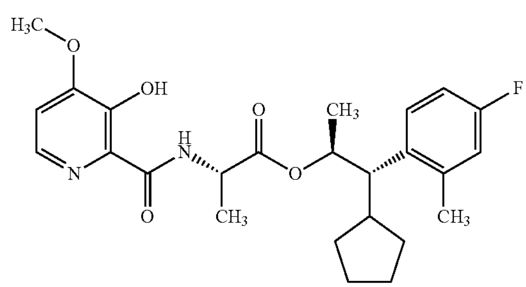 [SMILES: COc1ccnc(C(=O)N[C@@H](C)C(=O)O[C@@H](C)[C@H](c2ccc(F)cc2C)C2CCCC2)c1O] | Example 10 Steps 2 | Clear, Colorless Oil |
| 123 | 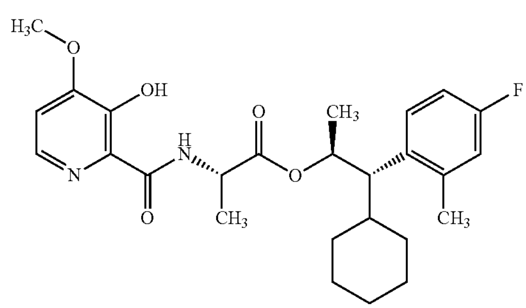 [SMILES: COc1ccnc(C(=O)N[C@@H](C)C(=O)O[C@@H](C)[C@H](c2ccc(F)cc2C)C2CCCCC2)c1O] | Example 10 Steps 2 | Clear, Colorless Oil |

TABLE 1-continued

Compound Structure, Appearance, and Preparation Method

| Cmpd. No. | Structure | As Prepared According To | Appearance |
|---|---|---|---|
| 124 | 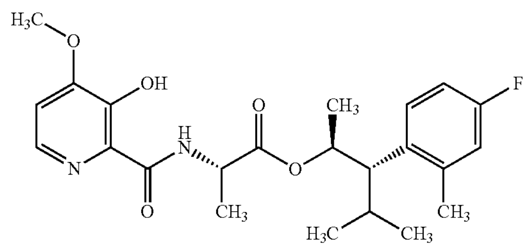 [SMILES: COc1ccnc(C(=O)N[C@@H](C)C(=O)O[C@@H](C)[C@H](c2ccc(F)cc2C)C(C)C)c1O] | Example 10 Steps 2 | Clear, Colorless Oil |
| 125 | 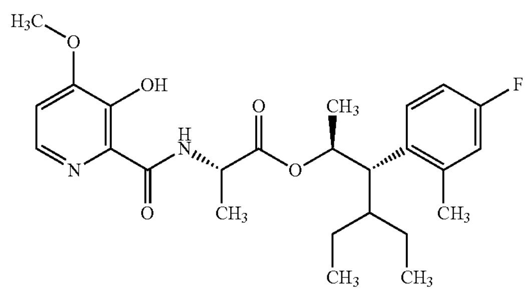 [SMILES: CCC(CC)[C@@H](c1ccc(F)cc1C)[C@H](C)OC(=O)[C@H](C)NC(=O)c1nccc(OC)c1O] | Example 10 Steps 2 | Clear, Colorless Oil |
| 126 | 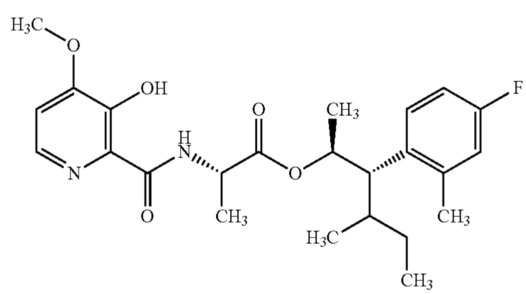 [SMILES: CCC(C)[C@@H](c1ccc(F)cc1C)[C@H](C)OC(=O)[C@H](C)NC(=O)c1nccc(OC)c1O] | Example 10 Steps 2 | Clear, Colorless Oil |
| 127 | 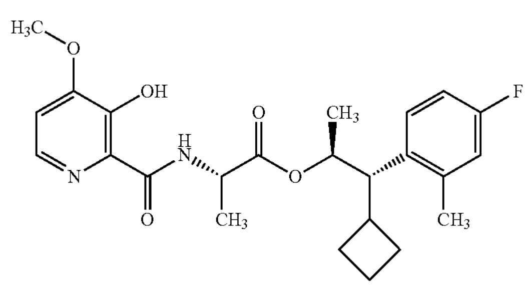 [SMILES: COc1ccnc(C(=O)N[C@@H](C)C(=O)O[C@@H](C)[C@H](c2ccc(F)cc2C)C2CCC2)c1O] | Example 10 Steps 2 | Clear, Colorless Oil |
| 128 | 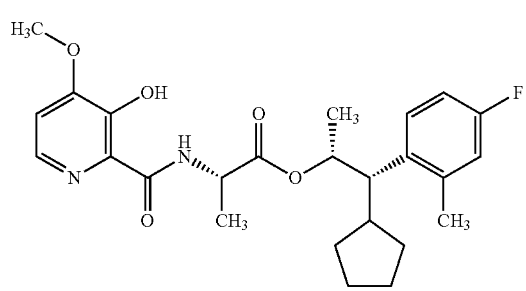 [SMILES: COc1ccnc(C(=O)N[C@@H](C)C(=O)O[C@H](C)[C@H](c2ccc(F)cc2C)C2CCCC2)c1O] | Example 10 Steps 2 | Clear, Colorless Oil |

TABLE 1-continued

Compound Structure, Appearance, and Preparation Method

| Cmpd. No. | Structure | As Prepared According To | Appearance |
|---|---|---|---|
| 129 | 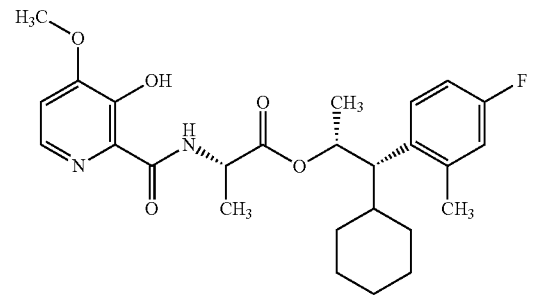 [SMILES: COc1ccnc(C(=O)N[C@@H](C)C(=O)O[C@H](C)[C@H](c2ccc(F)cc2C)C2CCCCC2)c1O] | Example 10 Steps 2 | Clear, Colorless Oil |
| 130 | 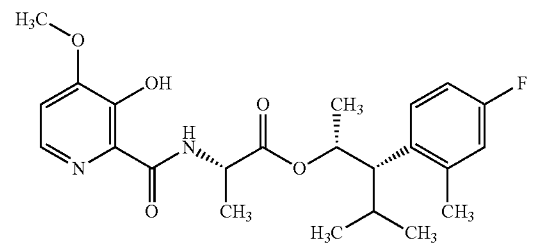 [SMILES: COc1ccnc(C(=O)N[C@@H](C)C(=O)O[C@H](C)[C@H](c2ccc(F)cc2C)C(C)C)c1O] | Example 10 Steps 2 | Clear, Colorless Oil |
| 131 | 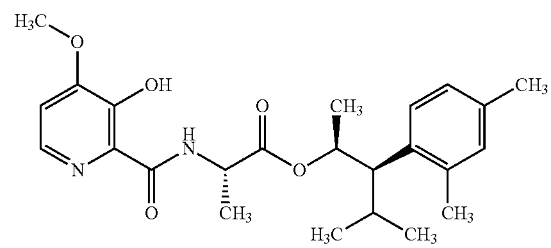 | Example 10 Steps 2 | Colorless Oil |
| 132 | 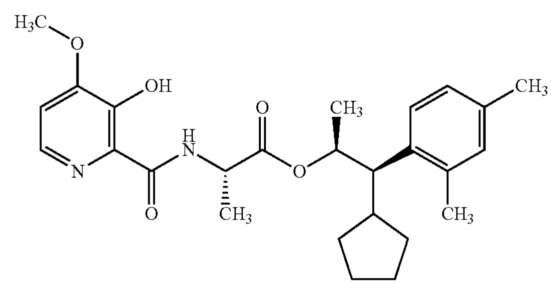 [SMILES: COc1ccnc(C(=O)N[C@@H](C)C(=O)O[C@@H](C)[C@@H](c2ccc(C)cc2C)C2CCCC2)c1O] | Example 10 Steps 2 | Colorless Oil |
| 133 | 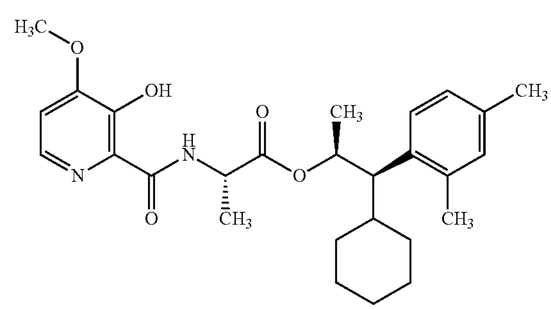 [SMILES: COc1ccnc(C(=O)N[C@@H](C)C(=O)O[C@@H](C)[C@@H](c2ccc(C)cc2C)C2CCCCC2)c1O] | Example 10 Steps 2 | White Wax |

TABLE 1-continued

Compound Structure, Appearance, and Preparation Method

| Cmpd. No. | Structure | As Prepared According To | Appearance |
|---|---|---|---|
| 134 | 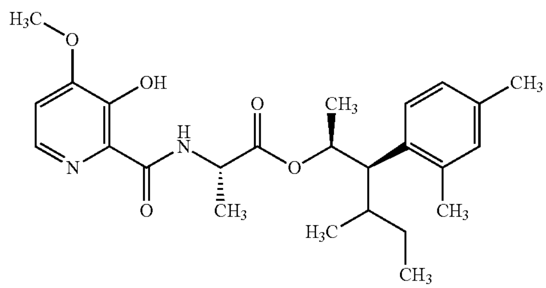 [SMILES: CCC(C)[C@H](c1ccc(C)cc1C)[C@H](C)OC(=O)[C@H](C)NC(=O)c1nccc(OC)c1O] | Example 10 Steps 2 | White Wax |
| 135 | 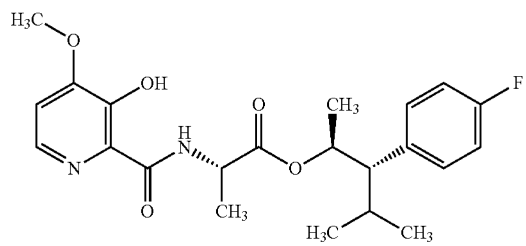 | Example 10 Steps 2 | Thick Oil |
| 136 | 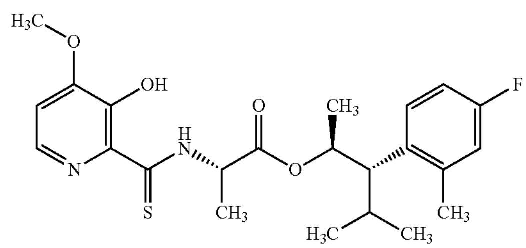 | Example 10 Steps 2 | Bright Yellow Semisolid |
| 137 | 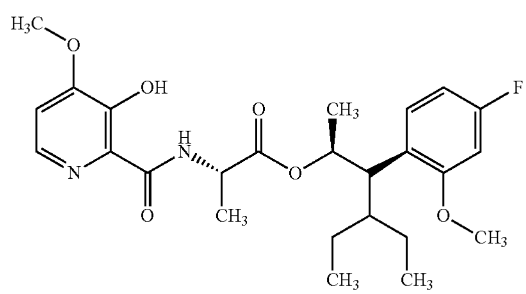 | Example 10 Steps 2 | Yellow Oil |
| 138 | 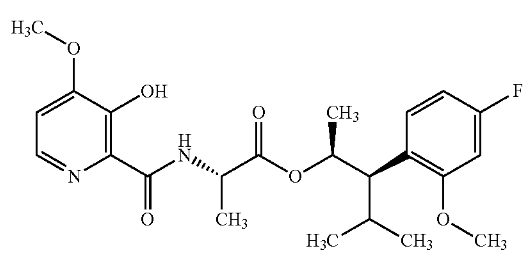 [SMILES: COc1cc(F)ccc1[C@@H](C(C)C)[C@H](C)OC(=O)[C@H](C)NC(=O)c1nccc(OC)c1O] | Example 10 Steps 2 | Pale Yellow Oil |

TABLE 1-continued

Compound Structure, Appearance, and Preparation Method

| Cmpd. No. | Structure | As Prepared According To | Appearance |
|---|---|---|---|
| 139 | 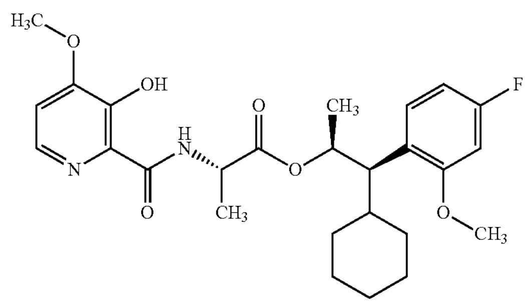 [SMILES: COc1cc(F)ccc1[C@@H](C1CCCCC1)[C@H](C)OC(=O)[C@H](C)NC(=O)c1nccc(OC)c1O] | Example 10 Steps 2 | Yellow Oil |
| 140 | 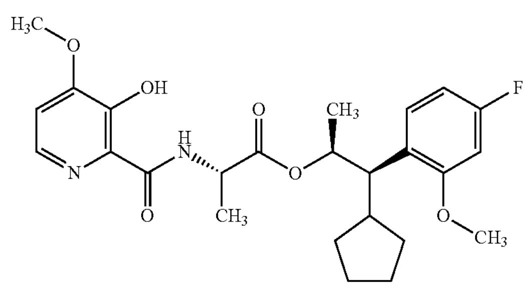 [SMILES: COc1cc(F)ccc1[C@@H](C1CCCC1)[C@H](C)OC(=O)[C@H](C)NC(=O)c1nccc(OC)c1O] | Example 10 Steps 2 | Pale Yellow Oil |
| 141 | 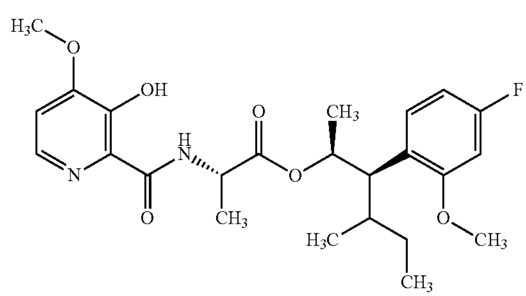 [SMILES: CCC(C)[C@H](c1ccc(F)cc1OC)[C@H](C)OC(=O)[C@H](C)NC(=O)c1nccc(OC)c1O] | Example 10 Steps 2 | Clear, Colorless Oil |
| 142 | 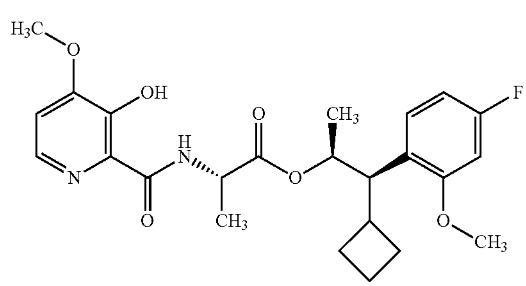 [SMILES: COc1cc(F)ccc1[C@@H](C1CCC1)[C@H](C)OC(=O)[C@H](C)NC(=O)c1nccc(OC)c1O] | Example 10 Steps 2 | Clear, Colorless Oil |
| 143 | 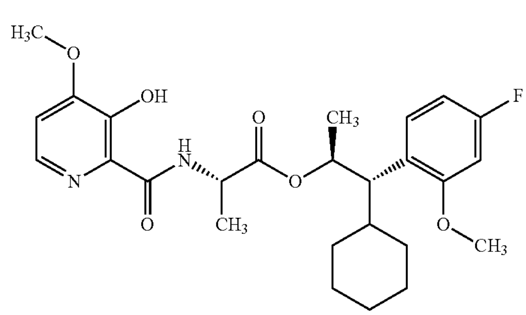 [SMILES: COc1cc(F)ccc1[C@H](C1CCCCC1)[C@H](C)OC(=O)[C@H](C)NC(=O)c1nccc(OC)c1O] | Example 10 Steps 2 | Clear, Colorless Oil |

TABLE 1-continued

Compound Structure, Appearance, and Preparation Method

| Cmpd. No. | Structure | As Prepared According To | Appearance |
|---|---|---|---|
| 144 | 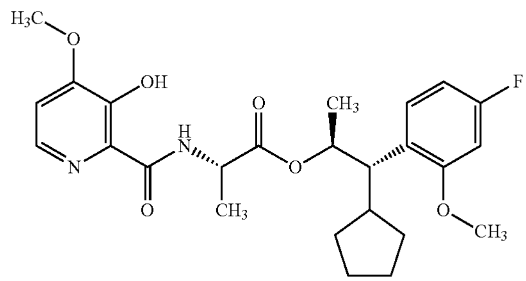 [SMILES: COc1cc(F)ccc1[C@H](C1CCCC1)[C@H](C)OC(=O)[C@H](C)NC(=O)c1nccc(OC)c1O] | Example 10 Steps 2 | Clear, Colorless Oil |
| 145 | 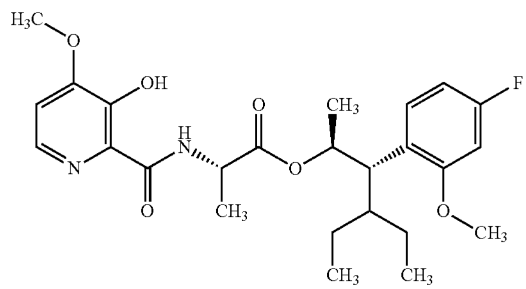 [SMILES: CCC(CC)[C@@H](c1ccc(F)cc1OC)[C@H](C)OC(=O)[C@H](C)NC(=O)c1nccc(OC)c1O] | Example 10 Steps 2 | Clear, Colorless Oil |
| 146 | 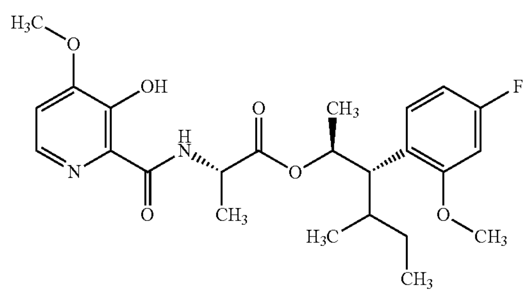 [SMILES: CCC(C)[C@@H](c1ccc(F)cc1OC)[C@H](C)OC(=O)[C@H](C)NC(=O)c1nccc(OC)c1O] | Example 10 Steps 2 | Clear, Colorless Oil |
| 147 | 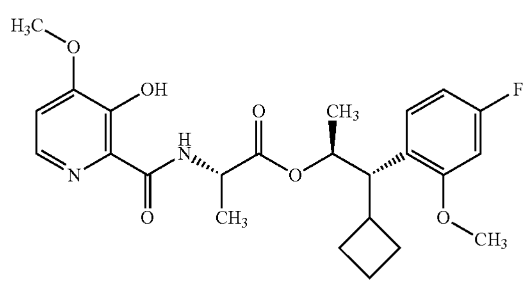 [SMILES: COc1cc(F)ccc1[C@H](C1CCC1)[C@H](C)OC(=O)[C@H](C)NC(=O)c1nccc(OC)c1O] | Example 10 Steps 2 | Clear, Colorless Oil |
| 148 | 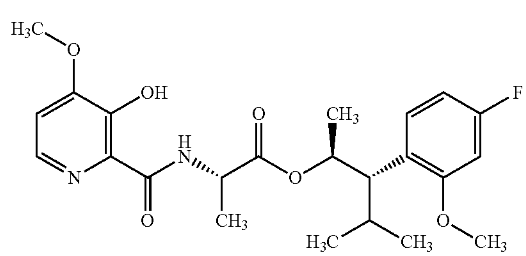 [SMILES: COc1cc(F)ccc1[C@H](C(C)C)[C@H](C)OC(=O)[C@H](C)NC(=O)c1nccc(OC)c1O] | Example 10 Steps 2 | Clear, Colorless Oil |

TABLE 1-continued

Compound Structure, Appearance, and Preparation Method

| Cmpd. No. | Structure | As Prepared According To | Appearance |
|---|---|---|---|
| 149 | 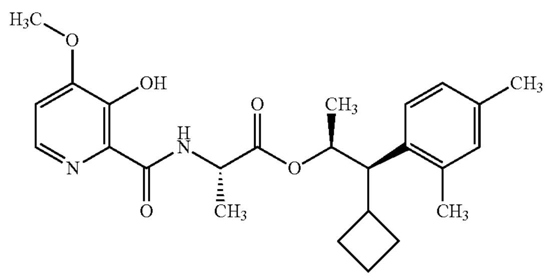 [SMILES: COc1ccnc(C(=O)N[C@@H](C)C(=O)O[C@@H](C)[C@@H](c2ccc(C)cc2C)C2CCC2)c1O] | Example 10 Steps 2 | Colorless Oil |
| 150 | 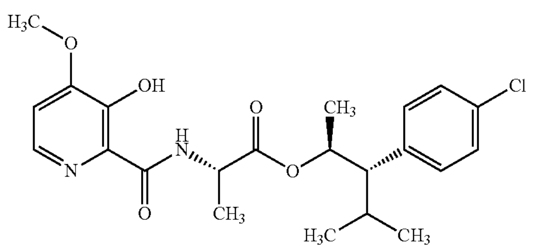 [SMILES: COc1ccnc(C(=O)N[C@@H](C)C(=O)O[C@@H](C)[C@H](c2ccc(Cl)cc2)C(C)C)c1O] | Example 10 Steps 2 | Colorless Oil |
| 151 | 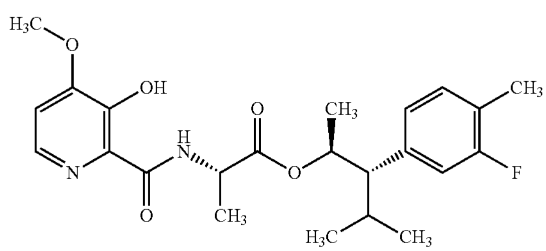 [SMILES: COc1ccnc(C(=O)N[C@@H](C)C(=O)O[C@@H](C)[C@H](c2ccc(C)c(F)c2)C(C)C)c1O] | Example 10 Steps 2 | Thick Oil |
| 152 | 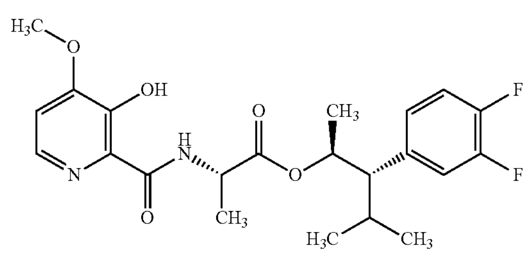 [SMILES: COc1ccnc(C(=O)N[C@@H](C)C(=O)O[C@@H](C)[C@H](c2ccc(F)c(F)c2)C(C)C)c1O] | Example 10 Steps 2 | Thick Oil |
| 153 | 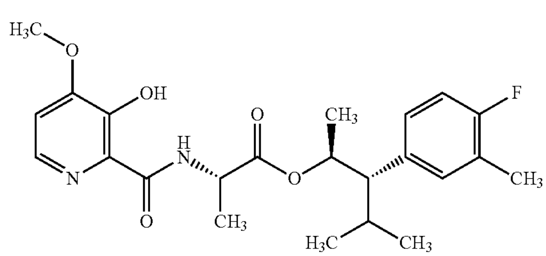 [SMILES: COc1ccnc(C(=O)N[C@@H](C)C(=O)O[C@@H](C)[C@H](c2ccc(F)c(C)c2)C(C)C)c1O] | Example 10 Steps 2 | Clear, Colorless Oil |
| 154 | 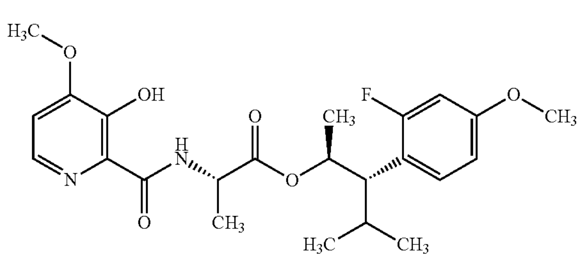 [SMILES: COc1ccc([C@H](C(C)C)[C@H](C)OC(=O)[C@H](C)NC(=O)c2nccc(OC)c2O)c(F)c1] | Example 10 Steps 2 | Clear, Colorless Oil |

TABLE 1-continued

Compound Structure, Appearance, and Preparation Method

| Cmpd. No. | Structure | As Prepared According To | Appearance |
|---|---|---|---|
| 155 | 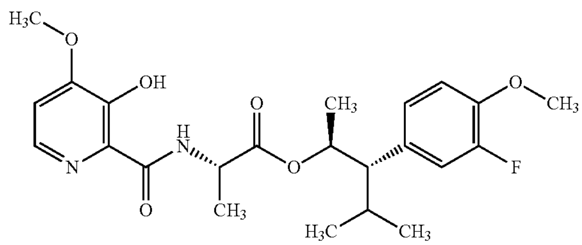 [SMILES: COc1ccc([C@H](C(C)C)[C@H](C)OC(=O)[C@H](C)NC(=O)c2nccc(OC)c2O)cc1F] | Example 10 Steps 2 | Clear, Colorless Oil |
| 156 | 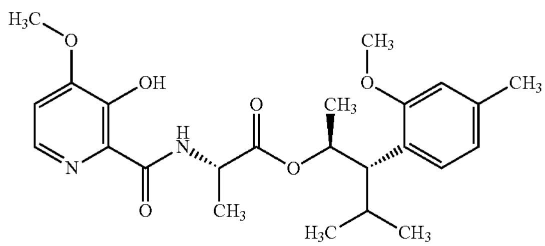 [SMILES: COc1cc(C)ccc1[C@H](C(C)C)[C@H](C)OC(=O)[C@H](C)NC(=O)c1nccc(OC)c1O] | Example 10 Steps 2 | Clear, Colorless Oil |
| 157 | 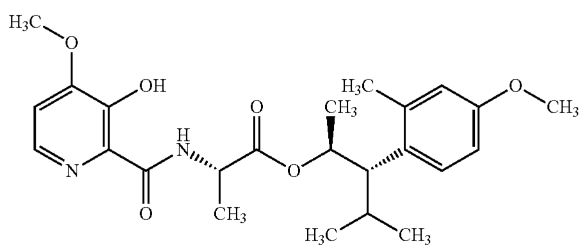 [SMILES: COc1ccc([C@H](C(C)C)[C@H](C)OC(=O)[C@H](C)NC(=O)c2nccc(OC)c2O)c(C)c1] | Example 10 Steps 2 | Clear, Colorless Oil |
| 158 | 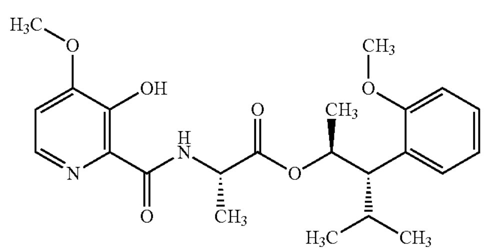 [SMILES: COc1ccccc1[C@H](C(C)C)[C@H](C)OC(=O)[C@H](C)NC(=O)c1nccc(OC)c1O] | Example 10 Steps 2 | Colorless Oil |
| 159 | 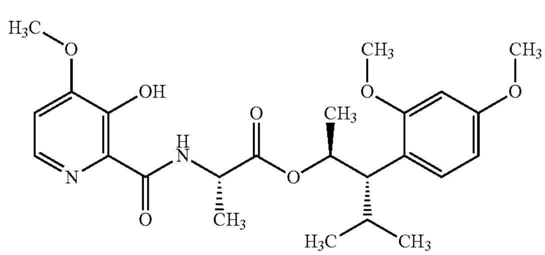 [SMILES: COc1ccc([C@H](C(C)C)[C@H](C)OC(=O)[C@H](C)NC(=O)c2nccc(OC)c2O)c(OC)c1] | Example 10 Steps 2 | Colorless Oil |
| 160 | 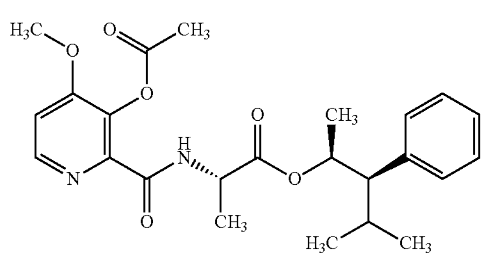 [SMILES: COc1ccnc(C(=O)N[C@@H](C)C(=O)O[C@@H](C)[C@@H](c2ccccc2)C(C)C)c1OC(C)=O] | Example 11A | Colorless Oil |

TABLE 1-continued

Compound Structure, Appearance, and Preparation Method

| Cmpd. No. | Structure | As Prepared According To | Appearance |
|---|---|---|---|
| 161 | 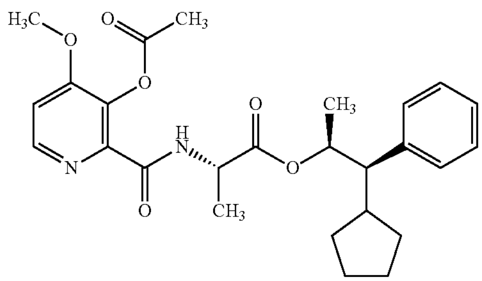 [SMILES: COc1ccnc(C(=O)N[C@@H](C)C(=O)O[C@@H](C)[C@@H](c2ccccc2)C2CCCC2)c1OC(C)=O] | Example 11A | Colorless Oil |
| 162 | 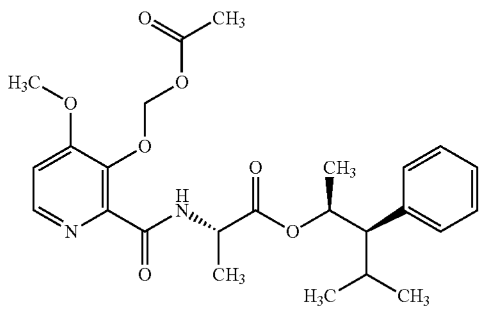 [SMILES: COc1ccnc(C(=O)N[C@@H](C)C(=O)O[C@@H](C)[C@@H](c2ccccc2)C(C)C)c1OCOC(C)=O] | Example 11B | Colorless Oil |
| 163 | 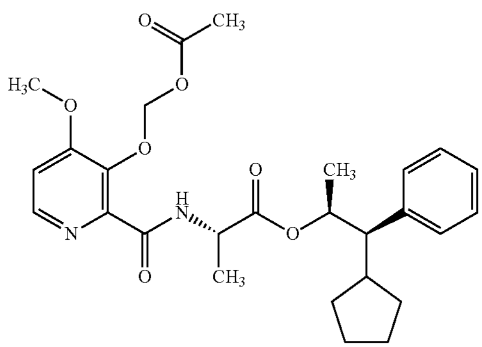 [SMILES: COc1ccnc(C(=O)N[C@@H](C)C(=O)O[C@@H](C)[C@@H](c2ccccc2)C2CCCC2)c1OCOC(C)=O] | Example 11B | Colorless Oil |
| 164 | 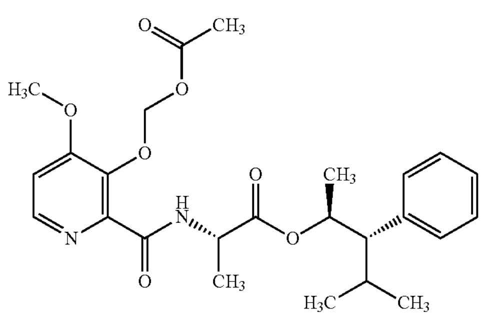 [SMILES: COc1ccnc(C(=O)N[C@@H](C)C(=O)O[C@@H](C)[C@H](c2ccccc2)C(C)C)c1OCOC(C)=O] | Example 11B | Colorless Oil |
| 165 | 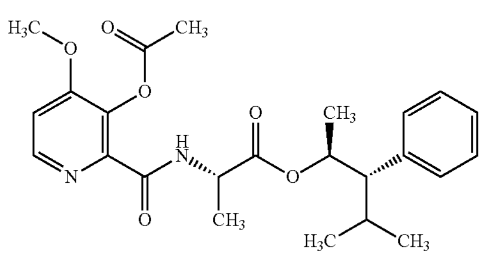 [SMILES: COc1ccnc(C(=O)N[C@@H](C)C(=O)O[C@@H](C)[C@H](c2ccccc2)C(C)C)c1OC(C)=O] | Example 11A | Colorless Oil |

TABLE 1-continued

Compound Structure, Appearance, and Preparation Method

| Cmpd. No. | Structure | As Prepared According To | Appearance |
|---|---|---|---|
| 166 | 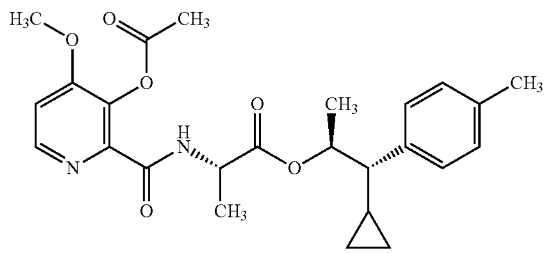 [SMILES: COc1ccnc(C(=O)N[C@@H](C)C(=O)O[C@@H](C)[C@H](c2ccc(C)cc2)C2CC2)c1OC(C)=O] | Example 11A | Colorless Oil |
| 167 | 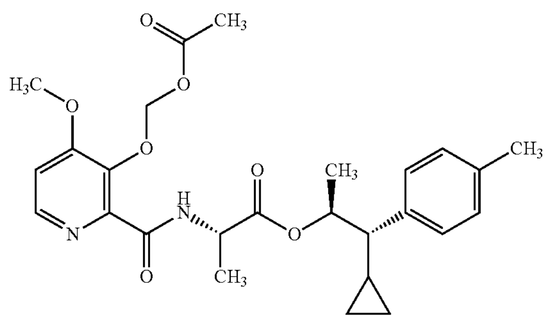 [SMILES: COc1ccnc(C(=O)N[C@@H](C)C(=O)O[C@@H](C)[C@H](c2ccc(C)cc2)C2CC2)c1OCOC(C)=O] | Example 11B | Colorless Oil |
| 168 | 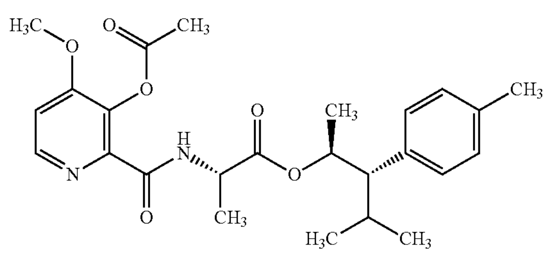 [SMILES: COc1ccnc(C(=O)N[C@@H](C)C(=O)O[C@@H](C)[C@H](c2ccc(C)cc2)C(C)C)c1OC(C)=O] | Example 11A | Clear, Colorless Oil |
| 169 | 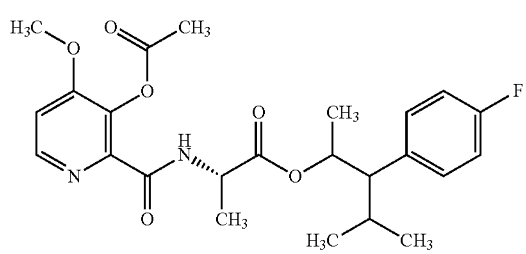 [SMILES: COc1ccnc(C(=O)N[C@@H](C)C(=O)OC(C)C(c2ccc(F)cc2)C(C)C)c1OC(C)=O] | Example 11A | Colorless Oil |
| 170 | 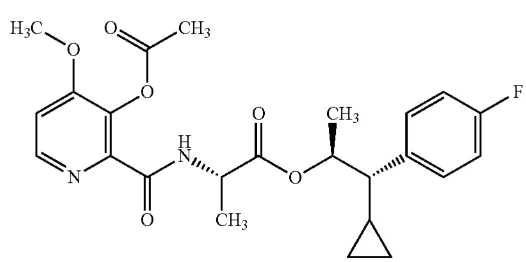 [SMILES: COc1ccnc(C(=O)N[C@@H](C)C(=O)O[C@@H](C)[C@H](c2ccc(F)cc2)C2CC2)c1OC(C)=O] | Example 11A | Colorless Oil |

TABLE 1-continued

Compound Structure, Appearance, and Preparation Method

| Cmpd. No. | Structure | As Prepared According To | Appearance |
|---|---|---|---|
| 171 | 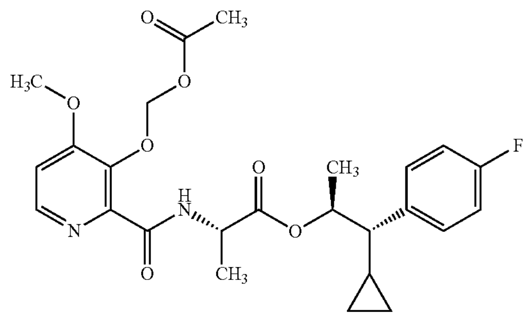 [SMILES: COc1ccnc(C(=O)N[C@@H](C)C(=O)O[C@@H](C)[C@H](c2ccc(F)cc2)C2CC2)c1OCOC(C)=O] | Example 11B | Colorless Oil |
| 172 | 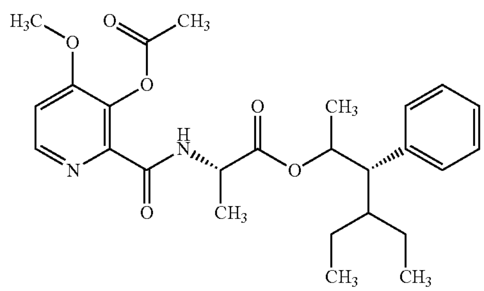 [SMILES: CCC(CC)[C@@H](c1ccccc1)C(C)OC(=O)[C@H](C)NC(=O)c1nccc(OC)c1OC(C)=O] | Example 11A | Colorless Oil |
| 173 | 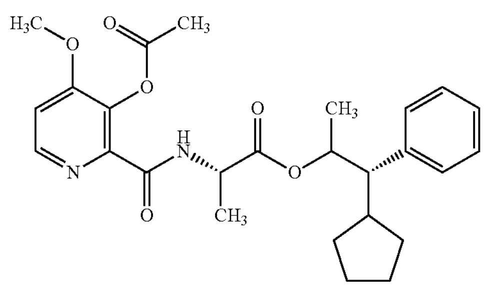 [SMILES: COc1ccnc(C(=O)N[C@@H](C)C(=O)OC(C)[C@H](c2ccccc2)C2CCCC2)c1OC(C)=O] | Example 11A | Colorless Oil |
| 174 | 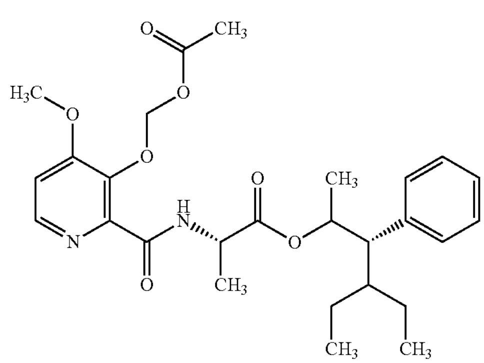 [SMILES: CCC(CC)[C@@H](c1ccccc1)C(C)OC(=O)[C@H](C)NC(=O)c1nccc(OC)c1OCOC(C)=O] | Example 11B | Colorless Oil |

TABLE 1-continued

Compound Structure, Appearance, and Preparation Method

| Cmpd. No. | Structure | As Prepared According To | Appearance |
|---|---|---|---|
| 175 | 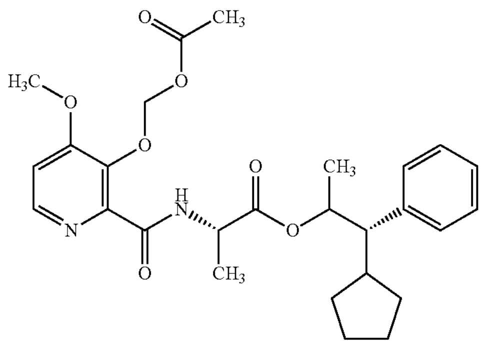 [SMILES: COc1ccnc(C(=O)N[C@@H](C)C(=O)OC(C)[C@H](c2ccccc2)C2CCCC2)c1OCOC(C)=O] | Example 11B | Colorless Oil |
| 176 | 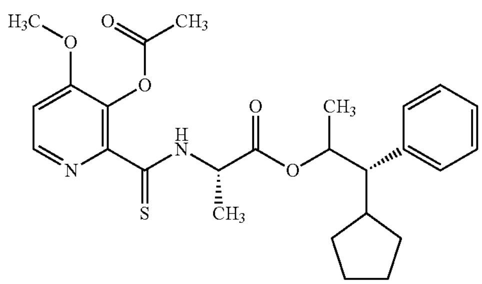 [SMILES: COc1ccnc(C(=S)N[C@@H](C)C(=O)OC(C)[C@H](c2ccccc2)C2CCCC2)c1OC(C)=O] | Example 12 | Orange Wax |
| 177 | 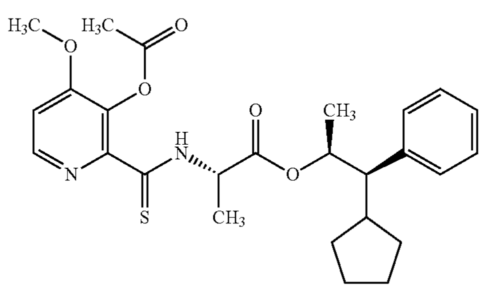 [SMILES: COc1ccnc(C(=S)N[C@@H](C)C(=O)O[C@@H](C)[C@@H](c2ccccc2)C2CCCC2)c1OC(C)=O] | Example 12 | Brown Oil |
| 178 | 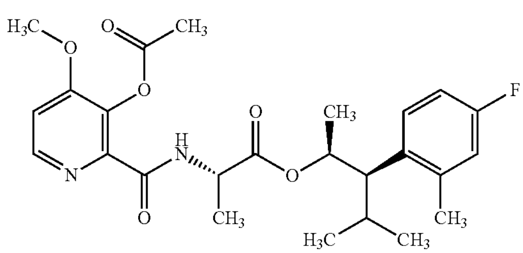 [SMILES: COc1ccnc(C(=O)N[C@@H](C)C(=O)O[C@@H](C)[C@@H](c2ccc(F)cc2C)C(C)C)c1OC(C)=O] | Example 11A | Clear, Colorless Oil |
| 179 | 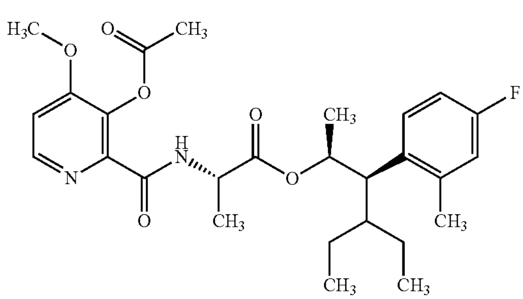 [SMILES: CCC(CC)[C@H](c1ccc(F)cc1C)[C@H](C)OC(=O)[C@H](C)NC(=O)c1nccc(OC)c1OC(C)=O] | Example 11A | Clear, Colorless Oil |

TABLE 1-continued
Compound Structure, Appearance, and Preparation Method
| Cmpd. No. | Structure | As Prepared According To | Appearance |
|---|---|---|---|
| 180 | 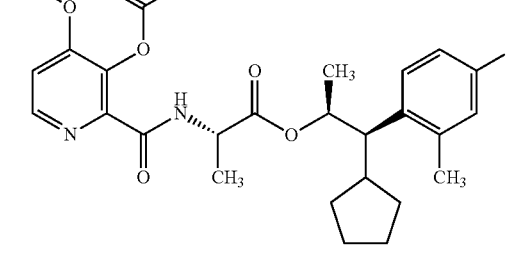 | Example 11A | Clear, Colorless Oil |
| 181 | 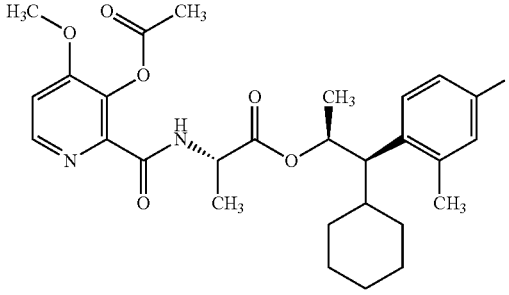 | Example 11A | Pale Yellow Oil |
| 182 | 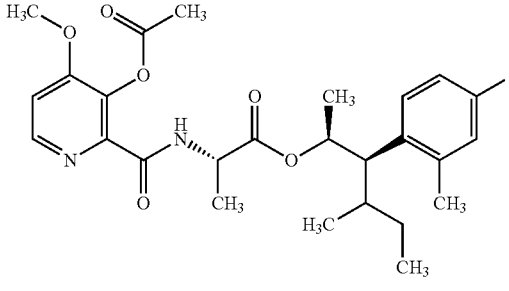 | Example 11A | Clear, Colorless Oil |
| 183 | 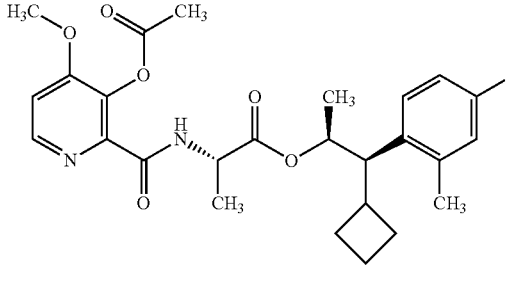 | Example 11A | Clear, Colorless Oil |
| 184 | 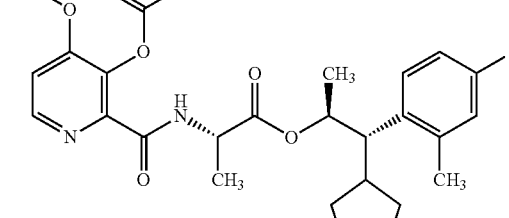 | Example 11A | Clear, Colorless Oil |

TABLE 1-continued

Compound Structure, Appearance, and Preparation Method

| Cmpd. No. | Structure | As Prepared According To | Appearance |
|---|---|---|---|
| 185 | 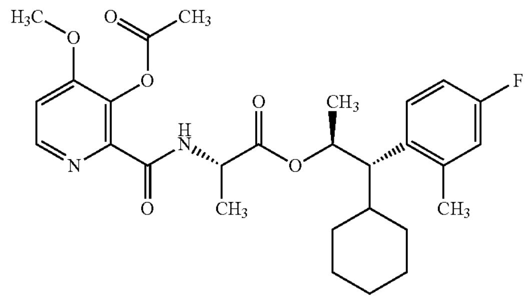 [SMILES: COc1ccnc(C(=O)N[C@@H](C)C(=O)O[C@@H](C)[C@H](c2ccc(F)cc2C)C2CCCCC2)c1OC(C)=O] | Example 11A | Clear, Colorless Oil |
| 186 | 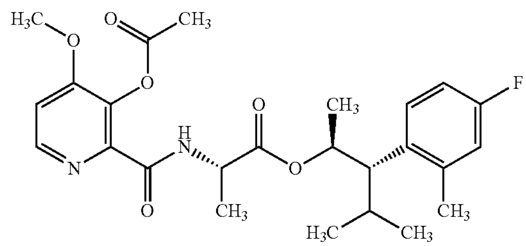 [SMILES: COc1ccnc(C(=O)N[C@@H](C)C(=O)O[C@@H](C)[C@H](c2ccc(F)cc2C)C(C)C)c1OC(C)=O] | Example 11A | Clear, Colorless Oil |
| 187 | 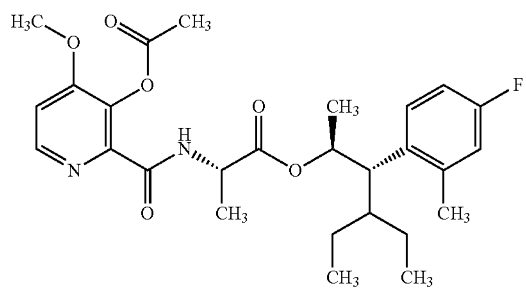 [SMILES: CCC(CC)[C@@H](c1ccc(F)cc1C)[C@H](C)OC(=O)[C@H](C)NC(=O)c1nccc(OC)c1OC(C)=O] | Example 11A | Clear, Colorless Oil |
| 188 | 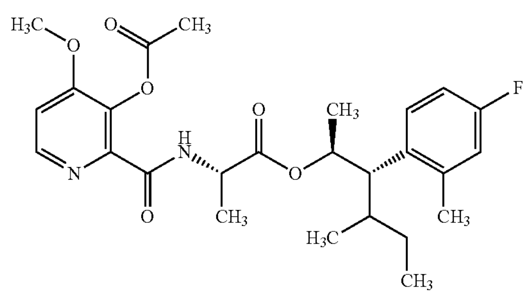 [SMILES: CCC(C)[C@@H](c1ccc(F)cc1C)[C@H](C)OC(=O)[C@H](C)NC(=O)c1nccc(OC)c1OC(C)=O] | Example 11A | Clear, Colorless Oil |
| 189 | 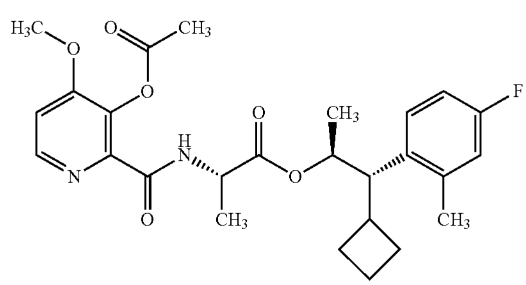 [SMILES: COc1ccnc(C(=O)N[C@@H](C)C(=O)O[C@@H](C)[C@H](c2ccc(F)cc2C)C2CCC2)c1OC(C)=O] | Example 11A | Clear, Colorless Oil |

TABLE 1-continued

Compound Structure, Appearance, and Preparation Method

| Cmpd. No. | Structure | As Prepared According To | Appearance |
|---|---|---|---|
| 190 | 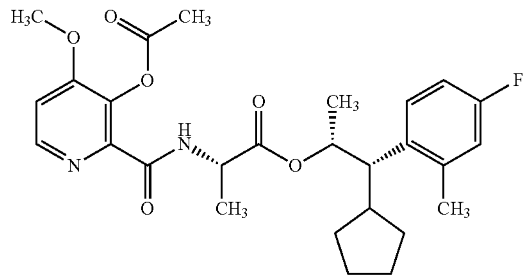 [SMILES: COc1ccnc(C(=O)N[C@@H](C)C(=O)O[C@H](C)[C@H](c2ccc(F)cc2C)C2CCCC2)c1OC(C)=O] | Example 11A | Clear, Colorless Oil |
| 191 | 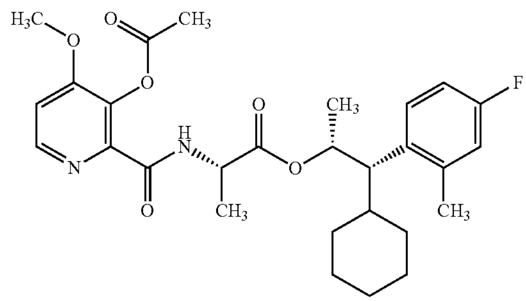 [SMILES: COc1ccnc(C(=O)N[C@@H](C)C(=O)O[C@H](C)[C@H](c2ccc(F)cc2C)C2CCCCC2)c1OC(C)=O] | Example 11A | Clear, Colorless Oil |
| 192 | 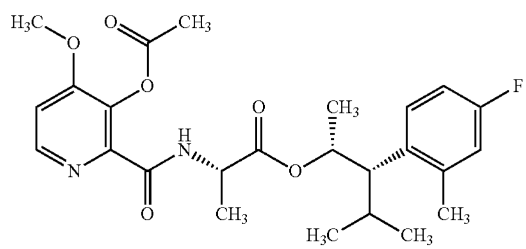 [SMILES: COc1ccnc(C(=O)N[C@@H](C)C(=O)O[C@H](C)[C@H](c2ccc(F)cc2C)C(C)C)c1OC(C)=O] | Example 11A | Clear, Colorless Oil |
| 193 | 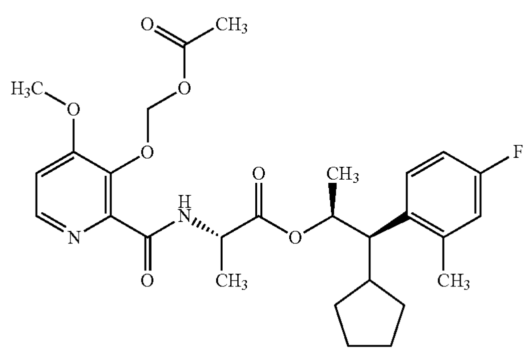 [SMILES: COc1ccnc(C(=O)N[C@@H](C)C(=O)O[C@@H](C)[C@@H](c2ccc(F)cc2C)C2CCCC2)c1OCOC(C)=O] | Example 11B | Clear, Colorless Oil |
| 194 | 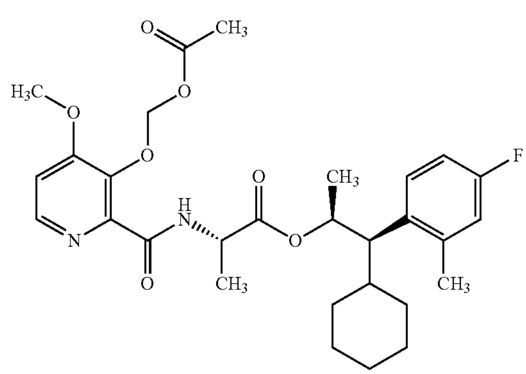 [SMILES: COc1ccnc(C(=O)N[C@@H](C)C(=O)O[C@@H](C)[C@@H](c2ccc(F)cc2C)C2CCCCC2)c1OCOC(C)=O] | Example 11B | Clear, Colorless Oil |

TABLE 1-continued

Compound Structure, Appearance, and Preparation Method

| Cmpd. No. | Structure | As Prepared According To | Appearance |
|---|---|---|---|
| 195 | 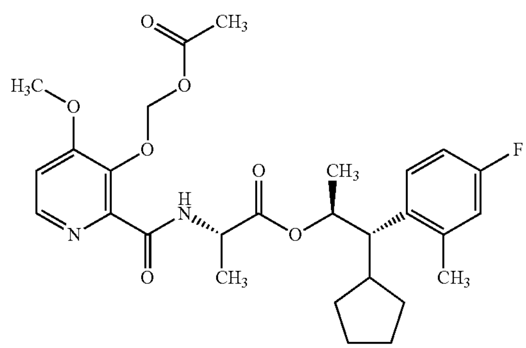 [SMILES: COc1ccnc(C(=O)N[C@@H](C)C(=O)O[C@@H](C)[C@H](c2ccc(F)cc2C)C2CCCC2)c1OCOC(C)=O] | Example 11B | Clear, Colorless Oil |
| 196 | 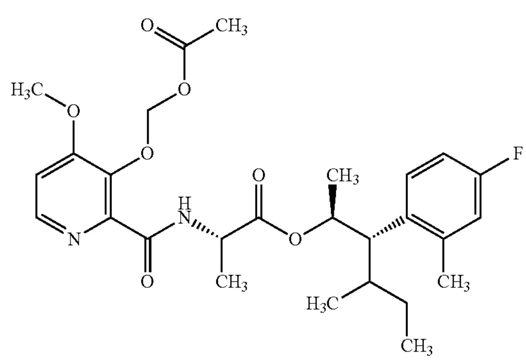 [SMILES: CCC(C)[C@@H](c1ccc(F)cc1C)[C@H](C)OC(=O)[C@H](C)NC(=O)c1nccc(OC)c1OCOC(C)=O] | Example 11B | Clear, Colorless Oil |
| 197 | 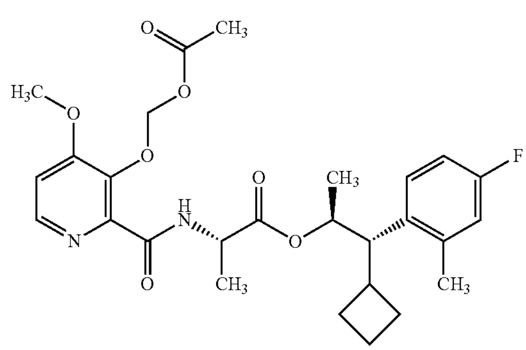 [SMILES: COc1ccnc(C(=O)N[C@@H](C)C(=O)O[C@@H](C)[C@H](c2ccc(F)cc2C)C2CCC2)c1OCOC(C)=O] | Example 11B | Clear, Colorless Oil |
| 198 | 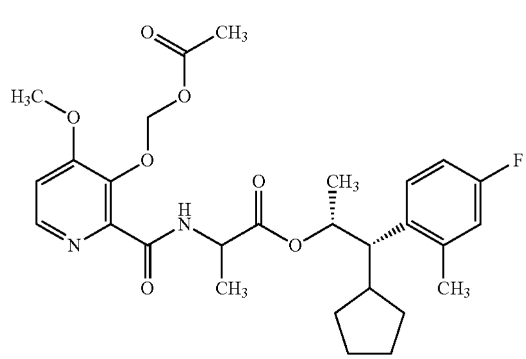 [SMILES: COc1ccnc(C(=O)NC(C)C(=O)O[C@H](C)[C@H](c2ccc(F)cc2C)C2CCCC2)c1OCOC(C)=O] | Example 11B | White Semisolid |

TABLE 1-continued

Compound Structure, Appearance, and Preparation Method

| Cmpd. No. | Structure | As Prepared According To | Appearance |
|---|---|---|---|
| 199 | 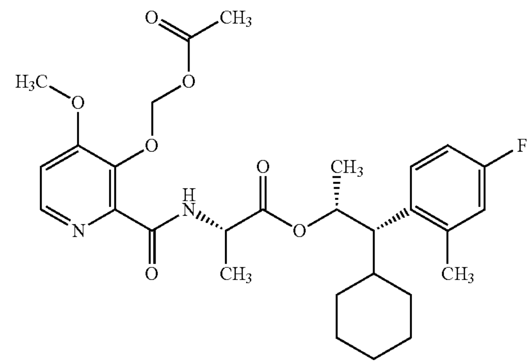 [SMILES: COc1ccnc(C(=O)N[C@@H](C)C(=O)O[C@H](C)[C@H](c2ccc(F)cc2C)C2CCCCC2)c1OCOC(C)=O] | Example 11B | Clear, Colorless Oil |
| 200 | 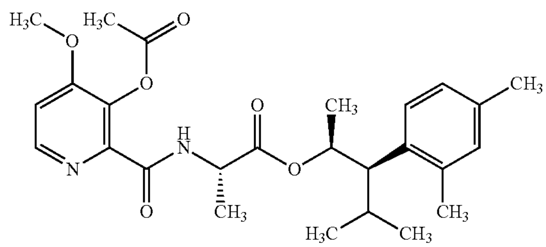 [SMILES: COc1ccnc(C(=O)N[C@@H](C)C(=O)O[C@@H](C)[C@@H](c2ccc(C)cc2C)C(C)C)c1OC(C)=O] | Example 11A | Colorless Oil |
| 201 | 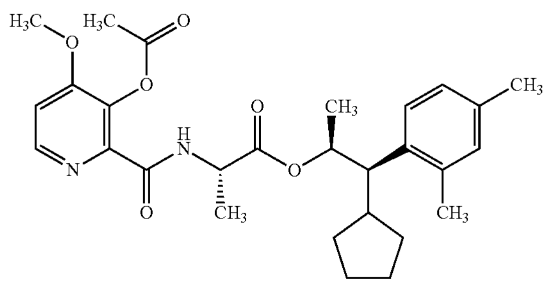 [SMILES: COc1ccnc(C(=O)N[C@@H](C)C(=O)O[C@@H](C)[C@@H](c2ccc(C)cc2C)C2CCCC2)c1OC(C)=O] | Example 11A | Colorless Oil |
| 202 | 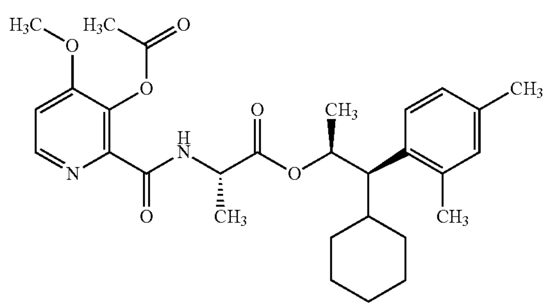 [SMILES: COc1ccnc(C(=O)N[C@@H](C)C(=O)O[C@@H](C)[C@@H](c2ccc(C)cc2C)C2CCCCC2)c1OC(C)=O] | Example 11A | Colorless Oil |
| 203 | 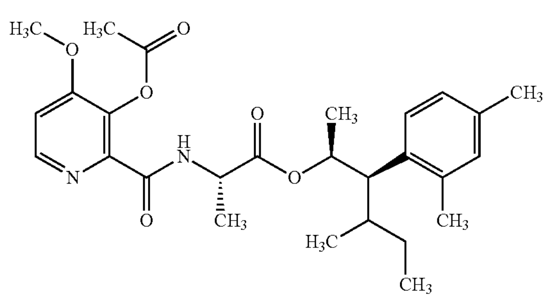 [SMILES: CCC(C)[C@H](c1ccc(C)cc1C)[C@H](C)OC(=O)[C@H](C)NC(=O)c1nccc(OC)c1OC(C)=O] | Example 11A | Colorless Oil |

TABLE 1-continued
Compound Structure, Appearance, and Preparation Method
| Cmpd. No. | Structure | As Prepared According To | Appearance |
|---|---|---|---|
| 204 | 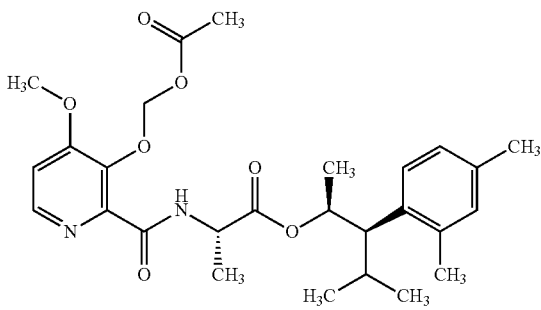 [SMILES: COc1ccnc(C(=O)N[C@@H](C)C(=O)O[C@@H](C)[C@@H](c2ccc(C)cc2C)C(C)C)c1OCOC(C)=O] | Example 11B | Colorless Oil |
| 205 | 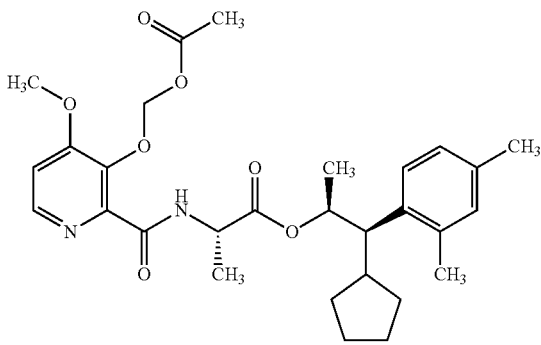 [SMILES: COc1ccnc(C(=O)N[C@@H](C)C(=O)O[C@@H](C)[C@@H](c2ccc(C)cc2C)C2CCCC2)c1OCOC(C)=O] | Example 11B | Colorless Oil |
| 206 | 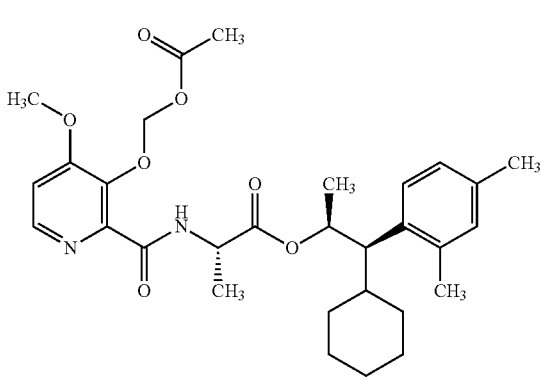 [SMILES: COc1ccnc(C(=O)N[C@@H](C)C(=O)O[C@@H](C)[C@@H](c2ccc(C)cc2C)C2CCCCC2)c1OCOC(C)=O] | Example 11B | Colorless Oil |
| 207 | 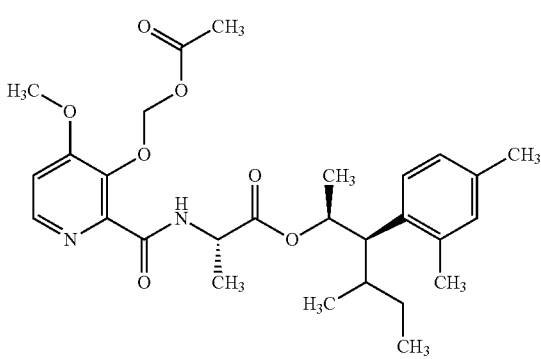 [SMILES: CCC(C)[C@H](c1ccc(C)cc1C)[C@H](C)OC(=O)[C@H](C)NC(=O)c1nccc(OC)c1OCOC(C)=O] | Example 11B | Colorless Oil |

TABLE 1-continued

Compound Structure, Appearance, and Preparation Method

| Cmpd. No. | Structure | As Prepared According To | Appearance |
|---|---|---|---|
| 208 | 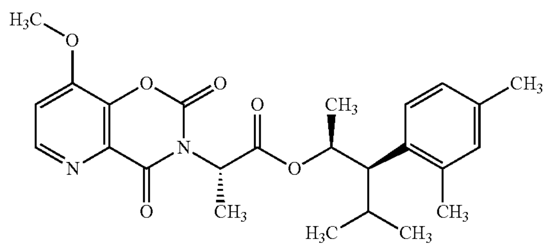 [SMILES: COc1ccnc2c(=O)n([C@@H](C)C(=O)O[C@@H](C)[C@@H](c3ccc(C)cc3C)C(C)C)c(=O)oc12] | Example 14 | Orange Oil |
| 209 | 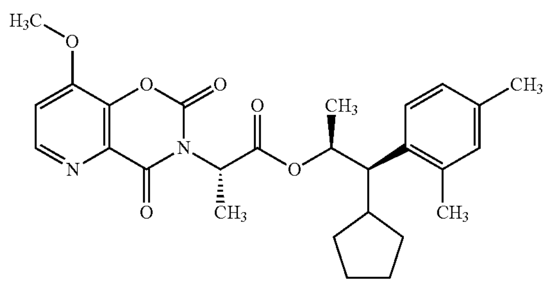 [SMILES: COc1ccnc2c(=O)n([C@@H](C)C(=O)O[C@@H](C)[C@@H](c3ccc(C)cc3C)C3CCCC3)c(=O)oc12] | Example 14 | Orange Oil |
| 210 | 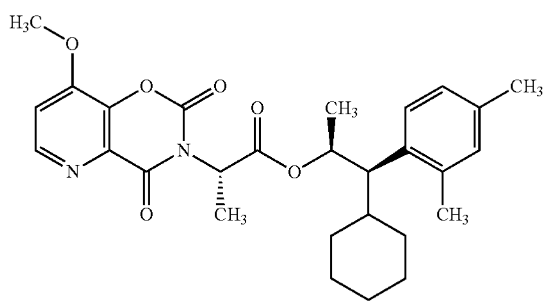 [SMILES: COc1ccnc2c(=O)n([C@@H](C)C(=O)O[C@@H](C)[C@@H](c3ccc(C)cc3C)C3CCCCC3)c(=O)oc12] | Example 14 | Orange Foam |
| 211 | 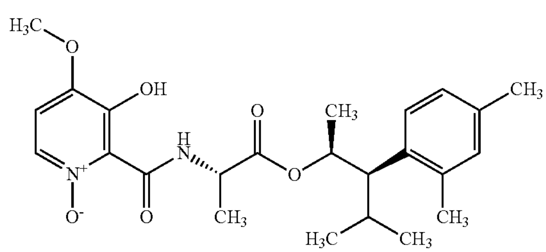 [SMILES: COc1cc[n+]([O-])c(C(=O)N[C@@H](C)C(=O)O[C@@H](C)[C@@H](c2ccc(C)cc2C)C(C)C)c1O] | Example 13 | Colorless Oil |
| 212 | 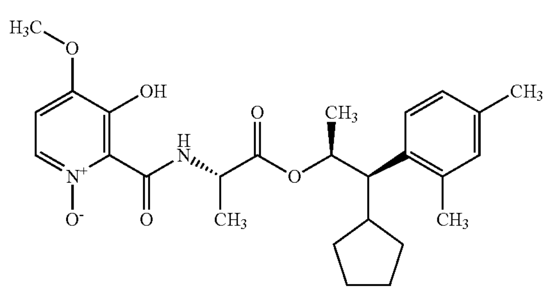 [SMILES: COc1cc[n+]([O-])c(C(=O)N[C@@H](C)C(=O)O[C@@H](C)[C@@H](c2ccc(C)cc2C)C2CCCC2)c1O] | Example 13 | Colorless Oil |

TABLE 1-continued

Compound Structure, Appearance, and Preparation Method

| Cmpd. No. | Structure | As Prepared According To | Appearance |
|---|---|---|---|
| 213 | 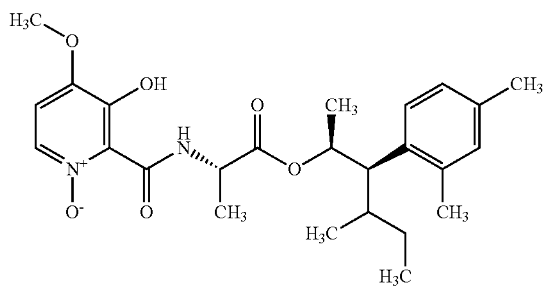 [SMILES: CCC(C)[C@H](c1ccc(C)cc1C)[C@H](C)OC(=O)[C@H](C)NC(=O)c1c(O)c(OC)cc[n+]1[O-]] | Example 13 | Colorless Oil |
| 214 | 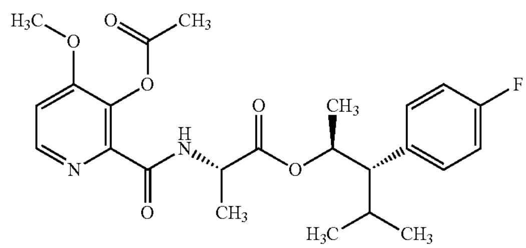 [SMILES: COc1ccnc(C(=O)N[C@@H](C)C(=O)O[C@@H](C)[C@H](c2ccc(F)cc2)C(C)C)c1OC(C)=O] | Example 11A | White Foam |
| 215 | 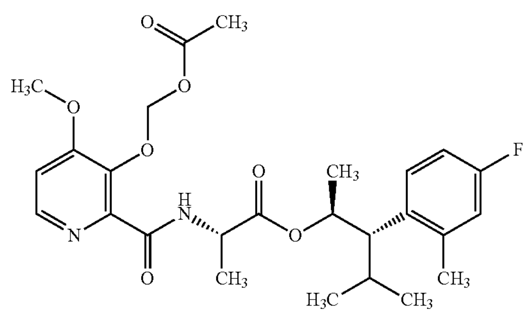 [SMILES: COc1ccnc(C(=O)N[C@@H](C)C(=O)O[C@@H](C)[C@H](c2ccc(F)cc2C)C(C)C)c1OCOC(C)=O] | Example 11B | Pale Yellow Oil |
| 216 | 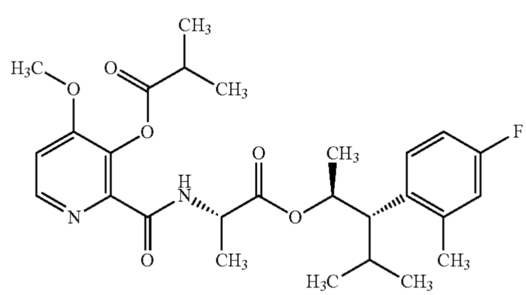 [SMILES: COc1ccnc(C(=O)N[C@@H](C)C(=O)O[C@@H](C)[C@H](c2ccc(F)cc2C)C(C)C)c1OC(=O)C(C)C] | Example 11C | Clear, Colorless Oil |
| 217 | 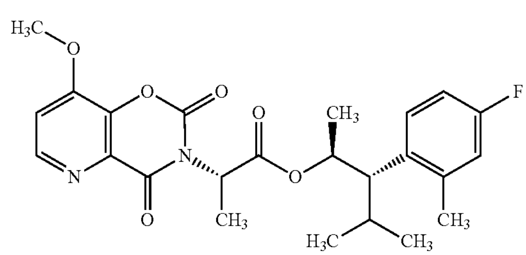 [SMILES: COc1ccnc2c(=O)n([C@@H](C)C(=O)O[C@@H](C)[C@H](c3ccc(F)cc3C)C(C)C)c(=O)oc12] | Example 14 | Pale Yellow Oil |

TABLE 1-continued

Compound Structure, Appearance, and Preparation Method

| Cmpd. No. | Structure | As Prepared According To | Appearance |
|---|---|---|---|
| 218 | 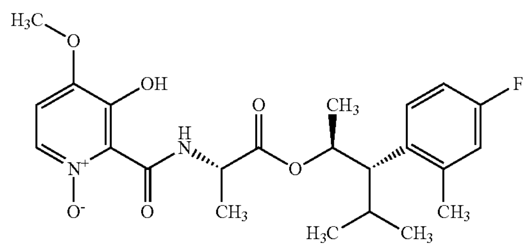 [SMILES: COc1cc[n+]([O-])c(C(=O)N[C@@H](C)C(=O)O[C@@H](C)[C@H](c2ccc(F)cc2C)C(C)C)c1O] | Example 13 | Clear, Colorless Oil |
| 219 | 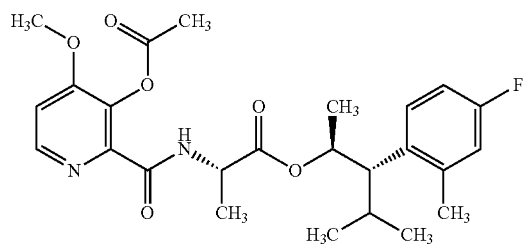 [SMILES: COc1ccnc(C(=O)N[C@@H](C)C(=O)O[C@@H](C)[C@H](c2ccc(F)cc2C)C(C)C)c1OC(C)=O] | Example 12 | Yellow Oil |
| 220 | 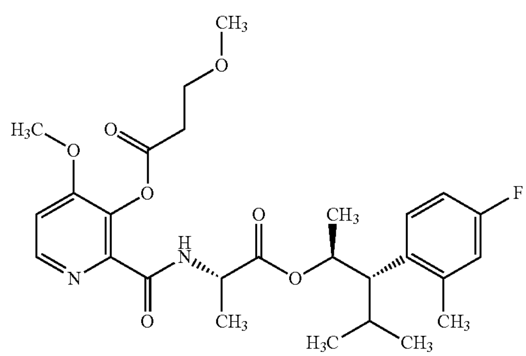 [SMILES: COCCC(=O)Oc1c(OC)ccnc1C(=O)N[C@@H](C)C(=O)O[C@@H](C)[C@H](c1ccc(F)cc1C)C(C)C] | Example 11C | Pale Yellow Oil |
| 221 | 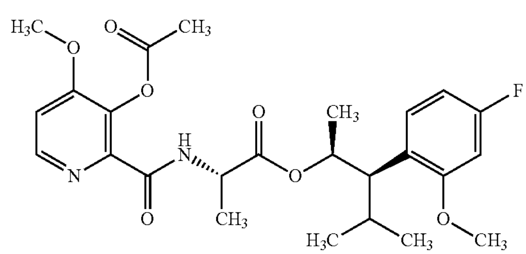 [SMILES: COc1cc(F)ccc1[C@@H](C(C)C)[C@H](C)OC(=O)[C@H](C)NC(=O)c1nccc(OC)c1OC(C)=O] | Example 11A | Pale Yellow Oil |
| 222 | 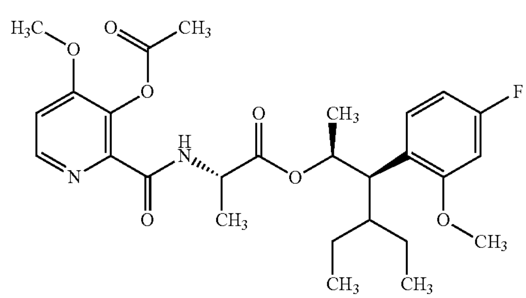 [SMILES: CCC(CC)[C@H](c1ccc(F)cc1OC)[C@H](C)OC(=O)[C@H](C)NC(=O)c1nccc(OC)c1OC(C)=O] | Example 11A | Yellow Oil |

TABLE 1-continued

Compound Structure, Appearance, and Preparation Method

| Cmpd. No. | Structure | As Prepared According To | Appearance |
|---|---|---|---|
| 223 | 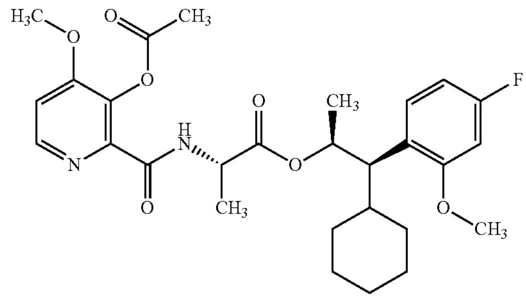 [SMILES: COc1cc(F)ccc1[C@@H](C1CCCCC1)[C@H](C)OC(=O)[C@H](C)NC(=O)c1nccc(OC)c1OC(C)=O] | Example 11A | Clear, Colorless Oil |
| 224 | 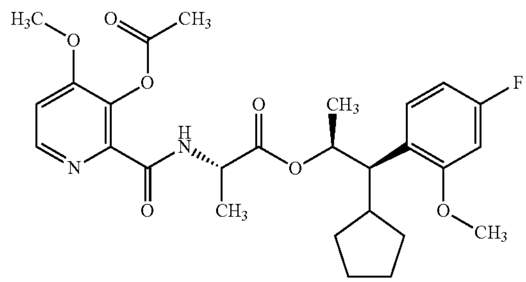 [SMILES: COc1cc(F)ccc1[C@@H](C1CCCC1)[C@H](C)OC(=O)[C@H](C)NC(=O)c1nccc(OC)c1OC(C)=O] | Example 11A | Clear, Colorless Oil |
| 225 | 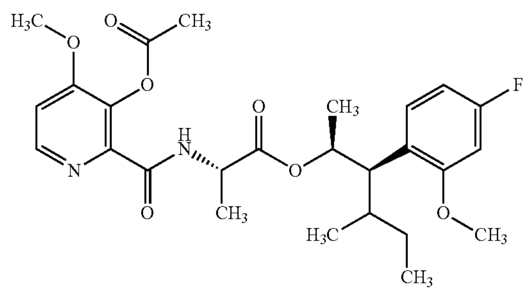 [SMILES: CCC(C)[C@H](c1ccc(F)cc1OC)[C@H](C)OC(=O)[C@H](C)NC(=O)c1nccc(OC)c1OC(C)=O] | Example 11A | Clear, Colorless Oil |
| 226 | 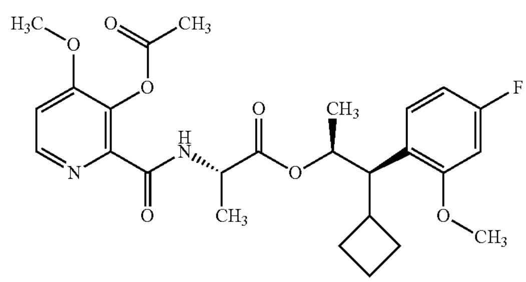 [SMILES: COc1cc(F)ccc1[C@@H](C1CCC1)[C@H](C)OC(=O)[C@H](C)NC(=O)c1nccc(OC)c1OC(C)=O] | Example 11A | Clear, Colorless Oil |
| 227 | 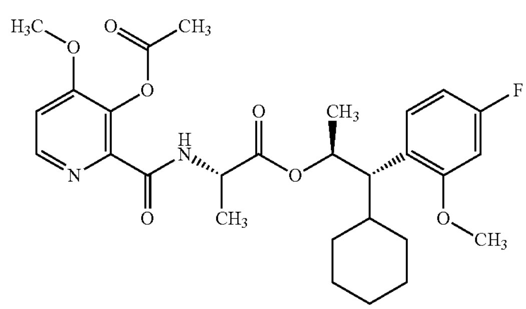 [SMILES: COc1cc(F)ccc1[C@H](C1CCCCC1)[C@H](C)OC(=O)[C@H](C)NC(=O)c1nccc(OC)c1OC(C)=O] | Example 11A | Clear, Colorless Oil |

TABLE 1-continued

Compound Structure, Appearance, and Preparation Method

| Cmpd. No. | Structure | As Prepared According To | Appearance |
|---|---|---|---|
| 228 | 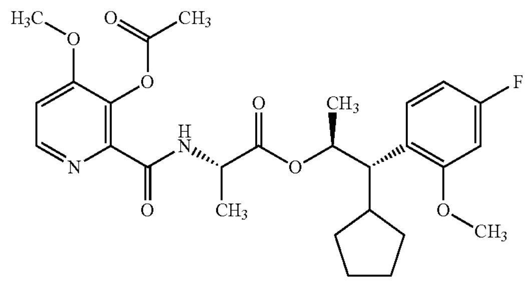 [SMILES: COc1cc(F)ccc1[C@H](C1CCCC1)[C@H](C)OC(=O)[C@H](C)NC(=O)c1nccc(OC)c1OC(C)=O] | Example 11A | Clear, Colorless Oil |
| 229 | 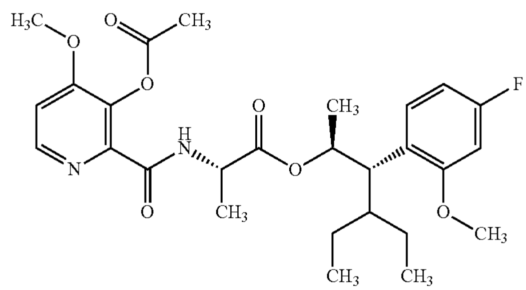 [SMILES: CCC(CC)[C@@H](c1ccc(F)cc1OC)[C@H](C)OC(=O)[C@H](C)NC(=O)c1nccc(OC)c1OC(C)=O] | Example 11A | Clear, Colorless Oil |
| 230 | 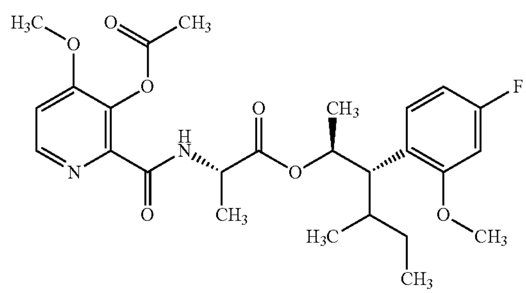 [SMILES: CCC(C)[C@@H](c1ccc(F)cc1OC)[C@H](C)OC(=O)[C@H](C)NC(=O)c1nccc(OC)c1OC(C)=O] | Example 11A | Clear, Colorless Oil |
| 231 | 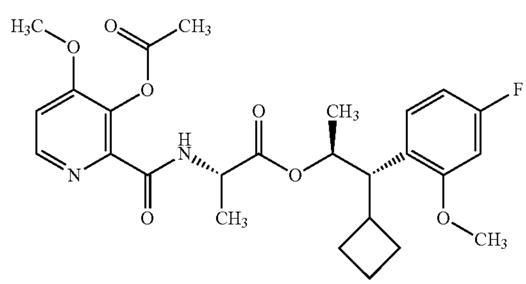 [SMILES: COc1cc(F)ccc1[C@H](C1CCC1)[C@H](C)OC(=O)[C@H](C)NC(=O)c1nccc(OC)c1OC(C)=O] | Example 11A | Clear, Colorless Oil |
| 232 | 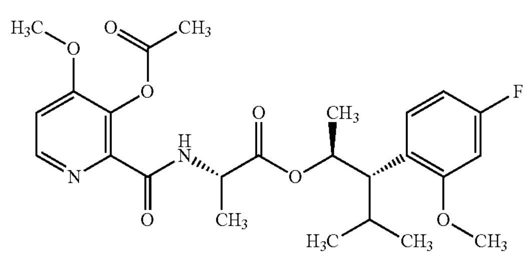 [SMILES: COc1cc(F)ccc1[C@H](C(C)C)[C@H](C)OC(=O)[C@H](C)NC(=O)c1nccc(OC)c1OC(C)=O] | Example 11A | Clear, Colorless Oil |

TABLE 1-continued

Compound Structure, Appearance, and Preparation Method

| Cmpd. No. | Structure | As Prepared According To | Appearance |
|---|---|---|---|
| 233 | 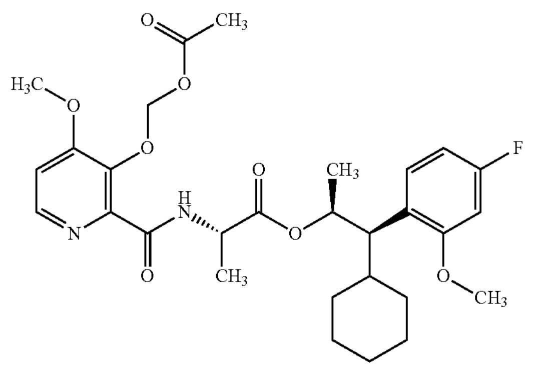 [SMILES: COc1cc(F)ccc1[C@@H](C1CCCCC1)[C@H](C)OC(=O)[C@H](C)NC(=O)c1nccc(OC)c1OCOC(C)=O] | Example 11B | Clear, Colorless Oil |
| 234 | 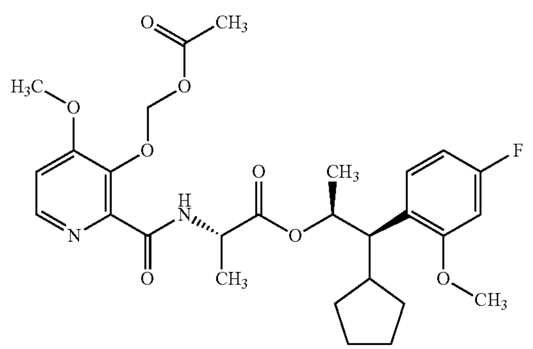 [SMILES: COc1cc(F)ccc1[C@@H](C1CCCC1)[C@H](C)OC(=O)[C@H](C)NC(=O)c1nccc(OC)c1OCOC(C)=O] | Example 11B | Clear, Colorless Oil |
| 235 | 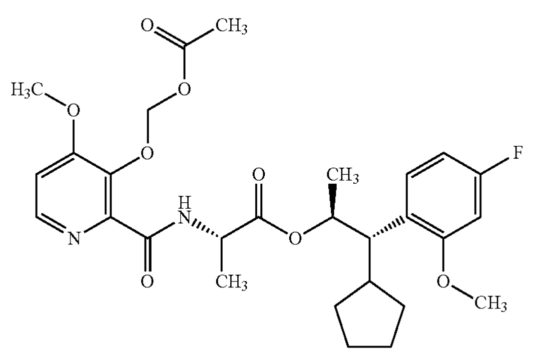 [SMILES: COc1cc(F)ccc1[C@H](C1CCCC1)[C@H](C)OC(=O)[C@H](C)NC(=O)c1nccc(OC)c1OCOC(C)=O] | Example 11B | Clear, Colorless Oil |
| 236 | 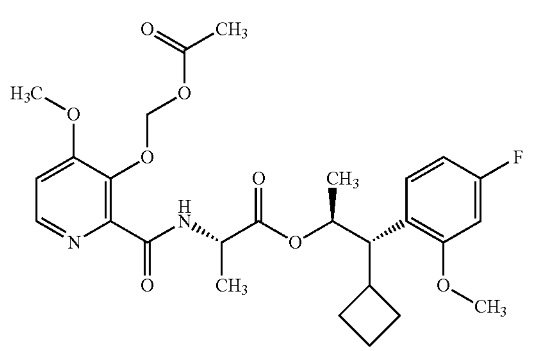 [SMILES: COc1cc(F)ccc1[C@H](C1CCC1)[C@H](C)OC(=O)[C@H](C)NC(=O)c1nccc(OC)c1OCOC(C)=O] | Example 11B | Clear, Colorless Oil |

TABLE 1-continued

Compound Structure, Appearance, and Preparation Method

| Cmpd. No. | Structure | As Prepared According To | Appearance |
|---|---|---|---|
| 237 | 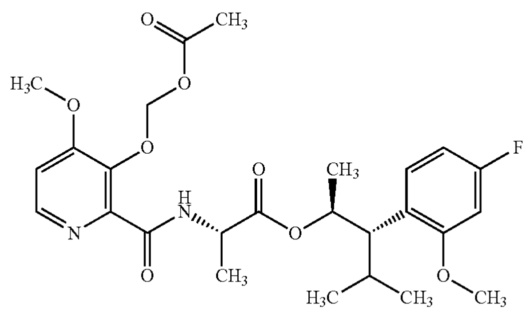 [SMILES: COc1cc(F)ccc1[C@H](C(C)C)[C@H](C)OC(=O)[C@H](C)NC(=O)c1nccc(OC)c1OCOC(C)=O] | Example 11B | Clear, Colorless Oil |
| 238 | 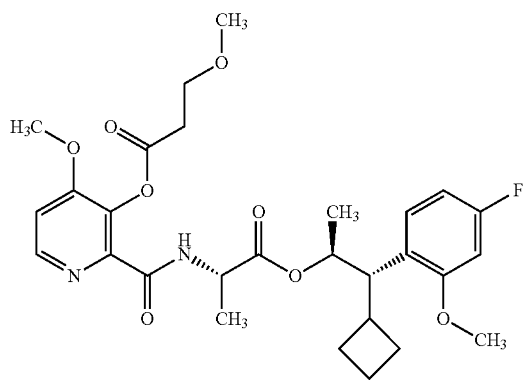 [SMILES: COCCC(=O)Oc1c(OC)ccnc1C(=O)N[C@@H](C)C(=O)O[C@@H](C)[C@H](c1ccc(F)cc1OC)C1CCC1] | Example 11C | Clear, Colorless Oil |
| 239 | 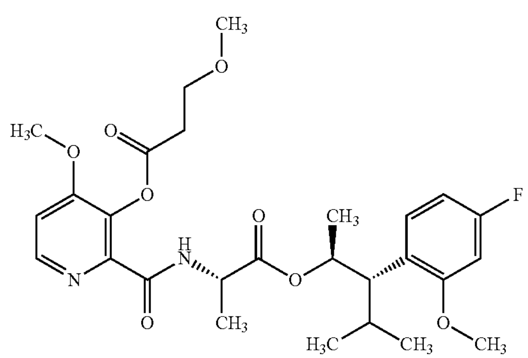 [SMILES: COCCC(=O)Oc1c(OC)ccnc1C(=O)N[C@@H](C)C(=O)O[C@@H](C)[C@H](c1ccc(F)cc1OC)C(C)C] | Example 11C | Clear, Colorless Oil |
| 240 | 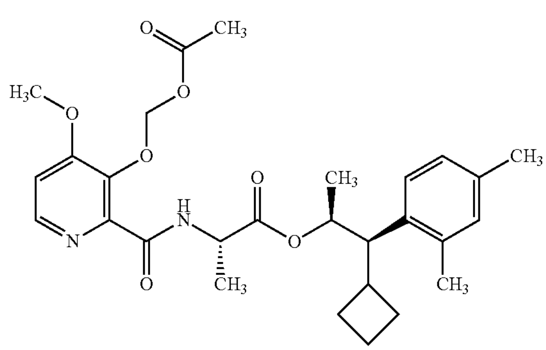 [SMILES: COc1ccnc(C(=O)N[C@@H](C)C(=O)O[C@@H](C)[C@@H](c2ccc(C)cc2C)C2CCC2)c1OCOC(C)=O] | Example 11B | Yellow Oil |

TABLE 1-continued

Compound Structure, Appearance, and Preparation Method

| Cmpd. No. | Structure | As Prepared According To | Appearance |
|---|---|---|---|
| 241 | 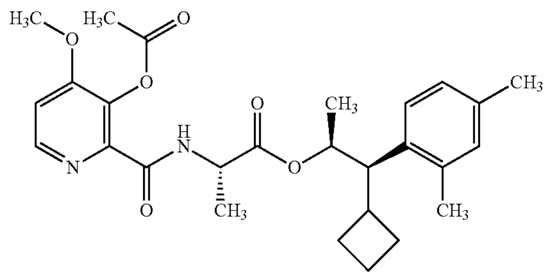 [SMILES: COc1ccnc(C(=O)N[C@@H](C)C(=O)O[C@@H](C)[C@@H](c2ccc(C)cc2C)C2CCC2)c1OC(C)=O] | Example 11A | Colorless Oil |
| 242 | 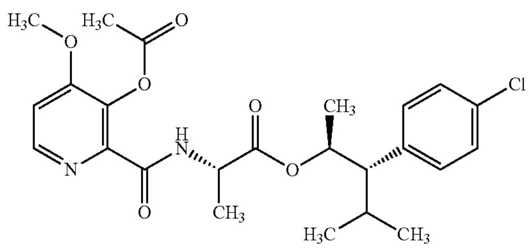 [SMILES: COc1ccnc(C(=O)N[C@@H](C)C(=O)O[C@@H](C)[C@H](c2ccc(Cl)cc2)C(C)C)c1OC(C)=O] | Example 11A | Thick Oil |
| 243 | 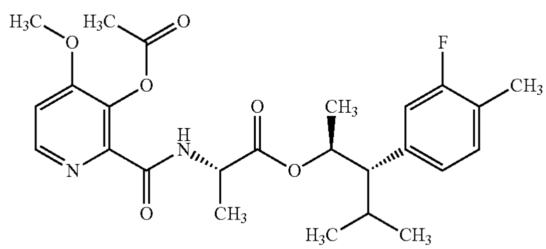 [SMILES: COc1ccnc(C(=O)N[C@@H](C)C(=O)O[C@@H](C)[C@H](c2ccc(C)c(F)c2)C(C)C)c1OC(C)=O] | Example 11A | White Foam |
| 244 | 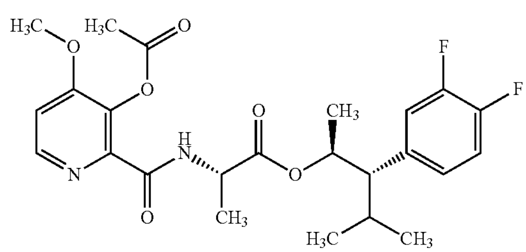 [SMILES: COc1ccnc(C(=O)N[C@@H](C)C(=O)O[C@@H](C)[C@H](c2ccc(F)c(F)c2)C(C)C)c1OC(C)=O] | Example 11A | Thick Oil |
| 245 | 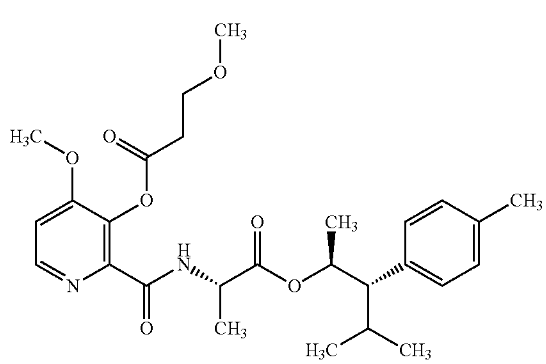 [SMILES: COCCC(=O)Oc1c(OC)ccnc1C(=O)N[C@@H](C)C(=O)O[C@@H](C)[C@H](c1ccc(C)cc1)C(C)C] | Example 11C | Pale Yellow Oil |

TABLE 1-continued
Compound Structure, Appearance, and Preparation Method
| Cmpd. No. | Structure | As Prepared According To | Appearance |
|---|---|---|---|
| 246 | 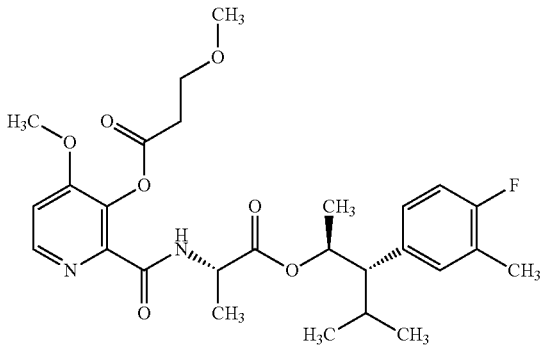 [SMILES: COCCC(=O)Oc1c(OC)ccnc1C(=O)N[C@@H](C)C(=O)O[C@@H](C)[C@H](c1ccc(F)c(C)c1)C(C)C] | Example 11C | Clear, Colorless Oil |
| 247 | 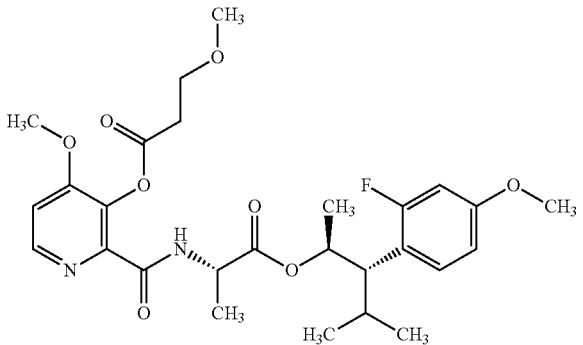 [SMILES: COCCC(=O)Oc1c(OC)ccnc1C(=O)N[C@@H](C)C(=O)O[C@@H](C)[C@H](c1ccc(OC)cc1F)C(C)C] | Example 11C | Pale Yellow Oil |
| 248 | 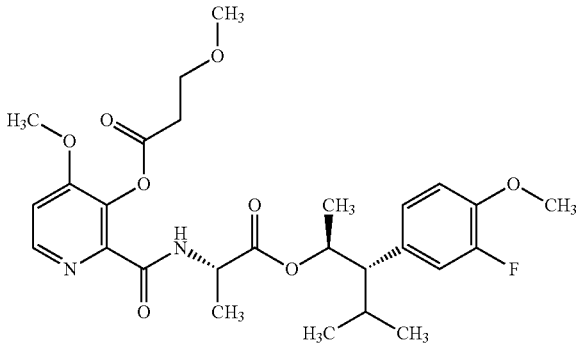 [SMILES: COCCC(=O)Oc1c(OC)ccnc1C(=O)N[C@@H](C)C(=O)O[C@@H](C)[C@H](c1ccc(OC)c(F)c1)C(C)C] | Example 11C | Pale Yellow Oil |
| 249 | 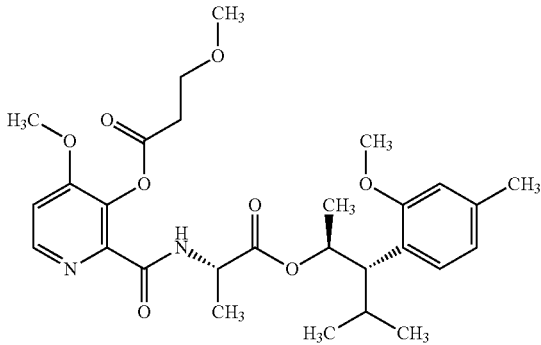 [SMILES: COCCC(=O)Oc1c(OC)ccnc1C(=O)N[C@@H](C)C(=O)O[C@@H](C)[C@H](c1ccc(C)cc1OC)C(C)C] | Example 11C | Clear, Colorless Oil |

TABLE 1-continued

Compound Structure, Appearance, and Preparation Method

| Cmpd. No. | Structure | As Prepared According To | Appearance |
|---|---|---|---|
| 250 | 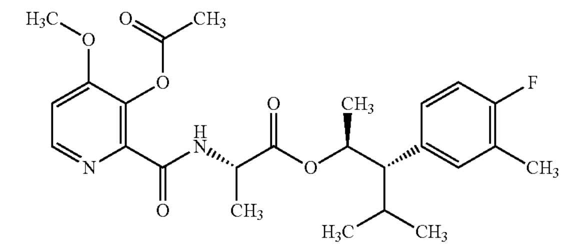 | Example 11A | Clear, Colorless Oil |
| 251 | 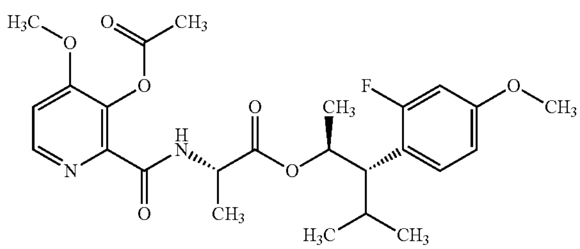 [SMILES: COc1ccc([C@H](C(C)C)[C@H](C)OC(=O)[C@H](C)NC(=O)c2nccc(OC)c2OC(C)=O)c(F)c1] | Example 11A | Clear, Colorless Oil |
| 252 | 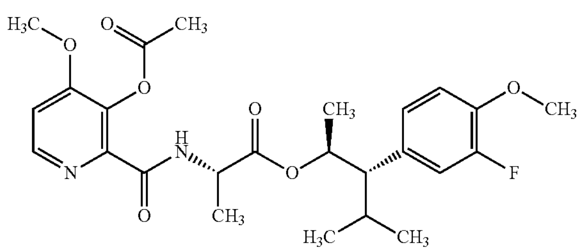 [SMILES: COc1ccc([C@H](C(C)C)[C@H](C)OC(=O)[C@H](C)NC(=O)c2nccc(OC)c2OC(C)=O)cc1F] | Example 11A | Clear, Colorless Oil |
| 253 | 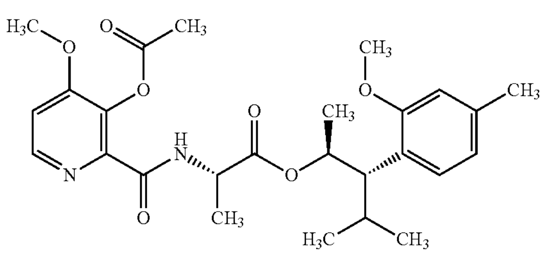 [SMILES: COc1cc(C)ccc1[C@H](C(C)C)[C@H](C)OC(=O)[C@H](C)NC(=O)c1nccc(OC)c1OC(C)=O] | Example 11A | Clear, Colorless Oil |
| 254 | 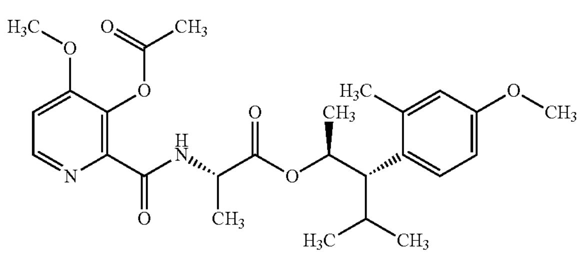 [SMILES: COc1ccc([C@H](C(C)C)[C@H](C)OC(=O)[C@H](C)NC(=O)c2nccc(OC)c2OC(C)=O)c(C)c1] | Example 11A | Clear, Colorless Oil |

TABLE 1-continued

Compound Structure, Appearance, and Preparation Method

| Cmpd. No. | Structure | As Prepared According To | Appearance |
|---|---|---|---|
| 255 | 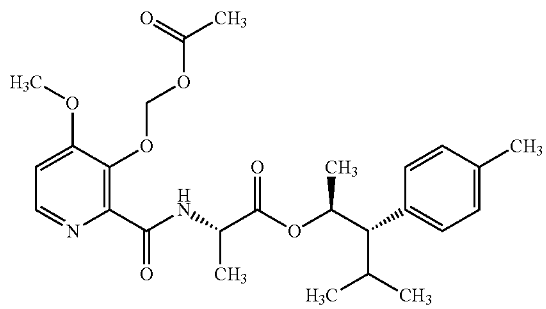 [SMILES: COc1ccnc(C(=O)N[C@@H](C)C(=O)O[C@@H](C)[C@H](c2ccc(C)cc2)C(C)C)c1OCOC(C)=O] | Example 11B | Clear, Colorless Oil |
| 256 | 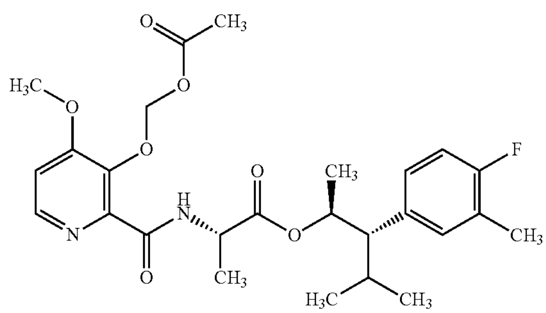 [SMILES: COc1ccnc(C(=O)N[C@@H](C)C(=O)O[C@@H](C)[C@H](c2ccc(F)c(C)c2)C(C)C)c1OCOC(C)=O] | Example 11B | Clear, Colorless Oil |
| 257 | 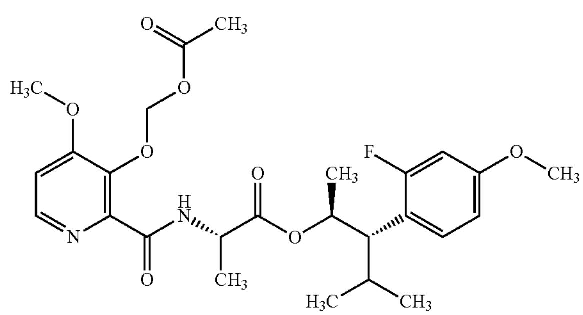 [SMILES: COc1ccc([C@H](C(C)C)[C@H](C)OC(=O)[C@H](C)NC(=O)c2nccc(OC)c2OCOC(C)=O)c(F)c1] | Example 11B | Clear, Colorless Oil |
| 258 | 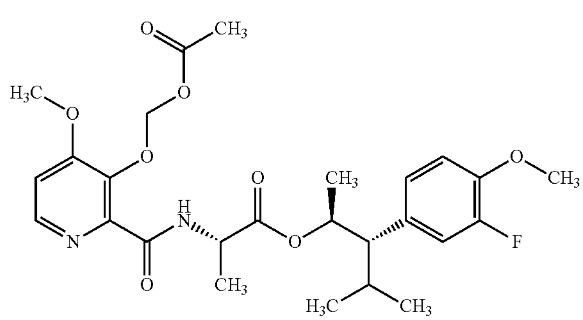 [SMILES: COc1ccc([C@H](C(C)C)[C@H](C)OC(=O)[C@H](C)NC(=O)c2nccc(OC)c2OCOC(C)=O)cc1F] | Example 11B | Clear, Colorless Oil |

TABLE 1-continued

Compound Structure, Appearance, and Preparation Method

| Cmpd. No. | Structure | As Prepared According To | Appearance |
|---|---|---|---|
| 259 | 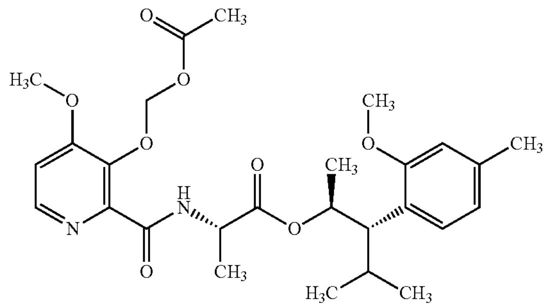 [SMILES: COc1cc(C)ccc1[C@H](C(C)C)[C@H](C)OC(=O)[C@H](C)NC(=O)c1nccc(OC)c1OCOC(C)=O] | Example 11B | Clear, Colorless Oil |
| 260 | 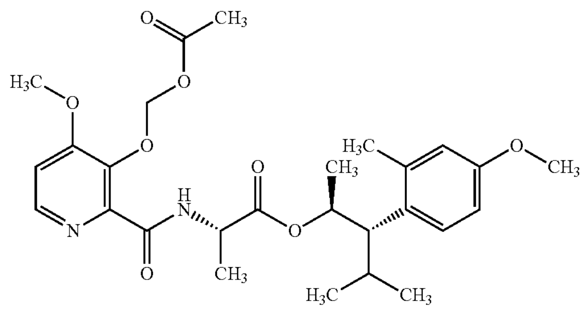 [SMILES: COc1ccc([C@H](C(C)C)[C@H](C)OC(=O)[C@H](C)NC(=O)c2nccc(OC)c2OCOC(C)=O)c(C)c1] | Example 11B | Clear, Colorless Oil |
| 261 | 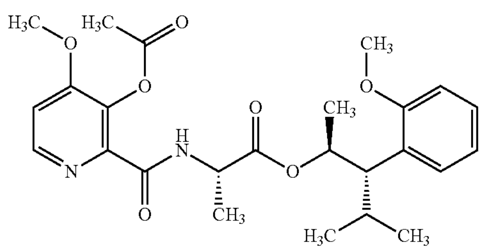 [SMILES: COc1ccccc1[C@H](C(C)C)[C@H](C)OC(=O)[C@H](C)NC(=O)c1nccc(OC)c1OC(C)=O] | Example 11A | Colorless Oil |
| 262 | 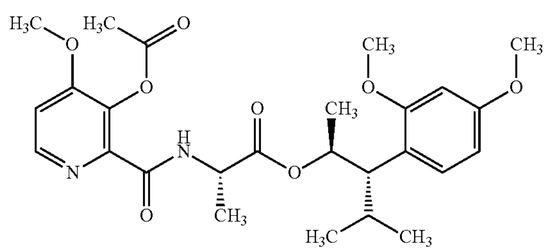 [SMILES: COc1ccc([C@H](C(C)C)[C@H](C)OC(=O)[C@H](C)NC(=O)c2nccc(OC)c2OC(C)=O)c(OC)c1] | Example 11A | Colorless Oil |
| 263 | 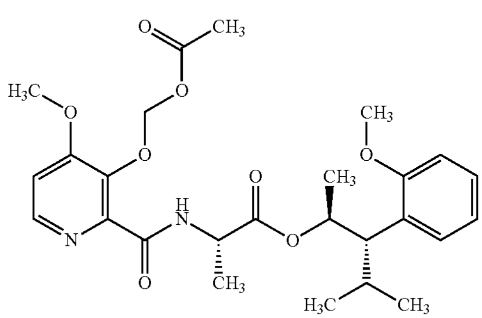 [SMILES: COc1ccccc1[C@H](C(C)C)[C@H](C)OC(=O)[C@H](C)NC(=O)c1nccc(OC)c1OCOC(C)=O] | Example 11B | Yellow Oil |

TABLE 1-continued

Compound Structure, Appearance, and Preparation Method

| Cmpd. No. | Structure | As Prepared According To | Appearance |
|---|---|---|---|
| 264 | 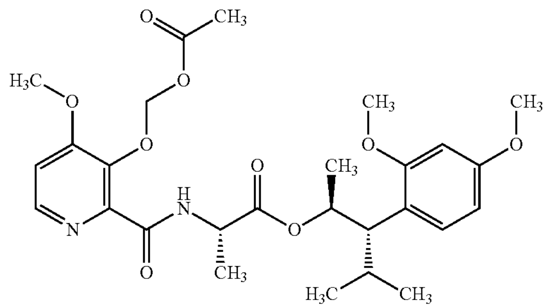 [SMILES: COc1ccc([C@H](C(C)C)[C@H](C)OC(=O)[C@H](C)NC(=O)c2nccc(OC)c2OCOC(C)=O)c(OC)c1] | Example 11B | Yellow Oil |
| 265 | 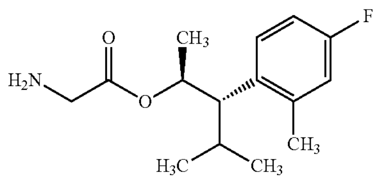 [SMILES: Cc1cc(F)ccc1[C@H](C(C)C)[C@H](C)OC(=O)CN] | Example 10 Steps 1 | Clear, Colorless Oil |
| 266 | 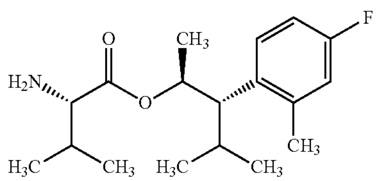 [SMILES: Cc1cc(F)ccc1[C@H](C(C)C)[C@H](C)OC(=O)[C@@H](N)C(C)C] | Example 10 Steps 1 | Clear, Colorless Oil |
| 267 | 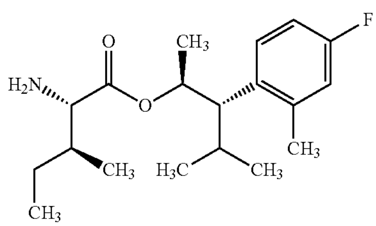 [SMILES: CC[C@H](C)[C@H](N)C(=O)O[C@@H](C)[C@H](c1ccc(F)cc1C)C(C)C] | Example 10 Steps 1 | Clear, Colorless Oil |
| 268 | 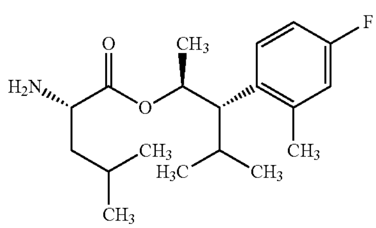 [SMILES: Cc1cc(F)ccc1[C@H](C(C)C)[C@H](C)OC(=O)[C@@H](N)CC(C)C] | Example 10 Steps 1 | White Semisolid |
| 269 | 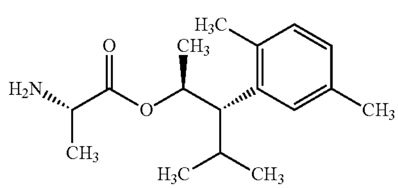 [SMILES: Cc1ccc(C)c([C@H](C(C)C)[C@H](C)OC(=O)[C@H](C)N)c1] | Example 10 Steps 1 | White Solid |
| 270 | 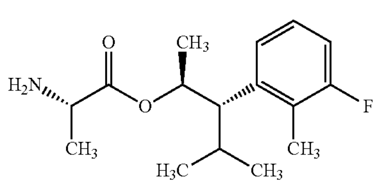 | Example 10 Steps 1 | White Solid |

TABLE 1-continued

Compound Structure, Appearance, and Preparation Method

| Cmpd. No. | Structure | As Prepared According To | Appearance |
|---|---|---|---|
| 271 | 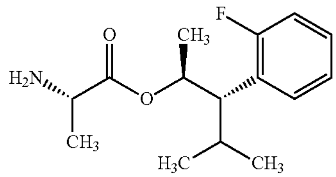 [SMILES: CC(C)[C@@H](c1ccccc1F)[C@H](C)OC(=O)[C@H](C)N] | Example 10 Steps 1 | White Solid |
| 272 | 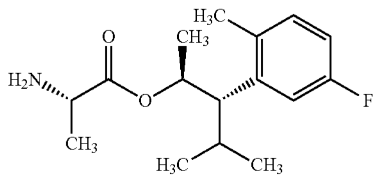 [SMILES: Cc1ccc(F)cc1[C@H](C(C)C)[C@H](C)OC(=O)[C@H](C)N] | Example 10 Steps 1 | White Solid |
| 273 | 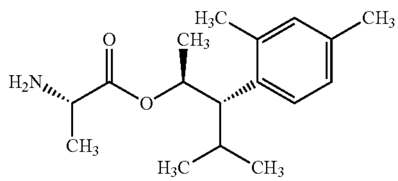 [SMILES: Cc1ccc([C@H](C(C)C)[C@H](C)OC(=O)[C@H](C)N)c(C)c1] | Example 10 Steps 1 | White Solid |
| 274 | 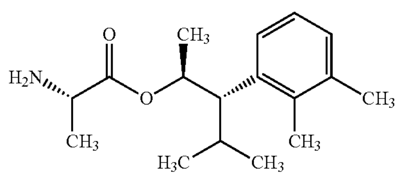 [SMILES: Cc1cccc([C@H](C(C)C)[C@H](C)OC(=O)[C@H](C)N)c1C] | Example 10 Steps 1 | White Solid |
| 275 | 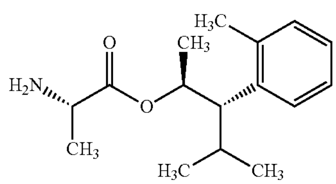 | Example 10 Steps 1 | White Solid |
| 276 | 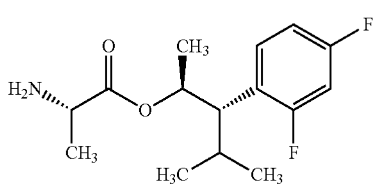 [SMILES: CC(C)[C@@H](c1ccc(F)cc1F)[C@H](C)OC(=O)[C@H](C)N] | Example 10 Steps 1 | Thick Oil |
| 277 | 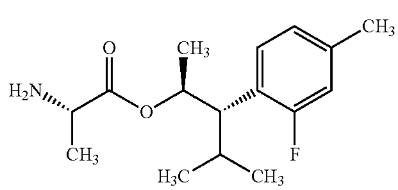 [SMILES: Cc1ccc([C@H](C(C)C)[C@H](C)OC(=O)[C@H](C)N)c(F)c1] | Example 10 Steps 1 | Thick Oil |
| 278 | 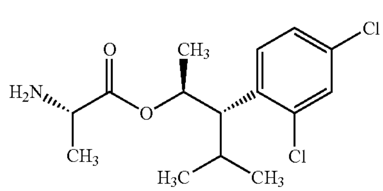 [SMILES: CC(C)[C@@H](c1ccc(Cl)cc1Cl)[C@H](C)OC(=O)[C@H](C)N] | Example 10 Steps 1 | Thick Oil |

TABLE 1-continued

Compound Structure, Appearance, and Preparation Method

| Cmpd. No. | Structure | As Prepared According To | Appearance |
|---|---|---|---|
| 279 | 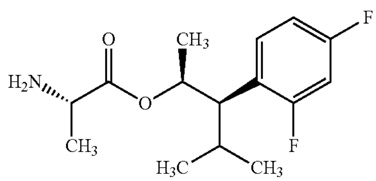 [SMILES: CC(C)[C@H](c1ccc(F)cc1F)[C@H](C)OC(=O)[C@H](C)N] | Example 10 Steps 1 | Thick Oil |
| 280 | 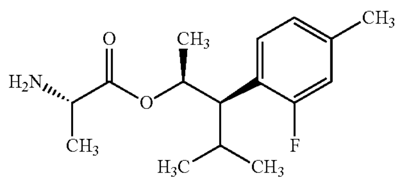 [SMILES: Cc1ccc([C@@H](C(C)C)[C@H](C)OC(=O)[C@H](C)N)c(F)c1] | Example 10 Steps 1 | Thick Oil |
| 281 | 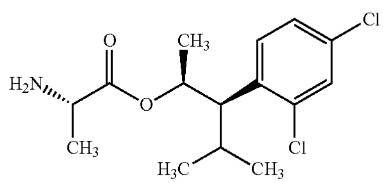 [SMILES: CC(C)[C@H](c1ccc(Cl)cc1Cl)[C@H](C)OC(=O)[C@H](C)N] | Example 10 Steps 1 | Thick Oil |
| 282 | 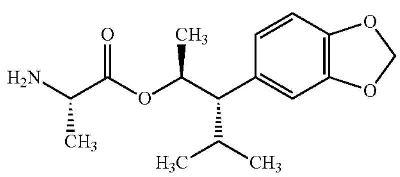 [SMILES: CC(C)[C@@H](c1ccc2c(c1)OCO2)[C@H](C)OC(=O)[C@H](C)N] | Example 10 Steps 1 | Yellow Oil |
| 283 | 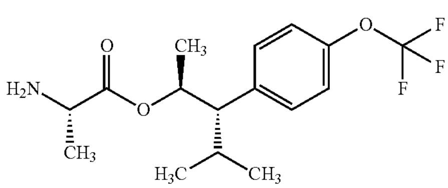 [SMILES: CC(C)[C@@H](c1ccc(OC(F)(F)F)cc1)[C@H](C)OC(=O)[C@H](C)N] | Example 10 Steps 1 | Colorless Semi-Solid |
| 284 | 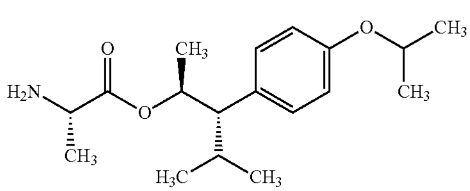 [SMILES: CC(C)Oc1ccc([C@H](C(C)C)[C@H](C)OC(=O)[C@H](C)N)cc1] | Example 10 Steps 1 | Yellow Oil |
| 285 | 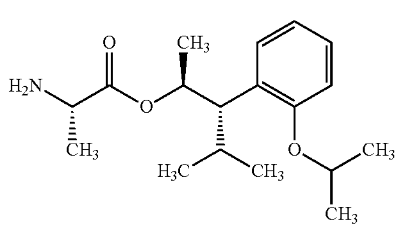 [SMILES: CC(C)Oc1ccccc1[C@H](C(C)C)[C@H](C)OC(=O)[C@H](C)N] | Example 10 Steps 1 | Yellow Oil |

TABLE 1-continued

Compound Structure, Appearance, and Preparation Method

| Cmpd. No. | Structure | As Prepared According To | Appearance |
|---|---|---|---|
| 286 | 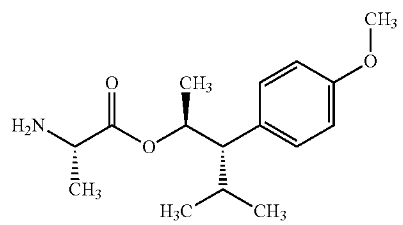 [SMILES: COc1ccc([C@H](C(C)C)[C@H](C)OC(=O)[C@H](C)N)cc1] | Example 10 Steps 1 | Colorless Oil |
| 287 | 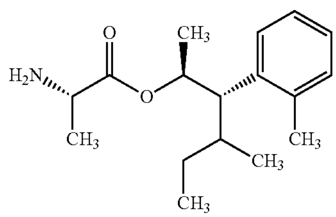 [SMILES: CCC(C)[C@@H](c1ccccc1C)[C@H](C)OC(=O)[C@H](C)N] | Example 10 Steps 1 | Residue |
| 288 | 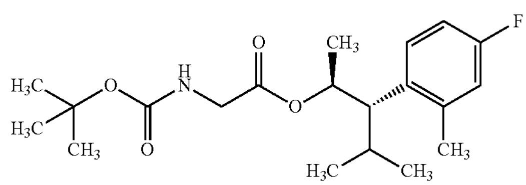 [SMILES: Cc1cc(F)ccc1[C@H](C(C)C)[C@H](C)OC(=O)CNC(=O)OC(C)(C)C] | Example 1D Example 2B Example 4A Example 4B Example 7 Example 8 | Clear, Colorless Oil |
| 289 | 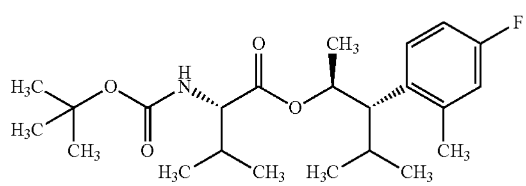 [SMILES: Cc1cc(F)ccc1[C@H](C(C)C)[C@H](C)OC(=O)[C@@H](NC(=O)OC(C)(C)C)C(C)C] | Example 1D Example 2B Example 4A Example 4B Example 7 Example 8 | Clear, Colorless Oil |
| 290 | 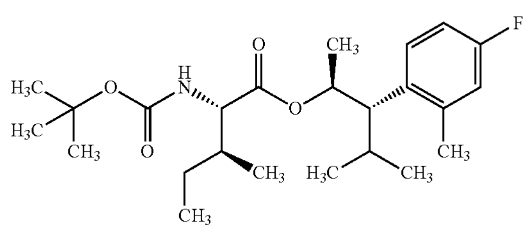 [SMILES: CC[C@H](C)[C@H](NC(=O)OC(C)(C)C)C(=O)O[C@@H](C)[C@H](c1ccc(F)cc1C)C(C)C] | Example 1D Example 2B Example 4A Example 4B Example 7 Example 8 | White Semisolid |
| 291 | 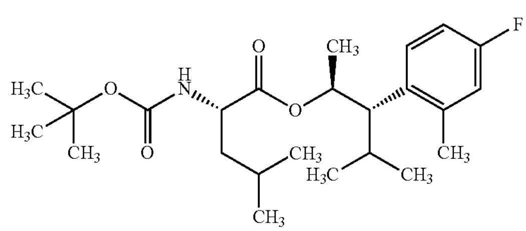 [SMILES: Cc1cc(F)ccc1[C@H](C(C)C)[C@H](C)OC(=O)[C@H](CC(C)C)NC(=O)OC(C)(C)C] | Example 1D Example 2B Example 4A Example 4B Example 7 Example 8 | Clear, Colorless Oil |
| 292 | 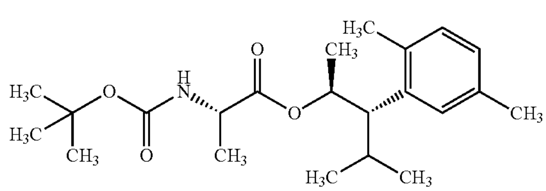 [SMILES: Cc1ccc(C)c([C@H](C(C)C)[C@H](C)OC(=O)[C@H](C)NC(=O)OC(C)(C)C)c1] | Example 6A Example 7 Example 8 | Colorless Oil |

TABLE 1-continued

Compound Structure, Appearance, and Preparation Method

| Cmpd. No. | Structure | As Prepared According To | Appearance |
|---|---|---|---|
| 293 | 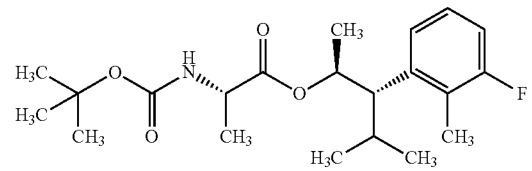 [SMILES: Cc1c(F)cccc1[C@H](C(C)C)[C@H](C)OC(=O)[C@H](C)NC(=O)OC(C)(C)C] | Example 6A Example 7 Example 8 | Colorless Oil |
| 294 | 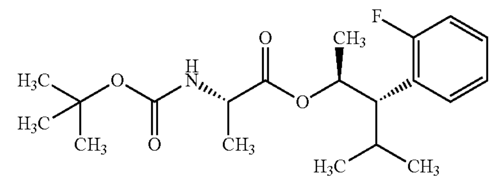 | Example 6A Example 7 Example 8 | Colorless Oil |
| 295 | 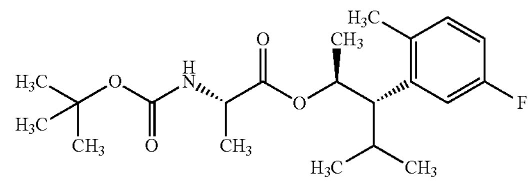 [SMILES: Cc1ccc(F)cc1[C@H](C(C)C)[C@H](C)OC(=O)[C@H](C)NC(=O)OC(C)(C)C] | Example 6A Example 7 Example 8 | Colorless Oil |
| 296 | 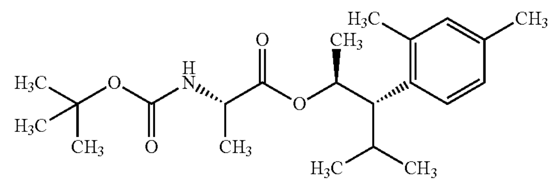 [SMILES: Cc1ccc([C@H](C(C)C)[C@H](C)OC(=O)[C@H](C)NC(=O)OC(C)(C)C)c(C)c1] | Example 6A Example 7 Example 8 | Colorless Oil |
| 297 | 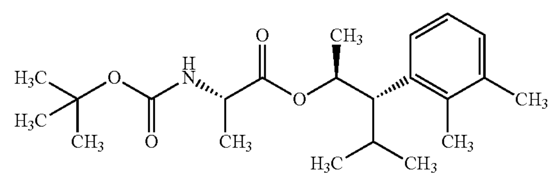 [SMILES: Cc1cccc([C@H](C(C)C)[C@H](C)OC(=O)[C@H](C)NC(=O)OC(C)(C)C)c1C] | Example 6A Example 7 Example 8 | Colorless Oil |
| 298 | 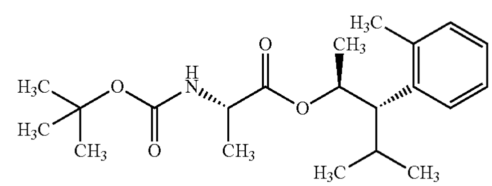 | Example 6A Example 7 Example 8 | Colorless Oil |
| 299 | 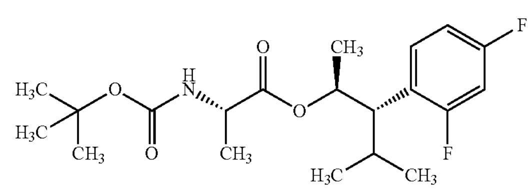 [SMILES: CC(C)[C@@H](c1ccc(F)cc1F)[C@H](C)OC(=O)[C@H](C)NC(=O)OC(C)(C)C] | Example 6A Example 7 Example 8 | Oil |
| 300 | 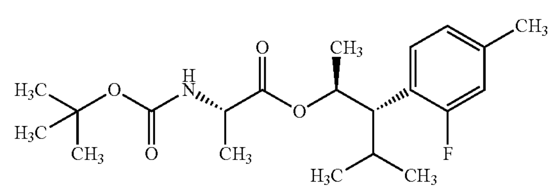 [SMILES: Cc1ccc([C@H](C(C)C)[C@H](C)OC(=O)[C@H](C)NC(=O)OC(C)(C)C)c(F)c1] | Example 6A Example 7 Example 8 | Oil |

TABLE 1-continued

Compound Structure, Appearance, and Preparation Method

| Cmpd. No. | Structure | As Prepared According To | Appearance |
|---|---|---|---|
| 301 | 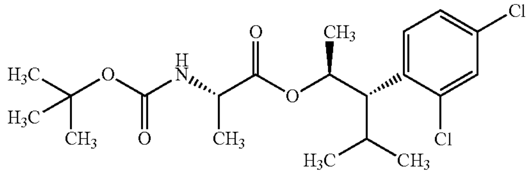 | Example 6A<br>Example 7<br>Example 8 | Oil |
| 302 | 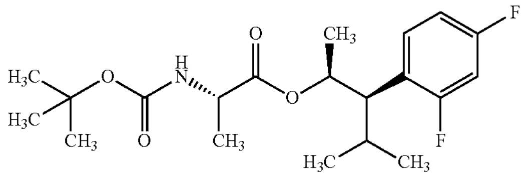 [SMILES: CC(C)[C@H](c1ccc(F)cc1F)[C@H](C)OC(=O)[C@H](C)NC(=O)OC(C)(C)C] | Example 6A<br>Example 7<br>Example 8 | Colorless Oil |
| 303 | 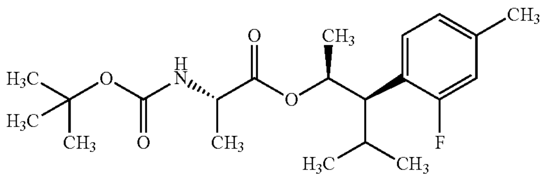 [SMILES: Cc1ccc([C@@H](C(C)C)[C@H](C)OC(=O)[C@H](C)NC(=O)OC(C)(C)C)c(F)c1] | Example 6A<br>Example 7<br>Example 8 | Oil |
| 304 | 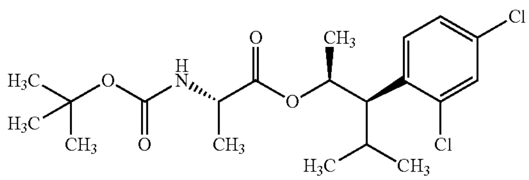 [SMILES: CC(C)[C@H](c1ccc(Cl)cc1Cl)[C@H](C)OC(=O)[C@H](C)NC(=O)OC(C)(C)C] | Example 6A<br>Example 7<br>Example 8 | Oil |
| 305 | 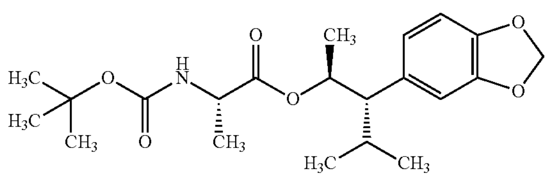 [SMILES: CC(C)[C@@H](c1ccc2c(c1)OCO2)[C@H](C)OC(=O)[C@H](C)NC(=O)OC(C)(C)C] | Example 6<br>Steps 2A, 6, 7, 4, 5<br>Example 7<br>Example 8 | Colorless Oil |
| 306 | 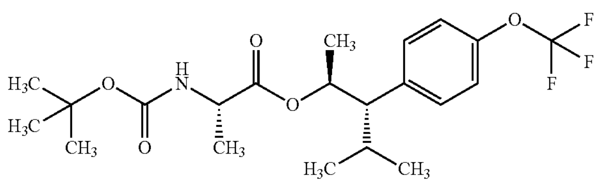 [SMILES: CC(C)[C@@H](c1ccc(OC(F)(F)F)cc1)[C@H](C)OC(=O)[C@H](C)NC(=O)OC(C)(C)C] | Example 6<br>Steps 2A, 6, 7, 4, 5<br>Example 7<br>Example 8 | Colorless Oil |
| 307 | 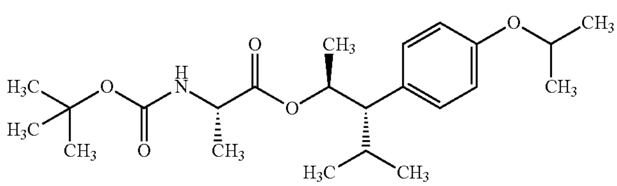 [SMILES: CC(C)Oc1ccc([C@H](C(C)C)[C@H](C)OC(=O)[C@H](C)NC(=O)OC(C)(C)C)cc1] | Example 6<br>Steps 2A, 6, 7, 4, 5<br>Example 7<br>Example 8 | White Wax |
| 308 | 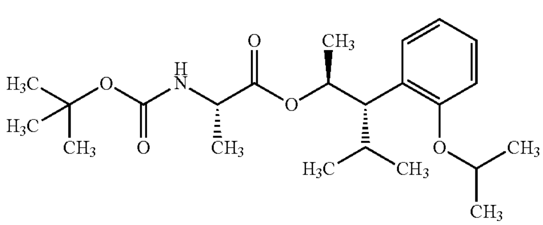 [SMILES: CC(C)Oc1ccccc1[C@H](C(C)C)[C@H](C)OC(=O)[C@H](C)NC(=O)OC(C)(C)C] | Example 6<br>Steps 2A, 6, 7, 4, 5<br>Example 7<br>Example 8 | Colorless Oil |

TABLE 1-continued

Compound Structure, Appearance, and Preparation Method

| Cmpd. No. | Structure | As Prepared According To | Appearance |
|---|---|---|---|
| 309 | 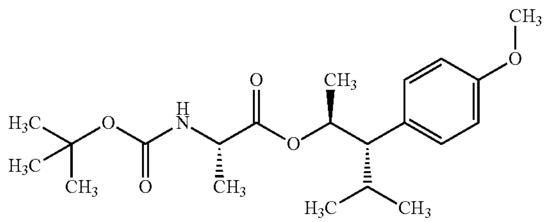 [SMILES: COc1ccc([C@H](C(C)C)[C@H](C)OC(=O)[C@H](C)NC(=O)OC(C)(C)C)cc1] | Example 6 Steps 1, 2, 6, 7, 4, 5 Example 8 | Colorless Oil |
| 310 | 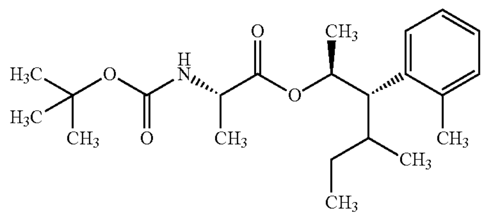 [SMILES: CCC(C)[C@@H](c1ccccc1C)[C@H](C)OC(=O)[C@H](C)NC(=O)OC(C)(C)C] | Example 1E Example 2B Example 3B Example 7 Example 8 | Residue |
| 311 | 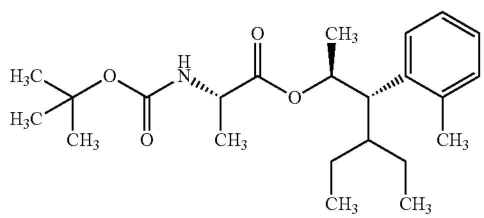 [SMILES: CCC(CC)[C@@H](c1ccccc1C)[C@H](C)OC(=O)[C@H](C)NC(=O)OC(C)(C)C] | Example 1E Example 2B Example 3B Example 7 Example 8 | Residue |
| 312 | 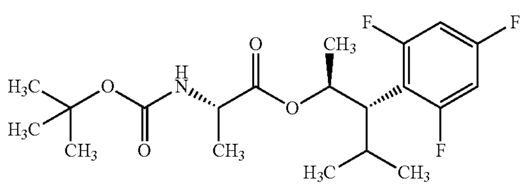 [SMILES: CC(C)[C@@H](c1c(F)cc(F)cc1F)[C@H](C)OC(=O)[C@H](C)NC(=O)OC(C)(C)C] | Example 6A Example 7 Example 8 | Residue |
| 313 | 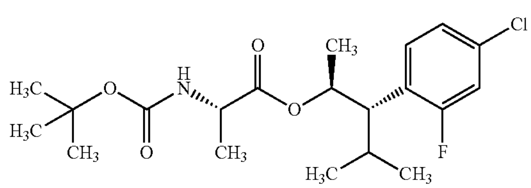 [SMILES: CC(C)[C@@H](c1ccc(Cl)cc1F)[C@H](C)OC(=O)[C@H](C)NC(=O)OC(C)(C)C] | Example 6A Example 7 Example 8 | Residue |
| 314 | 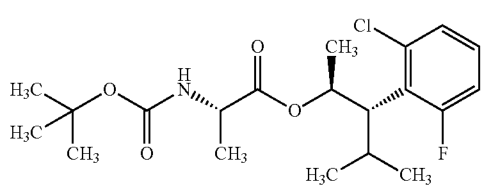 [SMILES: CC(C)[C@@H](c1c(F)cccc1Cl)[C@H](C)OC(=O)[C@H](C)NC(=O)OC(C)(C)C] | Example 6A Example 7 Example 8 | Residue |
| 315 | 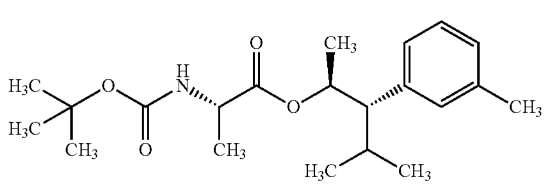 [SMILES: Cc1cccc([C@H](C(C)C)[C@H](C)OC(=O)[C@H](C)NC(=O)OC(C)(C)C)c1] | Example 6A Example 7 Example 8 | Residue |

| Cmpd. No. | Structure | As Prepared According To | Appearance |
|---|---|---|---|
| 316 | 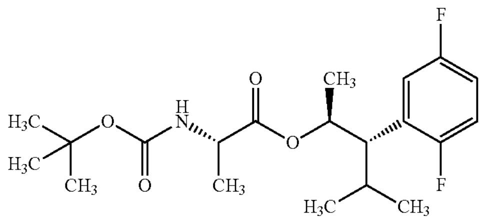 [SMILES: CC(C)[C@@H](c1cc(F)ccc1F)[C@H](C)OC(=O)[C@H](C)NC(=O)OC(C)(C)C] | Example 6A Example 7 Example 8 | Residue |
| 317 | 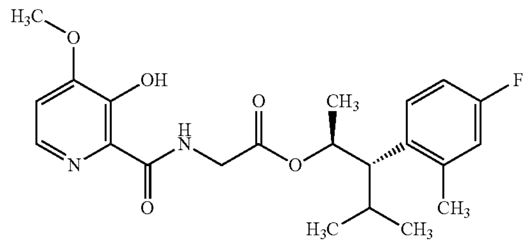 [SMILES: COc1ccnc(C(=O)NCC(=O)O[C@@H](C)[C@H](c2ccc(F)cc2C)C(C)C)c1O] | Example 10 Steps 2 | Clear, Colorless Oil |
| 318 | 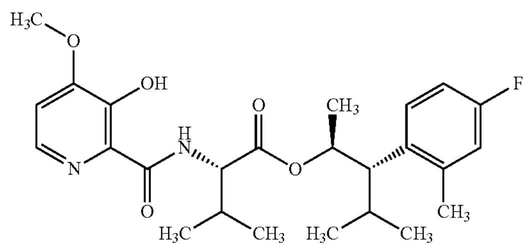 [SMILES: COc1ccnc(C(=O)N[C@H](C(=O)O[C@@H](C)[C@H](c2ccc(F)cc2C)C(C)C)C(C)C)c1O] | Example 10 Steps 2 | Clear, Colorless Oil |
| 319 | 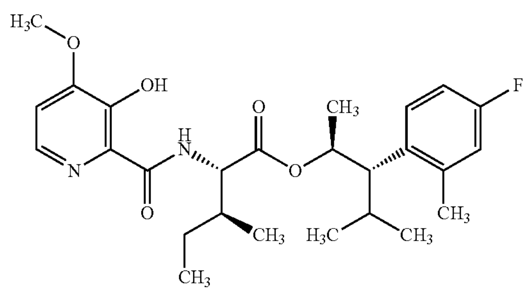 [SMILES: CC[C@H](C)[C@H](NC(=O)c1nccc(OC)c1O)C(=O)O[C@@H](C)[C@H](c1ccc(F)cc1C)C(C)C] | Example 10 Steps 2 | Clear, Colorless Oil |
| 320 | 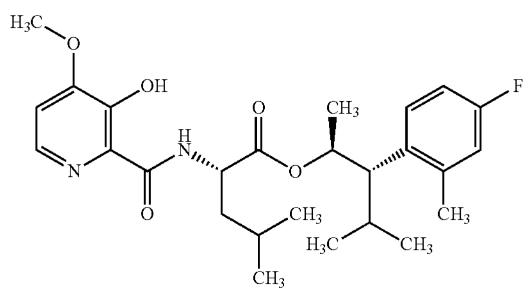 [SMILES: COc1ccnc(C(=O)N[C@@H](CC(C)C)C(=O)O[C@@H](C)[C@H](c2ccc(F)cc2C)C(C)C)c1O] | Example 10 Steps 2 | Clear, Colorless Oil |
| 321 | 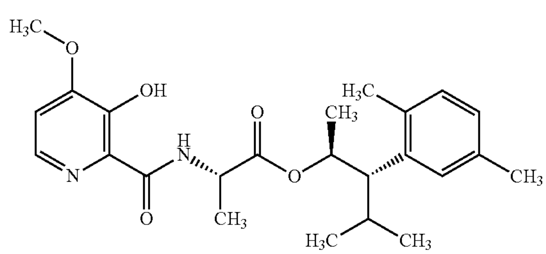 [SMILES: COc1ccnc(C(=O)N[C@@H](C)C(=O)O[C@@H](C)[C@H](c2cc(C)ccc2C)C(C)C)c1O] | Example 10 Steps 2 | Colorless Oil |

TABLE 1-continued

Compound Structure, Appearance, and Preparation Method

| Cmpd. No. | Structure | As Prepared According To | Appearance |
|---|---|---|---|
| 322 | 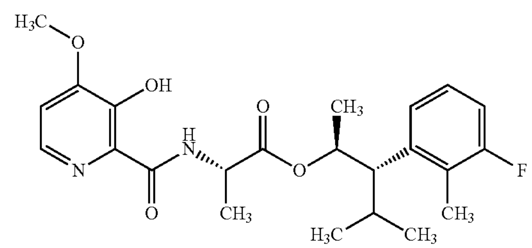 [SMILES: COc1ccnc(C(=O)N[C@@H](C)C(=O)O[C@@H](C)[C@H](c2cccc(F)c2C)C(C)C)c1O] | Example 10 Steps 2 | Colorless Oil |
| 323 | 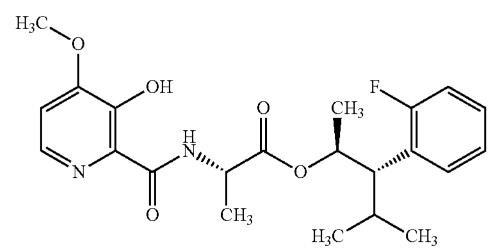 [SMILES: COc1ccnc(C(=O)N[C@@H](C)C(=O)O[C@@H](C)[C@H](c2ccccc2F)C(C)C)c1O] | Example 10 Steps 2 | Colorless Oil |
| 324 | 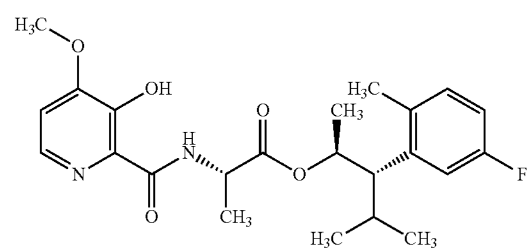 [SMILES: COc1ccnc(C(=O)N[C@@H](C)C(=O)O[C@@H](C)[C@H](c2cc(F)ccc2C)C(C)C)c1O] | Example 10 Steps 2 | Colorless Oil |
| 325 | 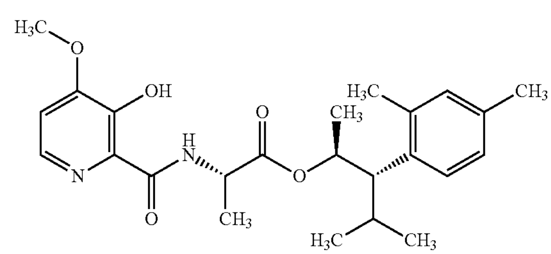 [SMILES: COc1ccnc(C(=O)N[C@@H](C)C(=O)O[C@@H](C)[C@H](c2ccc(C)cc2C)C(C)C)c1O] | Example 10 Steps 2 | Colorless Oil |
| 326 | 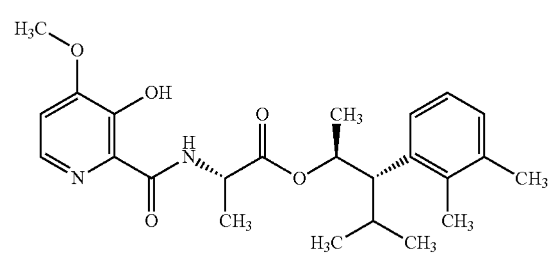 [SMILES: COc1ccnc(C(=O)N[C@@H](C)C(=O)O[C@@H](C)[C@H](c2cccc(C)c2C)C(C)C)c1O] | Example 10 Steps 2 | Colorless Oil |
| 327 | 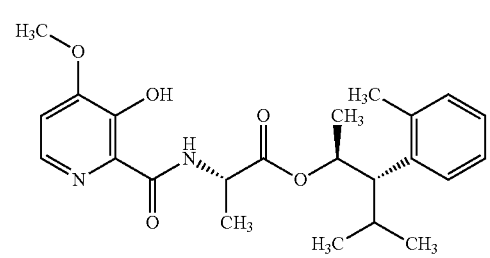 [SMILES: COc1ccnc(C(=O)N[C@@H](C)C(=O)O[C@@H](C)[C@H](c2ccccc2C)C(C)C)c1O] | Example 10 Steps 2 | Off-White Wax |

TABLE 1-continued

Compound Structure, Appearance, and Preparation Method

| Cmpd. No. | Structure | As Prepared According To | Appearance |
|---|---|---|---|
| 328 | 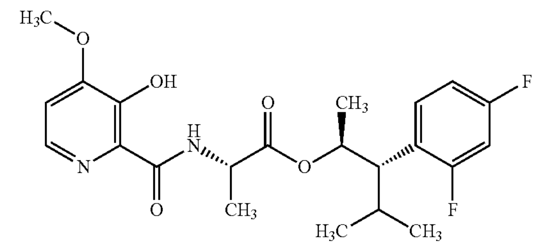 [SMILES: COc1ccnc(C(=O)N[C@@H](C)C(=O)O[C@@H](C)[C@H](c2ccc(F)cc2F)C(C)C)c1O] | Example 10 Steps 2 | White Foam |
| 329 | 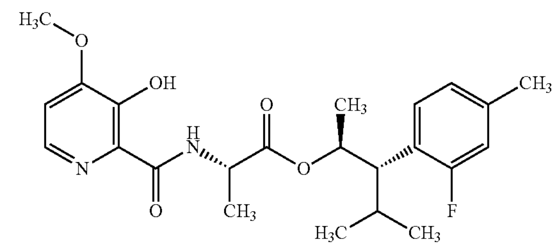 [SMILES: COc1ccnc(C(=O)N[C@@H](C)C(=O)O[C@@H](C)[C@H](c2ccc(C)cc2F)C(C)C)c1O] | Example 10 Steps 2 | White Foam |
| 330 | 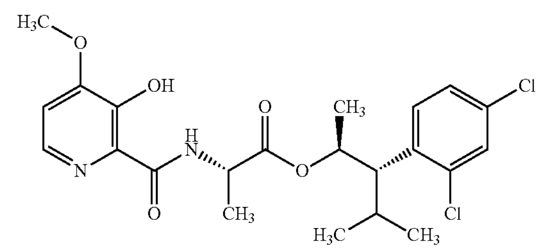 | Example 10 Steps 2 | Thick Oil |
| 331 | 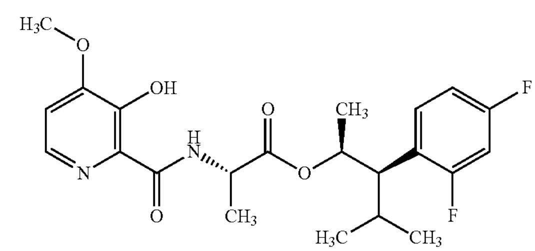 [SMILES: COc1ccnc(C(=O)N[C@@H](C)C(=O)O[C@@H](C)[C@@H](c2ccc(F)cc2F)C(C)C)c1O] | Example 10 Steps 2 | Thick Oil |
| 332 | 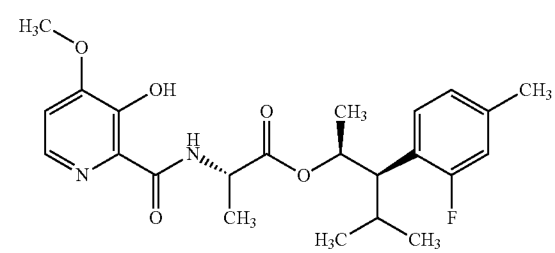 [SMILES: COc1ccnc(C(=O)N[C@@H](C)C(=O)O[C@@H](C)[C@@H](c2ccc(C)cc2F)C(C)C)c1O] | Example 10 Steps 2 | Thick Oil |
| 333 | 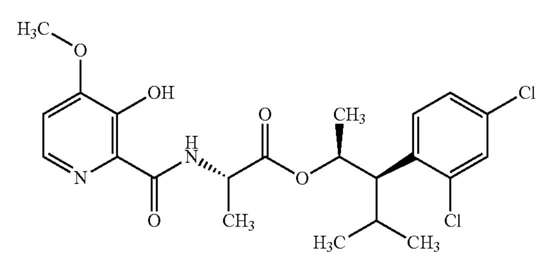 [SMILES: COc1ccnc(C(=O)N[C@@H](C)C(=O)O[C@@H](C)[C@@H](c2ccc(Cl)cc2Cl)C(C)C)c1O] | Example 10 Steps 2 | Thick Oil |

TABLE 1-continued
Compound Structure, Appearance, and Preparation Method
| Cmpd. No. | Structure | As Prepared According To | Appearance |
|---|---|---|---|
| 334 | 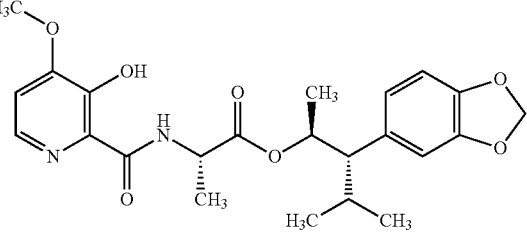 | Example 10 Steps 2 | Yellow Oil |
| 335 | 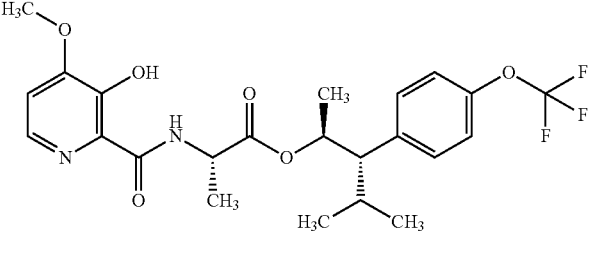 [SMILES: COc1ccnc(C(=O)N[C@@H](C)C(=O)O[C@@H](C)[C@H](c2ccc(OC(F)(F)F)cc2)C(C)C)c1O] | Example 10 Steps 2 | Yellow Oil |
| 336 | 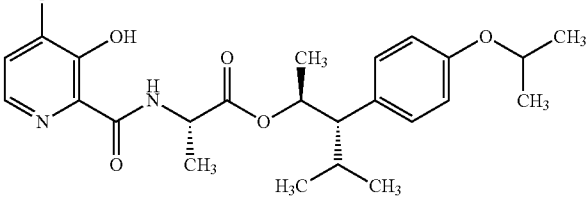 | Example 10 Steps 2 | Yellow Oil |
| 337 | 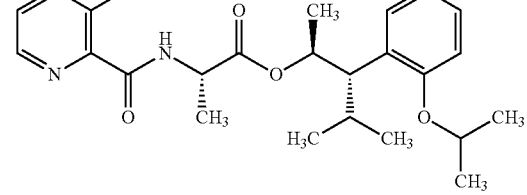 | Example 10 Steps 2 | Colorless Oil |
| 338 | 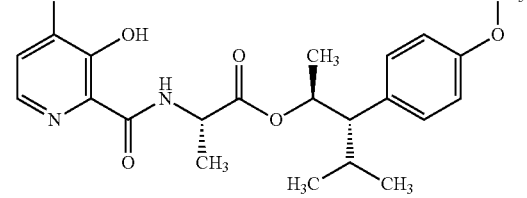 | Example 10 Steps 2 | Colorless Oil |

TABLE 1-continued

Compound Structure, Appearance, and Preparation Method

| Cmpd. No. | Structure | As Prepared According To | Appearance |
|---|---|---|---|
| 339 | 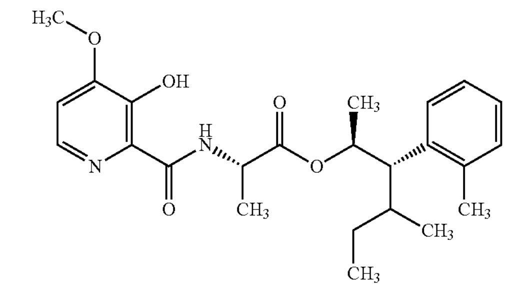 [SMILES: CCC(C)[C@@H](c1ccccc1C)[C@H](C)OC(=O)[C@H](C)NC(=O)c1nccc(OC)c1O] | Example 10 Steps 2 | Residue |
| 340 | 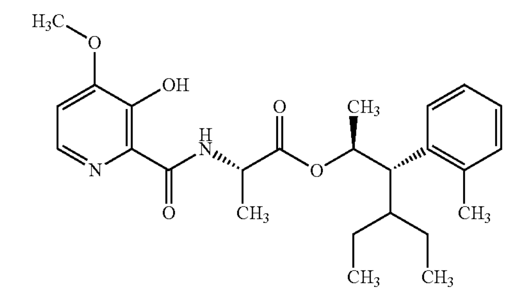 [SMILES: CCC(CC)[C@@H](c1ccccc1C)[C@H](C)OC(=O)[C@H](C)NC(=O)c1nccc(OC)c1O] | Example 10 Steps 2 | Residue |
| 341 | 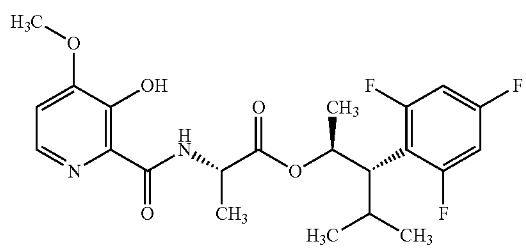 [SMILES: COc1ccnc(C(=O)N[C@@H](C)C(=O)O[C@@H](C)[C@H](c2c(F)cc(F)cc2F)C(C)C)c1O] | Example 10 Steps 2 | Residue |
| 342 | 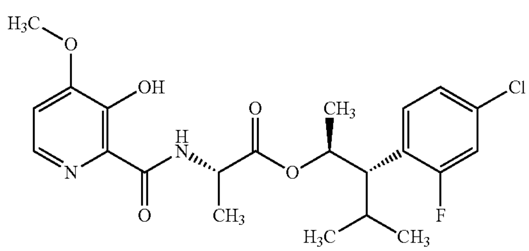 [SMILES: COc1ccnc(C(=O)N[C@@H](C)C(=O)O[C@@H](C)[C@H](c2ccc(Cl)cc2F)C(C)C)c1O] | Example 10 Steps 2 | Residue |
| 343 | 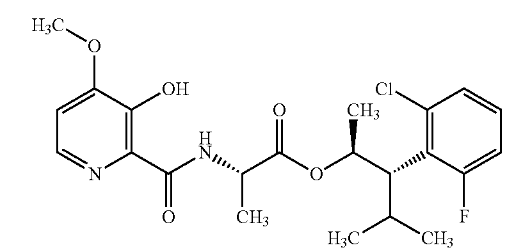 [SMILES: COc1ccnc(C(=O)N[C@@H](C)C(=O)O[C@@H](C)[C@H](c2c(F)cccc2Cl)C(C)C)c1O] | Example 10 Steps 2 | Residue |

TABLE 1-continued

Compound Structure, Appearance, and Preparation Method

| Cmpd. No. | Structure | As Prepared According To | Appearance |
|---|---|---|---|
| 344 | 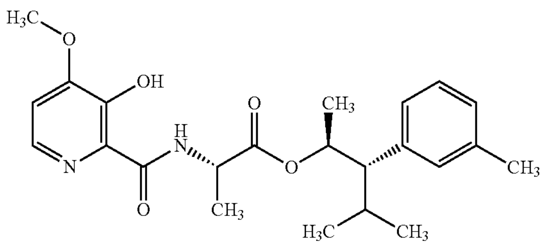 [SMILES: COc1ccnc(C(=O)N[C@@H](C)C(=O)O[C@@H](C)[C@H](c2cccc(C)c2)C(C)C)c1O] | Example 10 Steps 2 | Residue |
| 345 | 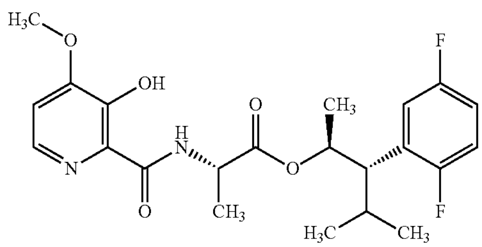 [SMILES: COc1ccnc(C(=O)N[C@@H](C)C(=O)O[C@@H](C)[C@H](c2cc(F)ccc2F)C(C)C)c1O] | Example 10 Steps 2 | Residue |
| 346 | 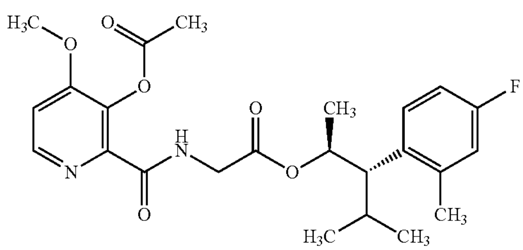 [SMILES: COc1ccnc(C(=O)NCC(=O)O[C@@H](C)[C@H](c2ccc(F)cc2C)C(C)C)c1OC(C)=O] | Example 11A | Clear, Colorless Oil |
| 347 | 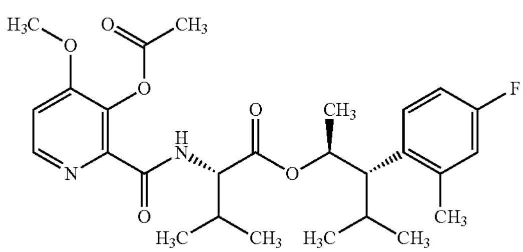 [SMILES: COc1ccnc(C(=O)N[C@H](C(=O)O[C@@H](C)[C@H](c2ccc(F)cc2C)C(C)C)C(C)C)c1OC(C)=O] | Example 11A | Clear, Colorless Oil |
| 348 | 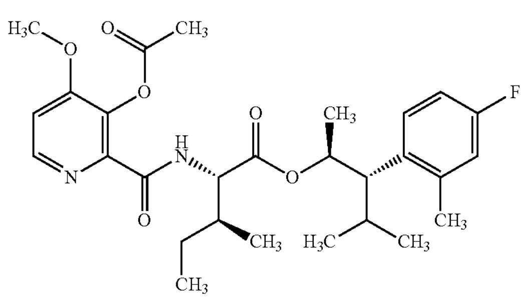 [SMILES: CC[C@H](C)[C@H](NC(=O)c1nccc(OC)c1OC(C)=O)C(=O)O[C@@H](C)[C@H](c1ccc(F)cc1C)C(C)C] | Example 11A | Clear, Colorless Oil |

TABLE 1-continued

Compound Structure, Appearance, and Preparation Method

| Cmpd. No. | Structure | As Prepared According To | Appearance |
|---|---|---|---|
| 349 | 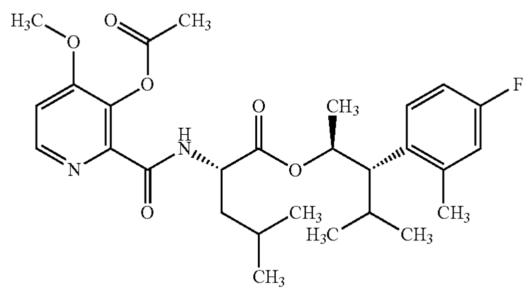 [SMILES: COc1ccnc(C(=O)N[C@@H](CC(C)C)C(=O)O[C@@H](C)[C@H](c2ccc(F)cc2C)C(C)C)c1OC(C)=O] | Example 11A | Clear, Colorless Oil |
| 350 | 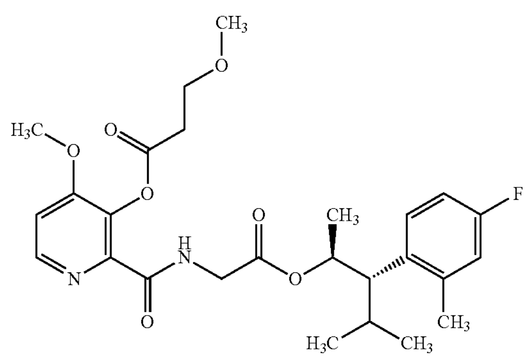 [SMILES: COCCC(=O)Oc1c(OC)ccnc1C(=O)NCC(=O)O[C@@H](C)[C@H](c1ccc(F)cc1C)C(C)C] | Example 11C | Clear, Colorless Oil |
| 351 | 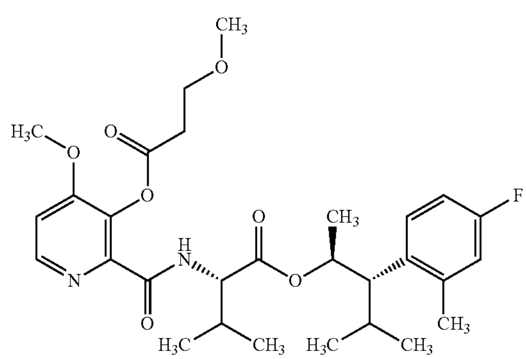 [SMILES: COCCC(=O)Oc1c(OC)ccnc1C(=O)N[C@H](C(=O)O[C@@H](C)[C@H](c1ccc(F)cc1C)C(C)C)C(C)C] | Example 11C | Clear, Colorless Oil |
| 352 | 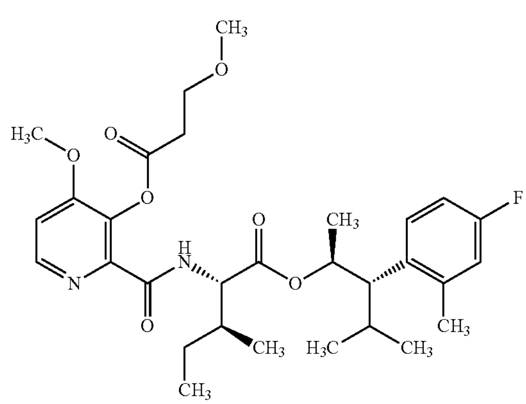 [SMILES: CC[C@H](C)[C@H](NC(=O)c1nccc(OC)c1OC(=O)CCOC)C(=O)O[C@@H](C)[C@H](c1ccc(F)cc1C)C(C)C] | Example 11C | Clear, Colorless Oil |

TABLE 1-continued

Compound Structure, Appearance, and Preparation Method

| Cmpd. No. | Structure | As Prepared According To | Appearance |
|---|---|---|---|
| 353 | 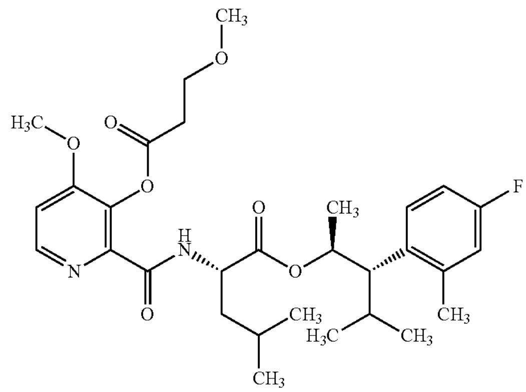 [SMILES: COCCC(=O)Oc1c(OC)ccnc1C(=O)N[C@@H](CC(C)C)C(=O)O[C@@H](C)[C@H](c1ccc(F)cc1C)C(C)C] | Example 11C | Clear, Colorless Oil |
| 354 | 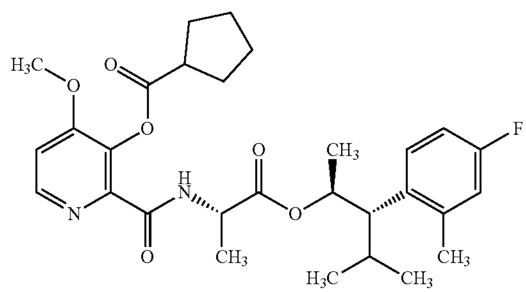 [SMILES: COc1ccnc(C(=O)N[C@@H](C)C(=O)O[C@@H](C)[C@H](c2ccc(F)cc2C)C(C)C)c1OC(=O)C1CCCC1] | Example 11C | Clear, Colorless Oil |
| 355 | 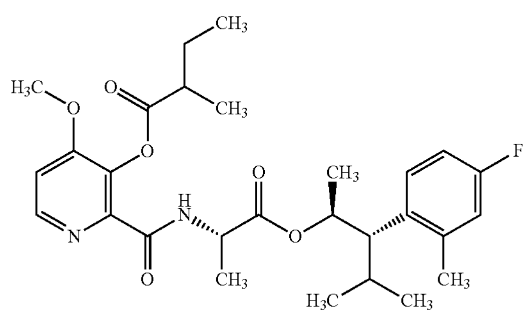 [SMILES: CCC(C)C(=O)Oc1c(OC)ccnc1C(=O)N[C@@H](C)C(=O)O[C@@H](C)[C@H](c1ccc(F)cc1C)C(C)C] | Example 11C | Pale Yellow Oil |
| 356 | 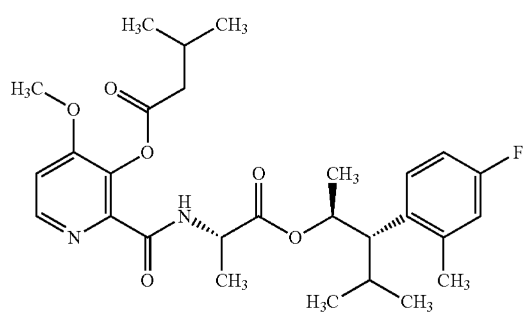 [SMILES: COc1ccnc(C(=O)N[C@@H](C)C(=O)O[C@@H](C)[C@H](c2ccc(F)cc2C)C(C)C)c1OC(=O)CC(C)C] | Example 11C | Clear, Colorless Oil |

TABLE 1-continued

Compound Structure, Appearance, and Preparation Method

| Cmpd. No. | Structure | As Prepared According To | Appearance |
|---|---|---|---|
| 357 | 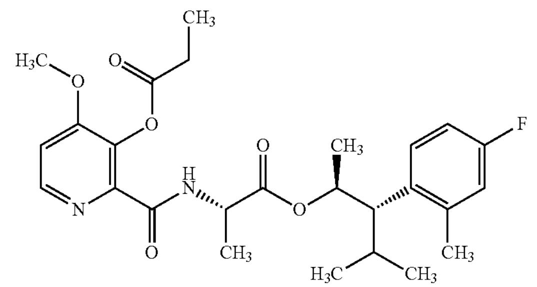 [SMILES: CCC(=O)Oc1c(OC)ccnc1C(=O)N[C@@H](C)C(=O)O[C@@H](C)[C@H](c1ccc(F)cc1C)C(C)C] | Example 11C | Clear, Colorless Oil |
| 358 | 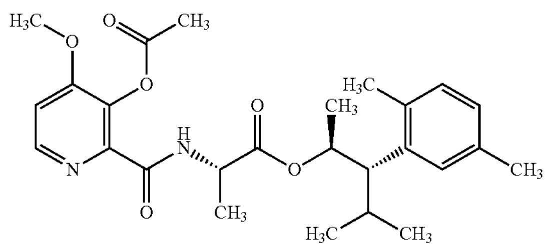 [SMILES: COc1ccnc(C(=O)N[C@@H](C)C(=O)O[C@@H](C)[C@H](c2cc(C)ccc2C)C(C)C)c1OC(C)=O] | Example 11A | White Foam |
| 359 | 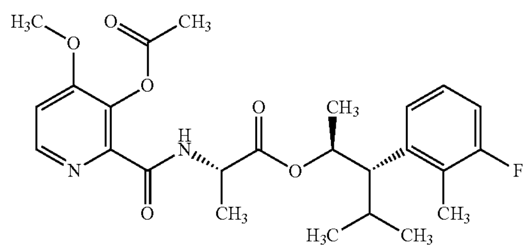 [SMILES: COc1ccnc(C(=O)N[C@@H](C)C(=O)O[C@@H](C)[C@H](c2cccc(F)c2C)C(C)C)c1OC(C)=O] | Example 11A | White Foam |
| 360 | 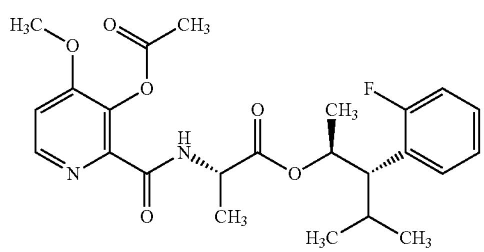 [SMILES: COc1ccnc(C(=O)N[C@@H](C)C(=O)O[C@@H](C)[C@H](c2ccccc2F)C(C)C)c1OC(C)=O] | Example 11A | Colorless Oil |
| 361 | 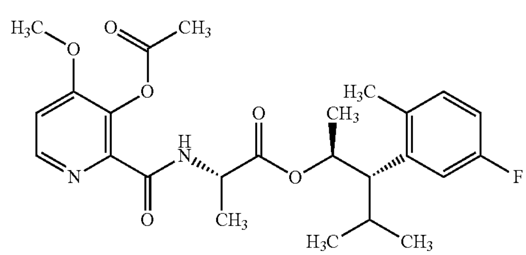 [SMILES: COc1ccnc(C(=O)N[C@@H](C)C(=O)O[C@@H](C)[C@H](c2cc(F)ccc2C)C(C)C)c1OC(C)=O] | Example 11A | Colorless Oil |
| 362 | 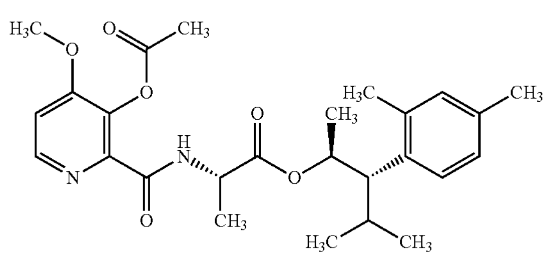 [SMILES: COc1ccnc(C(=O)N[C@@H](C)C(=O)O[C@@H](C)[C@H](c2ccc(C)cc2C)C(C)C)c1OC(C)=O] | Example 11A | Colorless Oil |

TABLE 1-continued

Compound Structure, Appearance, and Preparation Method

| Cmpd. No. | Structure | As Prepared According To | Appearance |
|---|---|---|---|
| 363 | 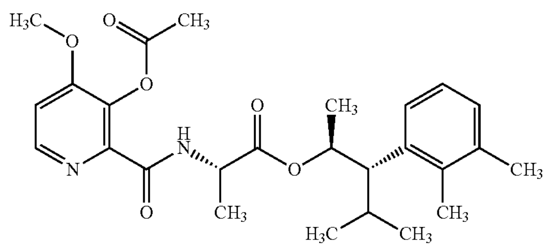 | Example 11A | Colorless Oil |
| 364 | 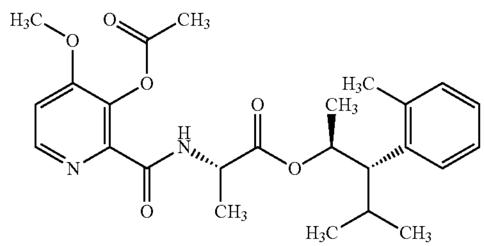 [SMILES: COc1ccnc(C(=O)N[C@@H](C)C(=O)O[C@@H](C)[C@H](c2ccccc2C)C(C)C)c1OC(C)=O] | Example 11A | Colorless Oil |
| 365 | 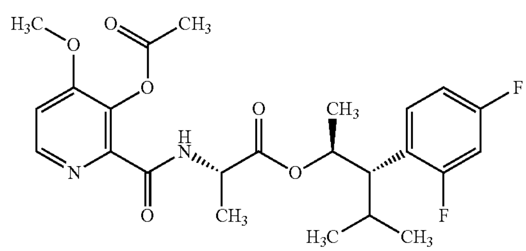 [SMILES: COc1ccnc(C(=O)N[C@@H](C)C(=O)O[C@@H](C)[C@H](c2ccc(F)cc2F)C(C)C)c1OC(C)=O] | Example 11A | White Foam |
| 366 | 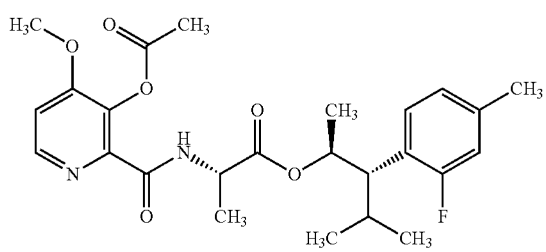 [SMILES: COc1ccnc(C(=O)N[C@@H](C)C(=O)O[C@@H](C)[C@H](c2ccc(C)cc2F)C(C)C)c1OC(C)=O] | Example 11A | White Foam |
| 367 | 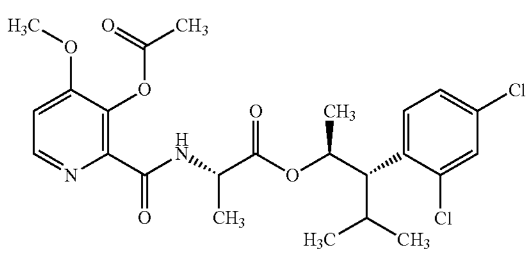 [SMILES: COc1ccnc(C(=O)N[C@@H](C)C(=O)O[C@@H](C)[C@H](c2ccc(Cl)cc2Cl)C(C)C)c1OC(C)=O] | Example 11A | White Foam |
| 368 | 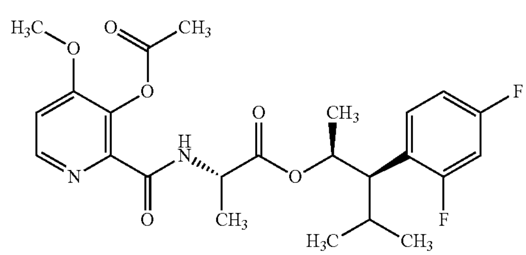 [SMILES: COc1ccnc(C(=O)N[C@@H](C)C(=O)O[C@@H](C)[C@@H](c2ccc(F)cc2F)C(C)C)c1OC(C)=O] | Example 11A | White Foam |

TABLE 1-continued

Compound Structure, Appearance, and Preparation Method

| Cmpd. No. | Structure | As Prepared According To | Appearance |
|---|---|---|---|
| 369 | 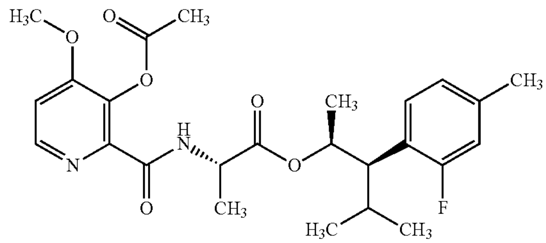 [SMILES: COc1ccnc(C(=O)N[C@@H](C)C(=O)O[C@@H](C)[C@@H](c2ccc(C)cc2F)C(C)C)c1OC(C)=O] | Example 11A | Thick Oil |
| 370 | 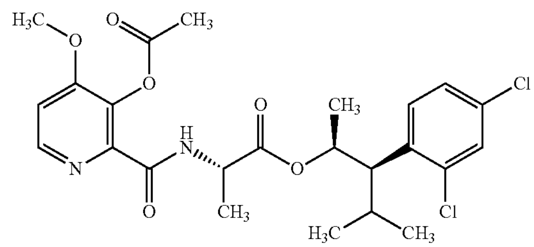 [SMILES: COc1ccnc(C(=O)N[C@@H](C)C(=O)O[C@@H](C)[C@@H](c2ccc(Cl)cc2Cl)C(C)C)c1OC(C)=O] | Example 11A | Thick Oil |
| 371 | 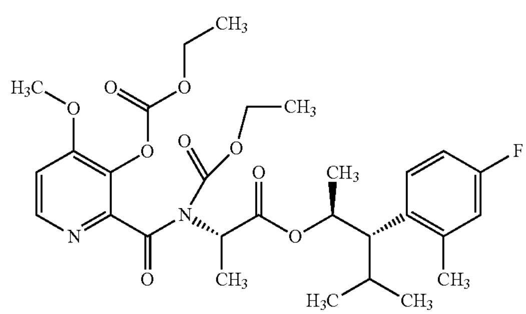 [SMILES: CCOC(=O)Oc1c(OC)ccnc1C(=O)N(C(=O)OCC)[C@@H](C)C(=O)O[C@@H](C)[C@H](c1ccc(F)cc1C)C(C)C] | Example 11C | White Foam |
| 372 | 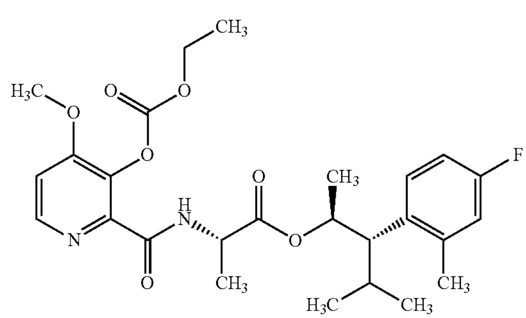 [SMILES: CCOC(=O)Oc1c(OC)ccnc1C(=O)N[C@@H](C)C(=O)O[C@@H](C)[C@H](c1ccc(F)cc1C)C(C)C] | Example 11C | Thick Oil |
| 373 | 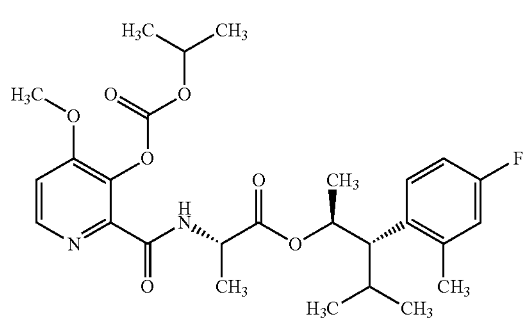 [SMILES: COc1ccnc(C(=O)N[C@@H](C)C(=O)O[C@@H](C)[C@H](c2ccc(F)cc2C)C(C)C)c1OC(=O)OC(C)C] | Example 11C | Colorless Oil |

TABLE 1-continued

Compound Structure, Appearance, and Preparation Method

| Cmpd. No. | Structure | As Prepared According To | Appearance |
|---|---|---|---|
| 374 | 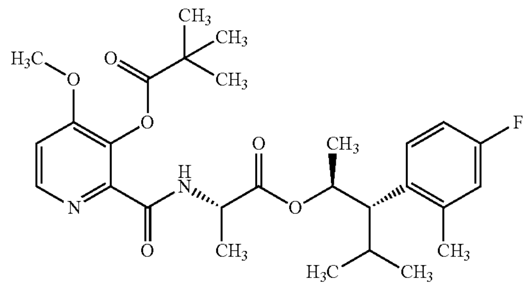 [SMILES: COc1ccnc(C(=O)N[C@@H](C)C(=O)O[C@@H](C)[C@H](c2ccc(F)cc2C)C(C)C)c1OC(=O)C(C)(C)C] | Example 11C | Thick Oil |
| 375 | 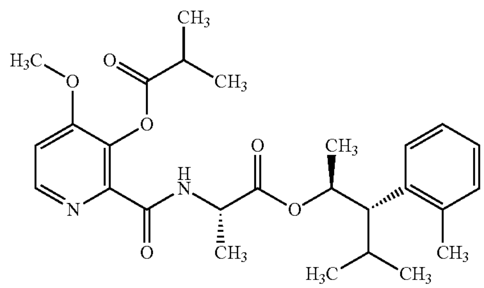 [SMILES: COc1ccnc(C(=O)N[C@@H](C)C(=O)O[C@@H](C)[C@H](c2ccccc2C)C(C)C)c1OC(=O)C(C)C] | Example 11C | Colorless Oil |
| 376 | 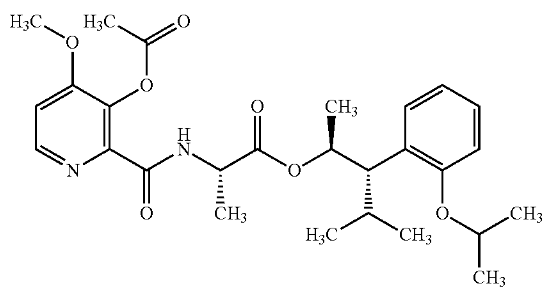 [SMILES: COc1ccnc(C(=O)N[C@@H](C)C(=O)O[C@@H](C)[C@H](c2ccccc2OC(C)C)C(C)C)c1OC(C)=O] | Example 11A | Colorless Oil |
| 377 | 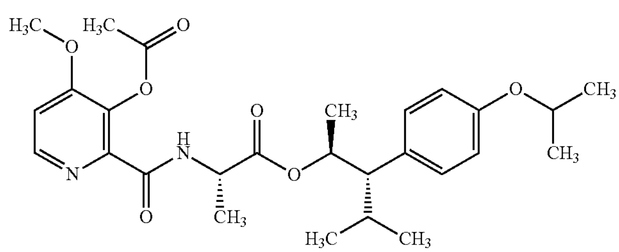 [SMILES: COc1ccnc(C(=O)N[C@@H](C)C(=O)O[C@@H](C)[C@H](c2ccc(OC(C)C)cc2)C(C)C)c1OC(C)=O] | Example 11A | Colorless Oil |
| 378 | 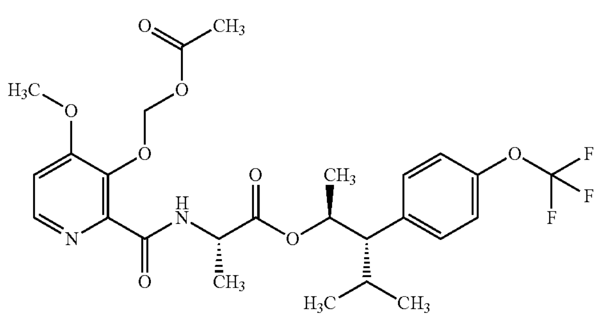 [SMILES: COc1ccnc(C(=O)N[C@@H](C)C(=O)O[C@@H](C)[C@H](c2ccc(OC(F)(F)F)cc2)C(C)C)c1OCOC(C)=O] | Example 11B | Yellow Oil |

TABLE 1-continued

Compound Structure, Appearance, and Preparation Method

| Cmpd. No. | Structure | As Prepared According To | Appearance |
|---|---|---|---|
| 379 | 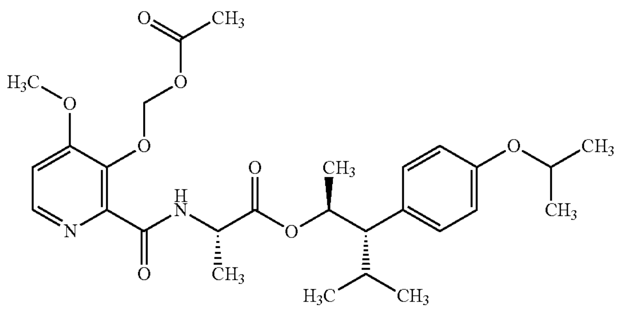 [SMILES: COc1ccnc(C(=O)N[C@@H](C)C(=O)O[C@@H](C)[C@H](c2ccc(OC(C)C)cc2)C(C)C)c1OCOC(C)=O] | Example 11B | Yellow Oil |
| 380 | 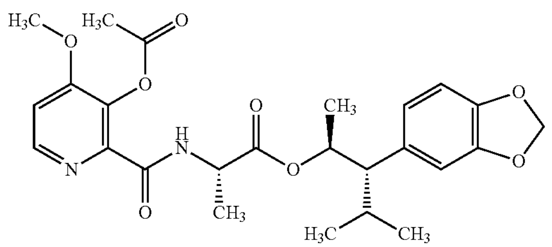 [SMILES: COc1ccnc(C(=O)N[C@@H](C)C(=O)O[C@@H](C)[C@H](c2ccc3c(c2)OCO3)C(C)C)c1OC(C)=O] | Example 11A | Glassy White Solid |
| 381 | 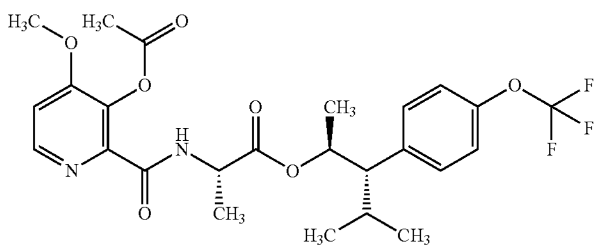 [SMILES: COc1ccnc(C(=O)N[C@@H](C)C(=O)O[C@@H](C)[C@H](c2ccc(OC(F)(F)F)cc2)C(C)C)c1OC(C)=O] | Example 11A | Colorless Oil |
| 382 | 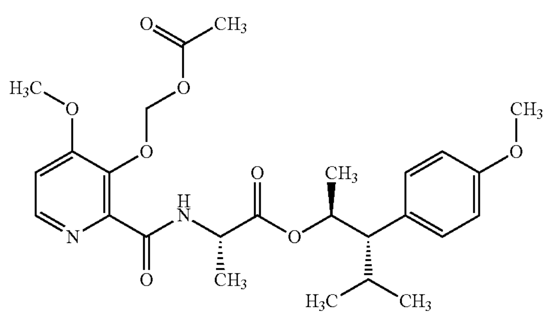 [SMILES: COc1ccc([C@H](C(C)C)[C@H](C)OC(=O)[C@H](C)NC(=O)c2nccc(OC)c2OCOC(C)=O)cc1] | Example 11B | Yellow Oil |
| 383 | 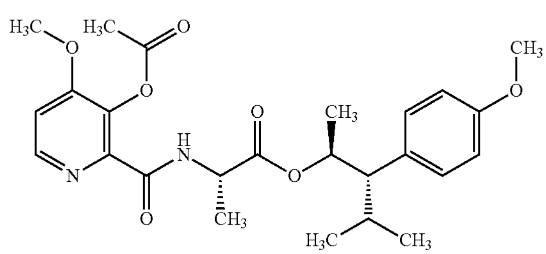 [SMILES: COc1ccc([C@H](C(C)C)[C@H](C)OC(=O)[C@H](C)NC(=O)c2nccc(OC)c2OC(C)=O)cc1] | Example 11A | Colorless Oil |

TABLE 1-continued

Compound Structure, Appearance, and Preparation Method

| Cmpd. No. | Structure | As Prepared According To | Appearance |
|---|---|---|---|
| 384 | 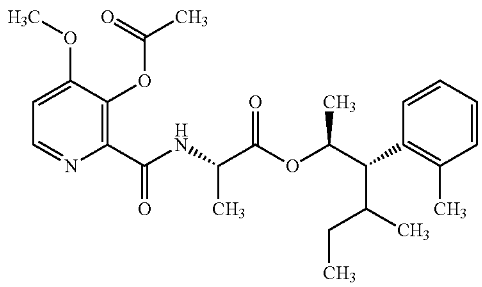 [SMILES: CCC(C)[C@@H](c1ccccc1C)[C@H](C)OC(=O)[C@H](C)NC(=O)c1nccc(OC)c1OC(C)=O] | Example 11A | Residue |
| 385 | 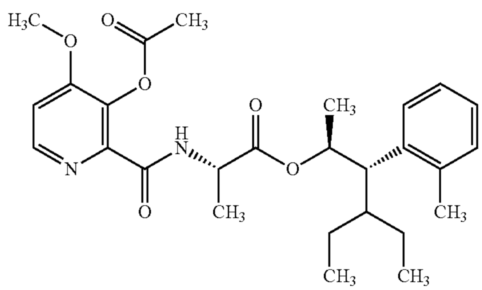 [SMILES: CCC(CC)[C@@H](c1ccccc1C)[C@H](C)OC(=O)[C@H](C)NC(=O)c1nccc(OC)c1OC(C)=O] | Example 11A | Residue |
| 386 | 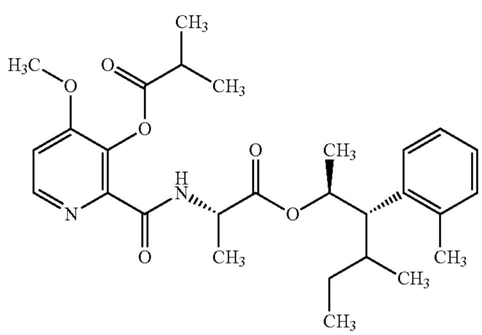 [SMILES: CCC(C)[C@@H](c1ccccc1C)[C@H](C)OC(=O)[C@H](C)NC(=O)c1nccc(OC)c1OC(=O)C(C)C] | Example 11C | Residue |
| 387 | 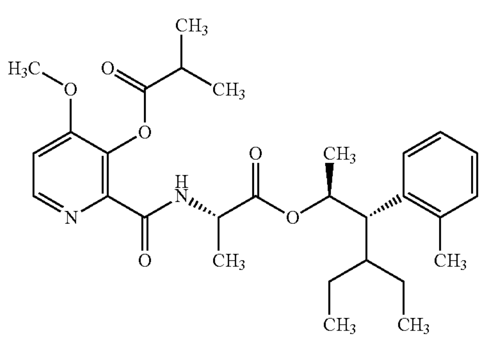 [SMILES: CCC(CC)[C@@H](c1ccccc1C)[C@H](C)OC(=O)[C@H](C)NC(=O)c1nccc(OC)c1OC(=O)C(C)C] | Example 11C | Residue |
| 388 | 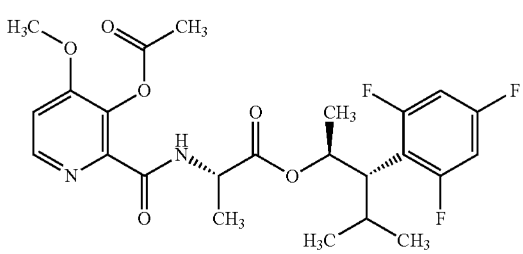 [SMILES: COc1ccnc(C(=O)N[C@@H](C)C(=O)O[C@@H](C)[C@H](c2c(F)cc(F)cc2F)C(C)C)c1OC(C)=O] | Example 11A | Residue |

TABLE 1-continued

Compound Structure, Appearance, and Preparation Method

| Cmpd. No. | Structure | As Prepared According To | Appearance |
|---|---|---|---|
| 389 | 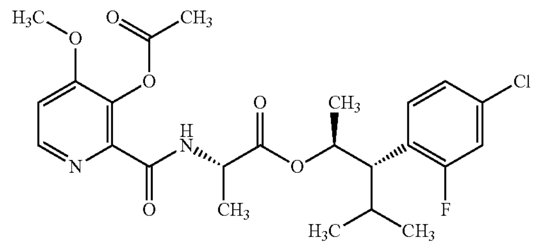 [SMILES: COc1ccnc(C(=O)N[C@@H](C)C(=O)O[C@@H](C)[C@H](c2ccc(Cl)cc2F)C(C)C)c1OC(C)=O] | Example 11A | Residue |
| 390 | 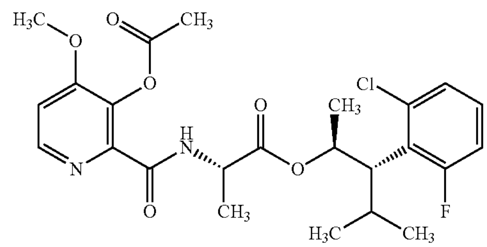 [SMILES: COc1ccnc(C(=O)N[C@@H](C)C(=O)O[C@@H](C)[C@H](c2c(F)cccc2Cl)C(C)C)c1OC(C)=O] | Example 11A | Residue |
| 391 | 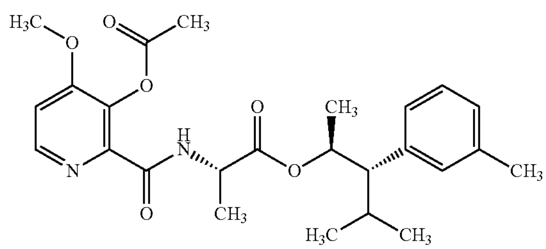 [SMILES: COc1ccnc(C(=O)N[C@@H](C)C(=O)O[C@@H](C)[C@H](c2cccc(C)c2)C(C)C)c1OC(C)=O] | Example 11A | Residue |
| 392 | 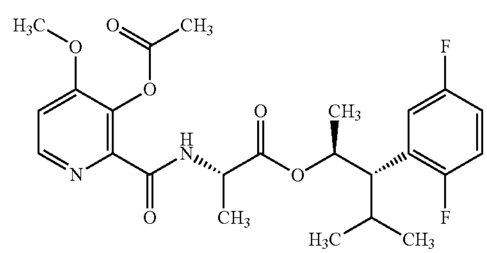 [SMILES: COc1ccnc(C(=O)N[C@@H](C)C(=O)O[C@@H](C)[C@H](c2cc(F)ccc2F)C(C)C)c1OC(C)=O] | Example 11A | Residue |

*Cmpd. No. - Compound Number

TABLE 2

Analytical Data

| Cmpd. No. | Melting Point (° C.) | IR (cm$^{-1}$) | MASS SPEC | NMR |
|---|---|---|---|---|
| 1 | | | ESIMS m/z 350.5 ([M + H]$^+$) | $^1$H NMR (400 MHz, CDCl$_3$) δ 7.31-7.12 (m, 5H), 5.50-5.38 (m, 1H), 5.02 (d, J = 7.8 Hz, 1H), 4.29-4.17 (m, 1H), 2.36 (dd, J = 8.4, 5.6 Hz, 1H), 2.13-1.96 (m, 1H), 1.44 (s, 9H), 1.14 (d, J = 7.2 Hz, 3H), 1.11 (d, J = 6.3 Hz, 3H), 0.94 (d, J = 6.6 Hz, 3H), 0.72 (d, J = 6.7 Hz, 3H). $^{13}$C NMR (101 MHz, CDCl$_3$) δ 172.83, 157.91, 139.85, 129.62, 127.92, 126.50, 79.70, 71.92, 58.00, 49.41, 29.18, 28.33, 21.29, 20.19, 18.97, 18.54. |
| 2 | | | ESIMS m/z 376.6 ([M + H]$^+$) | $^1$H NMR (400 MHz, CDCl$_3$) δ 7.38-7.14 (m, 5H), 5.33 (qd, J = 6.4, 3.9 Hz, 1H), 5.07 (d, J = 8.0 Hz, 1H), 4.40-4.23 (m, 1H), 2.41 (dd, J = 10.3, 4.0 |

TABLE 2-continued

Analytical Data

| Cmpd. No. | Melting Point (° C.) | IR (cm$^{-1}$) | MASS SPEC | NMR |
|---|---|---|---|---|
| | | | | Hz, 1H), 2.29-2.13 (m, 1H), 1.92-1.79 (m, 1H), 1.70-1.61 (m, 1H), 1.59-1.48 (m, 2H), 1.45 (s, 9H), 1.45-1.32 (m, 2H), 1.31 (d, J = 7.2 Hz, 3H), 1.27-1.13 (m, 1H), 1.06 (d, J = 6.3 Hz, 3H), 1.04-0.88 (m, 1H). $^{13}$C NMR (101 MHz, CDCl$_3$) δ 172.79, 155.00, 140.76, 129.49, 127.96, 126.49, 79.75, 73.15, 56.65, 49.52, 42.13, 31.61, 31.47, 28.34, 25.12, 24.53, 18.81. |
| 3 | | | ESIMS m/z 350.5 ([M + H]$^+$) | $^1$H NMR (300 MHz, CDCl$_3$) δ 7.36-7.20 (m, 3H), 7.16-7.03 (m, 2H), 5.40 (dq, J = 8.8, 6.2 Hz, 1H), 5.09 (d, J = 8.0 Hz, 1H), 4.39-4.15 (m, 1H), 2.70 (dd, J = 8.9, 6.3 Hz, 1H), 2.20-2.01 (m, 1H), 1.45 (s, 9H), 1.39 (d, J = 7.2 Hz, 3H), 1.08 (d, J = 6.2 Hz, 3H), 0.86 (d, J = 6.8 Hz, 3H), 0.76 (d, J = 6.8 Hz, 3H). |
| 4 | | | ESIMS m/z 365 ([M + H]$^+$) | $^1$H NMR (400 MHz, CDCl$_3$) δ 7.18-7.02 (m, 4H), 5.36-5.22 (m, 1H), 5.07 (s, 1H), 4.36-4.19 (m, 1H), 2.33 (s, 3H), 1.97 (dd, J = 10.0, 7.1 Hz, 1H), 1.45 (s, 9H), 1.36 (d, J = 7.2 Hz, 3H), 1.15 (d, J = 6.3 Hz, 3H), 1.12-1.00 (m, 1H), 0.73-0.57 (m, 1H), 0.47-0.27 (m, 2H), −0.01-−0.15 (m, 1H). $^{13}$C NMR (101 MHz, CDCl$_3$) δ 172.79, 155.03, 138.55, 136.15, 128.94, 128.28, 75.73, 68.48, 55.27, 49.50, 28.35, 21.01, 18.87, 18.19, 13.04, 6.90, 2.83. |
| 5 | | IR (thin film) 3358, 2976, 1715, 1514, 1366, 1167, 1052 cm$^{-1}$ | HRMS-ESI (m/z) [M + Na]$^+$ calcd for C$_{21}$H$_{33}$NNaO$_4$, 386.2302; found, 386.2306 | $^1$H NMR (400 MHz, CDCl$_3$) δ 7.13-7.05 (m, 2H), 7.00-6.94 (m, 2H), 5.38 (dq, J = 8.9, 6.3 Hz, 1H), 5.13 (d, J = 7.9 Hz, 1H), 4.28 (p, J = 7.5 Hz, 1H), 2.66 (dd, J = 8.9, 6.2 Hz, 1H), 2.33 (s, 3H), 2.09 (h, J = 6.8 Hz, 1H), 1.45 (s, 9H), 1.39 (d, J = 7.2 Hz, 3H), 1.07 (d, J = 6.3 Hz, 3H), 0.85 (d, J = 6.8 Hz, 3H), 0.76 (d, J = 6.7 Hz, 3H). $^{13}$C NMR (101 MHz, CDCl$_3$) δ 172.82, 155.03, 136.11, 135.47, 129.67, 128.65, 79.66, 72.59, 56.29, 49.56, 28.36, 28.16, 21.39, 21.00, 18.81, 18.42, 17.98. |
| 6 | | | ESIMS m/z 366 ([M + H]$^+$) | $^1$H NMR (400 MHz, CDCl$_3$) δ 7.22-7.12 (m, 2H), 7.03-6.94 (m, 2H), 5.32-5.20 (m, 1H), 5.04 (d, J = 8.0 Hz, 1H), 4.40-4.22 (m, 1H), 2.01 (dd, J = 10.1, 6.7 Hz, 1H), 1.45 (s, 9H), 1.34 (d, J = 7.2 Hz, 3H), 1.16 (d, J = 6.4 Hz, 3H), 1.13-1.07 (m, 1H), 0.76-0.63 (m, 1H), 0.46-0.31 (m, 2H), −0.03-−0.10 (m, 1H). $^{19}$F NMR (376 MHz, CDCl$_3$) δ −116.47. |
| 7 | | | ESIMS m/z 378 ([M + H]$^+$) | $^1$H NMR (400 MHz, CDCl$_3$) δ 7.32-7.02 (m, 5H), 5.48-5.34 (m, 1H), 5.10 (bs, 1H), 4.35-4.21 (m, 1H), 2.94 (dd, J = 8.6, 6.3 Hz, 1H), 1.64-1.55 (m, 1H), 1.45 (s, 9H), 1.66-1.54 (m, 2H), 1.30-1.12 (m, 2H), 1.39 (d, J = 7.2 Hz, 3H), 1.08 (d, J = 6.3 Hz, 3H), 0.96 (t, J = 7.4 Hz, 3H), 0.78 (t, J = 7.3 Hz, 3H). $^{13}$C NMR (101 MHz, CDCl$_3$) δ 172.72, 154.99, 138.99, 129.76, 127.94, 126.61, 72.12, 51.91, 49.49, 41.54, 28.35, 22.30, 19.03, 17.95, 11.68, 11.13. |
| 8 | | | ESIMS m/z 376 ([M + H]$^+$) | $^1$H NMR (400 MHz, CDCl$_3$) δ 7.36-7.04 (m, 5H), 5.34-5.26 (m, 1H), 5.14-4.97 (m, 1H), 4.28 (m, 1H), 2.76 (dd, J = 9.9, 6.1 Hz, 1H), 2.35-2.10 (m, 2H), 1.96-1.83 (m, 2H), 1.45 (s, 9H), 1.36 (d, J = 7.2 Hz, 3H), 1.33-0.98 m, 5H), 1.10 (d, J = 6.5 Hz, 3H). $^{13}$C NMR (101 MHz, CDCl$_3$) δ 172.62, 140.75, 140.10, 129.62, 127.90, 126.55, |

TABLE 2-continued

Analytical Data

| Cmpd. No. | Melting Point (° C.) | IR (cm$^{-1}$) | MASS SPEC | NMR |
|---|---|---|---|---|
| 9 | | IR (thin film) 3358, 2975, 1712, 1498, 1165, 862 cm$^{-1}$ | HRMS-ESI (m/z) [M + Na]$^+$ calcd for C$_{21}$H$_{32}$FNNaO$_4$, 404.2208; found, 404.2202 | 74.02, 55.12, 41.77, 31.46, 31.26, 28.35, 25.30, 24.45, 18.88, 16.30. $^1$H NMR (400 MHz, CDCl$_3$) δ 7.27 (q, J = 3.3 Hz, 1H), 6.91-6.82 (m, 2H), 5.45-5.33 (m, 1H), 5.03 (d, J = 7.9 Hz, 1H), 4.35-4.18 (m, 1H), 2.69 (dd, J = 9.2, 5.0 Hz, 1H), 2.28 (s, 3H), 2.02 (dp, J = 9.1, 6.7 Hz, 1H), 1.44 (s, 9H), 1.34-1.17 (m, 4H), 1.06 (d, J = 6.3 Hz, 3H), 0.98 (d, J = 6.5 Hz, 3H), 0.70 (d, J = 6.7 Hz, 3H). $^{13}$C NMR (101 MHz, CDCl$_3$) δ 172.75, 160.98 (d, J = 243.9 Hz), 155.01, 139.40 (d, J = 7.3 Hz), 134.70 (d, J = 2.9 Hz), 129.37 (d, J = 8.1 Hz), 116.46 (d, J = 20.4 Hz), 112.69 (d, J = 20.5 Hz), 79.81, 72.22, 50.66, 49.49, 30.41, 28.34, 20.99, 20.73 (d, J = 1.5 Hz), 20.44, 18.65, 18.40. $^{19}$F NMR (376 MHz, CDCl$_3$) δ −117.64. |
| 10 | | IR (thin film) 3358, 2966, 1715, 1498, 1167 cm$^{-1}$ | HRMS-ESI (m/z) [M + Na]$^+$ calcd for C$_{23}$H$_{36}$FNNaO$_4$, 432.2521; found, 432.2515 | $^1$H NMR (400 MHz, CDCl$_3$) δ 7.31 (dd, J = 8.4, 6.1 Hz, 1H), 6.86 (dd, J = 9.2, 7.4 Hz, 2H), 5.36 (qd, J = 6.3, 4.5 Hz, 1H), 5.05 (d, J = 8.0 Hz, 1H), 4.39-4.21 (m, 1H), 2.91 (dd, J = 10.0, 4.3 Hz, 1H), 2.30 (s, 3H), 1.74 (ddq, J = 14.1, 10.2, 4.6 Hz, 1H), 1.52 (ddt, J = 14.5, 7.4, 4.0 Hz, 1H), 1.44 (d, J = 2.1 Hz, 9H), 1.42-1.34 (m, 2H), 1.34-1.28 (m, 2H), 1.26-1.03 (m, 2H), 1.01 (d, J = 6.2 Hz, 3H), 0.88 (t, J = 7.4 Hz, 3H), 0.76 (q, J = 7.7 Hz, 1H), 0.70 (t, J = 7.4 Hz, 2H). $^{13}$C NMR (101 MHz, CDCl$_3$) δ 172.82, 160.98 (d, J = 244.1 Hz), 154.98, 139.43 (d, J = 7.3 Hz), 134.74 (d, J = 3.3 Hz), 129.78 (d, J = 8.0 Hz), 116.45 (d, J = 20.6 Hz), 112.75 (d, J = 20.7 Hz), 79.82, 71.95, 49.49, 45.70, 41.63, 28.36, 21.76, 21.12, 20.61, 18.83, 18.39, 10.77, 9.56. $^{19}$F NMR (376 MHz, CDCl$_3$) δ −117.60. |
| 11 | | IR (thin film) 3357, 2954, 1711, 1497, 1164, 860, 732 cm$^{-1}$ | HRMS-ESI (m/z) [M + Na]$^+$ calcd for C$_{23}$H$_{34}$FNNaO$_4$, 430.2364; found, 430.2361 | $^1$H NMR (400 MHz, CDCl$_3$) δ 7.30 (dd, J = 8.5, 6.1 Hz, 1H), 6.86 (t, J = 8.2 Hz, 2H), 5.31 (td, J = 6.5, 4.4 Hz, 1H), 5.06 (d, J = 7.8 Hz, 1H), 4.39-4.20 (m, 1H), 2.80 (dd, J = 10.3, 4.3 Hz, 1H), 2.30 (s, 3H), 2.26-2.10 (m, 1H), 1.88 (dtd, J = 11.0, 6.9, 3.3 Hz, 1H), 1.74-1.48 (m, 2H), 1.48-1.33 (m, 11H), 1.33-1.13 (m, 4H), 1.11-1.00 (m, 4H), 0.96-0.81 (m, 1H). $^{13}$C NMR (101 MHz, CDCl$_3$) δ 172.69, 160.94 (d, J = 243.9 Hz), 155.01, 138.84 (d, J = 7.2 Hz), 135.28 (d, J = 3.1 Hz), 129.66 (d, J = 8.1 Hz), 116.43 (d, J = 20.2 Hz), 112.70 (d, J = 20.4 Hz), 79.82, 73.45, 49.55, 49.41, 42.93, 31.61, 31.35, 28.35, 25.13, 24.42, 20.61, 18.72, 18.22. $^{19}$F NMR (376 MHz, CDCl$_3$) δ −117.66. |
| 12 | | IR (thin film) 3357, 2928, 1709, 1497, 1206, 860, 731 cm$^{-1}$ | HRMS-ESI (m/z) [M + Na]$^+$ calcd for C$_{24}$H$_{36}$FNNaO$_4$, 444.2521; found, 444.2514 | $^1$H NMR (400 MHz, CDCl$_3$) δ 7.32-7.26 (m, 1H), 6.90-6.81 (m, 2H), 5.47-5.35 (m, 1H), 5.07 (d, J = 7.9 Hz, 1H), 4.31 (q, J = 7.4 Hz, 1H), 2.76 (dd, J = 9.2, 4.9 Hz, 1H), 2.27 (s, 3H), 1.84 (dt, J = 12.6, 3.2 Hz, 1H), 1.79-1.53 (m, 3H), 1.45 (s, 9H), 1.41-1.30 (m, 1H), 1.30-1.25 (m, 3H), 1.25-0.87 (m, 8H), 0.80 (qt, J = 12.1, 6.1 Hz, 1H). $^{13}$C NMR (101 MHz, CDCl$_3$) δ 172.81, 160.94 (d, J = 243.9 Hz), 154.99, 139.46 (d, J = 7.2 Hz), 134.70 (d, J = 3.2 Hz), 129.43 (d, J = 7.9 Hz), 116.39 |

TABLE 2-continued

Analytical Data

| Cmpd. No. | Melting Point (° C.) | IR (cm$^{-1}$) | MASS SPEC | NMR |
|---|---|---|---|---|
| | | | | (d, J = 20.5 Hz), 112.73 (d, J = 20.5 Hz), 79.78, 71.54, 49.67, 49.44, 40.28, 31.31, 30.73, 28.38, 26.45, 26.40, 26.34, 20.73, 18.79, 18.29. $^{19}$F NMR (376 MHz, CDCl$_3$) δ −117.65. |
| 13 | | IR (thin film) 3357, 2971, 1712, 1498, 1164, 860 cm$^{-1}$ | HRMS-ESI (m/z) [M + Na]$^+$ calcd for C$_{22}$H$_{34}$FNNaO$_4$, 418.2364; found, 418.2360 | $^1$H NMR (400 MHz, CDCl$_3$) δ 7.27 (d, J = 6.3 Hz, 1H), 6.91-6.80 (m, 2H), 5.50-5.32 (m, 1H), 5.03 (s, 1H), 4.27 (dt, J = 13.6, 7.2 Hz, 1H), 2.79 (ddd, J = 43.4, 9.2, 5.1 Hz, 1H), 2.28 (d, J = 1.8 Hz, 3H), 1.81 (dtdd, J = 19.1, 9.5, 6.3, 3.1 Hz, 1H), 1.68-1.50 (m, 1H), 1.44 (d, J = 3.1 Hz, 9H), 1.36-1.13 (m, 3H), 1.13-0.57 (m, 10H). $^{19}$F NMR (376 MHz, CDCl$_3$) δ −117.61, −117.68. |
| 14 | | IR (thin film) 3355, 2976, 1713, 1498, 1166 cm$^{-1}$ | HRMS-ESI (m/z) [M + Na]$^+$ calcd for C$_{22}$H$_{32}$FNNaO$_4$, 416.2208; found, 416.2203 | $^1$H NMR (400 MHz, CDCl$_3$) δ 7.09 (dd, J = 8.3, 6.0 Hz, 1H), 6.82 (t, J = 8.4 Hz, 2H), 5.11 (t, J = 6.4 Hz, 1H), 4.95 (d, J = 8.0 Hz, 1H), 4.17 (t, J = 7.5 Hz, 1H), 3.02 (dd, J = 10.4, 6.7 Hz, 1H), 2.65 (q, J = 8.6, 7.8 Hz, 1H), 2.35 (s, 3H), 2.15 (dp, J = 7.4, 5.1, 4.1 Hz, 1H), 1.92-1.75 (m, 2H), 1.75-1.55 (m, 2H), 1.49-1.32 (m, 10H), 1.17 (d, J = 6.3 Hz, 3H), 1.06 (d, J = 7.2 Hz, 3H). $^{19}$F NMR (376 MHz, CDCl$_3$) δ −117.57. |
| 15 | | IR (thin film) 3356, 2954, 1711, 1497, 1163, 1056, 860, 732 cm$^{-1}$ | HRMS-ESI (m/z) [M + Na]$^+$ calcd for C$_{23}$H$_{34}$FNNaO$_4$, 430.2364; found, 430.2360 | $^1$H NMR (400 MHz, CDCl$_3$) δ 7.09 (dd, J = 9.5, 5.9 Hz, 1H), 6.91-6.82 (m, 2H), 5.26 (p, J = 6.5 Hz, 1H), 5.03 (s, 1H), 4.35-4.19 (m, 1H), 3.10 (t, J = 8.3 Hz, 1H), 2.30 (s, 3H), 2.21-2.06 (m, 1H), 1.85 (dtd, J = 11.2, 7.3, 3.5 Hz, 1H), 1.72-1.46 (m, 2H), 1.44 (s, 9H), 1.42-1.14 (m, 6H), 1.08 (d, J = 6.4 Hz, 3H), 1.03 (dd, J = 9.1, 6.4 Hz, 1H), 0.91 (dtt, J = 15.2, 7.8, 4.4 Hz, 1H). $^{19}$F NMR (376 MHz, CDCl$_3$) δ −117.51. |
| 16 | | IR (thin film) 2928, 1714, 1497, 1450, 1366, 1166, 1029, 861, 733 cm$^{-1}$ | HRMS-ESI (m/z) [M + Na]$^+$ calcd for C$_{24}$H$_{36}$FNNaO$_4$, 444.2521; found, 444.2516 | $^1$H NMR (400 MHz, CDCl$_3$) δ 7.05 (dd, J = 8.3, 5.9 Hz, 1H), 6.91-6.81 (m, 2H), 5.36 (dq, J = 9.2, 6.3 Hz, 1H), 5.08 (d, J = 7.8 Hz, 1H), 4.31 (d, J = 9.1 Hz, 1H), 3.11 (dd, J = 9.2, 6.0 Hz, 1H), 2.31 (s, 3H), 1.82-1.50 (m, 6H), 1.45 (s, 9H), 1.40 (d, J = 7.1 Hz, 3H), 1.35-1.06 (m, 2H), 1.02 (d, J = 6.3 Hz, 3H), 1.00-0.77 (m, 3H). $^{19}$F NMR (376 MHz, CDCl$_3$) δ −117.40. |
| 17 | | IR (thin film) 3355, 2965, 1714, 1499, 1366, 1167, 1052, 735 cm$^{-1}$ | HRMS-ESI (m/z) [M + Na]$^+$ calcd for C$_{21}$H$_{32}$FNNaO$_4$, 404.2208; found, 404.2201 | $^1$H NMR (400 MHz, CDCl$_3$) δ 7.05 (dd, J = 8.5, 6.0 Hz, 1H), 6.87 (ddt, J = 11.6, 8.3, 4.1 Hz, 2H), 5.33 (dq, J = 9.1, 6.2 Hz, 1H), 5.05 (d, J = 8.1 Hz, 1H), 4.28 (d, J = 7.6 Hz, 1H), 3.08 (dd, J = 9.2, 6.2 Hz, 1H), 2.32 (s, 3H), 2.18-2.06 (m, 1H), 1.45 (s, 9H), 1.39 (d, J = 7.2 Hz, 3H), 1.03 (d, J = 6.2 Hz, 3H), 0.85 (d, J = 6.8 Hz, 3H), 0.78 (d, J = 6.9 Hz, 3H). $^{19}$F NMR (376 MHz, CDCl$_3$) δ −117.34. |
| 18 | | IR (thin film) 2963, 1714, 1497, 1453, 1367, 1166, 1055, 860 cm$^{-1}$ | HRMS-ESI (m/z) [M + Na]$^+$ calcd for C$_{23}$H$_{36}$FNNaO$_4$, 432.2521; found, 432.2516 | $^1$H NMR (400 MHz, CDCl$_3$) δ 7.34 (dd, J = 9.7, 6.0 Hz, 1H), 6.86 (ddd, J = 8.3, 5.8, 2.9 Hz, 2H), 5.38 (dq, J = 8.1, 6.3 Hz, 1H), 5.05 (d, J = 8.2 Hz, 1H), 4.27 (qd, J = 6.4, 3.6 Hz, 1H), 2.74 (dd, J = 10.2, 3.6 Hz, 1H), 2.28 (s, 3H), 1.88 (ddq, J = 10.1, 6.2, 4.0, 3.2 Hz, 1H), 1.69-1.48 (m, 1H), 1.44 (s, 9H), 1.36 (d, J = 7.2 Hz, 1H), 1.35-1.11 (m, 2H), 1.10-0.83 (m, 6H), 0.74 (dt, J = 25.4, 7.3 Hz, 6H). $^{19}$F NMR (376 MHz, CDCl$_3$) δ −117.41, −118.02. |

TABLE 2-continued

Analytical Data

| Cmpd. No. | Melting Point (° C.) | IR (cm$^{-1}$) | MASS SPEC | NMR |
|---|---|---|---|---|
| 19 | | IR (thin film) 3442, 2965, 1713, 1497, 1453, 1367, 1165, 1055, 954, 860 cm$^{-1}$ | HRMS-ESI (m/z) [M + Na]$^+$ calcd for C$_{22}$H$_{34}$FNNaO$_4$, 418.2364; found, 418.2360 | $^1$H NMR (400 MHz, CDCl$_3$) δ 7.33 (dd, J = 9.5, 6.0 Hz, 1H), 6.86 (ddt, J = 12.5, 8.4, 3.6 Hz, 2H), 5.36 (ddq, J = 15.7, 9.5, 6.2 Hz, 1H), 5.08 (s, 1H), 4.28 (p, J = 6.3 Hz, 1H), 2.28 (d, J = 3.9 Hz, 3H), 2.04-1.57 (m, 1H), 1.45 (d, J = 1.9 Hz, 9H), 1.42-1.11 (m, 2H), 1.09-0.99 (m, 3H), 0.99-0.83 (m, 6H), 0.83-0.74 (m, 3H), 0.68 (d, J = 6.8 Hz, 1H). $^{19}$F NMR (376 MHz, CDCl$_3$) δ −117.94, −118.00. |
| 20 | | IR (thin film) 3356, 2977, 1708, 1498, 1163, 909, 731 cm$^{-1}$ | HRMS-ESI (m/z) [M + Na]$^+$ calcd for C$_{22}$H$_{32}$FNNaO$_4$, 416.2208; found, 416.2202 | $^1$H NMR (400 MHz, CDCl$_3$) δ 7.01 (dd, J = 8.4, 5.9 Hz, 1H), 6.85 (ddt, J = 11.3, 8.3, 4.1 Hz, 2H), 5.08 (dd, J = 14.2, 7.6 Hz, 2H), 4.36-4.05 (m, 1H), 3.23-3.03 (m, 1H), 2.70 (tt, J = 19.6, 9.3 Hz, 1H), 2.35 (s, 3H), 2.19-2.04 (m, 2H), 1.94-1.72 (m, 2H), 1.72-1.54 (m, 1H), 1.44 (s, 9H), 1.37 (d, J = 7.1 Hz, 4H), 1.05 (d, J = 6.3 Hz, 3H). $^{19}$F NMR (376 MHz, CDCl$_3$) δ −117.31. |
| 21 | | IR (thin film) 3355, 2954, 1711, 1497, 1163, 1066, 1019, 860, 733 cm$^{-1}$ | HRMS-ESI (m/z) [M + Na]$^+$ calcd for C$_{23}$H$_{34}$FNNaO$_4$, 430.2364; found, 430.2360 | $^1$H NMR (400 MHz, CDCl$_3$) δ 7.33 (dd, J = 8.4, 6.1 Hz, 1H), 6.86 (dd, J = 9.8, 2.8 Hz, 2H), 5.30 (qd, J = 6.1, 3.3 Hz, 1H), 5.05 (d, J = 7.7 Hz, 1H), 4.42-4.22 (m, 1H), 2.77 (dd, J = 10.8, 3.4 Hz, 1H), 2.30 (s, 3H), 2.28-2.10 (m, 2H), 1.93 (dtd, J = 11.5, 7.3, 3.4 Hz, 1H), 1.75-1.46 (m, 2H), 1.46-1.42 (m, 10H), 1.42-1.16 (m, 5H), 1.02 (d, J = 6.4 Hz, 3H), 0.86 (tdd, J = 12.0, 8.6, 6.0 Hz, 1H). $^{13}$C NMR (101 MHz, CDCl$_3$) δ 172.72, 160.92 (d, J = 243.9 Hz), 155.10, 138.76 (d, J = 7.3 Hz), 135.17 (d, J = 3.3 Hz), 129.94 (d, J = 7.8 Hz), 116.33 (d, J = 20.5 Hz), 112.67 (d, J = 20.6 Hz), 79.77, 73.09, 49.53, 42.66, 31.71, 28.31, 25.19, 24.50, 20.59, 18.55, 17.80. $^{19}$F NMR (376 MHz, CDCl$_3$) δ −117.74. |
| 22 | | IR (thin film) 3357, 2928, 1711, 1497, 1165, 860, 733 cm$^{-1}$ | HRMS-ESI (m/z) [M + Na]$^+$ calcd for C$_{24}$H$_{36}$FNNaO$_4$, 444.2521; found, 444.2515 | $^1$H NMR (400 MHz, CDCl$_3$) δ 7.33 (dd, J = 8.6, 6.1 Hz, 1H), 6.86 (ddt, J = 9.8, 7.1, 4.0 Hz, 2H), 5.47-5.36 (m, 1H), 5.10-4.94 (m, 1H), 4.37-4.21 (m, 1H), 2.72 (dd, J = 9.9, 4.0 Hz, 1H), 2.27 (s, 3H), 1.93 (d, J = 12.7 Hz, 1H), 1.80-1.48 (m, 4H), 1.44 (s, 10H), 1.29 (dd, J = 18.3, 7.7 Hz, 4H), 1.16-0.87 (m, 6H), 0.87-0.68 (m, 1H). $^{13}$C NMR (101 MHz, CDCl$_3$) δ 172.73, 160.93 (d, J = 244.0 Hz), 155.06, 139.41 (d, J = 7.3 Hz), 134.65 (d, J = 3.3 Hz), 129.67 (d, J = 7.8 Hz), 116.33 (d, J = 20.6 Hz), 112.74 (d, J = 20.5 Hz), 79.80, 71.03, 49.68, 39.93, 31.35, 28.35, 26.51, 26.37, 26.28, 20.74, 18.54, 17.99. $^{19}$F NMR (376 MHz, CDCl$_3$) δ −117.76. |
| 23 | | IR (thin film) 3356, 2975, 1712, 1498, 1366, 1165, 1063, 862, 735 cm$^{-1}$ | HRMS-ESI (m/z) [M + Na]$^+$ calcd for C$_{21}$H$_{32}$FNNaO$_4$, 404.2208; found, 404.2202 | $^1$H NMR (400 MHz, CDCl$_3$) δ 7.32 (dd, J = 8.4, 6.1 Hz, 1H), 6.92-6.82 (m, 2H), 5.40 (qd, J = 6.3, 3.9 Hz, 1H), 5.00 (d, J = 7.8 Hz, 1H), 4.41-4.18 (m, 1H), 2.63 (dd, J = 9.5, 4.3 Hz, 1H), 2.28 (s, 3H), 2.03 (dp, J = 9.7, 6.4 Hz, 1H), 1.44 (d, J = 3.7 Hz, 9H), 1.41-1.12 (m, 3H), 1.10-0.95 (m, 5H), 0.92-0.74 (m, 3H), 0.67 (d, J = 6.7 Hz, 3H). $^{19}$F NMR (376 MHz, CDCl$_3$) δ −117.72. |
| 24 | | IR (thin film) 3355, 2973, 2871, 1713, 1366, | HRMS-ESI (m/z) [M + Na]$^+$ calcd for C$_{22}$H$_{35}$NO$_4$Na, 400.2458; found, 400.2452 | $^1$H NMR (500 MHz, CDCl$_3$) δ 7.21-6.94 (m, 3H), 5.44-5.34 (m, 1H), 5.06 (d, J = 7.8 Hz, 1H), 4.33-4.23 (m, 1H), 2.68 (dd, J = 9.2, 4.9 Hz, 1H), 2.28 |

TABLE 2-continued

Analytical Data

| Cmpd. No. | Melting Point (° C.) | IR (cm$^{-1}$) | MASS SPEC | NMR |
|---|---|---|---|---|
| | | 1163, 733 cm$^{-1}$ | | (s, 3H), 2.25 (s, 3H), 2.03 (dp, J = 9.0, 6.6 Hz, 1H), 1.44 (s, 9H), 1.25 (d, J = 7.3 Hz, 3H), 1.05 (d, J = 6.3 Hz, 3H), 0.98 (d, J = 6.6 Hz, 3H), 0.70 (d, J = 6.7 Hz, 3H). |
| 25 | | IR (thin film) 3366, 2953, 1712, 1161, 731 cm$^{-1}$ | HRMS-ESI (m/z) [M + Na]$^+$ calcd for C$_{24}$H$_{37}$NO$_4$Na, 426.2615; found, 426.2608 | $^1$H NMR (500 MHz, CDCl$_3$) δ 7.24-6.91 (m, 3H), 5.30 (dq, J = 6.5, 3.4, 2.2 Hz, 1H), 5.08 (d, J = 8.2 Hz, 1H), 4.34-4.25 (m, 1H), 2.79 (dd, J = 10.3, 4.1 Hz, 1H), 2.29 (s, 3H), 2.27 (s, 3H), 2.25-2.14 (m, 1H), 1.97-1.80 (m, 1H), 1.70-1.61 (m, 1H), 1.58-1.35 (m, 12H), 1.34-1.17 (m, 5H), 1.07 (d, J = 6.3 Hz, 3H), 0.93-0.87 (m, 1H). |
| 26 | | IR (thin film) 3360, 2924, 1712, 1162, 732 cm$^{-1}$ | HRMS-ESI (m/z) [M + Na]$^+$ calcd for C$_{25}$H$_{39}$NO$_4$Na, 440.2771; found, 440.2765 | $^1$H NMR (500 MHz, CDCl$_3$) δ 7.21 (d, J = 7.9 Hz, 1H), 6.98-6.94 (m, 2H), 5.48-5.30 (m, 1H), 5.08 (d, J = 7.9 Hz, 1H), 4.38-4.23 (m, 1H), 2.75 (dd, J = 9.3, 4.8 Hz, 1H), 2.28 (s, 3H), 2.24 (s, 3H), 1.90-1.83 (m, 1H), 1.79-1.53 (m, 3H), 1.45 (s, 9H), 1.42-1.05 (m, 8H), 1.03 (d, J = 6.2 Hz, 3H), 1.01-0.73 (m, 2H). |
| 27 | | IR (thin film) 3358, 2970, 2931, 1713, 1163, 733 cm$^{-1}$ | HRMS-ESI (m/z) [M + Na]$^+$ calcd for C$_{23}$H$_{37}$NO$_4$Na, 414.2615; found, 414.2610 | $^1$H NMR (500 MHz, CDCl$_3$) δ 7.23-6.90 (m, 3H), 5.40 (dd, J = 7.7, 4.7 Hz, 1H), 5.06 (t, J = 9.1 Hz, 1H), 4.35-4.21 (m, 1H), 2.87-2.70 (m, 1H), 2.30-2.24 (m, 6H), 1.92-1.75 (m, 1H), 1.64-1.53 (m, 1H), 1.44 (d, J = 4.3 Hz, 9H), 1.35-1.14 (m, 3H), 1.15-0.62 (m, 10H). |
| 28 | | IR (thin film) 3358, 2973, 1711, 1501, 1163 cm$^{-1}$ | HRMS-ESI (m/z) [M + Na]$^+$ calcd for C$_{21}$H$_{32}$FNNaO$_5$, 420.2157; found, 420.2149 | $^1$H NMR (400 MHz, CDCl$_3$) δ 7.21 (dd, J = 8.5, 6.9 Hz, 1H), 6.69-6.53 (m, 2H), 5.39 (p, J = 5.9 Hz, 1H), 5.05 (d, J = 7.8 Hz, 1H), 4.33-4.17 (m, 1H), 3.78 (s, 3H), 3.06 (dd, J = 9.4, 5.0 Hz, 1H), 1.97 (dp, J = 9.2, 6.6 Hz, 1H), 1.44 (s, 9H), 1.27-1.20 (m, 3H), 1.05 (d, J = 6.2 Hz, 3H), 0.95 (d, J = 6.6 Hz, 3H), 0.68 (d, J = 6.7 Hz, 3H). $^{19}$F NMR (376 MHz, CDCl$_3$) δ -114.15. |
| 29 | | IR (thin film) 3358, 2965, 1714, 1501, 1165 cm$^{-1}$ | HRMS-ESI (m/z) [M + Na]$^+$ calcd for C$_{23}$H$_{36}$FNNaO$_5$, 448.2470; found, 448.2464 | $^1$H NMR (400 MHz, CDCl$_3$) δ 7.24 (dd, J = 8.6, 6.9 Hz, 1H), 6.68-6.50 (m, 2H), 5.44-5.30 (m, 1H), 5.05 (d, J = 8.1 Hz, 1H), 4.37-4.18 (m, 1H), 3.78 (s, 3H), 3.31 (dd, J = 9.7, 4.7 Hz, 1H), 1.76-1.56 (m, 2H), 1.44 (s, 9H), 1.41-1.17 (m, 5H), 1.02 (d, J = 6.2 Hz, 3H), 0.96 (ddd, J = 11.8, 9.1, 6.1 Hz, 1H), 0.88 (t, J = 7.4 Hz, 3H), 0.69 (t, J = 7.4 Hz, 3H). $^{13}$C NMR (101 MHz, CDCl$_3$) δ 172.81, 162.06 (d, J = 244.1 Hz), 159.15 (d, J = 9.2 Hz), 154.95, 130.14 (d, J = 9.1 Hz), 124.35 (d, J = 3.5 Hz), 106.70 (d, J = 20.5 Hz), 98.44 (d, J = 25.3 Hz), 79.73, 77.21, 72.04, 55.59, 49.46, 40.99, 28.34, 21.70, 21.48, 18.84, 18.42, 10.26, 10.03. $^{19}$F NMR (376 MHz, CDCl$_3$) δ -114.14. |
| 30 | | IR (thin film) 3356, 2929, 1714, 1502, 1165 cm$^{-1}$ | HRMS-ESI (m/z) [M + Na]$^+$ calcd for C$_{24}$H$_{36}$FNNaO$_5$, 460.2470; found, 460.2466 | $^1$H NMR (400 MHz, CDCl$_3$) δ 7.23 (t, J = 7.8 Hz, 1H), 6.69-6.48 (m, 2H), 5.47-5.33 (m, 1H), 5.07 (d, J = 8.2 Hz, 1H), 4.35-4.21 (m, 1H), 3.77 (s, 3H), 3.13 (s, 1H), 1.87-1.53 (m, 6H), 1.44 (s, 9H), 1.39-1.16 (m, 4H), 1.16-0.85 (m, 6H), 0.78 (qd, J = 12.2, 3.2 Hz, 1H). $^{19}$F NMR (376 MHz, CDCl$_3$) δ -114.17. |
| 31 | | IR (thin film) 3358, 2954, 1713, 1502, 1165 cm$^{-1}$ | HRMS-ESI (m/z) [M + H]$^+$ calcd for C$_{23}$H$_{34}$FNNaO$_5$, 446.2313; found, 446.2309 | $^1$H NMR (400 MHz, CDCl$_3$) δ 7.29-7.22 (m, 1H), 6.68-6.55 (m, 2H), 5.38-5.24 (m, 1H), 5.08 (d, J = 7.9 Hz, 1H), 4.38-4.21 (m, 1H), 3.78 (s, 3H), 3.12 (d, J = 10.7 Hz, 1H), 2.16 (qd, J = |

TABLE 2-continued

Analytical Data

| Cmpd. No. | Melting Point (° C.) | IR (cm$^{-1}$) | MASS SPEC | NMR |
|---|---|---|---|---|
| | | | | 10.0, 7.8, 2.9 Hz, 1H), 1.85 (ddt, J = 14.5, 11.1, 5.0 Hz, 1H), 1.74-1.59 (m, 1H), 1.52 (dtd, J = 15.4, 8.4, 3.7 Hz, 1H), 1.44 (d, J = 2.3 Hz, 9H), 1.43-1.14 (m, 6H), 1.03 (d, J = 6.3 Hz, 3H), 1.00-0.81 (m, 2H). $^{19}$F NMR (376 MHz, CDCl$_3$) δ −114.20. |
| 32 | | IR (thin film) 3358, 2968, 1711, 1501, 1163 cm$^{-1}$ | HRMS-ESI (m/z) [M + Na]$^+$ calcd for C$_{22}$H$_{34}$FNNaO$_5$, 434.2313; found, 434.2306 | $^1$H NMR (400 MHz, CDCl$_3$) δ 7.21 (ddd, J = 14.6, 8.6, 6.9 Hz, 1H), 6.61 (dddd, J = 15.1, 10.8, 4.4, 2.5 Hz, 2H), 5.47-5.33 (m, 1H), 5.05 (dd, J = 16.0, 7.7 Hz, 1H), 4.25 (dt, J = 23.5, 7.3 Hz, 1H), 3.78 (d, J = 1.3 Hz, 3H), 3.31-3.08 (m, 1H), 1.78 (ttd, J = 7.9, 6.3, 5.9, 3.5 Hz, 1H), 1.55-1.35 (m, 10H), 1.34-1.18 (m, 2H), 1.10 (td, J = 15.7, 14.1, 6.9 Hz, 3H), 1.04-0.81 (m, 5H), 0.77-0.61 (m, 3H). $^{19}$F NMR (376 MHz, CDCl$_3$) δ −114.11, −114.21. |
| 33 | | IR (thin film) 3352, 2964, 2932, 1712, 1605, 1509, 1452, 1366, 1224, 1160, 1052, 835 cm$^{-1}$ | HRMS-ESI (m/z) [M + Na]$^+$ calcd for C$_{20}$H$_{30}$FNO$_4$Na, 390.2051; found, 390.2044 | $^1$H NMR (400 MHz, CDCl$_3$) δ 7.06 (dd, J = 8.7, 5.6 Hz, 2H), 7.02-6.92 (m, 2H), 5.36 (dq, J = 8.7, 6.3 Hz, 1H), 5.05 (s, 1H), 4.37-4.19 (m, 1H), 2.69 (dd, J = 8.7, 6.4 Hz, 1H), 2.08 (h, J = 6.7 Hz, 1H), 1.45 (s, 8H), 1.38 (d, J = 7.2 Hz, 3H), 1.06 (d, J = 6.2 Hz, 3H), 0.86 (d, J = 6.8 Hz, 3H), 0.74 (d, J = 6.8 Hz, 3H). $^{13}$C NMR (126 MHz, CDCl$_3$) δ 172.79, 161.75 (d, J = 244.8 Hz), 155.03, 134.29, 131.03 (d, J = 7.6 Hz), 114.82 (d, J = 21.0 Hz), 79.79, 72.32, 55.88, 49.50, 28.34, 28.18, 21.30, 18.81, 18.41, 17.74. |
| 34 | | IR (thin film) 3358, 2976, 1710, 1501, 1276, 1164, 1035, 954, 833 cm$^{-1}$ | HRMS-ESI (m/z) [M + Na]$^+$ calcd for C$_{22}$H$_{32}$FNNaO$_5$, 432.2157; found, 432.2159 | $^1$H NMR (400 MHz, CDCl$_3$) δ 7.07 (dd, J = 8.3, 6.8 Hz, 1H), 6.63-6.53 (m, 2H), 5.19 (q, J = 6.2 Hz, 1H), 5.00 (d, J = 7.8 Hz, 1H), 4.18 (d, J = 7.4 Hz, 1H), 3.79 (s, 3H), 3.24 (s, 1H), 2.64 (h, J = 8.6 Hz, 1H), 2.11 (ddt, J = 11.6, 6.9, 4.3 Hz, 1H), 1.88-1.55 (m, 4H), 1.51-1.35 (m, 10H), 1.16 (d, J = 7.4 Hz, 3H), 1.11 (d, J = 6.4 Hz, 3H). $^{19}$F NMR (376 MHz, CDCl$_3$) δ −114.07. |
| 35 | | IR (thin film) 3358, 2928, 1712, 1502, 1450, 1163, 1033, 955, 834 cm$^{-1}$ | HRMS-ESI (m/z) [M + Na]$^+$ calcd for C$_{24}$H$_{36}$FNNaO$_5$, 460.2470; found, 460.2470 | $^1$H NMR (400 MHz, CDCl$_3$) δ 7.00 (dd, J = 8.3, 6.8 Hz, 1H), 6.60 (ddt, J = 10.7, 7.4, 4.1 Hz, 2H), 5.41 (s, 1H), 5.10 (d, J = 8.0 Hz, 1H), 4.37-4.17 (m, 1H), 3.76 (s, 3H), 3.36 (s, 1H), 1.76-1.48 m, 5H), 1.45 (s, 9H), 1.38 (d, J = 7.1 Hz, 3H), 1.32-1.16 (m, 2H), 1.16-0.92 (m, 5H), 0.92-0.72 (m, 2H). $^{19}$F NMR (376 MHz, CDCl$_3$) δ −113.94. |
| 36 | | IR (thin film) 3358, 2954, 1710, 1502, 1450, 1366, 1164, 1033, 953, 834, 732 cm$^{-1}$ | HRMS-ESI (m/z) [M + Na]$^+$ calcd for C$_{32}$H$_{34}$FNNaO$_5$, 446.2313; found, 446.2313 | $^1$H NMR (400 MHz, CDCl$_3$) δ 7.05 (t, J = 7.7 Hz, 1H), 6.67-6.53 (m, 2H), 5.29 (s, 1H), 5.07 (s, 1H), 4.23 (d, J = 7.9 Hz, 1H), 3.76 (s, 3H), 3.49 (d, J = 67.4 Hz, 1H), 2.11 (d, J = 53.5 Hz, 1H), 1.84 (dtd, J = 10.9, 7.1, 3.4 Hz, 1H), 1.70-1.58 (m, 1H), 1.58-1.37 (m, 12H), 1.34 (d, J = 7.1 Hz, 3H), 1.30-1.18 (m, 2H), 1.09 (d, J = 6.4 Hz, 3H), 0.99-0.83 (m, 1H). $^{19}$F NMR (376 MHz, CDCl$_3$) δ −114.07. |
| 37 | | IR (thin film) 3359, 2965, 1713, 1501, 1165, 1054, 1035, 955, 834 cm$^{-1}$ | HRMS-ESI (m/z) [M + Na]$^+$ calcd for C$_{23}$H$_{36}$FNNaO$_5$, 448.2470; found, 448.2469 | $^1$H NMR (400 MHz, CDCl$_3$) δ 7.04 (dd, J = 8.3, 6.8 Hz, 1H), 6.60 (ddt, J = 11.0, 7.6, 2.5 Hz, 2H), 5.40 (dt, J = 12.5, 6.3 Hz, 1H), 5.20-5.02 (m, 1H), 4.27 (s, 1H), 3.77 (s, 2H), 3.57 (d, J = 10.1 Hz, 1H), 1.55 (dt, J = 9.8, 6.7 Hz, 1H), 1.50-1.42 (m, 10H), 1.42-1.30 (m, 4H), 1.29-1.09 (m, 2H), 1.06 (d, J = 6.3 Hz, 3H), 0.94 (t, J = 7.4 Hz, 3H), 0.91- |

TABLE 2-continued

Analytical Data

| Cmpd. No. | Melting Point (° C.) | IR (cm$^{-1}$) | MASS SPEC | NMR |
|---|---|---|---|---|
| | | | | 0.78 (m, 1H), 0.75 (t, J = 7.2 Hz, 3H). $^{19}$F NMR (376 MHz, CDCl$_3$) δ −113.91. |
| 38 | | IR (thin film) 3358, 2966, 1711, 1600, 1502, 1452, 1366, 1164, 1053, 1035, 954, 834 cm$^{-1}$ | HRMS-ESI (m/z) [M + Na]$^+$ calcd for C$_{22}$H$_{34}$FNNaO$_5$, 434.2313; found, 434.2312 | $^1$H NMR (400 MHz, CDCl$_3$) δ 7.02 (t, J = 7.6 Hz, 1H), 6.66-6.56 (m, 2H), 5.40 (tt, J = 10.1, 5.5 Hz, 1H), 5.11 (s, 1H), 4.29 (dd, J = 15.4, 7.9 Hz, 1H), 3.77 (d, J = 2.3 Hz, 3H), 3.42 (d, J = 27.2 Hz, 1H), 1.80 (ddt, J = 8.9, 6.8, 4.4 Hz, 1H), 1.45 (d, J = 2.2 Hz, 9H), 1.36 (ddd, J = 14.4, 12.6, 6.9 Hz, 4H), 1.05 (dd, J = 8.1, 6.2 Hz, 3H), 0.97-0.82 (m, 4H), 0.76 (dd, J = 11.5, 7.0 Hz, 3H). $^{19}$F NMR (376 MHz, CDCl$_3$) δ −113.85, −113.92. |
| 39 | | IR (thin film) 3359, 2976, 1709, 1501, 1164, 1035, 954, 834, 732 cm$^{-1}$ | HRMS-ESI (m/z) [M + H]$^+$ calcd for C$_{22}$H$_{32}$FNNaO$_5$, 432.2157; found, 432.2147 | $^1$H NMR (400 MHz, CDCl$_3$) δ 7.00-6.93 (m, 1H), 6.58 (ddd, J = 10.0, 6.6, 2.0 Hz, 2H), 5.21-4.97 (m, 2H), 4.24 (d, J = 7.9 Hz, 1H), 3.79 (s, 3H), 3.31 (s, 1H), 2.76 (h, J = 8.5 Hz, 1H), 2.12 (dddd, J = 22.7, 20.7, 11.3, 6.7 Hz, 1H), 1.97-1.74 (m, 2H), 1.74-1.57 (m, 2H), 1.50-1.37 (m, 10H), 1.34 (d, J = 7.1 Hz, 3H), 1.06 (d, J = 6.4 Hz, 3H). $^{19}$F NMR (376 MHz, CDCl$_3$) δ −113.90. |
| 40 | | IR (thin film) 3359, 2964, 1710, 1502, 1164, 1050, 1034, 954, 834, 732 cm$^{-1}$ | HRMS-ESI (m/z) [M + Na]$^+$ calcd for C$_{21}$H$_{32}$FNNaO$_5$, 420.2157; found, 420.2154 | $^1$H NMR (400 MHz, CDCl$_3$) δ 7.01 (dd, J = 8.2, 6.7 Hz, 1H), 6.66-6.57 (m, 2H), 5.38 (t, J = 7.4 Hz, 1H), 5.09 (d, J = 7.7 Hz, 1H), 4.38-4.20 (m, 1H), 3.77 (s, 3H), 3.32 (s, 1H), 2.14-2.01 (m, 1H), 1.45 (s, 9H), 1.37 (d, J = 7.2 Hz, 3H), 1.05 (d, J = 6.2 Hz, 3H), 0.84 (d, J = 6.8 Hz, 3H), 0.73 (d, J = 6.7 Hz, 3H). $^{19}$F NMR (376 MHz, CDCl$_3$) δ −113.87. |
| 41 | | IR (thin film) 3358, 2975, 2935, 1713, 1164, 1021 cm$^{-1}$ | HRMS-ESI (m/z) [M + Na]$^+$ calcd for C$_{23}$H$_{35}$NO$_4$Na, 412.2458; found, 412.2463 | $^1$H NMR (500 MHz, CDCl$_3$) δ 7.09-6.87 (m, 3H), 5.21-5.07 (m, 1H), 4.98 (d, J = 7.9 Hz, 1H), 4.29-4.07 (m, 1H), 3.02 (dd, J = 10.5, 6.3 Hz, 1H), 2.68 (hept, J = 8.0, 7.1 Hz, 1H), 2.32 (s, 3H), 2.26 (s, 3H), 2.19-2.08 (m, 1H), 1.88-1.62 (m, 4H), 1.43 (s, 9H), 1.32-1.22 (m, 1H), 1.16 (d, J = 6.4 Hz, 3H), 1.07 (d, J = 7.1 Hz, 3H). |
| 42 | | IR (thin film) 3365, 2969, 2932, 2875, 1714, 1492, 1366, 1166, 1053 cm$^{-1}$ | HRMS-ESI (m/z) [M + Na]$^+$ calcd for C$_{20}$H$_{30}$ClNO$_4$, 409.1763; found, 409.1764 | $^1$H NMR (400 MHz, CDCl$_3$) δ 7.27 (d, J = 9.9 Hz, 2H), 7.03 (d, J = 8.5 Hz, 2H), 5.42-5.31 (m, 1H), 5.13-4.95 (m, 1H), 4.27 (t, 1H), 2.68 (dd, J = 8.6, 6.5 Hz, 1H), 2.16-1.98 (m, 1H), 1.45 (s, 9H), 1.38 (d, J = 7.2 Hz, 3H), 1.07 (d, J = 6.3 Hz, 3H), 0.86 (d, J = 6.8 Hz, 3H), 0.74 (d, J = 6.8 Hz, 3H). $^{13}$C NMR (126 MHz, CDCl$_3$) δ 172.76, 137.14, 132.52, 131.02, 128.15, 77.21, 72.15, 56.07, 49.49, 28.35, 28.15, 25.29, 21.27, 18.81, 18.47, 17.70, 14.13. |
| 43 | | IR (thin film) 3353, 2969, 2931, 1714, 1506, 1366, 1163, 1052 cm$^{-1}$ | HRMS-ESI (m/z) [M + Na]$^+$ calcd for C$_{21}$H$_{32}$FNO$_4$, 406.2268; found, 406.2269 | $^1$H NMR (400 MHz, CDCl$_3$) δ 7.09 (t, J = 8.0 Hz, 1H), 6.80-6.71 (m, 2H), 5.40-5.25 (m, 1H), 5.06 (s, 1H), 4.33-4.22 (m, 1H), 2.65 (dd, J = 8.7, 6.5 Hz, 1H), 2.25 (d, J = 1.8 Hz, 3H), 2.13-1.98 (m, 1H), 1.45 (s, 9H), 1.38 (d, J = 7.2 Hz, 3H), 1.08 (d, J = 6.3 Hz, 3H), 0.86 (d, J = 6.8 Hz, 3H), 0.76 (d, J = 6.8 Hz, 3H). $^{13}$C NMR (126 MHz, CDCl$_3$) δ 172.79, 161.92, 159.98, 138.35, 138.30, 130.82, 130.78, 125.20, 125.17, 123.01, 122.88, 116.22, 116.04, 79.77, 77.21, 72.28, 56.12, 49.50, 34.67, 31.59, 28.34, 28.19, 25.28, 21.29, 18.81, 18.51, 17.74, 14.21, 14.18, 14.13. |
| 44 | | IR (thin film) 3351, 2976, 1709, | HRMS-ESI (m/z) [M + Na]$^+$ calcd for C$_{20}$H$_{29}$F$_2$NO$_4$, 408.1957; found, 408.1956 | $^1$H NMR (400 MHz, CDCl$_3$) δ 7.09 (dt, J = 10.1, 8.3 Hz, 1H), 6.92 (ddd, J = 11.7, 7.6, 2.2 Hz, 1H), 6.86-6.76 (m, |

TABLE 2-continued

Analytical Data

| Cmpd. No. | Melting Point (° C.) | IR (cm⁻¹) | MASS SPEC | NMR |
|---|---|---|---|---|
| | | 1515, 1280, 1163, 1053, 771 cm⁻¹ | | 1H), 5.31 (dt, J = 8.5, 6.3 Hz, 1H), 5.03 (s, 1H), 4.27 (s, 1H), 2.72-2.62 (m, 1H), 2.13-1.96 (m, 1H), 1.45 (s, 9H), 1.37 (d, J = 7.2 Hz, 3H), 1.08 (d, J = 6.3 Hz, 3H), 0.88 (d, J = 6.8 Hz, 3H), 0.75 (d, J = 6.8 Hz, 3H). $^{13}$C NMR (126 MHz, CDCl$_3$) δ 172.72, 125.58, 118.35, 118.21, 116.77, 116.63, 79.84, 77.21, 71.98, 55.92, 49.48, 28.33, 28.24, 21.20, 18.75, 18.57, 17.51. |
| 45 | | IR (thin film) 2965, 1714, 1503, 1366, 1211, 1164, 1052 cm⁻¹ | HRMS-ESI (m/z) [M + Na]⁺ calcd for C$_{21}$H$_{32}$FNNaO$_4$, 404.2208; found, 404.2208 | $^1$H NMR (400 MHz, CDCl$_3$) δ 6.96-6.84 (m, 3H), 5.35 (dq, J = 8.8, 6.2 Hz, 1H), 5.11 (d, J = 7.8 Hz, 1H), 4.28 (p, J = 7.5 Hz, 1H), 2.65 (dd, J = 8.9, 6.3 Hz, 1H), 2.26 (d, J = 1.9 Hz, 3H), 2.13-2.03 (m, 1H), 1.45 (s, 9H), 1.39 (d, J = 7.2 Hz, 3H), 1.07 (d, J = 6.3 Hz, 3H), 0.85 (d, J = 6.8 Hz, 3H), 0.75 (d, J = 6.8 Hz, 3H). $^{13}$C NMR (101 MHz, CDCl$_3$) δ 172.82, 160.30 (d, J = 243.6 Hz), 155.04, 134.03 (d, J = 3.9 Hz), 132.62 (d, J = 4.9 Hz), 128.31 (d, J = 7.7 Hz), 124.13 (d, J = 17.1 Hz), 114.42 (d, J = 22.0 Hz), 79.75, 72.46, 55.89, 49.56, 28.36, 28.19, 21.34, 18.76, 18.46, 17.87, 14.64 (d, J = 3.5 Hz). $^{19}$F NMR (376 MHz, CDCl$_3$) δ −120.77. |
| 46 | | IR (thin film) 3369, 2965, 1714, 1508, 1366, 1293, 1165, 1053, 1032 cm⁻¹ | HRMS-ESI (m/z) [M + Na]⁺ calcd for C$_{21}$H$_{32}$FNNaO$_5$, 420.2157; found, 420.2158 | $^1$H NMR (400 MHz, CDCl$_3$) δ 7.03 (t, J = 8.5 Hz, 1H), 6.67 (ddd, J = 8.6, 2.6, 0.8 Hz, 1H), 6.60 (dd, J = 12.0, 2.6 Hz, 1H), 5.44-5.34 (m, 1H), 5.13 (d, J = 8.0 Hz, 1H), 4.28 (dd, J = 11.1, 4.2 Hz, 1H), 3.79 (s, 3H), 3.08 (dd, J = 8.5, 6.8 Hz, 1H), 2.15-2.05 (m, 1H), 1.45 (s, 9H), 1.38 (d, J = 7.2 Hz, 3H), 1.09 (d, J = 6.3 Hz, 3H), 0.90 (dd, J = 6.7, 1.0 Hz, 3H), 0.76 (d, J = 6.7 Hz, 3H). $^{13}$C NMR (101 MHz, CDCl$_3$) δ 172.80, 162.10 (d, J = 244.2 Hz), 159.37 (d, J = 11.4 Hz), 155.06, 130.68 (d, J = 6.6 Hz), 117.55 (d, J = 15.5 Hz), 109.59 (d, J = 3.0 Hz), 101.42 (d, J = 27.9 Hz), 79.66, 72.25, 55.44, 49.55, 47.97, 28.35, 21.11, 18.84, 18.60, 17.55. $^{19}$F NMR (376 MHz, CDCl$_3$) δ −113.07. |
| 47 | | IR (thin film) 3369, 2965, 1712, 1515, 1273, 1221, 1164, 1052, 1028 cm⁻¹ | HRMS-ESI (m/z) [M + Na]⁺ calcd for C$_{21}$H$_{32}$FNNaO$_5$, 420.2157; found, 420.2160 | $^1$H NMR (400 MHz, CDCl$_3$) δ 6.93-6.77 (m, 3H), 5.32 (dq, J = 8.6, 6.2 Hz, 1H), 5.17-5.04 (m, 1H), 4.28 (dd, J = 11.1, 4.1 Hz, 1H), 3.88 (s, 3H), 2.63 (dd, J = 8.7, 6.4 Hz, 1H), 2.13-2.00 (m, 1H), 1.45 (s, 9H), 1.38 (d, J = 7.2 Hz, 3H), 1.08 (d, J = 6.3 Hz, 3H), 0.86 (d, J = 6.8 Hz, 3H), 0.76 (d, J = 6.8 Hz, 3H). $^{13}$C NMR (101 MHz, CDCl$_3$) δ 172.78, 155.04, 151.97 (d, J = 245.2 Hz), 146.32 (d, J = 10.6 Hz), 131.77 (d, J = 5.7 Hz), 125.40 (d, J = 3.6 Hz), 117.21 (d, J = 18.3 Hz), 112.98 (d, J = 2.1 Hz), 79.75, 72.30, 56.25, 55.81, 49.53, 28.35, 28.25, 21.30, 18.75, 18.51, 17.72. $^{19}$F NMR (376 MHz, CDCl$_3$) δ −135.65. |
| 48 | | IR (thin film) 3355, 2963, 1714, 1506, 1454, 1366, 1256, 1163, 1050 cm⁻¹ | HRMS-ESI (m/z) [M + Na]⁺ calcd for C$_{22}$H$_{35}$NNaO$_5$, 416.2407; found, 416.2410 | $^1$H NMR (400 MHz, CDCl$_3$) δ 6.94 (d, J = 7.7 Hz, 1H), 6.72 (dd, J = 7.6, 1.5 Hz, 1H), 6.68 (d, J = 1.6 Hz, 1H), 5.40 (t, J = 7.7 Hz, 1H), 5.14 (d, J = 7.4 Hz, 1H), 4.35-4.20 (m, 1H), 3.76 (s, 3H), 3.32 (s, 1H), 2.33 (s, 3H), 2.08 (dq, J = 12.5, 6.3, 5.8 Hz, 1H), 1.45 (s, 9H), 1.38 (d, J = 7.2 Hz, 3H), 1.05 (d, J = 6.2 Hz, 3H), 0.84 (d, J = 6.8 Hz, 3H), 0.74 (d, J = 6.8 Hz, 3H). $^{13}$C NMR (101 MHz, CDCl$_3$) δ 172.75, |

TABLE 2-continued

Analytical Data

| Cmpd. No. | Melting Point (° C.) | IR (cm$^{-1}$) | MASS SPEC | NMR |
|---|---|---|---|---|
| | | | | 158.09, 155.01, 137.18, 129.51, 124.60, 120.74, 111.75, 79.60, 73.28, 55.34, 53.89, 49.67, 29.30, 28.76, 28.37, 21.44, 21.12, 18.79, 18.12. |
| 49 | | IR (thin film) 3364, 2961, 1712, 1502, 1453, 1366, 1250, 1162, 1048, 732 cm$^{-1}$ | HRMS-ESI (m/z) [M + Na]$^+$ calcd for C$_{22}$H$_{35}$NNaO$_5$, 416.2407; found, 416.2404 | $^1$H NMR (400 MHz, CDCl$_3$) δ 7.03-6.95 (m, 1H), 6.71 (d, J = 7.9 Hz, 2H), 5.33 (dq, J = 9.4, 6.2 Hz, 1H), 5.12 (d, J = 7.9 Hz, 1H), 4.38-4.20 (m, 1H), 3.78 (s, 3H), 3.05 (dd, J = 9.4, 5.9 Hz, 1H), 2.31 (s, 3H), 2.12 (dq, J = 13.4, 6.7 Hz, 1H), 1.45 (s, 9H), 1.40 (d, J = 7.2 Hz, 3H), 1.03 (d, J = 6.2 Hz, 3H), 0.84 (d, J = 6.8 Hz, 3H), 0.79 (d, J = 6.9 Hz, 3H). $^{13}$C NMR (101 MHz, CDCl$_3$) δ 172.89, 157.60, 155.00, 138.86, 129.96, 128.86, 115.89, 110.91, 79.71, 73.89, 55.04, 49.60, 49.24, 29.58, 28.35, 21.08, 20.98, 18.72, 18.64, 18.33. |
| 50 | | IR (thin film) 3363, 2962, 1712, 1505, 1207, 1157, 1045, 732 cm$^{-1}$ | HRMS-ESI (m/z) [M + Na]$^+$ calcd for C$_{22}$H$_{35}$NO$_6$Na, 432.2357; found, 432.2347 | $^1$H NMR (400 MHz, CDCl$_3$) δ 7.04-6.82 (m, 1H), 6.50-6.30 (m, 2H), 5.50-5.28 (m, 1H), 5.11 (d, J = 7.4 Hz, 1H), 4.36-4.17 (m, 1H), 3.80 (s, 3H), 3.76 (s, 3H), 3.44-3.00 (m, 1H), 2.06 (h, J = 6.7 Hz, 1H), 1.45 (s, 9H), 1.38 (d, J = 7.1 Hz, 3H), 1.05 (d, J = 6.2 Hz, 3H), 0.83 (d, J = 6.8 Hz, 3H), 0.73 (d, J = 6.8 Hz, 3H). |
| 51 | | IR (thin film) 3359, 2968, 1713, 1493, 1242, 1163, 1051, 755 cm$^{-1}$ | HRMS-ESI (m/z) [M + Na]$^+$ calcd for C$_{21}$H$_{33}$NO$_5$Na, 402.23; found, 402.2194 | $^1$H NMR (400 MHz, CDCl$_3$) δ 7.25-7.13 (m, 1H), 7.07 (dd, J = 7.6, 1.8 Hz, 1H), 6.95-6.81 (m, 2H), 5.58-5.36 (m, 1H), 5.20-5.02 (m, 1H), 4.38-4.17 (m, 1H), 3.78 (s, 3H), 3.55-3.08 (m, 1H), 2.10 (h, J = 6.7 Hz, 1H), 1.45 (s, 9H), 1.38 (d, J = 7.1 Hz, 3H), 1.06 (d, J = 6.2 Hz, 3H), 0.85 (d, J = 6.8 Hz, 3H), 0.74 (d, J = 6.8 Hz, 3H). |
| 52 | | | ESIMS m/z 250.4 ([M + H]$^+$) | |
| 53 | | | ESIMS m/z 375.5 ([M + Boc]$^+$) | |
| 54 | | | ESIMS m/z 250.4 ([M + H]$^+$) | |
| 55 | | | ESIMS m/z 262 ([M + H]$^+$) | |
| 56 | | | ESIMS m/z 264.3 ([M + H]$^+$) | |
| 57 | | | ESIMS m/z 264.4 ([M + H]$^+$) | |
| 58 | | | ESIMS m/z 268 ([M + H]$^+$) | |
| 59 | | | ESIMS m/z 266 ([M + H]$^+$) | |
| 60 | | | HRMS-ESI (m/z) [M + H]$^+$ calcd for C$_{17}$H$_{28}$NO$_2$, 278.2120; found, 278.2115 | |
| 61 | | | HRMS-ESI (m/z) [M + H]$^+$ calcd for C$_{17}$H$_{26}$NO$_2$, 276.1963; found, 276.1960 | |
| 62 | | | ESIMS m/z 282.2 ([M + H]$^+$) | |
| 63 | | | ESIMS m/z 310.2 ([M + H]$^+$) | |
| 64 | | | ESIMS m/z 308.2 ([M + H]$^+$) | |
| 65 | | | ESIMS m/z 322.2 ([M + H]$^+$) | |
| 66 | | | ESIMS m/z 296.2 ([M + H]$^+$) | |
| 67 | | | ESIMS m/z 294.2 ([M + H]$^+$) | |
| 68 | | | ESIMS m/z 308.2 ([M + H]$^+$) | |
| 69 | | | ESIMS m/z 322.2 ([M + H]$^+$) | |
| 70 | | | ESIMS m/z 282.1 ([M + H]$^+$) | |

TABLE 2-continued

Analytical Data

| Cmpd. No. | Melting Point (° C.) | IR (cm$^{-1}$) | MASS SPEC | NMR |
|---|---|---|---|---|
| 71 | | | ESIMS m/z 310.2 ([M + H]$^+$) | |
| 72 | | | ESIMS m/z 296.2 ([M + H]$^+$) | |
| 73 | | | ESIMS m/z 294.2 ([M + H]$^+$) | |
| 74 | | | ESIMS m/z 308.1 ([M + H]$^+$) | |
| 75 | | | ESIMS m/z 322.2 ([M + H]$^+$) | |
| 76 | | | ESIMS m/z 282.2 ([M + H]$^+$) | |
| 77 | | | HRMS-ESI (m/z) [M + H]$^+$ calcd for C$_{18}$H$_{30}$NO$_2$, 292.2271; found, 292.2268 | |
| 78 | | | HRMS-ESI (m/z) [M + H]$^+$ calcd for C$_{20}$H$_{32}$NO$_2$, 318.2428; found, 318.2525 | |
| 79 | | | HRMS-ESI (m/z) [M + H]$^+$ calcd for C$_{19}$H$_{30}$NO$_2$, 304.2271; found, 304.2267 | |
| 80 | | | HRMS-ESI (m/z) [M + H]$^+$ calcd for C$_{17}$H$_{28}$NO$_2$, 278.2115; found, 278.2112 | |
| 81 | | IR (thin film) 3383, 2960, 1737, 1603, 1509, 1460, 1386, 1223, 1117, 834 cm$^{-1}$ | HRMS-ESI (m/z) [M + H]$^+$ calcd for C$_{15}$H$_{23}$FNO$_2$, 268.1707; found, 268.1717 | |
| 82 | | | ESIMS m/z 298.3 ([M + H]$^+$) | |
| 83 | | | EIMS m/z 324.9 | |
| 84 | | | ESIMS m/z 338.3 ([M + H]$^+$) | |
| 85 | | | EIMS m/z 324.2 | |
| 86 | | | EIMS m/z 311.1 | |
| 87 | | | EIMS m/z 310.2 | |
| 88 | | | EIMS m/z 337.3 | |
| 89 | | | EIMS m/z 323.0 | |
| 90 | | | EIMS m/z 326.2 | |
| 91 | | | EIMS m/z 311.9 | |
| 92 | | | ESIMS m/z 310.0 ([M + H]$^+$) | |
| 93 | | | EIMS m/z 298.2 | |
| 94 | | | HRMS-ESI (m/z) [M + H]$^+$ calcd for C$_{18}$H$_{28}$NO$_2$, 290.2115; found, 290.2116 | |
| 95 | | IR (thin film) 3451, 3381, 2957, 2751, 2626, 2506, 1757, 1515, 1492, 1240, 1214, 1092, 832 cm$^{-1}$ | ESIMS m/z 284.1 ([M + H]$^+$) | |
| 96 | | IR (thin film) 2959, 2928, 1738, 1507, 1235, 1117, 731 cm$^{-1}$ | ESIMS m/z 282.2 ([M + H]$^+$) | |
| 97 | | IR (thin film) 3386, 2961, 1739, 1515, 1238, 1210, 1115 cm$^{-1}$ | ESIMS m/z 286.2 ([M + H]$^+$) | |
| 98 | | | ESIMS m/z 282.3 ([M + H]$^+$) | |
| 99 | | | ESIMS m/z 298.3 ([M + H]$^+$) | |

TABLE 2-continued

Analytical Data

| Cmpd. No. | Melting Point (° C.) | IR (cm$^{-1}$) | MASS SPEC | NMR |
|---|---|---|---|---|
| 100 | | | ESIMS m/z 298.3 ([M + H]$^+$) | |
| 101 | | | ESIMS m/z 294.3 ([M + H]$^+$) | |
| 102 | | | ESIMS m/z 294.3 ([M + H]$^+$) | |
| 103 | | | HRMS-ESI (m/z) [M + H]$^+$ calcd for C$_{16}$H$_{26}$NO$_3$, 280.1907; found, 280.1908 | |
| 104 | | | HRMS-ESI (m/z) [M + Na]$^+$ calcd for C$_{17}$H$_{27}$NO$_4$Na, 382.1832; found, 332.1811 | |
| 105 | | | HRMS-ESI (m/z) [M + H]$^+$ calcd for C$_{22}$H$_{29}$N$_2$O$_5$, 401.2076; found, 401.2078 | $^1$H NMR (400 MHz, CDCl$_3$) δ 12.15 (s, 1H), 8.46 (d, J = 8.0 Hz, 1H), 8.01 (d, J = 5.2 Hz, 1H), 7.27-7.08 (m, 5H), 6.88 (d, J = 5.2 Hz, 1H), 5.56-5.43 (m, 1H), 4.74-4.54 (m, 1H), 3.94 (s, 3H), 2.37 (dd, J = 8.4, 5.7 Hz, 1H), 2.03 (dh, J = 8.4, 6.6 Hz, 1H), 1.32 (d, J = 7.2 Hz, 3H), 1.13 (d, J = 6.3 Hz, 3H), 0.95 (d, J = 6.6 Hz, 3H), 0.71 (d, J = 6.7 Hz, 3H). $^{13}$C NMR (101 MHz, CDCl$_3$) δ 171.67, 168.64, 155.38, 148.77, 140.46, 139.69, 130.49, 129.58, 127.91, 126.49, 109.45, 72.39, 57.96, 56.07, 48.05, 29.19, 21.30, 20.17, 18.93, 18.06. |
| 106 | | | HRMS-ESI (m/z) [M + H]+ calcd for C$_{24}$H$_{31}$N$_2$O$_5$, 427.2233; found, 427.2235 | $^1$H NMR (400 MHz, CDCl$_3$) δ 12.17 (s, 1H), 8.52 (d, J = 8.0 Hz, 1H), 8.01 (d, J = 5.2 Hz, 1H), 7.31-7.12 (m, 5H), 6.88 (d, J = 5.2 Hz, 1H), 5.37 (qd, J = 6.3, 3.9 Hz, 1H), 4.81-4.58 (m, 1H), 3.94 (s, 3H), 2.42 (dd, J = 10.3, 4.1 Hz, 1H), 2.25-2.16 (m, 1H), 1.88 (dtd, J = 11.2, 7.2, 3.3 Hz, 1H), 1.69-1.50 (m, 3H), 1.49 (d, J = 7.2 Hz, 3H), 1.47-1.30 (m, 2H), 1.24-1.13 (m, 1H), 1.08 (d, J = 6.4 Hz, 3H), 0.99-0.85 (m, 1H). $^{13}$C NMR (101 MHz, CDCl$_3$) δ 171.60, 168.73, 155.39, 148.80, 140.63, 140.49, 130.45, 129.44, 127.93, 126.45, 109.49, 73.59, 56.60, 56.07, 48.21, 42.11, 31.63, 31.45, 25.07, 24.52, 18.73, 18.22. |
| 107 | | | HRMS-ESI (m/z) [M + H]$^+$ calcd for C$_{22}$H$_{29}$N$_2$O$_5$, 401.2076; found, 401.2073 | $^1$H NMR (300 MHz, CDCl$_3$) δ 12.16 (s, 1H), 8.50 (d, J = 7.9 Hz, 1H), 8.00 (d, J = 5.2 Hz, 1H), 7.38-7.17 (m, 3H), 7.13-7.04 (m, 2H), 6.88 (d, J = 5.2 Hz, 1H), 5.44 (dq, J = 8.6, 6.3 Hz, 1H), 4.81-4.59 (m, 1H), 3.95 (s, 3H), 2.72 (dd, J = 8.6, 6.5 Hz, 1H), 2.24-2.00 (m, 1H), 1.55 (d, J = 7.2 Hz, 3H), 1.11 (d, J = 6.3 Hz, 3H), 0.86 (d, J = 6.8 Hz, 3H), 0.76 (d, J = 6.7 Hz, 3H). $^{13}$C NMR (75 MHz, CDCl$_3$) δ 171.73, 168.72, 155.37, 148.75, 140.50, 138.53, 130.49, 129.78, 127.93, 126.66, 109.45, 73.04, 56.60, 56.11, 48.21, 28.31, 21.31, 18.65, 18.35, 17.76. |
| 108 | | | HRMS-ESI (m/z) [M + H]$^+$ calcd for C$_{23}$H$_{29}$N$_2$O$_5$, 413.2071; found, 413.2070 | $^1$H NMR (400 MHz, CDCl$_3$) δ 12.18 (s, 1H), 8.50 (d, J = 8.1 Hz, 1H), 8.00 (d, J = 5.2 Hz, 1H), 7.12-7.05 (m, 4H), 6.88 (d, J = 5.2 Hz, 1H), 5.42-5.24 (m, 1H), 4.82-4.63 (m, 1H), 3.95 (s, 3H), 2.32 (s, 3H), 1.99 (dd, J = 10.1, 7.0 Hz, 1H), 1.52 (d, J = 7.2 Hz, 3H), 1.18 (d, J = 6.4 Hz, 3H), 1.15-1.06 (m, 1H), 0.70-0.61 (m, 1H), 0.44-0.29 (m, 2H), −0.01-−0.10 (m, 1H). $^{13}$C NMR (101 MHz, CDCl$_3$) δ 171.66, 168.63, 155.40, 148.79, 140.43, 138.48, 136.16, 130.58, 128.94, 128.25, 109.44, 76.20, 56.06, 55.24, 48.15, 21.01, 18.39, 18.13, 12.99, 6.94, 2.89. |
| 109 | | IR (thin film) 3370, | HRMS-ESI (m/z) [M + H]$^+$ calcd for C$_{23}$H$_{31}$N$_2$O$_5$, | $^1$H NMR (400 MHz, CDCl$_3$) δ 12.17 (d, J = 0.6 Hz, 1H), 8.51 (d, J = 7.9 Hz, |

TABLE 2-continued

Analytical Data

| Cmpd. No. | Melting Point (° C.) | IR (cm⁻¹) | MASS SPEC | NMR |
|---|---|---|---|---|
| | | 2960, 1732, 1649, 1527, 1481, 1451, 1263, 1150, 1048, 799, 730 cm⁻¹ | 415.2227; found, 415.2222 | 1H), 8.00 (d, J = 5.2 Hz, 1H), 7.11-7.05 (m, 2H), 7.00-6.95 (m, 2H), 6.88 (d, J = 5.2 Hz, 1H), 5.42 (dq, J = 8.6, 6.3 Hz, 1H), 4.75-4.65 (m, 1H), 3.94 (s, 3H), 2.68 (dd, J = 8.6, 6.5 Hz, 1H), 2.31 (s, 3H), 2.09 (h, J = 6.7 Hz, 1H), 1.56 (d, J = 7.2 Hz, 3H), 1.11 (d, J = 6.2 Hz, 3H), 0.85 (d, J = 6.8 Hz, 3H), 0.76 (d, J = 6.8 Hz, 3H). $^{13}C$ NMR (101 MHz, CDCl$_3$) δ 171.72, 168.74, 155.39, 148.79, 140.47, 136.11, 135.40, 130.54, 129.64, 128.64, 109.47, 73.12, 56.22, 56.07, 48.23, 28.28, 21.32, 20.99, 18.65, 18.33, 17.75. |
| 110 | | | HRMS-ESI (m/z) [M + H]⁺ calcd for $C_{22}H_{28}FN_2O_5$, 419.1977; found, 419.1978 | $^1H$ NMR (400 MHz, CDCl$_3$) δ 12.15 (s, 1H), 8.61-8.38 (m, 1H), 8.06-7.94 (m, 1H), 7.12-6.82 (m, 5H), 5.51-5.33 (m, 1H), 4.75-4.60 (m, 1H), 3.95 (s, 3H), 2.77-2.63 (m, 1H), 2.16-1.99 (m, 1H), 1.59-1.47 (m, 3H), 1.16-1.04 (m, 3H), 0.94-0.83 (m, 3H), 0.79-0.71 (m, 3H). $^{19}F$ NMR (376 MHz, CDCl$_3$) δ −116.41, −116.47. |
| 111 | | | HRMS-ESI (m/z) [M + H]⁺ calcd for $C_{22}H_{26}FN_2O_5$, 417.1821; found, 417.1813 | $^1H$ NMR (400 MHz, CDCl$_3$) δ 12.15 (s, 1H), 8.46 (d, J = 8.1 Hz, 1H), 8.00 (d, J = 5.2 Hz, 1H), 7.21-7.07 (m, 2H), 7.02-6.92 (m, 2H), 6.88 (d, J = 5.2 Hz, 1H), 5.37-5.25 (m, 1H), 4.85-4.60 (m, 1H), 3.95 (s, 3H), 2.03 (dd, J = 10.2, 6.6 Hz, 1H), 1.51 (d, J = 7.2 Hz, 3H), 1.19 (d, J = 6.4 Hz, 3H), 1.16-1.03 (m, 1H), 0.74-0.62 (m, 1H), 0.49-0.29 (m, 2H), −0.02--0.12 (m, 1H). $^{19}F$ NMR (376 MHz, CDCl$_3$) δ −116.42. |
| 112 | | IR (thin film) 3372, 2962, 2934, 2879, 1734, 1650, 1576, 1528, 1481, 1452, 1324, 1280, 1264, 1213, 1149, 1059, 954, 802, 737, 705 cm⁻¹. | HRMS-ESI (m/z) [M + H]⁺ calcd for $C_{24}H_{33}N_2O_5$, 429.2389; found, 429.2385 | $^1H$ NMR (300 MHz, CDCl$_3$) δ 12.16 (s, 1H), 8.51 (d, J = 7.9 Hz, 1H), 8.00 (d, J = 5.2 Hz, 1H), 7.38-7.00 (m, 5H), 6.88 (d, J = 5.2 Hz, 1H), 5.59-5.37 (m, 1H), 4.70 (p, J = 7.2 Hz, 1H), 3.95 (s, 3H), 2.97 (dd, J = 8.5, 6.4 Hz, 1H), 1.55 (d, J = 7.2 Hz, 3H), 1.51-1.31 (m, 5H), 1.12 (d, J = 6.3 Hz, 3H), 0.93 (t, J = 7.4 Hz, 3H), 0.77 (t, J = 7.2 Hz, 3H). |
| 113 | | IR (thin film) 3370, 2943, 2868, 1731, 1648, 1527, 1450, 1263, 1144, 1038, 799, 734, 702 cm⁻¹. | HRMS-ESI (m/z) [M + H]⁺ calcd for $C_{24}H_{31}N_2O_5$, 427.2233; found, 427.2237 | $^1H$ NMR (300 MHz, CDCl$_3$) δ 12.17 (s, 1H), 8.48 (t, J = 8.9 Hz, 1H), 8.00 (d, J = 5.9 Hz, 1H), 7.33-7.03 (m, 5H), 6.93-6.83 (m, 1H), 5.41-5.26 (m, 1H), 4.80-4.58 (m, 1H), 3.95 (s, 3H), 2.78 (dd, J = 10.1, 5.9 Hz, 1H), 2.33-2.11 (m, 2H), 1.99-1.80 (m, 2H), 1.69-1.56 (m, 2H), 1.52 (dd, J = 7.2 Hz, 3H), 1.44-1.16 (m, 4H), 1.13 (d, J = 6.5 Hz, 3H). |
| 114 | | IR (thin film) 3254, 2947, 2867, 1729, 1512, 1485, 1273, 1207, 730 cm⁻¹ | HRMS-ESI (m/z) [M + H]⁺ calcd for $C_{24}H_{31}N_2O_4S$, 443.1999; found, 443.2026 | $^1H$ NMR (400 MHz, CDCl$_3$) δ 12.94 (s, 1H), 10.69 (s, 1H), 7.98 (s, 1H), 7.26-7.18 (m, 4H), 7.14-7.08 (m, 1H), 6.88 (s, 1H), 5.43-5.25 (m, 1H), 5.07 (dp, J = 17.6, 7.2 Hz, 1H), 3.97 (d, J = 3.1 Hz, 3H), 2.79 (dd, J = 9.9, 6.0 Hz, 1H), 2.45-2.27 (m, 1H), 2.27-2.12 (m, 1H), 2.00-1.77 (m, 1H), 1.61 (d, J = 7.1 Hz, 3H), 1.57-1.39 (m, 4H), 1.35-1.23 (m, 2H), 1.14 (d, J = 6.4 Hz, 3H). |
| 115 | | IR (CDCl3) 2951, 2868, 1733, 1581, 1514, 1486, 1454, 1377, 1342, 1274, | HRMS-ESI (m/z) [M + Na]⁺ calcd for $C_{24}H_{30}N_2O_4S$, 465.1818; found, 465.1830 | $^1H$ NMR (500 MHz, CDCl$_3$) δ 12.94 (s, 1H), 10.71 (s, 1H), 8.01 (d, J 1H), 7.22-7.17 (m, 3H), 7.15 (dd, J = 6.7, 3.0 Hz, 2H), 6.89 (d, J = 5.0 Hz, 1H), 5.39 (qd, J = 6.4, 4.0 Hz, 1H), 5.12-5.03 (m, 1H), 3.97 (s, 3H), 2.41 (dd, J = 10.4, 4.0 Hz, 1H), 2.25-2.14 (m, |

TABLE 2-continued

Analytical Data

| Cmpd. No. | Melting Point (° C.) | IR (cm⁻¹) | MASS SPEC | NMR |
|---|---|---|---|---|
| | | 1249, 1211, 1131, 1095, 992, 913, 860, 801, 736, 703 cm⁻¹ | | 1H), 1.95-1.84 (m, 1H), 1.69-1.59 (m, 1H), 1.56 (d, J = 7.2 Hz, 3H), 1.54-1.45 (m, 2H), 1.44-1.28 (m, 2H), 1.19 (dq, J = 12.3, 9.1 Hz, 1H), 1.09 (d, J = 6.4 Hz, 3H), 0.92 (ddt, J = 12.5, 10.0, 8.5 Hz, 1H). |
| 116 | | IR (thin film) 3369, 2967, 1733, 1650, 1529, 1481, 1264, 954, 801, 733 cm⁻¹ | HRMS-ESI (m/z) [M + Na]⁺ calcd for $C_{23}H_{29}FN_2NaO_5$, 455.1953; found, 455.1947 | ¹H NMR (400 MHz, CDCl₃) δ 12.13 (s, 1H), 8.46 (d, J = 8.0 Hz, 1H), 8.02 (d, J = 5.2 Hz, 1H), 7.22 (dd, J = 8.7, 6.0 Hz, 1H), 6.89 (d, J = 5.2 Hz, 1H), 6.83 (dd, J = 9.9, 2.7 Hz, 1H), 6.73 (td, J = 8.5, 2.9 Hz, 1H), 5.49-5.41 (m, 1H), 4.69 (p, J = 7.3 Hz, 1H), 3.95 (s, 3H), 2.69 (dd, J = 9.2, 5.0 Hz, 1H), 2.27 (s, 3H), 2.07-1.86 (m, 1H), 1.43 (d, J = 7.2 Hz, 3H), 1.07 (d, J = 6.3 Hz, 3H), 0.99 (d, J = 6.6 Hz, 3H), 0.68 (d, J = 6.7 Hz, 3H). ¹³C NMR (101 MHz, CDCl₃) δ 171.56, 168.72, 160.94 (d, J = 244.1 Hz), 155.46, 148.86, 140.50, 139.36 (d, J = 7.2 Hz), 134.57 (d, J = 3.3 Hz), 130.48, 129.32 (d, J = 8.2 Hz), 116.44 (d, J = 20.5 Hz), 112.67 (d, J = 20.5 Hz), 109.54, 72.65, 56.10, 50.65, 48.12, 30.45, 21.00, 20.72, 20.47, 18.37, 18.16. ¹⁹F NMR (376 MHz, CDCl₃) δ −117.61. |
| 117 | | IR (thin film) 3372, 2963, 1732, 1649, 1528, 1450, 1263, 1060, 954, 800, 731 cm⁻¹ | HRMS-ESI (m/z) [M + Na]⁺ calcd for $C_{25}H_{33}FN_2NaO_5$, 483.2266; found, 483.2262 | ¹H NMR (400 MHz, CDCl₃) δ 12.14 (s, 1H), 8.47 (d, J = 8.1 Hz, 1H), 8.03 (d, J = 5.2 Hz, 1H), 7.28-7.21 (m, 1H), 6.89 (d, J = 5.2 Hz, 1H), 6.82 (dd, J = 9.9, 2.8 Hz, 1H), 6.73 (td, J = 8.5, 2.9 Hz, 1H), 5.40 (qt, J = 6.2, 3.0 Hz, 1H), 4.71 (p, J = 7.3 Hz, 1H), 3.95 (s, 3H), 2.90 (dd, J = 10.0, 4.3 Hz, 1H), 2.27 (s, 3H), 1.63-1.46 (m, 4H), 1.46-1.32 (m, 1H), 1.15-0.83 (m, 9H), 0.65 (t, J = 7.4 Hz, 3H). ¹³C NMR (101 MHz, CDCl₃) δ 171.62, 168.78, 160.93 (d, J = 244.2 Hz), 155.49, 148.90, 140.52, 139.40 (d, J = 7.2 Hz), 134.65 (d, J = 3.2 Hz), 130.47, 129.74 (d, J = 7.9 Hz), 116.41 (d, J = 20.6 Hz), 112.73 (d, J = 20.5 Hz), 109.57, 72.33, 56.11, 48.24, 41.62, 29.30, 21.72, 21.09, 20.60, 18.28, 18.20, 10.79, 9.43. ¹⁹F NMR (376 MHz, CDCl₃) δ −117.60. |
| 118 | | IR (thin film) 3372, 2951, 1732, 1649, 1528, 1263, 1060, 952, 911, 800, 730 cm⁻¹ | HRMS-ESI (m/z) [M + Na]⁺ calcd for $C_{25}H_{31}FN_2NaO_5$, 481.2109; found, 481.2106 | ¹H NMR (400 MHz, CDCl₃) δ 12.14 (s, 1H), 8.47 (d, J = 8.1 Hz, 1H), 8.02 (d, J = 5.2 Hz, 1H), 7.22 (dd, J = 8.7, 6.0 Hz, 1H), 6.89 (d, J = 5.2 Hz, 1H), 6.82 (dd, J = 9.8, 2.9 Hz, 1H), 6.71 (td, J = 8.5, 2.9 Hz, 1H), 5.34 (qd, J = 6.4, 4.1 Hz, 1H), 4.71 (p, J = 7.3 Hz, 1H), 3.95 (s, 3H), 2.79 (dd, J = 10.3, 4.3 Hz, 1H), 2.28 (s, 3H), 2.20-2.08 (m, 1H), 1.90 (dtd, J = 11.3, 7.2, 3.6 Hz, 1H), 1.77-1.14 (m, 9H), 1.08 (d, J = 6.3 Hz, 3H), 0.85 (ddt, J = 12.4, 10.2, 8.4 Hz, 1H). ¹³C NMR (101 MHz, CDCl₃) δ 171.50, 168.76, 160.89 (d, J = 244.1 Hz), 155.47, 148.87, 140.51, 138.79 (d, J = 7.3 Hz), 135.16 (d, J = 3.3 Hz), 130.47, 129.60 (d, J = 8.0 Hz), 116.40 (d, J = 20.4 Hz), 112.67 (d, J = 20.6 Hz), 109.56, 73.88, 56.11, 49.39, 48.22, 42.94, 31.60, 31.38, 25.08, 24.42, 20.60, 18.19, 18.13. ¹⁹F NMR (376 MHz, CDCl₃) δ −117.66. |
| 119 | | IR (thin film) 3372, 2928, 1732, 1649, 1528, | HRMS-ESI (m/z) [M + H]⁺ calcd for $C_{26}H_{34}FN_2O_5$, 473.2446; found, 473.2440 | ¹H NMR (400 MHz, CDCl₃) δ 12.14 (s, 1H), 8.47 (d, J = 8.1 Hz, 1H), 8.02 (d, J = 5.2 Hz, 1H), 7.23 (dd, J = 8.7, 6.0 Hz, 1H), 6.89 (d, J = 5.2 Hz, 1H), 6.82 (dd, |

TABLE 2-continued

Analytical Data

| Cmpd. No. | Melting Point (° C.) | IR (cm⁻¹) | MASS SPEC | NMR |
|---|---|---|---|---|
| | | 1448, 1263, 1060, 954, 910, 730 cm⁻¹ | | J = 9.9, 2.9 Hz, 1H), 6.74 (td, J = 8.5, 2.9 Hz, 1H), 5.50-5.39 (m, 1H), 4.70 (p, J = 7.3 Hz, 1H), 3.95 (s, 3H), 2.75 (dd, J = 9.3, 4.8 Hz, 1H), 2.26 (s, 3H), 1.87 (dt, J = 12.7, 3.2 Hz, 1H), 1.80-1.70 (m, 1H), 1.70-1.52 (m, 3H), 1.45 (d, J = 7.2 Hz, 3H), 1.35-1.15 (m, 2H), 1.15-0.85 (m, 6H), 0.76 (qd, J = 12.2, 3.6 Hz, 1H). $^{13}$C NMR (101 MHz, CDCl$_3$) δ 171.59, 168.75, 160.90 (d, J = 243.9 Hz), 155.48, 148.86, 140.51, 139.44 (d, J = 7.2 Hz), 134.60 (d, J = 3.3 Hz), 130.48, 129.40 (d, J = 8.0 Hz), 116.37 (d, J = 20.5 Hz), 112.71 (d, J = 20.5 Hz), 109.56, 71.90, 56.11, 49.65, 48.16, 40.26, 31.30, 30.80, 26.44, 26.40, 26.30, 20.72, 18.19, 18.19. $^{19}$F NMR (376 MHz, CDCl$_3$) δ −117.64. |
| 120 | | IR (thin film) 3372, 2965, 1734, 1650, 1529, 1265, 954, 801, 734 cm⁻¹ | HRMS-ESI (m/z) [M + H]⁺ calcd for C$_{24}$H$_{32}$FN$_2$O$_5$, 447.2290; found, 447.2296 | $^{1}$H NMR (400 MHz, CDCl$_3$) δ 12.13 (d, J = 3.1 Hz, 1H), 8.45 (t, J = 6.7 Hz, 1H), 8.02 (dd, J = 5.2, 3.5 Hz, 1H), 7.22 (ddd, J = 8.8, 6.1, 4.0 Hz, 1H), 6.89 (t, J = 5.3, 1.7 Hz, 1H), 6.82 (dd, J = 10.0, 2.9 Hz, 1H), 6.73 (qd, J = 8.7, 2.9 Hz, 1H), 5.44 (tdd, J = 9.1, 6.4, 3.5 Hz, 1H), 4.68 (dp, J = 10.9, 7.3 Hz, 1H), 3.95 (s, 3H), 2.78 (ddd, J = 48.5, 9.2, 4.9 Hz, 1H), 2.27 (d, J = 3.9 Hz, 3H), 1.87-1.33 (m, 4H), 1.26 (s, 1H), 1.23-0.76 (m, 7H), 0.76-0.60 (m, 3H). $^{19}$F NMR (376 MHz, CDCl$_3$) δ −117.60, −117.64. |
| 121 | | IR (thin film) 3368, 2938, 1733, 1648, 1528, 1481, 1439, 1263, 953, 800, 730 cm⁻¹ | HRMS-ESI (m/z) [M + H]⁺ calcd for C$_{24}$H$_{30}$FN$_2$O$_5$, 445.2133; found, 445.2130 | $^{1}$H NMR (400 MHz, CDCl$_3$) δ 12.12 (s, 1H), 8.38 (d, J = 8.1 Hz, 1H), 7.99 (d, J = 5.1 Hz, 1H), 7.06 (dd, J = 8.6, 5.9 Hz, 1H), 6.87 (d, J = 5.2 Hz, 1H), 6.80 (dd, J = 9.9, 2.8 Hz, 1H), 6.74 (td, J = 8.5, 2.9 Hz, 1H), 5.16 (p, J = 6.3 Hz, 1H), 4.58 (p, J = 7.3 Hz, 1H), 3.94 (s, 3H), 3.03 (dd, J = 10.4, 6.6 Hz, 1H), 2.70-2.57 (m, 1H), 2.34 (s, 3H), 2.23-2.10 (m, 1H), 1.86-1.55 (m, 4H), 1.45-1.34 (m, 1H), 1.28-1.22 (m, 3H), 1.19 (d, J = 6.3 Hz, 3H). $^{13}$C NMR (101 MHz, CDCl$_3$) δ 171.39, 168.64, 160.91 (d, J = 243.9 Hz), 155.43, 148.81, 140.45, 139.10 (d, J = 6.7 Hz), 134.12 (d, J = 3.2 Hz), 130.49, 128.52 (d, J = 5.2 Hz), 116.50 (d, J = 20.4 Hz), 112.72 (d, J = 20.7 Hz), 109.49, 74.20, 56.09, 50.86, 47.99, 37.76, 29.39, 26.99, 20.45, 18.51, 18.19, 17.92. $^{19}$F NMR (376 MHz, CDCl$_3$) δ −117.49. |
| 122 | | IR (thin film) 3369, 2946, 1732, 1648, 1528, 1262, 1153, 953, 800, 730 cm⁻¹ | HRMS-ESI (m/z) [M + H]⁺ calcd for C$_{25}$H$_{32}$FN$_2$O$_5$, 459.2290; found, 459.2318 | $^{1}$H NMR (400 MHz, CDCl$_3$) δ 12.13 (s, 1H), 8.41 (d, J = 8.2 Hz, 1H), 7.98 (d, J = 5.2 Hz, 1H), 7.09 (dd, J = 8.6, 5.9 Hz, 1H), 6.92-6.80 (m, 2H), 6.77 (dd, J = 9.9, 2.8 Hz, 1H), 5.31 (p, J = 6.4 Hz, 1H), 4.75-4.64 (m, 1H), 3.95 (s, 3H), 3.10 (dt, J = 7.1, 5.4 Hz, 1H), 2.26 (s, 3H), 2.20-2.06 (m, 1H), 1.87 (qdd, J = 11.1, 8.9, 7.1, 3.8 Hz, 1H), 1.69-1.06 (m, 12H), 0.98-0.82 (m, 1H). $^{13}$C NMR (101 MHz, CDCl$_3$) δ 171.59, 168.65, 160.84 (d, J = 244.2 Hz), 155.41, 148.81, 140.44, 139.16 (d, J = 7.4 Hz), 134.99 (d, J = 3.0 Hz), 130.48, 129.07 (d, J = 8.3 Hz), 116.78 (d, J = 20.4 Hz), 112.48 (d, J = 20.6 Hz), 109.49, 75.73, 56.09, 48.21, 48.21, 43.47, 31.50, 31.09, 25.12, 24.13, |

TABLE 2-continued

Analytical Data

| Cmpd. No. | Melting Point (° C.) | IR (cm$^{-1}$) | MASS SPEC | NMR |
|---|---|---|---|---|
| 123 | | IR (thin film) 3371, 2928, 1733, 1650, 1528, 1450, 1264, 1155, 954, 800, 732 cm$^{-1}$ | HRMS-ESI (m/z) [M + H]$^+$ calcd for C$_{26}$H$_{34}$FN$_2$O$_5$, 473.2446; found, 473.2467 | 20.72, 18.23, 17.26. $^{19}$F NMR (376 MHz, CDCl$_3$) δ −117.47. $^1$H NMR (400 MHz, CDCl$_3$) δ 12.14 (s, 1H), 8.47 (d, J = 8.1 Hz, 1H), 7.99 (d, J = 5.2 Hz, 1H), 7.05 (dd, J = 8.6, 5.9 Hz, 1H), 6.92-6.75 (m, 4H), 5.40 (dq, J = 9.0, 6.3 Hz, 1H), 4.77-4.68 (m, 1H), 3.95 (s, 3H), 3.12 (dd, J = 9.0, 6.1 Hz, 1H), 2.29 (s, 3H), 1.82-1.59 (m, 3H), 1.53 (dd, J = 21.9, 7.2 Hz, 5H), 1.28-0.78 (m, 8H). $^{13}$C NMR (101 MHz, CDCl$_3$) δ 171.67, 168.67, 160.89 (d, J = 244.6 Hz), 155.42, 148.82, 140.47, 139.76 (d, J = 7.6 Hz), 133.87 (d, J = 3.3 Hz), 130.50, 129.20 (d, J = 7.2 Hz), 116.93 (d, J = 20.6 Hz), 112.37 (d, J = 20.7 Hz), 109.50, 73.49, 56.10, 49.06, 48.20, 40.18, 31.47, 29.14, 26.60, 26.55, 26.32, 20.95, 18.38, 17.98. |
| 124 | | IR (thin film) 3366, 2961, 1734, 1650, 1529, 1264, 1153, 1049, 955, 801, 735 cm$^{-1}$ | HRMS-ESI (m/z) [M + H]$^+$ calcd for C$_{23}$H$_{30}$FN$_2$O$_5$, 433.2133; found, 433.2129 | $^{19}$F NMR (376 MHz, CDCl$_3$) δ −117.35. $^1$H NMR (400 MHz, CDCl$_3$) δ 12.13 (s, 1H), 8.45 (d, J = 8.0 Hz, 1H), 7.99 (d, J = 5.2 Hz, 1H), 7.05 (dd, J = 8.6, 5.9 Hz, 1H), 6.93-6.77 (m, 3H), 5.38 (dq, J = 8.9, 6.3 Hz, 1H), 4.76-4.65 (m, 1H), 3.95 (s, 3H), 3.09 (dd, J = 8.9, 6.5 Hz, 1H), 2.29 (s, 3H), 2.11 (h, J = 6.8 Hz, 1H), 1.55 (d, J = 7.2 Hz, 3H), 1.08 (d, J = 6.2 Hz, 3H), 0.86 (d, J = 6.8 Hz, 3H), 0.78 (d, J = 6.7 Hz, 3H). |
| 125 | | IR (thin film) 3368, 2962, 1733, 1650, 1528, 1263, 1154, 1057, 954, 800, 733 cm$^{-1}$ | HRMS-ESI (m/z) [M + H]$^+$ calcd for C$_{25}$H$_{34}$FN$_2$O$_5$, 461.2446; found, 461.2442 | $^{19}$F NMR (376 MHz, CDCl$_3$) δ −117.30. $^1$H NMR (400 MHz, CDCl$_3$) δ 12.13 (s, 1H), 8.42 (d, J = 8.2 Hz, 1H), 7.98 (d, J = 5.3 Hz, 1H), 7.10 (dd, J = 8.7, 5.9 Hz, 1H), 6.88 (d, J = 5.1 Hz, 1H), 6.83 (td, J = 8.3, 2.8 Hz, 1H), 6.77 (dd, J = 9.9, 2.9 Hz, 1H), 5.46-5.40 (m, 1H), 4.75-4.66 (m, 1H), 3.95 (d, J = 2.2 Hz, 3H), 3.27 (t, J = 7.7 Hz, 1H), 2.27 (s, 2H), 1.67-1.24 (m, 8H), 1.14-0.82 (m, 7H), 0.76 (t, J = 7.4 Hz, 3H). |
| 126 | | IR thin film) 3369, 2964, 1733, 1649, 1528, 1262, 1056, 953, 800, 730 cm$^{-1}$ | HRMS-ESI (m/z) [M + H]$^+$ calcd for C$_{24}$H$_{32}$FN$_2$O$_5$, 447.2290; found, 447.2302 | $^{19}$F NMR (376 MHz, CDCl$_3$) δ −117.38. $^1$H NMR (400 MHz, CDCl$_3$) δ 12.13 (d, J = 4.6 Hz, 1H), 8.50-8.39 (m, 1H), 7.99 (dd, J = 5.3, 2.8 Hz, 1H), 7.07 (ddd, J = 8.9, 5.9, 3.1 Hz, 1H), 6.93-6.75 (m, 3H), 5.40 (ddq, J = 21.8, 9.3, 6.3 Hz, 1H), 4.77-4.64 (m, 1H), 3.95 (s, 3H), 3.16 (ddd, J = 24.5, 8.9, 6.4 Hz, 1H), 2.35-2.26 (m, 3H), 1.94-1.73 (m, 1H), 1.55 (t, J = 6.9 Hz, 3H), 1.52-1.33 (m, 1H), 1.08 (dd, J = 9.4, 6.2 Hz, 3H), 1.01-0.72 (m, 7H). |
| 127 | | IR (thin film) 3369, 2939, 1733, 1649, 1438, 1261, 1039, 953, 800, 729 cm$^{-1}$ | HRMS-ESI (m/z) [M + Na]$^+$ calcd for C$_{24}$H$_{29}$FN$_2$O$_5$, 467.1953; found, 467.1940 | $^{19}$F NMR (376 MHz, CDCl$_3$) δ −117.29, −117.34. $^1$H NMR (400 MHz, CDCl$_3$) δ 12.14 (s, 1H), 8.46 (d, J = 8.1 Hz, 1H), 8.00 (dd, J = 8.2, 5.2 Hz, 1H), 7.01 (ddd, J = 9.3, 4.6, 2.2 Hz, 1H), 6.88 (d, J = 5.2 Hz, 1H), 6.82 (dd, J = 8.0, 3.4 Hz, 2H), 5.12 (p, J = 6.3 Hz, 1H), 4.78-4.64 (m, 1H), 3.95 (s, 3H), 3.14 (dd, J = 10.0, 7.4 Hz, 1H), 2.74 (h, J = 8.3 Hz, 1H), 2.33 (s, 3H), 2.23-2.06 (m, 1H), 2.05-1.57 (m, 4H), 1.54 (d, J = 7.1 Hz, 3H), 1.45-1.33 (m, 1H), 1.09 (d, J = 6.3 Hz, 3H). |
| 128 | | IR thin film) 3369, 2951, 1735, 1650, 1529, | HRMS-ESI (m/z) [M + Na]$^+$ calcd for C$_{25}$H$_{31}$FN$_2$NaO$_5$, 481.2109; found, 481.2105 | $^{19}$F NMR (376 MHz, CDCl$_3$) δ −117.25. $^1$H NMR (400 MHz, CDCl$_3$) δ 12.14 (s, 1H), 8.45 (d, J = 7.7 Hz, 1H), 8.02 (d, J = 5.1 Hz, 1H), 7.30 (dd, J = 8.7, 6.1 Hz, 1H), 6.90 (d, J = 5.2 Hz, 1H), 6.82 (dd, |

TABLE 2-continued

Analytical Data

| Cmpd. No. | Melting Point (° C.) | IR (cm$^{-1}$) | MASS SPEC | NMR |
|---|---|---|---|---|
| | | 1264, 953, 733 cm$^{-1}$ | | J = 9.9, 2.9 Hz, 1H), 6.71 (td, J = 8.5, 2.9 Hz, 1H), 5.33 (qd, J = 6.3, 3.4 Hz, 1H), 4.71 (p, J = 7.3 Hz, 1H), 3.96 (s, 3H), 2.78 (dd, J = 10.5, 3.7 Hz, 1H), 2.29 (s, 3H), 2.28-2.16 (m, 1H), 1.92 (ddq, J = 10.8, 7.1, 3.4 Hz, 1H), 1.73-1.60 (m, 1H), 1.60-1.47 (m, 5H), 1.47-1.31 (m, 2H), 1.31-1.15 (m, 1H), 1.04 (d, J = 6.4 Hz, 3H), 0.92-0.77 (m, 1H). $^{19}$F NMR (376 MHz, CDCl$_3$) δ −117.71. |
| 129 | | IR (thin film) 3372, 2928, 1733, 1527, 1263, 955, 800, 730 cm$^{-1}$ | HRMS-ESI (m/z) [M + H]$^+$ calcd for C$_{26}$H$_{34}$FN$_2$O$_5$, 473.2446; found, 473.2455 | $^1$H NMR (400 MHz, CDCl$_3$) δ 12.15 (s, 1H), 8.42 (d, J = 7.7 Hz, 1H), 8.02 (d, J = 5.2 Hz, 1H), 7.30 (dd, J = 8.7, 6.1 Hz, 1H), 6.90 (d, J = 5.2 Hz, 1H), 6.81 (dd, J = 9.9, 2.8 Hz, 1H), 6.68 (td, J = 8.5, 2.9 Hz, 1H), 5.45 (qd, J = 6.2, 4.0 Hz, 1H), 4.70 (p, J = 7.2 Hz, 1H), 3.96 (s, 3H), 2.73 (dd, J = 9.9, 4.1 Hz, 1H), 2.26 (s, 3H), 1.92 (dt, J = 12.9, 3.2 Hz, 1H), 1.80-1.53 (m, 4H), 1.51 (d, J = 7.2 Hz, 3H), 1.35-1.03 (m, 4H), 1.00 (d, J = 6.3 Hz, 3H), 0.95 (td, J = 12.1, 3.7 Hz, 1H), 0.74 (qd, J = 12.2, 3.6 Hz, 1H). $^{19}$F NMR (376 MHz, CDCl$_3$) δ −117.72. |
| 130 | | IR (thin film) 3372, 2964, 1734, 1528, 1264, 954, 801, 732 cm$^{-1}$ | HRMS-ESI (m/z) [M + H]$^+$ calcd for C$_{23}$H$_{30}$FN$_2$O$_5$, 433.2133; found, 433.2130 | $^1$H NMR (400 MHz, CDCl$_3$) δ 12.12 (s, 1H), 8.43 (d, J = 8.3 Hz, 1H), 8.02 (d, J = 5.2 Hz, 1H), 7.33-7.23 (m, 1H), 6.90 (d, J = 5.2 Hz, 1H), 6.82 (dd, J = 10.0, 3.0 Hz, 1H), 6.66 (td, J = 8.5, 2.9 Hz, 1H), 5.44 (qd, J = 6.3, 4.0 Hz, 1H), 4.70 (p, J = 7.3 Hz, 1H), 3.96 (s, 3H), 2.68-2.62 (m, 1H), 2.27 (s, 3H), 2.15-1.82 (m, 1H), 1.50 (d, J = 7.2 Hz, 3H), 1.02 (dd, J = 6.4, 2.1 Hz, 6H), 0.67 (d, J = 6.7 Hz, 3H). $^{19}$F NMR (376 MHz, CDCl$_3$) δ −117.67. |
| 131 | | IR (thin film) 3369, 2968, 1732, 1649, 1527, 1263, 800, 730 cm$^{-1}$ | HRMS-ESI (m/z) [M + H]$^+$ calcd for C$_{24}$H$_{33}$N$_2$O$_5$, 451.2203; found, 451.2190 | $^1$H NMR (500 MHz, CDCl$_3$) δ 12.16 (s, 1H), 8.49 (d, J = 8.0 Hz, 1H), 8.01 (d, J = 5.2 Hz, 1H), 7.15 (d, J = 7.9 Hz, 1H), 6.93 (d, J = 1.8 Hz, 1H), 6.92-6.85 (m, 2H), 5.44 (qd, J = 6.2, 4.1 Hz, 1H), 4.76-4.60 (m, 1H), 3.94 (s, 3H), 2.70 (dd, J = 9.2, 5.0 Hz, 1H), 2.27 (s, 3H), 2.24 (s, 3H), 2.02 (dp, J = 9.1, 6.7 Hz, 1H), 1.42 (d, J = 7.2 Hz, 3H), 1.09 (d, J = 6.3 Hz, 3H), 0.99 (d, J = 6.6 Hz, 3H), 0.70 (d, J = 6.7 Hz, 3H). |
| 132 | | IR (thin film) 3369, 2947, 2868, 2256, 1713, 1527, 1263, 730 cm$^{-1}$ | HRMS-ESI (m/z) [M + H]$^+$ calcd for C$_{26}$H$_{35}$N$_2$O$_5$, 455.2540; found, 455.2536 | $^1$H NMR (500 MHz, CDCl$_3$) δ 12.17 (s, 1H), 8.50 (d, J = 8.0 Hz, 1H), 8.02 (d, J = 5.2 Hz, 1H), 7.16 (d, J = 7.9 Hz, 1H), 6.93 (d, J = 1.8 Hz, 1H), 6.91-6.85 (m, 2H), 5.33 (qd, J = 6.3, 4.2 Hz, 1H), 4.70 (p, J = 7.4 Hz, 1H), 3.94 (s, 3H), 2.80 (dd, J = 10.2, 4.2 Hz, 1H), 2.26 (s, 3H), 2.26 (s, 3H), 2.17 (dddd, J = 17.0, 10.2, 6.8, 3.1 Hz, 1H), 1.89 (dtd, J = 11.0, 7.1, 3.3 Hz, 1H), 1.69-1.31 (m, 8H), 1.21 (dq, J = 12.3, 9.2 Hz, 1H), 1.09 (d, J = 6.4 Hz, 3H), 0.92-0.81 (m, 1H). |
| 133 | | IR (thin film) 3369, 2925, 2850, 1731, 1527, 1262, 729 cm$^{-1}$ | HRMS-ESI (m/z) [M + H]$^+$ calcd for C$_{27}$H$_{37}$N$_2$O$_5$, 491.2516; found, 491.2520 | $^1$H NMR (500 MHz, CDCl$_3$) δ 12.17 (d, J = 0.6 Hz, 1H), 8.50 (d, J = 8.0 Hz, 1H), 8.02 (d, J = 5.2 Hz, 1H), 7.16 (d, J = 7.9 Hz, 1H), 6.92 (d, J = 1.9 Hz, 1H), 6.91-6.86 (m, 2H), 5.44 (qd, J = 6.3, 4.7 Hz, 1H), 4.75-4.64 (m, 1H), 3.94 (s, 3H), 2.76 (dd, J = 9.3, 4.8 Hz, 1H), 2.27 (s, 3H), 2.23 (s, 3H), 1.87 (dt, J = 12.5, 3.3 Hz, 1H), 1.78-1.47 (m, 4H), 1.44 (d, J = 7.2 Hz, 3H), 1.39-1.14 (m, 2H), 1.05 (d, J = 6.3 Hz, 3H), 1.03-0.69 (m, 4H). |

TABLE 2-continued

Analytical Data

| Cmpd. No. | Melting Point (° C.) | IR (cm$^{-1}$) | MASS SPEC | NMR |
|---|---|---|---|---|
| 134 | | IR (thin film) 3369, 2964, 2933, 2875, 1732, 1527, 1263, 800, 730 cm$^{-1}$ | HRMS-ESI (m/z) [M + H]$^+$ calcd for C$_{25}$H$_{35}$N$_2$O$_5$, 443.2540; found, 443.2562 | $^1$H NMR (500 MHz, CDCl$_3$) δ 12.15 (dd, J = 3.6, 0.6 Hz, 1H), 8.52-8.44 (m, 1H), 8.01 (t, J = 5.1 Hz, 1H), 7.15 (dd, J = 7.9, 2.0 Hz, 1H), 6.95-6.91 (m, 1H), 6.91-6.85 (m, 2H), 5.49-5.40 (m, 1H), 4.73-4.61 (m, 1H), 3.94 (s, 3H), 2.88-2.70 (m, 1H), 2.28-2.22 (m, 6H), 1.91-1.68 (m, 1H), 1.49-1.33 (m, 3H), 1.14-0.64 (m, 11H). |
| 135 | | IR (thin film) 3370, 2961, 1733, 1648, 1575, 1528, 1509, 1480, 1453, 1437, 1307, 1280, 1261, 1241, 1150, 801 cm$^{-1}$ | ESIMS m/z 419.1 ([M + H]$^+$) | $^1$H NMR (400 MHz, CDCl$_3$) δ 12.14 (s, 1H), 8.45 (d, J = 8.0 Hz, 1H), 8.00 (d, J = 5.2 Hz, 1H), 7.09-6.99 (m, 2H), 6.99-6.90 (m, 2H), 6.89 (d, J = 5.2 Hz, 1H), 5.40 (dq, J = 8.4, 6.3 Hz, 1H), 4.69 (p, J = 7.3 Hz, 1H), 3.96 (s, 3H), 3.71 (t, J = 6.9 Hz, 1H), 2.70 (dd, J = 8.3, 6.8 Hz, 1H), 1.54 (d, J = 7.1 Hz, 3H), 1.10 (d, J = 6.3 Hz, 3H), 0.87 (d, J = 6.8 Hz, 3H), 0.74 (d, J = 6.7 Hz, 3H). $^{13}$C NMR (126 MHz, CDCl$_3$) δ 171.63, 168.72, 168.30, 161.72 (d, J = 244.8 Hz), 155.40, 155.06, 150.14, 148.78, 140.49, 139.14, 134.23 (d, J = 3.3 Hz), 131.01 (d, J = 7.7 Hz), 130.46, 114.80, (d, J = 21.1 Hz), 109.47, 108.37, 72.80, 56.10, 55.83, 50.65, 48.19, 47.95, 28.35, 27.05, 23.40, 21.21, 18.75, 18.32, 17.41. |
| 136 | | IR (thin film) 3131, 2959, 1748, 1511, 1479, 1280, 1207, 1142, 797 cm$^{-1}$ | HRMS-ESI (m/z) [M + H]$^+$ calcd for C$_{23}$H$_{30}$FN$_2$O$_4$S, 449.1905; found, 449.1906 | $^1$H NMR (400 MHz, CDCl$_3$) δ 12.92 (s, 1H), 10.79-10.61 (m, 1H), 7.98 (d, J = 5.1 Hz, 1H), 7.05 (dd, J = 8.6, 5.9 Hz, 1H), 6.85 (ddt, J = 17.1, 9.5, 4.7 Hz, 3H), 5.40 (dq, J = 13.0, 6.4 Hz, 1H), 5.09 (p, J = 7.2 Hz, 1H), 3.97 (s, 3H), 3.11 (dd, J = 9.0, 6.3 Hz, 1H), 2.30 (s, 3H), 2.13 (dt, J = 13.5, 6.8 Hz, 1H), 1.64 (d, J = 7.1 Hz, 3H), 1.09 (d, J = 6.3 Hz, 3H), 0.86 (d, J = 6.7 Hz, 3H), 0.79 (d, J = 6.8 Hz, 3H). $^{19}$F NMR (376 MHz, CDCl$_3$) δ -117.20. |
| 137 | | IR (thin film) 3372, 2963, 1731, 1649, 1528, 1450, 1263, 1149, 1036, 953 cm$^{-1}$ | HRMS-ESI (m/z) [M + H]$^+$ calcd for C$_{25}$H$_{34}$FN$_2$O$_6$, 477.2395; found, 477.2392 | $^1$H NMR (400 MHz, CDCl$_3$) δ 12.15 (d, J = 0.6 Hz, 1H), 8.47 (d, J = 8.1 Hz, 1H), 8.02 (d, J = 5.3 Hz, 1H), 7.18 (dd, J = 8.5, 6.9 Hz, 1H), 6.89 (d, J = 5.1 Hz, 1H), 6.57 (dd, J = 11.0, 2.5 Hz, 1H), 6.51 (td, J = 8.4, 2.6 Hz, 1H), 5.40 (qd, J = 6.2, 4.5 Hz, 1H), 4.75-4.62 (m, 1H), 3.95 (s, 3H), 3.77 (s, 4H), 3.31 (dd, J = 9.9, 4.5 Hz, 1H), 1.63 (d, J = 12.1 Hz, 1H), 1.45 (d, J = 7.2 Hz, 3H), 1.42-1.27 (m, 1H), 1.24-1.08 (m, 1H), 1.03 (d, J = 6.2 Hz, 3H), 1.01-0.91 (m, 1H), 0.88 (t, J = 7.4 Hz, 3H), 0.65 (t, J = 7.4 Hz, 3H). $^{19}$F NMR (376 MHz, CDCl$_3$) δ -114.13. |
| 138 | | IR thin film) 3370, 2964, 1731, 1649, 1528, 1263, 1149, 953, 731 cm$^{-1}$ | HRMS-ESI (m/z) [M + H]$^+$ calcd for C$_{23}$H$_{30}$FN$_2$O$_6$, 449.2082; found, 449.2079 | $^1$H NMR (400 MHz, CDCl$_3$) δ 12.15 (s, 1H), 8.46 (d, J = 8.0 Hz, 1H), 8.01 (d, J = 5.2 Hz, 1H), 7.16 (dd, J = 8.5, 6.9 Hz, 1H), 6.89 (d, J = 5.2 Hz, 1H), 6.57 (dd, J = 11.1, 2.5 Hz, 1H), 6.51 (td, J = 8.3, 2.5 Hz, 1H), 5.49-5.40 (m, 1H), 4.74-4.61 (m, 1H), 3.95 (s, 3H), 3.77 (s, 3H), 3.06 (dd, J = 9.4, 5.0 Hz, 1H), 1.96 (ddq, J = 13.1, 9.1, 6.6 Hz, 1H), 1.42 (d, J = 7.2 Hz, 3H), 1.07 (d, J = 6.3 Hz, 3H), 0.97 (d, J = 6.6 Hz, 3H), 0.66 (d, J = 6.6 Hz, 3H). $^{19}$F NMR (376 MHz, CDCl$_3$) δ -114.12. |
| 139 | | IR (thin film) 3371, 2928, 1731, 1649, 1528, 1449, 1262, 1150, 1128, | HRMS-ESI (m/z) [M + H]$^+$ calcd for C$_{26}$H$_{34}$FN$_2$O$_6$, 489.2395; found, 489.2401 | $^1$H NMR (400 MHz, CDCl$_3$) δ 12.16 (s, 1H), 8.47 (d, J = 8.1 Hz, 1H), 8.02 (d, J = 5.2 Hz, 1H), 7.17 (t, J = 7.7 Hz, 1H), 6.89 (d, J = 5.2 Hz, 1H), 6.61-6.46 (m, 2H), 5.44 (p, J = 6.1 Hz, 1H), 4.69 (p, J = 7.3 Hz, 1H), 3.95 (s, 3H), 3.76 |

TABLE 2-continued

Analytical Data

| Cmpd. No. | Melting Point (° C.) | IR (cm⁻¹) | MASS SPEC | NMR |
|---|---|---|---|---|
| | | 1035, 953, 729 cm⁻¹ | | (s, 3H), 3.12 (d, J = 6.7 Hz, 1H), 1.84 (d, J = 13.0 Hz, 1H), 1.78-1.48 (m, 4H), 1.45 (d, J = 7.2 Hz, 3H), 1.37-1.05 (m, 4H), 1.04 (d, J = 6.3 Hz, 3H), 1.01-0.86 (m, 1H), 0.75 (qd, J = 12.1, 3.6 Hz, 1H). $^{19}$F NMR (376 MHz, CDCl$_3$) δ −114.15. |
| 140 | | IR (thin film) 3370, 2944, 1732, 1649, 1528, 1450, 1263, 1149, 1036, 952, 731 cm⁻¹ | HRMS-ESI (m/z) [M + H]⁺ calcd for C$_{25}$H$_{32}$FN$_2$O$_6$, 475.2239; found, 475.2233 | $^1$H NMR (400 MHz, CDCl$_3$) δ 12.17 (s, 1H), 8.48 (d, J = 8.0 Hz, 1H), 8.02 (d, J = 5.2 Hz, 1H), 7.21-7.13 (m, 1H), 6.89 (d, J = 5.2 Hz, 1H), 6.57 (dd, J = 11.1, 2.5 Hz, 1H), 6.48 (td, J = 8.3, 2.5 Hz, 1H), 5.34 (qd, J = 6.2, 3.3 Hz, 1H), 4.71 (p, J = 7.4 Hz, 1H), 3.95 (s, 3H), 3.77 (s, 3H), 3.18-3.06 (m, 1H), 2.21-2.05 (m, 1H), 1.87 (dtd, J = 11.2, 7.1, 3.5 Hz, 1H), 1.74-1.59 (m, 1H), 1.58-1.45 (m, 4H), 1.37 (dddd, J = 26.9, 11.8, 7.7, 3.1 Hz, 1H), 1.28-1.16 (m, 2H), 1.04 (d, J = 6.3 Hz, 3H), 1.02-0.97 (m, 1H), 0.95-0.82 (m, 1H). $^{19}$F NMR (376 MHz, CDCl$_3$) δ −114.21. |
| 141 | | IR (thin film) 3371, 2964, 1731, 1649, 1451, 1263, 1149, 1036, 952, 730 cm⁻¹ | HRMS-ESI (m/z) [M + H]⁺ calcd for C$_{24}$H$_{32}$FN$_2$O$_6$, 463.2239; found, 463.2234 | $^1$H NMR (400 MHz, CDCl$_3$) δ 12.15 (d, J = 5.4 Hz, 1H), 8.45 (dd, J = 13.9, 8.0 Hz, 1H), 8.01 (dd, J = 6.2, 5.2 Hz, 1H), 7.16 (ddd, J = 8.5, 6.9, 4.0 Hz, 1H), 6.88 (dd, J = 5.2, 3.9 Hz, 1H), 6.63-6.47 (m, 2H), 5.50-5.39 (m, 1H), 4.75-4.59 (m, 1H), 3.95 (d, J = 0.9 Hz, 3H), 3.77 (s, 3H), 3.29-3.06 (m, 1H), 1.82-1.66 (m, 1H), 1.49 (dd, J = 12.2, 7.1 Hz, 2H), 1.33 (d, J = 7.2 Hz, 1H), 1.20-1.00 (m, 4H), 1.00-0.78 (m, 4H), 0.74-0.63 (m, 3H). $^{19}$F NMR (376 MHz, CDCl$_3$) δ −114.11, −114.15. |
| 142 | | IR thin film) 3371, 2938, 1732, 1649, 1529, 1451, 1264, 1148, 953, 732 cm⁻¹ | HRMS-ESI (m/z) [M + H]⁺ calcd for C$_{24}$H$_{30}$FN$_2$O$_6$, 461.2082; found, 461.2073 | $^1$H NMR (400 MHz, CDCl$_3$) δ 12.16 (s, 1H), 8.41 (d, J = 8.0 Hz, 1H), 8.00 (d, J = 5.2 Hz, 1H), 7.03 (dd, J = 8.5, 6.8 Hz, 1H), 6.88 (d, J = 5.2 Hz, 1H), 6.55 (dd, J = 11.0, 2.5 Hz, 1H), 6.47 (td, J = 8.3, 2.5 Hz, 1H), 5.24 (q, J = 6.5 Hz, 1H), 4.61 (p, J = 7.3 Hz, 1H), 3.95 (s, 3H), 3.79 (s, 3H), 3.25 (s, 1H), 2.69-2.58 (m, 1H), 2.16-2.04 (m, 1H), 1.89-1.57 (m, 4H), 1.51-1.37 (m, 1H), 1.34 (d, J = 7.2 Hz, 3H), 1.13 (d, J = 6.4 Hz, 3H). $^{19}$F NMR (376 MHz, CDCl$_3$) δ −114.03. |
| 143 | | IR (thin film) 3369, 2927, 1732, 1649, 1528, 1450, 1278, 1263, 1035, 954, 731 cm⁻¹ | HRMS-ESI (m/z) [M + H]⁺ calcd for C$_{26}$H$_{34}$FN$_2$O$_6$, 489.2395; found, 489.2399 | $^1$H NMR (400 MHz, CDCl$_3$) δ 12.18 (s, 1H), 8.50 (d, J = 8.1 Hz, 1H), 7.98 (d, J = 5.2 Hz, 1H), 7.01 (dd, J = 8.5, 6.8 Hz, 1H), 6.88 (d, J = 5.2 Hz, 1H), 6.60 (td, J = 8.2, 2.6 Hz, 1H), 6.54 (dd, J = 11.0, 2.5 Hz, 1H), 5.46 (s, 1H), 4.76-4.62 (m, 1H), 3.95 (s, 3H), 3.75 (s, 3H), 3.39 (s, 1H), 1.80-1.59 (m, 5H), 1.59-1.46 (m, 4H), 1.17 (qt, J = 13.4, 3.6 Hz, 1H), 1.08 (d, J = 6.3 Hz, 3H), 1.07-0.91 (m, 2H), 0.82 (qt, J = 15.4, 7.4 Hz, 2H). $^{19}$F NMR (376 MHz, CDCl$_3$) δ −113.87. |
| 144 | | IR (thin film) 3370, 2943, 1731, 1528, 1450, 1279, 1263, 1148, 1034, 953, 731 cm⁻¹ | HRMS-ESI (m/z) [M + H]⁺ calcd for C$_{25}$H$_{32}$FN$_2$O$_6$, 475.2239; found, 475.2223 | $^1$H NMR (400 MHz, CDCl$_3$) δ 12.18 (s, 1H), 8.46 (d, J = 8.1 Hz, 1H), 7.96 (d, J = 5.2 Hz, 1H), 7.05 (t, J = 7.6 Hz, 1H), 6.87 (d, J = 5.2 Hz, 1H), 6.59 (td, J = 8.3, 2.5 Hz, 1H), 6.50 (dd, J = 11.1, 2.5 Hz, 1H), 5.34 (s, 1H), 4.77-4.59 (m, 1H), 3.95 (s, 3H), 3.73 (s, 3H), 3.65-3.13 (m, 1H), 2.30-2.02 (m, 1H), 1.84 (td, J = 11.6, 10.9, 6.8 Hz, 1H), 1.69-1.54 (m, 2H), 1.54-1.33 (m, 6H), 1.33-1.21 (m, 1H), 1.13 (d, J = 6.4 Hz, 3H), 0.98-0.81 (m, 1H). $^{19}$F NMR (376 MHz, CDCl$_3$) δ −114.03. |

TABLE 2-continued

Analytical Data

| Cmpd. No. | Melting Point (° C.) | IR (cm$^{-1}$) | MASS SPEC | NMR |
|---|---|---|---|---|
| 145 | | IR (thin film) 3370, 2962, 1762, 1649, 1528, 1451, 1262, 1150, 1034, 954, 731 cm$^{-1}$ | HRMS-ESI (m/z) [M + H]$^+$ calcd for C$_{25}$H$_{34}$FN$_2$O$_6$, 477.2395; found, 477.2389 | $^1$H NMR (400 MHz, CDCl$_3$) δ 12.18 (s, 1H), 8.48 (d, J = 7.9 Hz, 1H), 7.97 (d, J = 5.3 Hz, 1H), 7.04 (dd, J = 8.6, 6.8 Hz, 1H), 6.87 (d, J = 5.2 Hz, 1H), 6.59 (td, J = 8.2, 2.5 Hz, 1H), 6.52 (dd, J = 11.0, 2.6 Hz, 1H), 5.50-5.41 (m, 1H), 4.74-4.64 (m, 1H), 3.95 (s, 3H), 3.74 (s, 3H), 3.57 (d, J = 10.4 Hz, 1H), 1.65-1.55 (m, 1H), 1.53 (d, J = 7.2 Hz, 3H), 1.51-1.23 (m, 2H), 1.17 (dq, J = 14.2, 7.2 Hz, 1H), 1.10 (d, J = 6.2 Hz, 3H), 1.01-0.83 (m, 4H), 0.82-0.68 (m, 3H). $^{19}$F NMR (376 MHz, CDCl$_3$) δ −113.85. |
| 146 | | IR (thin film) 3370, 2963, 1732, 1649, 1527, 1451, 1278, 1263, 1149, 1035, 730 cm$^{-1}$ | HRMS-ESI (m/z) [M + H]$^+$ calcd for C$_{24}$H$_{32}$FN$_2$O$_6$, 463.2239; found, 463.2227 | $^1$H NMR (400 MHz, CDCl$_3$) δ 12.17 (s, 1H), 8.50 (q, J = 10.0, 8.1 Hz, 1H), 7.98 (t, J = 5.5 Hz, 1H), 7.02 (dd, J = 8.4, 6.8 Hz, 1H), 6.88 (d, J = 5.2 Hz, 1H), 6.66-6.48 (m, 2H), 5.45 (dd, J = 13.7, 7.1 Hz, 1H), 4.79-4.63 (m, 1H), 3.95 (s, 3H), 3.82-3.70 (m, 3H), 3.46 (s, 1H), 1.87-1.72 (m, 1H), 1.54 (dd, J = 14.3, 7.1 Hz, 3H), 1.43-1.23 (m, 1H), 1.09 (dd, J = 11.6, 6.2 Hz, 3H), 0.99-0.80 (m, 4H), 0.80-0.69 (m, 3H). $^{19}$F NMR (376 MHz, CDCl$_3$) δ −113.79, −113.87. |
| 147 | | IR (thin film) 3371, 2939, 1733, 1529, 1280, 1264, 11748, 954 cm$^{-1}$ | HRMS-ESI (m/z) [M + H]$^+$ calcd for C$_{24}$H$_{30}$FN$_2$O$_6$, 461.2082; found, 461.2060 | $^1$H NMR (400 MHz, CDCl$_3$) δ 12.18 (s, 1H), 8.47 (d, J = 8.1 Hz, 1H), 7.98 (d, J = 5.2 Hz, 1H), 6.97 (dd, J = 8.5, 6.7 Hz, 1H), 6.87 (d, J = 5.2 Hz, 1H), 6.61-6.50 (m, 2H), 5.19 (s, 1H), 4.74-4.60 (m, 1H), 3.95 (s, 3H), 3.78 (s, 3H), 3.34 (s, 1H), 2.79 (hept, J = 8.8, 7.9 Hz, 1H), 2.20-2.06 (m, 1H), 2.00-1.83 (m, 1H), 1.83-1.71 (m, 1H), 1.71-1.59 (m, 2H), 1.51 (d, J = 7.2, 2.7 Hz, 3H), 1.42 (qd, J = 9.6, 1.7 Hz, 1H), 1.10 (d, J = 6.4 Hz, 3H). $^{19}$F NMR (376 MHz, CDCl$_3$) δ −113.83. |
| 148 | | IR (thin film) 3371, 2961, 1732, 1528, 1280, 1262, 1149, 1034, 953, 730 cm$^{-1}$ | HRMS-ESI (m/z) [M + H]$^+$ calcd for C$_{23}$H$_{30}$FN$_2$O$_6$, 449.2082; found, 449.2063 | $^1$H NMR (400 MHz, CDCl$_3$) δ 12.18-12.16 (m, 1H), 8.50 (d, J = 7.9 Hz, 1H), 7.98 (d, J = 5.2 Hz, 1H), 7.01 (dd, J = 8.5, 6.7 Hz, 1H), 6.88 (d, J = 5.2 Hz, 1H), 6.61 (td, J = 8.3, 2.6 Hz, 1H), 6.55 (dd, J = 11.0, 2.5 Hz, 1H), 5.44 (d, J = 7.5 Hz, 1H), 4.76-4.64 (m, 1H), 4.12 (q, J = 7.2 Hz, OH), 3.95 (s, 3H), 3.75 (s, 3H), 3.34 (s, 1H), 2.14-2.02 (m, 1H), 1.54 (d, J = 7.2 Hz, 3H), 1.09 (d, J = 6.3 Hz, 3H), 0.85 (d, J = 6.7 Hz, 3H), 0.73 (d, J = 6.8 Hz, 3H). $^{19}$F NMR (376 MHz, CDCl$_3$) δ −113.80. |
| 149 | | IR (thin film) 2937, 1732, 1689, 1527, 1439, 910, 800, 729 cm$^{-1}$ | HRMS-ESI (m/z) [M + H]$^+$ calcd for C$_{25}$H$_{33}$F$_4$N$_2$O$_5$, 441.2384; found, 441.2378 | $^1$H NMR (500 MHz, CDCl$_3$) δ 12.15 (d, J = 0.6 Hz, 1H), 8.40 (d, J = 8.0 Hz, 1H), 7.99 (d, J = 5.2 Hz, 1H), 7.00 (d, J = 7.8 Hz, 1H), 6.93-6.83 (m, 3H), 5.24-5.12 (m, 1H), 4.65-4.51 (m, 1H), 3.94 (s, 3H), 3.04 (dd, J = 10.5, 6.5 Hz, 1H), 2.75-2.60 (m, 1H), 2.31 (s, 3H), 2.24 (s, 3H), 2.21-2.09 (m, 1H), 1.88-1.61 (m, 4H), 1.41 (pd, J = 10.1, 3.5 Hz, 1H), 1.24 (d, J = 7.2 Hz, 3H), 1.19 (d, J = 6.3 Hz, 3H). |
| 150 | | IR (thin film) 3370, 2962, 1735, 1649, 1529, 1481, 1264, 1152, 1052, 826, 801 cm$^{-1}$ | HRMS-ESI (m/z) [M + H]$^+$ calcd for C$_{22}$H$_{28}$ClN$_2$O$_5$, 435.1681; found, 435.168 | $^1$H NMR (400 MHz, CDCl$_3$) δ 12.14 (s, 1H), 8.44 (d, J = 8.0 Hz, 1H), 8.00 (d, J = 5.2 Hz, 1H), 7.22 (d, J = 8.4 Hz, 2H), 7.02 (d, J = 8.4 Hz, 2H), 6.89 (d, J = 5.2 Hz, 1H), 5.45-5.34 (m, 1H), 4.76-4.61 (m, 1H), 3.96 (s, 3H), 2.69 (t, J = 7.6 Hz, 1H), 2.13-2.00 (m, 1H), 1.54 (d, J = 6.6 Hz, 3H), 1.10 (d, J = 6.3 Hz, 3H), 0.88 (d, J = 6.7 Hz, 3H), 0.74 (d, J = 6.7 Hz, 3H). $^{13}$C NMR (126 MHz, CDCl$_3$) δ 171.59, |

TABLE 2-continued

Analytical Data

| Cmpd. No. | Melting Point (° C.) | IR (cm$^{-1}$) | MASS SPEC | NMR |
|---|---|---|---|---|
| | | | | 168.72, 155.41, 148.78, 140.51, 137.11, 132.47, 130.99, 130.44, 128.13, 109.49, 77.21, 72.62, 56.11, 56.01, 48.18, 28.32, 21.17, 18.86, 18.31, 17.31. |
| 151 | | IR (thin film) 3370, 2961, 1734, 1649, 1576, 1528, 1481, 1280, 1262, 800 cm$^{-1}$ | HRMS-ESI (m/z) [M + H]$^+$ calcd for C$_{23}$H$_{30}$FN$_2$O$_5$, 434.2165; found, 434.2169 | $^1$H NMR (400 MHz, CDCl$_3$) δ 12.14 (s, 1H), 8.48 (d, J = 7.9 Hz, 1H), 8.00 (d, J = 5.2 Hz, 1H), 7.06 (t, J = 7.9 Hz, 1H), 6.88 (d, J = 5.2 Hz, 1H), 6.81-6.71 (m, 2H), 5.43-5.32 (m, 1H), 4.73-4.63 (m, 1H), 3.95 (s, 3H), 2.67 (t, 1H), 2.24 (s, 3H), 2.12-1.99 (m, 1H), 1.55 (d, 3H), 1.11 (d, J = 6.3 Hz, 3H), 0.87 (d, J = 6.7 Hz, 3H), 0.76 (d, J = 6.8 Hz, 3H). $^{13}$C NMR (126 MHz, CDCl$_3$) δ 171.66, 168.71, 161.91, 159.97, 155.38, 148.76, 140.49, 138.29, 138.23, 130.83, 130.79, 130.48, 125.23, 125.20, 123.02, 122.88, 116.15, 115.98, 109.44, 77.22, 72.79, 56.09, 56.07, 48.17, 34.67, 31.59, 28.33, 25.28, 22.66, 21.22, 20.71, 18.75, 18.34, 17.51, 14.20, 14.17, 14.13. |
| 152 | | IR (thin film) 2963, 1736, 1649, 1517, 1481, 1281, 1264, 1212, 1053, 801 cm$^{-1}$ | HRMS-ESI (m/z) [M + H]$^+$ calcd for C$_{22}$H$_{27}$F$_2$N$_2$O$_5$, 438.1915; found, 438.1921 | $^1$H NMR (400 MHz, CDCl$_3$) δ 12.12 (s, 1H), 8.43 (d, J = 8.1 Hz, 1H), 8.00 (d, J = 5.2 Hz, 1H), 7.09-6.98 (m, 1H), 6.95-6.86 (m, 2H), 6.84-6.75 (m, 1H), 5.43-5.33 (m, 1H), 4.74-4.60 (m, 1H), 3.96 (s, 3H), 2.68 (t, J = 7.6 Hz, 1H), 2.11-2.00 (m, 1H), 1.53 (d, 3H), 1.12 (d, J = 6.3 Hz, 3H), 0.89 (d, J = 6.7 Hz, 3H), 0.75 (d, J = 6.7 Hz, 3H). $^{13}$C NMR (126 MHz, CDCl$_3$) δ 171.54, 168.73, 155.41, 148.78, 140.52, 130.40, 118.11, 109.49, 77.21, 72.45, 56.11, 55.86, 48.16, 28.43, 21.11, 18.94, 18.28, 17.15. |
| 153 | | IR (thin film) 2962, 1734, 1715, 1530, 1481, 1282, 1264, 1244, 1220, 801 cm$^{-1}$ | HRMS-ESI (m/z) [M + H]$^+$ calcd for C$_{23}$H$_{31}$FN$_2$O$_5$, 433.2133; found, 433.2129 | $^1$H NMR (400 MHz, CDCl$_3$) δ 12.15 (d, J = 0.6 Hz, 1H), 8.49 (d, J = 7.9 Hz, 1H), 8.00 (d, J = 5.2 Hz, 1H), 6.93-6.82 (m, 4H), 5.38 (dq, J = 8.6, 6.3 Hz, 1H), 4.73-4.63 (m, 1H), 3.95 (s, 3H), 2.66 (dd, J = 8.6, 6.6 Hz, 1H), 2.24 (d, J = 1.9 Hz, 3H), 2.06 (hept, J = 6.8 Hz, 1H), 1.55 (d, J = 7.2 Hz, 3H), 1.10 (d, J = 6.3 Hz, 3H), 0.85 (d, J = 6.7 Hz, 3H), 0.75 (d, J = 6.8 Hz, 3H). $^{13}$C NMR (101 MHz, CDCl$_3$) δ 171.65, 168.73, 160.27 (d, J = 243.5 Hz), 155.40, 148.79, 140.47, 133.95 (d, J = 3.8 Hz), 132.52 (d, J = 4.9 Hz), 130.50, 128.31 (d, J = 7.7 Hz), 124.11 (d, J = 17.0 Hz), 114.39 (d, J = 22.0 Hz), 109.48, 72.95, 56.07, 55.82, 48.20, 28.32, 21.25, 18.68, 18.29, 17.62, 14.61 (d, J = 3.5 Hz). $^{19}$F NMR (376 MHz, CDCl$_3$) δ -120.75. |
| 154 | | IR (thin film) 3367, 2963, 1734, 1649, 1530, 1508, 1282, 1264, 1149, 801, 731 cm$^{-1}$ | HRMS-ESI (m/z) [M + H]$^+$ calcd for C$_{23}$H$_{30}$FN$_2$O$_6$, 449.2082; found, 449.2076 | $^1$H NMR (400 MHz, CDCl$_3$) δ 12.16 (d, J = 0.6 Hz, 1H), 8.50 (d, J = 7.9 Hz, 1H), 7.99 (d, J = 5.2 Hz, 1H), 7.03 (t, J = 8.5 Hz, 1H), 6.91-6.84 (m, 1H), 6.66 (ddd, J = 8.6, 2.6, 0.8 Hz, 1H), 6.57 (dd, J = 12.0, 2.6 Hz, 1H), 5.44 (dqd, J = 7.6, 6.3, 1.2 Hz, 1H), 4.75-4.63 (m, 1H), 3.94 (s, 3H), 3.78 (s, 3H), 3.10 (t, J = 7.7 Hz, 1H), 2.09 (tt, J = 13.5, 6.6 Hz, 1H), 1.55 (d, J = 7.2 Hz, 3H), 1.12 (d, J = 6.3 Hz, 3H), 0.94-0.87 (m, 3H), 0.76 (d, J = 6.7 Hz, 3H). $^{13}$C NMR (101 MHz, CDCl$_3$) δ 171.68, 168.74, 162.09 (d, J = 244.2 Hz), 159.37 (d, J = 11.4 Hz), 155.38, 148.78, 140.47, 130.67 (d, J = 6.6 Hz), 130.56, 117.46 (d, J = 15.4 Hz), 109.59 (d, J = 3.0 Hz), 109.46, 101.41 (d, J = 27.9 Hz), 72.76, 56.07, 55.44, 48.21, 47.95, |

TABLE 2-continued

Analytical Data

| Cmpd. No. | Melting Point (° C.) | IR (cm$^{-1}$) | MASS SPEC | NMR |
|---|---|---|---|---|
| 155 | | IR (thin film) 3367, 2962, 1715, 1518, 1273, 1222, 801 cm$^{-1}$ | HRMS-ESI (m/z) [M + H]$^+$ calcd for C$_{23}$H$_{30}$FN$_2$O$_6$, 449.2082; found, 449.2082 | $^1$H NMR (400 MHz, CDCl$_3$) δ 12.15 (d, J = 0.6 Hz, 1H), 8.48 (d, J = 7.9 Hz, 1H), 8.00 (d, J = 5.2 Hz, 1H), 6.90-6.77 (m, 4H), 5.36 (dq, J = 8.4, 6.3 Hz, 1H), 4.73-4.64 (m, 1H), 3.95 (s, 3H), 3.87 (s, 3H), 2.68-2.60 (m, 1H), 2.05 (h, J = 6.7 Hz, 1H), 1.55 (d, J = 7.2 Hz, 3H), 1.11 (d, J = 6.3 Hz, 3H), 0.87 (d, J = 6.7 Hz, 3H), 0.76 (d, J = 6.7 Hz, 3H). $^{13}$C NMR (101 MHz, CDCl$_3$) δ 171.63, 168.76, 155.40, 151.94 (d, J = 245.1 Hz), 148.79, 146.29 (d, J = 10.7 Hz), 140.51, 131.69 (d, J = 5.6 Hz), 130.50, 125.45 (d, J = 3.5 Hz), 117.10 (d, J = 18.2 Hz), 112.94 (d, J = 2.2 Hz), 109.50, 72.80, 56.21, 56.08, 55.73, 48.21, 28.40, 21.21, 18.79, 18.30, 17.45. $^{19}$F NMR (376 MHz, CDCl$_3$) δ −135.65. |
| 156 | | IR thin film) 3367, 2960, 1732, 1649, 1528, 1262, 1041, 800, 730 cm$^{-1}$ | HRMS-ESI (m/z) [M + H]$^+$ calcd for C$_{24}$H$_{33}$N$_2$O$_6$, 445.2333; found, 445.2332 | $^1$H NMR (400 MHz, CDCl$_3$) δ 12.19 (d, J = 0.6 Hz, 1H), 8.53 (d, J = 7.9 Hz, 1H), 7.98 (d, J = 5.2 Hz, 1H), 6.94 (d, J = 7.7 Hz, 1H), 6.87 (d, J = 5.1 Hz, 1H), 6.71 (dt, J = 7.7, 1.1 Hz, 1H), 6.66 (d, J = 1.5 Hz, 1H), 5.51-5.35 (m, 1H), 4.75-4.64 (m, 1H), 3.94 (s, 3H), 3.76 (s, 3H), 3.34 (s, 1H), 2.32 (s, 3H), 2.09 (h, J = 6.7 Hz, 1H), 1.55 (d, J = 7.2 Hz, 3H), 1.09 (d, J = 6.2 Hz, 3H), 0.84 (d, J = 6.7 Hz, 3H), 0.74 (d, J = 6.8 Hz, 3H). |
| 157 | | IR (thin film) 2960, 1715, 1529, 1281, 1222, 1048, 801, 732 cm$^{-1}$ | HRMS-ES (m/z) [M + H]$^+$ calcd for C$_{24}$H$_{33}$N$_2$O$_6$, 445.2333; found, 445.2328 | $^1$H NMR (400 MHz, CDCl$_3$) δ 12.15 (d, J = 0.6 Hz, 1H), 8.51 (d, J = 7.9 Hz, 1H), 7.99 (d, J = 5.2 Hz, 1H), 7.00 (dd, J = 8.1, 0.8 Hz, 1H), 6.90-6.85 (m, 1H), 6.70 (d, J = 8.2 Hz, 2H), 5.37 (dq, J = 9.2, 6.2 Hz, 1H), 4.76-4.66 (m, 1H), 3.95 (s, 3H), 3.78 (s, 3H), 3.07 (dd, J = 9.2, 6.1 Hz, 1H), 2.29 (s, 3H), 2.11 (dq, J = 13.4, 6.8 Hz, 1H), 1.56 (d, J = 7.1 Hz, 3H), 1.07 (d, J = 6.2 Hz, 3H), 0.84 (d, J = 6.8 Hz, 3H), 0.79 (d, J = 6.8 Hz, 3H). $^{13}$C NMR (101 MHz, CDCl$_3$) δ 171.80, 168.71, 157.59, 155.39, 148.79, 140.47, 138.86, 130.54, 129.90, 128.80, 115.92, 110.88, 109.47, 74.41, 56.08, 55.04, 48.26, 29.71, 29.29, 21.08, 20.96, 18.76, 18.27, 18.23. |
| 158 | | IR (thin film) 3370, 2961, 1732, 1649, 1528, 1241, 1050, 755, 731 cm$^{-1}$ | HRMS-ESI (m/z) [M + H]$^+$ calcd for C$_{23}$H$_{31}$N$_2$O$_6$, 431.2177; found, 431.2155 | $^1$H NMR (400 MHz, CDCl$_3$) δ 12.18 (d, J = 0.6 Hz, 1H), 8.52 (d, J = 7.9 Hz, 1H), 7.99 (d, J = 5.2 Hz, 1H), 7.22-6.77 (m, 5H), 5.55-5.36 (m, 1H), 4.76-4.59 (m, 1H), 3.94 (s, 3H), 3.77 (s, 3H), 3.55-3.22 (m, 1H), 2.18-2.05 (m, 1H), 1.55 (d, J = 7.2 Hz, 3H), 1.09 (d, J = 6.3 Hz, 3H), 0.85 (d, J = 6.8 Hz, 3H), 0.74 (d, J = 6.8 Hz, 3H). |
| 159 | | IR (thin film) 3369, 2960, 1732, 1649, 1528, 1262, 1207, 1156, 1042, 730 cm$^{-1}$ | HRMS-ESI (m/z) [M + H]$^+$ calcd for C$_{24}$H$_{33}$N$_2$O$_7$, 461.2282; found, 461.2266 | $^1$H NMR (400 MHz, CDCl$_3$) δ 12.19 (s, 1H), 8.53 (d, J = 7.9 Hz, 1H), 7.99 (d, J = 5.2 Hz, 1H), 6.96 (d, J = 8.2 Hz, 1H), 6.87 (d, J = 5.3 Hz, 1H), 6.52-6.38 (m, 2H), 5.43 (s, 1H), 4.77-4.60 (m, 1H), 3.95 (s, 3H), 3.79 (s, 3H), 3.75 (s, 3H), 3.41-3.14 (m, 1H), 2.07 (dq, J = 13.4, 6.7 Hz, 1H), 1.55 (d, J = 7.1 Hz, 3H), 1.09 (d, J = 6.2 Hz, 3H), 0.83 (d, J = 6.7 Hz, 3H), 0.73 (d, J = 6.8 Hz, 3H). |
| 160 | | | HRMS-ESI (m/z) [M + H]$^+$ calcd for C$_{24}$H$_{31}$N$_2$O$_6$, 443.2182; found, 443.2187 | $^1$H NMR (300 MHz, CDCl$_3$) δ 8.54 (d, J = 8.0 Hz, 1H), 8.34 (d, J = 5.4 Hz, 1H), 7.33-7.10 (m, 5H), 7.00 (d, J = 5.4 Hz, 1H), 5.56-5.34 (m, 1H), 4.79-4.54 (m, 1H), 3.89 (s, 3H), 2.39 (s, 3H), 2.34 (dd, J = 8.7, 5.4 Hz, 1H), 2.14- |

TABLE 2-continued

Analytical Data

| Cmpd. No. | Melting Point (° C.) | IR (cm⁻¹) | MASS SPEC | NMR |
|---|---|---|---|---|
| | | | | 1.95 (m, 1H), 1.29 (d, J = 7.2 Hz, 3H), 1.09 (d, J = 6.2 Hz, 3H), 0.95 (d, J = 6.6 Hz, 3H), 0.71 (d, J = 6.7 Hz, 3H). $^{13}$C NMR (75 MHz, CDCl$_3$) δ 172.24, 168.91, 162.34, 159.46, 146.68, 141.49, 139.86, 137.49, 129.63, 127.90, 126.47, 109.79, 72.07, 58.01, 56.30, 56.26, 48.08, 29.24, 21.24, 20.74, 20.42, 18.92, 18.49. |
| 161 | | | HRMS-ESI (m/z) [M + H]$^+$ calcd for C$_{26}$H$_{33}$N$_2$O$_6$, 469.2338; found, 469.2345 | $^1$H NMR (300 MHz, CDCl$_3$) δ 8.58 (d, J = 8.0 Hz, 1H), 8.34 (d, J = 5.4 Hz, 1H), 7.33-7.09 (m, 5H), 7.01 (d, J = 5.5 Hz, 1H), 5.35 (qd, J = 6.3, 3.8 Hz, 1H), 4.83-4.65 (m, 1H), 3.89 (s, 3H), 2.43-2.38 (m, 1H), 2.40 (s, 3H), 2.29-2.14 (m, 1H), 1.93-1.78 (m, 1H), 1.70-1.50 (m, 3H), 1.45 (d, J = 7.2 Hz, 3H), 1.41-1.26 (m, 2H), 1.24-1.14 (m, 1H), 1.06 (d, J = 6.3 Hz, 3H), 0.95-0.77 (m, 1H). $^{13}$C NMR (75 MHz, CDCl$_3$) δ 172.20, 168.90, 162.36, 159.49, 146.67, 141.47, 140.72, 137.53, 129.49, 127.92, 126.44, 109.82, 73.34, 56.66, 56.31, 56.27, 48.20, 42.11, 31.70, 31.45, 25.11, 24.51, 20.74, 18.72. |
| 162 | | | HRMS-ESI (m/z) [M + H]$^+$ calcd for C$_{25}$H$_{33}$N$_2$O$_7$, 473.2288; found, 473.2294 | $^1$H NMR (300 MHz, CDCl$_3$) δ 8.36 (d, J = 7.9 Hz, 1H), 8.29 (d, J = 5.3 Hz, 1H), 7.28-7.11 (m, 5H), 6.96 (d, J = 5.4 Hz, 1H), 5.83-5.67 (m, 2H), 5.60-5.35 (m, 1H), 4.83-4.55 (m, 1H), 3.90 (s, 3H), 2.37 (dd, J = 8.5, 5.6 Hz, 1H), 2.12-2.00 (m, 1H), 2.06 (s, 3zH), 1.29 (d, J = 7.2 Hz, 3H), 1.12 (d, J = 6.2 Hz, 3H), 0.95 (d, J = 6.6 Hz, 3H), 0.72 (d, J = 6.7 Hz, 3H). $^{13}$C NMR (75 MHz, CDCl$_3$) δ 172.35, 170.26, 162.90, 160.29, 145.71, 143.99, 142.47, 139.82, 129.61, 127.90, 126.46, 109.58, 89.54, 72.07, 57.98, 56.20, 56.17, 48.26, 29.22, 21.27, 20.88, 20.85, 20.28, 18.93, 18.32. |
| 163 | | | HRMS-ESI (m/z) [M + H]$^+$ calcd for C$_{27}$H$_{35}$N$_2$O$_7$, 499.2444; found, 499.2449 | $^1$H NMR (300 MHz, CDCl$_3$) δ 8.41 (d, J = 7.8 Hz, 1H), 8.30 (d, J = 5.3 Hz, 1H), 7.30-7.15 (m, 5H), 6.97 (d, J = 5.4 Hz, 1H), 5.87-5.65 (m, 2H), 5.36 (qd, J = 6.4, 3.9 Hz, 1H), 4.94-4.63 (m, 1H), 3.91 (s, 3H), 2.42 (dd, J = 10.3, 3.9 Hz, 1H), 2.34-2.14 (m, 1H), 2.07 (s, 3H), 1.96-1.79 (m, 1H), 1.75-1.49 (m, 3H), 1.46 (d, J = 7.1 Hz, 3H), 1.45-1.28 (m, 2H), 1.27-1.16 (m, 1H), 1.08 (d, J = 6.3 Hz, 3H), 0.95-0.73 (m, 1H). $^{13}$C NMR (75 MHz, CDCl$_3$) δ 172.32, 170.28, 162.93, 160.32, 145.71, 144.05, 142.45, 140.73, 129.48, 127.94, 126.44, 109.60, 89.58, 73.34, 56.64, 56.22, 56.18, 48.39, 42.14, 31.64, 31.45, 25.10, 24.50, 20.89, 20.86, 18.76, 18.57. |
| 164 | | | HRMS-ESI (m/z) [M + H]$^+$ calcd for C$_{25}$H$_{33}$N$_2$O$_7$, 473.2288; found, 473.2279 | $^1$H NMR (300 MHz, CDCl$_3$) δ 8.38 (d, J = 7.7 Hz, 1H), 8.29 (d, J = 5.4 Hz, 1H), 7.30-7.19 (m, 3H), 7.17-7.06 (m, 2H), 6.96 (d, J = 5.4 Hz, 1H), 5.75 (s, 2H), 5.43 (dq, J = 8.7, 6.2 Hz, 1H), 4.90-4.52 (m, 1H), 3.92 (s, 3H), 2.72 (dd, J = 8.8, 6.4 Hz, 1H), 2.19-2.09 (m, 1H), 2.08 (s, 3H), 1.53 (d, J = 7.2 Hz, 3H), 1.10 (d, J = 6.3 Hz, 3H), 0.86 (d, J = 6.7 Hz, 3H), 0.77 (d, J = 6.8 Hz, 3H). $^{13}$C NMR (75 MHz, CDCl$_3$) δ 172.39, 170.32, 162.98, 160.29, 145.73, 144.03, 142.52, 138.62, 129.81, 127.90, 126.61, 109.56, 89.60, 72.72, 56.61, 56.22, |

TABLE 2-continued

Analytical Data

| Cmpd. No. | Melting Point (° C.) | IR (cm$^{-1}$) | MASS SPEC | NMR |
|---|---|---|---|---|
| | | | | 56.18, 48.41, 28.24, 21.34, 20.89, 18.54, 17.86. |
| 165 | | | HRMS-ESI (m/z) [M + H]$^+$ calcd for C$_{24}$H$_{31}$N$_2$O$_6$, 443.2182; found, 443.2177 | $^1$H NMR (400 MHz, CDCl$_3$) δ 8.54 (d, J = 8.1 Hz, 1H), 8.33 (d, J = 5.4 Hz, 1H), 7.30-7.17 (m, 3H), 7.14-7.05 (m, 2H), 7.00 (d, J = 5.4 Hz, 1H), 5.42 (dq, J = 8.7, 6.3 Hz, 1H), 4.69 (p, J = 7.3 Hz, 1H), 3.90 (s, 3H), 2.71 (dd, J = 8.6, 6.5 Hz, 1H), 2.39 (s, 3H), 2.17-2.03 (m, 1H), 1.50 (d, J = 7.2 Hz, 3H), 1.09 (d, J = 6.3 Hz, 3H), 0.86 (d, J = 6.8 Hz, 3H), 0.76 (d, J = 6.7 Hz, 3H). $^{13}$C NMR (101 MHz, CDCl$_3$) δ 172.22, 168.83, 162.38, 159.48, 146.63, 141.63, 138.69, 137.54, 129.79, 127.88, 126.58, 109.74, 72.74, 56.64, 56.26, 48.21, 28.26, 21.32, 20.72, 18.64, 18.62, 17.80. |
| 166 | | | HRMS-ESI (m/z) [M + H]$^+$ calcd for C$_{25}$H$_{31}$N$_2$O$_6$, 455.2177; found, 455.2169 | $^1$H NMR (400 MHz, CDCl$_3$) δ 8.60 (d, J = 8.0 Hz, 1H), 8.37 (d, J = 5.4 Hz, 1H), 7.18-7.10 (m, 4H), 7.05 (d, J = 5.5 Hz, 1H), 5.50-5.31 (m, 1H), 4.91-4.66 (m, 1H), 3.94 (s, 3H), 2.44 (s, 3H), 2.36 (s, 3H), 2.03 (dd, J = 10.0, 7.0 Hz, 1H), 1.52 (d, J = 7.1 Hz, 3H), 1.20 (d, J = 6.4 Hz, 3H), 1.19-1.08 (m, 1H), 0.76-0.62 (m, 1H), 0.51-0.34 (m, 2H), 0.05--0.08 (m, 1H). $^{13}$C NMR (101 MHz, CDCl$_3$) δ 172.21, 168.85, 162.33, 159.48, 146.64, 141.64, 138.58, 137.52, 136.08, 128.92, 128.29, 109.76, 75.92, 56.27, 55.25, 48.18, 21.01, 20.73, 18.68, 18.12, 13.03, 6.93, 2.87. |
| 167 | | | HRMS-ESI (m/z) [M + H]$^+$ calcd for C$_{26}$H$_{33}$N$_2$O$_7$, 485.2283; found, 485.2281 | $^1$H NMR (400 MHz, CDCl$_3$) δ 8.43 (d, J = 7.9 Hz, 1H), 8.33 (d, J = 5.3 Hz, 1H), 7.18-7.10 (m, 4H), 7.01 (d, J = 5.4 Hz, 1H), 5.80 (s, 2H), 5.46-5.25 (m, 1H), 4.90-4.72 (m, 1H), 3.96 (s, 3H), 2.37 (s, 3H), 2.12 (s, 3H), 2.05 (dd, J = 10.0, 7.0 Hz, 1H), 1.55 (d, J = 7.1 Hz, 3H), 1.22 (d, J = 6.3 Hz, 3H), 1.20-1.09 (m, 1H), 0.75-0.65 (m, 1H), 0.51-0.37 (m, 2H), 0.08--0.06 (m, 1H). $^{13}$C NMR (101 MHz, CDCl$_3$) δ 172.32, 170.20, 162.91, 160.30, 145.68, 143.99, 142.61, 138.58, 136.07, 128.91, 128.28, 109.57, 89.55, 75.89, 56.17, 55.24, 48.37, 21.00, 20.83, 18.53, 18.14, 13.01, 6.94, 2.87. |
| 168 | | IR (thin film) 3380, 2961, 1771, 1732, 1676, 1508, 1199, 1175, 908, 823, 802, 731 cm$^{-1}$ | HRMS-ESI (m/z) [M + H]$^+$ calcd for C$_{25}$H$_{33}$N$_2$O$_6$, 457.2333; found, 457.2328 | $^1$H NMR (400 MHz, CDCl$_3$) δ 8.55 (d, J = 8.0 Hz, 1H), 8.34 (d, J = 5.4 Hz, 1H), 7.06 (t, J = 6.4 Hz, 2H), 7.03-6.94 (m, 3H), 5.40 (dq, J = 8.7, 6.3 Hz, 1H), 4.74-4.62 (m, 1H), 3.91 (s, 3H), 2.67 (dd, J = 8.8, 6.3 Hz, 1H), 2.40 (s, 3H), 2.32 (s, 3H), 2.14-2.05 (m, 1H), 1.50 (d, J = 7.2 Hz, 3H), 1.08 (d, J = 6.3 Hz, 3H), 0.85 (d, J = 6.7 Hz, 3H), 0.75 (d, J = 6.7 Hz, 3H). $^{13}$C NMR (101 MHz, CDCl$_3$) δ 172.28, 168.90, 162.39, 159.49, 146.65, 141.67, 137.55, 136.06, 135.51, 129.68, 128.62, 109.73, 72.85, 56.29, 56.23, 48.23, 28.21, 21.36, 21.01, 20.75, 18.69, 18.56, 17.85. |
| 169 | | | HRMS-ESI (m/z) [M + H]$^+$ calcd for C$_{24}$H$_{30}$FN$_2$O$_6$, 461.2083; found, 461.2082 | $^1$H NMR (400 MHz, CDCl$_3$) δ 8.51 (d, J = 7.9 Hz, 1H), 8.39-8.28 (m, 1H), 7.12-6.89 (m, 5H), 5.50-5.32 (m, 1H), 4.78-4.60 (m, 1H), 3.91 (s, 3H), 2.77-2.64 (m, 1H), 2.41 (s, 3H), 2.14-2.02 (m, 1H), 1.54-1.35 (m, 3H), 1.12-0.97 (m, 3H), 0.94-0.83 (m, 3H), 0.79-0.68 (m, 3H). |

TABLE 2-continued

Analytical Data

| Cmpd. No. | Melting Point (° C.) | IR (cm$^{-1}$) | MASS SPEC | NMR |
|---|---|---|---|---|
| 170 | | | HRMS-ESI (m/z) [M + H]$^+$ calcd for C$_{24}$H$_{28}$FN$_2$O$_6$, 459.1926; found, 459.1923 | $^{19}$F NMR (376 MHz, CDCl$_3$) δ −116.57, −116.61. $^1$H NMR (400 MHz, CDCl$_3$) δ 8.51 (d, J = 8.3 Hz, 1H), 8.32 (d, J = 5.4 Hz, 1H), 7.22-7.10 (m, 2H), 7.09-6.86 (m, 3H), 5.39-5.19 (m, 1H), 4.71 (dq, J = 8.2, 7.2 Hz, 1H), 3.90 (s, 3H), 2.40 (s, 3H), 2.02 (dd, J = 10.1, 6.5 Hz, 1H), 1.46 (d, J = 7.2 Hz, 3H), 1.17 (d, J = 6.4 Hz, 3H), 1.12-1.03 (m, 1H), 0.73-0.62 (m, 1H), 0.47-0.31 (m, 2H), −0.01- −0.14 (m, 1H). |
| 171 | | | HRMS-ESI (m/z) [M + H]$^+$ calcd for C$_{25}$H$_{30}$FN$_2$O$_7$, 489.2032; found, 489.2027 | $^{19}$F NMR (376 MHz, CDCl$_3$) δ −116.54. $^1$H NMR (400 MHz, CDCl$_3$) δ 8.35 (d, J = 8.0 Hz, 1H), 8.31-8.19 (m, 1H), 7.23-7.14 (m, 2H), 7.03-6.82 (m, 3H), 5.75 (s, 2H), 5.36-5.19 (m, 1H), 4.82-4.65 (m, 1H), 3.92 (s, 3H), 2.07 (s, 3H), 2.03 (dd, J = 10.2, 6.5 Hz, 1H), 1.48 (d, J = 7.2 Hz, 3H), 1.18 (d, J = 6.4 Hz, 3H), 1.15-1.06 (m, 1H), 0.75-0.63 (m, 1H), 0.48-0.33 (m, 2H), −0.03- −0.12 (m, 1H). |
| 172 | | IR (thin film) 3382, 2962, 2933, 2875, 1771, 1732, 1676, 1505, 1309, 1193, 1174, 1040, 826, 734, 703 cm$^{-1}$. | HRMS-ESI (m/z) [M + H]$^+$ calcd for C$_{26}$H$_{35}$N$_2$O$_6$, 471.2495; found, 471.2494 | $^{19}$F NMR (376 MHz, CDCl$_3$) δ −116.54. $^1$H NMR (300 MHz, CDCl$_3$) δ 8.57 (d, J = 7.3 Hz, 1H), 8.33 (d, J = 5.4 Hz, 1H), 7.33-7.06 (m, 5H), 7.01 (d, J = 5.5 Hz, 1H), 5.52-5.36 (m, 1H), 4.70 (p, J = 7.1 Hz, 1H), 3.90 (s, 3H), 2.96 (dd, J = 8.6, 6.3 Hz, 1H), 2.40 (s, 3H), 1.50 (d, J = 7.2 Hz, 3H), 1.46-1.22 (m, 3H), 1.10 (d, J = 6.2 Hz, 3H), 0.99-0.82 (m, 5H), 0.78 (t, J = 7.2 Hz, 3H). |
| 173 | | IR (thin film) 3381, 2950, 1771, 1732, 1676, 1505, 1309, 1195, 1174, 1038, 826, 802, 734, 702 cm$^{-1}$. | HRMS-ESI (m/z) [M + H]$^+$ calcd for C$_{26}$H$_{33}$N$_2$O$_6$, 469.2338; found, 469.2342 | $^1$H NMR (300 MHz, CDCl$_3$) δ 8.53 (d, J = 7.8 Hz, 1H), 8.32 (d, J = 4.6 Hz, 1H), 7.33-7.06 (m, 5H), 7.01 (d, J = 5.5 Hz, 1H), 5.48-5.16 (m, 1H), 4.85-4.55 (m, 1H), 3.89 (s, 3H), 2.78 (dd, J = 10.0, 5.9 Hz, 1H), 2.39 (s, 3H), 1.98-1.80 (m, 1H), 1.73-1.19 (m, 11H), 1.11 (d, J = 6.5 Hz, 3H). |
| 174 | | IR (thin film) 3380, 2962, 2933, 1734, 1676, 1502, 1452, 1310, 1200, 1041, 1002, 967, 829, 735, 704 cm$^{-1}$. | HRMS-ESI (m/z) [M + H]$^+$ calcd for C$_{27}$H$_{37}$N$_2$O$_7$, 501.2601; found, 501.2606 | $^1$H NMR (300 MHz, CDCl$_3$) δ 8.40 (d, J = 7.9 Hz, 1H), 8.29 (d, J = 5.4 Hz, 1H), 7.34-7.06 (m, 5H), 6.96 (d, J = 5.4 Hz, 1H), 5.75 (s, 2H), 5.57-5.35 (m, 1H), 4.81-4.54 (m, 1H), 3.91 (s, 3H), 2.97 (dd, J = 8.6, 6.3 Hz, 1H), 2.07 (s, 3H), 1.53 (d, J = 7.2 Hz, 3H), 1.49-1.34 (m, 3H), 1.11 (d, J = 6.3 Hz, 3H), 0.95 (t, J = 7.3 Hz, 3H), 0.91-0.82 (m, 2H), 0.78 (t, J = 7.2 Hz, 3H). |
| 175 | | IR (thin film) 3382, 2948, 2869, 1733, 1501, 1437, 1310, 1200, 1040, 1002, 967, 829, 734, 703 cm$^{-1}$. | HRMS-ESI (m/z) [M + H]$^+$ calcd for C$_{27}$H$_{35}$N$_2$O$_7$, 499.2444; found, 499.2447 | $^1$H NMR (300 MHz, CDCl$_3$) δ 8.36 (d, J = 7.8 Hz, 1H), 8.28 (d, J = 5.2 Hz, 1H), 7.32-7.02 (m, 5H), 6.97 (dd, J = 5.4, 2.6 Hz, 1H), 5.75 (s, 2H), 5.45-5.17 (m, 1H), 4.85-4.40 (m, 1H), 3.91 (s, 3H) 2.79 (dd, J = 10.0, 5.9 Hz, 1H), 2.07 (s, 3H), 2.02-1.77 (m, 2H), 1.67-1.19 (m, 7H), 1.13-0.86 (m, 6H). |
| 176 | | IR (thin film) 2950, 1769, 1732, 1192, 1175, 730 cm$^{-1}$ | HRMS-ESI (m/z) [M + H]$^+$ calcd for C$_{26}$H$_{33}$N$_2$O$_5$S, 485.2105; found, 485.2171 | $^1$H NMR (400 MHz, CDCl$_3$, major) δ 9.94 (d, J = 6.5 Hz, 1H), 8.33 (d, J = 5.5 Hz, 1H), 7.26-7.20 (m, 3H), 7.14-7.10 (m, 2H), 7.00 (d, J = 5.5 Hz, 1H), 5.38-5.31 (m, 1H), 5.17-5.08 (m, 1H), 3.91 (s, 3H), 2.79 (dd, J = 9.9, 6.0 Hz, 1H), 2.36 (s, 3H), 2.28-2.12 (m, 1H), 1.98-1.82 (m, 2H), 1.57 (d, J = 7.2 Hz, 3H), 1.53-1.36 (m, 4H), 1.34-1.20 (m, 2H), 1.13 (d, J = 6.5 Hz, 3H). |
| 177 | | IR (thin film) 2950, | HRMS-ESI (m/z) [M + Na]$^+$ calcd for C$_{26}$H$_{32}$N$_2$O$_5$S, | $^1$H NMR (500 MHz, CDCl$_3$) δ 9.98 (d, J = 7.3 Hz, 1H), 8.35 (d, J = 5.4 Hz, |

TABLE 2-continued

Analytical Data

| Cmpd. No. | Melting Point (° C.) | IR (cm$^{-1}$) | MASS SPEC | NMR |
|---|---|---|---|---|
| | | 2868, 1770, 1731, 1585, 1496, 1438, 1365, 1311, 1278, 1193, 1175, 1131, 1102, 1040, 1010, 909, 847, 824, 759, 703 cm$^{-1}$ | 507.1924; found, 507.1920 | 1H), 7.25-7.13 (m, 5H), 7.01 (d, J = 5.5 Hz, 1H), 5.39 (qd, J = 6.3, 4.1 Hz, 1H), 5.16 (p, J = 7.2 Hz, 1H), 3.91 (s, 3H), 2.42 (dd, J = 10.3, 4.0 Hz, 1H), 2.35 (s, 3H), 2.28-2.19 (m, 1H), 1.93-1.83 (m, 1H), 1.68-1.59 (m, 1H), 1.52 (d, J = 7.2 Hz, 3H), 1.50-1.31 (m, 4H), 1.20 (dq, J = 12.5, 9.1 Hz, 1H), 1.08 (d, J = 6.4 Hz, 3H), 0.97-0.90 (m, 1H). |
| 178 | | IR (thin film) 3384, 2968, 1772, 1733, 1677, 1499, 1176, 825, 734 cm$^{-1}$ | HRMS-ESI (m/z) [M + Na]$^+$ calcd for $C_{25}H_{31}FN_2NaO_6$, 497.2058; found, 497.2056 | $^1$H NMR (400 MHz, CDCl$_3$) δ 8.52 (s, 1H), 8.35 (d, J = 5.4 Hz, 1H), 7.31-7.22 (m, 1H), 7.02 (d, J = 5.5 Hz, 1H), 6.84 (dd, J = 9.9, 2.9 Hz, 1H), 6.76 (td, J = 8.5, 2.8 Hz, 1H), 5.48-5.36 (m, 1H), 4.76-4.62 (m, 1H), 3.91 (s, 3H), 2.67 (dd, J = 9.4, 4.8 Hz, 1H), 2.39 (s, 3H), 2.27 (s, 3H), 2.01 (dp, J = 9.2, 6.6 Hz, 1H), 1.39 (d, J = 7.2 Hz, 3H), 1.05 (d, J = 6.3 Hz, 3H), 0.99 (d, J = 6.6 Hz, 3H), 0.68 (d, J = 6.7 Hz, 3H). $^{19}$F NMR (376 MHz, CDCl$_3$) δ −117.72. |
| 179 | | IR (thin film) 3384, 2963, 1771, 1732, 1676, 1498, 1174, 825, 731 cm$^{-1}$ | HRMS-ESI (m/z) [M + Na]$^+$ calcd for $C_{27}H_{35}FN_2NaO_6$, 525.2371; found, 525.2364 | $^1$H NMR (400 MHz, CDCl$_3$) δ 8.54 (d, J = 7.6 Hz, 1H), 8.35 (d, J = 5.5 Hz, 1H), 7.30 (dd, J = 8.8, 6.2 Hz, 1H), 7.02 (dd, J = 5.5, 2.6 Hz, 1H), 6.83 (dd, J = 9.9, 2.9 Hz, 1H), 6.75 (td, J = 8.6, 2.9 Hz, 1H), 5.38 (qd, J = 6.3, 4.0 Hz, 1H), 4.79-4.65 (m, 1H), 3.91 (s, 3H), 2.90 (dd, J = 10.1, 4.2 Hz, 1H), 2.39 (s, 3H), 2.27 (d, J = 3.5 Hz, 3H), 1.82-1.67 (m, 1H), 1.58-1.28 (m, 4H), 1.26 (s, 1H), 1.19-1.05 (m, 1H), 0.99 (dd, J = 10.0, 6.3 Hz, 3H), 0.94-0.81 (m, 4H), 0.72-0.63 (m, 3H). $^{19}$F NMR (376 MHz, CDCl$_3$) δ −117.69. |
| 180 | | IR (thin film) 3384, 2950, 1771, 1731, 1675, 1498, 1175, 907, 730 cm$^{-1}$ | HRMS-ESI (m/z) [M + Na]$^+$ calcd for $C_{27}H_{33}FN_2NaO_6$, 523.2215; found, 523.2210 | $^1$H NMR (400 MHz, CDCl$_3$) δ 8.54 (d, J = 8.0 Hz, 1H), 8.35 (d, J = 5.4 Hz, 1H), 7.31-7.22 (m, 1H), 7.02 (d, J = 5.4 Hz, 1H), 6.83 (dd, J = 9.9, 2.8 Hz, 1H), 6.73 (td, J = 8.5, 2.8 Hz, 1H), 5.32 (qd, J = 6.4, 3.9 Hz, 1H), 4.72 (p, J = 7.3 Hz, 1H), 3.91 (s, 3H), 2.78 (dd, J = 10.4, 4.2 Hz, 1H), 2.39 (s, 3H), 2.29 (s, 3H), 2.25-2.10 (m, 1H), 1.89 (ddt, J = 14.4, 10.9, 5.2 Hz, 1H), 1.74-1.30 (m, 7H), 1.30-1.13 (m, 2H), 1.06 (d, J = 6.3 Hz, 3H), 1.00-0.78 (m, 1H). $^{13}$C NMR (101 MHz, CDCl$_3$) δ 172.09, 168.86, 162.37, 160.90 (d, J = 243.9 Hz), 159.56, 146.64, 141.54, 138.75 (d, J = 7.2 Hz), 137.63, 135.25 (d, J = 3.2 Hz), 129.77 (d, J = 8.1 Hz), 116.34 (d, J = 20.2 Hz), 112.67 (d, J = 20.5 Hz), 109.82, 73.60, 56.31, 49.43, 48.20, 42.91, 31.62, 31.42, 25.12, 24.42, 20.73, 20.61, 18.63, 18.13. $^{19}$F NMR (376 MHz, CDCl$_3$) δ −117.78. |
| 181 | | IR (thin film) 3383, 2928, 1771, 1675, 1498, 1174, 1038, 825, 732 cm$^{-1}$ | HRMS-ESI (m/z) [M + H]$^+$ calcd for $C_{28}H_{36}FN_2O_6$, 515.2552; found, 515.2557 | $^1$H NMR (400 MHz, CDCl$_3$) δ 8.54 (d, J = 7.5 Hz, 1H), 8.35 (d, J = 5.4 Hz, 1H), 7.31-7.27 (m, 1H), 7.02 (d, J = 5.4 Hz, 1H), 6.87-6.73 (m, 2H), 5.42 (qd, J = 6.3, 4.3 Hz, 1H), 4.77-4.66 (m, 1H), 3.91 (s, 3H), 2.74 (dd, J = 9.5, 4.7 Hz, 1H), 2.40 (s, 3H), 2.31-2.21 (m, 3H), 1.86 (d, J = 12.9 Hz, 1H), 1.78-1.49 (m, 3H), 1.41 (d, J = 7.2 Hz, 3H), 1.36-1.15 (m, 3H), 1.15-0.84 (m, 6H), 0.84-0.70 (m, 1H). $^{13}$C NMR (101 MHz, CDCl$_3$) δ 172.20, 168.87, 162.36, 160.91 (d, J = 243.8 Hz), 159.55, 146.65, 141.55, 139.40 (d, J = 7.1 Hz), 137.60, 134.70 (d, J = 3.4 |

TABLE 2-continued

Analytical Data

| Cmpd. No. | Melting Point (° C.) | IR (cm$^{-1}$) | MASS SPEC | NMR |
|---|---|---|---|---|
| | | | | Hz), 129.50 (d, J = 7.7 Hz), 116.32 (d, J = 20.6 Hz), 112.74 (d, J = 20.2 Hz), 109.82, 71.63, 56.31, 49.64, 48.13, 40.27, 31.28, 30.87, 29.30, 26.47, 26.37, 26.27, 20.74, 18.66, 18.19. $^{19}$F NMR (376 MHz, CDCl$_3$) δ −117.74. |
| 182 | | IR (thin film) 3384, 2965, 1771, 1732, 1674, 1498, 1175, 908, 731 cm$^{-1}$ | HRMS-ESI (m/z) [M + Na]$^+$ calcd for C$_{26}$H$_{33}$FN$_2$NaO$_6$, 511.2215; found, 511.2207 | $^1$H NMR (400 MHz, CDCl$_3$) δ 8.59-8.45 (m, 1H), 8.35 (dd, J = 5.4, 1.3 Hz, 1H), 7.31-7.23 (m, 1H), 7.04-6.95 (m, 1H), 6.83 (dd, J = 9.9, 2.7 Hz, 1H), 6.76 (dtd, J = 8.5, 5.3, 2.6 Hz, 1H), 5.42 (ddt, J = 8.6, 6.1, 3.5 Hz, 1H), 4.76-4.64 (m, 1H), 3.91 (s, 3H), 2.77 (ddd, J = 42.7, 9.3, 4.8 Hz, 1H), 2.39 (d, J = 2.0 Hz, 3H), 2.33-2.23 (m, 3H), 1.97-1.50 (m, 2H), 1.48-1.31 (m, 3H), 1.26 (s, 1H), 1.23-0.93 (m, 4H), 0.94-0.58 (m, 5H). $^{19}$F NMR (376 MHz, CDCl$_3$) δ −117.69, −117.74. |
| 183 | | IR (thin film) 3380, 2938, 1771, 1732, 1674, 1498, 1175, 908, 730 cm$^{-1}$ | HRMS-ESI (m/z) [M + Na]$^+$ calcd for C$_{26}$H$_{31}$FN$_2$NaO$_6$, 509.2058; found, 509.2056 | $^1$H NMR (400 MHz, CDCl$_3$) δ 8.49-8.39 (m, 1H), 8.33 (d, J = 5.4 Hz, 1H), 7.09 (dd, J = 8.6, 6.0 Hz, 1H), 7.00 (d, J = 5.5 Hz, 1H), 6.81 (dd, J = 9.9, 2.9 Hz, 1H), 6.74 (td, J = 8.4, 2.8 Hz, 1H), 5.14 (p, J = 6.4 Hz, 1H), 4.59 (p, J = 7.4 Hz, 1H), 3.90 (s, 3H), 3.02 (dd, J = 10.4, 6.4 Hz, 1H), 2.70-2.59 (m, 1H), 2.39 (s, 3H), 2.34 (s, 3H), 2.17 (d, J = 6.0 Hz, 1H), 1.88-1.59 (m, 4H), 1.42-1.33 (m, 1H), 1.20 (d, J = 7.2 Hz, 3H), 1.17 (d, J = 6.3 Hz, 3H). $^{19}$F NMR (376 MHz, CDCl$_3$) δ −117.62. |
| 184 | | IR (thin film) 3379, 2949, 1770, 1731, 1675, 1499, 1175, 907, 730 cm$^{-1}$ | HRMS-ESI (m/z) [M + Na]$^+$ calcd for C$_{27}$H$_{33}$FN$_2$NaO$_6$, 523.2215; found, 523.2202 | $^1$H NMR (400 MHz, CDCl$_3$) δ 8.47 (d, J = 8.1 Hz, 1H), 8.31 (d, J = 5.4 Hz, 1H), 7.09 (dd, J = 8.7, 5.9 Hz, 1H), 7.01 (d, J = 5.5 Hz, 1H), 6.84 (td, J = 8.3, 3.1 Hz, 1H), 6.76 (dd, J = 9.9, 2.8 Hz, 1H), 5.29 (p, J = 6.7 Hz, 1H), 4.74-4.63 (m, 1H), 3.91 (s, 3H), 3.10 (dd, J = 9.2, 7.1 Hz, 1H), 2.40 (d, J = 2.6 Hz, 3H), 2.21-2.07 (m, 1H), 1.86 (dtd, J = 14.8, 7.9, 7.1, 4.5 Hz, 1H), 1.67-1.30 (m, 9H), 1.30-1.16 (m, 2H), 1.16-1.08 (m, 4H), 0.98-0.81 (m, 1H). $^{19}$F NMR (376 MHz, CDCl$_3$) δ −117.62. |
| 185 | | IR (thin film) 3379, 2928, 1771, 1733, 1676, 1499, 1193, 1175, 825, 732 cm$^{-1}$ | HRMS-ESI (m/z) [M + H]$^+$ calcd for C$_{28}$H$_{36}$FN$_2$O$_6$, 515.2552; found, 515.2568 | $^1$H NMR (400 MHz, CDCl$_3$) δ 8.52 (d, J = 8.0 Hz, 1H), 8.33 (d, J = 5.4 Hz, 1H), 7.05 (dd, J = 8.6, 5.9 Hz, 1H), 7.01 (d, J = 5.5 Hz, 1H), 6.88-6.78 (m, 2H), 5.41-5.36 (m, 1H), 4.77-4.67 (m, 1H), 3.91 (s, 3H), 3.11 (dd, J = 9.0, 6.1 Hz, 1H), 2.40 (s, 3H), 2.28 (s, 3H), 1.83-1.39 (m, 10H), 1.31-0.95 (m, 5H), 0.95-0.81 (m, 2H). $^{19}$F NMR (376 MHz, CDCl$_3$) δ −117.48. |
| 186 | | IR (thin film) 3381, 2961, 1771, 1732, 1675, 1499, 1174, 1045, 908, 731 cm$^{-1}$ | HRMS-ESI (m/z) [M + Na]$^+$ calcd for C$_{25}$H$_{31}$FN$_2$NaO$_6$, 497.2058; found, 497.2048 | $^1$H NMR (400 MHz, CDCl$_3$) δ 8.51 (d, J = 8.0 Hz, 1H), 8.33 (d, J = 5.4 Hz, 1H), 7.05 (dd, J = 8.5, 6.0 Hz, 1H), 7.01 (d, J = 5.5 Hz, 1H), 6.84 (qd, J = 10.0, 9.2, 2.8 Hz, 2H), 5.36 (dq, J = 9.3, 6.2 Hz, 1H), 4.75-4.65 (m, 1H), 3.91 (d, J = 1.9 Hz, 3H), 3.08 (dd, J = 8.9, 6.5 Hz, 1H), 2.40 (d, J = 2.1 Hz, 3H), 2.29 (s, 3H), 2.12 (h, J = 6.8 Hz, 1H), 1.50 (dd, J = 7.2, 2.0 Hz, 3H), 1.06 (d, J = 6.2 Hz, 3H), 0.86 (dd, J = 6.9, 1.9 Hz, 3H), 0.77 (d, J = 6.8 Hz, 3H). $^{13}$C NMR (101 MHz, CDCl$_3$) δ 172.23, 168.88, 162.36, 160.94 (d, J = 244.3 Hz), 159.51, 146.65, 141.57, 139.90 (d, J = 6.5 Hz), 137.56, 133.65 (d, J = 2.9 Hz), 129.31-129.08 (m), 116.96 (d, J = 20.5 Hz), 112.33 (d, J = 20.7 Hz), 109.77, 73.76, 56.30, 48.22, 29.69, |

TABLE 2-continued

Analytical Data

| Cmpd. No. | Melting Point (° C.) | IR (cm$^{-1}$) | MASS SPEC | NMR |
|---|---|---|---|---|
| 187 | | IR (thin film) 3379, 2963, 1771, 1732, 1675, 1499, 1175, 907, 730 cm$^{-1}$ | HRMS-ESI (m/z) [M + H]$^+$ calcd for C$_{27}$H$_{36}$FN$_2$O$_6$, 503.2552; found, 503.2557 | 29.30, 20.93, 20.91, 20.75, 18.92, 18.59, 17.91. $^{19}$F NMR (376 MHz, CDCl$_3$) δ −117.42. $^1$H NMR (400 MHz, CDCl$_3$) δ 8.47 (d, J = 8.3 Hz, 1H), 8.31 (d, J = 5.5 Hz, 1H), 7.09 (dd, J = 8.7, 5.9 Hz, 1H), 7.01 (dd, J = 5.4, 2.2 Hz, 1H), 6.83 (td, J = 8.5, 3.3 Hz, 1H), 6.76 (dd, J = 9.9, 2.9 Hz, 1H), 5.41 (dq, J = 7.8, 6.2 Hz, 1H), 4.70 (dt, J = 8.0, 6.0 Hz, 1H), 3.91 (d, J = 1.7 Hz, 3H), 3.25 (q, J = 8.0 Hz, 1H), 2.40 (s, 3H), 2.27 (s, 2H), 1.62 (d, J = 10.7 Hz, 2H), 1.54-1.24 (m, 6H), 1.09 (d, J = 6.2 Hz, 3H), 1.07-0.81 (m, 4H), 0.81-0.64 (m, 3H). |
| 188 | | IR (thin film) 3379, 2964, 1771, 1733, 1676, 1500, 1176, 1059, 732 cm$^{-1}$ | HRMS-ESI (m/z) [M + Na]$^+$ calcd for C$_{26}$H$_{33}$FN$_2$NaO$_6$, 511.2215; found, 511.2209 | $^{19}$F NMR (376 MHz, CDCl$_3$) δ −117.52. $^1$H NMR (400 MHz, CDCl$_3$) δ 8.56-8.45 (m, 1H), 8.32 (dd, J = 5.4, 3.2 Hz, 1H), 7.06 (ddd, J = 9.1, 5.8, 3.2 Hz, 1H), 7.01 (d, J = 5.5 Hz, 1H), 6.83 (qd, J = 10.4, 9.3, 5.1 Hz, 2H), 5.38 (ddt, J = 18.2, 9.3, 6.3 Hz, 1H), 4.76-4.63 (m, 1H), 3.91 (s, 3H), 3.22-3.07 (m, 1H), 2.40 (d, J = 1.3 Hz, 3H), 2.35-2.25 (m, 3H), 1.95-1.75 (m, 1H), 1.54-1.33 (m, 4H), 1.06 (dd, J = 8.1, 6.2 Hz, 3H), 1.00-0.81 (m, 4H), 0.78 (dt, J = 7.1, 3.7 Hz, 3H). |
| 189 | | IR (thin film) 3379, 2939, 1770, 1732, 1674, 1499, 1175, 908, 730 cm$^{-1}$ | HRMS-ESI (m/z) [M + Na]$^+$ calcd for C$_{26}$H$_{31}$FN$_2$NaO$_6$, 509.2059; found, 509.2039 | $^{19}$F NMR (376 MHz, CDCl$_3$) δ −117.43, −117.48. $^1$H NMR (400 MHz, CDCl$_3$) δ 8.49 (d, J = 8.1 Hz, 1H), 8.33 (d, J = 5.5 Hz, 1H), 7.05-6.97 (m, 2H), 6.87-6.77 (m, 2H), 5.17-5.04 (m, 1H), 4.74-4.62 (m, 1H), 3.91 (s, 3H), 3.13 (t, J = 8.7 Hz, 1H), 2.72 (dt, J = 19.2, 9.6 Hz, 1H), 2.40 (s, 3H), 2.33 (s, 3H), 2.19-2.06 (m, 1H), 1.92-1.71 (m, 2H), 1.71-1.56 (m, 2H), 1.48 (d, J = 7.1 Hz, 3H), 1.44-1.20 (m, 1H), 1.07 (d, J = 6.3 Hz, 3H). |
| 190 | | IR (thin film) 3383, 2951, 1771, 1732, 1675, 1498, 1175, 908, 730 cm$^{-1}$ | HRMS-ESI (m/z) [M + Na]$^+$ calcd for C$_{27}$H$_{33}$FN$_2$NaO$_6$, 523.2215; found, 523.2201 | $^{19}$F NMR (376 MHz, CDCl$_3$) δ −117.38. $^1$H NMR (400 MHz, CDCl$_3$) δ 8.61-8.49 (m, 1H), 8.35 (d, J = 5.4 Hz, 1H), 7.33 (dd, J = 8.7, 6.1 Hz, 1H), 7.02 (d, J = 5.5 Hz, 1H), 6.86-6.72 (m, 2H), 5.32 (qd, J = 6.4, 3.5 Hz, 1H), 4.74 (p, J = 7.2 Hz, 1H), 3.92 (s, 3H), 2.77 (dd, J = 10.6, 3.5 Hz, 1H), 2.40 (s, 3H), 2.29 (s, 3H), 2.27-2.15 (m, 1H), 1.99-1.86 (m, 1H), 1.74-1.29 (m, 7H), 1.29-1.15 (m, 2H), 1.03 (d, J = 6.4 Hz, 3H), 0.93-0.78 (m, 1H). $^{13}$C NMR (101 MHz, CDCl$_3$) δ 172.03, 168.89, 162.41, 160.91 (d, J = 243.8 Hz), 159.55, 146.65, 141.52, 138.75 (d, J = 7.2 Hz), 137.62, 135.15 (d, J = 3.2 Hz), 129.97 (d, J = 8.1 Hz), 116.32 (d, J = 20.6 Hz), 112.63 (d, J = 20.5 Hz), 109.81, 73.36, 56.31, 49.51, 48.10, 42.71, 31.73, 31.70, 25.18, 24.52, 20.74, 20.62, 18.55, 17.78. |
| 191 | | IR (thin film) 3380, 2928, 1771, 1732, 1675, 1498, 1173, 909, 730 cm$^{-1}$ | HRMS-ESI (m/z) [M + Na]$^+$ calcd for C$_{28}$H$_{35}$FN$_2$NaO$_6$, 537.2371; found, 537.2380 | $^{19}$F NMR (376 MHz, CDCl$_3$) δ −117.80. $^1$H NMR (400 MHz, CDCl$_3$) δ 8.53 (s, 1H), 8.35 (d, J = 5.4 Hz, 1H), 7.33 (dd, J = 8.7, 6.1 Hz, 1H), 7.03 (d, J = 5.4 Hz, 1H), 6.88-6.69 (m, 2H), 5.42 (pd, J = 8.5, 7.4, 3.3 Hz, 1H), 4.78-4.67 (m, 1H), 3.92 (s, 3H), 2.71 (dd, J = 9.9, 3.9 Hz, 1H), 2.40 (s, 3H), 2.26 (s, 3H), 1.92 (d, J = 12.8 Hz, 1H), 1.79-1.49 (m, 4H), 1.44 (d, J = 7.2 Hz, 3H), 1.38-1.16 (m, 3H), 1.16-0.84 (m, 5H), 0.82-0.66 (m, 1H). $^{13}$C NMR (101 MHz, CDCl$_3$) δ 172.01, 168.88, 162.37, 160.90 (d, J = 243.9 Hz), 159.57, 146.64, 141.51, 139.38 (d, J = 7.3 Hz), 137.64, 134.61 (d, J = 3.1 |

TABLE 2-continued

Analytical Data

| Cmpd. No. | Melting Point (° C.) | IR (cm$^{-1}$) | MASS SPEC | NMR |
|---|---|---|---|---|
| | | | | Hz), 129.69 (d, J = 7.8 Hz), 116.28 (d, J = 20.6 Hz), 112.68 (d, J = 20.6 Hz), 109.82, 71.31, 56.32, 49.62, 48.11, 39.95, 31.32, 31.20, 29.29, 26.51, 26.37, 26.24, 20.74, 18.52, 17.93. $^{19}$F NMR (376 MHz, CDCl$_3$) δ −117.81. |
| 192 | | IR (thin film) 3380, 2963, 1771, 1732, 1676, 1499, 1176, 733 cm$^{-1}$ | HRMS-ESI (m/z) [M + Na]$^+$ calcd for C$_{25}$H$_{31}$FN$_2$NaO$_6$, 497.2058; found, 497.2059 | $^1$H NMR (400 MHz, CDCl$_3$) δ 8.57-8.43 (m, 1H), 8.35 (d, J = 5.4 Hz, 1H), 7.32 (dd, J = 8.7, 6.1 Hz, 1H), 7.02 (d, J = 5.4 Hz, 1H), 6.83 (dd, J = 9.9, 2.9 Hz, 1H), 6.79-6.71 (m, 1H), 5.43 (qd, J = 6.4, 3.9 Hz, 1H), 4.76-4.68 (m, 1H), 3.92 (s, 3H), 2.67-2.60 (m, 1H), 2.40 (s, 3H), 2.27 (s, 3H), 2.12-1.94 (m, 1H), 1.44 (d, J = 7.2 Hz, 3H), 1.01 (dd, J = 6.4, 3.0 Hz, 6H), 0.67 (d, J = 6.7 Hz, 3H). $^{19}$F NMR (376 MHz, CDCl$_3$) δ −117.77. |
| 193 | | IR (thin film) 3378, 2951, 1732, 1674, 1497, 1201, 1003, 968, 730 cm$^{-1}$ | HRMS-ESI (m/z) [M + Na]$^+$ calcd for C$_{28}$H$_{35}$FN$_2$NaO$_7$, 553.2321; found, 553.2310 | $^1$H NMR (400 MHz, CDCl$_3$) δ 8.37 (d, J = 7.9 Hz, 1H), 8.30 (d, J = 5.4 Hz, 1H), 7.31-7.27 (m, 1H), 6.97 (d, J = 5.4 Hz, 1H), 6.83 (dd, J = 9.9, 2.8 Hz, 1H), 6.75 (td, J = 8.5, 2.9 Hz, 1H), 5.75 (d, J = 2.4 Hz, 2H), 5.33 (qd, J = 6.3, 4.0 Hz, 1H), 4.74 (p, J = 7.3 Hz, 1H), 3.92 (s, 3H), 2.80 (dd, J = 10.3, 4.2 Hz, 1H), 2.29 (s, 3H), 2.25-2.11 (m, 1H), 2.07 (s, 3H), 1.89 (dtd, J = 10.9, 7.1, 3.4 Hz, 1H), 1.77-1.29 (m, 7H), 1.29-1.13 (m, 2H), 1.08 (d, J = 6.3 Hz, 3H), 0.96-0.79 (m, 1H). $^{13}$C NMR (101 MHz, CDCl$_3$) δ 172.21, 170.25, 162.95, 160.90 (d, J = 243.9 Hz), 160.39, 145.69, 144.14, 142.51, 138.78 (d, J = 7.2 Hz), 135.27 (d, J = 3.2 Hz), 129.70 (d, J = 8.1 Hz), 116.37 (d, J = 20.5 Hz), 112.69 (d, J = 20.6 Hz), 109.63, 89.63, 73.62, 56.21, 49.42, 48.41, 42.95, 31.62, 31.38, 25.11, 24.41, 20.86, 20.62, 18.50, 18.17. $^{19}$F NMR (376 MHz, CDCl$_3$) δ −117.76. |
| 194 | | IR (thin film) 3379, 2929, 1733, 1675, 1498, 1202, 1004, 969, 829, 731 cm$^{-1}$ | HRMS-ESI (m/z) [M + H]$^+$ calcd for C$_{29}$H$_{38}$FN$_2$O$_7$, 545.2658; found, 545.2652 | $^1$H NMR (400 MHz, CDCl$_3$) δ 8.29 (d, J = 7.8 Hz, 1H), 8.29 (d, J = 5.4 Hz, 1H), 7.30 (dd, J = 8.7, 6.1 Hz, 1H), 6.96 (d, J = 5.4 Hz, 1H), 6.87-6.76 (m, 2H), 5.75 (d, J = 1.6 Hz, 2H), 5.48-5.38 (m, 1H), 4.73 (p, J = 7.3 Hz, 1H), 3.91 (s, 3H), 2.76 (dd, J = 9.3, 4.8 Hz, 1H), 2.27 (s, 3H), 2.07 (s, 3H), 1.86 (d, J = 12.8 Hz, 1H), 1.81-1.51 (m, 3H), 1.42 (d, J = 7.1 Hz, 3H), 1.33 (d, J = 12.7 Hz, 1H), 1.28-0.89 (m, 8H), 0.85-0.72 (m, 1H). $^{13}$C NMR (101 MHz, CDCl$_3$) δ 172.32, 170.25, 162.94, 160.91 (d, J = 244.0 Hz), 160.37, 145.69, 144.10, 142.54, 139.42 (d, J = 7.3 Hz), 134.70 (d, J = 3.3 Hz), 129.47 (d, J = 8.1 Hz), 116.34 (d, J = 20.3 Hz), 112.75 (d, J = 20.5 Hz), 109.62, 89.62, 71.67, 56.21, 49.66, 48.34, 40.30, 31.30, 30.79, 26.45, 26.40, 26.32, 20.86, 20.74, 18.54, 18.23. $^{19}$F NMR (376 MHz, CDCl$_3$) δ −117.73. |
| 195 | | IR (thin film) 3379, 2950, 1756, 1676, 1498, 1201, 1003, 969, 829, 731 cm$^{-1}$ | HRMS-ESI (m/z) [M + Na]$^+$ calcd for C$_{28}$H$_{35}$FN$_2$NaO$_7$, 553.2321; found, 553.2326 | $^1$H NMR (400 MHz, CDCl$_3$) δ 8.31 (d, J = 8.1 Hz, 1H), 8.26 (d, J = 5.4 Hz, 1H), 7.09 (dd, J = 8.6, 5.9 Hz, 1H), 6.96 (d, J = 5.4 Hz, 1H), 6.89-6.72 (m, 2H), 5.74 (s, 2H), 5.36-5.22 (m, 1H), 4.71 (p, J = 7.2 Hz, 1H), 3.92 (s, 3H), 3.11 (dd, J = 9.2, 7.2 Hz, 1H), 2.27 (s, 2H), 2.20-2.10 (m, 2H), 2.07 (s, 4H), 1.87 (dtd, J = 14.8, 7.1, 3.4 Hz, 1H), 1.75-1.30 (m, 7H), 1.30-1.16 (m, 1H), 1.11 (d, J = 6.4 Hz, 3H), 0.99-0.81 (m, 1H). $^{19}$F NMR (376 MHz, CDCl$_3$) δ −117.60. |
| 196 | | IR (thin film) 3379, | HRMS-ESI (m/z) [M + Na]$^+$ calcd for C$_{27}$H$_{35}$FN$_2$NaO$_7$, | $^1$H NMR (400 MHz, CDCl$_3$) δ 8.34 (t, J = 8.5 Hz, 1H), 8.28 (dd, J = 5.4, 2.6 Hz, |

TABLE 2-continued

Analytical Data

| Cmpd. No. | Melting Point (° C.) | IR (cm$^{-1}$) | MASS SPEC | NMR |
|---|---|---|---|---|
| | | 2964, 1734, 1675, 1498, 1202, 1003, 968, 829, 731 cm$^{-1}$ | 541.2321; found, 541.2306 | 1H), 7.07 (ddd, J = 9.0, 6.0, 3.1 Hz, 1H), 6.96 (d, J = 5.4 Hz, 1H), 6.90-6.75 (m, 2H), 5.75 (d, J = 2.7 Hz, 2H), 5.39 (ddq, J = 18.7, 9.3, 6.2 Hz, 1H), 4.72 (td, J = 7.4, 6.2 Hz, 1H), 3.92 (s, 3H), 3.16 (ddd, J = 24.9, 9.0, 6.3 Hz, 1H), 2.35-2.20 (m, 3H), 2.07 (d, J = 0.9 Hz, 3H), 1.97-1.72 (m, 1H), 1.58-1.34 (m, 4H), 1.07 (dd, J = 7.7, 6.2 Hz, 3H), 1.02-0.82 (m, 4H), 0.78 (dd, J = 7.3, 5.2 Hz, 3H). $^{19}$F NMR (376 MHz, CDCl$_3$) δ -117.41, -117.46. |
| 197 | | IR (thin film) 3379, 2977, 1733, 1674, 1498, 1201, 1041, 1003, 968, 829, 730 cm$^{-1}$ | HRMS-ESI (m/z) [M + H]$^+$ calcd for C$_{27}$H$_{34}$FN$_2$O$_7$, 517.2345; found, 517.2340 | $^1$H NMR (400 MHz, CDCl$_3$) δ 8.33 (d, J = 7.9 Hz, 1H), 8.28 (d, J = 5.4 Hz, 1H), 7.06-6.98 (m, 1H), 6.95 (d, J = 5.4 Hz, 1H), 6.83 (dd, J = 9.5, 2.3 Hz, 2H), 5.75 (s, 2H), 5.17-5.01 (m, 1H), 4.71 (p, J = 7.2 Hz, 1H), 3.91 (s, 3H), 3.14 (t, J = 8.7 Hz, 1H), 2.73 (p, J = 8.8 Hz, 1H), 2.34 (s, 3H), 2.23-2.09 (m, 1H), 2.07 (s, 3H), 1.95-1.72 (m, 2H), 1.72-1.55 (m, 2H), 1.50 (d, J = 7.1 Hz, 3H), 1.37 (p, J = 10.0 Hz, 1H), 1.08 (d, J = 6.3 Hz, 3H). $^{19}$F NMR (376 MHz, CDCl$_3$) δ -117.38. |
| 198 | | IR (thin film) 3384, 2951, 1734, 1677, 1499, 1202, 1005, 970, 830 cm$^{-1}$ | HRMS-ESI (m/z) [M + Na]$^+$ calcd for C$_{28}$H$_{35}$FN$_2$NaO$_7$, 553.2321; found, 553.2313 | $^1$H NMR (400 MHz, CDCl$_3$) δ 8.37 (d, J = 7.7 Hz, 1H), 8.30 (d, J = 5.3 Hz, 1H), 7.34 (dd, J = 8.7, 6.1 Hz, 1H), 6.97 (d, J = 5.4 Hz, 1H), 6.83 (dd, J = 9.9, 2.8 Hz, 1H), 6.74 (td, J = 8.5, 3.0 Hz, 1H), 5.77 (d, J = 6.4 Hz, 1H), 5.71 (d, J = 6.4 Hz, 1H), 5.32 (qd, J = 6.4, 3.2 Hz, 1H), 4.76 (p, J = 7.3 Hz, 1H), 3.92 (s, 3H), 2.77 (dd, J = 10.7, 3.5 Hz, 1H), 2.34-2.20 (m, 4H), 2.08 (s, 3H), 1.99-1.86 (m, 1H), 1.74-1.30 (m, 8H), 1.30-1.16 (m, 1H), 1.10-0.99 (m, 3H), 0.84 (ddt, J = 12.2, 10.3, 5.9 Hz, 1H). $^{13}$C NMR (101 MHz, CDCl$_3$) δ 172.14, 170.25, 162.99, 160.92 (d, J = 243.9 Hz), 160.41, 145.70, 144.13, 142.50, 138.76 (d, J = 7.3 Hz), 135.17 (d, J = 3.4 Hz), 129.97 (d, J = 8.1 Hz), 116.32 (d, J = 20.7 Hz), 112.61 (d, J = 20.6 Hz), 109.63, 89.62, 73.34, 56.22, 49.52, 48.31, 42.72, 31.73, 31.70, 25.20, 24.53, 20.86, 20.61, 18.46, 17.80. $^{19}$F NMR (376 MHz, CDCl$_3$) δ -117.78. |
| 199 | | IR (thin film) 3379, 2928, 1733, 1675, 1497, 1201, 1003, 969, 911, 829, 730 cm$^{-1}$ | HRMS-ESI (m/z) [M + Na]$^+$ calcd for C$_{29}$H$_{37}$FN$_2$NaO$_7$, 567.2477; found, 567.2486 | $^1$H NMR (400 MHz, CDCl$_3$) δ 8.36 (d, J = 7.6 Hz, 1H), 8.30 (d, J = 5.4 Hz, 1H), 7.33 (dd, J = 8.7, 6.1 Hz, 1H), 6.98 (d, J = 5.5 Hz, 1H), 6.82 (dd, J = 9.9, 2.8 Hz, 1H), 6.71 (td, J = 8.5, 2.9 Hz, 1H), 5.77 (d, J = 6.4 Hz, 1H), 5.70 (d, J = 6.4 Hz, 1H), 5.43 (qd, J = 6.2, 3.8 Hz, 1H), 4.74 (p, J = 7.2 Hz, 1H), 3.92 (s, 3H), 2.72 (dd, J = 9.9, 4.0 Hz, 1H), 2.26 (s, 3H), 2.07 (s, 3H), 1.99-1.87 (m, 1H), 1.82-1.51 (m, 3H), 1.51-1.39 (m, 3H), 1.37-1.01 (m, 6H), 0.99 (d, J = 6.3 Hz, 3H), 0.84-0.67 (m, 1H). $^{13}$C NMR (101 MHz, CDCl$_3$) δ 172.12, 170.24, 162.93, 160.90 (d, J = 243.7 Hz), 160.44, 145.68, 144.17, 142.45, 139.38 (d, J = 7.2 Hz), 134.63 (d, J = 2.9 Hz), 129.67 (d, J = 8.0 Hz), 116.28 (d, J = 20.5 Hz), 112.64 (d, J = 20.5 Hz), 109.64, 89.64, 71.28, 56.22, 49.62, 48.34, 39.99, 31.31, 31.21, 26.51, 26.37, 26.27, 20.86, 20.73, 18.45, 17.94. $^{19}$F NMR (376 MHz, CDCl$_3$) δ -117.79. |
| 200 | | IR (thin film) 3383, 2969, 1772, | HRMS-ESI (m/z) [M + H]$^+$ calcd for C$_{26}$H$_{35}$N$_2$O$_6$, 471.2490; found, 471.2485 | $^1$H NMR (500 MHz, CDCl$_3$) δ 8.56 (s, 1H), 8.35 (d, J = 5.4 Hz, 1H), 7.19 (d, J = 7.9 Hz, 1H), 7.00 (d, J = 5.4 Hz, 1H), |

TABLE 2-continued

Analytical Data

| Cmpd. No. | Melting Point (° C.) | IR (cm⁻¹) | MASS SPEC | NMR |
|---|---|---|---|---|
| | | 1733, 1679, 1200, 1176 cm⁻¹ | | 6.94 (d, J = 1.9 Hz, 1H), 6.90 (dd, J = 7.9, 1.9 Hz, 1H), 5.41 (qd, J = 6.3, 4.7 Hz, 1H), 4.77-4.61 (m, 1H), 3.91 (s, 3H), 2.68 (dd, J = 9.3, 4.8 Hz, 1H), 2.39 (s, 3H), 2.27 (s, 3H), 2.25 (s, 3H), 2.03 (dp, J = 9.2, 6.6 Hz, 1H), 1.38 (d, J = 7.2 Hz, 3H), 1.05 (d, J = 6.3 Hz, 3H), 0.99 (d, J = 6.6 Hz, 3H), 0.69 (d, J = 6.8 Hz, 3H). |
| 201 | | IR (thin film) 3383, 2950, 1773, 1734, 1679, 1507, 1201, 1177 cm⁻¹ | HRMS-ESI (m/z) [M + H]⁺ calcd for $C_{28}H_{37}N_2O_6$, 497.2646; found, 497.2640 | ¹H NMR (500 MHz, CDCl$_3$) δ 8.58 (s, 1H), 8.35 (d, J = 5.5 Hz, 1H), 7.20 (d, J = 7.9 Hz, 1H), 7.01 (d, J = 5.4 Hz, 1H), 6.97-6.86 (m, 2H), 5.31 (qd, J = 6.3, 3.9 Hz, 1H), 4.78-4.64 (m, 1H), 3.91 (s, 3H), 2.79 (dd, J = 10.4, 4.1 Hz, 1H), 2.40 (s, 3H), 2.27 (s, 3H), 2.26 (s, 3H), 2.26-2.16 (m, 1H), 1.93-1.82 (m, 1H), 1.71-1.59 (m, 1H), 1.59-1.23 (m, 7H), 1.29-1.15 (m, 1H), 1.07 (d, J = 6.4 Hz, 3H), 0.92-0.83 (m, 1H). |
| 202 | | IR (thin film) 3382, 2929, 1173, 1735, 1679, 1508, 1201, 1176, 735 cm⁻¹ | HRMS-ESI (m/z) [M + Na]⁺ calcd for $C_{29}H_{38}N_2O_6Na$, 533.2622; found, 533.2615 | ¹H NMR (500 MHz, CDCl$_3$) δ 8.58 (s, 1H), 8.35 (d, J = 5.4 Hz, 1H), 7.21 (d, J = 7.8 Hz, 1H), 7.01 (d, J = 5.5 Hz, 1H), 6.96-6.88 (m, 2H), 5.42 (qd, J = 6.3, 4.5 Hz, 1H), 4.76-4.67 (m, 1H), 3.91 (s, 3H), 2.75 (dd, J = 9.4, 4.6 Hz, 1H), 2.40 (s, 3H), 2.28 (s, 3H), 2.24 (s, 3H), 1.90-1.50 (m, 5H), 1.41 (d, J = 7.2 Hz, 3H), 1.39-1.31 (m, 1H), 1.29-1.14 (m, 1H), 1.14-1.04 (m, 2H), 1.03 (d, J = 6.3 Hz, 3H), 1.01-0.86 (m, 1H), 0.84-0.73 (m, 1H). |
| 203 | | IR (thin film) 2968, 29333, 1773, 1734, 1679, 1507, 1200, 1177 cm⁻¹ | HRMS-ESI (m/z) [M + H]⁺ calcd for $C_{27}H_{37}N_2O_6$, 485.2646; found, 485.2643 | ¹H NMR (500 MHz, CDCl$_3$) δ 8.56 (s, 1H), 8.35 (dd, J = 5.4, 2.6 Hz, 1H), 7.20 (t, J = 7.2 Hz, 1H), 7.06-6.87 (m, 3H), 5.42 (dtd, J = 10.6, 6.3, 4.5 Hz, 1H), 4.77-4.62 (m, 1H), 3.91 (s, 3H), 2.88-2.68 (m, 1H), 2.39 (s, 3H), 2.29-2.24 (m, 6H), 1.94-1.53 (m, 1H), 1.46-0.62 (m, 14H). |
| 204 | | IR (thin film) 3380, 2969, 1732, 1675, 1502, 1200, 1003, 967, 829 cm⁻¹ | HRMS-ESI (m/z) [M + H]⁺ calcd for $C_{27}H_{37}N_2O_7$, 501.2595; found, 501.2589 | ¹H NMR (500 MHz, CDCl$_3$) δ 8.38 (d, J = 7.9 Hz, 1H), 8.29 (d, J = 5.4 Hz, 1H), 7.20 (d, J = 7.9 Hz, 1H), 7.00-6.87 (m, 3H), 5.80-5.69 (m, 2H), 5.42 (qd, J = 6.2, 4.7 Hz, 1H), 4.71 (p, J = 7.2 Hz, 1H), 3.91 (s, 3H), 2.69 (dd, J = 9.2, 4.9 Hz, 1H), 2.27 (s, 3H), 2.25 (s, 3H), 2.10-1.97 (m, 1H), 2.06 (s, 3H), 1.39 (d, J = 7.2 Hz, 3H), 1.07 (d, J = 6.3 Hz, 3H), 0.99 (d, J = 6.6 Hz, 3H), 0.70 (d, J = 6.7 Hz, 3H). |
| 205 | | IR (thin film) 3380, 2950, 1756, 1735, 1678, 1504, 1202, 1005 cm⁻¹ | HRMS-ESI (m/z) [M + H]⁺ calcd for $C_{29}H_{39}N_2O_7$, 527.2752; found, 527.2744 | ¹H NMR (500 MHz, CDCl$_3$) δ 8.39 (d, J = 7.9 Hz, 1H), 8.29 (d, J = 5.4 Hz, 1H), 7.21 (d, J = 7.9 Hz, 1H), 6.98-6.86 (m, 3H), 5.82-5.69 (m, 2H), 5.32 (qd, J = 6.3, 4.1 Hz, 1H), 4.73 (p, J = 7.3 Hz, 1H), 3.91 (s, 3H), 2.81 (dd, J = 10.3, 4.2 Hz, 1H), 2.27 (s, 3H), 2.27 (s, 3H), 2.25-2.19 (m, 1H), 2.07 (s, 3H), 1.95-1.82 (m, 1H), 1.69-1.60 (m, 1H), 1.57-1.34 (m, 7H), 1.29-1.15 (m, 1H), 1.08 (d, J = 6.3 Hz, 3H), 0.89 (tdd, J = 11.7, 9.4, 7.6 Hz, 1H). |
| 206 | | IR (thin film) 3380, 2963, 1756, 1735, 1678, 1504, 1202, 1005, 970 cm⁻¹ | HRMS-ESI (m/z) [M + Na]⁺ calcd for $C_{30}H_{40}N_2O_7Na$, 563.2728; found, 563.2725 | ¹H NMR (500 MHz, CDCl$_3$) δ 8.39 (d, J = 7.9 Hz, 1H), 8.29 (d, J = 5.3 Hz, 1H), 7.23 (d, J = 7.7 Hz, 1H), 6.97-6.90 (m, 3H), 5.81-5.68 (m, 2H), 5.42 (qd, J = 6.2, 4.6 Hz, 1H), 4.77-4.69 (m, 1H), 3.91 (s, 3H), 2.76 (dd, J = 9.4, 4.7 Hz, 1H), 2.28 (s, 3H), 2.24 (s, 3H), 2.06 (s, 3H), 1.91-1.51z (m, 5H), 1.42 (d, J = 7.2 Hz, 3H), 1.40-1.33 (m, 1H), 1.25-0.91 (m, 7H), 0.85-0.73 (m, 1H). |
| 207 | | IR (thin film) 3381, | HRMS-ESI (m/z) [M + H]⁺ calcd for $C_{28}H_{39}N_2O_7$, | ¹H NMR (500 MHz, CDCl$_3$) δ 8.38 (d, J = 16.9, 7.8 Hz, 1H), 8.32-8.26 (m, |

TABLE 2-continued

Analytical Data

| Cmpd. No. | Melting Point (° C.) | IR (cm⁻¹) | MASS SPEC | NMR |
|---|---|---|---|---|
| | | 2968, 2933, 1757, 1735, 1678, 1504, 1202, 1005 cm⁻¹ | 515.2752; found, 515.2746 | 1H), 7.21 (t, J = 8.3 Hz, 1H), 7.00-6.86 (m, 3H), 5.81-5.66 (m, 2H), 5.48-5.37 (m, 1H), 4.77-4.63 (m, 1H), 3.91 (s, 3H), 2.88-2.70 (m, 1H), 2.32-2.23 (m, 6H), 2.06 (s, 3H), 1.90-1.52 (m, 1H), 1.46-0.66 (m, 14H). |
| 208 | | IR (thin film) 2958, 1770, 1715, 1371, 1244, 734 cm⁻¹ | HRMS-ESI (m/z) [M + H]⁺ calcd for $C_{25}H_{31}N_2O_6$, 455.2177; found, 455.2171 | ¹H NMR (500 MHz, CDCl₃) δ 8.62 (d, J = 5.3 Hz, 1H), 7.15 (d, J = 5.4 Hz, 1H), 6.90 (d, J = 7.9 Hz, 1H), 6.87-6.83 (m, 1H), 6.32-6.24 (m, 1H), 5.65 (q, J = 7.1 Hz, 1H), 5.43 (qd, J = 6.4, 3.2 Hz, 1H), 4.05 (s, 3H), 2.53 (dd, J = 10.4, 3.2 Hz, 1H), 2.18 (s, 3H), 2.10 (s, 3H), 2.06-1.96 (m, 1H), 1.71 (d, J = 7.0 Hz, 3H), 1.04 (d, J = 6.5 Hz, 3H), 0.95 (d, J = 6.3 Hz, 3H), 0.60 (d, J = 6.6 Hz, 3H). |
| 209 | | IR (thin film) 2949, 1770, 1715, 1502, 1371, 1243 cm⁻¹ | HRMS-ESI (m/z) [M + H]⁺ calcd for $C_{27}H_{33}N_2O_6$, 481.2333; found, 481.2325 | ¹H NMR (500 MHz, CDCl₃) δ 8.62 (d, J = 5.3 Hz, 1H), 7.15 (d, J = 5.4 Hz, 1H), 6.93 (d, J = 7.9 Hz, 1H), 6.87-6.82 (m, 1H), 6.33-6.28 (m, 1H), 5.67 (q, J = 7.0 Hz, 1H), 5.29 (qd, J = 6.5, 2.9 Hz, 1H), 4.05 (s, 3H), 2.68 (dd, J = 10.9, 2.8 Hz, 1H), 2.30-2.18 (m, 4H), 2.09 (s, 3H), 1.93 (dtd, J = 11.2, 7.2, 3.4 Hz, 1H), 1.71 (d, J = 7.1 Hz, 3H), 1.68-1.05 (m, 6H), 0.98 (d, J = 6.4 Hz, 3H), 0.83-0.72 (m, 1H). |
| 210 | | IR (thin film) 2928, 1771, 1715, 1502, 1371, 1243 cm⁻¹ | HRMS-ESI (m/z) [M + H]⁺ calcd for $C_{28}H_{35}N_2O_6$, 495.2490; found, 495.2485 | ¹H NMR (500 MHz, CDCl₃) δ 8.63 (d, J = 5.3 Hz, 1H), 7.15 (d, J = 5.3 Hz, 1H), 6.90 (d, J = 7.9 Hz, 1H), 6.86-6.83 (m, 1H), 6.29-6.24 (m, 1H), 5.67 (q, J = 7.0 Hz, 1H), 5.43 (qd, J = 6.3, 3.1 Hz, 1H), 4.06 (s, 3H), 2.66-2.60 (m, 1H), 2.17 (s, 3H), 2.10 (s, 3H), 2.01-1.94 (m, 1H), 1.78-1.54 (m, 6H), 1.53-1.43 (m, 1H), 1.34-1.19 (m, 2H), 1.14-0.88 (m, 6H), 0.76-0.58 (m, 1H). |
| 211 | | IR (thin film) 2964, 1734, 1644, 1571, 1480, 1302, 1216 cm⁻¹ | HRMS-ESI (m/z) [M + H]⁺ calcd for $C_{24}H_{33}N_2O_6$, 445.2333; found, 445.2370 | ¹H NMR (500 MHz, CDCl₃) δ 14.37 (s, 1H), 12.78 (d, J = 7.0 Hz, 1H), 7.88 (d, J = 7.1 Hz, 1H), 7.15 (d, J = 7.7 Hz, 1H), 6.90 (d, J = 8.0 Hz, 2H), 6.77 (d, J = 7.2 Hz, 1H), 5.42 (qd, J = 6.3, 5.0 Hz, 1H), 4.69-4.61 (m, 1H), 3.96 (s, 3H), 2.69 (dd, J = 9.1, 5.0 Hz, 1H), 2.25 (s, 3H), 2.23 (s, 3H), 2.00 (dp, J = 8.8, 6.6 Hz, 1H), 1.44 (d, J = 7.2 Hz, 3H), 1.08 (d, J = 6.3 Hz, 3H), 0.98 (d, J = 6.6 Hz, 3H), 0.69 (d, J = 6.8 Hz, 3H). |
| 212 | | IR (thin film) 2948, 2868, 1734, 1570, 1480, 1301, 1218 cm⁻¹ | HRMS-ESI (m/z) [M + H]⁺ calcd for $C_{26}H_{35}N_2O_6$, 471.2490; found, 471.2515 | ¹H NMR (500 MHz, CDCl₃) δ 14.38 (s, 1H), 12.79 (d, J = 7.2 Hz, 1H), 7.90 (d, J = 7.1 Hz, 1H), 7.17 (d, J = 7.9 Hz, 1H), 6.96-6.85 (m, 2H), 6.77 (d, J = 7.1 Hz, 1H), 5.31 (qd, J = 6.3, 4.0 Hz, 1H), 4.72-4.60 (m, 1H), 3.96 (s, 3H), 2.80 (dd, J = 10.3, 4.2 Hz, 1H), 2.28-2.24 (m, 6H), 2.21-2.10 (m, 1H), 1.95-1.85 (m, 1H), 1.69-1.30 (m, 8H), 1.20 (dq, J = 12.3, 9.2 Hz, 1H), 1.08 (d, J = 6.3 Hz, 3H), 0.94-0.81 (m, 1H). |
| 213 | | IR (thin film) 2963, 2931, 1733, 1569, 1479, 1453, 1301, 1213, 729 cm⁻¹ | HRMS-ESI (m/z) [M + H]⁺ calcd for $C_{25}H_{35}N_2O_6$, 459.2490; found, 459.2527 | ¹H NMR (500 MHz, CDCl₃) δ 14.37 (d, J = 6.2 Hz, 1H), 12.75 (dd, J = 15.8, 7.1 Hz, 1H), 7.98-7.81 (m, 1H), 7.21-6.71 (m, 4H), 5.50-5.33 (m, 1H), 4.72-4.58 (m, 1H), 3.96 (s, 3H), 2.92-2.70 (m, 1H), 2.31-2.19 (m, 6H), 1.88-1.69 (m, 1H), 1.44 (dd, J = 48.4, 7.2 Hz, 3H), 1.25-0.58 (m, 11H). |
| 214 | | IR (thin film) 3382, 2962, 1770, 1731, 1674, 1590, 1571, 1507, 1452, | ESIMS m/z 461.1 ([M + H]⁺) | ¹H NMR (500 MHz, CDCl₃) δ 8.50 (d, J = 8.0 Hz, 1H), 8.33 (d, J = 5.4 Hz, 1H), 7.17-6.99 (m, 3H), 6.99-6.86 (m, 2H), 5.38 (dq, J = 8.2, 6.2 Hz, 1H), 4.75-4.60 (m, 1H), 3.92 (s, 3H), 2.69 (dd, J = 8.3, 6.9 Hz, 1H), 2.40 (s, 3H), 2.14-2.00 |

TABLE 2-continued

Analytical Data

| Cmpd. No. | Melting Point (° C.) | IR (cm⁻¹) | MASS SPEC | NMR |
|---|---|---|---|---|
| | | 1435, 1309, 1198, 1174, 1159, 1045, 906, 833, 803, 729 cm⁻¹ | | (m, 1H), 1.49 (d, J = 7.2 Hz, 3H), 1.08 (d, J = 6.3 Hz, 3H), 0.87 (d, J = 6.7 Hz, 3H), 0.74 (d, J = 6.7 Hz, 3H). $^{13}$C NMR (126 MHz, CDCl$_3$) δ 172.15, 168.93, 162.38, 161.69 (d, J = 244.5 Hz), 159.48, 146.65, 141.52, 137.54, 134.34 (d, J = 3.3 Hz), 131.04 (d, J = 7.7 Hz), 114.75 (d, J = 20.9 Hz), 109.77, 72.50, 56.31, 55.80, 48.17, 28.29, 21.24, 20.77, 18.75, 18.65, 17.41. |
| 215 | | IR (thin film) 3381, 2962, 1756, 1677, 1499, 1203, 1044, 1004, 971, 830 cm⁻¹ | HRMS-ESI (m/z) [M + H]⁺ calcd for C$_{26}$H$_{34}$FN$_2$O$_7$, 505.2345; found, 505.2345 | $^1$H NMR (400 MHz, CDCl$_3$) δ 8.34 (d, J = 7.8 Hz, 1H), 8.28 (d, J = 5.3 Hz, 1H), 7.05 (dd, J = 8.5, 5.9 Hz, 1H), 6.96 (d, J = 5.4 Hz, 1H), 6.91-6.77 (m, 2H), 5.75 (s, 2H), 5.36 (dq, J = 9.0, 6.2 Hz, 1H), 4.72 (p, J = 7.2 Hz, 1H), 3.92 (s, 3H), 3.09 (dd, J = 9.0, 6.4 Hz, 1H), 2.30 (s, 3H), 2.13 (q, J = 6.8 Hz, 1H), 2.08 (s, 3H), 1.52 (d, J = 7.2 Hz, 3H), 1.07 (d, J = 6.3 Hz, 3H), 0.86 (d, J = 6.7 Hz, 3H), 0.78 (d, J = 6.8 Hz, 3H). $^{13}$C NMR (101 MHz, CDCl$_3$) δ 172.35, 170.26, 162.95, 160.94 (d, J = 244.4 Hz), 160.33, 145.69, 144.07, 142.53, 139.88 (d, J = 7.3 Hz), 133.64 (d, J = 3.0 Hz), 129.16 (d, J = 6.0 Hz), 116.96 (d, J = 20.5 Hz), 112.34 (d, J = 20.7 Hz), 109.59, 89.61, 73.75, 56.20, 48.43, 29.70, 29.30, 20.92, 20.87, 18.88, 18.44, 17.99. $^{19}$F NMR (376 MHz, CDCl$_3$) δ −117.40. |
| 216 | | IR (thin film) 3382, 2971, 1733, 1678, 1499, 1210, 1153, 1123, 1045, 731 cm⁻¹ | HRMS-ESI (m/z) [M + H]⁺ calcd for C$_{27}$H$_{36}$FN$_2$O$_6$, 503.2552; found, 503.2553 | $^1$H NMR (400 MHz, CDCl$_3$) δ 8.45 (d, J = 7.7 Hz, 1H), 8.32 (d, J = 5.4 Hz, 1H), 7.05 (dd, J = 8.6, 5.9 Hz, 1H), 6.99 (d, J = 5.4 Hz, 1H), 6.90-6.73 (m, 2H), 5.35 (dq, J = 8.9, 6.2 Hz, 1H), 4.78-4.64 (m, 1H), 3.90 (s, 3H), 3.08 (dd, J = 8.9, 6.5 Hz, 1H), 2.95 (p, J = 7.0 Hz, 1H), 2.29 (s, 3H), 2.11 (h, J = 6.7 Hz, 1H), 1.49 (d, J = 7.2 Hz, 3H), 1.37 (s, 3H), 1.35 (s, 3H), 1.06 (d, J = 6.2 Hz, 3H), 0.86 (d, J = 6.8 Hz, 3H), 0.77 (d, J = 6.8 Hz, 3H). $^{13}$C NMR (101 MHz, CDCl$_3$) δ 174.67, 172.31, 162.33, 160.93 (d, J = 244.3 Hz), 159.48, 146.54, 141.94, 139.89 (d, J = 7.3 Hz), 137.73, 133.69 (d, J = 2.9 Hz), 129.15 (d, J = 7.1 Hz), 116.95 (d, J = 20.5 Hz), 112.31 (d, J = 20.7 Hz), 109.62, 73.70, 56.30, 48.19, 33.97, 29.70, 20.93, 20.90, 20.89, 18.95, 18.82, 18.62, 17.90. $^{19}$F NMR (376 MHz, CDCl$_3$) δ −117.44. |
| 217 | | IR thin film) 2960, 1714, 1500, 1371, 1243, 1083, 731 cm⁻¹ | HRMS-ESI (m/z) [M + H]⁺ calcd for C$_{24}$H$_{28}$FN$_2$O$_6$, 459.1926; found, 459.1926 | $^1$H NMR (400 MHz, CDCl$_3$) δ 8.60 (d, J = 5.3 Hz, 1H), 7.14 (d, J = 5.3 Hz, 1H), 6.97 (dd, J = 8.7, 6.0 Hz, 1H), 6.62 (td, J = 8.5, 2.9 Hz, 1H), 6.23 (dd, J = 10.0, 2.8 Hz, 1H), 5.49 (q, J = 7.0 Hz, 1H), 5.34 (p, J = 6.3 Hz, 1H), 4.07 (s, 3H), 2.87 (dd, J = 9.9, 6.1 Hz, 1H), 2.12 (s, 3H), 1.95 (dp, J = 9.8, 6.6 Hz, 1H), 1.63 (d, J = 7.0 Hz, 3H), 1.15 (d, J = 6.3 Hz, 3H), 1.00 (d, J = 6.5 Hz, 3H), 0.63 (d, J = 6.6 Hz, 3H). $^{19}$F NMR (376 MHz, CDCl$_3$) δ −117.44, −117.49. |
| 218 | | IR (thin film) 2962, 1736, 1533, 1481, 1302, 1241, 1155, 1030, 953, 815, 758 cm⁻¹ | HRMS-ESI (m/z) [M + H]⁺ calcd for C$_{23}$H$_{30}$FN$_2$O$_6$, 449.2082; found, 449.2085 | $^1$H NMR (400 MHz, CDCl$_3$) δ 14.33 (s, 1H), 12.78 (d, J = 7.0 Hz, 1H), 7.88 (d, J = 7.2 Hz, 1H), 7.05 (dd, J = 8.3, 5.9 Hz, 1H), 6.88-6.75 (m, 3H), 5.37 (dq, J = 8.9, 6.3 Hz, 1H), 4.66 (p, J = 7.1 Hz, 1H), 3.98 (s, 3H), 3.08 (dd, J = 9.0, 6.5 Hz, 1H), 2.30 (s, 3H), 2.09 (hept, J = 6.9 Hz, 1H), 1.57 (d, J = 7.2 Hz, 3H), |

TABLE 2-continued

Analytical Data

| Cmpd. No. | Melting Point (° C.) | IR (cm⁻¹) | MASS SPEC | NMR |
|---|---|---|---|---|
| | | | | 1.07 (d, J = 6.2 Hz, 3H), 0.85 (d, J = 6.8 Hz, 3H), 0.77 (d, J = 6.8 Hz, 3H). $^{13}$C NMR (101 MHz, CDCl$_3$) δ 171.09, 165.57, 160.90 (d, J = 244.3 Hz), 152.59, 149.34, 139.86 (d, J = 7.3 Hz), 133.66 (d, J = 3.1 Hz), 130.96, 129.20 (d, J = 7.4 Hz), 123.74, 116.84 (d, J = 20.5 Hz), 112.33 (d, J = 20.8 Hz), 107.74, 73.95, 56.55, 48.90, 29.73, 29.30, 20.93, 20.92, 18.96, 17.83, 17.59. $^{19}$F NMR (376 MHz, CDCl$_3$) δ −117.36. |
| 219 | | IR (thin film) 3281, 2962, 1770, 1733, 1498, 1192, 1175, 1104, 821, 730 cm⁻¹ | ESIMS m/z 491.2 ([M + H]⁺) | $^1$H NMR (400 MHz, CDCl$_3$) δ 9.94 (d, J = 7.5 Hz, 1H), 8.32 (d, J = 5.4 Hz, 1H), 7.05 (dd, J = 8.4, 5.9 Hz, 1H), 7.00 (d, J = 5.5 Hz, 1H), 6.90-6.80 (m, 2H), 5.39 (dq, J = 9.1, 6.3 Hz, 1H), 5.18 (p, J = 7.1 Hz, 1H), 3.91 (s, 3H), 3.10 (dd, J = 9.1, 6.3 Hz, 1H), 2.36 (s, 3H), 2.30 (s, 3H), 2.19-2.09 (m, 1H), 1.60 (d, J = 7.1 Hz, 3H), 1.08 (d, J = 6.2 Hz, 3H), 0.86 (d, J = 6.7 Hz, 3H), 0.79 (d, J = 6.8 Hz, 3H). $^{13}$C NMR (101 MHz, CDCl$_3$) δ 189.28, 171.51, 168.58, 160.96 (d, J = 244.5 Hz), 159.87, 146.29, 145.03, 139.87 (d, J = 7.4 Hz), 136.90, 133.53 (d, J = 2.9 Hz), 129.16 (d, J = 6.9 Hz), 117.00 (d, J = 20.5 Hz), 112.38 (d, J = 20.7 Hz), 109.27, 74.11, 56.43, 53.08, 29.66, 29.29, 21.26, 20.94, 20.91, 18.78, 18.10, 16.84. $^{19}$F NMR (376 MHz, CDCl$_3$) δ −117.27. |
| 220 | | IR (thin film) 3382, 2961, 1732, 1676, 1499, 1151, 1110, 1049, 730 cm⁻¹ | HRMS-ESI (m/z) [M + H]⁺ calcd for C$_{27}$H$_{36}$FN$_2$O$_7$, 519.2501; found, 519.2497 | $^1$H NMR (400 MHz, CDCl$_3$) δ 8.49 (d, J = 7.9 Hz, 1H), 8.32 (d, J = 5.4 Hz, 1H), 7.05 (dd, J = 8.6, 5.9 Hz, 1H), 7.01 (d, J = 5.5 Hz, 1H), 6.89-6.77 (m, 2H), 5.36 (dp, J = 8.9, 6.2 Hz, 1H), 4.74-4.64 (m, 1H), 3.91 (s, 3H), 3.81 (t, J = 6.6 Hz, 2H), 3.41 (s, 3H), 3.08 (dd, J = 8.9, 6.5 Hz, 1H), 2.99 (t, J = 6.6 Hz, 2H), 2.29 (s, 3H), 2.11 (h, J = 6.7 Hz, 1H), 1.49 (d, J = 7.1 Hz, 3H), 1.06 (d, J = 6.3 Hz, 3H), 0.86 (d, J = 6.8 Hz, 3H), 0.77 (d, J = 6.8 Hz, 3H). $^{13}$C NMR (101 MHz, CDCl$_3$) δ 172.23, 169.40, 162.30, 160.93 (d, J = 244.3 Hz), 159.51, 146.69, 141.58, 139.89 (d, J = 7.4 Hz), 137.41, 133.65 (d, J = 3.2 Hz), 129.15 (d, J = 9.6 Hz), 116.96 (d, J = 20.5 Hz), 112.32 (d, J = 20.8 Hz), 109.77, 73.74, 67.62, 58.76, 56.33, 48.22, 34.67, 29.70, 20.93, 20.90, 18.95, 18.58, 17.90. $^{19}$F NMR (376 MHz, CDCl$_3$) δ −117.42. |
| 221 | | IR (thin film) 3375, 2964, 1771, 1676, 1502, 1193, 1035, 953, 832 cm⁻¹ | HRMS-ESI (m/z) [M + H]⁺ calcd for C$_{25}$H$_{32}$FN$_2$O$_7$, 491.2188; found, 491.2184 | $^1$H NMR (400 MHz, CDCl$_3$) δ 8.53 (s, 1H), 8.35 (d, J = 5.4 Hz, 1H), 7.21 (dd, J = 8.5, 6.9 Hz, 1H), 7.01 (d, J = 5.4 Hz, 1H), 6.62-6.48 (m, 2H), 5.46-5.37 (m, 1H), 4.74-4.64 (m, 1H), 3.91 (s, 3H), 3.77 (s, 3H), 3.04 (dd, J = 9.5, 4.8 Hz, 1H), 2.39 (s, 3H), 1.61 (s, 1H), 1.39 (d, J = 7.2 Hz, 3H), 1.03 (d, J = 6.3 Hz, 3H), 0.97 (d, J = 6.6 Hz, 3H), 0.67 (d, J = 6.7 Hz, 3H). $^{19}$F NMR (376 MHz, CDCl$_3$) δ −114.24. |
| 222 | | IR (thin film) 3379, 2963, 1772, 1733, 1677, 1502, 1194, 1177, 1036, 954, 834 cm⁻¹ | HRMS-ESI (m/z) [M + H]⁺ calcd for C$_{27}$H$_{36}$FN$_2$O$_7$, 519.2501; found, 519.2499 | $^1$H NMR (400 MHz, CDCl$_3$) δ 8.54 (s, 1H), 8.35 (d, J = 5.5 Hz, 1H), 7.23 (dd, J = 8.5, 6.9 Hz, 1H), 7.01 (d, J = 5.5 Hz, 1H), 6.60-6.49 (m, 2H), 5.43-5.33 (m, 1H), 4.75-4.65 (m, 1H), 3.91 (s, 3H), 3.77 (s, 3H), 3.30 (dd, J = 10.0, 4.4 Hz, 1H), 2.39 (s, 3H), 1.77-1.59 (m, 2H), 1.51-1.39 (m, 3H), 1.33 (dq, J = 14.4, 7.2 Hz, 1H), 1.19 (dtd, J = |

TABLE 2-continued

Analytical Data

| Cmpd. No. | Melting Point (° C.) | IR (cm$^{-1}$) | MASS SPEC | NMR |
|---|---|---|---|---|
| | | | | 14.9, 7.5, 3.3 Hz, 1H), 1.01 (d, J = 6.2 Hz, 3H), 0.99-0.91 (m, 1H), 0.88 (t, J = 7.4 Hz, 3H), 0.67 (t, J = 7.4 Hz, 3H). |
| 223 | | IR (thin film) 3381, 2929, 1771, 1731, 1675, 1501, 1193, 1175, 953, 731 cm$^{-1}$ | HRMS-ESI (m/z) [M + H]$^+$ calcd for C$_{28}$H$_{36}$FN$_2$O$_7$, 531.2501; found, 531.2496 | $^{19}$F NMR (376 MHz, CDCl$_3$) δ −114.23.<br>$^1$H NMR (400 MHz, CDCl$_3$) δ 8.54 (d, J = 7.8 Hz, 1H), 8.35 (d, J = 5.4 Hz, 1H), 7.22 (t, J = 7.7 Hz, 1H), 7.01 (d, J = 5.4 Hz, 1H), 6.56 (ddd, J = 9.5, 7.3, 4.1 Hz, 2H), 5.42 (t, J = 5.8 Hz, 1H), 4.70 (p, J = 7.3 Hz, 1H), 3.91 (s, 3H), 3.76 (s, 3H), 3.11 (s, 1H), 2.40 (s, 3H), 1.78 (dd, J = 46.1, 13.0 Hz, 2H), 1.59 (dd, J = 20.5, 8.6 Hz, 3H), 1.42 (dd, J = 11.2, 7.1 Hz, 3H), 1.37-0.85 (m, 8H), 0.83-0.67 (m, 1H). |
| 224 | | IR (thin film) 3382, 2946, 1771, 1731, 1675, 1501, 1192, 1176, 1149, 951, 731 cm$^{-1}$ | HRMS-ESI (m/z) [M + H]$^+$ calcd for C$_{27}$H$_{34}$FN$_2$O$_7$, 517.2345; found, 517.2341 | $^{19}$F NMR (376 MHz, CDCl$_3$) δ −114.25.<br>$^1$H NMR (400 MHz, CDCl$_3$) δ 8.55 (s, 1H), 8.35 (d, J = 5.4 Hz, 1H), 7.23 (t, J = 7.7 Hz, 1H), 7.02 (d, J = 5.4 Hz, 1H), 6.57 (dd, J = 11.1, 2.6 Hz, 1H), 6.50 (td, J = 8.4, 2.5 Hz, 1H), 5.32 (dt, J = 10.1, 5.0 Hz, 1H), 4.72 (p, J = 7.2 Hz, 1H), 3.92 (s, 3H), 3.77 (s, 3H), 3.11 (d, J = 10.7 Hz, 1H), 2.40 (s, 3H), 2.22-2.06 (m, 1H), 1.86 (dtd, J = 11.2, 6.9, 3.4 Hz, 1H), 1.71-1.59 (m, 2H), 1.59-1.29 (m, 5H), 1.29-1.16 (m, 2H), 1.02 (d, J = 6.3 Hz, 3H), 0.88 (dq, J = 11.9, 8.4, 8.0 Hz, 1H). |
| 225 | | IR (thin film) 3378, 2964, 1771, 1731, 1675, 1501, 1193, 1175, 1035, 952, 833, 732 cm$^{-1}$ | HRMS-ESI (m/z) [M + H]$^+$ calcd for C$_{26}$H$_{34}$FN$_2$O$_7$, 505.2345; found, 505.2341 | $^{19}$F NMR (376 MHz, CDCl$_3$) δ −114.34.<br>$^1$H NMR (400 MHz, CDCl$_3$) δ 8.52 (s, 1H), 8.34 (dd, J = 5.5, 3.2 Hz, 1H), 7.21 (ddd, J = 11.8, 8.4, 6.9 Hz, 1H), 7.01 (dd, J = 5.5, 3.5 Hz, 1H), 6.55 (dddt, J = 13.6, 8.1, 5.3, 2.7 Hz, 2H), 5.48-5.36 (m, 1H), 4.75-4.58 (m, 1H), 3.94-3.87 (m, 3H), 3.77 (d, J = 1.1 Hz, 3H), 3.16 (ddd, J = 47.2, 9.4, 4.9 Hz, 1H), 2.39 (d, J = 2.9 Hz, 3H), 1.86-1.71 (m, 1H), 1.61-1.36 (m, 2H), 1.34-1.21 (m, 3H), 1.11-0.93 (m, 4H), 0.89 (td, J = 7.3, 3.6 Hz, 2H), 0.75-0.61 (m, 3H). |
| 226 | | IR (thin film) 3379, 2938, 1771, 1731, 1675, 1502, 1193, 1176, 1035, 953, 733 cm$^{-1}$ | HRMS-ESI (m/z) [M + H]$^+$ calcd for C$_{26}$H$_{32}$FN$_2$O$_7$, 503.2188; found, 503.2181 | $^{19}$F NMR (376 MHz, CDCl$_3$) δ −114.21, −114.28.<br>$^1$H NMR (400 MHz, CDCl$_3$) δ 8.47 (s, 1H), 8.33 (d, J = 5.4 Hz, 1H), 7.06 (dd, J = 8.5, 6.8 Hz, 1H), 7.01 (d, J = 5.4 Hz, 1H), 6.55 (dd, J = 11.0, 2.6 Hz, 1H), 6.48 (td, J = 8.3, 2.5 Hz, 1H), 5.21 (q, J = 6.1 Hz, 1H), 4.62 (p, J = 7.3 Hz, 1H), 3.91 (s, 3H), 3.78 (s, 3H), 3.25 (s, 1H), 2.65 (d, J = 14.9 Hz, 1H), 2.40 (s, 3H), 2.15-2.06 (m, 1H), 1.87-1.58 (m, 4H), 1.43 (dt, J = 17.2, 8.4 Hz, 1H), 1.30 (d, J = 7.1 Hz, 3H), 1.11 (d, J = 6.3 Hz, 3H). |
| 227 | | IR (thin film) 3381, 2927, 1770, 1732, 1675, 1502, 1192, 1175, 1034, 953, 908, 730 cm$^{-1}$ | HRMS-ESI (m/z) [M + H]$^+$ calcd for C$_{28}$H$_{36}$FN$_2$O$_7$, 531.2501; found, 531.2493 | $^{19}$F NMR (376 MHz, CDCl$_3$) δ −114.16.<br>$^1$H NMR (400 MHz, CDCl$_3$) δ 8.54 (d, J = 7.8 Hz, 1H), 8.31 (d, J = 5.4 Hz, 1H), 7.00 (q, J = 4.9 Hz, 2H), 6.60 (td, J = 8.3, 2.5 Hz, 1H), 6.53 (dd, J = 11.0, 2.5 Hz, 1H), 5.54-5.31 (m, 1H), 4.78-4.63 (m, 1H), 3.91 (s, 3H), 3.73 (s, 3H), 3.47 (d, J = 69.3 Hz, 1H), 2.40 (s, 3H), 1.81-1.51 (m, 5H), 1.49 (d, J = 7.1 Hz, 3H), 1.37-1.08 (m, 2H), 1.08-1.04 (m, 4H), 1.04-0.70 (m, 3H). |
| 228 | | IR (thin film) 3379, 2944, 1770, 1732, 1675, 1502, 1192, 1176, 1149, 1033, 952, | HRMS-ESI (m/z) [M + H]$^+$ calcd for C$_{27}$H$_{34}$FN$_2$O$_7$, 517.2345; found, 517.2333 | $^{19}$F NMR (376 MHz, CDCl$_3$) δ −114.00.<br>$^1$H NMR (400 MHz, CDCl$_3$) δ 8.50 (s, 1H), 8.28 (d, J = 5.4 Hz, 1H), 7.05 (t, J = 7.7 Hz, 1H), 7.00 (d, J = 5.5 Hz, 1H), 6.58 (td, J = 8.2, 2.5 Hz, 1H), 6.49 (dd, J = 11.1, 2.5 Hz, 1H), 5.32 (s, 1H), 4.71-4.59 (m, 1H), 3.91 (s, 3H), 3.71 (s, 3H), 3.48 (d, J = 40.6 Hz, 1H), 2.40 (s, 3H), |

TABLE 2-continued

Analytical Data

| Cmpd. No. | Melting Point (° C.) | IR (cm⁻¹) | MASS SPEC | NMR |
|---|---|---|---|---|
| | | 732 cm⁻¹ | | 2.18 (s, 1H), 1.92-1.78 (m, 1H), 1.63 (s, 1H), 1.56-1.34 (m, 6H), 1.34-1.20 (m, 2H), 1.11 (d, J = 6.4 Hz, 3H), 0.89 (td, J = 9.3, 8.3, 3.7 Hz, 1H). $^{19}$F NMR (376 MHz, CDCl$_3$) δ −114.18. |
| 229 | | IR (thin film) 2963, 1772, 1733, 1677, 1503, 1194, 1177, 1035, 954 cm⁻¹ | HRMS-ESI (m/z) [M + H]⁺ calcd for C$_{27}$H$_{36}$FN$_2$O$_7$, 519.2501; found, 519.2499 | $^1$H NMR (400 MHz, CDCl$_3$) δ 8.53 (s, 1H), 8.30 (d, J = 5.4 Hz, 1H), 7.09-6.97 (m, 2H), 6.58 (td, J = 8.2, 2.5 Hz, 1H), 6.51 (dd, J = 11.0, 2.6 Hz, 1H), 5.49-5.37 (m, 1H), 4.74-4.63 (m, 1H), 3.91 (s, 3H), 3.73 (s, 3H), 3.58 (s, 1H), 2.40 (s, 3H), 1.61 (d, J = 18.5 Hz, 1H), 1.48 (d, J = 7.1 Hz, 3H), 1.45-1.28 (m, 2H), 1.27-1.12 (m, 1H), 1.09 (d, J = 6.2 Hz, 3H), 1.00-0.83 (m, 4H), 0.74 (t, J = 7.3 Hz, 3H). $^{19}$F NMR (376 MHz, CDCl$_3$) δ −113.98. |
| 230 | | IR (thin film) 2964, 1770, 1732, 1675, 1502, 1193, 1175, 1034, 953, 834, 731 cm⁻¹ | HRMS-ESI (m/z) [M + H]⁺ calcd for C$_{26}$H$_{34}$FN$_2$O$_7$, 505.2345; found, 505.2333 | $^1$H NMR (400 MHz, CDCl$_3$) δ 8.55 (s, 1H), 8.31 (dd, J = 8.1, 5.4 Hz, 1H), 7.08-6.97 (m, 2H), 6.65-6.55 (m, 1H), 6.55-6.48 (m, 1H), 5.45 (d, J = 11.2 Hz, 1H), 4.69 (ddd, J = 14.1, 8.0, 7.1 Hz, 1H), 3.91 (s, 3H), 3.74 (d, J = 9.6 Hz, 3H), 3.51 (d, J = 44.9 Hz, 1H), 2.40 (d, J = 1.8 Hz, 3H), 1.90-1.58 (m, 1H), 1.55-1.44 (m, 3H), 1.41-1.26 (m, 1H), 1.07 (dd, J = 11.1, 6.2 Hz, 3H), 0.99-0.80 (m, 4H), 0.75 (t, J = 7.4 Hz, 3H). $^{19}$F NMR (376 MHz, CDCl$_3$) δ −113.91, −114.00. |
| 231 | | IR (thin film) 3381, 2939, 1770, 1731, 1674, 1502, 1193, 1175, 1148, 1035, 953, 731 cm⁻¹ | HRMS-ESI (m/z) [M + H]⁺ calcd for C$_{26}$H$_{32}$FN$_2$O$_7$, 503.2188; found, 503.2173 | $^1$H NMR (400 MHz, CDCl$_3$) δ 8.51 (d, J = 7.6 Hz, 1H), 8.31 (d, J = 5.4 Hz, 1H), 7.02-6.94 (m, 2H), 6.65-6.49 (m, 2H), 5.16 (s, 1H), 4.73-4.59 (m, 1H), 3.91 (s, 3H), 3.77 (s, 3H), 3.33 (s, 1H), 2.78 (hept, J = 8.6, 7.8 Hz, 1H), 2.40 (s, 3H), 2.17-2.04 (m, 1H), 1.97-1.56 (m, 4H), 1.45 (d, J = 7.1 Hz, 3H), 1.43-1.36 (m, 1H), 1.08 (d, J = 6.4 Hz, 3H). $^{19}$F NMR (376 MHz, CDCl$_3$) δ −113.98. |
| 232 | | IR (thin film) 3379, 2962, 1770, 1732, 1674, 1502, 1192, 1175, 1150, 1034, 953, 731 cm⁻¹ | HRMS-ESI (m/z) [M + H]⁺ calcd for C$_{25}$H$_{32}$FN$_2$O$_7$, 491.2188; found, 491.2179 | $^1$H NMR (400 MHz, CDCl$_3$) δ 8.54 (d, J = 7.3 Hz, 1H), 8.31 (d, J = 5.4 Hz, 1H), 7.05-6.97 (m, 2H), 6.60 (td, J = 8.3, 2.6 Hz, 1H), 6.54 (dd, J = 11.1, 2.5 Hz, 1H), 5.48-5.31 (m, 1H), 4.77-4.64 (m, 1H), 3.91 (s, 3H), 3.74 (s, 3H), 3.33 (s, 1H), 2.40 (s, 3H), 2.14-2.01 (m, 1H), 1.66 (s, 1H), 1.49 (d, J = 7.1 Hz, 2H), 1.07 (d, J = 6.2 Hz, 3H), 0.85 (d, J = 6.7 Hz, 3H), 0.72 (d, J = 6.8 Hz, 3H). $^{19}$F NMR (376 MHz, CDCl$_3$) δ −113.95. |
| 233 | | IR (thin film) 3381, 2928, 1733, 1675, 1501, 1201, 1004, 953, 831, 730 cm⁻¹ | HRMS-ESI (m/z) [M + H]⁺ calcd for C$_{29}$H$_{38}$FN$_2$O$_8$, 561.2607; found, 561.2602 | $^1$H NMR (400 MHz, CDCl$_3$) δ 8.36 (d, J = 7.9 Hz, 1H), 8.29 (d, J = 5.4 Hz, 1H), 7.26-7.22 (m, 1H), 6.96 (d, J = 5.4 Hz, 1H), 6.61-6.52 (m, 2H), 5.78-5.72 (m, 2H), 5.42 (q, J = 5.9 Hz, 1H), 4.72 (p, J = 7.1 Hz, 1H), 3.91 (s, 3H), 3.77 (s, 3H), 3.13 (s, 1H), 2.07 (s, 3H), 1.89-1.51 (m, 7H), 1.42 (d, J = 7.1 Hz, 3H), 1.37-1.05 (m, 3H), 1.03 (d, J = 6.2 Hz, 2H), 1.01-0.68 (m, 2H). $^{19}$F NMR (376 MHz, CDCl$_3$) δ −114.24. |
| 234 | | IR (thin film) 3381, 2948, 1732, 1674, 1501, 1200, 1004, 951, 831 cm⁻¹ | HRMS-ESI (m/z) [M + H]⁺ calcd for C$_{28}$H$_{36}$FN$_2$O$_8$, 547.2450; found, 547.2445 | $^1$H NMR (400 MHz, CDCl$_3$) δ 8.37 (d, J = 7.9 Hz, 1H), 8.29 (d, J = 5.4 Hz, 1H), 7.28-7.21 (m, 1H), 6.96 (d, J = 5.4 Hz, 1H), 6.57 (dd, J = 11.1, 2.5 Hz, 1H), 6.52 (td, J = 8.4, 2.5 Hz, 1H), 5.81-5.71 (m, 2H), 5.33 (qd, J = 6.4, 3.8 Hz, 1H), 4.73 (p, J = 7.2 Hz, 1H), 3.92 (s, 3H), 3.77 (s, 3H), 3.12 (d, J = 10.4 Hz, 1H), 2.18 (s, 1H), 2.07 (s, 3H), 1.98-1.80 (m, 1H), 1.64 (d, J = 6.5 Hz, 2H), 1.58-1.29 (m, 5H), 1.29-1.15 (m, 2H), 1.02 (dd, J = 14.6, 6.3 Hz, |

TABLE 2-continued

Analytical Data

| Cmpd. No. | Melting Point (° C.) | IR (cm$^{-1}$) | MASS SPEC | NMR |
|---|---|---|---|---|
| 235 | | IR (thin film) 3379, 2945, 1733, 1674, 1501, 1200, 1035, 1003, 953, 831, 731 cm$^{-1}$ | HRMS-ESI (m/z) [M + H]$^+$ calcd for C$_{28}$H$_{36}$FN$_2$O$_8$, 547.2450; found, 547.2444 | 3H), 0.94-0.83 (m, 1H). $^{19}$F NMR (376 MHz, CDCl$_3$) δ −114.31. $^1$H NMR (400 MHz, CDCl$_3$) δ 8.32 (d, J = 7.8 Hz, 1H), 8.25 (d, J = 5.4 Hz, 1H), 7.05 (t, J = 7.7 Hz, 1H), 6.95 (d, J = 5.4 Hz, 1H), 6.59 (td, J = 8.2, 2.5 Hz, 1H), 6.50 (dd, J = 11.1, 2.5 Hz, 1H), 5.74 (s, 2H), 5.32 (s, 1H), 4.68 (p, J = 7.2 Hz, 1H), 3.91 (s, 3H) 3.73 (s, 3H), 3.49 (d, J = 46.2 Hz, 1H), 2.07 (s, 3H), 1.90-1.78 (m, 1H), 1.63 (d, J = 24.2 Hz, 1H), 1.55-1.31 (m, 8H), 1.31-1.19 (m, 1H), 1.12 (d, J = 6.4 Hz, 3H), 0.90 (td, J = 9.4, 8.3, 3.6 Hz, 1H). |
| 236 | | IR (thin film) 3381, 2939, 1733, 1674, 1501, 1200, 1147, 1037, 1003, 953, 831, 731 cm$^{-1}$ | HRMS-ESI (m/z) [M + H]$^+$ calcd for C$_{27}$H$_{34}$FN$_2$O$_8$, 533.2294; found, 533.2286 | $^{19}$F NMR (376 MHz, CDCl$_3$) δ −114.15. $^1$H NMR (400 MHz, CDCl$_3$) δ 8.33 (d, J = 7.9 Hz, 1H), 8.27 (d, J = 5.4 Hz, 1H), 7.02-6.92 (m, 2H), 6.60-6.47 (m, 2H), 5.80-5.70 (m, 2H), 5.16 (s, 1H), 4.78-4.63 (m, 1H), 3.91 (s, 3H), 3.78 (s, 3H), 3.34 (s, 3H), 2.79 (h, J = 8.6 Hz, 1H), 2.20-2.09 (m, 1H), 2.07 (s, 3H), 1.99-1.57 (m, 4H), 1.48 (dd, J = 7.1, 3.0 Hz, 3H), 1.45-1.37 (m, 1H), 1.09 (d, J = 6.4 Hz, 3H). |
| 237 | | IR (thin film) 3379, 2962, 1733, 1674, 1501, 1200, 1036, 1003, 953, 831, 731 cm$^{-1}$ | HRMS-ESI (m/z) [M + H]$^+$ calcd for C$_{26}$H$_{34}$FN$_2$O$_8$, 521.2294; found, 521.2284 | $^{19}$F NMR (376 MHz, CDCl$_3$) δ −113.97. $^1$H NMR (400 MHz, CDCl$_3$) δ 8.36 (d, J = 7.8 Hz, 1H), 8.27 (d, J = 5.3 Hz, 1H), 7.01 (dd, J = 8.5, 6.8 Hz, 1H), 6.95 (d, J = 5.4 Hz, 1H), 6.60 (td, J = 8.3, 2.5 Hz, 1H), 6.55 (dd, J = 11.1, 2.5 Hz, 1H), 5.75 (s, 2H), 5.56-5.31 (m, 1H), 4.71 (p, J = 7.3 Hz, 1H), 3.92 (s, 3H), 3.75 (s, 3H), 3.34 (s, 1H), 2.07 (s, 3H), 1.67 (s, 1H), 1.51 (d, J = 7.1 Hz, 3H), 1.08 (d, J = 6.3 Hz, 3H), 0.85 (d, J = 6.8 Hz, 3H), 0.73 (d, J = 6.8 Hz, 3H). |
| 238 | | IR (thin film) 3380, 2937, 1768, 1732, 1675, 1502, 1146, 1110, 1035, 953, 833, 731 cm$^{-1}$ | HRMS-ESI (m/z) [M + H]$^+$ calcd for C$_{28}$H$_{36}$FN$_2$O$_8$, 547.2450; found, 547.2439 | $^{19}$F NMR (376 MHz, CDCl$_3$) δ −113.93. $^1$H NMR (400 MHz, CDCl$_3$) δ 8.49 (s, 1H), 8.31 (d, J = 5.4 Hz, 1H), 6.98 (dd, J = 15.2, 6.2 Hz, 2H), 6.61-6.46 (m, 2H), 5.16 (s, 1H), 4.70-4.59 (m, 1H), 3.90 (s, 3H), 3.82 (t, J = 6.6 Hz, 2H), 3.77 (s, 3H), 3.41 (s, 3H), 3.37-3.23 (m, 1H), 2.99 (t, J = 6.7 Hz, 2H), 2.77 (h, J = 8.8, 8.4 Hz, 1H), 2.16-2.05 (m, 1H), 1.97-1.55 (m, 5H), 1.44 (d, J = 7.2 Hz, 3H), 1.08 (d, J = 6.4 Hz, 3H). |
| 239 | | IR (thin film) 3377, 2961, 1768, 1675, 1502, 1310, 1148, 1112, 1034, 953, 833, 732 cm$^{-1}$ | HRMS-ESI (m/z) [M + H]$^+$ calcd for C$_{27}$H$_{36}$FN$_2$O$_8$, 535.2450; found, 535.2441 | $^{19}$F NMR (376 MHz, CDCl$_3$) δ −113.97. $^1$H NMR (400 MHz, CDCl$_3$) δ 8.52 (s, 1H), 8.31 (d, J = 5.4 Hz, 1H), 7.07-6.97 (m, 2H), 6.60 (td, J = 8.3, 2.6 Hz, 1H), 6.54 (dd, J = 11.0, 2.5 Hz, 1H), 5.49-5.35 (m, 1H), 4.72-4.60 (m, 1H), 3.90 (s, 3H), 3.81 (t, J = 6.6 Hz, 2H), 3.74 (s, 3H), 3.41 (s, 3H), 3.28 (d, J = 41.3 Hz, 1H), 2.99 (t, J = 6.6 Hz, 2H), 2.08 (dp, J = 13.6, 7.0 Hz, 1H), 1.48 (d, J = 7.1 Hz, 3H), 1.07 (d, J = 6.2 Hz, 3H), 0.85 (d, J = 6.7 Hz, 3H), 0.72 (d, J = 6.9 Hz, 3H). |
| 240 | | IR (thin film) 1733, 1674, 1503, 1201, 1003, 968, 911, 729 cm$^{-1}$ | HRMS-ESI (m/z) [M + H]$^+$ calcd for C$_{28}$H$_{37}$N$_2$O$_7$, 513.2595; found, 513.2591 | $^{19}$F NMR (376 MHz, CDCl$_3$) δ −113.94. $^1$H NMR (500 MHz, CDCl$_3$) δ 8.35-8.23 (m, 2H), 7.02 (d, J = 7.9 Hz, 1H), 6.95-6.84 (m, 3H), 5.79-5.68 (m, 2H), 5.20-5.08 (m, 1H), 4.66-4.55 (m, 1H), 3.90 (s, 3H), 3.04 (dd, J = 10.5, 6.3 Hz, 1H), 2.70 (dh, J = 16.8, 8.8, 8.2 Hz, 1H), 2.32 (s, 3H), 2.24 (s, 3H), 2.19-2.10 (m, 1H), 2.06 (s, 3H), 1.89-1.63 (m, 4H), 1.46-1.36 (m, 1H), 1.21 (d, J = 7.2 Hz, 3H), 1.18 (d, J = 6.3 Hz, 3H). |
| 241 | | IR (thin film) 2938, | HRMS-ESI (m/z) [M + H]$^+$ calcd for C$_{27}$H$_{35}$N$_2$O$_6$, | $^1$H NMR (500 MHz, CDCl$_3$) δ 8.48 (s, 1H), 8.33 (d, J = 5.5 Hz, 1H), 7.04- |

TABLE 2-continued

Analytical Data

| Cmpd. No. | Melting Point (° C.) | IR (cm⁻¹) | MASS SPEC | NMR |
|---|---|---|---|---|
| | | 1771, 1675, 1505, 1199, 1175, 908, 730 cm⁻¹ | 483.2490; found, 483.2484 | 6.85 (m, 4H), 5.20-5.10 (m, 1H), 4.65-4.52 (m, 1H), 3.90 (s, 3H), 3.03 (dd, J= 10.5, 6.3 Hz, 1H), 2.69 (h, J = 9.1 Hz, 1H), 2.39 (s, 3H), 2.32 (s, 3H), 2.25 (s, 3H), 2.20-2.10 (m, 1H), 1.88-1.63 (m, 4H), 1.46-1.35 (m, 1H), 1.20 (d, J = 7.1 Hz, 3H), 1.16 (d, J = 6.4 Hz, 3H). |
| 242 | | IR (thin film) 3380, 2961, 1771, 1734, 1676, 1508, 1310, 1200, 1175, 1061, 827 cm⁻¹ | HRMS-ESI (m/z) [M + H]⁺ calcd for $C_{24}H_{30}ClN_2O_6$, 479.1769; found, 479.1772 | ¹H NMR (400 MHz, CDCl₃) δ 8.49 (d, J = 8.1 Hz, 1H), 8.34 (d, J = 5.5 Hz, 1H), 7.21 (d, J = 8.4 Hz, 2H), 7.07-6.97 (m, 3H), 5.46-5.33 (m, 1H), 4.75-4.61 (m, 1H), 3.92 (s, 3H), 2.68 (t, J = 7.6 Hz, 1H), 2.40 (s, 3H), 2.12-2.02 (m, 1H), 1.49 (d, J = 7.1 Hz, 3H), 1.08 (d, J = 6.3 Hz, 3H), 0.88 (d, J = 6.6 Hz, 3H), 0.73 (d, J = 6.8 Hz, 3H). |
| 243 | | IR (thin film) 3380, 2962, 1772, 1735, 1677, 1508, 1202, 1176, 1061 cm⁻¹ | HRMS-ESI (m/z) [M + H]⁺ calcd for $C_{25}H_{32}FN_2O_6$, 476.2271; found, 476.2275 | ¹H NMR (400 MHz, CDCl₃) δ 8.54 (s, 1H), 8.34 (d, J = 5.4 Hz, 1H), 7.11-6.97 (m, 2H), 6.83-6.64 (m, 2H), 5.44-5.29 (m, 1H), 4.77-4.60 (m, 1H), 3.92 (s, 3H), 2.71-2.60 (m, 1H), 2.40 (s, 3H), 2.24 (d, J = 1.8 Hz, 3H), 2.13-2.00 (m, 1H), 1.49 (d, J = 7.1 Hz, 3H), 1.09 (d, J = 6.3 Hz, 3H), 0.86 (d, J = 6.8 Hz, 3H), 0.75 (d, J = 6.7 Hz, 3H). |
| 244 | | IR (thin film) 3382, 2963, 1771, 1734, 1676, 1513, 1203, 1175, 1061 cm⁻¹ | HRMS-ESI (m/z) [M + H]⁺ calcd for $C_{24}H_{29}F_2N_2O_6$, 480.202; found, 480.202 | ¹H NMR (400 MHz, CDCl₃) δ 8.48 (d, J = 8.1 Hz, 1H), 8.33 (d, J = 5.4 Hz, 1H), 7.08-6.97 (m, 2H), 6.92 (ddd, J = 11.7, 7.6, 2.2 Hz, 1H), 6.85-6.72 (m, 1H), 5.41-5.26 (m, 1H), 4.75-4.63 (m, 1H), 3.92 (s, 3H), 2.73-2.57 (m, 1H), 2.40 (s, 3H), 2.12-1.99 (m, 1H), 1.48 (d, J = 7.1 Hz, 3H), 1.09 (d, J = 6.3 Hz, 3H), 0.89 (d, J = 6.5 Hz, 3H), 0.74 (d, J = 6.7 Hz, 3H). |
| 245 | | IR (thin film) 3380, 2960, 1769, 1732, 1676, 1508, 1210, 1111, 1061, 823 cm⁻¹ | HRMS-ESI (m/z) [M + H]⁺ calcd for $C_{27}H_{37}N_2O_7$, 501.2595; found, 501.2589 | ¹H NMR (400 MHz, CDCl₃) δ 8.53 (d, J = 8.0 Hz, 1H), 8.34 (d, J = 5.5 Hz, 1H), 7.06 (t, J = 7.0 Hz, 2H), 7.02-6.95 (m, 3H), 5.39 (dq, J = 8.7, 6.2 Hz, 1H), 4.74-4.63 (m, 1H), 3.90 (s, 3H), 3.81 (t, J = 6.6 Hz, 2H), 3.40 (s, 3H), 2.99 (t, J = 6.6 Hz, 2H), 2.67 (dd, J = 8.7, 6.3 Hz, 1H), 2.32 (s, 3H), 2.09 (h, J = 6.7 Hz, 1H), 1.50 (d, J = 7.1 Hz, 3H), 1.08 (d, J = 6.3 Hz, 3H), 0.85 (d, J = 6.8 Hz, 3H), 0.75 (d, J = 6.8 Hz, 3H). ¹³C NMR (101 MHz, CDCl₃) δ 172.29, 169.42, 162.35, 159.50, 146.71, 141.69, 137.40, 136.06, 135.51, 129.68, 128.62, 109.74, 72.83, 67.62, 58.76, 56.32, 56.24, 48.23, 34.66, 28.22, 21.36, 21.01, 18.68, 18.57, 17.84. |
| 246 | | IR (thin film) 3380, 2961, 1733, 1676, 1503, 1208, 1115, 1051, 731 cm⁻¹ | HRMS-ESI (m/z) [M + H]⁺ calcd for $C_{27}H_{36}FN_2O_7$, 519.2501; found, 519.2498 | ¹H NMR (400 MHz, CDCl₃) δ 8.51 (d, J = 7.7 Hz, 1H), 8.33 (d, J = 5.5 Hz, 1H), 7.01 (d, J = 5.5 Hz, 1H), 6.93-6.80 (m, 3H), 5.36 (dq, J = 8.6, 6.3 Hz, 1H), 4.73-4.62 (m, 1H), 3.91 (s, 3H), 3.81 (t, J = 6.6 Hz, 2H), 3.40 (s, 3H), 2.99 (t, J = 6.6 Hz, 2H), 2.65 (dd, J = 8.6, 6.6 Hz, 1H), 2.24 (d, J = 1.9 Hz, 3H), 2.08 (hept, J = 6.7 Hz, 1H), 1.49 (d, J = 7.2 Hz, 3H), 1.08 (d, J = 6.3 Hz, 3H), 0.85 (d, J = 6.7 Hz, 3H), 0.74 (d, J = 6.8 Hz, 3H). ¹³C NMR (101 MHz, CDCl₃) δ 172.24, 169.42, 162.36, 160.27 (d, J = 243.5 Hz), 159.52, 146.72, 141.64, 137.42, 134.08 (d, J = 3.9 Hz), 132.56 (d, J = 5.0 Hz), 128.37 (d, J = 7.7 Hz), 124.07 (d, J = 17.1 Hz), 114.38 (d, J = 22.0 Hz), 109.78, 72.67, 67.62, 58.76, 56.33, 55.84, 48.22, 34.67, 28.28, 21.30, 18.67, 18.63, 17.67, 14.63 (d, J = 3.6 Hz). ¹⁹F NMR (376 MHz, CDCl₃) δ -120.90. |

TABLE 2-continued

Analytical Data

| Cmpd. No. | Melting Point (° C.) | IR (cm$^{-1}$) | MASS SPEC | NMR |
|---|---|---|---|---|
| 247 | | IR (thin film) 3377, 2962, 1734, 1676, 1507, 1209, 1113, 1061, 833, 731 cm$^{-1}$ | HRMS-ESI (m/z) [M + H]$^+$ calcd for C$_{27}$H$_{36}$FN$_2$O$_8$, 535.2450; found, 535.2446 | $^1$H NMR (400 MHz, CDCl$_3$) δ 8.53 (d, J = 7.7 Hz, 1H), 8.33 (d, J = 5.4 Hz, 1H), 7.06-6.97 (m, 2H), 6.69-6.62 (m, 1H), 6.58 (dd, J = 12.0, 2.6 Hz, 1H), 5.40 (ddt, J = 8.6, 6.8, 3.4 Hz, 1H), 4.75-4.60 (m, 1H), 3.90 (s, 3H), 3.81 (t, J = 6.6 Hz, 2H), 3.78 (s, 3H), 3.40 (s, 3H), 3.09 (t, J = 7.6 Hz, 1H), 2.99 (t, J = 6.6 Hz, 2H), 2.10 (h, J = 6.8 Hz, 1H), 1.49 (d, J = 7.1 Hz, 3H), 1.10 (d, J = 6.3 Hz, 3H), 0.93-0.87 (m, 3H), 0.75 (d, J = 6.7 Hz, 3H). $^{13}$C NMR (101 MHz, CDCl$_3$) δ 172.25, 169.41, 162.33, 162.10 (d, J = 244.3 Hz), 159.48, 159.32 (d, J = 11.2 Hz), 146.71, 141.67, 137.38, 130.69 (d, J = 6.6 Hz), 117.57 (d, J = 15.3 Hz), 109.73, 109.58 (d, J = 2.9 Hz), 101.39 (d, J = 28.0 Hz), 72.48, 67.62, 58.76, 56.31, 55.44, 48.21, 34.66, 29.29, 28.36, 21.10, 18.97, 18.50, 17.43. $^{19}$F NMR (376 MHz, CDCl$_3$) δ −112.98. |
| 248 | | IR (thin film) 3380, 2962, 1732, 1676, 1511, 1273, 1210, 1113, 731 cm$^{-1}$ | HRMS-ESI (m/z) [M + H]$^+$ calcd for C$_{27}$H$_{36}$FN$_2$O$_8$, 535.2450; found, 535.2444 | $^1$H NMR (400 MHz, CDCl$_3$) δ 8.51 (d, J = 7.9 Hz, 1H), 8.34 (d, J = 5.4 Hz, 1H), 7.01 (d, J = 5.5 Hz, 1H), 6.92-6.75 (m, 3H), 5.34 (dq, J = 8.3, 6.2 Hz, 1H), 4.66 (dt, J = 8.1, 7.1 Hz, 1H), 3.90 (s, 3H), 3.86 (s, 3H), 3.81 (t, J = 6.6 Hz, 2H), 3.40 (s, 3H), 2.99 (t, J = 6.6 Hz, 2H), 2.64 (dd, J = 8.6, 6.5 Hz, 1H), 2.05 (h, J = 6.8 Hz, 1H), 1.49 (d, J = 7.2 Hz, 3H), 1.09 (d, J = 6.3 Hz, 3H), 0.87 (d, J = 6.7 Hz, 3H), 0.75 (d, J = 6.7 Hz, 3H). $^{13}$C NMR (101 MHz, CDCl$_3$) δ 172.19, 169.42, 162.36, 159.51, 151.94 (d, J = 245.0 Hz), 146.73, 146.25 (d, J = 10.8 Hz), 141.62, 137.42, 131.84 (d, J = 5.6 Hz), 125.47 (d, J = 3.6 Hz), 117.15 (d, J = 18.2 Hz), 113.05-112.84 (m), 109.77, 72.51, 67.62, 58.76, 56.33, 56.24, 55.74, 48.21, 34.67, 28.35, 21.25, 18.77, 18.63, 17.47. $^{19}$F NMR (376 MHz, CDCl$_3$) δ −135.76. |
| 249 | | IR (thin film) 3379, 2960, 1769, 1732, 1678, 1506, 1311, 1210, 1111, 1041, 808 cm$^{-1}$ | HRMS-ESI (m/z) [M + H]$^+$ calcd for C$_{28}$H$_{39}$N$_2$O$_8$, 531.2701; found, 531.2703 | $^1$H NMR (400 MHz, CDCl$_3$) δ 8.53 (s, 1H), 8.32 (d, J = 5.4 Hz, 1H), 6.99 (d, J = 5.5 Hz, 1H), 6.94 (d, J = 7.7 Hz, 1H), 6.75-6.69 (m, 1H), 6.65 (d, J = 1.6 Hz, 1H), 5.41 (d, J = 7.8 Hz, 1H), 4.73-4.62 (m, 1H), 3.90 (s, 3H), 3.82 (t, J = 6.6 Hz, 2H), 3.75 (s, 3H), 3.40 (s, 3H), 2.99 (t, J = 6.7 Hz, 2H), 2.31 (s, 3H), 2.09 (h, J = 6.7 Hz, 1H), 1.69 (s, 1H), 1.49 (d, J = 7.1 Hz, 3H), 1.07 (d, J = 6.2 Hz, 3H) 0.84 (d, J = 6.7 Hz, 3H), 0.74 (d, J = 6.8 Hz, 3H). $^{13}$C NMR (101 MHz, CDCl$_3$) δ 172.30, 169.43, 162.30, 159.47, 158.10, 146.70, 141.75, 137.36, 137.15, 124.61, 120.69, 111.71, 109.69, 73.50, 67.63, 58.76, 56.31, 55.31, 48.32, 34.67, 29.30, 28.80, 21.43, 21.12, 18.87, 18.61, 18.11. |
| 250 | | IR (thin film) 3381, 2962, 1771, 1733, 1677, 1503, 1311, 1203, 1176, 1049, 733 cm$^{-1}$ | HRMS-ESI (m/z) [M + H]$^+$ calcd for C$_{25}$H$_{32}$FN$_2$O$_6$, 475.2239; found, 475.2236 | $^1$H NMR (400 MHz, CDCl$_3$) δ 8.53 (d, J = 8.0 Hz, 1H), 8.34 (d, J = 5.4 Hz, 1H), 7.01 (d, J = 5.5 Hz, 1H), 6.92-6.84 (m, 3H), 5.36 (dq, J = 8.6, 6.3 Hz, 1H), 4.69 (dq, J = 8.1, 7.1 Hz, 1H), 3.91 (s, 3H), 2.70-2.62 (m, 1H), 2.40 (s, 3H), 2.24 (d, J = 1.9 Hz, 3H), 2.07 (h, J = 6.7 Hz, 1H), 1.50 (d, J = 7.1 Hz, 3H), 1.08 (d, J = 6.2 Hz, 3H), 0.85 (d, J = 6.7 Hz, 3H), 0.74 (d, J = 6.8 Hz, 3H). $^{13}$C NMR (101 MHz, CDCl$_3$) δ 172.23, 168.89, 162.41, 160.27 (d, J = 243.4 Hz), 159.51, 146.66, 141.63, 137.57, 134.08 (d, J = 3.8 Hz), 132.56 (d, J = |

TABLE 2-continued

Analytical Data

| Cmpd. No. | Melting Point (° C.) | IR (cm$^{-1}$) | MASS SPEC | NMR |
|---|---|---|---|---|
| | | | | 4.9 Hz), 128.37 (d, J = 7.7 Hz), 124.08 (d, J = 17.2 Hz), 114.38 (d, J = 22.0 Hz), 109.78, 72.69, 56.30, 55.84, 48.22, 28.28, 21.30, 20.75, 18.67, 18.64, 17.67, 14.63 (d, J = 3.6 Hz). $^{19}$F NMR (376 MHz, CDCl$_3$) δ −120.91. |
| 251 | | IR (thin film) 3376, 2963, 1771, 1733, 1675, 1507, 1195, 1175, 1150, 1033, 833, 731 cm$^{-1}$ | HRMS-ESI (m/z) [M + H]$^+$ calcd for C$_{25}$H$_{32}$FN$_2$O$_7$, 491.2188; found, 491.2183 | $^1$H NMR (400 MHz, CDCl$_3$) δ 8.55 (d, J = 7.7 Hz, 1H), 8.33 (d, J = 5.4 Hz, 1H), 7.06-6.97 (m, 2H), 6.65 (ddd, J = 8.6, 2.6, 0.8 Hz, 1H), 6.58 (dd, J = 12.0, 2.6 Hz, 1H), 5.41 (dqd, J = 7.6, 6.2, 1.2 Hz, 1H), 4.68 (dq, J = 8.1, 7.2 Hz, 1H), 3.91 (s, 3H), 3.78 (s, 3H), 3.15-3.03 (m, 1H), 2.40 (s, 3H), 2.14-2.05 (m, 1H), 1.50 (d, J = 7.2 Hz, 3H), 1.10 (d, J = 6.3 Hz, 3H), 0.90 (dd, J = 6.7, 0.8 Hz, 3H), 0.75 (d, J = 6.7 Hz, 3H). $^{13}$C NMR (101 MHz, CDCl$_3$) δ 172.24, 168.89, 162.39, 162.11 (d, J = 244.3 Hz), 159.49, 159.34 (d, J = 11.2 Hz), 146.66, 141.67, 137.54, 130.71 (d, J = 6.5 Hz), 117.58 (d, J = 15.5 Hz), 109.73, 109.59 (d, J = 3.0 Hz), 101.40 (d, J = 27.9 Hz), 72.50, 56.29, 55.45, 48.22, 29.30, 28.37, 21.10, 20.75, 18.98, 18.51, 17.42. $^{19}$F NMR (376 MHz, CDCl$_3$) δ −112.96. |
| 252 | | IR (thin film) 3379, 2962, 1770, 1732, 1675, 1512, 1202, 1176, 1030, 731 cm$^{-1}$ | HRMS-ESI (m/z) [M + H]$^+$ calcd for C$_{25}$H$_{32}$FN$_2$O$_7$, 491.2188; found, 491.2182 | $^1$H NMR (400 MHz, CDCl$_3$) δ 8.53 (d, J = 8.0 Hz, 1H), 8.34 (d, J = 5.4 Hz, 1H), 7.01 (d, J = 5.5 Hz, 1H), 6.90-6.76 (m, 3H), 5.34 (dq, J = 8.4, 6.3 Hz, 1H), 4.73-4.63 (m, 1H), 3.91 (s, 3H), 3.86 (s, 3H), 2.68-2.61 (m, 1H), 2.40 (s, 3H), 2.05 (dq, J = 13.5, 6.8 Hz, 1H), 1.49 (d, J = 7.2 Hz, 3H), 1.09 (d, J = 6.3 Hz, 3H), 0.87 (d, J = 6.7 Hz, 3H), 0.75 (d, J = 6.7 Hz, 3H). $^{13}$C NMR (101 MHz, CDCl$_3$) δ 172.17, 168.90, 162.41, 159.50, 151.94 (d, J = 245.0 Hz), 146.68, 146.25 (d, J = 10.6 Hz), 141.59, 137.56, 131.84 (d, J = 5.7 Hz), 125.48 (d, J = 3.6 Hz), 117.13 (d, J = 18.2 Hz), 112.94 (d, J = 1.6 Hz), 109.77, 72.53, 56.27 (d, J = 6.4 Hz), 55.73, 48.21, 29.29, 28.35, 21.25, 20.75, 18.76, 18.64, 17.47. $^{19}$F NMR (376 MHz, CDCl$_3$) δ −135.76. |
| 253 | | IR (thin film) 3381, 2961, 1772, 1732, 1678, 1507, 1201, 1176, 1041, 733 cm$^{-1}$ | HRMS-ESI (m/z) [M + H]$^+$ calcd for C$_{26}$H$_{35}$N$_2$O$_7$, 487.2439; found, 487.2430 | $^1$H NMR (400 MHz, CDCl$_3$) δ 8.57 (d, J = 7.9 Hz, 1H), 8.32 (d, J = 5.4 Hz, 1H), 7.00 (d, J = 5.5 Hz, 1H), 6.94 (d, J = 7.7 Hz, 1H), 6.75-6.68 (m, 1H), 6.65 (d, J = 1.6 Hz, 1H), 5.51-5.39 (m, 1H), 4.76-4.60 (m, 1H), 3.90 (s, 3H), 3.75 (s, 3H), 3.33 (s, 1H), 2.40 (s, 3H), 2.31 (s, 3H), 2.09 (h, J = 6.7 Hz, 1H), 1.50 (d, J = 7.1 Hz, 3H), 1.07 (d, J = 6.2 Hz, 3H), 0.84 (d, J = 6.8 Hz, 3H), 0.74 (d, J = 6.8 Hz, 3H). $^{13}$C NMR (101 MHz, CDCl$_3$) δ 172.29, 168.90, 162.35, 159.46, 158.10, 146.65, 141.73, 137.51, 137.15, 124.61, 120.69, 111.71, 109.69, 73.52, 56.28, 55.31, 48.33, 29.30, 28.80, 21.43, 21.13, 20.75, 18.85, 18.62, 18.11. |
| 254 | | IR (thin film) 3379, 2959, 1771, 1731, 1677, 1503, 1201, 1175, 1046, 733 cm$^{-1}$ | HRMS-ESI (m/z) [M + H]$^+$ calcd for C$_{26}$H$_{35}$N$_2$O$_7$, 487.2439; found, 487.2436 | $^1$H NMR (400 MHz, CDCl$_3$) δ 8.55 (d, J = 8.0 Hz, 1H), 8.33 (d, J = 5.4 Hz, 1H), 7.06-6.92 (m, 2H), 6.70 (d, J = 8.1 Hz, 2H), 5.35 (dq, J = 9.2, 6.2 Hz, 1H), 4.70 (dq, J = 8.1, 7.1 Hz, 1H), 3.91 (s, 3H), 3.78 (s, 3H), 3.06 (dd, J = 9.3, 6.0 Hz, 1H), 2.40 (s, 3H), 2.29 (s, 3H), 2.12 (dq, J = 13.4, 6.7 Hz, 1H), 1.51 (d, J = 7.1 Hz, 3H), 1.05 (d, J = 6.2 Hz, |

TABLE 2-continued

Analytical Data

| Cmpd. No. | Melting Point (° C.) | IR (cm$^{-1}$) | MASS SPEC | NMR |
|---|---|---|---|---|
| | | | | 3H), 0.84 (d, J = 6.8 Hz, 3H), 0.79 (d, J = 6.9 Hz, 3H).<br>$^{13}$C NMR (101 MHz, CDCl$_3$) δ 172.34, 168.88, 162.37, 159.49, 157.56, 146.65, 141.65, 138.91, 137.54, 130.04, 128.84, 115.90, 110.86, 109.74, 74.13, 56.29, 55.05, 48.27, 29.64, 29.30, 21.09, 20.99, 20.75, 18.74, 18.61, 18.26. |
| 255 | | IR (thin film) 3379, 2961, 1756, 1675, 1503, 1201, 1042, 1003, 969, 827, 731 cm$^{-1}$ | HRMS-ESI (m/z) [M + H]$^+$ calcd for C$_{26}$H$_{35}$N$_2$O$_7$, 487.2439; found, 487.2433 | $^1$H NMR (400 MHz, CDCl$_3$) δ 8.37 (d, J = 7.8 Hz, 1H), 8.29 (d, J = 5.3 Hz, 1H), 7.11-7.03 (m, 2H), 7.03-6.93 (m, 3H), 5.75 (d, J = 0.6 Hz, 2H), 5.40 (dq, J = 8.8, 6.3 Hz, 1H), 4.79-4.66 (m, 1H), 3.91 (s, 3H), 2.68 (dd, J = 8.8, 6.3 Hz, 1H), 2.32 (s, 3H), 2.16-2.03 (m, 4H), 1.53 (d, J = 7.1 Hz, 3H), 1.09 (d, J = 6.3 Hz, 3H), 0.85 (d, J = 6.8 Hz, 3H), 0.76 (d, J = 6.8 Hz, 3H).<br>$^{13}$C NMR (101 MHz, CDCl$_3$) δ 172.40, 170.26, 162.98, 160.32, 145.70, 144.04, 142.66, 136.08, 135.50, 129.69, 128.62, 109.55, 89.63, 72.83, 56.26, 56.19, 48.44, 28.23, 21.36, 21.01, 20.87, 18.57, 18.54, 17.89. |
| 256 | | IR (thin film) 3380, 2962, 1735, 1674, 1503, 1203, 1043, 1004, 969, 829, 731 cm$^{-1}$ | HRMS-ESI (m/z) [M + H]$^+$ calcd for C$_{26}$H$_{34}$FN$_2$O$_7$, 505.2345; found, 505.2339 | $^1$H NMR (400 MHz, CDCl$_3$) δ 8.36 (d, J = 7.7 Hz, 1H), 8.29 (d, J = 5.4 Hz, 1H), 6.96 (d, J = 5.4 Hz, 1H), 6.93-6.85 (m, 3H), 5.75 (s, 2H), 5.37 (dq, J = 8.6, 6.2 Hz, 1H), 4.78-4.65 (m, 1H), 3.92 (s, 3H), 2.67 (dd, J = 8.6, 6.5 Hz, 1H), 2.24 (d, J = 2.0 Hz, 3H), 2.07 (s, 4H), 1.52 (d, J = 7.2 Hz, 3H), 1.09 (d, J = 6.3 Hz, 3H), 0.85 (d, J = 6.7 Hz, 3H), 0.75 (d, J = 6.8 Hz, 3H).<br>$^{13}$C NMR (101 MHz, CDCl$_3$) δ 172.35, 170.27, 163.00, 160.33, 160.28 (d, J = 243.4 Hz), 145.71, 144.07, 142.60, 134.07 (d, J = 3.8 Hz), 132.59 (d, J = 4.9 Hz), 128.35 (d, J = 7.7 Hz), 124.09 (d, J = 17.2 Hz), 114.38 (d, J = 22.1 Hz), 109.59, 89.62, 72.67, 56.20, 55.85, 48.43, 28.28, 21.31, 20.87, 18.62, 18.51, 17.74, 14.63 (d, J = 3.5 Hz).<br>$^{19}$F NMR (376 MHz, CDCl$_3$) δ -120.87. |
| 257 | | IR (thin film) 3380, 2963, 1736, 1676, 1507, 1200, 1040, 1004, 969, 831 cm$^{-1}$ | HRMS-ESI (m/z) [M + H]$^+$ calcd for C$_{26}$H$_{34}$FN$_2$O$_8$, 521.2294; found, 521.2286 | $^1$H NMR (400 MHz, CDCl$_3$) δ 8.37 (d, J = 7.8 Hz, 1H), 8.28 (d, J = 5.4 Hz, 1H), 7.03 (t, J = 8.5 Hz, 1H), 6.95 (d, J = 5.4 Hz, 1H), 6.66 (ddd, J = 8.6, 2.6, 0.7 Hz, 1H), 6.58 (dd, J = 12.0, 2.6 Hz, 1H), 5.78-5.68 (m, 2H), 5.47-5.36 (m, 1H), 4.75-4.65 (m, 1H), 3.91 (s, 3H), 3.79 (s, 3H), 3.10 (t, J = 7.7 Hz, 1H), 2.07 (s, 4H), 1.52 (d, J = 7.2 Hz, 3H), 1.11 (d, J = 6.3 Hz, 3H), 0.90 (dd, J = 6.7, 0.8 Hz, 3H), 0.76 (d, J = 6.7 Hz, 3H).<br>$^{13}$C NMR (101 MHz, CDCl$_3$) δ 172.36, 170.27, 162.99, 162.11 (d, J = 244.3 Hz), 160.32, 159.34 (d, J = 11.2 Hz), 145.70, 144.04, 142.64, 130.70 (d, J = 5.5 Hz), 117.58 (d, J = 15.5 Hz), 109.58 (d, J = 3.3 Hz), 109.55, 101.40 (d, J = 27.9 Hz), 89.63, 72.58-72.37 (m), 56.19, 55.45, 48.42, 29.30, 28.39, 21.10, 20.87, 18.98, 18.37, 17.44.<br>$^{19}$F NMR (376 MHz, CDCl$_3$) δ -112.98. |
| 258 | | IR (thin film) 3378, 2962, 1736, 1674, 1513, 1203, 1043, 1004, 969, 732 cm$^{-1}$ | HRMS-ESI (m/z) [M + H]$^+$ calcd for C$_{26}$H$_{34}$FN$_2$O$_8$, 521.2294; found, 521.2288 | $^1$H NMR (400 MHz, CDCl$_3$) δ 8.36 (d, J = 7.8 Hz, 1H), 8.29 (d, J = 5.4 Hz, 1H), 6.96 (d, J = 5.4 Hz, 1H), 6.90-6.76 (m, 3H), 5.75 (s, 2H), 5.35 (dq, J = 8.5, 6.3 Hz, 1H), 4.70 (p, J = 7.2 Hz, 1H), 3.92 (s, 3H), 3.87 (s, 3H), 2.69-2.60 (m, 1H), 2.13-2.01 (m, 4H), 1.52 (d, J = 7.1 Hz, 3H), 1.10 (d, J = 6.3 Hz, 3H), 0.87 (d, J = 6.7 Hz, 3H), 0.76 (d, J = 6.7 Hz, 3H). |

TABLE 2-continued

Analytical Data

| Cmpd. No. | Melting Point (° C.) | IR (cm$^{-1}$) | MASS SPEC | NMR |
|---|---|---|---|---|
| | | | | $^{13}$C NMR (101 MHz, CDCl$_3$) δ 172.31, 170.27, 163.01, 160.33, 151.95 (d, J = 245.4 Hz), 146.27 (d, J = 10.8 Hz), 145.72, 144.07, 142.57, 131.82 (d, J = 5.8 Hz), 125.46 (d, J = 3.5 Hz), 117.16 (d, J = 18.0 Hz), 113.05-112.84 (m), 109.59, 89.62, 72.51, 56.22 (d, J = 5.0 Hz), 55.76, 48.41, 29.30, 28.35, 21.26, 20.87, 18.70, 18.51, 17.55. $^{19}$F NMR (376 MHz, CDCl$_3$) δ −135.75. |
| 259 | | IR (thin film) 3376, 2960, 1737, 1678, 1505, 1203, 1042, 1004, 971, 736 cm$^{-1}$ | HRMS-ESI (m/z) [M + H]$^+$ calcd for C$_{27}$H$_{37}$N$_2$O$_8$, 517.2544; found, 517.2539 | $^1$H NMR (400 MHz, CDCl$_3$) δ 8.39 (d, J = 7.7 Hz, 1H), 8.28 (d, J = 5.4 Hz, 1H), 6.97-6.92 (m, 2H), 6.76-6.68 (m, 1H), 6.66 (d, J = 1.6 Hz, 1H), 5.80-5.72 (m, 2H), 5.42 (d, J = 8.1 Hz, 1H), 4.76-4.65 (m, 1H), 3.91 (s, 3H), 3.76 (s, 3H), 3.34 (s, 1H), 2.32 (s, 3H), 2.15-2.02 (m, 4H), 1.52 (d, J = 7.1 Hz, 3H), 1.07 (d, J = 6.2 Hz, 3H), 0.84 (d, J = 6.8 Hz, 3H), 0.74 (d, J = 6.8 Hz, 3H). $^{13}$C NMR (101 MHz, CDCl$_3$) δ 172.43, 170.26, 162.95, 160.30, 158.11, 145.71, 143.99, 142.75, 137.16, 124.61, 120.70, 111.72, 109.51, 89.64, 73.51, 56.18, 55.32, 48.52, 29.30, 28.82, 21.43, 21.14, 20.87, 18.83, 18.49, 18.17. |
| 260 | | IR (thin film) 3379, 2960, 1732, 1674, 1502, 1201, 1043, 1003, 969, 830, 730 cm$^{-1}$ | HRMS-ESI (m/z) [M + H]$^+$ calcd for C$_{27}$H$_{37}$N$_2$O$_8$, 517.2544; found, 517.2536 | $^1$H NMR (400 MHz, CDCl$_3$) δ 8.37 (d, J = 7.8 Hz, 1H), 8.28 (d, J = 5.4 Hz, 1H), 7.04-6.97 (m, 1H), 6.95 (d, J = 5.4 Hz, 1H), 6.70 (d, J = 7.5 Hz, 2H), 5.75 (d, J = 0.7 Hz, 2H), 5.36 (dq, J = 9.3, 6.2 Hz, 1H), 4.77-4.65 (m, 1H), 3.91 (s, 3H), 3.78 (s, 3H), 3.07 (dd, J = 9.3, 6.0 Hz, 1H), 2.30 (s, 3H), 2.18-2.09 (m, 1H), 2.07 (s, 3H), 1.53 (d, J = 7.1 Hz, 3H), 1.06 (d, J = 6.2 Hz, 3H), 0.84 (d, J = 6.8 Hz, 3H), 0.79 (d, J = 6.8 Hz, 3H). $^{13}$C NMR (101 MHz, CDCl$_3$) δ 172.47, 170.26, 162.97, 160.31, 157.57, 145.70, 144.04, 142.62, 138.90, 130.02, 128.86, 115.89, 110.88, 109.56, 89.62, 74.11, 56.19, 55.05, 48.48, 29.65, 29.30, 21.09, 20.99, 20.87, 18.71, 18.47, 18.31. |
| 261 | | IR (thin film) 3379, 2961, 1770, 1732, 1675, 1508, 1175, 731 cm$^{-1}$ | HRMS-ESI (m/z) [M + H]$^+$ calcd for C$_{25}$H$_{33}$N$_2$O$_7$, 473.2282; found, 473.2264 | $^1$H NMR (400 MHz, CDCl$_3$) δ 8.58 (d, J = 7.7 Hz, 1H), 8.32 (d, J = 5.4 Hz, 1H), 7.22-7.13 (m, 1H), 7.07 (dd, J = 7.6, 1.8 Hz, 1H), 7.00 (d, J = 5.6 Hz, 1H), 6.97-6.80 (m, 2H), 5.64-5.28 (m, 1H), 4.77-4.57 (m, 1H), 3.91 (s, 3H), 3.77 (s, 3H), 3.55-3.28 (m, 1H), 2.40 (s, 3H), 2.12 (dq, J = 13.4, 6.7 Hz, 1H), 1.50 (d, J = 7.1 Hz, 3H), 1.08 (d, J = 6.3 Hz, 3H), 0.85 (d, J = 6.8 Hz, 3H), 0.74 (d, J = 6.7 Hz, 3H). |
| 262 | | IR (thin film) 3379, 2960, 1770, 1732, 1676, 1505, 1205, 730 cm$^{-1}$ | HRMS-ESI (m/z) [M + H]$^+$ calcd for C$_{26}$H$_{35}$N$_2$O$_8$, 503.2388; found, 503.2374 | $^1$H NMR (400 MHz, CDCl$_3$) δ 8.58 (s, 1H), 8.32 (d, J = 5.4 Hz, 1H), 7.00 (d, J = 5.5 Hz, 1H), 6.96 (d, J = 8.2 Hz, 1H), 6.47-6.39 (m, 2H), 5.42 (d, J = 9.2 Hz, 1H), 4.79-4.61 (m, 1H), 3.91 (s, 3H), 3.78 (s, 3H), 3.74 (s, 3H), 3.45-3.16 (m, 1H), 2.40 (s, 3H), 2.13-2.01 (m, 1H), 1.50 (d, J = 7.1 Hz, 3H), 1.07 (d, J = 6.3 Hz, 3H), 0.83 (d, J = 6.7 Hz, 3H), 0.73 (d, J = 6.8 Hz, 3H). |
| 263 | | IR (thin film) 3379, 2961, 1735, 1674, 1493, 1203, 969, 733 cm$^{-1}$ | HRMS-ESI (m/z) [M + H]$^+$ calcd for C$_{26}$H35N$_2$O$_8$, 503.2388; found, 503.2359 | $^1$H NMR (400 MHz, CDCl$_3$) δ 8.38 (d, J = 7.8 Hz, 1H), 8.27 (d, J = 5.4 Hz, 1H), 7.22-7.13 (m, 1H), 7.07 (dd, J = 7.6, 1.8 Hz, 1H), 6.94 (d, J = 5.4 Hz, 1H), 6.92-6.75 (m, 2H), 5.82-5.69 (m, 2H), 5.45 (s, 1H), 4.81-4.59 (m, 1H), 3.91 (s, 3H), 3.77 (s, 3H), 3.53-3.23 (m, 1H), 2.16-2.05 (m, 4H), 1.52 (d, J = 7.1 Hz, 3H), 1.08 (d, J = 6.2 Hz, 3H), 0.85 (d, J = 6.7 Hz, 3H), 0.74 (d, J = 6.8 Hz, 3H). |

TABLE 2-continued

Analytical Data

| Cmpd. No. | Melting Point (° C.) | IR (cm$^{-1}$) | MASS SPEC | NMR |
|---|---|---|---|---|
| 264 | | IR (thin film) 3379, 2960, 1734, 1675, 1505, 1204, 1041, 830, 731 cm$^{-1}$ | HRMS-ESI (m/z) [M + H]$^+$ calcd for C$_{27}$H$_{37}$N$_2$O$_9$, 533.2494; found, 533.2488 | $^1$H NMR (400 MHz, CDCl$_3$) δ 8.38 (d, J = 7.8 Hz, 1H), 8.27 (d, J = 5.4 Hz, 1H), 7.03-6.84 (m, 2H), 6.43 (d, J = 7.8 Hz, 2H), 5.74 (d, J = 1.2 Hz, 2H), 5.46-5.34 (m, 1H), 4.78-4.62 (m, 1H), 3.90 (s, 3H), 3.78 (s, 3H), 3.74 (s, 3H), 3.42-2.96 (m, 1H), 2.15-2.04 (m, 4H), 1.51 (d, J = 7.2 Hz, 3H), 1.07 (d, J = 6.2 Hz, 3H), 0.82 (d, J = 6.7 Hz, 3H), 0.73 (d, J = 6.8 Hz, 3H). |
| 265 | | | ESIMS m/z 268.3 ([M + H]$^+$) | |
| 266 | | | ESIMS m/z 310.3 ([M + H]$^+$) | |
| 267 | | | ESIMS m/z 324.3 ([M + H]$^+$) | |
| 268 | | | ESIMS m/z 324.3 ([M + H]$^+$) | |
| 269 | | IR (thin film) 2969, 1743, 1502, 1449, 1365, 1230, 1216, 1203, 1120, 1053, 805 cm$^{-1}$ | HRMS-ESI (m/z) [M + H]$^+$ calcd for C$_{17}$H$_{28}$NO$_2$, 278.2115; found, 278.2108 | |
| 270 | | IR (thin film) 2961, 2826, 1739, 1578, 1508, 1466, 1368, 1253, 1235, 1197, 1166, 1094, 1044, 786, 754 cm$^{-1}$ | HRMS-ESI (m/z) [M + H]$^+$ calcd for C$_{16}$H$_{25}$FNO$_2$, 282.1864; found, 282.1877 | |
| 271 | | IR (thin film) 2959, 2851, 1739, 1583, 1491, 1454, 1248, 1231, 1197, 1120, 1051, 761 cm$^{-1}$ | HRMS-ESI (m/z) [M + H]$^+$ calcd for C$_{15}$H$_{23}$FNO$_2$, 268.1707; found, 268.1718 | |
| 272 | | IR (thin film) 2959, 2873, 1737, 1587, 1530, 1498, 1457, 1284, 1238, 1190, 1114, 1047, 873, 813 cm$^{-1}$ | HRMS-ESI (m/z) [M + H]$^+$ calcd for C$_{16}$H$_{25}$FNO$_2$, 282.1864; found, 282.1869 | |
| 273 | | IR (thin film) 2870, 1742, 1594, 1502, 1454, 1377, 1251, 1226, 1199, 1118, 1048, 887, 818 cm$^{-1}$ | HRMS-ESI (m/z) [M + H]$^+$ calcd for C$_{17}$H$_{28}$NO$_2$, 278.2115; found, 278.2119 | |
| 274 | | IR (thin film) 2871, 1740, 1588, 1407, 1455, 1384, 1252, 1239, 1200, 1117, 1044, 783 cm$^{-1}$ | HRMS-ESI (m/z) [M + H]$^+$ calcd for C$_{17}$H$_{28}$NO$_2$, 278.2115; found, 278.2110 | |
| 275 | | IR (thin film) 2871, 1738, 1586, 1505, 1455, | HRMS-ESI (m/z) [M + H]$^+$ calcd for C$_{16}$H$_{26}$NO$_2$, 264.1958; found, 264.1953 | |

TABLE 2-continued

Analytical Data

| Cmpd. No. | Melting Point (° C.) | IR (cm$^{-1}$) | MASS SPEC | NMR |
|---|---|---|---|---|
| | | 1244, 1196, 1162, 1119, 1053, 754 cm$^{-1}$ | | |
| 276 | | IR (thin film) 2961, 2872, 1754, 1740, 1602, 1501, 1244, 1116, 1082, 967, 846 cm$^{-1}$ | HRMS-ESI (m/z) [M + H]$^+$ calcd for C$_{15}$H$_{22}$F$_2$NO$_2$, 286.1613; found, 286.1628 | |
| 277 | | IR (thin film) 2960, 1757, 1508, 1458, 1269, 1236, 1212, 1124, 1050, 853, 819 cm$^{-1}$ | HRMS-ESI (m/z) [M + H]$^+$ calcd for C$_{16}$H$_{25}$FNO$_2$, 282.1864; found, 282.1871 | |
| 278 | | IR (thin film) 2967, 2873, 1737, 1589, 1476, 1382, 1251, 1229, 1121, 1107, 1043, 871, 845, 824 cm$^{-1}$ | | |
| 279 | | IR (thin film) 2963, 1740, 1602, 1501, 1458, 1234, 1207, 1172, 1113, 964, 846 cm$^{-1}$ | HRMS-ESI (m/z) [M + H]$^+$ calcd for C$_{15}$H$_{22}$F$_2$NO$_2$, 286.1613; found, 286.1637 | |
| 280 | | IR (thin film) 2961, 1740, 1506, 1456, 1235, 1207, 1115, 939 cm$^{-1}$ | HRMS-ESI (m/z) [M + H]$^+$ calcd for C$_{16}$H$_{25}$FNO$_2$, 282.1864; found, 282.1878 | |
| 281 | | IR (thin film) 2962, 1739, 1470, 1381, 1233, 1192, 1109, 1044, 1007, 806 cm$^{-1}$ | HRMS-ESI (m/z) [M + H]$^+$ calcd for C$_{15}$H$_{22}$Cl$_2$NO$_2$, 318.1022; found, 318.1022 | |
| 282 | | IR (thin film) 3391, 2959, 2875, 1736, 1488, 1231, 1196, 1114, 1035 cm$^{-1}$ | | |
| 283 | | | HRMS-ESI (m/z) [M + H]$^+$ calcd for C$_{16}$H$_{23}$F$_3$NO$_3$, 334.1625; found, 334.1616 | |
| 284 | | IR (thin film) 2973, 1738, 1509, 1237, 1117, 831 cm$^{-1}$ | | |
| 285 | | | HRMS-ESI (m/z) [M + H]$^+$ calcd for C$_{18}$H$_{30}$NO$_3$, 308.2226; found, 308.2074 | |
| 286 | | | HRMS-ESI (m/z) [M + Na]$^+$ calcd for C$_{16}$H$_{25}$NO$_3$Na, 302.1727; found, 302.1723 | |
| 287 | | | | |
| 288 | | IR (thin film) 3367, | HRMS-ESI (m/z) [M + Na]$^+$ calcd for C$_{20}$H$_{30}$FNNaO$_4$, | $^1$H NMR (400 MHz, CDCl$_3$) δ 7.04 (dd, J = 8.5, 5.9 Hz, 1H), 6.87 (ddt, J = 11.6, |

TABLE 2-continued

Analytical Data

| Cmpd. No. | Melting Point (°C.) | IR (cm$^{-1}$) | MASS SPEC | NMR |
|---|---|---|---|---|
| | | 2964, 1713, 1498, 1366, 1164, 1052, 954, 862 cm$^{-1}$ | 390.2051; found, 390.2053 | 8.3, 4.1 Hz, 2H), 5.40 (dq, J = 8.3, 6.3 Hz, 1H), 5.02 (s, 1H), 3.93-3.85 (m, 2H), 3.02 (t, J = 7.7 Hz, 1H), 2.31 (s, 3H), 2.07 (h, J = 6.8 Hz, 1H), 1.46 (s, 9H), 1.04 (d, J = 6.3 Hz, 3H), 0.91 (d, J = 6.7 Hz, 3H), 0.77 (d, J = 6.8 Hz, 3H). $^{13}$C NMR (101 MHz, CDCl$_3$) δ 169.85, 160.98 (d, J = 244.6 Hz), 155.63, 139.89 (d, J = 8.0 Hz), 133.68 (d, J = 2.8 Hz), 129.24 (d, J = 7.3 Hz), 117.01 (d, J = 20.5 Hz), 112.37 (d, J = 20.8 Hz), 79.96, 73.61, 49.56, 42.78, 29.85, 28.33, 20.96, 20.78, 19.55, 17.64. $^{19}$F NMR (376 MHz, CDCl$_3$) δ −117.37. |
| 289 | | IR (thin film) 2964, 1712, 1498, 1366, 1158, 1049, 863 cm$^{-1}$ | HRMS-ESI (m/z) [M + Na]$^+$ calcd for C$_{23}$H$_{36}$FNNaO$_4$, 432.2521; found, 432.2521 | $^1$H NMR (400 MHz, CDCl$_3$) δ 7.04 (dd, J = 8.6, 6.0 Hz, 1H), 6.87 (qd, J = 9.3, 8.4, 2.8 Hz, 2H), 5.33 (dq, J = 9.5, 6.2 Hz, 1H), 4.97 (d, J = 9.4 Hz, 1H), 4.24 (dd, J = 9.3, 4.4 Hz, 1H), 3.09 (dd, J = 9.5, 5.7 Hz, 1H), 2.33 (s, 3H), 2.26-2.07 (m, 2H), 1.46 (s, 9H), 1.02 (d, J = 6.2 Hz, 3H), 1.00 (d, J = 6.9 Hz, 3H), 0.88 (d, J = 6.9 Hz, 3H), 0.83 (d, J = 6.8 Hz, 3H), 0.80 (d, J = 6.9 Hz, 3H). $^{13}$C NMR (101 MHz, CDCl$_3$) δ 171.82, 160.99 (d, J = 244.4 Hz), 155.66, 139.90 (d, J = 7.6 Hz), 133.39 (d, J = 2.7 Hz), 129.26 (d, J = 7.4 Hz), 117.04 (d, J = 20.5 Hz), 112.37 (d, J = 20.6 Hz), 79.70, 73.46, 58.88, 49.31, 31.26, 29.27, 28.34, 20.91, 19.38, 18.39, 17.03. $^{19}$F NMR (376 MHz, CDCl$_3$) δ −117.33. |
| 290 | | IR (thin film) 2964, 1712, 1498, 1366, 1158, 1049, 863 cm$^{-1}$ | HRMS-ESI (m/z) [M + Na]$^+$ calcd for C$_{24}$H$_{38}$FNNaO$_4$, 446.2677; found, 446.2681 | $^1$H NMR (400 MHz, CDCl$_3$) δ 7.04 (dd, J = 8.6, 5.9 Hz, 1H), 6.93-6.81 (m, 2H), 5.33 (dq, J = 9.5, 6.2 Hz, 1H), 4.96 (d, J = 9.3 Hz, 1H), 4.28 (dd, J = 9.3, 4.5 Hz, 1H), 3.10 (dd, J = 9.6, 5.5 Hz, 1H), 2.33 (s, 3H), 2.14 (dt, J = 13.5, 6.7 Hz, 1H), 1.99-1.83 (m, 1H), 1.54-1.32 (m, 10H), 1.21-1.08 (m, 1H), 1.02 (d, J = 6.2 Hz, 3H), 0.97 (d, J = 6.8 Hz, 3H), 0.91 (t, J = 7.4 Hz, 3H), 0.82 (d, J = 6.9 Hz, 3H), 0.80 (d, J = 6.9 Hz, 3H). $^{13}$C NMR (101 MHz, CDCl$_3$) δ 171.79, 161.00 (d, J = 244.4 Hz), 155.59, 139.90 (d, J = 7.3 Hz), 133.33 (d, J = 2.9 Hz), 129.28 (d, J = 7.6 Hz), 117.05 (d, J = 20.5 Hz), 112.37 (d, J = 20.7 Hz), 79.69, 73.41, 58.61, 49.35, 37.97, 29.19, 28.35, 24.40, 20.92, 18.45, 18.21, 15.71, 11.56. $^{19}$F NMR (376 MHz, CDCl$_3$) δ −117.32. |
| 291 | | IR (thin film) 3365, 2960, 1714, 1499, 1367, 1165, 1049, 863 cm$^{-1}$ | HRMS-ESI (m/z) [M + Na]$^+$ calcd for C$_{24}$H$_{38}$FNNaO$_4$, 446.2677; found, 446.2675 | $^1$H NMR (400 MHz, CDCl$_3$) δ 7.05 (dd, J = 8.5, 5.9 Hz, 1H), 6.93-6.82 (m, 2H), 5.31 (dq, J = 9.2, 6.2 Hz, 1H), 4.85 (d, J = 8.8 Hz, 1H), 4.29 (td, J = 9.1, 4.8 Hz, 1H), 3.08 (dd, J = 9.2, 6.1 Hz, 1H), 2.33 (s, 3H), 2.12 (h, J = 6.7 Hz, 1H), 1.70 (dq, J = 13.1, 6.8 Hz, 1H), 1.58 (ddd, J = 13.5, 8.4, 5.1 Hz, 1H), 1.52-1.36 (m, 10H), 1.03 (d, J = 6.2 Hz, 3H), 0.95 (dd, J = 6.6, 3.0 Hz, 6H), 0.85 (d, J = 6.8 Hz, 3H), 0.78 (d, J = 6.8 Hz, 3H). $^{13}$C NMR (101 MHz, CDCl$_3$) δ 172.88, 160.98 (d, J = 244.5 Hz), 155.31, 139.86 (d, J = 7.3 Hz), 133.62 (d, J = 2.9 Hz), 129.25 (d, J = 8.4 Hz), 116.99 (d, J = 20.5 Hz), 112.37 (d, J = 20.6 Hz), 79.73, 73.45, 52.55, 49.36, 41.84, 29.51, 28.33, 24.82, 23.05, 21.82, 20.95, 18.75, 18.09. $^{19}$F NMR (376 MHz, CDCl$_3$) δ −117.42. |
| 292 | | IR (thin film) 3357, | HRMS-ESI (m/z) [M + Na]$^+$ calcd for C$_{22}$H$_{35}$NO$_4$Na, | $^1$H NMR (500 MHz, CDCl$_3$) δ 7.04 (d, J = 7.6 Hz, 1H), 6.92 (dd, J = 7.7, 1.7 Hz, |

TABLE 2-continued

Analytical Data

| Cmpd. No. | Melting Point (° C.) | IR (cm$^{-1}$) | MASS SPEC | NMR |
|---|---|---|---|---|
| | | 2963, 2874, 1712, 1501, 1451, 1365, 1160, 1049 cm$^{-1}$ | 400.2458; found, 400.2450 | 1H), 6.89 (s, 1H), 5.35 (dq, J = 9.4, 6.2 Hz, 1H), 5.08 (d, J = 7.9 Hz, 1H), 4.30 (t, J = 7.6 Hz, 1H), 3.09 (dd, J = 9.4, 6.0 Hz, 1H), 2.29 (s, 3H), 2.28 (s, 3H), 2.14 (dq, J = 13.5, 6.7 Hz, 1H), 1.45 (s, 9H), 1.40 (d, J = 7.1 Hz, 3H), 1.04 (d, J = 6.2 Hz, 3H), 0.84 (d, J = 6.8 Hz, 3H), 0.81 (d, J = 6.9 Hz, 3H). |
| 293 | | IR (thin film) 3356, 2965, 1712, 1500, 1455, 1365, 1245, 1161, 1045, 820 cm$^{-1}$ | HRMS-ESI (m/z) [M + Na]$^+$ calcd for C$_{21}$H$_{32}$FNO$_4$Na, 404.2208; found, 404.2208 | $^1$H NMR (500 MHz, CDCl$_3$) δ 7.11 (td, J = 7.9, 5.9 Hz, 1H), 6.99-6.82 (m, 2H), 5.36 (dq, J = 9.1, 6.2 Hz, 1H), 5.05 (d, J = 7.8 Hz, 1H), 4.29 (t, J = 7.5 Hz, 1H), 3.14 (dd, J = 9.0, 6.4 Hz, 1H), 2.24 (d, J = 2.3 Hz, 3H), 2.14 (dq, J = 13.4, 6.7 Hz, 1H), 1.45 (s, 9H), 1.39 (d, J = 7.2 Hz, 3H), 1.04 (d, J = 6.2 Hz, 3H), 0.86 (d, J = 6.8 Hz, 3H), 0.79 (d, J = 6.8 Hz, 3H). |
| 294 | | IR (thin film) 3363, 2965, 2933, 1712, 1491, 1453, 1365, 1162, 1052, 757 cm$^{-1}$ | HRMS-ESI (m/z) [M + Na]$^+$ calcd for C$_{20}$H$_{30}$FNO$_4$Na, 390.2051; found, 390.2053 | $^1$H NMR (500 MHz, CDCl$_3$) δ 7.25-7.19 (m, 1H), 7.12 (dtd, J = 22.9, 7.6, 1.6 Hz, 2H), 7.03 (ddd, J = 9.7, 8.1, 1.3 Hz, 1H), 5.43 (dqd, J = 7.5, 6.3, 1.3 Hz, 1H), 5.06 (d, J = 7.9 Hz, 1H), 4.39-4.15 (m, 1H), 3.18 (t, J = 7.7 Hz, 1H), 2.22-2.03 (m, 1H), 1.45 (s, 9H), 1.38 (d, J = 7.2 Hz, 3H), 1.10 (d, J = 6.3 Hz, 3H), 1.04-0.86 (m, 3H), 0.77 (d, J = 6.7 Hz, 3H). |
| 295 | | IR (thin film) 3356, 2969, 1712, 1497, 1365, 1243, 1161, 1050, 731 cm$^{-1}$ | HRMS-ESI (m/z) [M + Na]$^+$ calcd for C$_{21}$H$_{32}$FNO$_4$Na, 404.2208; found, 404.2204 | $^1$H NMR (500 MHz, CDCl$_3$) δ 7.12 (dd, J = 8.5, 6.0 Hz, 1H), 6.88-6.75 (m, 2H), 5.31 (dq, J = 9.0, 6.3 Hz, 1H), 5.05 (d, J = 7.9 Hz, 1H), 4.43-4.15 (m, 1H), 3.10 (t, J = 7.4 Hz, 1H), 2.29 (s, 3H), 2.12 (h, J = 6.8 Hz, 1H), 1.45 (s, 9H), 1.38 (d, J = 7.2 Hz, 3H), 1.06 (d, J = 6.3 Hz, 3H), 0.87 (d, J = 6.7 Hz, 3H), 0.81 (d, J = 6.8 Hz, 3H). |
| 296 | | IR (thin film) 3356, 2962, 1713, 1501, 1451, 1365, 1160, 1049, 732 cm$^{-1}$ | HRMS-ESI (m/z) [M + Na]$^+$ calcd for C$_{22}$H$_{35}$NO$_4$Na, 400.2458; found, 400.2462 | $^1$H NMR (500 MHz, CDCl$_3$) δ 7.04-6.91 (m, 3H), 5.35 (dq, J = 9.3, 6.3 Hz, 1H), 5.07 (s, 1H), 4.29 (t, J = 7.6 Hz, 1H), 3.08 (dd, J = 9.4, 6.0 Hz, 1H), 2.29 (s, 3H), 2.29 (s, 3H), 2.12 (dq, J = 13.4, 6.8 Hz, 1H), 1.45 (s, 9H), 1.39 (d, J = 7.2 Hz, 3H), 1.03 (d, J = 6.2 Hz, 3H), 0.84 (d, J = 6.7 Hz, 3H), 0.80 (d, J = 6.9 Hz, 3H). |
| 297 | | IR (thin film) 3352, 2964, 1712, 1499, 1452, 1365, 1160, 1050, 731 cm$^{-1}$ | HRMS-ESI (m/z) [M + NH4]$^+$ calcd for C$_{22}$H$_{35}$NO$_4$NH$_4$, 395.2904; found, 395.2889 | $^1$H NMR (500 MHz, CDCl$_3$) δ 7.07-7.01 (m, 2H), 6.95 (dd, J = 7.0, 2.3 Hz, 1H), 5.37 (dq, J = 9.2, 6.3 Hz, 1H), 5.08 (s, 1H), 4.30 (t, J = 7.8 Hz, 1H), 3.23 (dd, J = 9.3, 6.0 Hz, 1H), 2.30 (s, 3H), 2.24 (s, 3H), 2.13 (dq, J = 13.4, 6.7 Hz, 1H), 1.45 (s, 9H), 1.40 (d, J = 7.1 Hz, 3H), 1.03 (d, J = 6.2 Hz, 3H), 0.84 (d, J = 6.8 Hz, 3H), 0.79 (d, J = 6.9 Hz, 3H). |
| 298 | | IR (thin film) 3359, 2965, 2875, 1714, 1161, 1054 cm$^{-1}$ | HRMS-ESI (m/z) [M + Na]$^+$ calcd for C$_{21}$H$_{33}$NO$_4$Na, 386.2302; found, 386.2301 | $^1$H NMR (500 MHz, CDCl$_3$) δ 7.20-7.06 (m, 4H), 5.37 (dq, J = 9.3, 6.2 Hz, 1H), 5.07 (d, J = 7.8 Hz, 1H), 4.29 (t, J = 7.2 Hz, 1H), 3.13 (dd, J = 9.2, 6.1 Hz, 1H), 2.34 (s, 3H), 2.15 (dq, J = 13.4, 6.8 Hz, 1H), 1.45 (s, 9H), 1.39 (d, J = 7.2 Hz, 3H), 1.04 (d, J = 6.2 Hz, 3H), 0.86 (d, J = 6.8 Hz, 3H), 0.81 (d, J = 6.8 Hz, 3H). |
| 299 | | IR (thin film) 3365, 2966, 1712, 1503, 1454, 1366, 1165, 1053, 966, 849 cm$^{-1}$ | HRMS-ESI (m/z) [M + Na]$^+$ calcd for C$_{20}$H$_{29}$F$_2$NO$_4$Na, 408.1957; found, 408.1955 | $^1$H NMR (500 MHz, CDCl$_3$) δ 7.10 (td, J = 8.4, 6.4 Hz, 1H), 6.93-6.74 (m, 2H), 5.39 (tt, J = 7.0, 5.5 Hz, 1H), 5.04 (d, J = 7.9 Hz, 1H), 4.26 (t, J = 7.6 Hz, 1H), 3.13 (t, J = 7.7 Hz, 1H), 2.10 (h, J = 6.8 Hz, 1H), 1.45 (s, 9H), 1.37 (d, J = 7.2 Hz, 3H), 1.09 (d, J = 6.3 Hz, 3H), 0.91 (d, J = 6.8 Hz, 3H), 0.75 (d, J = 6.7 Hz, 3H). |
| 300 | | IR (thin film) 2969, 1716, 1506, 1456, 1365, 1164, 1053 | HRMS-ESI (m/z) [M + Na]$^+$ calcd for C$_{21}$H$_{32}$FNO$_4$Na, 404.2208; found, 404.2202 | $^1$H NMR (500 MHz, CDCl$_3$) δ 7.00 (t, J = 7.7 Hz, 1H), 6.90 (dd, J = 7.9, 1.7 Hz, 1H), 6.87-6.74 (m, 1H), 5.40 (tt, J = 6.9, 5.5 Hz, 1H), 5.07 (d, J = 8.1 Hz, 1H), 4.33-4.16 (m, 1H), 3.11 (t, J = 7.7 Hz, |

TABLE 2-continued

Analytical Data

| Cmpd. No. | Melting Point (° C.) | IR (cm$^{-1}$) | MASS SPEC | NMR |
|---|---|---|---|---|
| | | cm$^{-1}$ | | 1H), 2.33 (s, 3H), 2.10 (h, J = 6.8 Hz, 1H), 1.45 (s, 9H), 1.38 (d, J = 7.2 Hz, 3H), 1.09 (d, J = 6.3 Hz, 3H), 0.90 (d, J = 6.7 Hz, 3H), 0.76 (d, J = 6.7 Hz, 3H). |
| 301 | | IR (thin film) 3358, 2966, 1712, 1500, 1474, 1453, 1365, 1162, 1045 cm$^{-1}$ | HRMS-ESI (m/z) [M + Na]$^+$ calcd for C$_{20}$H$_{29}$Cl$_2$NO$_4$Na, 440.1366; found, 440.1366 | $^1$H NMR (500 MHz, CDCl$_3$) δ 7.42 (d, J = 2.3 Hz, 1H), 7.23 (dd, J = 8.5, 2.2 Hz, 1H), 7.13 (d, J = 8.5 Hz, 1H), 5.47-5.25 (m, 1H), 5.03 (d, J = 7.6 Hz, 1H), 4.28 (d, J = 7.7 Hz, 1H), 3.51 (s, 1H), 2.24-1.99 (m, 1H), 1.45 (s, 9H), 1.39 (d, J = 7.2 Hz, 3H), 1.08 (d, J = 6.4 Hz, 3H), 0.92 (d, J = 6.8 Hz, 3H), 0.77 (d, J = 6.8 Hz, 3H). |
| 302 | | IR (thin film) 3346, 2975, 1710, 1502, 1366, 1249, 1163, 1064, 965, 847 cm$^{-1}$ | HRMS-ESI (m/z) [M + Na]$^+$ calcd for C$_{20}$H$_{29}$F$_2$NO$_4$Na, 408.1957; found, 408.1956 | $^1$H NMR (500 MHz, CDCl$_3$) δ 7.33-7.27 (m, 1H), 6.90-6.82 (m, 1H), 6.82-6.75 (m, 1H), 5.54-5.30 (m, 1H), 5.01 (d, J = 8.6 Hz, 1H), 4.35-4.18 (m, 1H), 2.84 (dd, J = 9.1, 5.2 Hz, 1H), 2.09-1.87 (m, 1H), 1.44 (s, 9H), 1.24 (d, J = 7.3 Hz, 3H), 1.10 (d, J = 6.3 Hz, 3H), 0.97 (d, J = 6.5 Hz, 3H), 0.72 (d, J = 6.8 Hz, 3H). |
| 303 | | IR (thin film) 3364, 2974, 2932, 1714, 1506, 1454, 1336, 1167, 1065 cm$^{-1}$ | HRMS-ESI (m/z) [M + Na]$^+$ calcd for C$_{21}$H$_{32}$FNO$_4$Na, 404.2208; found, 404.2206 | $^1$H NMR (500 MHz, CDCl$_3$) δ 7.17 (t, J = 7.8 Hz, 1H), 6.90 (d, J = 7.6 Hz, 1H), 6.84 (dd, J = 11.0, 1.8 Hz, 1H), 5.44-5.38 (m, 1H), 5.04 (d, J = 7.4 Hz, 1H), 4.46-4.15 (m, 1H) 2.83 (dd, J = 9.0, 5.1 Hz, 1H), 2.33 (d, J = 3.0 Hz, 3H), 2.11-1.97 (m, 1H), 1.44 (s, 9H), 1.22 (d, J = 7.2 Hz, 3H), 1.10 (d, J = 6.3 Hz, 3H), 0.97 (d, J = 6.6 Hz, 3H), 0.73 (d, J = 6.9 Hz, 3H). |
| 304 | | IR (thin film) 3353, 2975, 1710, 1472, 1366, 1163, 1111, 1020, 863, 809 cm$^{-1}$ | HRMS-ESI (m/z) [M + Na]$^+$ calcd for C$_{20}$H$_{29}$Cl$_2$NO$_4$Na, 440.1366; found, 440.1360 | $^1$H NMR (500 MHz, CDCl$_3$) δ 7.40 (d, J = 2.2 Hz, 1H), 7.36 (d, J = 8.5 Hz, 1H), 7.24-7.06 (m, 1H), 5.62-5.20 (m, 1H), 5.02 (d, J = 8.1 Hz, 1H), 4.46-4.13 (m, 1H), 3.13 (dd, J = 9.6, 4.6 Hz, 1H), 2.20-1.92 (m, 1H), 1.44 (s, 9H), 1.37-1.26 (m, 3H), 1.06 (d, J = 6.3 Hz, 3H), 1.01 (d, J = 6.6 Hz, 3H), 0.70 (d, J = 6.8 Hz, 3H). |
| 305 | | IR (thin film) 3375, 2969, 1711, 1504, 1488, 1160, 1038, 731 cm$^{-1}$ | HRMS-ESI (m/z) [M + Na]$^+$ calcd for C$_{21}$H$_{31}$NO$_6$Na, 416.2044; found, 416.2040 | $^1$H NMR (500 MHz, CDCl$_3$) δ 6.74 (d, J = 7.9 Hz, 1H), 6.60 (d, J = 1.8 Hz, 1H), 6.54 (dd, J = 8.0, 1.7 Hz, 1H), 5.94 (s, 2H), 5.31 (dq, J = 8.8, 6.3 Hz, 1H), 5.07 (d J = 7.8 Hz, 1H), 4.33-4.20 (m, 1H), 2.61 (dd, J = 8.8, 6.4 Hz, 1H), 2.12-1.98 (m, J = 6.8 Hz, 1H), 1.45 (s, 9H), 1.38 (d, J = 7.2 Hz, 3H), 1.08 (d, J = 6.2 Hz, 3H), 0.85 (d, J = 6.7 Hz, 3H), 0.76 (d, J = 6.7 Hz, 3H). |
| 306 | | IR thin film) 3361, 2970, 1715, 1366, 1262, 1218, 1165 cm$^{-1}$ | | $^1$H NMR (500 MHz, CDCl$_3$) δ 7.13 (q, J = 8.8 Hz, 4H), 5.37 (dq, J = 8.7, 6.3 Hz, 1H), 5.04 (d, J = 8.0 Hz, 1H), 4.37-4.22 (m, 1H), 2.72 (dd, J = 8.6, 6.6 Hz, 1H), 2.10 (h, J = 6.7 Hz, 1H), 1.45 (s, 9H), 1.37 (d, J = 7.2 Hz, 3H), 1.07 (d, J = 6.3 Hz, 3H), 0.87 (d, J = 6.8 Hz, 3H), 0.75 (d, J = 6.7 Hz, 3H). $^{19}$F NMR (471 MHz, CDCl$_3$) δ -57.9. |
| 307 | | IR (thin film) 3363, 2976, 2933, 2875, 1712, 1508, 1238, 1165, 1050 cm$^{-1}$ | | $^1$H NMR (500 MHz, CDCl$_3$) δ 7.06-6.91 (m, 2H), 6.90-6.75 (m, 2H), 5.35 (dq, J = 8.9, 6.3 Hz, 1H), 5.08 (d, J = 8.0 Hz, 1H), 4.52 (hept, J = 6.1 Hz, 1H), 4.36-4.22 (m, 1H), 2.63 (dd, J = 9.0, 6.1 Hz, 1H), 2.14-2.00 (m, 1H), 1.45 (s, 9H), 1.38 (d, J = 7.2 Hz, 3H), 1.33 (d, J = 6.1 Hz, 6H), 1.06 (d, J = 6.2 Hz, 3H), 0.84 (d, J = 6.8 Hz, 3H), 0.75 (d, J = 6.7 Hz, 3H). $^{13}$C NMR (126 MHz, CDCl$_3$) δ 172.8, 156.6, 155.0, 130.6, 130.3, 115.2, 79.7, 72.7, 69.7, 60.4, 55.8, 49.5, 28.3, 28.2, 22.1, 21.4, 18.9, 18.3, 18.0. |

TABLE 2-continued

Analytical Data

| Cmpd. No. | Melting Point (° C.) | IR (cm$^{-1}$) | MASS SPEC | NMR |
|---|---|---|---|---|
| 308 | | IR (thin film) 3357, 2976, 2933, 2874, 1712, 1489, 1238, 1160, 1050, 732 cm$^{-1}$ | HRMS-ESI (m/z) [M + Na]$^+$ calcd for C$_{23}$H$_{37}$NO$_5$Na, 430.2569; found, 430.2431 | $^1$H NMR (500 MHz, CDCl$_3$) δ 7.23-7.11 (m, 1H), 7.06 (dd, J = 7.8, 1.8 Hz, 1H), 6.92-6.78 (m, 2H), 5.42 (s, 1H), 5.13 (d, J = 7.7 Hz, 1H), 4.56 (hept, J = 6.1 Hz, 1H), 4.30 (t, J = 7.5 Hz, 1H), 3.44 (s, 1H), 2.12 (h, J = 6.7 Hz, 1H), 1.45 (s, 9H), 1.40 (d, J = 7.2 Hz, 3H), 1.39-1.26 (m, 6H), 1.04 (d, J = 6.2 Hz, 3H), 0.83 (d, J = 6.8 Hz, 3H), 0.76 (d, J = 6.8 Hz, 3H). |
| 309 | | IR (thin film) 3361, 2962, 1713, 1512, 1246, 1165, 1050 cm$^{-1}$ | HRMS-ESI (m/z) [M + Na]$^+$ calcd for C$_{21}$H$_{33}$NO$_5$Na, 402.2251; found, 402.2221 | $^1$H NMR (400 MHz, CDCl$_3$) δ 7.09-6.90 (m, 2H), 6.90-6.77 (m, 2H), 5.35 (dq, J = 8.9, 6.3 Hz, 1H), 5.07 (s, 1H), 4.28 (t, J = 7.6 Hz, 1H), 3.80 (s, 3H), 2.64 (dd, J = 8.9, 6.2 Hz, 1H), 2.07 (h, J = 6.7 Hz, 1H), 1.45 (s, 9H), 1.38 (d, J = 7.2 Hz, 3H), 1.06 (d, J = 6.2 Hz, 3H), 0.84 (d, J = 6.8 Hz, 3H), 0.75 (d, J = 6.8 Hz, 3H). |
| 310 | | | ESIMS m/z 400 ([M + Na]$^+$) | $^1$H NMR (400 MHz, CDCl$_3$) δ 7.23-7.04 (m, 4H), 5.38 (dq, J = 9.6, 6.1 Hz, 1H), 5.09 (s, 1H), 4.41-4.22 (m, 1H), 3.32-3.07 (m, 1H), 2.34 (d, J = 2.6 Hz, 3H), 1.89 (dtd, J = 12.5, 6.2, 5.6, 3.2 Hz, 1H), 1.54-1.33 (m, 12H), 1.32-1.20 (m, 1H), 1.14-0.69 (m, 10H). |
| 311 | | | ESIMS m/z 392 ([M + H]$^+$) | $^1$H NMR (400 MHz, CDCl$_3$) δ 7.20-7.03 (m, 4H), 5.41 (dq, J = 8.3, 6.2 Hz, 1H), 5.06 (s, 1H), 4.27 (s, 1H), 3.30 (t, J = 7.6 Hz, 1H), 2.33 (s, 3H), 1.72-1.58 (m, 1H), 1.44 (s, 10H), 1.36 (dd, J = 10.9, 7.2 Hz, 5H), 1.08 (d, J = 6.3 Hz, 4H), 0.93 (t, J = 7.4 Hz, 3H), 0.78 (t, J = 7.3 Hz, 3H). |
| 312 | | | | $^1$H NMR (400 MHz, CDCl$_3$) δ 6.67 (d, J = 9.3 Hz, 2H), 5.54 (ddt, J = 8.1, 6.3, 2.0 Hz, 1H), 5.04 (s, 1H), 4.27 (d, J = 8.5 Hz, 1H), 3.17 (t, J = 7.7 Hz, 1H), 2.30-2.15 (m, 1H), 1.45 (s, 9H), 1.37 (d, J = 7.3 Hz, 3H), 1.12 (dt, J = 6.3, 1.2 Hz, 3H), 0.95 (d, J = 6.6 Hz, 3H), 0.77 (dt, J = 6.8, 1.4 Hz, 3H). $^{19}$F NMR (376 MHz, CDCl$_3$) δ −103.51, −108.05, −110.09. |
| 313 | | | | $^1$H NMR (400 MHz, CDCl$_3$) δ 7.09 (dtt, J = 8.3, 5.6, 2.7 Hz, 3H), 5.47-5.32 (m, 1H), 5.03 (s, 1H), 4.26 (s, 1H), 3.13 (t, J = 7.7 Hz, 1H), 2.10 (q, J = 6.8 Hz, 1H), 1.45 (s, 9H), 1.37 (d, J = 7.2 Hz, 3H), 1.09 (d, J = 6.3 Hz, 3H), 0.99-0.85 (m, 3H), 0.75 (d, J = 6.8 Hz, 3H). $^{19}$F NMR (376 MHz, CDCl$_3$) δ −112.35. |
| 314 | | | | $^1$H NMR (400 MHz, CDCl$_3$) δ 7.23 (dd, J = 8.4, 1.2 Hz, 1H), 7.16 (td, J = 8.0, 5.6 Hz, 1H), 6.96 (ddd, J = 10.9, 8.1, 1.5 Hz, 1H), 5.58 (ddq, J = 12.5, 9.1, 3.1 Hz, 1H), 5.07 (s, 1H), 4.30 (d, J = 8.5 Hz, 1H), 3.60-3.48 (m, 1H), 2.24 (dqd, J = 13.7, 6.8, 2.1 Hz, 1H), 1.45 (s, 9H), 1.40 (d, J = 7.2 Hz, 3H), 1.08 (dd, J = 6.3, 1.8 Hz, 3H), 0.99 (d, J = 6.8 Hz, 3H), 0.78 (dd, J = 6.8, 2.8 Hz, 3H). $^{19}$F NMR (376 MHz, CDCl$_3$) δ −105.00 |
| 315 | | | | $^1$H NMR (400 MHz, CDCl$_3$) δ 7.17 (t, J = 7.8 Hz, 1H), 7.05 (d, J = 7.6 Hz, 1H), 6.89 (s, 2H), 5.45-5.32 (m, 1H), 5.08 (s, 1H), 4.28 (s, 1H), 2.65 (dd, J = 8.9, 6.2 Hz, 1H), 2.33 (s, 3H), 2.14-2.04 (m, 1H), 1.45 (s, 9H), 1.39 (d, J = 7.3 Hz, 3H), 1.07 (d, J = 6.2 Hz, 3H), 0.85 (d, J = 6.8 Hz, 3H), 0.76 (d, J = 6.8 Hz, 3H). |
| 316 | | | ESIMS m/z 386 ([M + H]$^+$) | $^1$H NMR (400 MHz, CDCl$_3$) δ 7.00 (td, J = 9.1, 4.7 Hz, 1H), 6.88 (dddd, J = |

TABLE 2-continued

Analytical Data

| Cmpd. No. | Melting Point (° C.) | IR (cm⁻¹) | MASS SPEC | NMR |
|---|---|---|---|---|
| | | | | 24.6, 8.9, 6.3, 3.3 Hz, 2H), 5.49-5.28 (m, 1H), 5.04 (s, 1H), 4.26 (d, J = 9.3 Hz, 1H), 3.15 (t, J = 7.7 Hz, 1H), 2.09 (d, J = 7.3 Hz, 3H), 1.12 (d, J = 6.3 Hz, 3H), 0.94 (d, J = 6.7 Hz, 3H), 0.78 (d, J = 6.7 Hz, 3H). $^{19}$F NMR (376 MHz, CDCl$_3$) δ -118.45- -122.20 (m). |
| 317 | | IR (thin film) 3371, 2961, 1740, 1650, 1533, 1497, 1437, 1262, 1240, 1215, 1188, 801, 729 cm⁻¹ | HRMS-ESI (m/z) [M + H]⁺ calcd for C$_{22}$H$_{28}$FN$_2$O$_5$, 419.1977; found, 419.1976 | $^1$H NMR (400 MHz, CDCl$_3$) δ 12.06-12.02 (m, 1H), 8.47 (t, J = 5.8 Hz, 1H), 7.99 (d, J = 5.3 Hz, 1H), 7.05 (dd, J = 8.3, 5.9 Hz, 1H), 6.90-6.81 (m, 3H), 5.45 (dq, J = 8.2, 6.3 Hz, 1H), 4.19 (d, J = 5.7 Hz, 2H), 3.95 (s, 3H), 3.04 (t, J = 7.7 Hz, 1H), 2.30 (s, 3H), 2.08 (h, J = 6.8 Hz, 1H), 1.09 (d, J = 6.3 Hz, 3H), 0.93 (d, J = 6.7 Hz, 3H), 0.77 (d, J = 6.8 Hz, 3H). $^{13}$C NMR (101 MHz, CDCl$_3$) δ 169.35, 168.66, 160.95 (d, J = 244.4 Hz), 155.42, 148.73, 140.59, 139.90 (d, J = 7.5 Hz), 133.63 (d, J = 3.3 Hz), 130.43, 129.20 (d, J = 6.9 Hz), 116.98 (d, J = 20.5 Hz), 112.35 (d, J = 20.7 Hz), 109.57, 74.06, 56.09, 49.55, 41.17, 29.95, 20.95, 20.80, 19.71, 17.46. $^{19}$F NMR (376 MHz, CDCl$_3$) δ -117.31. |
| 318 | | IR (thin film) 3371, 2963, 1731, 1651, 1527, 1262, 1240, 730 cm⁻¹ | HRMS-ESI (m/z) [M + H]⁺ calcd for C$_{25}$H$_{34}$FN$_2$O$_5$, 461.2446; found, 461.2453 | $^1$H NMR (400 MHz, CDCl$_3$) δ 12.16 (s, 1H), 8.43 (d, J = 9.5 Hz, 1H), 7.99 (d, J = 5.2 Hz, 1H), 7.03 (dd, J = 8.7, 5.9 Hz, 1H), 6.89 (d, J = 5.2 Hz, 1H), 6.83 (td, J = 8.4, 2.9 Hz, 1H), 6.77 (dd, J = 9.9, 2.8 Hz, 1H), 5.37 (dq, J = 9.1, 6.1 Hz, 1H), 4.66 (dd, J = 9.5, 4.9 Hz, 1H), 3.96 (s, 3H), 3.09 (dd, J = 9.2, 6.1 Hz, 1H), 2.42-2.29 (m, 1H), 2.27 (s, 3H), 2.20-2.06 (m, 1H), 1.07 (d, J = 6.2 Hz, 3H), 1.06 (d, J = 6.9 Hz, 3H), 1.01 (d, J = 6.9 Hz, 3H), 0.82 (d, J = 6.8 Hz, 3H), 0.76 (d, J = 6.9 Hz, 3H). $^{13}$C NMR (101 MHz, CDCl$_3$) δ 170.53, 169.10, 160.93 (d, J = 244.6 Hz), 155.43, 148.78, 140.48, 139.88 (d, J = 7.3 Hz), 133.35 (d, J = 3.3 Hz), 130.52, 129.15 (d, J = 7.9 Hz), 116.98 (d, J = 20.5 Hz), 112.31 (d, J = 20.6 Hz), 109.50, 73.81, 57.39, 56.10, 49.30, 31.34, 29.46, 20.88, 19.48, 18.63, 18.11, 17.43. $^{19}$F NMR (376 MHz, CDCl$_3$) δ -117.29. |
| 319 | | IR (thin film) 3374, 2963, 1731, 1651, 1526, 1261, 1240, 1046, 800, 730 cm⁻¹ | HRMS-ESI (m/z) [M + H]⁺ calcd for C$_{26}$H$_{36}$FN$_2$O$_5$, 475.2603; found, 475.2599 | $^1$H NMR (400 MHz, CDCl$_3$) δ 12.17 (s, 1H), 8.42 (d, J = 9.5 Hz, 1H), 7.98 (d, J = 5.2 Hz, 1H), 7.03 (dd, J = 8.7, 5.9 Hz, 1H), 6.89 (d, J = 5.3 Hz, 1H), 6.83 (td, J = 8.4, 2.9 Hz, 1H), 6.77 (dd, J = 9.9, 2.8 Hz, 1H), 5.37 (dq, J = 9.2, 6.2 Hz, 1H), 4.71 (dd, J = 9.5, 4.9 Hz, 1H), 3.96 (s, 3H), 3.09 (dd, J = 9.3, 6.0 Hz, 1H), 2.27 (s, 3H), 2.19-2.03 (m, 2H), 1.54 (dddd, J = 14.9, 11.4, 6.8, 4.0 Hz, 1H), 1.28 (tdd, J = 14.3, 9.8, 7.3 Hz, 1H), 1.07 (d, J = 6.2 Hz, 3H), 1.04 (d, J = 6.8 Hz, 3H), 1.01-0.87 (m, 3H), 0.81 (d, J = 6.8 Hz, 3H), 0.76 (d, J = 6.9 Hz, 3H). $^{13}$C NMR (101 MHz, CDCl$_3$) δ 170.48, 168.99, 160.93 (d, J = 244.4 Hz), 155.43, 148.77, 140.47, 139.89 (d, J = 7.3 Hz), 133.30 (d, J = 3.3 Hz), 130.53, 129.16 (d, J = 7.8 Hz), 116.98 (d, J = 20.5 Hz), 112.30 (d, J = 20.6 Hz), 109.49, 73.77, 56.98, 56.10, 49.29, 37.88, 29.40, 24.69, 20.88, 18.48, 18.15, 15.83, 11.48. $^{19}$F NMR (376 MHz, CDCl$_3$) δ -117.28. |

TABLE 2-continued

Analytical Data

| Cmpd. No. | Melting Point (° C.) | IR (cm⁻¹) | MASS SPEC | NMR |
|---|---|---|---|---|
| 320 | | IR (thin film) 3367, 2959, 1733, 1650, 1529, 1263, 1244, 1049, 800, 731 cm⁻¹ | HRMS-ESI (m/z) [M + H]⁺ calcd for $C_{26}H_{36}FN_2O_5$, 475.2603; found, 475.2600 | ¹H NMR (400 MHz, CDCl₃) δ 12.15 (s, 1H), 8.28 (d, J = 9.0 Hz, 1H), 7.98 (d, J = 5.2 Hz, 1H), 7.04 (dd, J = 8.7, 5.9 Hz, 1H), 6.89 (d, J = 5.2 Hz, 1H), 6.83 (td, J = 8.4, 2.9 Hz, 1H), 6.77 (dd, J = 9.9, 2.8 Hz, 1H), 5.35 (dq, J = 8.8, 6.2 Hz, 1H), 4.79-4.68 (m, 1H), 3.95 (s, 3H), 3.07 (dd, J = 8.8, 6.6 Hz, 1H), 2.27 (s, 3H), 2.08 (h, J = 6.8 Hz, 1H), 1.80-1.66 (m, 2H), 1.08 (d, J = 6.2 Hz, 3H), 1.05-0.86 (m, 7H), 0.84 (d, J = 6.7 Hz, 3H), 0.75 (d, J = 6.8 Hz, 3H ). ¹³C NMR (101 MHz, CDCl₃) δ 171.49, 168.88, 160.90 (d, J = 244.3 Hz), 155.43, 148.80, 140.41, 139.83 (d, J = 7.3 Hz), 133.54 (d, J = 3.3 Hz), 130.45, 129.10 (d, J = 7.1 Hz), 116.91 (d, J = 20.4 Hz), 112.28 (d, J = 20.7 Hz), 109.48, 73.83, 56.08, 50.94, 49.28, 41.40, 29.68, 24.91, 23.00, 21.70, 20.89, 18.98, 17.74. ¹⁹F NMR (376 MHz, CDCl₃) δ −117.37. |
| 321 | | IR (thin film) 3370, 2959, 2873, 1731, 1648, 1576, 1526, 1480, 1450, 1325, 1280, 1262, 1241, 1149, 1046, 953, 800, 730 cm⁻¹ | ESIMS m/z 429.2 ([M + H]⁺) | ¹H NMR (500 MHz, CDCl₃) δ 12.15 (s, 1H), 8.50 (d, J = 7.9 Hz, 1H), 8.00 (d, J = 5.2 Hz, 1H), 7.02 (d, J = 7.6 Hz, 1H), 6.95-6.86 (m, 3H), 5.39 (dq, J = 9.3, 6.2 Hz, 1H), 4.81-4.60 (m, 1H), 3.95 (s, 3H), 3.20-2.96 (m, 1H), 2.30 (s, 3H), 2.27 (s, 3H), 2.14 (dq, J = 13.4, 6.7 Hz, 1H), 1.57 (d, J = 7.2 Hz, 3H), 1.07 (d, J = 6.2 Hz, 3H), 0.84 (d, J = 6.8 Hz, 3H), 0.81 (d, J = 6.8 Hz, 3H). |
| 322 | | IR (thin film) 3370, 2962, 2875, 1734, 1649, 1576, 1527, 1480, 1453, 1324, 1280, 1263, 1241, 1163, 1043, 786, 732 cm⁻¹ | ESIMS m/z 433.2 ([M + H]⁺) | ¹H NMR (500 MHz, CDCl₃) δ 12.12 (s, 1H), 8.48 (d, J = 7.9 Hz, 1H), 8.00 (d, J = 5.2 Hz, 1H), 7.12 (td, J = 8.0, 5.9 Hz, 1H), 6.94-6.85 (m, 3H), 5.40 (dq, J = 9.0, 6.2 Hz, 1H), 4.70 (p, J = 7.3 Hz, 1H), 3.95 (s, 3H), 3.15 (t, J = 7.7 Hz, 1H), 2.22 (d, J = 2.4 Hz, 3H), 2.14 (h, J = 6.8 Hz, 1H), 1.56 (d, J = 7.2 Hz, 3H), 1.08 (d, J = 6.2 Hz, 3H), 0.86 (d, J = 6.8 Hz, 3H), 0.79 (d, J = 6.9 Hz, 3H). |
| 323 | | IR (thin film) 3370, 2962, 1733, 1648, 1576, 1527, 1480, 1452, 1280, 1262, 1241, 1216, 1148, 1049, 849, 800, 757, 730 cm⁻¹ | ESIMS m/z 419.2 ([M + H]⁺) | ¹H NMR (500 MHz, CDCl₃) δ 12.15 (s, 1H), 8.49 (d, J = 7.9 Hz, 1H), 8.00 (d, J = 5.2 Hz, 1H), 7.24-7.18 (m, 1H), 7.15 (td, J = 7.4, 1.9 Hz, 1H), 7.09 (td, J = 7.5, 1.3 Hz, 1H), 7.00 (ddd, J = 10.3, 8.2, 1.2 Hz, 1H), 6.88 (d, J = 5.2 Hz, 1H), 5.47 (dqd, J = 7.6, 6.4, 1.2 Hz, 1H), 4.73-4.62 (m, 1H), 3.95 (s, 3H), 3.20 (t, J = 7.7 Hz, 1H), 2.18-2.08 (m, 1H), 1.55 (d, J = 7.3 Hz, 3H), 1.13 (d, J = 6.3 Hz, 3H), 0.92 (d, J = 6.8 Hz, 3H), 0.77 (d, J = 6.7 Hz, 3H). |
| 324 | | IR (thin film) 3370, 2959, 1731, 1648, 1576, 1526, 1480, 1450, 1438, 1280, 1262, 1241, 1149, 1046, 953, 819, 799, 730 cm⁻¹ | ESIMS m/z 433.2 ([M + H]⁺) | ¹H NMR (500 MHz, CDCl₃) δ 12.12 (s, 1H), 8.46 (d, J = 8.0 Hz, 1H), 7.99 (d, J = 5.2 Hz, 1H), 7.07 (dd, J = 8.3, 6.2 Hz, 1H), 6.88 (d, J = 5.2 Hz, 1H), 6.84-6.76 (m, 2H), 5.36 (dq, J = 8.7, 6.2 Hz, 1H), 4.75-4.61 (m, 1H), 3.95 (s, 3H), 3.11 (t, J = 7.9 Hz, 1H), 2.27 (s, 3H), 2.11 (h, J = 6.7 Hz, 1H), 1.55 (d, J = 7.2 Hz, 3H), 1.10 (d, J = 6.3 Hz, 3H), 0.88 (d, J = 6.8 Hz, 3H), 0.80 (d, J = 6.8 Hz, 3H). |
| 325 | | IR (thin film) 3370, 2961, 1733, 1648, 1576, 1527, 1497, 1451, 1280, 1261, 1240, | ESIMS m/z 429.2 ([M + H]⁺) | ¹H NMR (500 MHz, CDCl₃) δ 12.15 (s, 1H), 8.50 (d, J = 7.9 Hz, 1H), 8.00 (d, J = 5.2 Hz, 1H), 7.02-6.94 (m, 3H), 6.88 (d, J = 5.2 Hz, 1H), 5.39 (dq, J = 9.2, 6.2 Hz, 1H), 4.71 (p, J = 7.3 Hz, 1H), 3.95 (s, 3H), 3.10 (dd, J = 9.3, 6.1 Hz, 1H), 2.28 (s, 6H), 2.12 (dq, J = 13.4, 6.8 |

TABLE 2-continued

Analytical Data

| Cmpd. No. | Melting Point (° C.) | IR (cm⁻¹) | MASS SPEC | NMR |
|---|---|---|---|---|
| | | 1148, 1048, 952, 800, 730 cm⁻¹ | | Hz, 1H), 1.56 (d, J = 7.2 Hz, 3H), 1.07 (d, J = 6.2 Hz, 3H), 0.84 (d, J = 6.8 Hz, 3H), 0.80 (d, J = 6.8 Hz, 3H). |
| 326 | | IR (thin film) 3369, 2961, 1732, 1648, 1576, 1526, 1480, 1451, 1384, 1359, 1262, 1241, 1213, 1150, 1045, 849, 800, 779, 729 cm⁻¹ | ESIMS m/z 429.2 ([M + H]⁺) | ¹H NMR (500 MHz, CDCl₃) δ 12.15 (s, 1H), 8.51 (d, J = 7.7 Hz, 1H), 8.00 (d, J = 2873, 5.2 Hz, 1H), 7.09-7.00 (m, 2H), 6.95 (dd, J = 7.4, 1.8 Hz, 1H), 6.88 (d, J = 5.3 Hz, 1H), 5.41 (dq, J = 9.0, 6.2 Hz, 1H), 4.76-4.63 (m, 1H), 3.95 (s, 3H), 3.25 (dd, J = 9.2, 6.1 Hz, 1H), 2.28 (s, 3H), 2.23 (s, 3H), 2.18-2.08 (m, 1H), 1.57 (d, J = 7.2 Hz, 3H), 1.06 (d, J = 6.3 Hz, 3H), 0.84 (d, J = 6.7 Hz, 3H), 0.79 (d, J = 6.8 Hz, 3H). |
| 327 | | IR (thin film) 3369, 2960, 2932, 2874, 1732, 1649, 1527, 1451, 1150, 1053, 731 cm⁻¹ | ESIMS m/z 415 ([M + H]⁺) | ¹H NMR (500 MHz, CDCl₃) δ 12.15 (d, J = 0.6 Hz, 1H), 8.50 (d, J = 7.9 Hz, 1H), 8.00 (d, J = 5.2 Hz, 1H), 7.19-7.06 (m, 4H), 6.88 (d, J = 5.2 Hz, 1H), 5.41 (dq, J = 9.2, 6.2 Hz, 1H), 4.76-4.66 (m, 1H), 3.95 (s, 3H), 3.15 (dd, J = 9.2, 6.2 Hz, 1H), 2.32 (s, 3H), 2.15 (dq, J = 13.4, 6.7 Hz, 1H), 1.56 (d, J = 7.2 Hz, 3H), 1.08 (d, J = 6.2 Hz, 3H), 0.86 (d, J = 6.8 Hz, 3H), 0.81 (d, J = 6.8 Hz, 3H). |
| 328 | | IR (thin film) 2964, 1733, 1714, 1652, 1528, 1503, 1280, 1263, 966, 848 cm⁻¹ | HRMS-ESI (m/z) [M + H]⁺ calcd for C₂₂H₂₇F₂N₂O₅, 437.1883; found, 437.1879 | ¹H NMR (500 MHz, CDCl₃) δ 12.14 (d, J = 0.6 Hz, 1H), 8.45 (d, J = 7.9 Hz, 1H), 7.99 (d, J = 5.2 Hz, 1H), 7.10 (td, J = 8.4, 6.4 Hz, 1H), 6.88 (d, J = 5.2 Hz, 1H), 6.86-6.81 (m, 1H), 6.74 (ddd, J = 10.2, 8.9, 2.6 Hz, 1H), 5.52-5.31 (m, 1H), 4.79-4.55 (m, 1H), 3.95 (s, 3H), 3.14 (t, J = 7.7 Hz, 1H), 2.09 (h, J = 6.8 Hz, 1H), 1.58-1.53 (m, 3H), 1.12 (d, J = 6.3 Hz, 3H), 0.93 (d, J = 6.7 Hz, 3H), 0.75 (d, J = 6.7 Hz, 3H). |
| 329 | | IR (thin film) 2962, 1733, 1650, 1576, 1528, 1481, 1450, 1362, 1327, 1263, 1242, 1149, 1050, 800 cm⁻¹ | HRMS-ESI (m/z) [M + H]⁺ calcd for C₂₃H₃₀FN₂O₅, 433.2133; found, 433.2129 | ¹H NMR (500 MHz, CDCl₃) δ 12.16 (d, J = 0.7 Hz, 1H), 8.49 (d, J = 8.0 Hz, 1H), 8.00 (d, J = 5.2 Hz, 1H), 7.01 (t, J = 7.7 Hz, 1H), 6.93-6.84 (m, 2H), 6.83-6.78 (m, 1H), 5.45 (dqd, J = 7.6, 6.3, 1.2 Hz, 1H), 4.73-4.60 (m, 1H), 3.95 (s, 3H), 3.14 (t, J = 7.7 Hz, 1H), 2.32 (s, 3H), 2.10 (h, J = 6.8 Hz, 1H), 1.55 (d, J = 7.2 Hz, 3H), 1.12 (d, J = 6.3 Hz, 3H), 1.01-0.88 (m, 3H), 0.76 (d, J = 6.7 Hz, 3H). |
| 330 | | IR (thin film) 2963, 1734, 1648, 1576, 1527, 1478, 1451, 1438, 1262, 1150, 1044, 799, 730 cm⁻¹ | HRMS-ESI (m/z) [M + H]⁺ calcd for C₂₂H₂₇Cl₂N₂O₅, 469.1292; found, 469.1293 | ¹H NMR (500 MHz, CDCl₃) δ 12.13 (d, J = 0.6 Hz, 1H), 8.44 (d, J = 8.0 Hz, 1H), 7.99 (d, J = 5.2 Hz, 1H), 7.34 (d, J = 2.2 Hz, 1H), 7.22 (dd, J = 8.4, 2.2 Hz, 1H), 7.13 (d, J = 8.4 Hz, 1H), 6.88 (d, J = 5.2 Hz, 1H), 5.45-5.32 (m, 1H), 4.78-4.61 (m, 1H), 3.95 (s, 3H), 3.52 (s, 1H), 2.09 (dt, J = 13.7, 6.9 Hz, 1H), 1.55 (d, J = 7.2 Hz, 3H), 1.12 (d, J = 6.3 Hz, 3H), 0.93 (d, J = 6.7 Hz, 3H), 0.76 (d, J = 6.8 Hz, 3H). |
| 331 | | IR (thin film) 2965, 1734, 1648, 1576, 1528, 1502, 1480, 1438, 1322, 1263, 1241, 1150, 1060, 964, 848, 800, 731 cm⁻¹ | HRMS-ESI (m/z) [M + H]⁺ calcd for C₂₂H₂₇F₂N₂O₅, 437.1883; found, 437.1887 | ¹H NMR (500 MHz, CDCl₃) δ 12.24-11.76 (m, 1H), 8.42 (d, J = 8.0 Hz, 1H), 8.01 (d, J = 5.2 Hz, 1H), 7.25-7.10 (m, 1H), 6.89 (d, J = 5.1 Hz, 1H), 6.74 (dddd, J = 14.1, 11.6, 7.5, 1.9 Hz, 2H), 5.50-5.41 (m, 1H), 4.78-4.62 (m, 1H), 3.95 (s, 3H), 2.84 (dd, J = 9.1, 5.1 Hz, 1H), 2.00 (dq, J = 9.0, 6.9 Hz, 1H), 1.42 (d, J = 7.2 Hz, 3H), 1.12 (d, J = 6.3 Hz, 3H), 0.99 (d, J = 6.6 Hz, 3H), 0.70 (d, J = 6.7 Hz, 3H). |
| 332 | | IR (thin film) 2964, 1733, 1648, 1576, 1527, 1438, 1323, 1262, 1132, | | ¹H NMR (500 MHz, CDCl₃) δ 12.14 (d, J = 0.7 Hz, 1H), 8.46 (d, J = 8.0 Hz, 1H), 8.01 (d, J = 5.2 Hz, 1H), 7.13 (t, J = 7.9 Hz, 1H), 6.88 (d, J = 5.3 Hz, 1H), 6.86-6.71 (m, 2H), 5.55-5.40 (m, 1H), 4.80-4.59 (m, 1H), 3.95 (s, 3H), 2.85 (dd, J = |

TABLE 2-continued

Analytical Data

| Cmpd. No. | Melting Point (° C.) | IR (cm$^{-1}$) | MASS SPEC | NMR |
|---|---|---|---|---|
| | | 800, 730 cm$^{-1}$ | | 8.9, 5.3 Hz, 1H), 2.30 (s, 3H), 2.02 (dp, J = 13.6, 6.8 Hz, 1H), 1.40 (d, J = 7.2 Hz, 3H), 1.13 (d, J = 6.2 Hz, 3H), 1.01-0.89 (m, 3H), 0.72 (d, J = 6.6 Hz, 3H). $^{13}$C NMR (126 MHz, CDCl$_3$) δ 171.60, 168.63, 161.50 (d, J = 243.0 Hz), 155.39, 148.77, 140.46, 138.17, 130.49, 124.61, 123.34 (d, J = 14.9 Hz), 115.43 (d, J = 23.9 Hz), 109.44, 72.12, 56.09, 48.06, 34.67, 31.59, 29.04, 20.91, 18.19. |
| 333 | | IR (thin film) 2964, 2872, 1734, 1649, 1576, 1528, 1472, 1438, 1323, 1263, 1241, 1129, 800 cm$^{-1}$ | HRMS-ESI (m/z) [M + H]$^+$ calcd for C$_{22}$H$_{27}$Cl$_2$N$_2$O$_5$, 469.1292; found, 469.1282 | $^1$H NMR (500 MHz, CDCl$_3$) δ 12.14 (d, J = 0.6 Hz, 1H), 8.43 (d, J = 7.9 Hz, 1H), 8.02 (d, J = 5.3 Hz, 1H), 7.37 (d, J = 2.2 Hz, 1H), 7.28 (d, J = 8.5 Hz, 1H), 7.05 (dd, J = 8.5, 2.3 Hz, 1H), 6.90 (d, J = 5.1 Hz, 1H), 5.46 (qd, J = 6.3, 4.7 Hz, 1H), 4.77-4.65 (m, 1H), 3.96 (s, 3H), 3.12 (dd, J = 9.6, 4.5 Hz, 1H), 2.02-1.92 (m, 1H), 1.48 (d, J = 7.2 Hz, 3H), 1.08 (d, J = 6.3 Hz, 3H), 1.02 (d, J = 6.6 Hz, 3H), 0.68 (d, J = 6.7 Hz, 3H). $^{13}$C NMR (126 MHz, CDCl$_3$) δ 171.40, 168.71, 155.48, 148.85, 140.54, 136.78, 136.31, 132.55, 130.48, 130.37, 128.95, 127.06, 109.56, 72.00, 56.13, 51.39, 48.06, 34.53, 30.14, 20.75, 20.47, 18.22. |
| 334 | | IR (thin film) 3368, 2961, 1731, 1648, 1528, 1482, 1438, 1240, 1037, 729 cm$^{-1}$ | HRMS-ESI (m/z) [M + H]$^+$ calcd for C$_{23}$H$_{29}$N$_2$O$_7$, 445.1969; found, 445.1961 | $^1$H NMR (500 MHz, CDCl$_3$) δ 12.14 (s, 1H), 8.48 (d, J = 7.9 Hz, 1H), 7.99 (d, J = 5.2 Hz, 1H), 6.87 (d, J = 5.2 Hz, 1H), 6.69 (d, J = 8.0 Hz, 1H), 6.59 (d, J = 1.7 Hz, 1H), 6.53 (dd, J = 8.0, 1.7 Hz, 1H), 5.92 (q, J = 1.6 Hz, 2H), 5.34 (dq, J = 8.5, 6.3 Hz, 1H), 4.75-4.60 (m, 1H), 3.94 (s, 3H), 2.63 (dd, J = 8.5, 6.6 Hz, 1H), 2.03 (dq, J = 13.5, 6.8 Hz, 1H), 1.54 (d, J = 7.2 Hz, 3H), 1.11 (d, J = 6.3 Hz, 3H), 0.85 (d, J = 6.7 Hz, 3H), 0.76 (d, J = 6.7 Hz, 3H). |
| 335 | | IR (thin film) 3370, 2964, 1735, 1649, 1528, 1258, 1217, 1153 cm$^{-1}$ | HRMS-ESI (m/z) [M + H]$^+$ calcd for C$_{23}$H$_{28}$F$_3$N$_2$O$_6$, 485.1894; found, 485.1896 | $^1$H NMR (500 MHz, CDCl$_3$) δ 12.13 (d, J = 0.6 Hz, 1H), 8.44 (d, J = 7.9 Hz, 1H), 7.99 (d, J = 5.2 Hz, 1H), 7.15-7.05 (m, 4H), 6.88 (d, J = 5.2 Hz, 1H), 5.41 (dq, J = 8.2, 6.3 Hz, 1H), 4.76-4.59 (m, 1H), 3.95 (s, 3H), 2.73 (dd, J = 8.2, 7.0 Hz, 1H), 2.09 (h, J = 6.8 Hz, 1H), 1.54 (d, J = 7.2 Hz, 3H), 1.10 (d, J = 6.4 Hz, 3H), 0.88 (d, J = 6.7 Hz, 3H), 0.74 (d, J = 6.7 Hz, 3H). $^{19}$F NMR (471 MHz, CDCl$_3$) δ −57.8. |
| 336 | | IR (thin film) 3369, 2974, 1732, 1649, 1527, 1509, 1239, 953, 730 cm$^{-1}$ | HRMS-ESI (m/z) [M + H]$^+$ calcd for C$_{25}$H$_{35}$N$_2$O$_6$, 459.2490; found, 459.2468 | $^1$H NMR (500 MHz, CDCl$_3$) δ 12.16 (s, 1H), 8.50 (d, J = 7.8 Hz, 1H), 8.00 (d, J = 5.2 Hz, 1H), 7.08-6.94 (m, 2H), 6.87 (d, J = 5.2 Hz, 1H), 6.84-6.75 (m, 2H), 5.38 (dq, J = 8.7, 6.3 Hz, 1H), 4.79-4.58 (m, 1H), 4.50 (hept, J = 6.1 Hz, 1H), 3.95 (s, 3H), 2.65 (dd, J = 8.7, 6.3 Hz, 1H), 2.15-1.97 (m, 1H), 1.55 (d, J = 7.2 Hz, 3H), 1.33 (d, J = 6.0 Hz, 6H), 1.10 (d, J = 6.3 Hz, 3H), 0.84 (d, J = 6.7 Hz, 3H), 0.75 (d, J = 6.7 Hz, 3H). |
| 337 | | IR (thin film) 3369, 2972, 1733, 1649, 1527, 1450, 1238, 953, 752, 732 cm$^{-1}$ | HRMS-ESI (m/z) [M + H]$^+$ calcd for C$_{25}$H$_{35}$N$_2$O$_6$, 459.2490; found, 459.2476 | $^1$H NMR (500 MHz, CDCl$_3$) δ 12.16 (s, 1H), 8.54 (d, J = 7.9 Hz, 1H), 7.99 (d, J = 5.2 Hz, 1H), 7.14 (ddd, J = 8.5, 7.5, 1.7 Hz, 1H), 7.06 (dd, J = 7.6, 1.8 Hz, 1H), 6.93-6.74 (m, 3H), 5.47 (s, 1H), 4.84-4.62 (m, 1H), 4.54 (hept, J = 6.0 Hz, 1H), 3.94 (s, 3H), 3.45 (s, 1H), 2.12 (hept, J = 6.8 Hz, 1H), 1.57 (d, J = 7.2 Hz, 3H), 1.33 (d, J = 6.0 Hz, 3H), 1.31 (d, J = 6.0 Hz, 3H), 1.08 (d, J = 6.2 Hz, 3H), 0.83 (d, J = 6.8 Hz, 3H), 0.76 (d, J = 6.8 Hz, 3H). |
| 338 | | IR (thin film) 3368, | HRMS-ESI (m/z) [M + Na]$^+$ calcd for C$_{23}$H$_{30}$N$_2$O$_6$Na, | $^1$H NMR (500 MHz, CDCl$_3$) δ 12.16 (s, 1H), 8.49 (d, J = 7.9 Hz, 1H), 8.00 (d, J = |

TABLE 2-continued

Analytical Data

| Cmpd. No. | Melting Point (° C.) | IR (cm$^{-1}$) | MASS SPEC | NMR |
|---|---|---|---|---|
| | | 2960, 1732, 1649, 1512, 1453, 1241, 800, 730 cm$^{-1}$ | 453.1996; found, 453.1983 | 5.2 Hz, 1H), 7.00 (d, J = 8.6 Hz, 2H), 6.88 (d, J = 5.2 Hz, 1H), 6.84-6.75 (m, 2H), 5.39 (dq, J = 8.6, 6.3 Hz, 1H), 4.76-4.63 (m, 1H), 3.95 (s, 3H), 3.79 (s, 3H), 2.66 (dd, J = 8.7, 6.4 Hz, 1H), 2.07 (h, J = 6.8 Hz, 1H), 1.55 (d, J = 7.2 Hz, 3H), 1.10 (d, J = 6.2 Hz, 3H), 0.85 (d, J = 6.8 Hz, 3H), 0.75 (d, J = 6.7 Hz, 3H). |
| 339 | | IR (thin film) 2963, 1734, 1650, 1528, 1452, 1264 cm$^{-1}$ | HRMS-ESI (m/z) [M + H]$^+$ calcd for C$_{24}$H$_{33}$N$_2$O$_5$, 429.2310; found, 429.2381 | $^1$H NMR (400 MHz, CDCl$_3$) δ 12.15 (s, 1H), 8.50 (d, J = 7.8 Hz, 1H), 8.00 (d, J = 5.2 Hz, 1H), 7.21-7.02 (m, 4H), 6.88 (d, J = 5.2 Hz, 1H), 5.43 (ddq, J = 12.3, 9.6, 6.2 Hz, 1H), 4.77-4.59 (m, 1H), 3.95 (s, 3H), 3.31-3.11 (m, 1H), 2.33 (d, J = 4.9 Hz, 3H), 2.00-1.79 (m, 1H), 1.55 (d, J = 6.6 Hz, 2H), 1.41 (ddd, J = 12.2, 7.3, 4.5 Hz, 1H), 1.34-1.19 (m, 1H), 1.12-0.67 (m, 10H). |
| 340 | | IR (thin film) 3370, 2961, 1528, 1263, 1057 cm$^{-1}$ | HRMS-ESI (m/z) [M + H]$^+$ calcd for C$_{25}$H$_{35}$N$_2$O$_5$, 443.2465; found, 443.2536 | $^1$H NMR (400 MHz, CDCl$_3$) δ 12.15 (s, 1H), 8.47 (d, J = 8.1 Hz, 1H), 7.99 (d, J = 5.2 Hz, 1H), 7.19-7.04 (m, 4H), 6.88 (d, J = 5.2 Hz, 1H), 5.46 (dq, J = 8.5, 6.2 Hz, 1H), 4.70 (p, J = 7.5 Hz, 1H), 3.95 (s, 3H), 3.32 (t, J = 7.6 Hz, 1H), 2.31 (s, 3H), 1.75-1.59 (m, 1H), 1.54 (d, J = 7.2 Hz, 3H), 1.49-1.17 (m, 3H), 1.14-0.97 (m, 4H), 0.90 (t, J = 7.4 Hz, 3H), 0.77 (t, J = 7.3 Hz, 3H). |
| 341 | | | ESIMS m/z 455 ([M + H]$^+$) | $^1$H NMR (400 MHz, CDCl$_3$) δ 12.14 (s, 1H), 8.47 (d, J = 8.0 Hz, 1H), 7.99 (d, J = 5.2 Hz, 1H), 6.88 (d, J = 5.2 Hz, 1H), 6.62 (s, 2H), 5.58 (ddt, J = 8.0, 6.4, 1.9 Hz, 1H), 4.68 (dq, J = 9.3, 7.3 Hz, 1H), 3.95 (s, 3H), 3.19 (t, J = 7.7 Hz, 1H), 2.35-2.19 (m, 1H), 1.54 (d, J = 7.2 Hz, 3H), 1.15 (dt, J = 6.4, 1.3 Hz, 3H), 0.96 (d, J = 6.7 Hz, 3H), 0.78 (dt, J = 6.8, 1.3 Hz, 3H). $^{19}$F NMR (376 MHz, CDCl$_3$) δ −105.84 (d, J = 1667.9 Hz), −110.02. |
| 342 | | | | $^1$H NMR (400 MHz, CDCl$_3$) δ 12.13 (s, 1H), 8.44 (d, J = 8.0 Hz, 1H), 7.99 (d, J = 5.2 Hz, 1H), 7.08 (dd, J = 3.8, 2.0 Hz, 2H), 7.04-6.96 (m, 1H), 6.86 (dd, J = 19.5, 5.2 Hz, 1H), 5.44 (ddd, J = 7.7, 6.4, 1.3 Hz, 1H), 4.80-4.49 (m, 1H), 3.95 (s, 3H), 3.14 (t, J = 7.8 Hz, 1H), 2.09 (q, J = 6.9 Hz, 1H), 1.54 (d, J = 7.2 Hz, 3H), 1.12 (d, J = 6.3 Hz, 3H), 0.93 (d, J = 6.6 Hz, 3H), 0.75 (d, J = 6.7 Hz, 3H). $^{19}$F NMR (376 MHz, CDCl$_3$) δ −112.37. |
| 343 | | | | $^1$H NMR (400 MHz, CDCl$_3$) δ 12.15 (s, 1H), 8.50 (d, J = 8.0 Hz, 1H), 7.99 (d, J = 5.2 Hz, 1H), 7.24-7.07 (m, 3H), 6.96 (dddd, J = 9.5, 8.1, 2.8, 1.5 Hz, 1H), 6.87 (d, J = 5.2 Hz, 1H), 5.82-5.37 (m, 1H), 4.71 (dd, J = 7.9, 7.1 Hz, 1H), 3.62-3.24 (m, 1H), 2.31-2.21 (m, 1H), 1.57 (d, J = 7.2 Hz, 3H), 1.36 (s, 1H), 1.18-0.96 (m, 7H), 0.78 (ddd, J = 6.8, 2.7, 0.9 Hz, 3H). $^{13}$C NMR (101 MHz, CDCl$_3$) δ 171.59, 168.70, 155.38, 148.78, 140.43, 137.03 (d, J = 9.3 Hz), 129.07-127.37 (m), 125.68 (d, J = 3.5 Hz), 114.81 (dd, J = 24.5, 2.1 Hz), 109.43, 73.22 (d, J = 5.4 Hz), 72.04 (d, J = 5.2 Hz), 56.06, 52.18-50.01 (m), 48.25, 29.65 (d, J = 3.2 Hz), 21.72 (d, J = 3.8 Hz), 20.38, 18.59 (d, J = 2.4 Hz), 18.16. $^{19}$F NMR (376 MHz, CDCl$_3$) δ −105.04 (d, J = 14.1 Hz). |

TABLE 2-continued

Analytical Data

| Cmpd. No. | Melting Point (° C.) | IR (cm$^{-1}$) | MASS SPEC | NMR |
|---|---|---|---|---|
| 344 | | | ESIMS m/z 415 ([M + H]$^+$) | $^1$H NMR (400 MHz, CDCl$_3$) δ 12.16 (s, 1H), 8.51 (d, J = 7.9 Hz, 1H), 8.01 (dd, J = 5.2, 3.5 Hz, 1H), 7.17 (q, J = 8.2 Hz, 1H), 7.04 (t, J = 6.0 Hz, 1H), 6.89 (td, J = 5.2, 4.7, 2.6 Hz, 3H), 5.41 (ddt, J = 17.9, 8.7, 6.2 Hz, 1H), 4.69 (p, J = 7.3 Hz, 1H), 3.94 (d, J = 5.1 Hz, 2H), 2.66 (ddd, J = 12.1, 8.8, 6.4 Hz, 1H), 2.33 (d, J = 4.2 Hz, 3H), 1.70-1.48 (m, 6H), (dd, J = 8.0, 6.8 Hz, 3H), 0.76 (d, J = 6.8 Hz, 3H). $^{13}$C NMR (101 MHz, CDCl$_3$) δ 171.75, 168.73, 155.40, 148.81, 140.46, 137.37, 130.65, 130.57, 127.73, 127.39, 126.82, 109.45, 108.39, 73.18, 72.02, 56.07, 48.22, 28.31, 21.49, 21.33, 18.66, 18.33, 17.89. |
| 345 | | | ESIMS m/z 437 ([M + H]$^+$) | $^1$H NMR (400 MHz, CDCl$_3$) δ 12.13 (s, 1H), 8.46 (d, J = 8.0 Hz, 1H), 8.00 (dd, J = 8.4, 5.2 Hz, 1H), 7.09-6.65 (m, 4H), 5.59-5.25 (m, 1H), 4.85-4.56 (m, 1H), 3.94 (d, J = 5.0 Hz, 4H), 3.27-3.08 (m, 1H), 1.54 (d, J = 7.2 Hz, 3H), 1.15 (d, J = 6.3 Hz, 3H), 0.95 (d, J = 6.7 Hz, 3H), 0.78 (d, J = 6.7 Hz, 3H). |
| 346 | | IR (thin film) 3391, 2962, 1770, 1743, 1677, 1513, 1499, 1311, 1192, 1175, 1009, 732 cm$^{-1}$ | HRMS-ESI (m/z) [M + H]$^+$ calcd for C$_{24}$H$_{30}$FN$_2$O$_6$, 461.2082; found, 461.2077 | $^1$H NMR (400 MHz, CDCl$_3$) δ 8.48 (t, J = 5.4 Hz, 1H), 8.34 (d, J = 5.4 Hz, 1H), 7.08-6.97 (m, 2H), 6.86 (ddd, J = 9.5, 6.3, 2.4 Hz, 2H), 5.43 (dq, J = 8.5, 6.4 Hz, 1H), 4.16 (d, J = 5.4 Hz, 2H), 3.92 (s, 3H), 3.03 (t, J = 7.7 Hz, 1H), 2.40 (s, 3H), 2.30 (s, 3H), 2.13-2.02 (m, 1H), 1.07 (d, J = 6.3 Hz, 3H), 0.92 (d, J = 6.7 Hz, 3H), 0.76 (d, J = 6.7 Hz, 3H). $^{19}$F NMR (376 MHz, CDCl$_3$) δ −117.43. |
| 347 | | IR (thin film) 3382, 2963, 1771, 1730, 1681, 1499, 1311, 1191, 1173, 907, 731 cm$^{-1}$ | HRMS-ESI (m/z) [M + H]$^+$ calcd for C$_{27}$H$_{36}$FN$_2$O$_6$, 503.2552; found, 503.2554 | $^1$H NMR (400 MHz, CDCl$_3$) δ 8.46 (d, J = 9.5 Hz, 1H), 8.32 (d, J = 5.5 Hz, 1H), 7.03 (dd, J = 9.1, 5.7 Hz, 2H), 6.83 (td, J = 8.4, 2.9 Hz, 1H), 6.77 (dd, J = 10.0, 2.8 Hz, 1H), 5.35 (dq, J = 9.1, 6.2 Hz, 1H), 4.66 (dd, J = 9.6, 4.8 Hz, 1H), 3.92 (s, 3H), 3.07 (dd, J = 9.1, 6.1 Hz, 1H), 2.40 (s, 3H), 2.36-2.22 (m, 4H), 2.14 (td, J = 13.4, 12.6, 5.9 Hz, 1H), 1.05 (d, J = 6.2 Hz, 3H), 1.02 (d, J = 6.8 Hz, 3H), 0.97 (d, J = 6.9 Hz, 3H), 0.82 (d, J = 6.8 Hz, 3H), 0.76 (d, J = 6.8 Hz, 3H). $^{13}$C NMR (101 MHz, CDCl$_3$) δ 171.03, 168.84, 162.69, 160.91 (d, J = 244.3 Hz), 159.51, 146.61, 141.66, 139.97 (d, J = 7.3 Hz), 137.57, 133.48 (d, J = 3.2 Hz), 129.19 (d, J = 7.8 Hz), 116.95 (d, J = 20.4 Hz), 112.24 (d, J = 20.7 Hz), 109.74, 73.47, 57.33, 56.31, 49.32, 31.55, 29.38, 20.91, 20.89-20.83 (m), 20.77, 19.38, 18.63, 18.10, 17.51. $^{19}$F NMR (376 MHz, CDCl$_3$) δ −117.47. |
| 348 | | IR (thin film) 3383, 2963, 1771, 1730, 1680, 1499, 1191, 1173, 731 cm$^{-1}$ | HRMS-ESI (m/z) [M + H]$^+$ calcd for C$_{28}$H$_{37}$FN$_2$O$_6$, 517.2708; found, 517.2715 | $^1$H NMR (400 MHz, CDCl$_3$) δ 8.45 (d, J = 9.5 Hz, 1H), 8.31 (d, J = 5.4 Hz, 1H), 7.03 (dd, J = 9.5, 5.6 Hz, 2H), 6.83 (td, J = 8.4, 2.9 Hz, 1H), 6.77 (dd, J = 9.9, 2.8 Hz, 1H), 5.35 (dq, J = 9.2, 6.2 Hz, 1H), 4.71 (dd, J = 9.5, 4.9 Hz, 1H), 3.92 (s, 3H), 3.08 (dd, J = 9.2, 6.0 Hz, 1H), 2.40 (s, 3H), 2.26 (s, 3H), 2.14 (td, J = 13.3, 12.8, 6.1 Hz, 1H), 2.09-1.98 (m, 1H), 1.51 (dtd, J = 16.7, 7.4, 3.6 Hz, 1H), 1.30-1.18 (m, 1H), 1.04 (d, J = 6.2 Hz, 3H), 1.00 (d, J = 6.8 Hz, 3H), 0.93 (t, J = 7.4 Hz, 3H), 0.82 (d, J = 6.8 Hz, 3H), 0.76 (d, J = 6.9 Hz, 3H). $^{13}$C NMR (101 MHz, CDCl$_3$) δ 170.99, 168.84, 162.59, 160.91 (d, J = 244.3 Hz), 159.51, 146.60, 141.67, 139.98 (d, |

TABLE 2-continued

Analytical Data

| Cmpd. No. | Melting Point (° C.) | IR (cm$^{-1}$) | MASS SPEC | NMR |
|---|---|---|---|---|
| | | | | J = 7.5 Hz), 137.58, 133.44 (d, J = 3.3 Hz), 129.21 (d, J = 7.6 Hz), 116.95 (d, J = 20.5 Hz), 112.23 (d, J = 20.8 Hz), 109.72, 73.43, 56.98, 56.31, 49.32, 38.12, 29.31, 24.73, 20.92, 20.90-20.83 (m), 20.78, 18.48, 18.16, 15.72, 11.56. $^{19}$F NMR (376 MHz, CDCl$_3$) δ -117.47. |
| 349 | | IR (thin film) 3378, 2959, 1772, 1733, 1679, 1499, 1191, 1173, 1049, 825 cm$^{-1}$ | HRMS-ESI (m/z) [M + H]$^+$ calcd for C$_{28}$H$_{38}$FN$_2$O$_6$, 517.2708; found, 517.2707 | $^1$H NMR (400 MHz, CDCl$_3$) δ 8.31 (t, J = 5.8 Hz, 2H), 7.08-6.96 (m, 2H), 6.84 (td, J = 8.4, 2.9 Hz, 1H), 6.78 (dd, J = 9.9, 2.8 Hz, 1H), 5.33 (dq, J = 8.9, 6.3 Hz, 1H), 4.72 (dt, J = 9.0, 7.0 Hz, 1H), 3.91 (s, 3H), 3.06 (dd, J = 8.9, 6.5 Hz, 1H), 2.39 (s, 3H), 2.26 (s, 3H), 2.15-2.04 (m, 1H), 1.78-1.59 (m, 3H), 1.05 (d, J = 6.2 Hz, 3H), 0.99-0.93 (m, 6H), 0.84 (d, J = 6.8 Hz, 3H), 0.75 (d, J = 6.8 Hz, 3H). $^{13}$C NMR (101 MHz, CDCl$_3$) δ 172.05, 168.83, 162.46, 160.90 (d, J = 244.3 Hz), 159.52, 146.57, 141.63, 139.94 (d, J = 7.5 Hz), 137.58, 133.69 (d, J = 3.3 Hz), 129.18 (d, J = 6.9 Hz), 116.90 (d, J = 20.5 Hz), 112.25 (d, J = 20.6 Hz), 109.74, 73.52, 56.30, 51.04, 49.33, 41.69, 29.59, 24.93, 23.03, 21.98, 20.94, 20.92-20.86 (m), 20.76, 18.94, 17.82. $^{19}$F NMR (376 MHz, CDCl$_3$) δ -117.54. |
| 350 | | IR (thin film) 3387, 2961, 1767, 1742, 1678, 1498, 1208, 1112, 1047, 1009, 730 cm$^{-1}$ | HRMS-ESI (m/z) [M + H]$^+$ calcd for C$_{26}$H$_{34}$FN$_2$O$_7$, 505.2345; found, 505.2339 | $^1$H NMR (400 MHz, CDCl$_3$) δ 8.46 (t, J = 5.4 Hz, 1H), 8.33 (d, J = 5.4 Hz, 1H), 7.08-6.99 (m, 2H), 6.90-6.80 (m, 2H), 5.43 (dq, J = 8.2, 6.3 Hz, 1H), 4.15 (d, J = 5.4 Hz, 2H), 3.91 (s, 3H), 3.82 (t, J = 6.6 Hz, 2H), 3.41 (s, 3H), 3.09-2.95 (m, 3H), 2.30 (s, 3H), 2.07 (h, J = 6.8 Hz, 1H), 1.07 (d, J = 6.3 Hz, 3H), 0.92 (d, J = 6.7 Hz, 3H), 0.76 (d, J = 6.8 Hz, 3H). $^{19}$F NMR (376 MHz, CDCl$_3$) δ -117.43. |
| 351 | | IR (thin film) 3383, 2963, 1769, 1730, 1681, 1499, 1311, 1110, 826 cm$^{-1}$ | HRMS-ESI (m/z) [M + H]$^+$ calcd for C$_{29}$H$_{40}$FN$_2$O$_7$, 547.2814; found, 547.2813 | $^1$H NMR (400 MHz, CDCl$_3$) δ 8.44 (d, J = 9.5 Hz, 1H), 8.32 (d, J = 5.4 Hz, 1H), 7.09-6.98 (m, 2H), 6.83 (td, J = 8.4, 2.9 Hz, 1H), 6.77 (dd, J = 10.0, 2.8 Hz, 1H), 5.35 (dq, J = 9.1, 6.2 Hz, 1H), 4.65 (dd, J = 9.5, 4.8 Hz, 1H), 3.91 (s, 3H), 3.81 (t, J = 6.6 Hz, 2H), 3.40 (s, 3H), 3.07 (dd, J = 9.1, 6.1 Hz, 1H), 2.99 (t, J = 6.7 Hz, 2H), 2.34-2.21 (m, 4H), 2.14 (dq, J = 13.4, 6.5 Hz, 1H), 1.05 (d, J = 6.2 Hz, 3H), 1.01 (d, J = 6.8 Hz, 3H), 0.97 (d, J = 6.9 Hz, 3H), 0.82 (d, J = 6.8 Hz, 3H), 0.76 (d, J = 6.9 Hz, 3H). $^{19}$F NMR (376 MHz, CDCl$_3$) δ -117.47. |
| 352 | | IR (thin film) 3382, 2963, 1769, 1730, 1681, 1499, 1111, 1046, 825, 731 cm$^{-1}$ | HRMS-ESI (m/z) [M + H]$^+$ calcd for C$_{30}$H$_{42}$FN$_2$O$_7$, 561.2971; found, 561.2969 | $^1$H NMR (400 MHz, CDCl$_3$) δ 8.43 (d, J = 9.4 Hz, 1H), 8.31 (d, J = 5.4 Hz, 1H), 7.06-6.96 (m, 2H), 6.83 (td, J = 8.4, 2.9 Hz, 1H), 6.77 (dd, J = 10.0, 2.8 Hz, 1H), 5.35 (dq, J = 9.1, 6.2 Hz, 1H), 4.69 (dd, J = 9.5, 4.9 Hz, 1H), 3.91 (s, 3H), 3.81 (t, J = 6.6 Hz, 2H), 3.41 (s, 3H), 3.07 (dd, J = 9.2, 6.0 Hz, 1H), 2.99 (t, J = 6.7 Hz, 2H), 2.26 (s, 3H), 2.18-2.08 (m, 1H), 2.08-1.97 (m, 1H), 1.50 (dddd, J = 13.3, 11.3, 6.8, 3.8 Hz, 1H), 1.29-1.17 (m, 1H), 1.04 (d, J = 6.2 Hz, 3H), 0.99 (d, J = 6.9 Hz, 3H), 0.93 (t, J = 7.4 Hz, 3H), 0.82 (d, J = 6.8 Hz, 3H), 0.76 (d, J = 6.8 Hz, 3H). $^{13}$C NMR (101 MHz, CDCl$_3$) δ 170.99, 169.35, 162.55, 160.91 (d, J = 243.9 Hz), 159.52, 146.64, 141.69, 139.97 (d, J = 7.5 Hz), 137.44, 133.44 (d, J = 3.1 Hz), 129.20 (d, J = 8.2 Hz), 116.95 (d, J = 20.3 Hz), 112.24 (d, J = 20.7 Hz), 109.72, 73.43, 67.65, 58.75, 56.97, |

TABLE 2-continued

Analytical Data

| Cmpd. No. | Melting Point (° C.) | IR (cm⁻¹) | MASS SPEC | NMR |
|---|---|---|---|---|
| 353 | | IR (thin film) 3377, 2958, 1769, 1733, 1679, 1499, 1309, 1110, 1049, 826 cm⁻¹ | HRMS-ESI (m/z) [M + H]⁺ calcd for $C_{30}H_{42}FN_2O_7$, 561.2971; found, 561.2974 | 56.34, 49.30, 38.13, 34.69, 29.32, 24.73, 20.92, 20.90-20.86 (m), 18.49, 18.15, 15.72, 11.55. ¹⁹F NMR (376 MHz, CDCl₃) δ −117.46. ¹H NMR (400 MHz, CDCl₃) δ 8.31 (t, J = 3.9 Hz, 2H), 7.08-6.98 (m, 2H), 6.84 (td, J = 8.4, 2.9 Hz, 1H), 6.78 (dd, J = 10.0, 2.8 Hz, 1H), 5.37-5.27 (m, 1H), 4.79-4.63 (m, 1H), 3.91 (s, 3H), 3.81 (t, J = 6.7 Hz, 2H), 3.40 (s, 3H), 3.06 (dd, J = 8.9, 6.5 Hz, 1H), 2.98 (t, J = 6.7 Hz, 2H), 2.26 (s, 3H), 2.09 (h, J = 6.8 Hz, 1H), 1.75-1.62 (m, 3H), 1.05 (d, J = 6.2 Hz, 3H), 0.99-0.93 (m, 6H), 0.84 (d, J = 6.8 Hz, 3H), 0.74 (d, J = 6.8 Hz, 3H). ¹³C NMR (101 MHz, CDCl₃) δ 172.06, 169.33, 162.42, 160.91 (d, J = 244.3 Hz), 159.53, 146.61, 141.64, 139.93 (d, J = 7.6 Hz), 137.45, 133.69 (d, J = 3.1 Hz), 129.19 (d, J = 8.0 Hz), 116.91 (d, J = 20.5 Hz), 112.25 (d, J = 20.6 Hz), 109.74, 73.51, 67.65, 58.74, 56.33, 51.03, 49.32, 41.74, 34.69, 29.60, 24.91, 23.05, 21.97, 21.01-20.80 (m), 20.94, 18.95, 17.82. |
| 354 | | IR (thin film) 3383, 2960, 1736, 1499, 1208, 1122, 730 cm⁻¹ | HRMS-ESI (m/z) [M + H]⁺ calcd for $C_{29}H_{38}FN_2O_6$, 529.2708; found, 529.2705 | ¹⁹F NMR (376 MHz, CDCl₃) δ −117.54. ¹H NMR (400 MHz, CDCl₃) δ 8.45 (d, J = 8.1 Hz, 1H), 8.31 (d, J = 5.4 Hz, 1H), 7.05 (dd, J = 8.6, 5.9 Hz, 1H), 6.99 (d, J = 5.5 Hz, 1H), 6.90-6.77 (m, 2H), 5.35 (dq, J = 8.9, 6.2 Hz, 1H), 4.77-4.64 (m, 1H), 3.89 (s, 3H), 3.15 (q, J = 8.0 Hz, 1H), 3.11-3.03 (m, 1H), 2.29 (s, 3H), 2.21-1.97 (m, 6H), 1.83-1.70 (m, 2H), 1.70-1.57 (m, 1H), 1.49 (d, J = 7.2 Hz, 3H), 1.06 (d, J = 6.2 Hz, 3H), 0.86 (d, J = 6.8 Hz, 3H), 0.77 (d, J = 6.8 Hz, 3H). |
| 355 | | IR (thin film) 3382, 2968, 1734, 1679, 1499, 1155, 1109, 1059, 731 cm⁻¹ | HRMS-ESI (m/z) [M + H]⁺ calcd for $C_{28}H_{38}FN_2O_6$, 517.2708; found, 517.2702 | ¹⁹F NMR (376 MHz, CDCl₃) δ −117.44. ¹H NMR (400 MHz, CDCl₃) δ 8.42 (d, J = 10.8 Hz, 1H), 8.32 (d, J = 5.4 Hz, 1H), 7.05 (dd, J = 8.6, 5.9 Hz, 1H), 6.99 (d, J = 5.5 Hz, 1H), 6.91-6.77 (m, 2H), 5.35 (dq, J = 8.7, 6.2 Hz, 1H), 4.77-4.66 (m, 1H), 3.89 (s, 3H), 3.07 (dd, J = 8.8, 6.5 Hz, 1H), 2.77 (q, J = 6.9 Hz, 1H), 2.29 (s, 3H), 2.11 (h, J = 6.7 Hz, 1H), 1.92 (dp, J = 14.2, 7.0 Hz, 1H), 1.65 (dt, J = 13.9, 7.2 Hz, 1H), 1.49 (d, J = 7.2 Hz, 3H), 1.37-1.30 (m, 3H), 1.05 (dd, J = 7.8, 7.0 Hz, 6H), 0.86 (d, J = 6.8 Hz, 3H), 0.77 (d, J = 6.8 Hz, 3H). |
| 356 | | IR thin film) 3380, 2960, 1678, 1499, 1311, 1149, 1049, 731 cm⁻¹ | HRMS-ESI (m/z) [M + H]⁺ calcd for $C_{28}H_{38}FN_2O_6$, 517.2708; found, 517.2706 | ¹⁹F NMR (376 MHz, CDCl₃) δ −117.44. ¹H NMR (400 MHz, CDCl₃) δ 8.47 (d, J = 8.1 Hz, 1H), 8.32 (d, J = 5.4 Hz, 1H), 7.05 (dd, J = 8.6, 5.9 Hz, 1H), 7.00 (d, J = 5.4 Hz, 1H), 6.88-6.77 (m, 2H), 5.36 (dq, J = 8.9, 6.3 Hz, 1H), 4.70 (dq, J = 8.2, 7.2 Hz, 1H), 3.90 (s, 3H), 3.08 (dd, J = 8.9, 6.5 Hz, 1H), 2.58 (d, J = 7.1 Hz, 2H), 2.35-2.20 (m, 4H), 2.17-2.05 (m, 1H), 1.49 (d, J = 7.2 Hz, 3H), 1.09-1.03 (m, 9H), 0.86 (d, J = 6.7 Hz, 3H), 0.77 (d, J = 6.8 Hz, 3H). |
| 357 | | IR (thin film) 3379, 2961, 1734, 1676, 1310, 1211, 1125, 1049, 731 cm⁻¹ | HRMS-ESI (m/z) [M + H]⁺ calcd for $C_{26}H_{34}FN_2O_6$, 489.2395; found, 489.2389 | ¹⁹F NMR (376 MHz, CDCl₃) δ −117.43. ¹H NMR (400 MHz, CDCl₃) δ 8.50 (d, J = 8.0 Hz, 1H), 8.32 (d, J = 5.5 Hz, 1H), 7.05 (dd, J = 8.6, 5.9 Hz, 1H), 7.01 (d, J = 5.4 Hz, 1H), 6.89-6.78 (m, 2H), 5.36 (dq, J = 8.9, 6.2 Hz, 1H), 4.76-4.64 (m, 1H), 3.91 (s, 3H), 3.08 (dd, J = 8.9, 1499, 6.5 Hz, 1H), 2.73 (q, J = 7.5 Hz, 2H), 2.29 (s, 3H), 2.11 (h, J = 6.8 Hz, 1H), 1.50 (d, J = 7.2 Hz, 3H), 1.28 (t, J = 7.5 Hz, 3H), 1.06 (d, J = 6.3 Hz, 3H), |

TABLE 2-continued

Analytical Data

| Cmpd. No. | Melting Point (° C.) | IR (cm$^{-1}$) | MASS SPEC | NMR |
|---|---|---|---|---|
| | | | | 0.86 (d, J = 6.8 Hz, 3H), 0.77 (d, J = 6.8 Hz, 3H). $^{19}$F NMR (376 MHz, CDCl$_3$) δ −117.43. |
| 358 | | IR (thin film) 3378, 2959, 1770, 1731, 1675, 1504, 1451, 1435, 1365, 1309, 1199, 1174, 1044, 907, 804, 729 cm$^{-1}$ | ESIMS m/z 471.2 ([M + H]$^+$) | $^1$H NMR (500 MHz, CDCl$_3$) δ 8.56 (s, 1H), 8.34 (d, J = 5.5 Hz, 1H), 7.04-6.98 (m, 2H), 6.95-6.84 (m, 2H), 5.37 (dq, J = 9.4, 6.2 Hz, 1H), 4.76-4.65 (m, 1H), 3.91 (s, 3H), 3.10 (dd, J = 9.1, 5.9 Hz, 1H), 2.40 (s, 3H), 2.29 (s, 3H), 2.27 (s, 3H), 2.14 (dp, J = 14.1, 7.4, 6.9 Hz, 1H), 1.52 (d, J = 7.1 Hz, 3H), 1.05 (d, J = 6.2 Hz, 3H), 0.84 (d, J = 6.8 Hz, 3H), 0.80 (d, J = 6.8 Hz, 3H). |
| 359 | | IR (thin film) 3381, 2961, 1770, 1732, 1675, 1506, 1457, 1436, 1366, 1310, 1199, 1164, 1041, 907, 785, 731 cm$^{-1}$ | ESIMS m/z 475.2 ([M + H]$^+$) | $^1$H NMR (500 MHz, CDCl$_3$) δ 8.53 (s, 1H), 8.34 (d, J = 5.5 Hz, 1H), 7.11 (td, J = 8.0, 5.9 Hz, 1H), 7.01 (d, J = 5.5 Hz, 1H), 6.90 (dt, J = 8.8, 4.9 Hz, 2H), 5.38 (dq, J = 8.9, 6.2 Hz, 1H), 4.75-4.63 (m, 1H), 3.91 (s, 3H), 3.14 (t, J = 7.7 Hz, 1H), 2.40 (s, 3H), 2.22 (d, J = 2.4 Hz, 3H), 2.14 (dq, J = 13.5, 6.9 Hz, 1H), 1.51 (d, J = 7.1 Hz, 3H), 1.06 (d, J = 6.3 Hz, 3H), 0.86 (d, J = 6.8 Hz, 3H), 0.78 (d, J = 6.9 Hz, 3H). |
| 360 | | IR (thin film) 3381, 2963, 1771, 1734, 1676, 1508, 1490, 1453, 1436, 1366, 1310, 1202, 1175, 1050, 907, 759, 732 cm$^{-1}$ | ESIMS m/z 461.2 ([M + H]$^+$) | $^1$H NMR (500 MHz, CDCl$_3$) δ 8.55 (s, 1H), 8.34 (d, J = 5.4 Hz, 1H), 7.22-7.17 (m, 1H), 7.14 (td, J = 7.5, 1.9 Hz, 1H), 7.08 (td, J = 7.5, 1.2 Hz, 1H), 7.00 (d, J = 5.4 Hz, 2H), 5.52-5.37 (m, 1H), 4.75-4.60 (m, 1H), 3.91 (s, 3H), 3.19 (t, J = 7.7 Hz, 1H), 2.40 (s, 3H), 2.18-2.09 (m, 1H), 1.50 (d, J = 7.2 Hz, 3H), 1.11 (d, J = 6.3 Hz, 3H), 0.91 (d, J = 6.7 Hz, 3H), 0.77 (d, J = 6.7 Hz, 3H). |
| 361 | | IR (thin film) 3377, 2961, 1770, 1734, 1676, 1500, 1453, 1436, 1365, 1310, 1201, 1175, 1048, 907, 805, 731 cm$^{-1}$ | ESIMS m/z 475.2 ([M + H]$^+$) | $^1$H NMR (500 MHz, CDCl$_3$) δ 8.53 (s, 1H), 8.33 (d, J = 5.4 Hz, 1H), 7.07 (dd, J = 8.2, 6.2 Hz, 1H), 7.01 (d, J = 5.4 Hz, 1H), 6.88-6.73 (m, 2H), 5.41-5.24 (m, 1H), 4.76-4.64 (m, 1H), 3.91 (s, 3H), 3.10 (t, J = 7.8 Hz, 1H), 2.40 (s, 3H), 2.27 (s, 3H), 2.16-2.08 (m, 1H), 1.50 (d, J = 7.2 Hz, 3H), 1.08 (d, J = 6.3 Hz, 3H), 0.88 (d, J = 6.8 Hz, 3H), 0.80 (d, J = 6.8 Hz, 3H). |
| 362 | | IR (thin film) 3376, 2959, 1771, 1731, 1676, 1505, 1452, 1437, 1200, 1175, 1045, 823 cm$^{-1}$ | ESIMS m/z 471.2 ([M + H]$^+$) | $^1$H NMR (400 MHz, CDCl$_3$) δ 8.56 (s, 1H), 8.34 (d, J = 5.5 Hz, 1H), 7.01 (d, J = 5.5 Hz, 1H), 6.96 (d, J = 2.9 Hz, 3H), 5.46-5.29 (m, 1H), 4.77-4.65 (m, 1H), 3.91 (s, 3H), 3.09 (dd, J = 9.2, 5.9 Hz, 1H), 2.36 (s, 3H), 2.28 (s, 6H), 2.19-2.07 (m, 1H), 1.51 (d, J = 7.1 Hz, 3H), 1.04 (d, J = 6.2 Hz, 3H), 0.84 (d, J = 6.8 Hz, 3H), 0.79 (d, J = 6.8 Hz, 3H). |
| 363 | | IR (thin film) 3377, 2961, 1771, 1733, 1677, 1507, 1452, 1437, 1365, 1310, 1202, 1175, 1043 cm$^{-1}$ | ESIMS m/z 471.2 ([M + H]$^+$) | $^1$H NMR (400 MHz, CDCl$_3$) δ 8.57 (s, 1H), 8.34 (d, J = 5.4 Hz, 1H), 7.06-6.99 (m, 3H), 6.97-6.92 (m, 1H), 5.39 (dq, J = 12.5, 6.5 Hz, 1H), 4.69 (dt, J = 8.1, 7.1 Hz, 1H), 3.91 (s, 3H), 3.25 (dd, J = 9.2, 6.0 Hz, 1H), 2.36 (s, 3H), 2.28 (s, 3H), 2.23 (s, 3H), 2.13 (dt, J = 14.1, 7.1 Hz, 1H), 1.52 (d, J = 7.2 Hz, 3H), 1.04 (d, J = 6.2 Hz, 3H), 0.84 (d, J = 6.7 Hz, 3H), 0.79 (d, J = 6.9 Hz, 3H). |
| 364 | | IR (thin film) 3382, 2960, 1771, 1732, 1676, 1507, 1200, 1175, 731 cm$^{-1}$ | HRMS-ESI (m/z) [M + H]$^+$ calcd for C$_{25}$H$_{33}$N$_2$O$_6$, 457.2333; found, 457.2332 | $^1$H NMR (500 MHz, CDCl$_3$) δ 8.55 (s, 1H), 8.34 (d, J = 5.5 Hz, 1H), 7.18-7.06 (m, 4H), 7.01 (d, J = 5.4 Hz, 1H), 5.39 (dq, J = 9.3, 6.2 Hz, 1H), 4.75-4.66 (m, 1H), 3.91 (s, 3H), 3.14 (dd, J = 9.3, 6.2 Hz, 1H), 2.40 (s, 3H), 2.32 (s, 3H), 2.21-2.10 (m, 1H), 1.51 (d, J = 7.1 Hz, 3H), 1.05 (d, J = 6.2 Hz, 3H), 0.86 (d, J = 6.9 Hz, 3H), 0.80 (d, J = 6.9 Hz, 3H). |

TABLE 2-continued

Analytical Data

| Cmpd. No. | Melting Point (° C.) | IR (cm⁻¹) | MASS SPEC | NMR |
|---|---|---|---|---|
| 365 | | IR (thin film) 2964, 1770, 1734, 1675, 1502, 1453, 1309, 1192, 1174, 1049, 965, 907, 846, 730 cm⁻¹ | ESIMS m/z 479.2 ([M + H]⁺) | $^1$H NMR (500 MHz, CDCl$_3$) δ 8.52 (s, 1H), 8.33 (d, J = 5.4 Hz, 1H), 7.10 (td, J = 8.4, 6.4 Hz, 1H), 7.01 (d, J = 5.5 Hz, 1H), 6.85-6.79 (m, 1H), 6.75 (ddd, J = 10.2, 8.9, 2.6 Hz, 1H), 5.41 (tt, J = 7.1, 5.8 Hz, 1H), 4.83-4.58 (m, 1H), 3.91 (s, 3H), 3.13 (t, J = 7.7 Hz, 1H), 2.40 (s, 3H), 2.09 (td, J = 13.3, 6.5 Hz, 1H), 1.49 (d, J = 7.2 Hz, 3H), 1.10 (d, J = 6.3 Hz, 3H), 0.92 (d, J = 6.8 Hz, 3H), 0.75 (d, J = 6.7 Hz, 3H). |
| 366 | | IR (thin film) 2962, 1770, 1733, 1676, 1506, 1452, 1310, 1197, 1174, 1049, 907, 823, 731 cm⁻¹ | ESIMS m/z 475.2 ([M + H]⁺) | $^1$H NMR (500 MHz, CDCl$_3$) δ 8.55 (s, 1H), 8.34 (d, J = 5.5 Hz, 1H), 7.05-6.95 (m, 2H), 6.89 (dd, J = 7.6, 1.5 Hz, 1H), 6.85-6.77 (m, 1H), 5.50-5.38 (m, 1H), 4.83-4.55 (m, 1H), 3.91 (s, 3H), 3.13 (t, J = 7.7 Hz, 1H), 2.40 (s, 3H), 2.32 (s, 3H), 2.10 (dt, J = 13.5, 6.8 Hz, 1H), 1.50 (d, J = 7.1 Hz, 3H), 1.10 (d, J = 6.3 Hz, 3H), 0.90 (d, J = 6.7 Hz, 3H), 0.76 (d, J = 6.7 Hz, 3H). $^{13}$C NMR (126 MHz, CDCl$_3$) δ 172.25, 168.92, 162.36, 160.50, 159.45, 146.65, 141.61, 138.33 (d, J = 8.2 Hz), 137.50, 130.10, 124.31 (d, J = 3.0 Hz), 122.50 (d, J = 15.0 Hz), 115.94 (d, J = 23.8 Hz), 109.70, 72.47, 56.28, 48.17, 28.32, 21.07, 20.90, 20.77, 18.96, 18.52, 17.42. |
| 367 | | IR (thin film) 2963, 1771, 1735, 1677, 1508, 1365, 1310, 1200, 1175, 1044, 825, 732 cm⁻¹ | ESIMS m/z 511.1 ([M]⁺) | $^1$H NMR (500 MHz, CDCl$_3$) δ 8.51 (s, 1H), 8.33 (d, J = 5.4 Hz, 1H), 7.36 (d, J = 2.2 Hz, 1H), 7.22 (dd, J = 8.5, 2.2 Hz, 1H), 7.13 (d, J = 8.4 Hz, 1H), 7.01 (d, J = 5.4 Hz, 1H), 5.37 (t, J = 7.3 Hz, 1H), 4.83-4.56 (m, 1H), 3.91 (s, 3H), 3.51 (s, 1H), 2.40 (s, 3H), 2.16-1.99 (m, 1H), 1.50 (d, J = 7.2 Hz, 3H), 1.10 (d, J = 6.3 Hz, 3H), 0.92 (d, J = 6.7 Hz, 3H), 0.76 (d, J = 6.8 Hz, 3H). |
| 368 | | IR (thin film) 3379, 2967, 1770, 1733, 1675, 1502, 1192, 1173, 965, 846, 731 cm⁻¹ | ESIMS m/z 479.2 ([M + H]⁺) | $^1$H NMR (500 MHz, CDCl$_3$) δ 8.49 (s, 1H), 8.34 (d, J = 5.4 Hz, 1H), 7.26 (s, 1H), 7.02 (dd, J = 5.5, 2.3 Hz, 1H), 6.82-6.71 (m, 2H), 5.45 (td, J = 6.2, 4.7 Hz, 1H), 4.75-4.59 (m, 1H), 3.92 (d, J = 2.5 Hz, 3H), 2.82 (dd, J = 9.3, 4.8 Hz, 1H), 2.39 (s, 3H), 2.01 (ddt, J = 15.8, 13.3, 6.8 Hz, 1H), 1.39 (d, J 3H), 1.08 (d, J = 6.3 Hz, 3H), 0.99 (d, J = 6.6 Hz, 3H), 0.70 (d, J = 6.6 Hz, 3H). |
| 369 | | IR (thin film) 2965, 1771, 1732, 1676, 1506, 1437, 1310, 1190, 1175, 1061, 1008, 821, 803 cm⁻¹ | ESIMS m/z 475.2 ([M + H]⁺) | $^1$H NMR (500 MHz, CDCl$_3$) δ 8.62 (dt, J = 4.3, 1.8 Hz, 1H), 8.35 (d, J = 5.5 Hz, 1H), 7.70 (tt, J = 7.7, 1.8 Hz, 1H), 7.31 (dd, J = 7.7, 5.8 Hz, 1H), 7.01 (d, J = 5.5 Hz, 1H), 6.82 (dd, J = 9.4, 7.0 Hz, 2H), 5.53-5.33 (m, 1H), 4.76-4.54 (m, 1H), 3.91 (s, 3H), 2.83 (dd, J = 9.2, 5.0 Hz, 1H), 2.39 (s, 3H), 2.31 (s, 3H), 1.36 (d, J = 7.1 Hz, 3H), 1.10 (d, J = 6.3 Hz, 3H), 0.98 (d, J = 6.6 Hz, 3H), 0.72 (d, J = 6.8 Hz, 3H). |
| 370 | | IR (thin film) 2964, 1771, 1733, 1714, 1676, 1506, 1472, 1365, 1310, 1192, 1175, 826, 804, 734 cm⁻¹ | ESIMS m/z 511.1 ([M + H]⁺) | $^1$H NMR (500 MHz, CDCl$_3$) δ 8.50 (s, 1H), 8.35 (d, J = 5.4 Hz, 1H), 7.41-7.30 (m, 2H), 7.07 (dd, J = 8.5, 2.2 Hz, 1H), 7.03 (d, J = 5.4 Hz, 1H), 5.44 (qd, J = 6.2, 4.3 Hz, 1H), 4.80-4.61 (m, 1H), 3.92 (d, J = 1.9 Hz, 3H), 3.10 (dd, J = 9.8, 4.3 Hz, 1H), 2.40 (s, 3H), 2.04-1.88 (m, 1H), 1.44 (d, J = 7.2 Hz, 3H), 1.05 (d, J = 6.3 Hz, 3H), 1.02 (d, J = 6.6 Hz, 3H), 0.68 (d, J = 6.7 Hz, 3H). $^{13}$C NMR (126 MHz, CDCl$_3$) δ 171.98, 168.88, 162.37, 159.57, 149.73, 146.66, 141.41, 137.63, 136.93, 136.28, 132.49, 130.70, 128.86, 127.08, 123.76, 109.88, |

TABLE 2-continued

Analytical Data

| Cmpd. No. | Melting Point (° C.) | IR (cm$^{-1}$) | MASS SPEC | NMR |
|---|---|---|---|---|
| | | | | 71.68, 56.33, 48.10, 30.13, 20.73, 20.64, 18.62, 18.30. |
| 371 | | IR (thin film) 2961, 1773, 1742, 1685, 1594, 1490, 1441, 1375, 1342, 1306, 1246, 1217, 1201, 1090 cm$^{-1}$ | ESIMS m/z 577.3 ([M + H]$^+$) | $^1$H NMR (400 MHz, CDCl$_3$) δ 8.33 (d, J = 5.5 Hz, 1H), 7.04 (dd, J = 8.6, 5.9 Hz, 1H), 6.95 (d, J = 5.6 Hz, 1H), 6.91-6.79 (m, 2H), 5.44-5.31 (m, 1H), 5.25 (q, J = 7.0 Hz, 1H), 4.31 (q, J = 7.1 Hz, 2H), 3.98-3.85 (m, 5H), 3.01 (t, J = 7.6 Hz, 1H), 2.31 (s, 3H), 2.15-2.04 (m, 1H), 1.63 (d, J = 7.0 Hz, 3H), 1.36 (t, J = 7.2 Hz, 3H), 1.01 (d, J = 6.3 Hz, 3H), 0.90 (d, J = 6.8 Hz, 3H), 0.87 (t, J = 7.2 Hz, 3H), 0.77 (d, J = 6.7 Hz, 3H). |
| 372 | | IR (thin film) 3379, 2962, 1767, 1734, 1678, 1499, 1312, 1251, 1215, 1051, 731 cm$^{-1}$ | ESIMS m/z 505.3 ([M + H]$^+$) | $^1$H NMR (500 MHz, CDCl$_3$) δ 8.47 (d, J = 8.1 Hz, 1H), 8.34 (d, J = 5.5 Hz, 1H), 7.08-6.99 (m, 2H), 6.88-6.79 (m, 2H), 5.36 (dq, J = 8.9, 6.3 Hz, 1H), 4.81-4.69 (m, 1H), 4.36 (q, J = 7.1 Hz, 2H), 3.94 (s, 3H), 3.08 (dd, J = 8.9, 6.5 Hz, 1H), 2.29 (m, 3H), 2.15-2.05 (m, 1H), 1.50 (d, J = 7.1 Hz, 3H), 1.41 (t, J = 7.1 Hz, 3H), 1.06 (d, J = 6.3 Hz, 3H), 0.86 (d, J = 6.8 Hz, 3H), 0.77 (d, J = 6.8 Hz, 3H). |
| 373 | | IR (thin film) 3384, 2981, 1764, 1736, 1681, 1500, 1313, 1259, 1217, 1180, 1100, 915 cm$^{-1}$ | ESIMS m/z 519.3 ([M + H]$^+$) | $^1$H NMR (400 MHz, CDCl$_3$) δ 8.44 (d, J = 8.1 Hz, 1H), 8.33 (d, J = 5.4 Hz, 1H), 7.08-6.97 (m, 2H), 6.91-6.75 (m, 2H), 5.44-5.31 (m, 1H), 4.98 (dq, J = 12.9, 6.4 Hz, 1H), 4.81-4.61 (m, 1H), 3.93 (s, 3H), 3.08 (dd, J = 8.9, 6.5 Hz, 1H), 2.29 (s, 3H), 2.11 (dt, J = 13.5, 6.8 Hz, 1H), 1.50 (d, J = 7.1 Hz, 3H), 1.41 (d, J = 6.3 Hz, 6H), 1.06 (d, J = 6.3 Hz, 3H), 0.86 (d, J = 6.8 Hz, 3H), 0.77 (d, J = 6.8 Hz, 3H). |
| 374 | | IR (thin film) 3382, 2968, 2874, 1756, 1735, 1681, 1611, 1500, 1311, 1274, 1208, 1154, 1108, 1060, 819, 730 cm$^{-1}$ | ESIMS m/z 517.3 ([M + H]$^+$) | $^1$H NMR (400 MHz, CDCl$_3$) δ 8.40 (s, 1H), 8.31 (d, J = 5.4 Hz, 1H), 7.05 (dd, J = 8.5, 5.9 Hz, 1H), 6.98 (d, J = 5.5 Hz, 1H), 6.91-6.72 (m, 2H), 5.35 (dq, J = 8.9, 6.3 Hz, 1H), 4.77-4.62 (m, 1H), 3.89 (s, 3H), 3.07 (dd, J = 8.8, 6.6 Hz, 1H), 2.29 (s, 3H), 2.11 (h, J = 6.7 Hz, 1H), 1.49 (d, J = 7.1 Hz, 3H), 1.41 (s, 9H), 1.05 (d, J = 6.3 Hz, 3H), 0.86 (d, J = 6.8 Hz, 3H), 0.77 (d, J = 6.8 Hz, 3H). $^{13}$C NMR (126 MHz, CDCl$_3$) δ 176.05, 172.39, 162.25, 160.89 (d, J = 244.3 Hz), 159.38, 146.49, 142.15, 139.92, 137.85, 133.67, 116.93 (d, J = 20.4 Hz), 112.29 (d, J = 20.6 Hz), 109.49, 73.65, 56.29, 53.43, 49.29, 48.13, 39.15, 29.67, 27.17, 20.92, 18.92, 18.66, 17.87. |
| 375 | | IR (thin film) 3382, 2970, 2875, 1762, 1733, 1678, 1504, 1208, 730 cm$^{-1}$ | HRMS-ESI (m/z) [M + H]$^+$ calcd for C$_{27}$H$_{37}$N$_2$O$_6$, 485.2646; found, 485.2642 | $^1$H NMR (500 MHz, CDCl$_3$) δ 8.49 (s, 1H), 8.33 (d, J = 5.4 Hz, 1H), 7.18-7.06 (m, 4H), 6.99 (d, J = 5.5 Hz, 1H), 5.39 (dq, J = 9.2, 6.2 Hz, 1H), 4.76-4.66 (m, 1H), 3.89 (s, 3H), 3.13 (dd, J = 9.2, 6.2 Hz, 1H), 2.95 (p, J = 7.0 Hz, 1H), 2.32 (s, 3H), 2.21-2.10 (m, 1H), 1.50 (d, J = 7.1 Hz, 3H), 1.36 (dd, J = 7.0, 0.9 Hz, 6H), 1.05 (d, J = 6.2 Hz, 3H), 0.86 (d, J = 6.8 Hz, 3H), 0.80 (d, J = 6.8 Hz, 3H). |
| 376 | | IR (thin film) 3383, 2974, 1771, 1732, 1676, 1506, 1193, 1174, 751 cm$^{-1}$ | HRMS-ESI (m/z) [M + H]$^+$ calcd for C$_{27}$H$_{37}$N$_2$O$_7$, 501.2601; found, 501.2515 | $^1$H NMR (500 MHz, CDCl$_3$) δ 8.59 (s, 1H), 8.33 (d, J = 5.5 Hz, 1H), 7.14 (td, J = 7.8, 1.7 Hz, 1H), 7.06 (dd, J = 7.5, 1.7 Hz, 1H), 7.00 (d, J = 5.5 Hz, 1H), 6.94-6.73 (m, 2H), 5.45 (s, 1H), 4.86-4.64 (m, 1H), 4.54 (hept, J = 6.0 Hz, 1H), 3.90 (s, 3H), 3.44 (s, 1H), 2.40 (s, 3H), 2.14 (dq, J = 13.3, 6.4 Hz, 1H), 1.52 (d, J = 7.1 Hz, 3H), 1.33 (d, J = 6.0 Hz, 3H), 1.31 (d, J = 6.0 Hz, 3H), 1.05 (d, J = 6.1 Hz, 3H), 0.83 (d, J = 6.8 Hz, 3H), 0.76 (d, J = 6.8 Hz, 3H). |
| 377 | | IR (thin film) 3381, | HRMS-ESI (m/z) [M + H]$^+$ calcd for C$_{27}$H$_{37}$N$_2$O$_7$, | $^1$H NMR (500 MHz, CDCl$_3$) δ 8.56 (s, 1H), 8.34 (d, J = 5.4 Hz, 1H), 7.00 (d, |

TABLE 2-continued

Analytical Data

| Cmpd. No. | Melting Point (° C.) | IR (cm$^{-1}$) | MASS SPEC | NMR |
|---|---|---|---|---|
| | | 2975, 1771, 1732, 1676, 1507, 1175, 730 cm$^{-1}$ | 501.2601; found, 501.2493 | J = 5.5 Hz, 1H), 6.99-6.96 (m, 2H), 6.81-6.76 (m, 2H), 5.36 (dq, J = 8.6, 6.2 Hz, 1H), 4.75-4.62 (m, 1H), 4.51 (hept, J = 6.0 Hz, 1H), 3.91 (s, 3H), 2.64 (dd, J = 8.8, 6.3 Hz, 1H), 2.40 (s, 3H), 2.12-2.02 (m, 1H), 1.50 (d, J = 7.1 Hz, 3H), 1.33 (d, J = 6.0 Hz, 6H), 1.08 (d, J = 6.3 Hz, 3H), 0.84 (d, J = 6.8 Hz, 3H), 0.75 (d, J = 6.7 Hz, 3H). |
| 378 | | IR (thin film) 3381, 2964, 1737, 1677, 1506, 1256, 1201, 1160, 1004 cm$^{-1}$ | HRMS-ESI (m/z) [M + H]$^+$ calcd for C$_{26}$H$_{32}$F$_3$N$_2$O$_8$, 557.2107; found, 557.2107 | $^1$H NMR (500 MHz, CDCl$_3$) δ 8.33 (d, J = 7.8 Hz, 1H), 8.28 (d, J = 5.3 Hz, 1H), 7.15-7.04 (m, 4H), 6.96 (d, J = 5.4 Hz, 1H), 5.75 (s, 2H), 5.40 (dq, J = 8.3, 6.3 Hz, 1H), 4.70 (p, J = 7.3 Hz, 1H), 3.92 (s, 3H), 2.73 (dd, J = 8.3, 6.9 Hz, 1H), 2.15-2.04 (m, 4H), 1.51 (d, J = 7.2 Hz, 3H), 1.09 (d, J = 6.3 Hz, 3H), 0.88 (d, J = 6.7 Hz, 3H), 0.74 (d, J = 6.8 Hz, 3H). |
| 379 | | IR (thin film) 3382, 2976, 1755, 1733, 1675, 1506, 1236, 1201, 955, 829 cm$^{-1}$ | HRMS-ESI (m/z) [M + H]$^+$ calcd for C$_{28}$H$_{39}$N$_2$O$_8$, 531.2701; found, 531.2688 | $^1$H NMR (500 MHz, CDCl$_3$) δ 8.38 (d, J = 7.8 Hz, 1H), 8.29 (d, J = 5.3 Hz, 1H), 6.98 (d, J = 8.7 Hz, 2H), 6.95 (d, J = 5.4 Hz, 1H), 6.79 (d, J = 8.6 Hz, 2H), 5.80-5.71 (m, 2H), 5.37 (dq, J = 8.8, 6.3 Hz, 1H), 4.80-4.64 (m, 1H), 4.51 (hept, J = 6.1 Hz, 1H), 3.91 (s, 3H), 2.65 (dd, J = 8.8, 6.3 Hz, 1H), 2.15-2.00 (m, 4H), 1.52 (d, J = 7.2 Hz, 3H), 1.33 (d, J = 6.1 Hz, 6H), 1.08 (d, J = 6.3 Hz, 3H), 0.84 (d, J = 6.7 Hz, 3H), 0.75 (d, J = 6.8 Hz, 3H). |
| 380 | | IR (thin film) 3380, 2961, 1770, 1731, 1675, 1504, 1488, 1192, 1175, 1037, 730 cm$^{-1}$ | HRMS-ESI (m/z) [M + H]$^+$ calcd for C$_{25}$H$_{31}$N$_2$O$_8$, 487.2080; found, 487.2065 | $^1$H NMR (500 MHz, CDCl$_3$) δ 8.54 (s, 1H), 8.34 (d, J = 5.5 Hz, 1H), 7.01 (d, J = 5.5 Hz, 1H), 6.70 (d, J = 7.9 Hz, 1H), 6.60 (d, J = 1.6 Hz, 1H), 6.54 (dd, J = 8.0, 1.7 Hz, 1H), 5.93 (q, J = 1.5 Hz, 2H), 5.33 (dq, J = 8.6, 6.3 Hz, 1H), 4.75-4.63 (m, 1H), 3.91 (s, 3H), 2.63 (dd, J = 8.5, 6.6 Hz, 1H), 2.40 (s, 3H), 2.09-2.00 (m, 1H), 1.49 (d, J = 7.2 Hz, 3H), 1.09 (d, J = 6.3 Hz, 3H), 0.86 (d, J = 6.7 Hz, 3H), 0.76 (d, J = 6.8 Hz, 3H). |
| 381 | | IR (thin film) 3385, 2964, 1772, 1734, 1677, 1507, 1258, 1199, 1162 cm$^{-1}$ | HRMS-ESI (m/z) [M + H]$^+$ calcd for C$_{25}$H$_{30}$F$_3$N$_2$O$_7$, 527.2000; found, 527.2000 | $^1$H NMR (500 MHz, CDCl$_3$) δ 8.49 (d, J = 7.5 Hz, 1H), 8.33 (d, J = 5.5 Hz, 1H), 7.16-7.05 (m, 4H), 7.01 (d, J = 5.5 Hz, 1H), 5.39 (dq, J = 8.2, 6.3 Hz, 1H), 4.74, 4.60 (m, 1H), 3.91 (s, 3H), 2.72 (dd, J = 8.1, 7.0 Hz, 1H), 2.40 (s, 3H), 2.15-2.02 (m, 1H), 1.48 (d, J = 7.2 Hz, 3H), 1.08 (d, J = 6.3 Hz, 3H), 0.88 (d, J = 6.7 Hz, 3H), 0.74 (d, J = 6.8 Hz, 3H). |
| 382 | | IR (thin film) 3378, 2960, 1733, 1675, 1511, 1201, 1038, 968, 829 cm$^{-1}$ | HRMS-ESI (m/z) [M + H]$^+$ calcd for C$_{26}$H$_{35}$N$_2$O$_8$, 503.2388; found, 503.2356 | $^1$H NMR (300 MHz, CDCl$_3$) δ 8.38 (d, J = 7.7 Hz, 1H), 8.29 (d, J = 5.4 Hz, 1H), 7.05-6.98 (m, 2H), 6.96 (d, J = 5.4 Hz, 1H), 6.87-6.75 (m, 2H), 5.75 (s, 2H), 5.45-5.30 (m, 1H), 4.80-4.60 (m, 1H), 3.92 (s, 3H), 3.79 (s, 3H), 2.67 (dd, J = 8.8, 6.3 Hz, 1H), 2.19-1.98 (m, 4H), 1.53 (d, J = 7.2 Hz, 3H), 1.09 (d, J = 6.3 Hz, 3H), 0.85 (d, J = 6.8 Hz, 3H), 0.75 (d, J = 6.8 Hz, 3H). |
| 383 | | IR (thin film) 3378, 2960, 1770, 1732, 1675, 1511, 1176, 1035, 730 cm$^{-1}$ | HRMS-ESI (m/z) [M + H]$^+$ calcd for C$_{25}$H$_{33}$N$_2$O$_7$, 473.2282; found, 473.2259 | $^1$H NMR (500 MHz, CDCl$_3$) δ 8.55 (s, 1H), 8.34 (d, J = 5.4 Hz, 1H), 7.07-6.95 (m, 3H), 6.88-6.74 (m, 2H), 5.37 (dq, J = 8.7, 6.3 Hz, 1H), 4.75-4.61 (m, 1H), 3.91 (s, 3H), 3.79 (s, 3H), 2.66 (dd, J = 8.7, 6.4 Hz, 1H), 2.40 (s, 3H), 2.08 (dq, J = 13.4, 6.7 Hz, 1H), 1.50 (d, J = 7.2 Hz, 3H), 1.07 (d, J = 6.2 Hz, 3H), 0.84 (d, J = 6.8 Hz, 3H), 0.75 (d, J = 6.8 Hz, 3H). |
| 384 | | IR (thin film) 2963, 1772, 1678, 1507, 1200, 733 cm$^{-1}$ | HRMS-ESI (m/z) [M + H]$^+$ calcd for C$_{26}$H$_{35}$N$_2$O$_6$, 471.2416; found, 471.2487 | $^1$H NMR (400 MHz, CDCl$_3$) δ 8.56 (s, 1H), 8.34 (dd, J = 5.4, 2.0 Hz, 1H), 7.19-7.06 (m, 4H), 7.01 (d, J = 5.5 Hz, 1H), 5.40 (dq, J = 12.1, 6.6 Hz, 1H), 4.72 (p, J = 7.3 Hz, 1H), 3.91 (s, 3H), 3.39- |

TABLE 2-continued

Analytical Data

| Cmpd. No. | Melting Point (° C.) | IR (cm⁻¹) | MASS SPEC | NMR |
|---|---|---|---|---|
| | | | | 3.05 (m, 1H), 2.40 (d, J = 1.7 Hz, 3H), 2.33 (d, J = 5.7 Hz, 3H), 1.90 (s, 1H), 1.55-1.18 (m, 5H), 1.04 (d, J = 6.3 Hz, 3H), 1.01-0.71 (m, 6H). |
| 385 | | IR (thin film) 2961, 1771, 1732, 1677, 1506, 1198, 1175, 731 cm⁻¹ | HRMS-ESI (m/z) [M + H]⁺ calcd for C$_{27}$H$_{37}$N$_2$O$_6$, 485.2572; found, 485.2643 | ¹H NMR (400 MHz, CDCl$_3$) δ 8.53 (s, 1H), 8.33 (d, J = 5.4 Hz, 1H), 7.22-7.05 (m, 4H), 7.01 (d, J = 5.5 Hz, 1H), 5.43 (dq, J = 8.3, 6.2 Hz, 1H), 4.69 (p, J = 7.3 Hz, 1H), 3.91 (s, 3H), 3.31 (t, J = 7.6 Hz, 1H), 2.39 (s, 3H), 2.31 (s, 3H), 1.63 (d, J = 6.2 Hz, 1H), 1.54-1.17 (m, 6H), 1.17-0.85 (m, 7H), 0.77 (t, J = 7.3 Hz, 3H). |
| 386 | | IR (thin film) 2970, 1736, 1506, 1210, 7.33 cm⁻¹ | HRMS-ESI (m/z) [M + H]⁺ calcd for C$_{28}$H$_{39}$N$_2$O$_6$, 499.2729; found, 499.2729 | ¹H NMR (400 MHz, CDCl$_3$) δ 8.49 (s, 1H), 8.33 (dd, J = 5.4, 2.1 Hz, 1H), 7.22-7.05 (m, 4H), 6.99 (d, J = 5.5 Hz, 1H), 5.39 (dq, J = 9.6, 6.7, 6.2 Hz, 1H), 4.72 (p, J = 7.3 Hz, 1H), 3.89 (s, 3H), 3.30-3.12 (m, 1H), 2.95 (tt, J = 7.0, 6.0 Hz, 1H), 2.33 (s, 3H), 1.88 (d, J = 13.8 Hz, 1H), 1.43 (dd, J = 59.5, 7.0 Hz, 11H), 1.04 (d, J = 6.3 Hz, 3H), 0.83 (qd, J = 15.1, 13.7, 7.1 Hz, 6H). |
| 387 | | IR (thin film) 2964, 1681, 1505, 1211, 1111 cm⁻¹ | HRMS-ESI (m/z) [M + H]⁺ calcd for C$_{29}$H$_{41}$N$_2$O$_6$, 513.2883; found, 513.2953 | ¹H NMR (400 MHz, CDCl$_3$) δ 8.46 (s, 1H), 8.32 (d, J =5.5 Hz, 1H), 7.17-7.03 (m, 5H), 6.99 (d, J = 5.5 Hz, 1H), 5.50-5.36 (m, 1H), 4.69 (p, J = 7.3 Hz, 1H), 3.89 (s, 3H), 3.31 (t, J = 7.6 Hz, 1H), 2.94 (p, J = 7.0, 1H), 2.31 (s, 3H), 1.61 (s, 1H), 1.51-0.94 (m, 15H), 0.90 (t, J = 7.4 Hz, 3H), 0.77 (t, J = 7.3 Hz, 3H). |
| 388 | | | ESIMS m/z 497 ([M + H]⁺) | ¹H NMR (400 MHz, CDCl$_3$) δ 8.53 (d, J = 8.0 Hz, 1H), 8.43-8.20 (m, 1H), 7.01 (d, J = 5.5 Hz, 1H), 6.62 (t, J = 9.0 Hz, 2H), 5.65-5.47 (m, 1H), 4.68 (dq, J = 8.3, 7.2 Hz, 1H), 3.91 (s, 3H), 3.19 (t, J = 7.7 Hz, 1H), 2.40 (s, 3H), 2.31-2.13 (dt, J = 6.4, 1.2 Hz, 3H), 0.96 (dd, J = 6.7, 3.5 Hz, 3H), 0.77 (dt, J = 6.7, 1.3 Hz, 3H). ¹⁹F NMR (376 MHz, CDCl$_3$) δ −105.79 (d, J = 1613.0 Hz), −110.18 (t, J = 6.4 Hz). |
| 389 | | | ESIMS m/z 495 ([M + H]⁺) | ¹H NMR (400 MHz, CDCl$_3$) δ 8.51 (d, J = 6.7 Hz, 1H), 8.33 (d, J = 5.4 Hz, 1H), 7.13-6.92 (m, 4H), 5.42 (dqd, J = 7.6, 6.4, 1.2 Hz, 1H), 4.75-4.51 (m, 1H), 3.91 (s, 3H), 3.13 (t, J = 7.7 Hz, 1H), 2.40 (s, 3H), 2.20-2.01 (m, 1H), 1.49 (d, J = 7.2 Hz, 3H), 1.10 (d, J = 6.3 Hz, 3H), 0.93 (d, J = 6.5 Hz, 3H), 0.75 (d, J = 6.7 Hz, 3H). ¹⁹F NMR (376 MHz, CDCl$_3$) δ −112.27. |
| 390 | | | ESIMS m/z 495 ([M + H]⁺) | ¹H NMR (400 MHz, CDCl$_3$) δ 8.40-8.29 (m, 1H), 7.25-7.08 (m, 3H), 7.06-6.90 (m, 2H), 5.75-5.47 (m, 1H), 4.89-4.39 (m, 1H), 3.91 (s, 3H), 3.62-3.47 (m, 1H), 2.40 (s, 3H), 2.33-2.17 (m, 1H), 1.47 (dd, J = 38.1, 7.2 Hz, 3H), 1.14-1.06 (m, 3H), 0.99 (dd, J = 6.8, 5.6 Hz, 3H), 0.78 (dt, J = 6.9, 2.4 Hz, 3H). ¹⁹F NMR (376 MHz, CDCl$_3$) δ −105.07 (d, J = 18.2 Hz). |
| 391 | | | ESIMS m/z 457 ([M + H]⁺) | ¹H NMR (400 MHz, CDCl$_3$) δ 8.57 (d, J = 8.1 Hz, 1H), 8.34 (d, J = 5.4 Hz, 1H), 7.22-7.10 (m, 1H), 7.09-6.98 (m, 2H), 6.89 (d, J = 6.0 Hz, 2H), 5.47-5.24 (m, 1H), 4.62 (dp, J = 51.8, 7.2 Hz, 1H), 3.91 (s, 3H), 2.67 (dt, J = 8.7, 6.9 Hz, 1H), 2.40 (s, 3H), 2.33 (d, J = 5.2 Hz, 3H), 2.10 (dt, J = 13.6, 6.8 Hz, 1H), 1.46 (dd, J = 37.4, 7.2 Hz, 3H), 1.09 (d, J = 6.3 Hz, 3H), 0.86 (t, J = 7.0 Hz, 3H), 0.76 (d, J = 6.7 Hz, 3H). |

TABLE 2-continued

Analytical Data

| Cmpd. No. | Melting Point (° C.) | IR (cm$^{-1}$) | MASS SPEC | NMR |
|---|---|---|---|---|
| 392 | | | ESIMS m/z 479 ([M + H]$^+$) | $^1$H NMR (400 MHz, CDCl$_3$) δ 8.53 (d, J = 7.8 Hz, 1H), 8.33 (d, J = 5.5 Hz, 1H), 7.07-6.78 (m, 4H), 5.45-5.34 (m, 1H), 4.76-4.62 (m, 1H), 3.91 (s, 3H), 3.22-3.08 (m, 1H), 2.40 (s, 3H), 2.09 (dt, J = 13.5, 6.8 Hz, 1H), 1.49 (d, J = 7.1 Hz, 3H), 1.13 (d, J = 6.3 Hz, 3H), 0.95 (t, J = 5.2 Hz, 3H), 0.77 (d, J = 6.7 Hz, 3H). $^{19}$F NMR (376 MHz, CDCl$_3$) δ −119.17, −120.97. |

*Cmpd. No. - Compound Number

TABLE 3

Biological Testing Rating Scale

Rating Table for Fungal Pathogens

| % Control | Rating |
|---|---|
| >80 | A |
| ≤80 | B |
| Not Tested | C |
| ≤0 | D |

TABLE 4

Biological Activity - PUCCRT and SEPTTR Disease Control in High and Low Volume Applications

| | HV activity at 100 ppm | | | | LV activity at 121.5 g/H | | | |
|---|---|---|---|---|---|---|---|---|
| Cmpd. | PUCCRT* | | SEPTTR* | | PUCCRT* | | SEPTTR* | |
| No. | 1DP* | 3DC* | 1DP* | 3DC* | 1DP* | 3DC* | 1DP* | 3DC* |
| 105 | A | D | B | B | C | C | C | C |
| 106 | B | D | D | D | C | C | C | C |
| 112 | A | A | A | A | C | C | C | C |
| 113 | A | A | A | A | C | C | C | C |
| 114 | A | B | A | B | C | C | C | C |
| 115 | D | D | B | D | C | C | C | C |
| 116 | A | D | D | B | C | C | C | C |
| 117 | A | D | A | A | C | C | C | C |
| 118 | A | B | B | B | C | C | C | C |
| 119 | A | B | A | A | C | C | C | C |
| 120 | A | D | D | B | C | C | C | C |
| 121 | A | B | B | A | C | C | C | C |
| 122 | A | A | A | B | C | C | C | C |
| 123 | A | A | A | A | C | C | C | C |
| 124 | A | A | A | A | C | C | C | C |
| 125 | A | B | A | A | C | C | C | C |
| 126 | A | B | A | A | C | C | C | C |
| 127 | A | A | A | B | C | C | C | C |
| 128 | B | D | D | B | C | C | C | C |
| 129 | A | D | A | B | C | C | C | C |
| 130 | A | B | B | B | C | C | C | C |
| 131 | A | B | A | B | C | C | C | C |
| 132 | A | A | A | B | C | C | C | C |
| 133 | A | B | A | B | C | C | C | C |
| 134 | B | B | B | B | C | C | C | C |
| 135 | B | A | B | A | C | C | C | C |
| 136 | A | A | A | A | C | C | C | C |
| 138 | A | B | D | D | C | C | C | C |
| 139 | A | B | A | D | C | C | C | C |
| 140 | A | A | D | B | C | C | C | C |
| 141 | B | A | D | A | C | C | C | C |
| 142 | A | A | D | B | C | C | C | C |
| 143 | A | A | A | B | C | C | C | C |
| 144 | A | A | B | A | C | C | C | C |
| 145 | A | A | B | A | C | C | C | C |
| 146 | A | A | B | A | C | C | C | C |
| 147 | A | A | D | B | C | C | C | C |
| 148 | B | A | D | B | C | C | C | C |
| 149 | B | B | B | A | C | C | C | C |
| 160 | C | C | C | C | A | B | B | A |
| 161 | C | C | C | C | A | B | B | A |
| 162 | C | C | C | C | A | A | B | A |
| 163 | C | C | C | C | A | B | B | A |
| 164 | C | C | C | C | A | A | A | A |
| 165 | C | C | C | C | A | A | A | A |
| 166 | C | C | C | C | A | A | B | A |
| 167 | C | C | C | C | A | A | A | A |
| 168 | C | C | C | C | A | A | B | B |
| 169 | C | C | C | C | A | A | B | A |
| 170 | C | C | C | C | A | A | A | A |
| 171 | C | C | C | C | A | A | A | A |
| 172 | C | C | C | C | A | A | A | A |
| 173 | C | C | C | C | A | B | A | A |
| 174 | C | C | C | C | A | A | A | A |
| 175 | C | C | C | C | A | A | A | A |
| 176 | C | C | C | C | A | B | A | A |
| 177 | C | C | C | C | B | D | B | D |
| 178 | C | C | C | C | A | B | D | B |
| 179 | C | C | C | C | A | D | A | A |
| 180 | C | C | C | C | A | B | B | B |
| 181 | C | C | C | C | B | B | B | A |
| 182 | C | C | C | C | A | B | B | A |
| 183 | C | C | C | C | B | B | B | A |
| 184 | C | C | C | C | A | A | A | A |
| 185 | C | C | C | C | A | B | A | A |
| 186 | C | C | C | C | A | A | A | A |
| 187 | C | C | C | C | A | B | A | A |
| 188 | C | C | C | C | A | B | A | A |
| 189 | C | C | C | C | A | B | A | A |
| 190 | C | C | C | C | D | D | D | B |
| 191 | C | C | C | C | D | B | B | B |
| 192 | C | C | C | C | A | B | D | A |
| 193 | C | C | C | C | B | B | D | B |
| 194 | C | C | C | C | B | D | B | A |
| 195 | C | C | C | C | A | A | A | A |
| 196 | C | C | C | C | A | A | A | A |
| 197 | C | C | C | C | A | A | A | A |
| 198 | C | C | C | C | B | D | B | B |
| 199 | C | C | C | C | B | D | A | B |
| 200 | C | C | C | C | B | B | D | B |

TABLE 4-continued

Biological Activity - PUCCRT and SEPTTR Disease Control in High and Low Volume Applications

| Cmpd. No. | HV activity at 100 ppm ||||  LV activity at 121.5 g/H ||||
|---|---|---|---|---|---|---|---|---|
| | PUCCRT* || SEPTTR* || PUCCRT* || SEPTTR* ||
| | 1DP* | 3DC* | 1DP* | 3DC* | 1DP* | 3DC* | 1DP* | 3DC* |
| 201 | C | C | C | C | A | B | B | B |
| 202 | C | C | C | C | A | D | B | B |
| 203 | C | C | C | C | B | B | B | B |
|

TABLE 4-continued

Biological Activity - PUCCRT and SEPTTR Disease Control in High and Low Volume Applications

| Cmpd. No. | HV activity at 100 ppm | | | | LV activity at 121.5 g/H | | | |
|---|---|---|---|---|---|---|---|---|
| | PUCCRT* | | SEPTTR* | | PUCCRT* | | SEPTTR* | |
| | 1DP* | 3DC* | 1DP* | 3DC* | 1DP* | 3DC* | 1DP* | 3DC* |
| 391 | C | C | C | C | A | B |

TABLE 6

Biological Activity - Disease Control in 1DP* test at 100 ppm

| Cmpd. No.* | ALTESO* | CERCBE* | COLLLA* | LEPTNO* |
|---|---|---|---|---|
| 186 | A | A | D | A |
| 187 | B | A | A | B |
| 216 | B | A | B | A |
| 217 | B | A | D | A |
| 218 | D | A | B | A |
| 219 | B | A | B | A |
| 220 | B | A | B | A |
| 354 | B | A | A | A |
| 355 | A | A | A | A |
| 356 | A | A | B | A |
| 357 | B | A | A | A |
| 359 | B | A | A | A |
| 363 | D | A | B | B |
| 364 | B | A | A | B |
| 371 | B | A | A | A |
| 372 | A | A | A | A |
| 373 | B | A | A | A |
| 374 | B | A | B | A |
| 375 | B | A | A | A |

*Cmpd. No.—Compound Number
*ALTESO—Tomato Early Blight (*Alternaria solani*)
*CERCBE—Leaf Spot of Sugar Beets (*Cercospora beticola*)
*COLLLA—Cucumber Anthracnose (*Glomerella lagenarium*; Anamorph: *Colletotricum lagenarium*)
*LEPTNO—Wheat Glume Blotch (*Parastagonospora nodorum*)

TABLE 7

Biological Activity - Disease Control in 1DP* Test at 100 ppm

| Cmpd. No.* | PSPECU* | PYRIOR* | RHYNSE* | UNCINE* |
|---|---|---|---|---|
| 186 | B | A | B | A |
| 187 | D | A | A | A |
| 216 | B | A | B | A |
| 217 | D | A | B | A |
| 218 | D | A | B | A |
| 219 | B | A | B | A |
| 220 | D | A | B | A |
| 354 | A | B | B | A |
| 355 | B | B | B | A |
| 356 | B | B | B | A |
| 357 | B | B | B | A |
| 359 | B | A | A | A |
| 363 | D | A | B | A |
| 364 | B | A | B | A |
| 371 | B | B | B | A |
| 372 | A | B | B | A |
| 373 | B | B | B | A |
| 374 | B | B | B | A |
| 375 | B | A | B | A |

*Cmpd. No.—Compound Number
*PSPECU—Cucumber Downy Midlew (*Pseudoperonospora cubensis*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*1DP—1 Day Protectant

What is claimed is:

1. A composition for the control of a fungal pathogen including mixtures of at least one of the compounds of Formula I

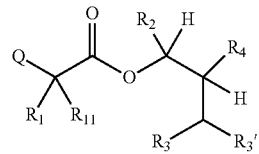

wherein:

Q is

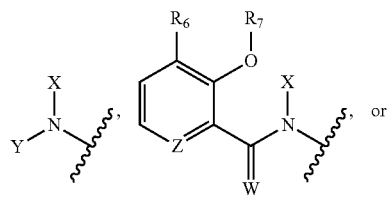

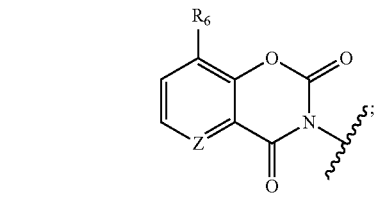

X is hydrogen or $C(O)R_5$;

Y is hydrogen or $C(O)R_5$;

Z is N or $N^+ \rightarrow O^-$ and W is O or S;

$R_1$ is hydrogen or alkyl, substituted with 0, 1 or multiple $R_8$;

$R_2$ is methyl;

$R_3$ and $R_{3'}$ are independently chosen from $C_2$-$C_6$ alkyl, $C_3$-$C_6$ cycloalkyl, aryl or heteroaryl, each optionally substituted with 0, 1 or multiple $R_8$; Alternatively, $R_3$ and $R_{3'}$ may be taken together to form a 3-6 membered saturated or partially saturated carbocycle or heterocycle, optionally substituted with 0, 1 or multiple $R_8$;

$R_4$ is chosen from aryl or heteroaryl, each optionally substituted with 0, 1 or multiple $R_8$;

$R_5$ is chosen from alkoxy or benzyloxy, each optionally substituted with 0, 1, or multiple $R_8$;

$R_6$ is chosen from hydrogen, alkoxy, or halo, each optionally substituted with 0, 1, or multiple $R_8$;

$R_7$ is chosen from hydrogen, —$C(O)R_9$, or —$CH_2OC(O)R_9$;

$R_8$ is chosen from hydrogen, alkyl, aryl, acyl, halo, alkenyl, alkynyl, alkoxy, cyano, or heterocyclyl, each optionally substituted with 0, 1, or multiple $R_{10}$;

$R_9$ is chosen from alkyl, alkoxy, or aryl, each optionally substituted with 0, 1, or multiple $R_8$;

$R_{10}$ is chosen from hydrogen, alkyl, aryl, acyl, halo, alkenyl, alkoxy, or heterocyclyl;

$R_{11}$ is chosen from hydrogen or alkyl, each substituted with 0, 1 or multiple $R_8$; and a phytologically acceptable carrier material.

2. The composition according to claim 1, wherein O is

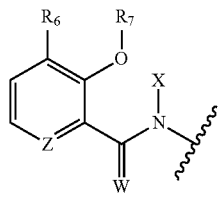

wherein X is hydrogen.

3. The composition according to claim 2 wherein Z is N.

4. The composition according to claim 3 wherein W is O.

5. The composition according to claim 4, wherein $R_6$ is alkoxy.

6. The composition according to claim 5, wherein $R_7$ is hydrogen.

7. The composition according to claim 6, wherein $R_1$ and $R_{11}$ are independently chosen from hydrogen or alkyl, $R_3$ and $R_{3'}$ are independently chosen from $C_1$-$C_6$ alkyl or taken together to form a 3-6 membered saturated carbocycle, each optionally substituted with 0, 1 or multiple $R_8$, and $R_4$ is aryl, optionally substituted with 0, 1 or multiple $R_8$.

8. The composition according to claim 5, wherein $R_7$ is chosen from —C(O)$R_9$ or —CH$_2$OC(O)$R_9$.

9. The composition according to claim 8, wherein $R_9$ is alkyl, optionally substituted with 0, 1 or multiple $R_8$.

10. The composition according to claim 9, wherein $R_1$ and $R_n$ are independently chosen from hydrogen or alkyl, $R_3$ and $R_{3'}$ are independently chosen from $C_1$-$C_6$ alkyl or taken together to form a 3-6 membered saturated carbocycle, each optionally substituted with 0, 1 or multiple $R_8$, and $R_4$ is aryl, optionally substituted with 0, 1 or multiple $R_8$.

11. The composition according to claim 1 wherein the fungal pathogen is one of Leaf Blotch of Wheat (*Zymoseptoria tritici*), Wheat Brown Rust (*Puccinia triticina*), Stripe Rust (*Puccinia stritformis*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Pyricularia oryzae*), Rust of Soybean (*Phakopsora pachyrhizi*), Glume Blotch of Wheat (*Parastagonospora nodorum*), Powdery Mildew of Wheat (*Blumeria graminis* f. sp. *tritici*), Powdery Mildew of Barley (*Blumeria graminis* f. sp. *hordes*), Powdery Mildew of Cucurbits (*Erysiphe cichoracearum*), Anthracnose of Cucurbits (*Colletotrichum lagenarium*), Leaf Spot of Beet (*Cercospora beticola*), Early Blight of Tomato (*Alternaria solani*), and Net Blotch of Barley (*Pyrenophora teres*).

12. The composition according to claim 7 wherein the fungal pathogen is one of Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Parastagonospora nodorum*), Anthracnose of Cucurbits (*Colletotrichum lagenarium*), Leaf Spot of Beet (*Cercospora beticola*), and Early Blight of Tomato (*Alternaria solani*).

13. The composition according to claim 8 wherein the fungal pathogen is one of Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Parastagonospora nodorum*), Anthracnose of Cucurbits (*Colletotrichum lagenarium*), Leaf Spot of Beet (*Cercospora beticola*), and Early Blight of Tomato (*Alternaria solani*).

14. The composition according to claim 10 wherein the fungal pathogen is one of Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Parastagonospora nodorum*), Anthracnose of Cucurbits (*Colletotrichum lagenarium*), Leaf Spot of Beet (*Cercospora beticola*), and Early Blight of Tomato (*Alternaria solani*).

15. A method for the control and prevention of fungal attack on a plant, the method including the step of:
applying a fungicidally effective amount of at least one of the compositions of claim 7 to at least one of the plant, an area adjacent to the plant, soil adapted to support growth of the plant, a root of the plant, and foliage of the plant.

16. A method for the control and prevention of fungal attack on a plant, the method including the step of:
applying a fungicidally effective amount of at least one of the compositions of claim 10 to at least one of the plant, an area adjacent to the plant, soil adapted to support growth of the plant, a root of the plant, and foliage of the plant.

17. A method for the control and prevention of fungal attack on a plant, the method including the step of:
applying a fungicidally effective amount of at least one of the compositions of claim 11 to at least one of the plant, an area adjacent to the plant, soil adapted to support growth of the plant, a root of the plant, and foliage of the plant.

18. A method for the control and prevention of fungal attack on a plant, the method including the step of:
applying a fungicidally effective amount of at least one of the compositions of claim 14 to at least one of the plant, an area adjacent to the plant, soil adapted to support growth of the plant, a root of the plant, and foliage of the plant.

* * * * *